US012612414B2

(12) United States Patent
Kubota et al.

(10) Patent No.: US 12,612,414 B2
(45) Date of Patent: Apr. 28, 2026

(54) NITRILE SUMO INHIBITORS AND USES THEREOF

(71) Applicant: SUVALENT THERAPEUTICS, INC., Thousand Oaks, CA (US)

(72) Inventors: Miles Douglas Kubota, Monrovia, CA (US); Andrew S. Tasker, Simi Valley, CA (US); Fang-Tsao Hong, Thousand Oaks, CA (US); Mary Walton, Camarillo, CA (US); Victor J. Cee, Thousand Oaks, CA (US); Peter Buchowiecki, Thousand Oaks, CA (US)

(73) Assignee: CIT THERAPEUTICS, INC., La Jolla, CA (US)

( * ) Notice: Subject to any disclaimer, the term of this patent is extended or adjusted under 35 U.S.C. 154(b) by 7 days.

(21) Appl. No.: 18/576,128

(22) PCT Filed: Jul. 21, 2022

(86) PCT No.: PCT/US2022/073985
§ 371 (c)(1),
(2) Date: Jan. 3, 2024

(87) PCT Pub. No.: WO2023/004376
PCT Pub. Date: Jan. 26, 2023

(65) Prior Publication Data
US 2024/0360148 A1 Oct. 31, 2024

Related U.S. Application Data

(60) Provisional application No. 63/224,040, filed on Jul. 21, 2021.

(51) Int. Cl.
*C07D 495/04* (2006.01)
*A61K 31/4365* (2006.01)
*A61K 31/444* (2006.01)

(52) U.S. Cl.
CPC ........ *C07D 495/04* (2013.01); *A61K 31/4365* (2013.01); *A61K 31/444* (2013.01)

(58) Field of Classification Search
CPC .................................................... C07D 495/04
See application file for complete search history.

(56) References Cited

U.S. PATENT DOCUMENTS 8,217,031 B2 7/2012 Matsuoka et al.
2023/0303584 A1 * 9/2023 Ouyang .................. A61P 35/00

FOREIGN PATENT DOCUMENTS

WO WO-2008120761 A1 10/2008
WO WO-2012114252 A1 8/2012
WO 2020/191151 A1 9/2020
WO 2021/150918 A1 7/2021

OTHER PUBLICATIONS

Berge et al., Pharmaceutical Salts, J. Pharm. Sci., 66(1): 1-19 (1977).
International Application No. PCT/US2022/073985, International Search Report and Written Opinion, mailed Oct. 19, 2022.
Weidmann et al., Copying Life: Synthesis of an Enzymatically Active Mirror-Image DNA-Ligase Made of D-Amino Acids, Cell Chemical Biology, 26:645-656 (2019).
Wilen et al., Strategies in optical resolutions, Tetrahedron, 33(21):2725-2736 (1997).

* cited by examiner

*Primary Examiner* — Valerie Rodriguez-Garcia
(74) *Attorney, Agent, or Firm* — MARSHALL, GERSTEIN & BORUN LLP

(57) ABSTRACT

The present invention relates to cyano-containing compounds and compositions capable of acting as inhibitors of small ubiquitin-like modifier (SUMO) family of proteins. The compounds and compositions may be used in the treatment of cancer. There are disclosed, inter alia, methods of inhibiting an E1 enzyme, and compounds useful for inhibiting an E1 enzyme.

Formula I

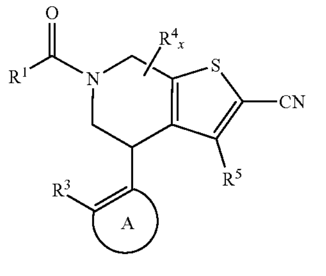

18 Claims, No Drawings

Specification includes a Sequence Listing.

SEQUENCE LISTING

```
Sequence total quantity: 6
SEQ ID NO: 1            moltype = AA  length = 13
FEATURE                 Location/Qualifiers
REGION                  1..13
                        note = Synthetic
source                  1..13
                        mol_type = protein
                        organism = synthetic construct
SEQUENCE: 1
LVGAGAIGCE LLK                                                       13

SEQ ID NO: 2            moltype = AA  length = 13
FEATURE                 Location/Qualifiers
REGION                  1..13
                        note = Synthetic
source                  1..13
                        mol_type = protein
                        organism = synthetic construct
SEQUENCE: 2
VVGAGGIGCE LLK                                                       13

SEQ ID NO: 3            moltype = AA  length = 13
FEATURE                 Location/Qualifiers
REGION                  1..13
                        note = Synthetic
source                  1..13
                        mol_type = protein
                        organism = synthetic construct
SEQUENCE: 3
VIGAGGLGCE LLK                                                       13

SEQ ID NO: 4            moltype = AA  length = 13
FEATURE                 Location/Qualifiers
REGION                  1..13
                        note = Synthetic
source                  1..13
                        mol_type = protein
                        organism = synthetic construct
SEQUENCE: 4
IVGCGGLGCP LAQ                                                       13
```

-continued

```
SEQ ID NO: 5           moltype = AA  length = 13
FEATURE                Location/Qualifiers
REGION                 1..13
                       note = Synthetic
source                 1..13
                       mol_type = protein
                       organism = synthetic construct
SEQUENCE: 5
LVGAGAIGCE LLK                                                    13

SEQ ID NO: 6           moltype = AA  length = 13
FEATURE                Location/Qualifiers
REGION                 1..13
                       note = Synthetic
source                 1..13
                       mol_type = protein
                       organism = synthetic construct
SEQUENCE: 6
LLGAGTLGCN VAR                                                    13
```

NITRILE SUMO INHIBITORS AND USES THEREOF

STATEMENT OF GOVERNMENT SUPPORT

This invention was made with government support under grant number SBIR Grant 1R43CA239820 awarded by the National Institutes of Health from the National Cancer Institute. The government has certain rights in the invention.

INCORPORATION BY REFERENCE OF MATERIALS SUBMITTED ELECTRONICALLY

The application contains, as a separate part of the disclosure, a Sequence Listing in .XML format: Filename: 54043_Seglisting.XML; Size: 8,251 Bytes; Created: Jul. 15, 2022, which is incorporated by reference in its entirety.

FIELD OF THE INVENTION

The present invention relates to compounds and compositions capable of acting as inhibitors of the small ubiquitin-like modifier (SUMO) family of proteins. The compounds and compositions may be used in the treatment of cancer.

BACKGROUND OF THE INVENTION

Post-translational modifications of cellular proteins by the small ubiquitin-like modifier (SUMO) family of proteins are important epigenetic mechanisms for regulating various cellular functions. Aberrations in post-translational modification of cellular proteins by the small ubiquitin-like modifier (SUMO) family of proteins are associated with the pathogenesis of life-threatening diseases, such as cancer, neurodegenerative disorders, and viral infection. Indeed, the enzymes catalyzing SUMO-modification (e.g., E1 disclosed herein) are present in higher levels in cancer tissues versus normal tissues and in metastasized tumors versus normal cells, and play an important role in cancer proliferation and metastasis. Without wishing to be bound by any theory, it is believed that E1 is a target for the development of therapeutics (e.g., cancer therapeutics). Thus, there are disclosed herein methods of inhibiting an E1 enzyme, and compounds useful for inhibiting an E1 enzyme.

DESCRIPTION OF THE INVENTION

One embodiment relates to compounds of the structure of Formula

[I]

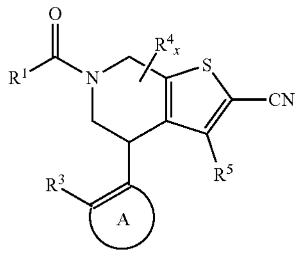

wherein ring A is selected from a) 5-7 membered cycloalkenyl, b) phenyl, c) 5- or 6-membered heteroaryl, d) 9-, 10- or 11-membered fused partially saturated heterocyclyl, and e) 9- or 10-membered fused heteroaryl;

wherein ring A is unsubstituted or substituted with one, two or three $R^2$ substituents;

$R^1$ is substituted or unsubstituted alkenyl or substituted or unsubstituted alkynyl;

Each $R^2$ is independently selected from halo, alkoxy, hydroxy, amino, alkyl, haloalkyl, cyano, alkylcarbonylamino, alkylsulfonylamino, and alkylaminocarbonylamino;

$R^3$ is selected from substituted or unsubstituted nitrogen containing 5-membered heteroaryl, substituted or unsubstituted 5- or 6-membered cycloalkenyl, substituted or unsubstituted nitrogen containing 5- or 6-membered partially unsaturated heterocyclyl and substituted or unsubstituted nitrogen containing 6-10 membered heteroaryl;

Each $R^4$ is independently selected from hydroxy and $C_1$-$C_3$ alkyl;

$R^5$ is selected from H, halo and $C_1$-$C_3$ alkyl; and x is 0, 1, or 2;

or an isomer or stereoisomer of any of the foregoing, or a mixture thereof or a pharmaceutically acceptable salt thereof.

In one embodiment, at least one $R^2$ is selected from H, fluoro, chloro, $C_1$-$C_3$ alkoxy, hydroxy, amino, $C_1$-$C_3$ alkyl, $C_1$-$C_3$ haloalkyl, cyano, $C_1$-$C_3$ alkylcarbonylamino, $C_1$-$C_3$ alkylsulfonylamino, and $C_1$-$C_3$ alkylaminocarbonylamino; or in isomer or stereoisomer of any of the foregoing, or a mixture thereof or a pharmaceutically acceptable salt thereof; or an isomer or a pharmaceutically acceptable salt thereof.

In one embodiment, at least one $R^2$ is selected from fluoro, chloro, methylcarbonylamino, hydroxy, methyl, difluoromethyl, methylsulfonylamino, and methylaminocarbonylamino and cyano; or an isomer or stereoisomer of any of the foregoing, or a mixture thereof or a pharmaceutically acceptable salt thereof.

In one embodiment, ring A is unsubstituted with $R^2$.

In one embodiment, $R^3$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or stereoisomer of any of the foregoing, or a mixture thereof or a pharmaceutically acceptable salt thereof.

In one embodiment, $R^3$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or stereoisomer of any of the foregoing, or a mixture thereof or a pharmaceutically acceptable salt thereof.

In one embodiment, $R^3$ is substituted 4-pyrazolyl; or an isomer or stereoisomer of any of the foregoing, or a mixture thereof or a pharmaceutically acceptable salt thereof.

In one embodiment, $R^3$ is 5-pyrimidinyl, 2-methyl-5-pyrimidinyl, 4-methyl-5-pyrimidinyl, 4,6-dimethoxy-5-pyrimidinyl, 4,6-dimethyl-5-pyrimidinyl, 4-trifluoromethyl-5-pyrimidinyl, 4-pyrimidinyl, 2-methyl-4-pyrimidinyl, 4-methyl-6-pyrimidinyl, 2,4-dimethyl-6-pyrimidinyl, 3-pyridinyl, 2-pyridinyl, 4-methyl-2-pyridinyl, 2-trifluoromethyl-3-pyridinyl, 4-trifluoromethyl-3-pyridinyl, 2-methyl-3-pyridinyl, 2,5-dimethyl-3-pyridinyl, 2,6-dimethyl-3-pyridinyl, 2,4-dimethyl-3-pyridinyl, 2-ethyl-3-pyridinyl, 5-methyl-3-pyridinyl, 2-ethoxy-3-pyridinyl, 2-ethoxy-5-methyl-3-pyridinyl, 2-methoxy-3-pyridinyl, 2-methoxy-6-methyl-3-pyridinyl, 2-ethoxy-6-methyl-3-pyridinyl, 2-isopropoxy-3-pyridinyl, 2-(3-pentoxy)-3-pyridinyl, 2-methoxyethoxy-3-pyridinyl, 2-cyclopropoxy-3-pyridinyl, 2-cyclopentyloxy-3-pyridinyl, 2-cyclohexloxy-3-pyridinyl, 2-fluoro-3-pyridinyl, 2-chloro-3-pyridinyl, 2-phenyl-3-pyridinyl, 2-fluoro-3-methyl-5-pyridinyl, 2-fluoro-3-chloro-5-pyridinyl, 3-fluoro-5-pyridinyl, 3-chloro-5-pyridinyl, 2-chloro-4-methyl-5-pyridinyl, 2-methoxy-5-pyridinyl, 3-methoxy-5-pyridinyl, 2-ethoxy-5-pyridinyl, 3-ethoxy-5-pyridinyl, 3-trifluoromethyl-5-pyridinyl, 3-ethyl-5-pyridinyl, 2,3-dimethyl-5-pyridinyl, 2-(2-hydroxymethylpyrrolidin-1-yl)-5-pyridinyl, 2-(morpholin-1-yl)-3-chloro-5-pyridinyl, 2-(dimethylaminoethoxy)-5-pyridinyl, 2-(2-dimethylaminomethylpyrrolidin-1-yl)-5-pyridinyl, 2-phenyl-5-pyridinyl, 2-methyl-6-pyridinyl, 2,4-dimethyl-6-pyridinyl or 2-ethyl-6-pyridinyl; or an isomer or stereoisomer of any of the foregoing, or a mixture thereof or a pharmaceutically acceptable salt thereof.

In one embodiment, $R^3$ is 2-trifluoromethyl-3-pyridinyl; or an isomer or stereoisomer of any of the foregoing, or a mixture thereof or a pharmaceutically acceptable salt thereof.

In one embodiment, $R^3$ is selected from substituted or unsubstituted tetrahydroquinolinyl; substituted or unsubstituted 1-pyrrolin-3-yl, substituted or unsubstituted 1-imidazolidinyl, and substituted or unsubstituted dihydropyridin-3-yl; or an isomer or stereoisomer of my of the foregoing, or a mixture thereof or a pharmaceutically acceptable salt thereof.

In one embodiment, $R^3$ is selected from 1-methoxy-4-isoquinolinyl, 1-chloro-4-isoquinolinyl, 6-methyl-4-isoquinolinyl, 1-oxo-2-methyl-4-isoquinolinyl, 5-pyrrolopyridinyl, [1,3,3a]-triazainden-5-yl, 1-ethyl-3-pyrrolopyridinyl, 1-methyl-5-pyrrolopyridinyl, 3-quinolinyl, 4-isoquinolinyl and 4-quinolinyl; or an isomer or stereoisomer of any of the foregoing, or a mixture thereof or a pharmaceutically acceptable salt thereof.

In one embodiment, $R^3$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-trifluoromethyl-pyrazol-4-yl, 1-methyl-3-difluoromethyl-pyrazol-4-yl, 1-butyl-3-trifluoromethyl-pyrazol-4-yl, 1-propynyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-(2-fluoroethyl)-3-trifluoromethyl-pyrazol-4-yl, 1-(2,2-difluoroethyl)-3-trifluoromethyl-pyrazol-4-yl, 1-(2,2,2-trifluoroethyl)-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[1-aminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-[1-(N-methylaminocarbonyl)ethyl]-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanopropyl-3-trifluoromethyl-pyrazol-4-yl, 1-cyanoethyl-3-trifluoromethyl-pyrazol-4-yl, 2-cyanoethyl-3-trifluoromethyl-pyrazol-4-yl, cyanomethyl-3-trifluoromethyl-pyrazol-4-yl, 1-[N,N-dimethylaminocarbonylethyl]-3-trifluoromethyl-pyrazol-4-yl, 1-carboxypropyl-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethoxycarbonylmethyl-3-trifluoromethyl-pyrazol-4-yl, 1-ethoxycarbonylethyl-3-trifluoromethyl-pyrazol-4-yl, 1-ethoxycarbonylpropyl-3-trifluoromethyl-pyrazol-4-yl, 1-methylsulfonyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-[[1,3,4-oxadiazol-2-yl]methyl]-3-trifluoromethyl-pyrazol-4-yl, 1-[[1,2,4-oxadiazol-5-yl]methyl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-[3-chloro-5-fluoro-4-pyridyl]-3-trifluoromethyl-pyrazol-4-yl, 1-[2-amino-4-pyridyl]-3-trifluoromethyl-pyrazol-4-yl, 1-[3,5-difluoro-4-pyridyl]-3-trifluoromethyl-pyrazol-4-yl, 1-[3-fluoro-4-pyridyl]-3-trifluoromethyl-pyrazol-4-yl, 1-[3-fluoro-2-pyridyl]-3-trifluoromethyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl or 4-methyl-5-thiazolyl; or an isomer or stereoisomer of any of the foregoing, or a mixture thereof or a pharmaceutically acceptable salt thereof.

One embodiment relates to compounds wherein $R^3$ is substituted or unsubstituted 4-isoquinolinyl or substituted or unsubstituted 4-quinolinyl; or an isomer or a pharmaceutically acceptable salt thereof.

In one embodiment, ring A is selected from phenyl, thienyl, pyrazolyl, cyclopentenyl, cyclohexenyl, 4-pyridyl, and indolyl; or an isomer or stereoisomer of any of the foregoing, or a mixture thereof or a pharmaceutically acceptable salt thereof.

In one embodiment, ring A is phenyl; or an isomer or stereoisomer of any of the foregoing, or a mixture thereof or a pharmaceutically acceptable salt thereof.

One embodiment relates to compounds wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

One embodiment relates to compounds wherein $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

One embodiment relates to compounds wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an iso Tier or stereoisomer of any of the foregoing, or a mixture thereof or a pharmaceutically acceptable salt thereof.

One embodiment relates to compounds wherein $R^1$ is selected from ethenyl, dimethylaminopropenyl, and dimethylaminopropynyl; or an isomer or stereoisomer of any of the foregoing, or a mixture thereof or a pharmaceutically acceptable salt thereof.

One embodiment relates to compounds wherein x is 0; or an isomer or stereoisomer of any of the foregoing, or a mixture thereof or a pharmaceutically acceptable salt thereof.

One embodiment relates to compounds wherein $R^5$ is H; or an isomer or stereoisomer of any of the foregoing, or a mixture thereof or a pharmaceutically acceptable salt thereof.

One embodiment relates to compounds of Formula II

[II]

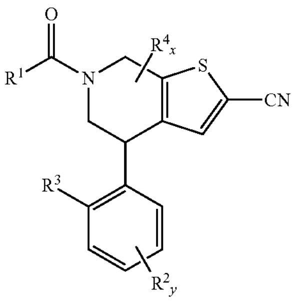

wherein $R^1$ is substituted or unsubstituted $C_2$-$C_6$ alkenyl, or substituted or unsubstituted $C_2$-$C_6$ alkynyl;

each $R^2$ is independently selected from halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^3$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl;

each $R^4$ is independently $C_1$-$C_3$ alkyl;

x is 0, 1, or 2; and y is 0, 1, or 2;

or an isomer or stereoisomer of any of the foregoing, or a mixture thereof or a pharmaceutically acceptable salt thereof.

In one embodiment $R^3$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or stereoisomer of any of the foregoing, or a mixture thereof or a pharmaceutically acceptable salt thereof In one embodiment $R^3$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or stereoisomer of any of the foregoing, or a mixture thereof or a pharmaceutically acceptable salt thereof.

In one embodiment $R^3$ is substituted 4-pyrazolyl; or an isomer or stereoisomer of any of the foregoing, or a mixture thereof or a pharmaceutically acceptable salt thereof.

In one embodiment $R^3$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-trifluoromethyl-pyrazol-4-yl, 1-methyl-3-difluoromethyl-pyrazol-4-yl, 1-butyl-3-trifluoromethyl-pyrazol-4-yl, 1-propynyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-(2-fluoroethyl)-3-trifluoromethyl-pyrazol-4-yl, 1-(2,2-difluoroethyl)-3-trifluoromethyl-pyrazol-4-yl, 1-(2,2,2-trifluoroethyl)-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[1-aminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-[1-(N-methylamino- carbonyl)ethyl]-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanopropyl-3-trifluoromethyl-pyrazol-4-yl, 1-cyanoethyl-3-trifluoromethyl-pyrazol-4-yl, 2-cyanoethyl-3-trifluoromethyl-pyrazol-4-yl, cyanomethyl-3-trifluoromethyl-pyrazol-4-yl, 1-[N,N-dimethylaminocarbonylethyl]-3-trifluoromethyl-pyrazol-4-yl, 1-carboxypropyl-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethoxycarbonylmethyl-3-trifluoromethyl-pyrazol-4-yl, 1-ethoxycarbonylethyl-3-trifluoromethyl-pyrazol-4-yl, 1-ethoxycarbonylpropyl-3-trifluoromethyl-pyrazol-4-yl, 1-methylsulfonyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-[[1,3,4-oxadiazol-2-yl]methyl]-3-trifluoromethyl-pyrazol-4-yl, 1-[[1,2,4-oxadiazol-5-yl]methyl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-[3-chloro-5-fluoro-4-pyridyl]-3-trifluoromethyl-pyrazol-4-yl, 1-[2-amino-4-pyridyl]-3-trifluoromethyl-pyrazol-4-yl, 1-[3,5-difluoro-4-pyridyl]-3-trifluoromethyl-pyrazol-4-yl, 1-[3-fluoro-4-pyridyl]-3-trifluoromethyl-pyrazol-4-yl, 1-[3-fluoro-2-pyridyl]-3-trifluoromethyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl or 4-methyl-5-thiazolyl; or an isomer or stereoisomer of any of the foregoing, or a mixture thereof or a pharmaceutically acceptable salt thereof.

One embodiment relates to compounds wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl-substituted $C_2$-$C_6$ alkynyl, substituted or unsubstituted 3-7 membered cycloalkyl-substituted $C_2$-$C_6$ alkenyl, substituted or unsubstituted 3-7 membered oxygen-containing heterocyclyl-substituted $C_2$-$C_6$ alkenyl, substituted or unsubstituted 3-7 membered oxygen-containing heterocyclyl-substituted $C_2$-$C_6$ alkynyl, substituted or unsubstituted 3-7 membered nitrogen-containing heterocyclyl-substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

In one embodiment $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

In one embodiment $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxybutenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino) propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

In one embodiment, y is 0; or an isomer or stereoisomer of any of the foregoing, or a mixture thereof or a pharmaceutically acceptable salt thereof.

In one embodiment at least one $R^2$ is selected from fluoro, amino, methylcarbonylamino, chloro, hydroxy, methyl, difluoromethyl, methylsulfonylamino, methylaminocarbonylamino and cyano; or an isomer or stereoisomer of any of the foregoing, or a mixture thereof or a pharmaceutically acceptable salt thereof.

In one embodiment, x is 0; or an isomer or stereoisomer of any of the foregoing, or a mixture thereof or a pharmaceutically acceptable salt thereof.

One embodiment relates to compounds of Formula III

[III]

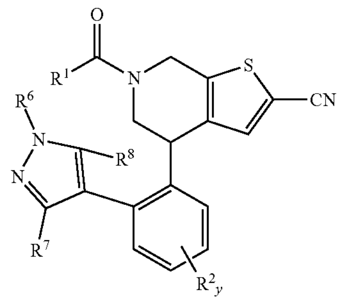

wherein $R^1$ is substituted or unsubstituted $C_2$-$C_6$ alkenyl, or substituted or unsubstituted $C_2$-$C_6$ alkynyl;

each $R^2$ is independently selected from halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

y is 0, 1, or 2;

$R^6$ is selected from H, $C_{1-6}$ alkyl, $C_2$-$C_4$ alkynyl, $C_{1-6}$ hydroxyalkyl, $C_{1-6}$ alkoxy, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl; and $R^8$ is selected from H, carboxy, cyano, $C_{1-4}$ alkyl, $C_{1-3}$ haloalkyl, and $C_{1-6}$ alkylaminocarbonyl;

or an isomer or stereoisomer of any of the foregoing, or a mixture thereof or a pharmaceutically acceptable salt thereof.

One embodiment relates to compounds wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

In one embodiment $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

In one embodiment $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

In one embodiment $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methylaminocarbonylmethyl, aminocarbonylmethyl, aminocarbonylethyl, 1-aminocarbonylethyl, aminocarbonyl-1,1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl]methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl; or in isomer or stereoisomer of any of the foregoing, or a mixture thereof or a pharmaceutically acceptable salt thereof.

In one embodiment $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl; or an isomer or stereoisomer of any of the foregoing, or a mixture thereof or a pharmaceutically acceptable salt thereof.

In one embodiment $R^8$ is selected from H, trifluoromethyl, methyl, ethyl, carboxy, cyano and methylaminocarbonyl; or an isomer or stereoisomer of any of the foregoing, or a mixture thereof or a pharmaceutically acceptable salt thereof.

In one embodiment, y is 0; or an isomer or stereoisomer of any of the foregoing, or a mixture thereof or a pharmaceutically acceptable salt thereof.

In one embodiment at least one $R^2$ is selected from fluoro, methylcarbonylamino, chloro, hydroxy, methyl, difluoromethyl, methylsulfonylamino, and methylaminocarbonylamino and cyano; or an isomer or stereoisomer of any of the foregoing, or a mixture thereof or a pharmaceutically acceptable salt thereof.

In one embodiment $R^6$ is ethyl; $R^7$ is trifluoromethyl; and $R^8$ is H; or an isomer or stereoisomer of any of the foregoing, or a mixture thereof or a pharmaceutically acceptable salt thereof.

One embodiment relates to compounds of Formula IV

IV

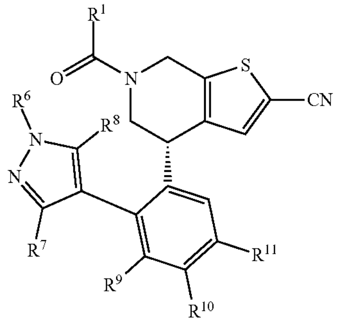

$R^1$ is substituted or unsubstituted $C_2$-$C_6$ alkenyl, or substituted or unsubstituted $C_2$-$C_6$ alkynyl;

$R^6$ is selected from H, $C_{1-6}$ alkyl, $C_{2-4}$ alkynyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^8$ is selected from H, carboxy, cyano, $C_{1-4}$ alkyl, $C_{1-3}$ haloalkyl, and $C_{1-6}$ alkylaminocarbonyl;

$R^9$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^{10}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino; and $R^{11}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino or an isomer or stereoisomer of any of the foregoing, or a mixture thereof or a pharmaceutically acceptable salt thereof.

In an embodiment, $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

In an embodiment, $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

In an embodiment, $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

In an embodiment, $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methylaminocarbonylmethyl, aminocarbonylmethyl, aminocarbonylethyl, 1-aminocarbonylethyl, aminocarbonyl-1,1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl] methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl; or an isomer or stereoisomer of any of the foregoing, or a mixture thereof or a pharmaceutically acceptable salt thereof.

In an embodiment, $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl; or an isomer or stereoisomer of any of the foregoing, or a mixture thereof or a pharmaceutically acceptable salt thereof.

In an embodiment, $R^8$ is selected from H, trifluoromethyl, methyl, ethyl, carboxy, cyano and methylaminocarbonyl; or an isomer or stereoisomer of any of the foregoing, or a mixture thereof or a pharmaceutically acceptable salt thereof.

In an embodiment, $R^9$ is selected from H, fluoro, chloro, methyl, and cyano; or an isomer or stereoisomer of any of the foregoing, or a mixture thereof or a pharmaceutically acceptable salt thereof.

In an embodiment, $R^{10}$ is selected from H, fluoro, methylcarbonylamino, chloro, amino, hydroxy, methyl, difluoromethyl, methylsulfonylamino, and methylaminocarbonylamino; or an isomer or stereoisomer of any of the foregoing, or a mixture thereof or a pharmaceutically acceptable salt thereof.

In an embodiment, $R^{11}$ is H, or fluoro; or an isomer or stereoisomer of any of the foregoing, or a mixture thereof or a pharmaceutically acceptable salt thereof.

In an embodiment, $R^6$ is ethyl; $R^7$ is trifluoromethyl; and $R^8$ is H; or an isomer or stereoisomer of any of the foregoing, or a mixture thereof or a pharmaceutically acceptable salt thereof.

One embodiment relates to compounds of Formula V

V

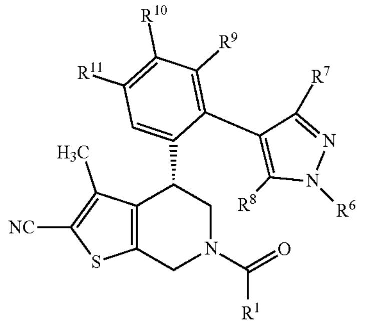

$R^1$ is substituted or unsubstituted $C_2$-$C_6$ alkenyl, or substituted or unsubstituted $C_2$-$C_6$ alkynyl;

$R^6$ is selected from H, $C_{1-6}$ alkyl, $C_{2-4}$ alkynyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^8$ is selected from H, carboxy, cyano, $C_{1-4}$ alkyl, $C_{1-3}$ haloalkyl, and $C_{1-6}$ alkylaminocarbonyl;

$R^9$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^{10}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino; and $R^{11}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino or in isomer or stereoisomer of any of the foregoing, or a mixture thereof or a pharmaceutically acceptable salt thereof.

In an embodiment, $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

In an embodiment, $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

In an embodiment, $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

In an embodiment, $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methylaminocarbonylmethyl, aminocarbonylmethyl, aminocarbonylethyl, 1-aminocarbonylethyl, aminocarbonyl-1,1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl]methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl.

In an embodiment, $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl.

In an embodiment, $R^8$ is selected from H, trifluoromethyl, methyl, ethyl, carboxy, cyano and methylaminocarbonyl.

In an embodiment, $R^9$ is selected from H, fluoro, chloro, methyl, and cyano.

In an embodiment, $R^9$ is H or fluoro.

In an embodiment, $R^{10}$ is selected from H, fluoro, methylcarbonylamino, chloro, amino, hydroxy, methyl, difluoromethyl, methylsulfonylamino, and methylaminocarbonylamino.

In an embodiment, $R^{11}$ is H, or fluoro.

In an embodiment, $R^{10}$ and $R^{11}$ is H.

In an embodiment, $R^6$ is ethyl; $R^7$ is trifluoromethyl; and $R^8$ is H.

In one embodiment, $R^6$ is ethyl; $R^7$ is trifluoromethyl; and $R^8$ is H;

In one embodiment, $R^6$ is methyl; $R^7$ is trifluoromethyl; and $R^8$ is H.

In one embodiment, $R^6$ is H; $R^7$ is trifluoromethyl; and $R^8$ is H.

In one embodiment, $R^6$ is 3,5-difluoropyridin-4-yl; $R^7$ is trifluoromethyl; and $R^8$ is H.

In one embodiment, $R^1$ is ethenyl.

In one embodiment, $R^1$ is dimethylaminopropenyl;

In one embodiment, $R^1$ is methylaminopropenyl.

In one embodiment, $R^1$ is 3,3-difluoropropenyl.

In one embodiment, $R^1$ is 2-(azetin-2-yl)ethenyl.

In one embodiment, $R^1$ is 2-(2-methyl-pyrrolidiny-5-yl) ethenyl.

In one embodiment, $R^1$ is 3-(methylamino)butenyl.

In one embodiment, $R^1$ is ethylaminopropenyl.

In one embodiment, $R^1$ is 2-(3-methoxypyrrolidiny-5-yl) ethenyl.

In one embodiment, $R^1$ is 2-(3-fluoropyrrolidiny-5-yl) ethenyl.

In one embodiment, $R^1$ is 2-(pyrrolidiny-2-yl)ethenyl.

In one embodiment, $R^1$ is aminopropenyl.

In one embodiment, $R^9$ is fluoro; $R^{10}$ is H; and $R^{11}$ is H.

In one embodiment, the compound has a plasma protein binding (PPB) of less than about 99.5% in rat plasma or human plasma. In some embodiments, the compounds have a PPB in rat plasma of less than about 99.0%, about 98.5%, about 98.0%, about 97.5% or about 97.0%. In some embodiments, the compounds have a PPB in human plasma of less than 99.0%, about 98.5%, about 98.0%, about 97.5% or about 97.0%.

In one embodiment, the compound has a permeability in CACO-2 cells greater than about 3.0 ucm/s. In some embodiments, the compounds have CACO-2 cell permeability of about 4, about 5, about 6, about 7, about 8, about 9, about 10, about 11, about 12, about 13 about 14, or about 15 ucm/s.

In one embodiment, the compound has solubility in simulated gastric fluid (SGF) greater than about 20 μM.

In some embodiments, the compound has a solubility in SGF of about 25 μM, about 30 μM, about 40 μM, about 50 μM, or greater than 50 μM.

In one embodiment, the compound has solubility in simulated intestinal fluid (SIF) greater than about 30 μM. In some embodiments, the compound has a solubility in SIF of about 35 μM, about 40 μM, about 50 μM, or greater than 50 μM.

In one embodiment, the compound has solubility in phosphate buffered saline (PBS) [pH 7.4] greater than about 40 μM. In some embodiments, the compound has a solubility in PBS of about 45 μM, about 50 μM, about 55 μM, about 60 μM, or greater than 60 μM.

In one embodiment, the compound has an $IC_{50}$ in HCT-116 cells less than about 0.20 μM. In some embodiments, the compound has an 1050 in HCT-116 cells less than 0.15 μM or less than 0.10 μM.

In one embodiment, the compound is as recited in Table A, below, or a pharmaceutically acceptable salt thereof.

TABLE A

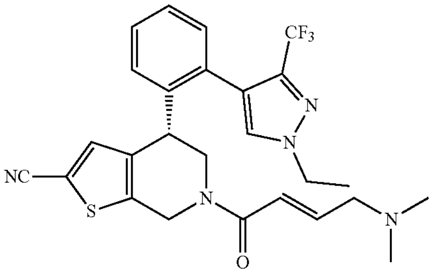 [SMILES: CCn1cc(-c2ccccc2[C@@H]2CN(C(=O)/C=C/CN(C)C)Cc3sc(C#N)cc32)c(C(F)(F)F)n1]

TABLE A-continued

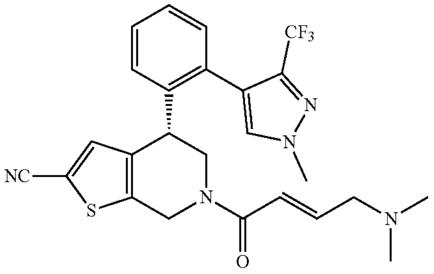 [SMILES: CN(C)C/C=C/C(=O)N1Cc2sc(C#N)cc2[C@H](c2ccccc2-c2cn(C)nc2C(F)(F)F)C1]

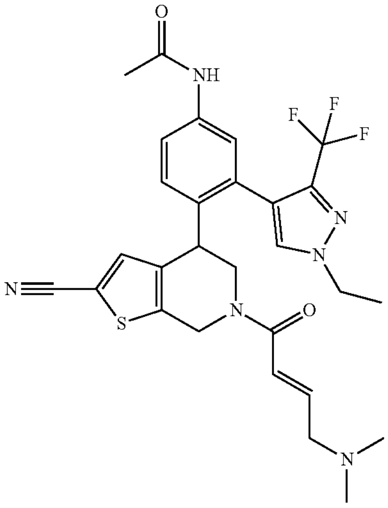 [SMILES: CCn1cc(-c2cc(NC(C)=O)ccc2C2CN(C(=O)/C=C/CN(C)C)Cc3sc(C#N)cc32)c(C(F)(F)F)n1]

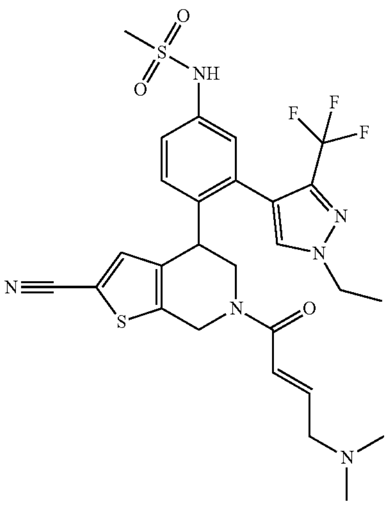 [SMILES: CCn1cc(-c2cc(NS(C)(=O)=O)ccc2C2CN(C(=O)/C=C/CN(C)C)Cc3sc(C#N)cc32)c(C(F)(F)F)n1]

TABLE A-continued
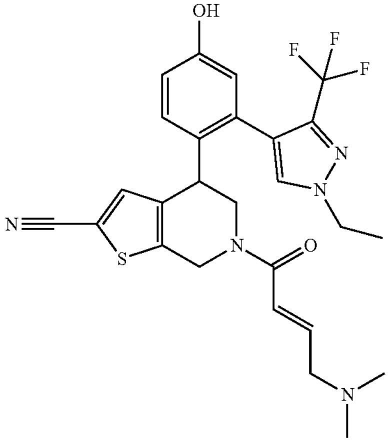 [SMILES: CCn1cc(-c2cc(O)ccc2C2CN(C(=O)/C=C/CN(C)C)Cc3sc(C#N)cc32)c(C(F)(F)F)n1]
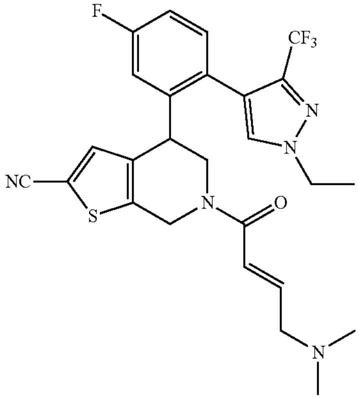 [SMILES: CCn1cc(-c2ccc(F)cc2C2CN(C(=O)/C=C/CN(C)C)Cc3sc(C#N)cc32)c(C(F)(F)F)n1]
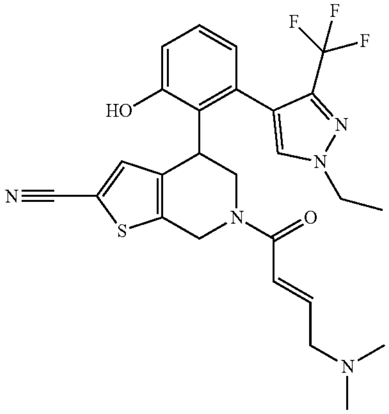 [SMILES: CCn1cc(-c2cccc(O)c2C2CN(C(=O)/C=C/CN(C)C)Cc3sc(C#N)cc32)c(C(F)(F)F)n1]
TABLE A-continued
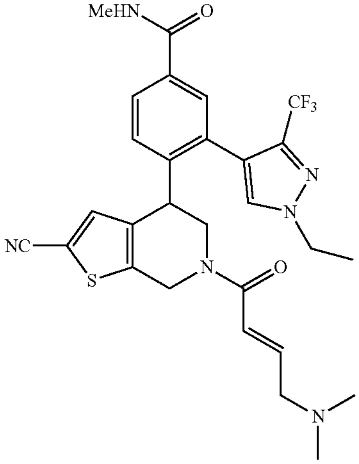 [SMILES: CCn1cc(-c2cc(C(=O)NC)ccc2C2CN(C(=O)/C=C/CN(C)C)Cc3sc(C#N)cc32)c(C(F)(F)F)n1]
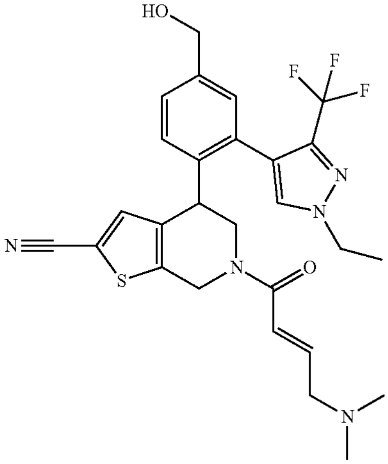 [SMILES: CCn1cc(-c2cc(CO)ccc2C2CN(C(=O)/C=C/CN(C)C)Cc3sc(C#N)cc32)c(C(F)(F)F)n1]
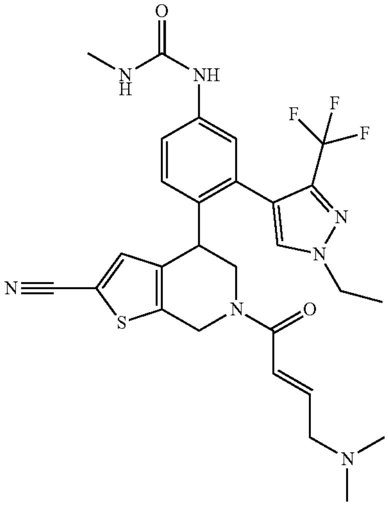 [SMILES: CCn1cc(-c2cc(NC(=O)NC)ccc2C2CN(C(=O)/C=C/CN(C)C)Cc3sc(C#N)cc32)c(C(F)(F)F)n1]

TABLE A-continued
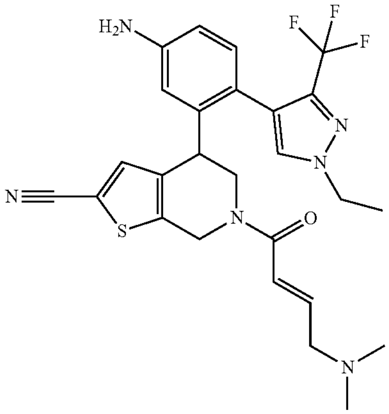 [SMILES: CCn1cc(-c2ccc(N)cc2C2CN(C(=O)/C=C/CN(C)C)Cc3sc(C#N)cc32)c(C(F)(F)F)n1]
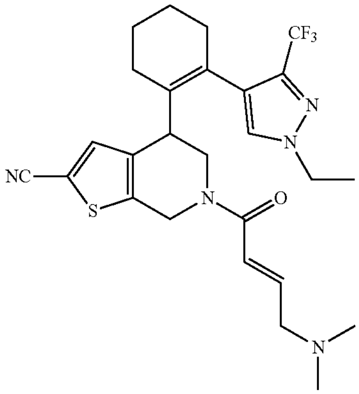 [SMILES: CCn1cc(C2=C(C3CN(C(=O)/C=C/CN(C)C)Cc4sc(C#N)cc43)CCCC2)c(C(F)(F)F)n1]
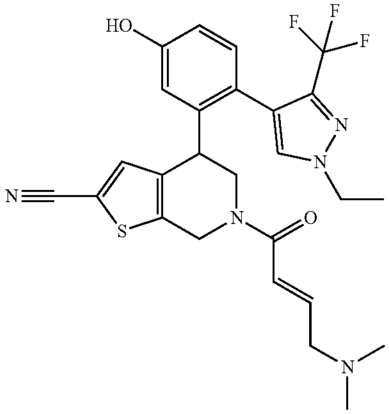 [SMILES: CCn1cc(-c2ccc(O)cc2C2CN(C(=O)/C=C/CN(C)C)Cc3sc(C#N)cc32)c(C(F)(F)F)n1]
TABLE A-continued
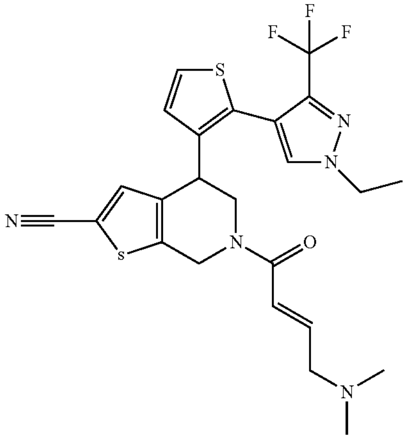
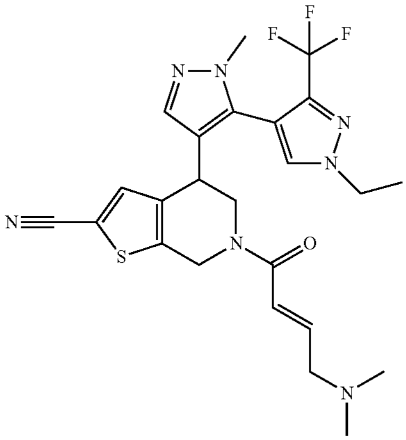 [SMILES: CCn1cc(-c2c(C3CN(C(=O)/C=C/CN(C)C)Cc4sc(C#N)cc43)cnn2C)c(C(F)(F)F)n1]
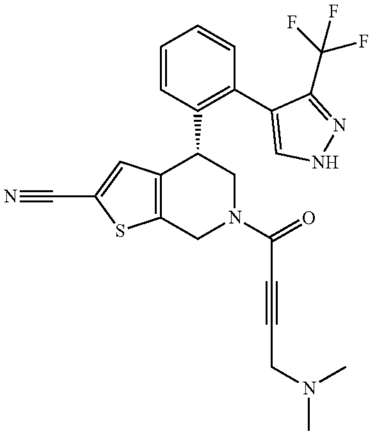 [SMILES: CN(C)CC#CC(=O)N1Cc2sc(C#N)cc2[C@H](c2ccccc2-c2c[nH]nc2C(F)(F)F)C1]

TABLE A-continued
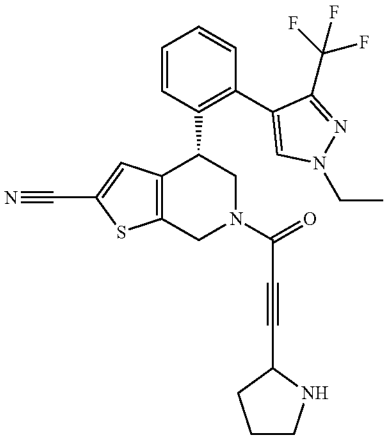 [SMILES: CCn1cc(-c2ccccc2[C@@H]2CN(C(=O)C#CC3CCCN3)Cc3sc(C#N)cc32)c(C(F)(F)F)n1]
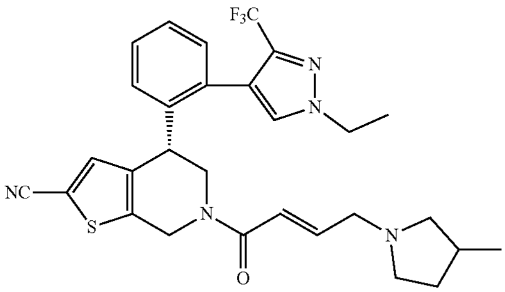 [SMILES: CCn1cc(-c2ccccc2[C@@H]2CN(C(=O)/C=C/CN3CCC(C)C3)Cc3sc(C#N)cc32)c(C(F)(F)F)n1]
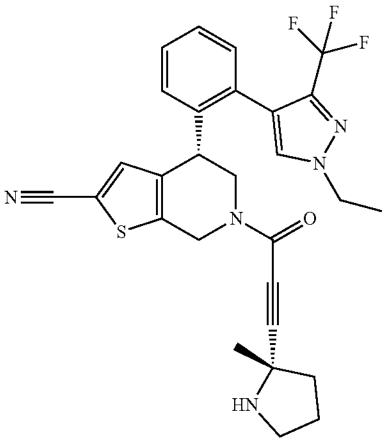 [SMILES: CCn1cc(-c2ccccc2[C@@H]2CN(C(=O)C#C[C@]3(C)CCCN3)Cc3sc(C#N)cc32)c(C(F)(F)F)n1]
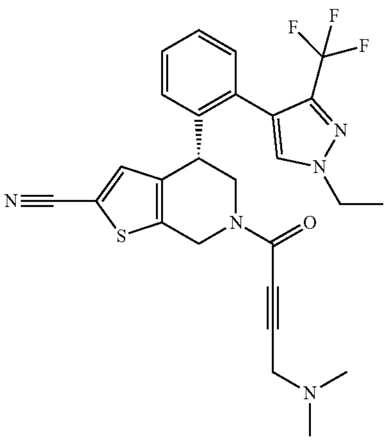 [SMILES: CCn1cc(-c2ccccc2[C@@H]2CN(C(=O)C#CCN(C)C)Cc3sc(C#N)cc32)c(C(F)(F)F)n1]
TABLE A-continued
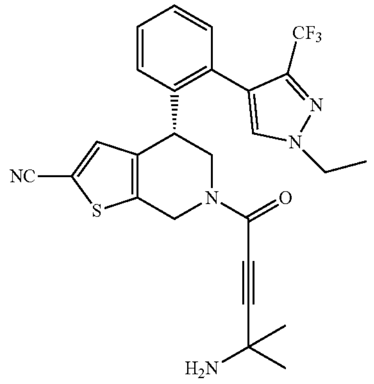 [SMILES: CCn1cc(-c2ccccc2[C@@H]2CN(C(=O)C#CC(C)(C)N)Cc3sc(C#N)cc32)c(C(F)(F)F)n1]
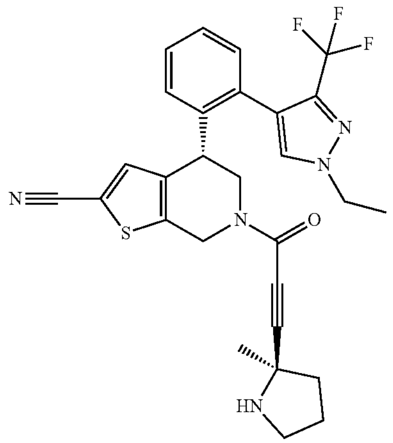 [SMILES: CCn1cc(-c2ccccc2[C@@H]2CN(C(=O)C#C[C@@]3(C)CCCN3)Cc3sc(C#N)cc32)c(C(F)(F)F)n1]
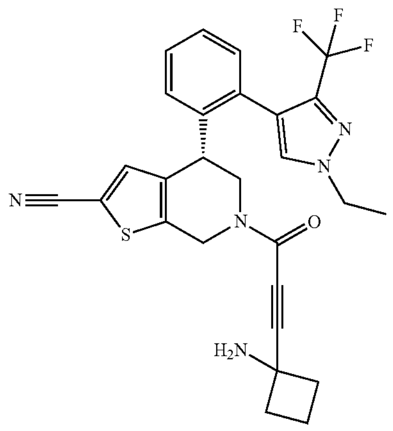 [SMILES: CCn1cc(-c2ccccc2[C@@H]2CN(C(=O)C#CC3(N)CCC3)Cc3sc(C#N)cc32)c(C(F)(F)F)n1]

TABLE A-continued
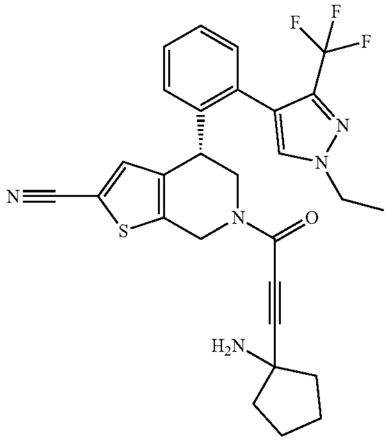 [SMILES: CCn1cc(-c2ccccc2[C@@H]2CN(C(=O)C#CC3(N)CCCC3)Cc3sc(C#N)cc32)c(C(F)(F)F)n1]
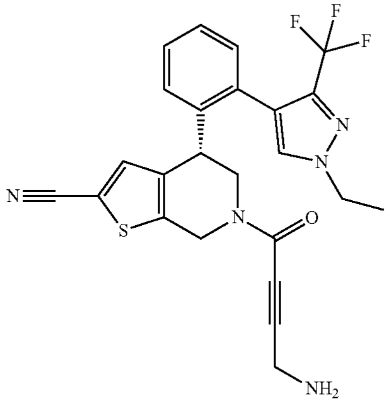 [SMILES: CCn1cc(-c2ccccc2[C@@H]2CN(C(=O)C#CCN)Cc3sc(C#N)cc32)c(C(F)(F)F)n1]
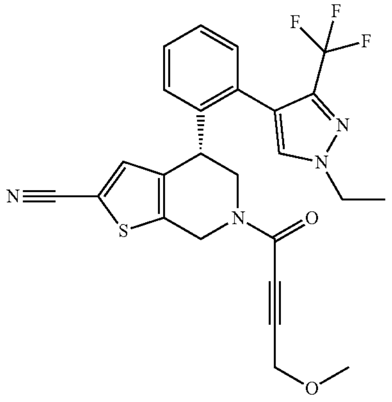 [SMILES: CCn1cc(-c2ccccc2[C@@H]2CN(C(=O)C#CCOC)Cc3sc(C#N)cc32)c(C(F)(F)F)n1]
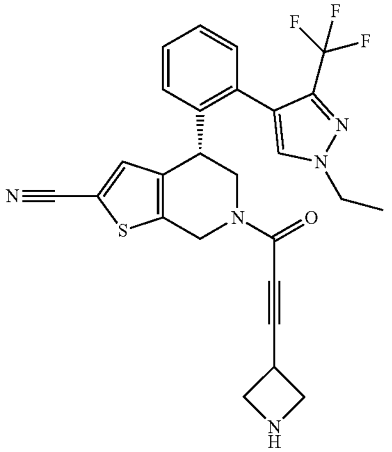 [SMILES: CCn1cc(-c2ccccc2[C@@H]2CN(C(=O)C#CC3CNC3)Cc3sc(C#N)cc32)c(C(F)(F)F)n1]
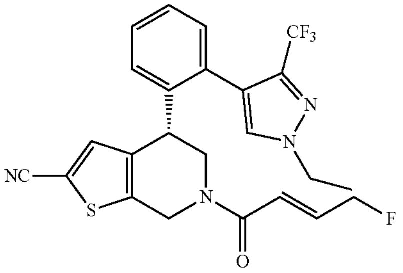 [SMILES: CCn1cc(-c2ccccc2[C@@H]2CN(C(=O)/C=C/CF)Cc3sc(C#N)cc32)c(C(F)(F)F)n1]
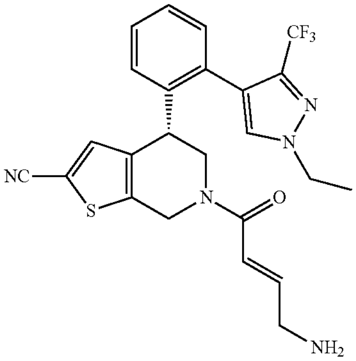 [SMILES: CCn1cc(-c2ccccc2[C@@H]2CN(C(=O)/C=C/CN)Cc3sc(C#N)cc32)c(C(F)(F)F)n1]
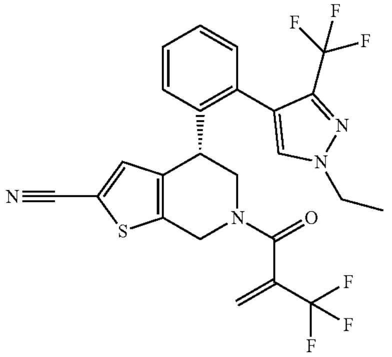 [SMILES: C=C(C(=O)N1Cc2sc(C#N)cc2[C@H](c2ccccc2-c2cn(CC)nc2C(F)(F)F)C1)C(F)(F)F]

TABLE A-continued
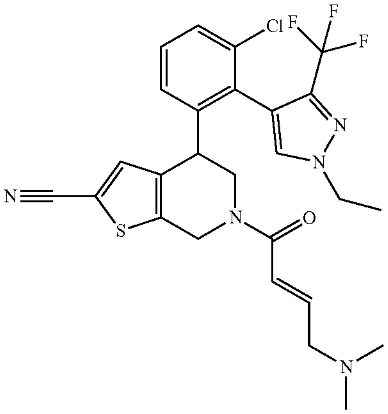 [SMILES: CCn1cc(-c2c(Cl)cccc2C2CN(C(=O)/C=C/CN(C)C)Cc3sc(C#N)cc32)c(C(F)(F)F)n1]
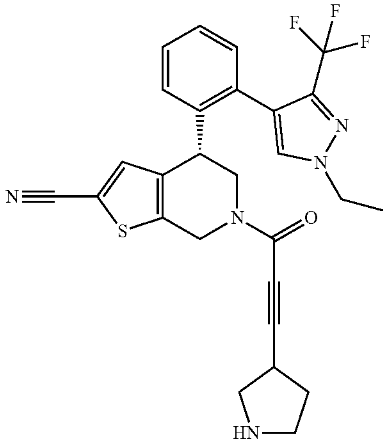
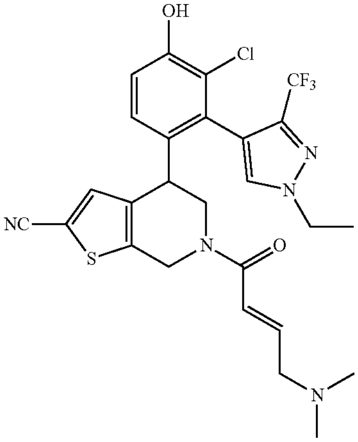 [SMILES: CCn1cc(-c2c(C3CN(C(=O)/C=C/CN(C)C)Cc4sc(C#N)cc43)ccc(O)c2Cl)c(C(F)(F)F)n1]
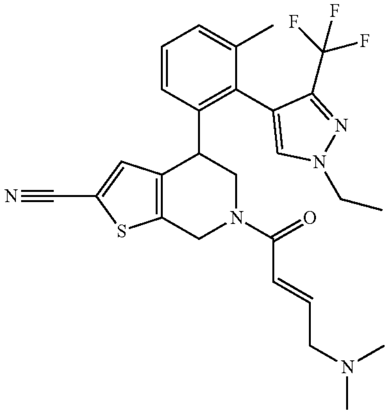
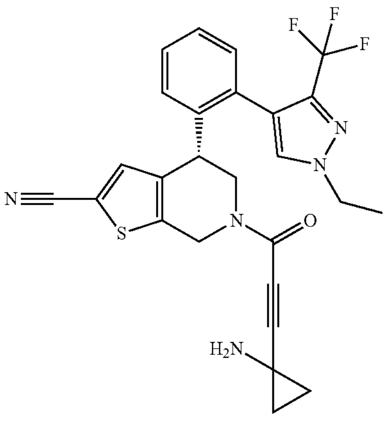 [SMILES: CCn1cc(-c2ccccc2[C@@H]2CN(C(=O)C#CC3(N)CC3)Cc3sc(C#N)cc32)c(C(F)(F)F)n1]
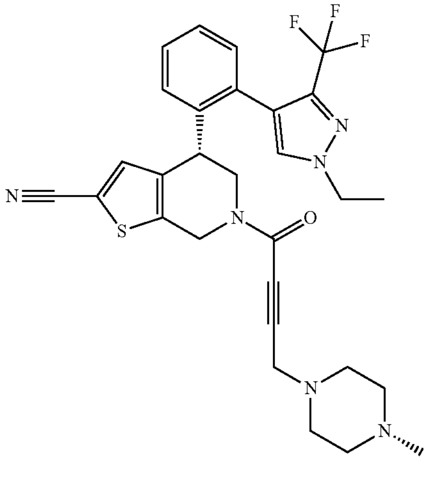

TABLE A-continued
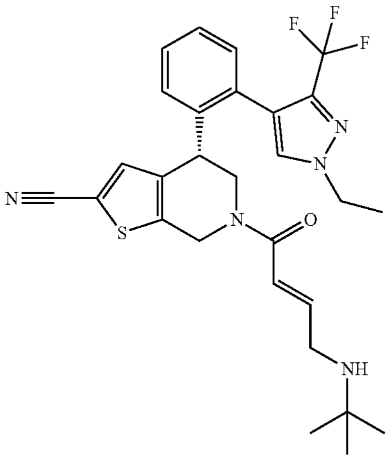 [SMILES: CCn1cc(-c2ccccc2[C@@H]2CN(C(=O)/C=C/CNC(C)(C)C)Cc3sc(C#N)cc32)c(C(F)(F)F)n1]
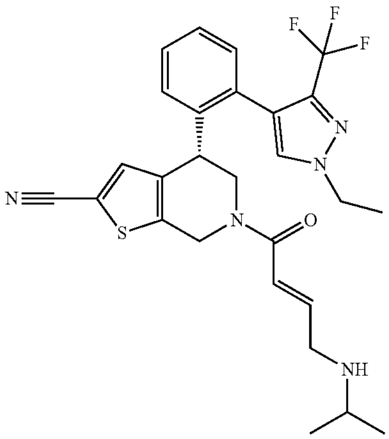 [SMILES: CCn1cc(-c2ccccc2[C@@H]2CN(C(=O)/C=C/CNC(C)C)Cc3sc(C#N)cc32)c(C(F)(F)F)n1]
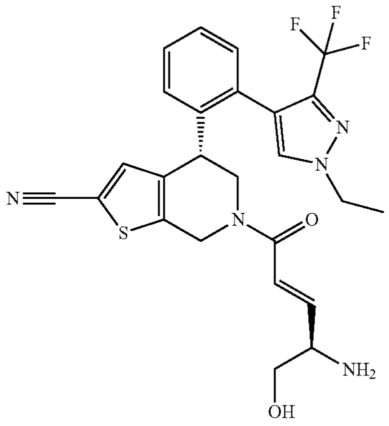 [SMILES: CCn1cc(-c2ccccc2[C@@H]2CN(C(=O)/C=C/[C@@H](N)CO)Cc3sc(C#N)cc32)c(C(F)(F)F)n1]
TABLE A-continued
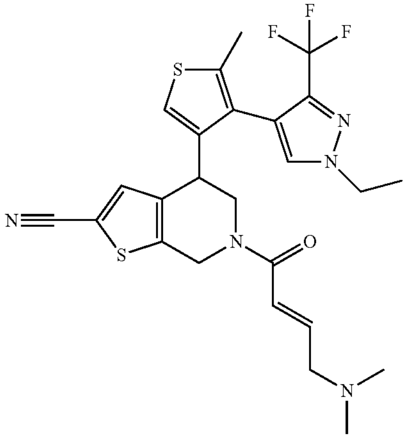 [SMILES: CCn1cc(-c2c(C3CN(C(=O)/C=C/CN(C)C)Cc4sc(C#N)cc43)csc2C)c(C(F)(F)F)n1]
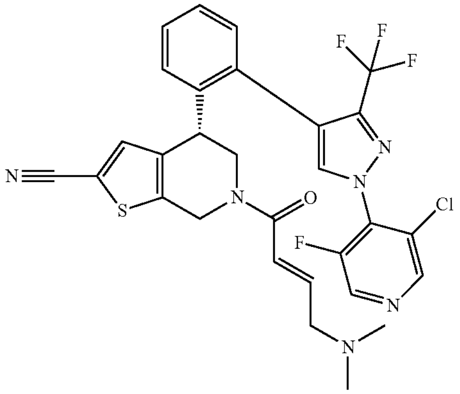 [SMILES: CN(C)C/C=C/C(=O)N1Cc2sc(C#N)cc2[C@H](c2ccccc2-c2cn(-c3c(F)cncc3Cl)nc2C(F)(F)F)C1]
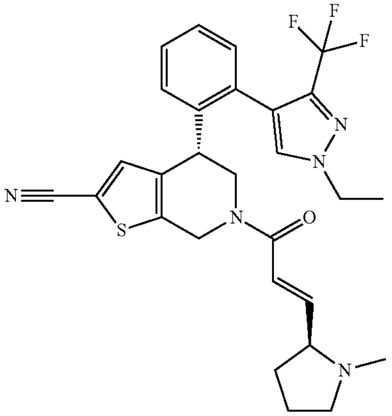 [SMILES: CCn1cc(-c2ccccc2[C@@H]2CN(C(=O)/C=C/[C@@H]3CCCN3C)Cc3sc(C#N)cc32)c(C(F)(F)F)n1]
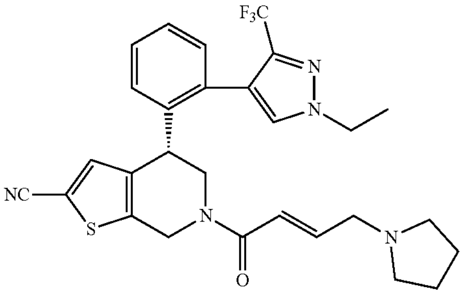 [SMILES: CCn1cc(-c2ccccc2[C@@H]2CN(C(=O)/C=C/CN3CCCC3)Cc3sc(C#N)cc32)c(C(F)(F)F)n1]

TABLE A-continued
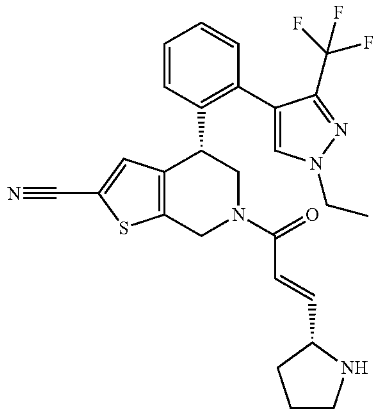 [SMILES: CCn1cc(-c2ccccc2[C@@H]2CN(C(=O)/C=C/[C@H]3CCCN3)Cc3sc(C#N)cc32)c(C(F)(F)F)n1]
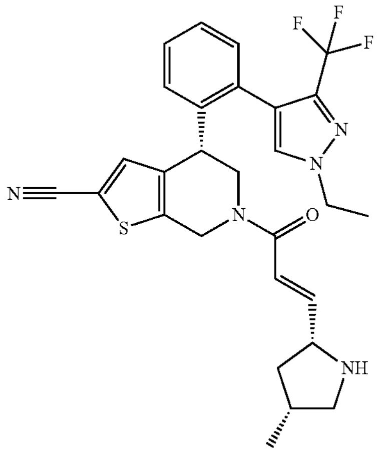 [SMILES: CCn1cc(-c2ccccc2[C@@H]2CN(C(=O)/C=C/[C@H]3C[C@@H](C)CN3)Cc3sc(C#N)cc32)c(C(F)(F)F)n1]
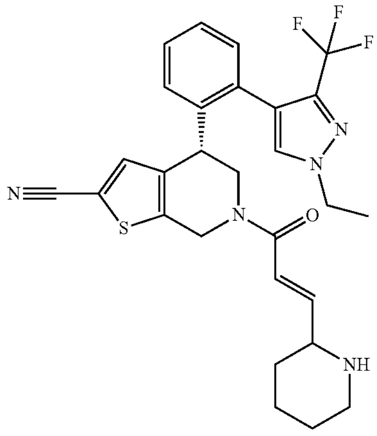 [SMILES: CCn1cc(-c2ccccc2[C@@H]2CN(C(=O)/C=C/C3CCCCN3)Cc3sc(C#N)cc32)c(C(F)(F)F)n1]
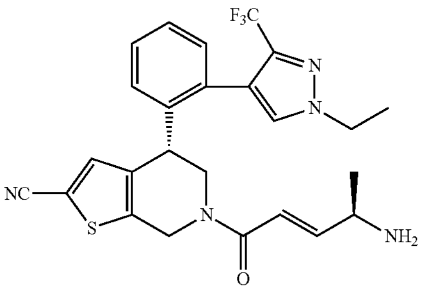 [SMILES: CCn1cc(-c2ccccc2[C@@H]2CN(C(=O)/C=C/[C@@H](C)N)Cc3sc(C#N)cc32)c(C(F)(F)F)n1]
TABLE A-continued
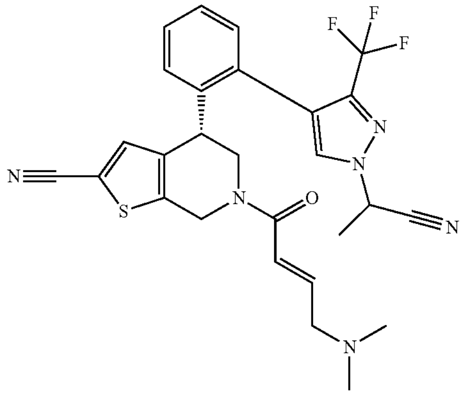 [SMILES: CC(C#N)n1cc(Cc2ccccc2[C@@H]2CN(C(=O)/C=C/CN(C)C)Cc3sc(C#N)cc32)c(C(F)(F)F)n1]
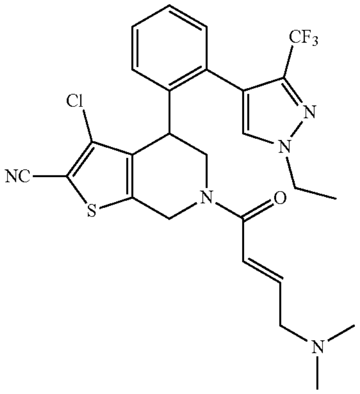 [SMILES: CCn1cc(-c2ccccc2C2CN(C(=O)/C=C/CN(C)C)Cc3sc(C#N)c(Cl)c32)c(C(F)(F)F)n1]
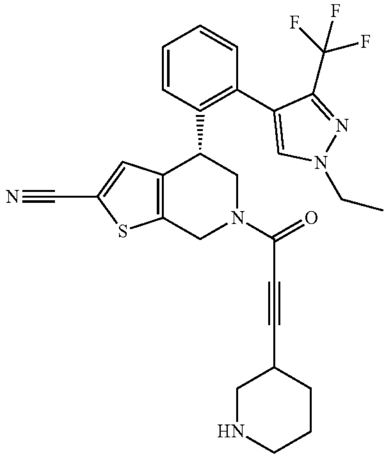 [SMILES: CCn1cc(-c2ccccc2[C@@H]2CN(C(=O)C#CC3CCCNC3)Cc3sc(C#N)cc32)c(C(F)(F)F)n1]

TABLE A-continued
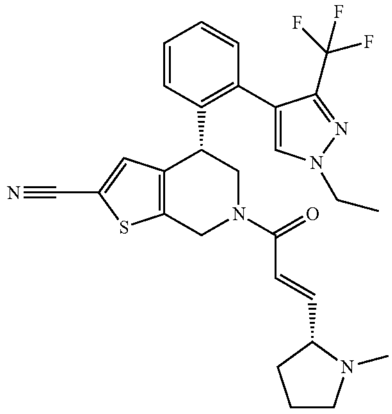 [SMILES: CCn1cc(-c2ccccc2[C@@H]2CN(C(=O)/C=C/[C@H]3CCCN3C)Cc3sc(C#N)cc32)c(C(F)(F)F)n1]
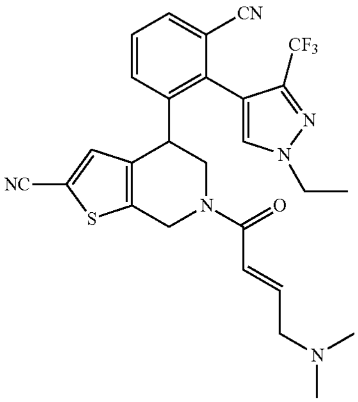 [SMILES: CCn1cc(-c2c(C#N)cccc2C2CN(C(=O)/C=C/CN(C)C)Cc3sc(C#N)cc32)c(C(F)(F)F)n1]
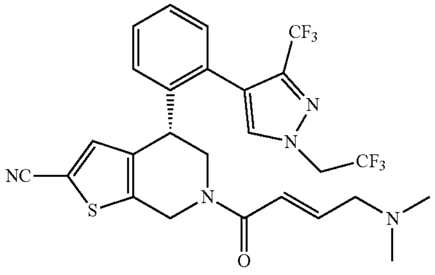 [SMILES: CN(C)C/C=C/C(=O)N1Cc2sc(C#N)cc2[C@H](c2ccccc2-c2cn(CC(F)(F)F)nc2C(F)(F)F)C1]
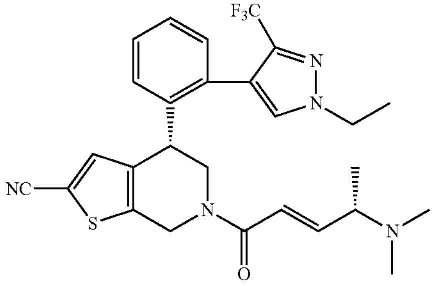 [SMILES: CCn1cc(-c2ccccc2[C@@H]2CN(C(=O)/C=C/[C@H](C)N(C)C)Cc3sc(C#N)cc32)c(C(F)(F)F)n1]
TABLE A-continued
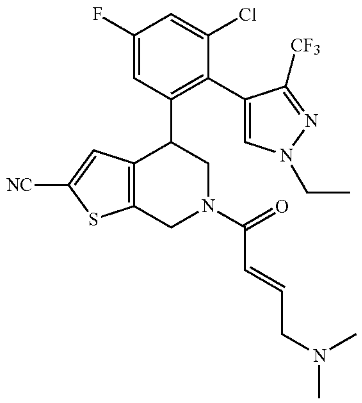 [SMILES: CCn1cc(-c2c(Cl)cc(F)cc2C2CN(C(=O)/C=C/CN(C)C)Cc3sc(C#N)cc32)c(C(F)(F)F)n1]
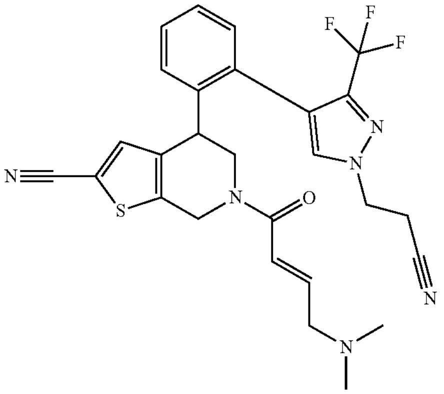 [SMILES: CN(C)C/C=C/C(=O)N1Cc2sc(C#N)cc2C(c2ccccc2Cc2cn(CCC#N)nc2C(F)(F)F)C1]
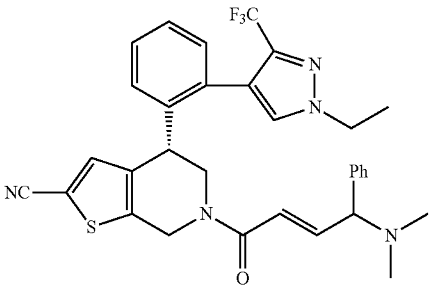 [SMILES: CCn1cc(-c2ccccc2[C@@H]2CN(C(=O)/C=C/C(c3ccccc3)N(C)C)Cc3sc(C#N)cc32)c(C(F)(F)F)n1]
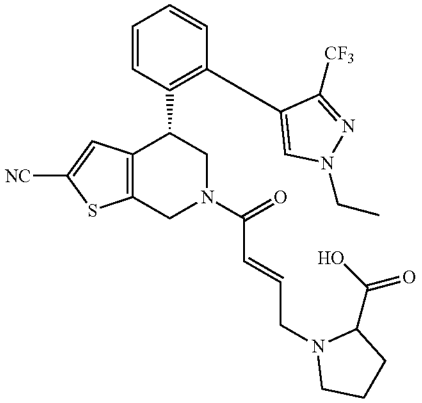 [SMILES: CCn1cc(Cc2ccccc2[C@@H]2CN(C(=O)/C=C/CN3CCCC3C(=O)O)Cc3sc(C#N)cc32)c(C(F)(F)F)n1]

TABLE A-continued
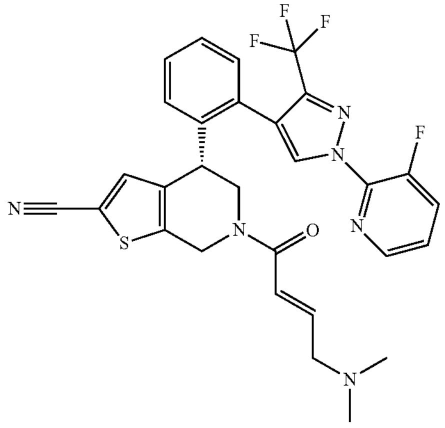 [SMILES: CN(C)C/C=C/C(=O)N1Cc2sc(C#N)cc2[C@H](c2ccccc2-c2cn(-c3ncccc3F)nc2C(F)(F)F)C1]
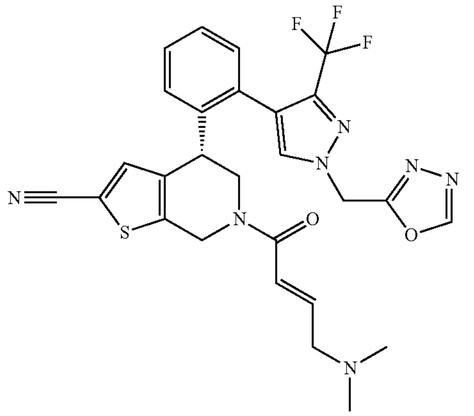 [SMILES: CN(C)C/C=C/C(=O)N1Cc2sc(C#N)cc2[C@H](c2ccccc2-c2cn(Cc3nnco3)nc2C(F)(F)F)C1]
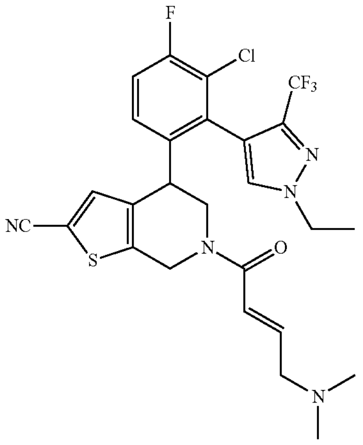 [SMILES: CCn1cc(-c2c(C3CN(C(=O)/C=C/CN(C)C)Cc4sc(C#N)cc43)ccc(F)c2Cl)c(C(F)(F)F)n1]
TABLE A-continued
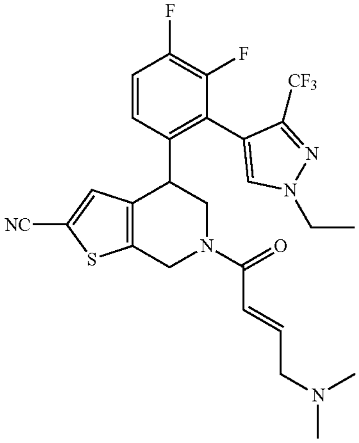 [SMILES: CCn1cc(-c2c(C3CN(C(=O)/C=C/CN(C)C)Cc4sc(C#N)cc43)ccc(F)c2F)c(C(F)(F)F)n1]
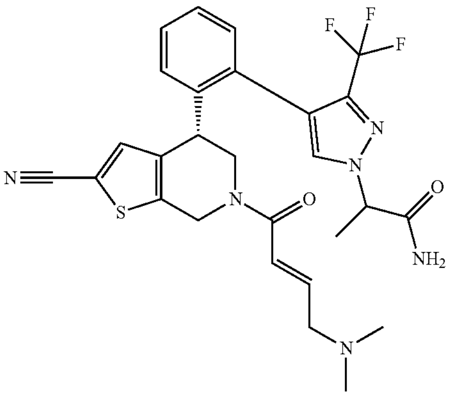 [SMILES: CC(C(N)=O)n1cc(Cc2ccccc2[C@@H]2CN(C(=O)/C=C/CN(C)C)Cc3sc(C#N)cc32)c(C(F)(F)F)n1]
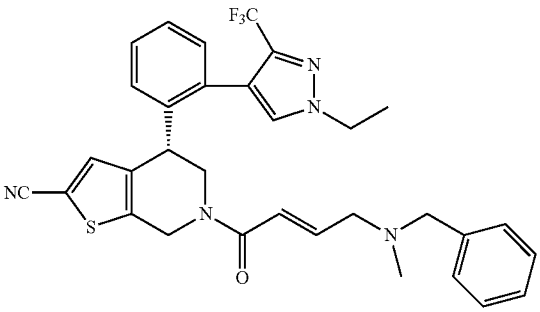 [SMILES: CCn1cc(-c2ccccc2[C@@H]2CN(C(=O)/C=C/CN(C)Cc3ccccc3)Cc3sc(C#N)cc32)c(C(F)(F)F)n1]
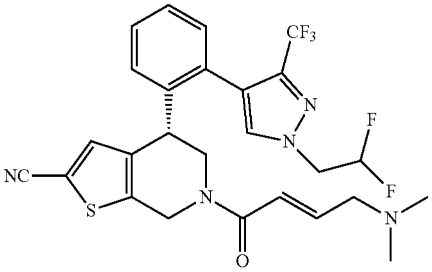 [SMILES: CN(C)C/C=C/C(=O)N1Cc2sc(C#N)cc2[C@H](c2ccccc2-c2cn(CC(F)F)nc2C(F)(F)F)C1]

TABLE A-continued
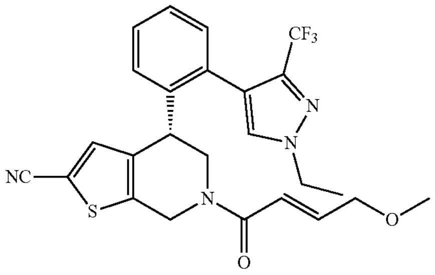 [SMILES: CCn1cc(-c2ccccc2[C@@H]2CN(C(=O)/C=C/COC)Cc3sc(C#N)cc32)c(C(F)(F)F)n1]
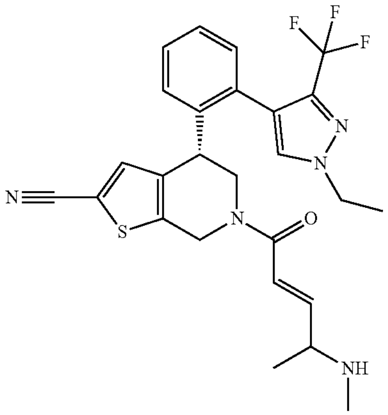 [SMILES: CCn1cc(-c2ccccc2[C@@H]2CN(C(=O)/C=C/C(C)NC)Cc3sc(C#N)cc32)c(C(F)(F)F)n1]
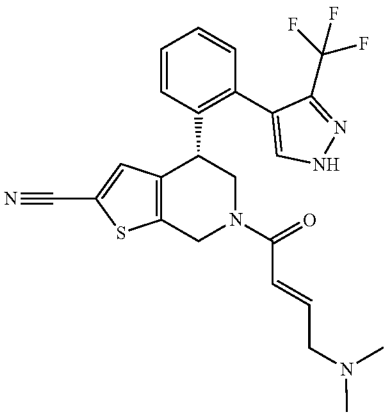 [SMILES: CN(C)C/C=C/C(=O)N1Cc2sc(C#N)cc2[C@H](c2ccccc2-c2c[nH]nc2C(F)(F)F)C1]
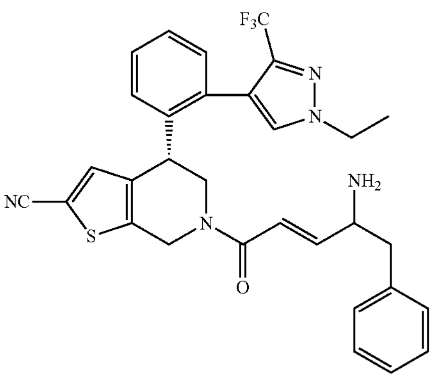 [SMILES: CCn1cc(-c2ccccc2[C@@H]2CN(C(=O)/C=C/C(N)Cc3ccccc3)Cc3sc(C#N)cc32)c(C(F)(F)F)n1]
TABLE A-continued
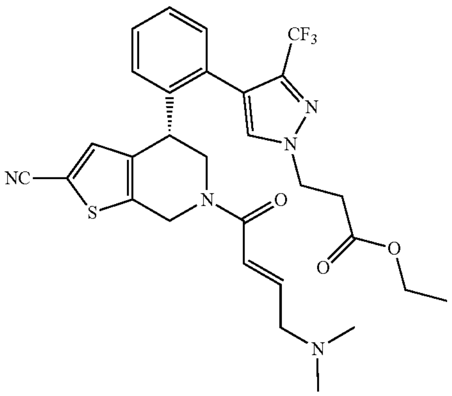 [SMILES: CCOC(=O)CCn1cc(-c2ccccc2[C@@H]2CN(C(=O)/C=C/CN(C)C)Cc3sc(C#N)cc32)c(C(F)(F)F)n1]
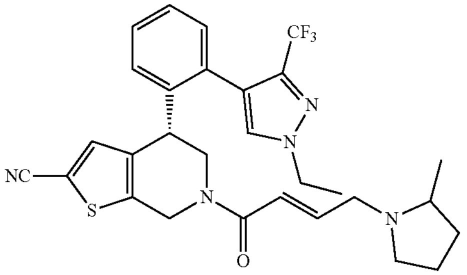 [SMILES: CCn1cc(-c2ccccc2[C@@H]2CN(C(=O)/C=C/CN3CCCC3C)Cc3sc(C#N)cc32)c(C(F)(F)F)n1]
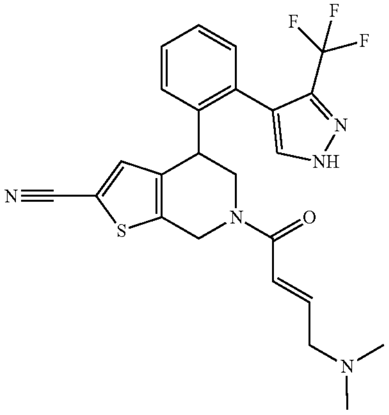 [SMILES: CN(C)C/C=C/C(=O)N1Cc2sc(C#N)cc2C(c2ccccc2-c2c[nH]nc2C(F)(F)F)C1]
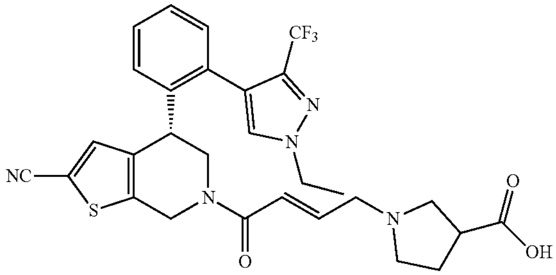 [SMILES: CCn1cc(-c2ccccc2[C@@H]2CN(C(=O)/C=C/CN3CCC(C(=O)O)C3)Cc3sc(C#N)cc32)c(C(F)(F)F)n1]

TABLE A-continued
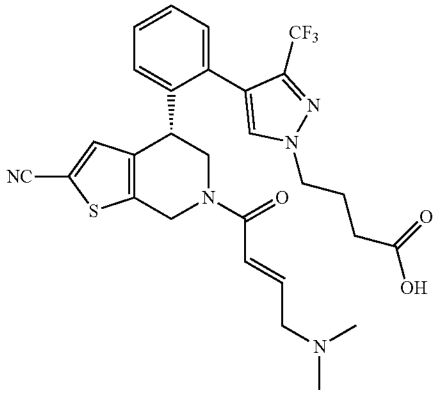 [SMILES: CN(C)C/C=C/C(=O)N1Cc2sc(C#N)cc2[C@H](c2ccccc2-c2cn(CCCC(=O)O)nc2C(F)(F)F)C1]
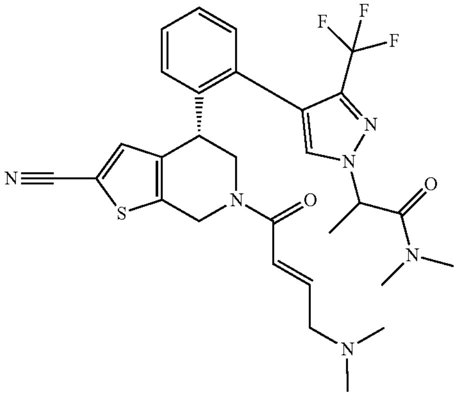 [SMILES: CC(C(=O)N(C)C)n1cc(-c2ccccc2[C@@H]2CN(C(=O)/C=C/CN(C)C)Cc3sc(C#N)cc32)c(C(F)(F)F)n1]
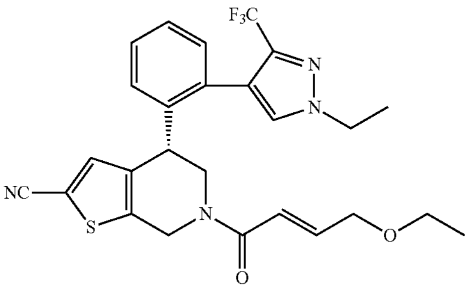 [SMILES: CCOC/C=C/C(=O)N1Cc2sc(C#N)cc2[C@H](c2ccccc2-c2cn(CC)nc2C(F)(F)F)C1]
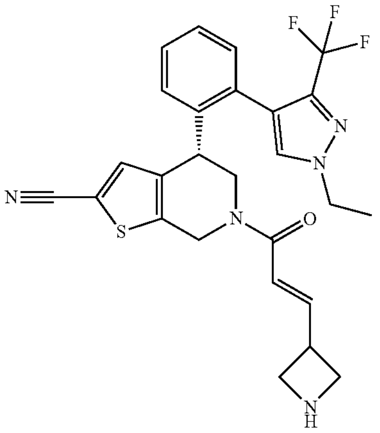 [SMILES: CCn1cc(-c2ccccc2[C@@H]2CN(C(=O)/C=C/C3CNC3)Cc3sc(C#N)cc32)c(C(F)(F)F)n1]
TABLE A-continued
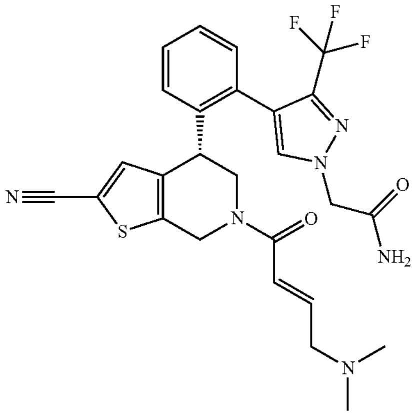 [SMILES: CN(C)C/C=C/C(=O)N1Cc2sc(C#N)cc2[C@H](c2ccccc2-c2cn(CC(N)=O)nc2C(F)(F)F)C1]
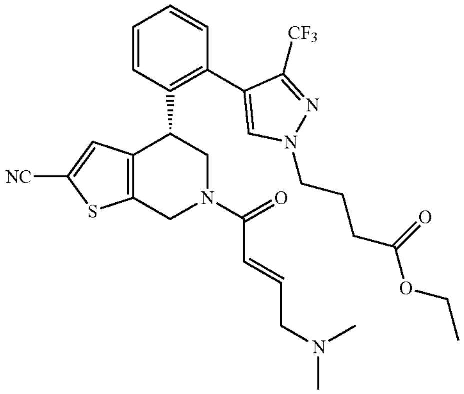 [SMILES: CCOC(=O)CCCn1cc(-c2ccccc2[C@@H]2CN(C(=O)/C=C/CN(C)C)Cc3sc(C#N)cc32)c(C(F)(F)F)n1]
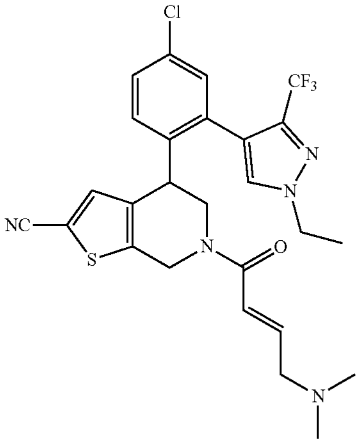 [SMILES: CCn1cc(-c2cc(Cl)ccc2C2CN(C(=O)/C=C/CN(C)C)Cc3sc(C#N)cc32)c(C(F)(F)F)n1]
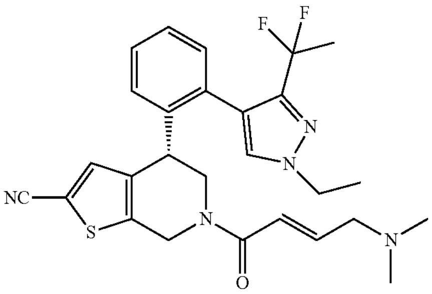 [SMILES: CCn1cc(-c2ccccc2[C@@H]2CN(C(=O)/C=C/CN(C)C)Cc3sc(C#N)cc32)c(C(C)(F)F)n1]

TABLE A-continued
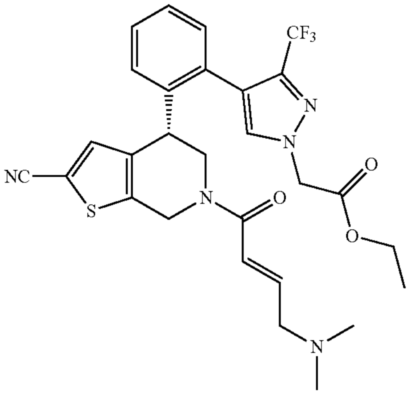 [SMILES: CCOC(=O)Cn1cc(-c2ccccc2[C@@H]2CN(C(=O)/C=C/CN(C)C)Cc3sc(C#N)cc32)c(C(F)(F)F)n1]
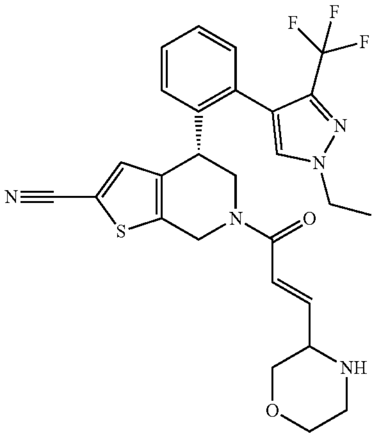 [SMILES: CCn1cc(-c2ccccc2[C@@H]2CN(C(=O)/C=C/C3COCCN3)Cc3sc(C#N)cc32)c(C(F)(F)F)n1]
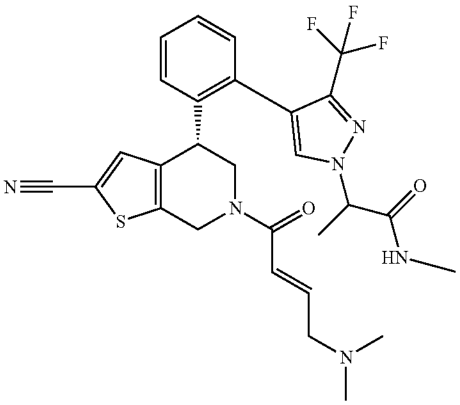 [SMILES: CNC(=O)C(C)n1cc(-c2ccccc2[C@@H]2CN(C(=O)/C=C/CN(C)C)Cc3sc(C#N)cc32)c(C(F)(F)F)n1]
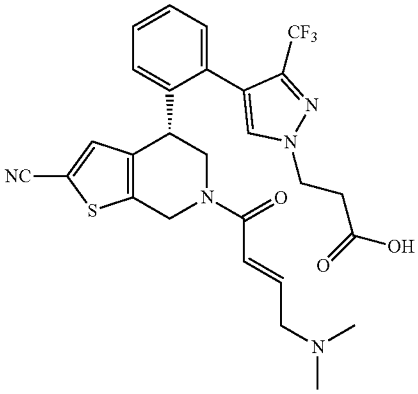 [SMILES: CN(C)C/C=C/C(=O)N1Cc2sc(C#N)cc2[C@H](c2ccccc2-c2cn(CCC(=O)O)nc2C(F)(F)F)C1]
TABLE A-continued
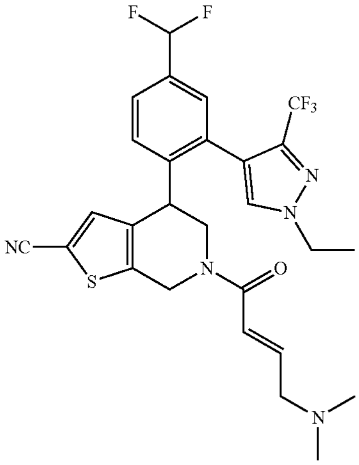 [SMILES: CCn1cc(-c2cc(C(F)F)ccc2C2CN(C(=O)/C=C/CN(C)C)Cc3sc(C#N)cc32)c(C(F)(F)F)n1]
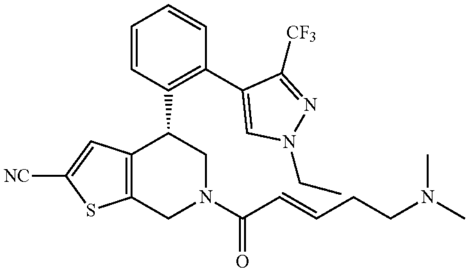 [SMILES: CCn1cc(-c2ccccc2[C@@H]2CN(C(=O)/C=C/CCN(C)C)Cc3sc(C#N)cc32)c(C(F)(F)F)n1]
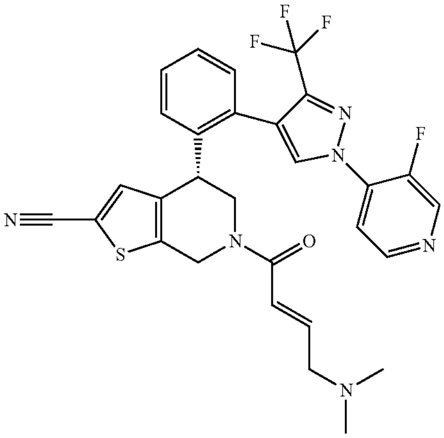 [SMILES: CN(C)C/C=C/C(=O)N1Cc2sc(C#N)cc2[C@H](c2ccccc2-c2cn(-c3ccncc3F)nc2C(F)(F)F)C1]
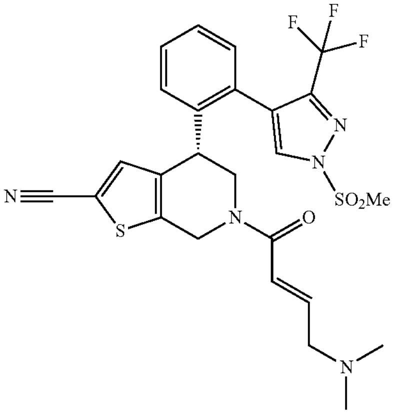 [SMILES: CN(C)C/C=C/C(=O)N1Cc2sc(C#N)cc2[C@H](c2ccccc2-c2cn(S(C)(=O)=O)nc2C(F)(F)F)C1]

TABLE A-continued
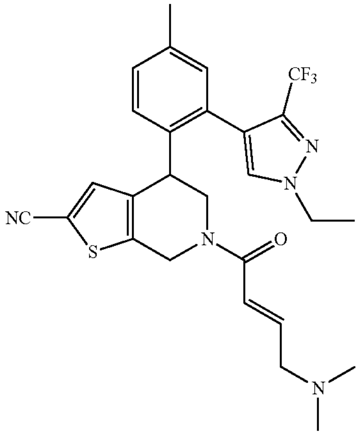 [SMILES: CCn1cc(-c2cc(C)ccc2C2CN(C(=O)/C=C/CN(C)C)Cc3sc(C#N)cc32)c(C(F)(F)F)n1]
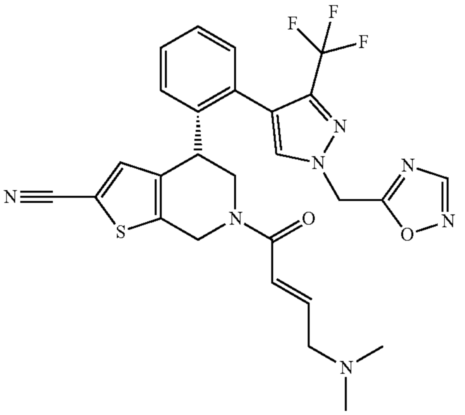
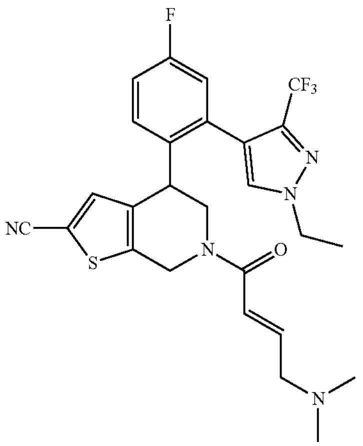 [SMILES: CCn1cc(-c2cc(F)ccc2C2CN(C(=O)/C=C/CN(C)C)Cc3sc(C#N)cc32)c(C(F)(F)F)n1]
TABLE A-continued
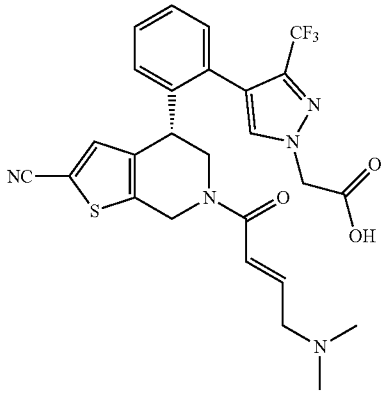 [SMILES: CN(C)C/C=C/C(=O)N1Cc2sc(C#N)cc2[C@H](c2ccccc2-c2cn(CC(=O)O)nc2C(F)(F)F)C1]
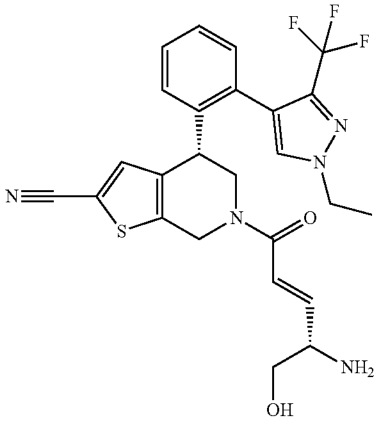 [SMILES: CCn1cc(-c2ccccc2[C@@H]2CN(C(=O)/C=C/[C@H](N)CO)Cc3sc(C#N)cc32)c(C(F)(F)F)n1]
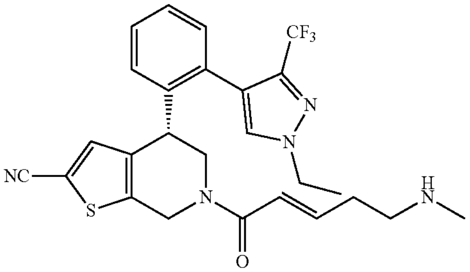 [SMILES: CCn1cc(-c2ccccc2[C@@H]2CN(C(=O)/C=C/CCNC)Cc3sc(C#N)cc32)c(C(F)(F)F)n1]
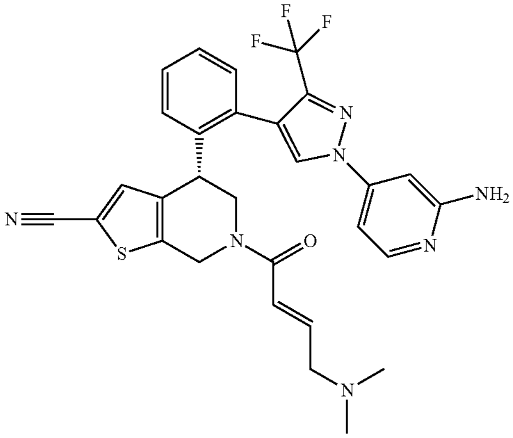 [SMILES: CN(C)C/C=C/C(=O)N1Cc2sc(C#N)cc2[C@H](c2ccccc2-c2cn(-c3ccnc(N)c3)nc2C(F)(F)F)C1]

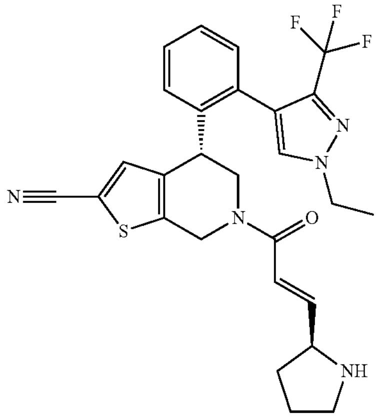 [SMILES: CCn1cc(-c2ccccc2[C@@H]2CN(C(=O)/C=C/[C@@H]3CCCN3)Cc3sc(C#N)cc32)c(C(F)(F)F)n1]
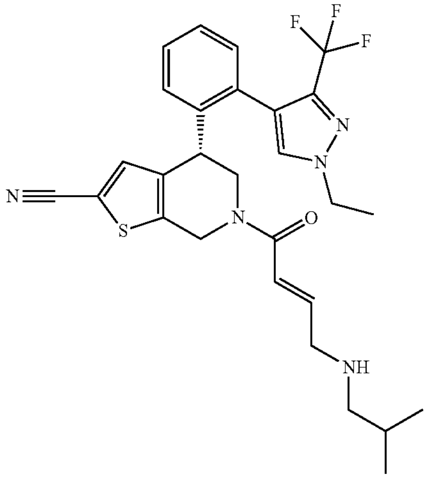 [SMILES: CCn1cc(-c2ccccc2[C@@H]2CN(C(=O)/C=C/CNCC(C)C)Cc3sc(C#N)cc32)c(C(F)(F)F)n1]
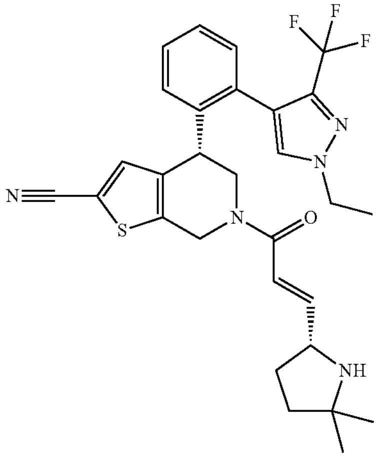 [SMILES: CCn1cc(-c2ccccc2[C@@H]2CN(C(=O)/C=C/[C@H]3CCC(C)(C)N3)Cc3sc(C#N)cc32)c(C(F)(F)F)n1]
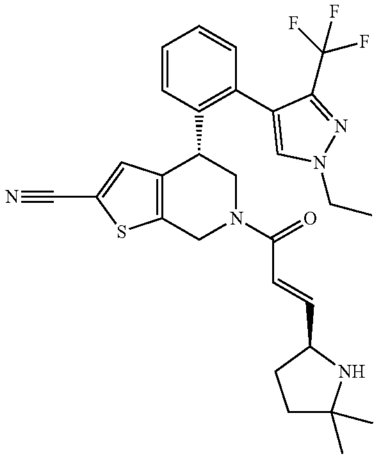 [SMILES: CCn1cc(-c2ccccc2[C@@H]2CN(C(=O)/C=C/[C@@H]3CCC(C)(C)N3)Cc3sc(C#N)cc32)c(C(F)(F)F)n1]
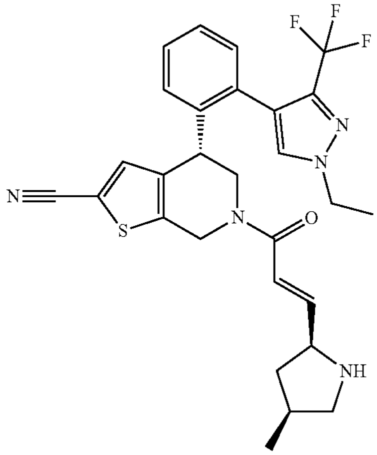 [SMILES: CCn1cc(-c2ccccc2[C@@H]2CN(C(=O)/C=C/[C@@H]3C[C@H](C)CN3)Cc3sc(C#N)cc32)c(C(F)(F)F)n1]
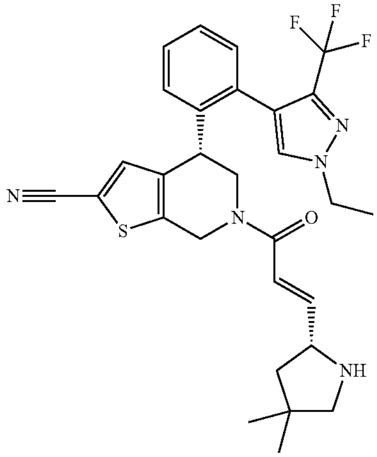 [SMILES: CCn1cc(-c2ccccc2[C@@H]2CN(C(=O)/C=C/[C@H]3CC(C)(C)CN3)Cc3sc(C#N)cc32)c(C(F)(F)F)n1]

TABLE A-continued
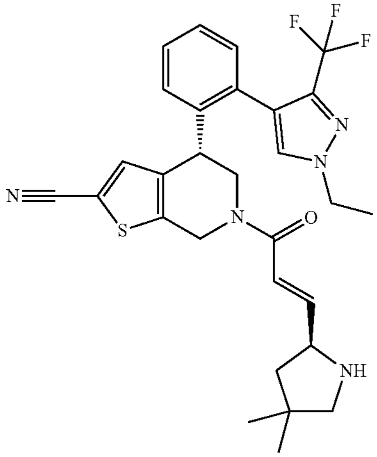 [SMILES: CCn1cc(-c2ccccc2[C@@H]2CN(C(=O)/C=C/[C@@H]3CC(C)(C)CN3)Cc3sc(C#N)cc32)c(C(F)(F)F)n1]
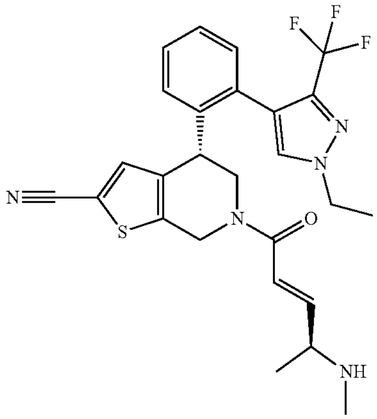 [SMILES: CCn1cc(-c2ccccc2[C@@H]2CN(C(=O)/C=C/[C@H](C)NC)Cc3sc(C#N)cc32)c(C(F)(F)F)n1]
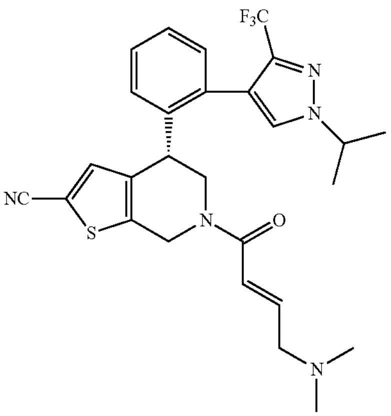 [SMILES: CC(C)n1cc(-c2ccccc2[C@@H]2CN(C(=O)/C=C/CN(C)C)Cc3sc(C#N)cc32)c(C(F)(F)F)n1]
TABLE A-continued
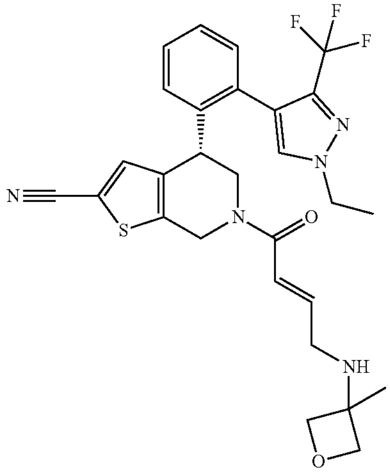 [SMILES: CCn1cc(-c2ccccc2[C@@H]2CN(C(=O)/C=C/CNC3(C)COC3)Cc3sc(C#N)cc32)c(C(F)(F)F)n1]
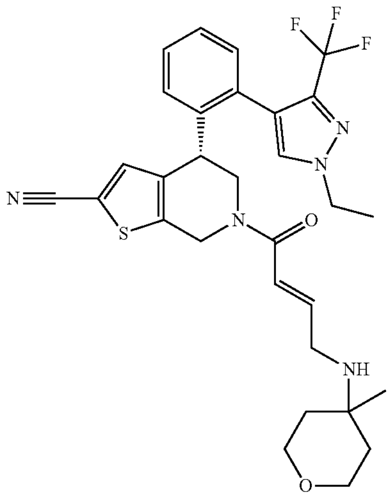 [SMILES: CCn1cc(-c2ccccc2[C@@H]2CN(C(=O)/C=C/CNC3(C)CCOCC3)Cc3sc(C#N)cc32)c(C(F)(F)F)n1]
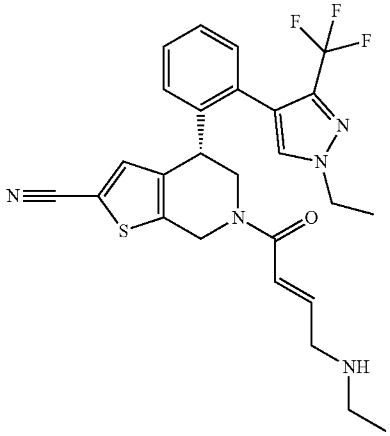 [SMILES: CCNC/C=C/C(=O)N1Cc2sc(C#N)cc2[C@H](c2ccccc2-c2cn(CC)nc2C(F)(F)F)C1]

TABLE A-continued
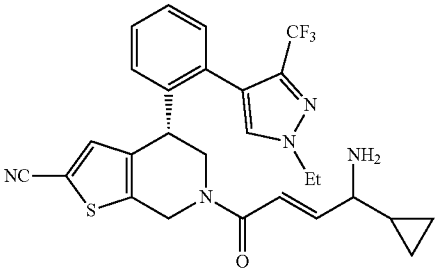 [SMILES: CCn1cc(-c2ccccc2[C@@H]2CN(C(=O)/C=C/C(N)C3CC3)Cc3sc(C#N)cc32)c(C(F)(F)F)n1]
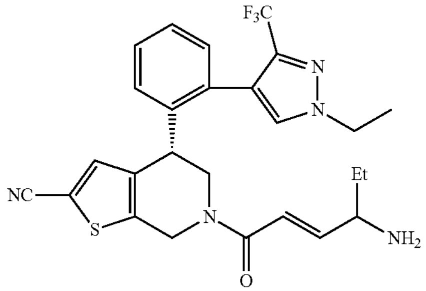 [SMILES: CCC(N)/C=C/C(=O)N1Cc2sc(C#N)cc2[C@H](c2ccccc2-c2cn(CC)nc2C(F)(F)F)C1]
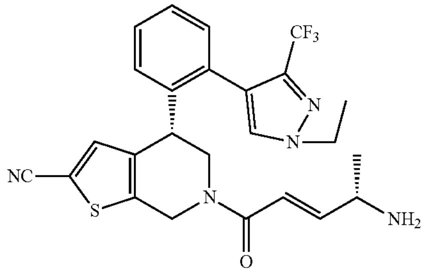 [SMILES: CCn1cc(-c2ccccc2[C@@H]2CN(C(=O)/C=C/[C@H](C)N)Cc3sc(C#N)cc32)c(C(F)(F)F)n1]
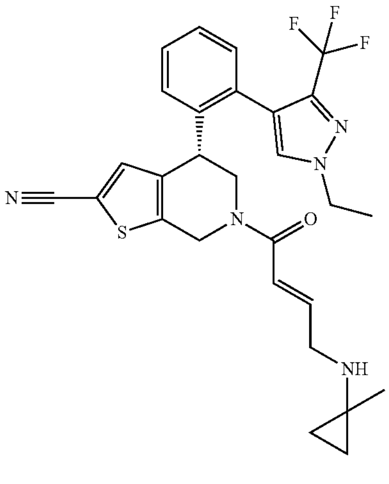 [SMILES: CCn1cc(-c2ccccc2[C@@H]2CN(C(=O)/C=C/CNC3(C)CC3)Cc3sc(C#N)cc32)c(C(F)(F)F)n1]
TABLE A-continued
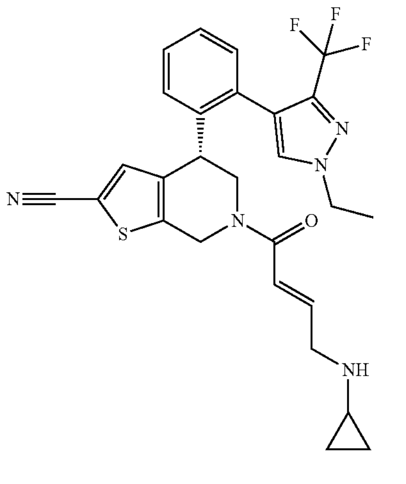 [SMILES: CCn1cc(-c2ccccc2[C@@H]2CN(C(=O)/C=C/CNC3CC3)Cc3sc(C#N)cc32)c(C(F)(F)F)n1]
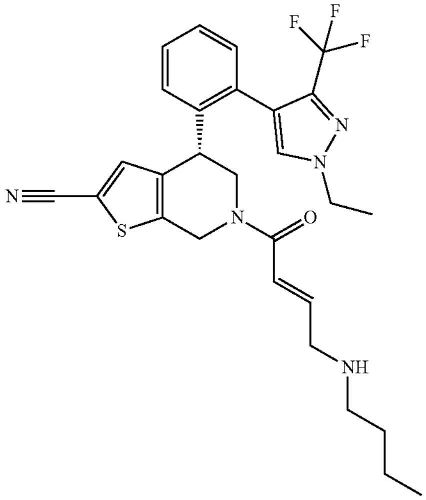 [SMILES: CCCCNC/C=C/C(=O)N1Cc2sc(C#N)cc2[C@H](c2ccccc2-c2cn(CC)nc2C(F)(F)F)C1]
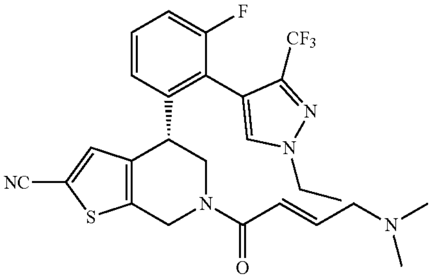 [SMILES: CCn1cc(-c2c(F)cccc2[C@@H]2CN(C(=O)/C=C/CN(C)C)Cc3sc(C#N)cc32)c(C(F)(F)F)n1]
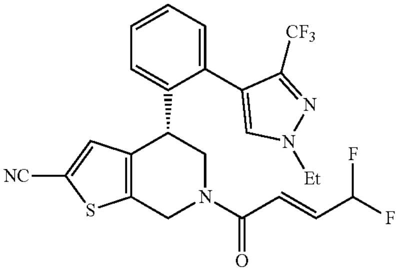 [SMILES: CCn1cc(-c2ccccc2[C@@H]2CN(C(=O)/C=C/C(F)F)Cc3sc(C#N)cc32)c(C(F)(F)F)n1]

TABLE A-continued
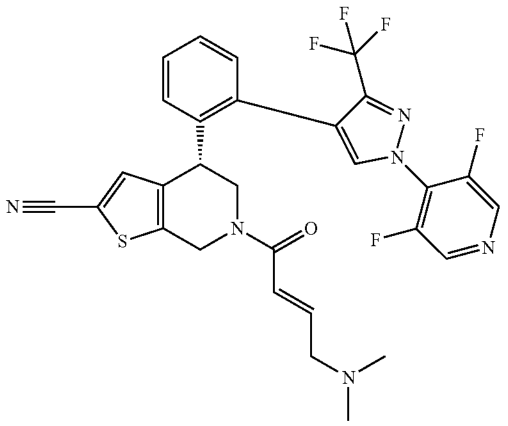 [SMILES: CN(C)C/C=C/C(=O)N1Cc2sc(C#N)cc2[C@H](c2ccccc2-c2cn(-c3c(F)cncc3F)nc2C(F)(F)F)C1]
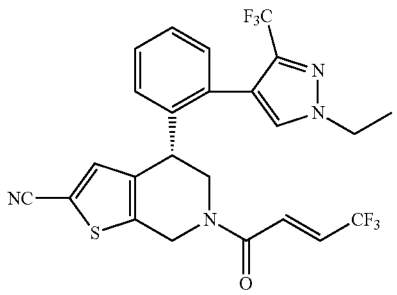 [SMILES: CCn1cc(-c2ccccc2[C@@H]2CN(C(=O)/C=C/C(F)(F)F)Cc3sc(C#N)cc32)c(C(F)(F)F)n1]
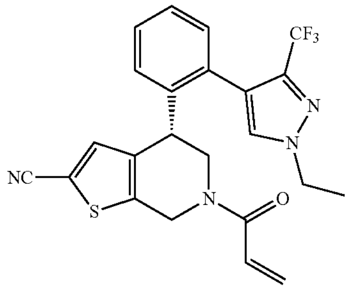 [SMILES: C=CC(=O)N1Cc2sc(C#N)cc2[C@H](c2ccccc2-c2cn(CC)nc2C(F)(F)F)C1]
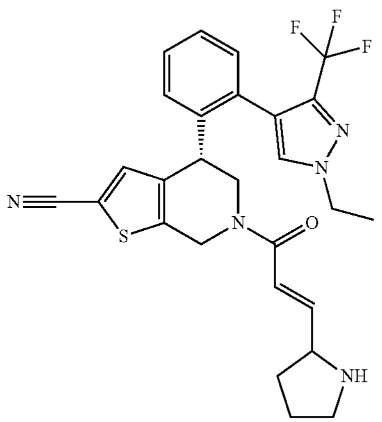 [SMILES: CCn1cc(-c2ccccc2[C@@H]2CN(C(=O)/C=C/C3CCCN3)Cc3sc(C#N)cc32)c(C(F)(F)F)n1]
TABLE A-continued
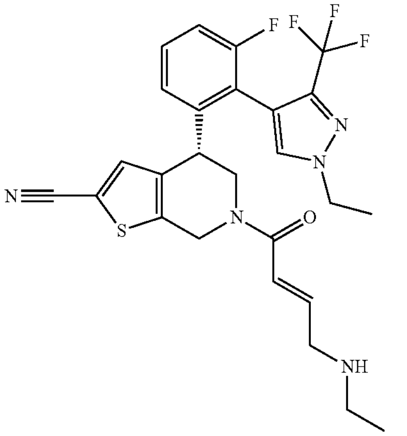 [SMILES: CCNC/C=C/C(=O)N1Cc2sc(C#N)cc2[C@H](c2cccc(F)c2-c2cn(CC)nc2C(F)(F)F)C1]
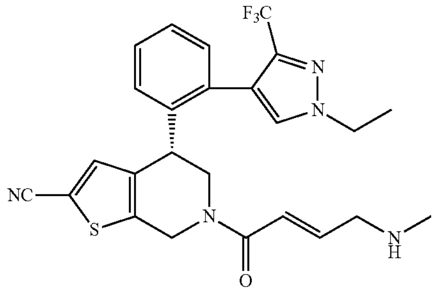 [SMILES: CCn1cc(-c2ccccc2[C@@H]2CN(C(=O)/C=C/CNC)Cc3sc(C#N)cc32)c(C(F)(F)F)n1]
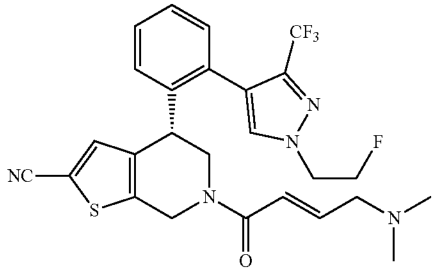 [SMILES: CN(C)C/C=C/C(=O)N1Cc2sc(C#N)cc2[C@H](c2ccccc2-c2cn(CCF)nc2C(F)(F)F)C1]
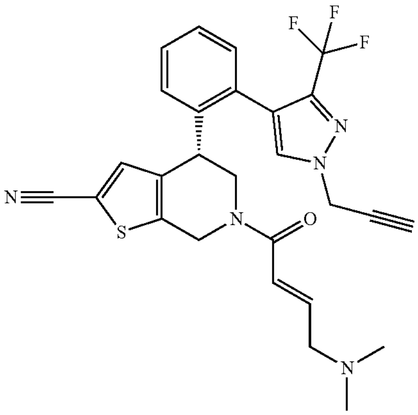 [SMILES: C#CCn1cc(-c2ccccc2[C@@H]2CN(C(=O)/C=C/CN(C)C)Cc3sc(C#N)cc32)c(C(F)(F)F)n1]

TABLE A-continued
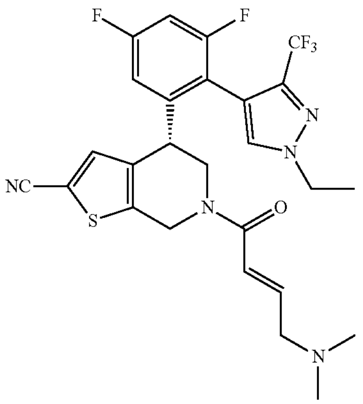 [SMILES: CCn1cc(-c2c(F)cc(F)cc2[C@@H]2CN(C(=O)/C=C/CN(C)C)Cc3sc(C#N)cc32)c(C(F)(F)F)n1]
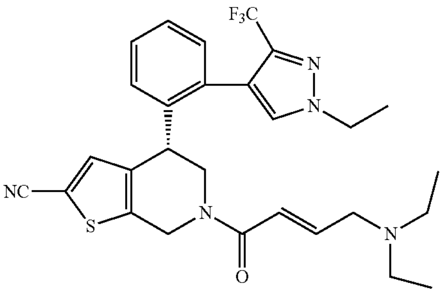 [SMILES: CCN(CC)C/C=C/C(=O)N1Cc2sc(C#N)cc2[C@H](c2ccccc2-c2cn(CC)nc2C(F)(F)F)C1]
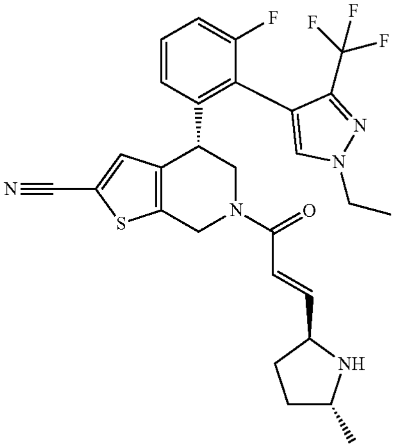 [SMILES: CCn1cc(-c2c(F)cccc2[C@@H]2CN(C(=O)/C=C/[C@@H]3CC[C@@H](C)N3)Cc3sc(C#N)cc32)c(C(F)(F)F)n1]
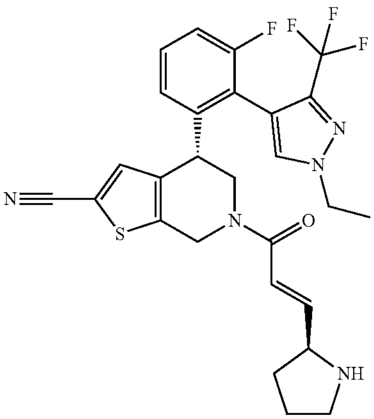 [SMILES: CCn1cc(-c2c(F)cccc2[C@@H]2CN(C(=O)/C=C/[C@@H]3CCCN3)Cc3sc(C#N)cc32)c(C(F)(F)F)n1]
TABLE A-continued
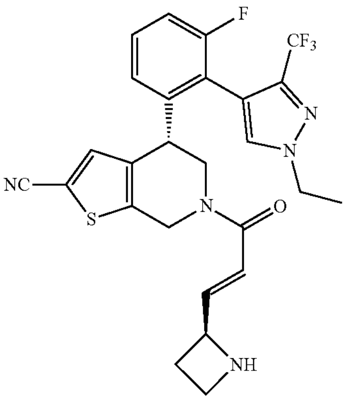 [SMILES: CCn1cc(-c2c(F)cccc2[C@@H]2CN(C(=O)/C=C/[C@@H]3CCN3)Cc3sc(C#N)cc32)c(C(F)(F)F)n1]
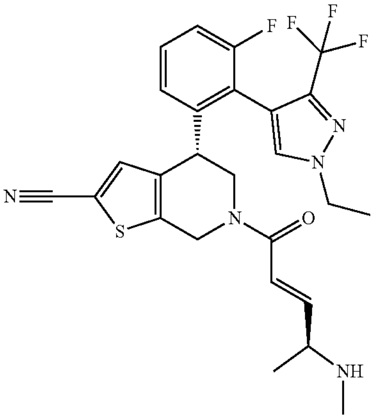 [SMILES: CCn1cc(-c2c(F)cccc2[C@@H]2CN(C(=O)/C=C/[C@H](C)NC)Cc3sc(C#N)cc32)c(C(F)(F)F)n1]
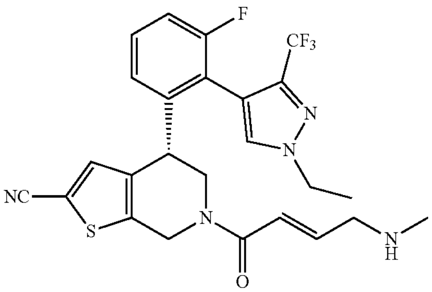 [SMILES: CCn1cc(-c2c(F)cccc2[C@@H]2CN(C(=O)/C=C/CNC)Cc3sc(C#N)cc32)c(C(F)(F)F)n1]
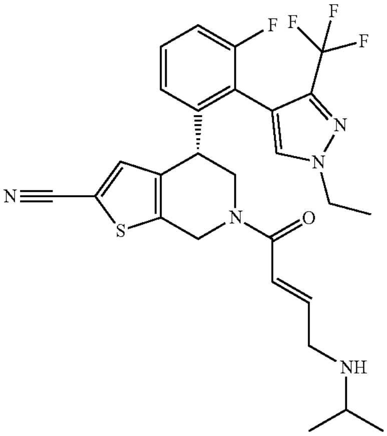 [SMILES: CCn1cc(-c2c(F)cccc2[C@@H]2CN(C(=O)/C=C/CNC(C)C)Cc3sc(C#N)cc32)c(C(F)(F)F)n1]

TABLE A-continued
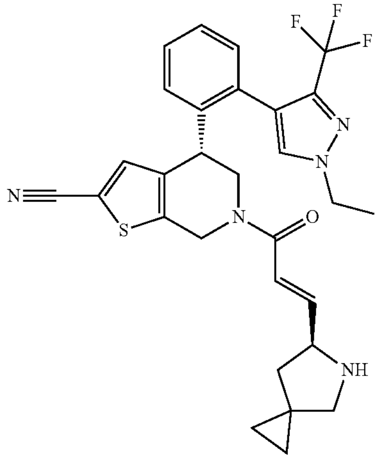 [SMILES: CCn1cc(-c2ccccc2[C@@H]2CN(C(=O)/C=C/[C@@H]3CC4(CC4)CN3)Cc3sc(C#N)cc32)c(C(F)(F)F)n1]
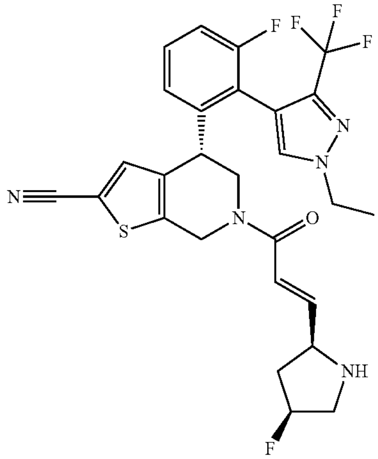 [SMILES: CCn1cc(-c2c(F)cccc2[C@@H]2CN(C(=O)/C=C/[C@@H]3C[C@H](F)CN3)Cc3sc(C#N)cc32)c(C(F)(F)F)n1]
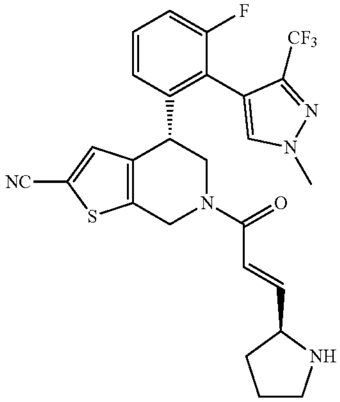 [SMILES: Cn1cc(-c2c(F)cccc2[C@@H]2CN(C(=O)/C=C/[C@@H]3CCCN3)Cc3sc(C#N)cc32)c(C(F)(F)F)n1]
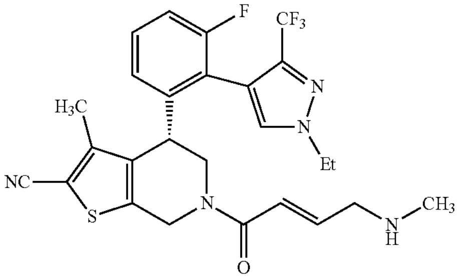 [SMILES: CCn1cc(-c2c(F)cccc2[C@@H]2CN(C(=O)/C=C/CNC)Cc3sc(C#N)c(C)c32)c(C(F)(F)F)n1]
TABLE A-continued
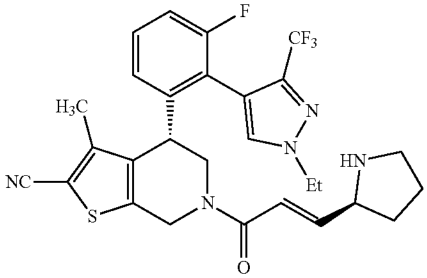 [SMILES: CCn1cc(-c2c(F)cccc2[C@@H]2CN(C(=O)/C=C/[C@@H]3CCCN3)Cc3sc(C#N)c(C)c32)c(C(F)(F)F)n1]
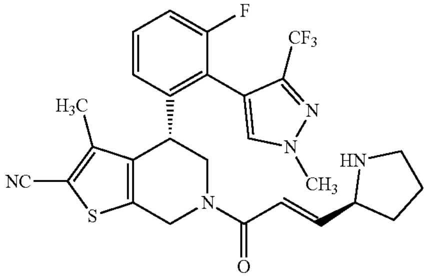 [SMILES: Cc1c(C#N)sc2c1[C@H](c1cccc(F)c1-c1cn(C)nc1C(F)(F)F)CN(C(=O)/C=C/[C@@H]1CCCN1)C2]
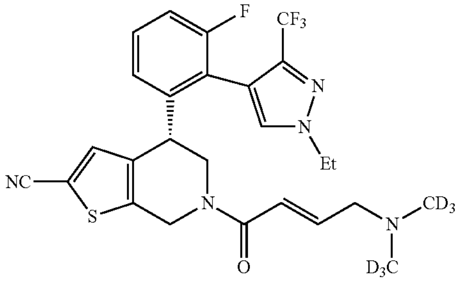 [SMILES: [2H]C([2H])([2H])N(C/C=C/C(=O)N1Cc2sc(C#N)cc2[C@H](c2cccc(F)c2-c2cn(CC)nc2C(F)(F)F)C1)C([2H])([2H])[2H]]
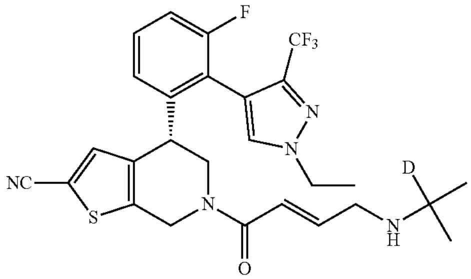 [SMILES: [2H]C(C)(C)NC/C=C/C(=O)N1Cc2sc(C#N)cc2[C@H](c2cccc(F)c2-c2cn(CC)nc2C(F)(F)F)C1]
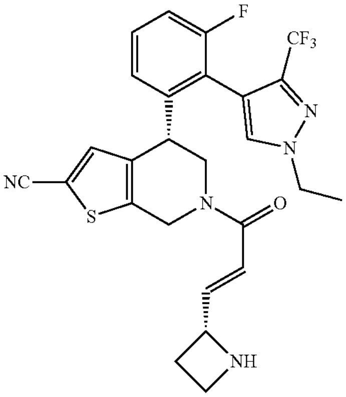 [SMILES: CCn1cc(-c2c(F)cccc2[C@@H]2CN(C(=O)/C=C/[C@H]3CCN3)Cc3sc(C#N)cc32)c(C(F)(F)F)n1]

TABLE A-continued
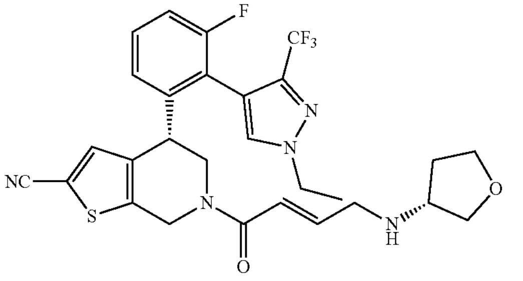 [SMILES: CCn1cc(-c2c(F)cccc2[C@@H]2CN(C(=O)/C=C/CN[C@@H]3CCOC3)Cc3sc(C#N)cc32)c(C(F)(F)F)n1]
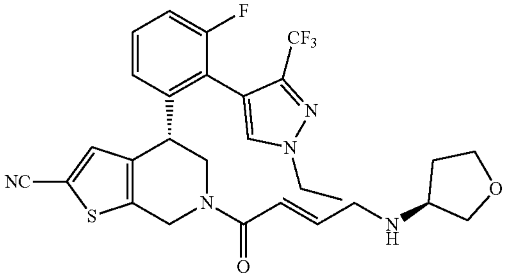 [SMILES: CCn1cc(-c2c(F)cccc2[C@@H]2CN(C(=O)/C=C/CN[C@H]3CCOC3)Cc3sc(C#N)cc32)c(C(F)(F)F)n1]
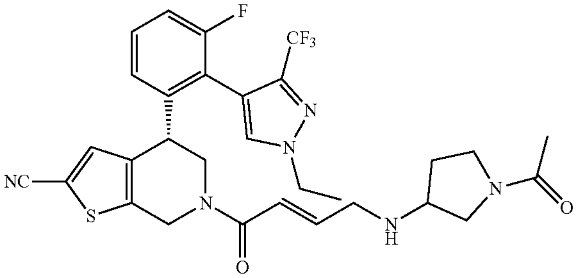 [SMILES: CCn1cc(-c2c(F)cccc2[C@@H]2CN(C(=O)/C=C/CNC3CCN(C(C)=O)C3)Cc3sc(C#N)cc32)c(C(F)(F)F)n1]
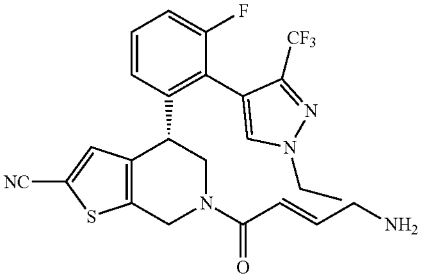 [SMILES: CCn1cc(-c2c(F)cccc2[C@@H]2CN(C(=O)/C=C/CN)Cc3sc(C#N)cc32)c(C(F)(F)F)n1]
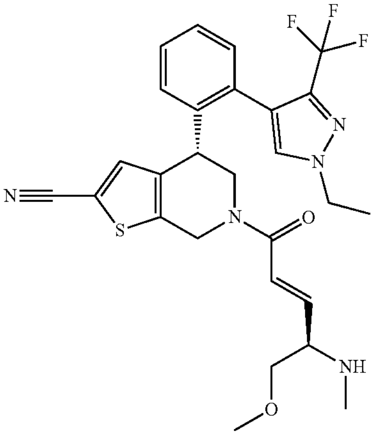 [SMILES: CCn1cc(-c2ccccc2[C@@H]2CN(C(=O)/C=C/[C@H](COC)NC)Cc3sc(C#N)cc32)c(C(F)(F)F)n1]
TABLE A-continued
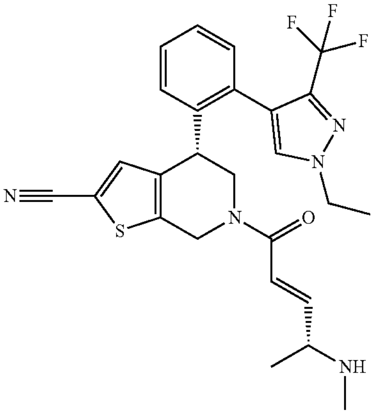 [SMILES: CCn1cc(-c2ccccc2[C@@H]2CN(C(=O)/C=C/[C@@H](C)NC)Cc3sc(C#N)cc32)c(C(F)(F)F)n1]
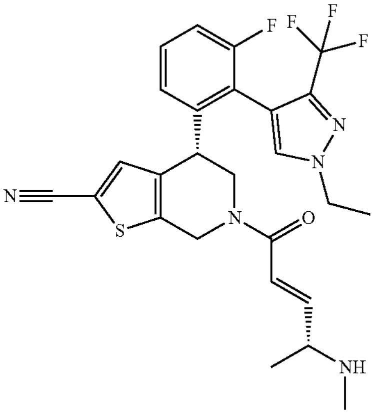 [SMILES: CCn1cc(-c2c(F)cccc2[C@@H]2CN(C(=O)/C=C/[C@@H](C)NC)Cc3sc(C#N)cc32)c(C(F)(F)F)n1]
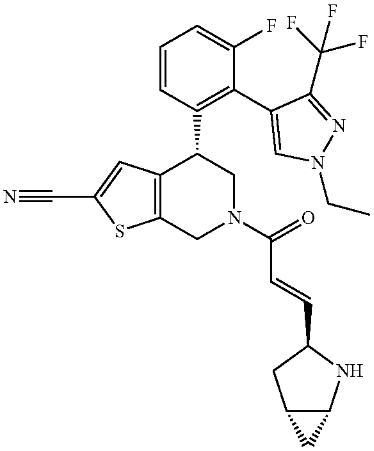 [SMILES: CCn1cc(-c2c(F)cccc2[C@@H]2CN(C(=O)/C=C/[C@@H]3C[C@H]4C[C@H]4N3)Cc3sc(C#N)cc32)c(C(F)(F)F)n1]

TABLE A-continued
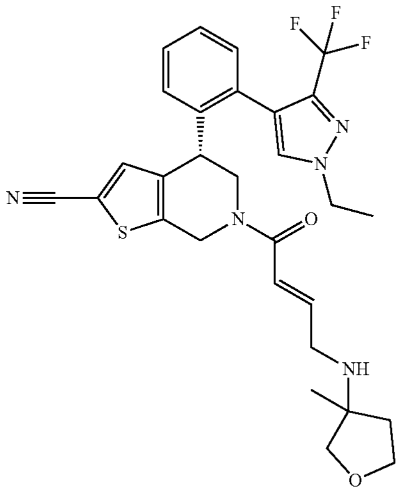 [SMILES: CCn1cc(-c2ccccc2[C@@H]2CN(C(=O)/C=C/CNC3(C)CCOC3)Cc3sc(C#N)cc32)c(C(F)(F)F)n1]
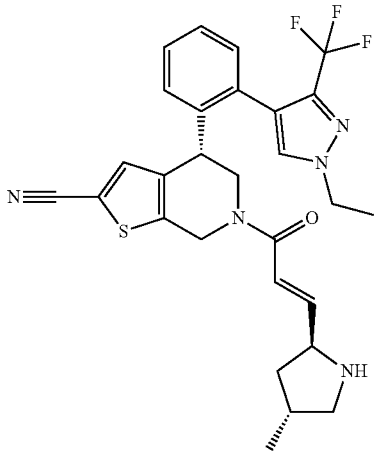 [SMILES: CCn1cc(-c2ccccc2[C@@H]2CN(C(=O)/C=C/[C@@H]3C[C@@H](C)CN3)Cc3sc(C#N)cc32)c(C(F)(F)F)n1]
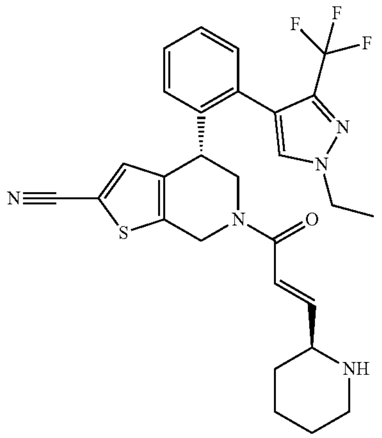 [SMILES: CCn1cc(-c2ccccc2[C@@H]2CN(C(=O)/C=C/[C@@H]3CCCCN3)Cc3sc(C#N)cc32)c(C(F)(F)F)n1]
TABLE A-continued
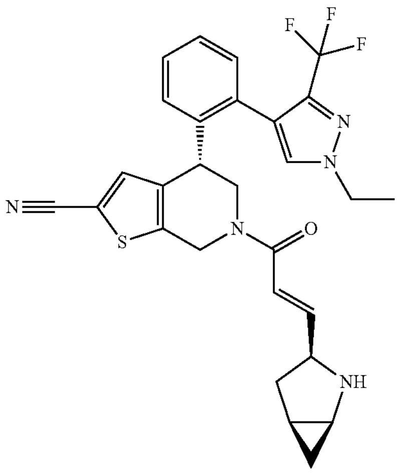 [SMILES: CCn1cc(-c2ccccc2[C@@H]2CN(C(=O)/C=C/[C@@H]3C[C@@H]4C[C@@H]4N3)Cc3sc(C#N)cc32)c(C(F)(F)F)n1]
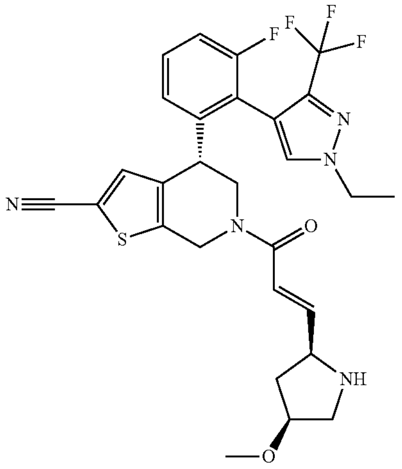 [SMILES: CCn1cc(-c2c(F)cccc2[C@@H]2CN(C(=O)/C=C/[C@@H]3C[C@H](OC)CN3)Cc3sc(C#N)cc32)c(C(F)(F)F)n1]
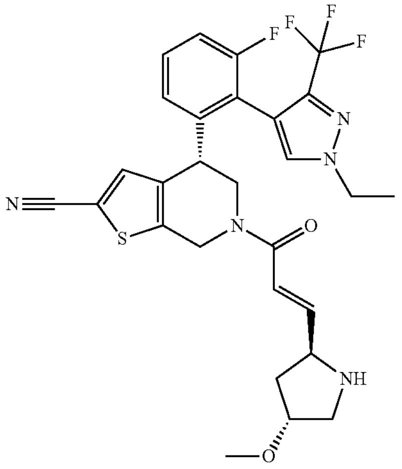 [SMILES: CCn1cc(-c2c(F)cccc2[C@@H]2CN(C(=O)/C=C/[C@@H]3C[C@@H](OC)CN3)Cc3sc(C#N)cc32)c(C(F)(F)F)n1]

TABLE A-continued
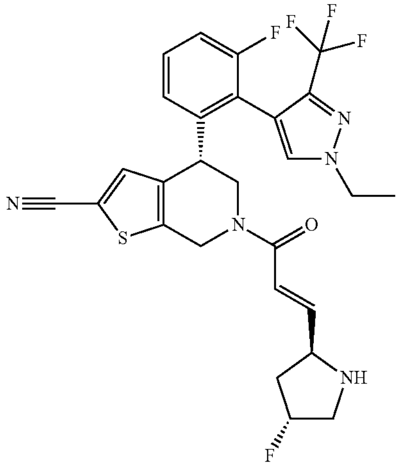 [SMILES: CCn1cc(-c2c(F)cccc2[C@@H]2CN(C(=O)/C=C/[C@@H]3C[C@@H](F)CN3)Cc3sc(C#N)cc32)c(C(F)(F)F)n1]
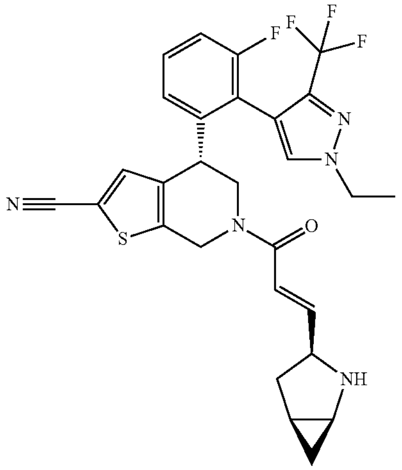 [SMILES: CCn1cc(-c2c(F)cccc2[C@@H]2CN(C(=O)/C=C/[C@@H]3C[C@@H]4C[C@@H]4N3)Cc3sc(C#N)cc32)c(C(F)(F)F)n1]
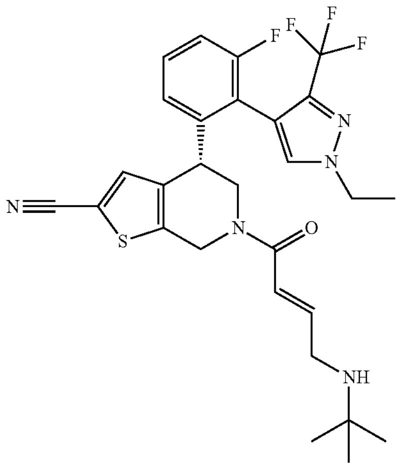 [SMILES: CCn1cc(-c2c(F)cccc2[C@@H]2CN(C(=O)/C=C/CNC(C)(C)C)Cc3sc(C#N)cc32)c(C(F)(F)F)n1]
TABLE A-continued
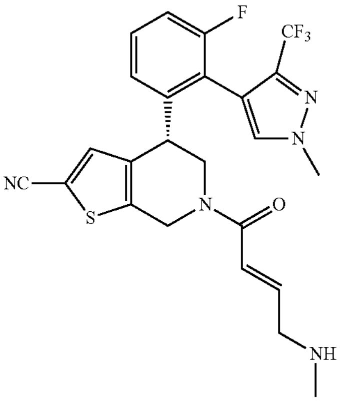 [SMILES: CNC/C=C/C(=O)N1Cc2sc(C#N)cc2[C@H](c2cccc(F)c2-c2cn(C)nc2C(F)(F)F)C1]
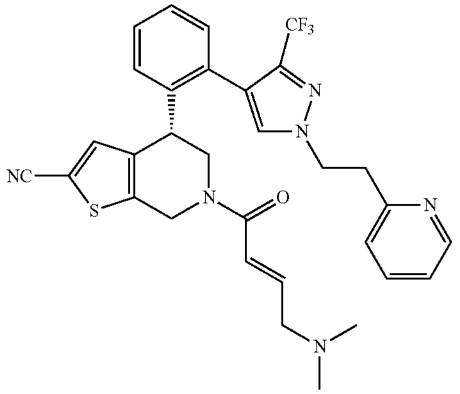 [SMILES: CN(C)C/C=C/C(=O)N1Cc2sc(C#N)cc2[C@H](c2ccccc2-c2cn(CCc3ccccn3)nc2C(F)(F)F)C1]
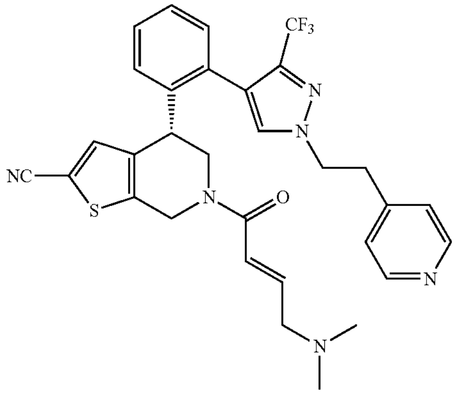 [SMILES: CN(C)C/C=C/C(=O)N1Cc2sc(C#N)cc2[C@H](c2ccccc2-c2cn(CCc3ccncc3)nc2C(F)(F)F)C1]
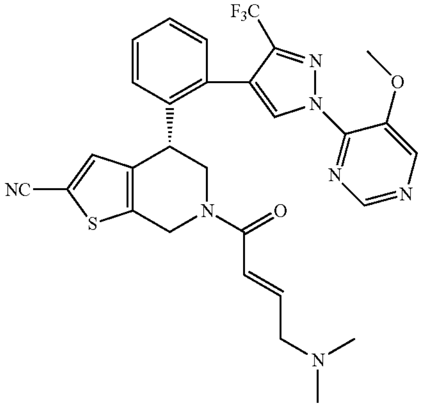 [SMILES: COc1cncnc1-n1cc(-c2ccccc2[C@@H]2CN(C(=O)/C=C/CN(C)C)Cc3sc(C#N)cc32)c(C(F)(F)F)n1]

TABLE A-continued
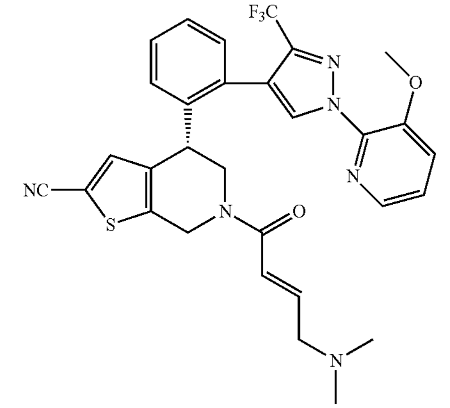 [SMILES: COc1cccnc1-n1cc(-c2ccccc2[C@@H]2CN(C(=O)/C=C/CN(C)C)Cc3sc(C#N)cc32)c(C(F)(F)F)n1]
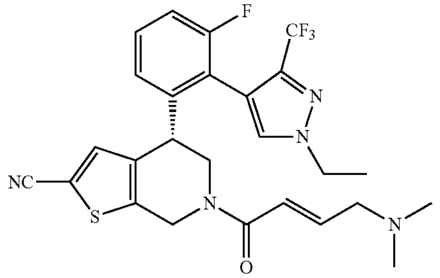 [SMILES: CCn1cc(-c2c(F)cccc2[C@@H]2CN(C(=O)/C=C/CN(C)C)Cc3sc(C#N)cc32)c(C(F)(F)F)n1]
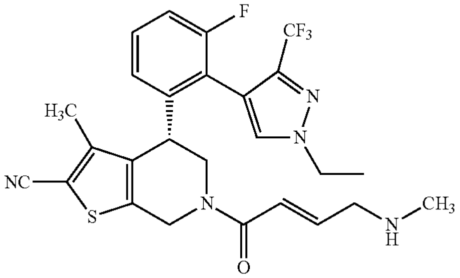 [SMILES: CCn1cc(-c2c(F)cccc2[C@@H]2CN(C(=O)/C=C/CNC)Cc3sc(C#N)c(C)c32)c(C(F)(F)F)n1]
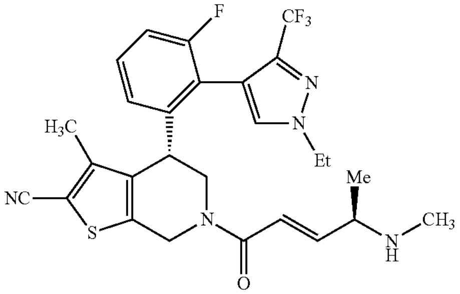 [SMILES: CCn1cc(-c2c(F)cccc2[C@@H]2CN(C(=O)/C=C/[C@@H](C)NC)Cc3sc(C#N)c(C)c32)c(C(F)(F)F)n1]
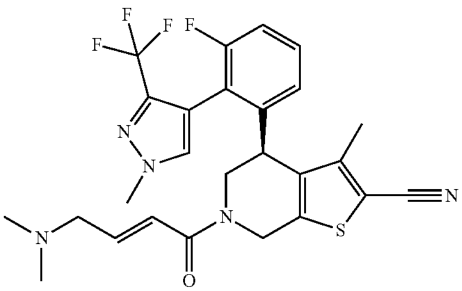 [SMILES: Cc1c(C#N)sc2c1[C@H](c1cccc(F)c1-c1cn(C)nc1C(F)(F)F)CN(C(=O)/C=C/CN(C)C)C2]
TABLE A-continued
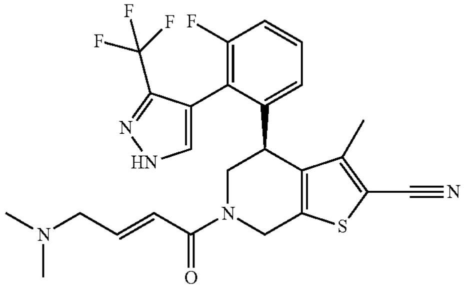 [SMILES: Cc1c(C#N)sc2c1[C@H](c1cccc(F)c1-c1c[nH]nc1C(F)(F)F)CN(C(=O)/C=C/CN(C)C)C2]
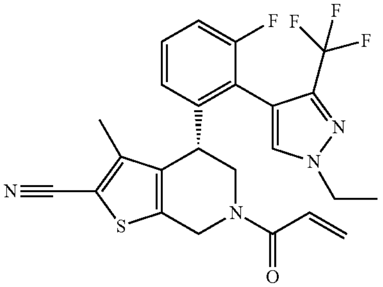 [SMILES: C=CC(=O)N1Cc2sc(C#N)c(C)c2[C@H](c2cccc(F)c2-c2cn(CC)nc2C(F)(F)F)C1]
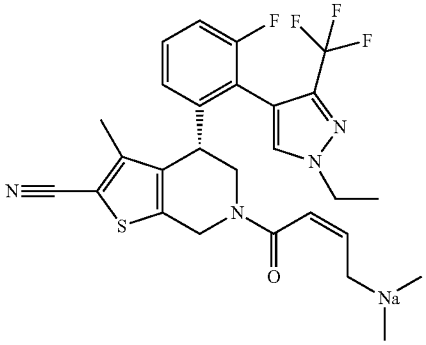
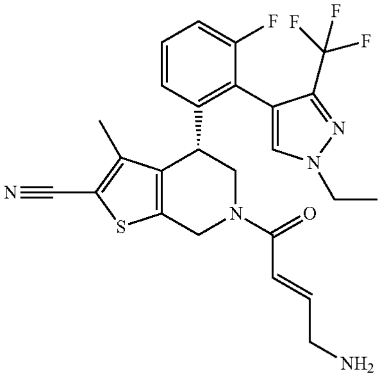 [SMILES: CCn1cc(-c2c(F)cccc2[C@@H]2CN(C(=O)/C=C/CN)Cc3sc(C#N)c(C)c32)c(C(F)(F)F)n1]

TABLE A-continued
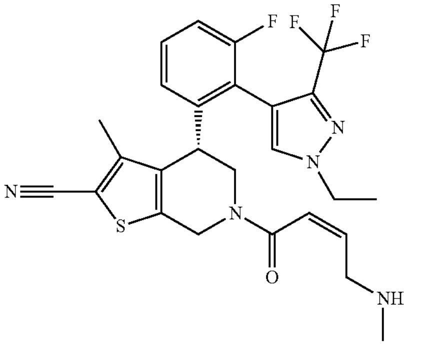 [SMILES: CCn1cc(-c2c(F)cccc2[C@@H]2CN(C(=O)/C=C\CNC)Cc3sc(C#N)c(C)c32)c(C(F)(F)F)n1]
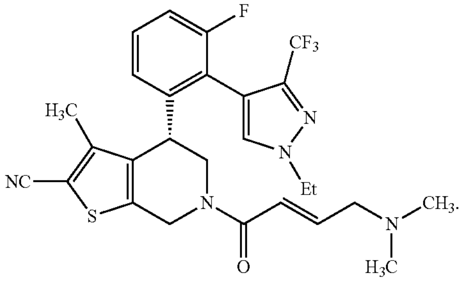 [SMILES: CCn1cc(-c2c(F)cccc2[C@@H]2CN(C(=O)/C=C/CN(C)C)Cc3sc(C#N)c(C)c32)c(C(F)(F)F)n1]
In one embodiment, the compound is as recited in Table B, below, or a pharmaceutically acceptable salt thereof.
TABLE B
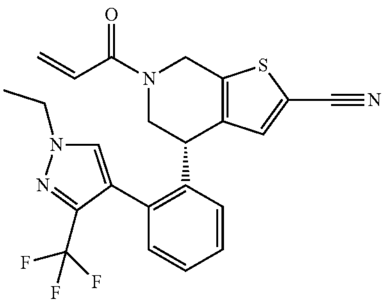 [SMILES: C=CC(=O)N1Cc2sc(C#N)cc2[C@H](c2ccccc2-c2cn(CC)nc2C(F)(F)F)C1]
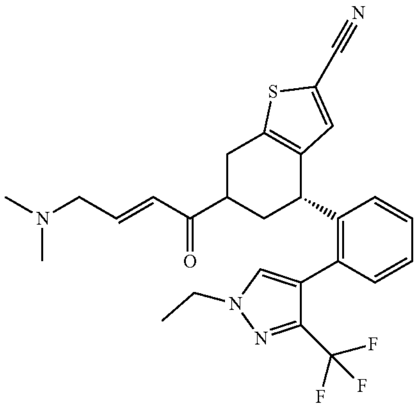 [SMILES: CCn1cc(-c2ccccc2[C@@H]2CC(C(=O)/C=C/CN(C)C)Cc3sc(C#N)cc32)c(C(F)(F)F)n1]
TABLE B-continued
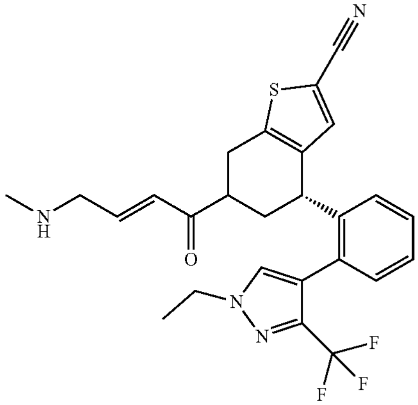 [SMILES: CCn1cc(-c2ccccc2[C@@H]2CC(C(=O)/C=C/CNC)Cc3sc(C#N)cc32)c(C(F)(F)F)n1]
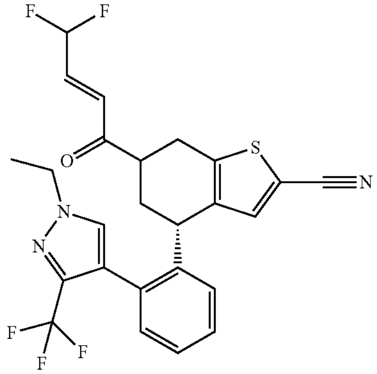 [SMILES: CCn1cc(-c2ccccc2[C@@H]2CC(C(=O)/C=C/C(F)F)Cc3sc(C#N)cc32)c(C(F)(F)F)n1]
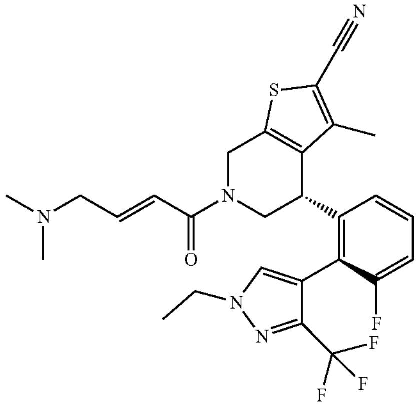
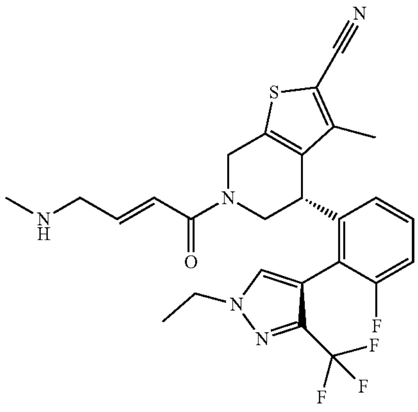

TABLE B-continued
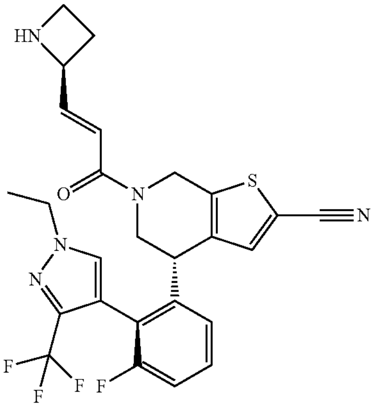
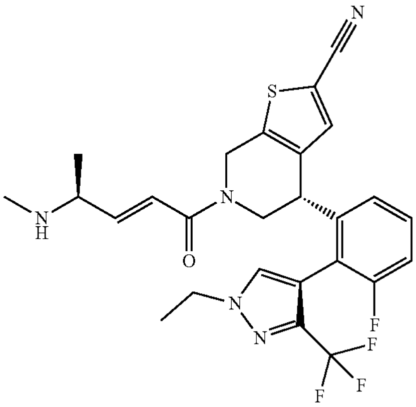
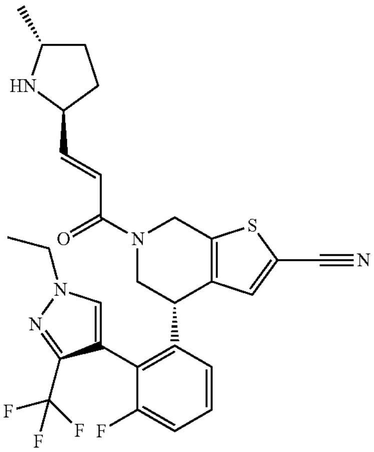
TABLE B-continued
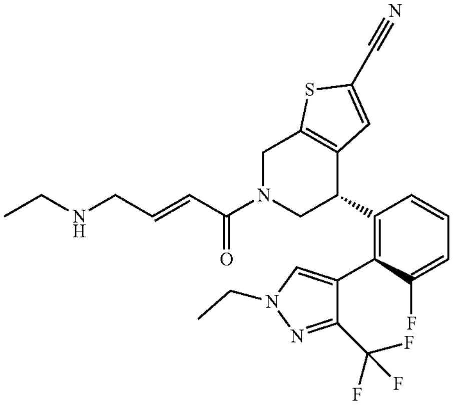
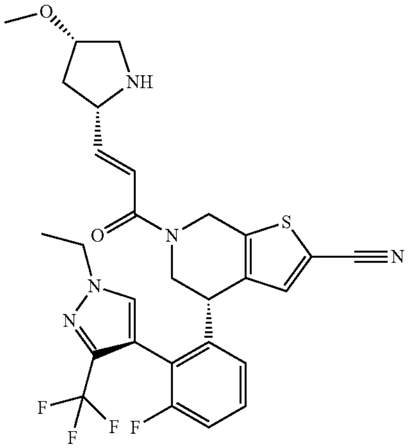
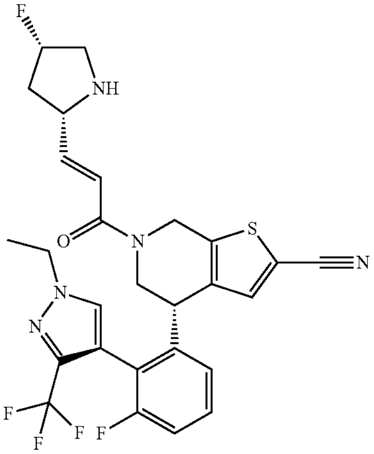
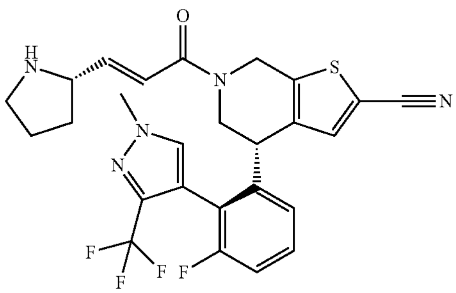

TABLE B-continued
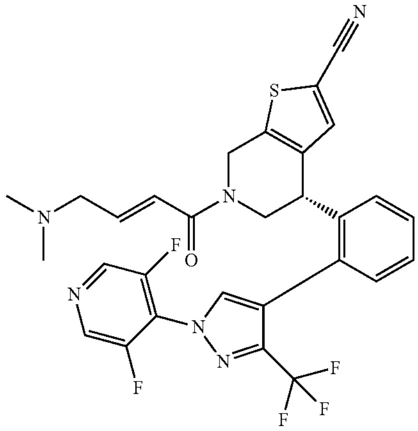 [SMILES: CN(C)C/C=C/C(=O)N1Cc2sc(C#N)cc2[C@H](c2ccccc2-c2cn(-c3c(F)cncc3F)nc2C(F)(F)F)C1]
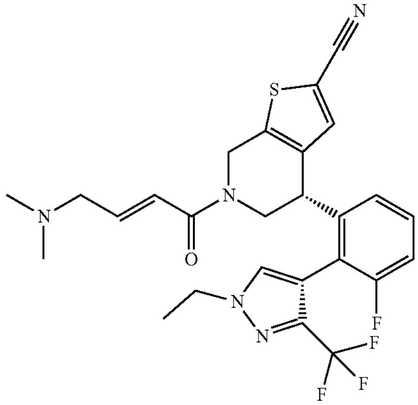
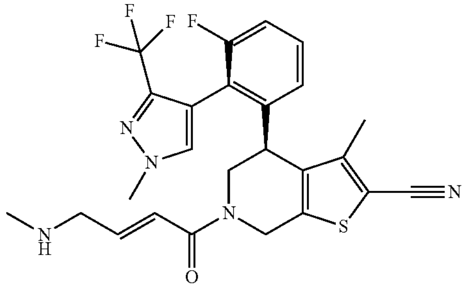
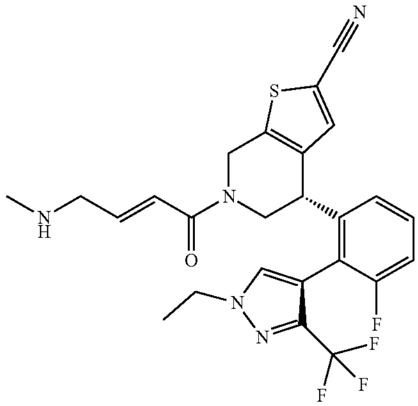
TABLE B-continued
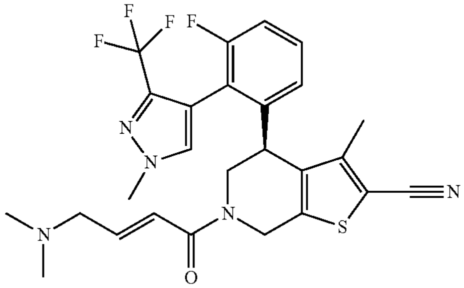 [SMILES: Cc1c(C#N)sc2c1[C@H](c1cccc(F)c1-c1cn(C)nc1C(F)(F)F)CN(C(=O)/C=C/CN(C)C)C2]
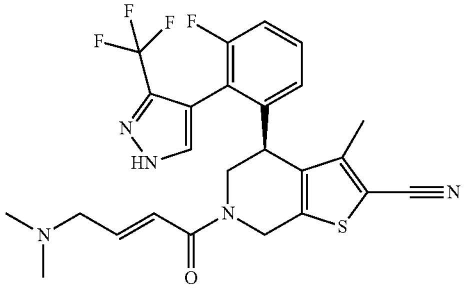 [SMILES: Cc1c(C#N)sc2c1[C@H](c1cccc(F)c1-c1c[nH]nc1C(F)(F)F)CN(C(=O)/C=C/CN(C)C)C2]
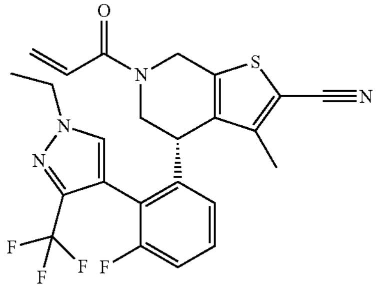 [SMILES: C=CC(=O)N1Cc2sc(C#N)c(C)c2[C@H](c2cccc(F)c2-c2cn(CC)nc2C(F)(F)F)C1]
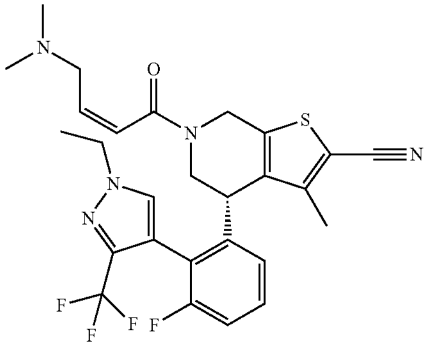 [SMILES: CCn1cc(-c2c(F)cccc2[C@@H]2CN(C(=O)/C=C\CN(C)C)Cc3sc(C#N)c(C)c32)c(C(F)(F)F)n1]
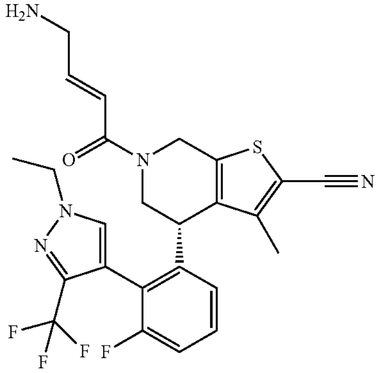 [SMILES: CCn1cc(-c2c(F)cccc2[C@@H]2CN(C(=O)/C=C/CN)Cc3sc(C#N)c(C)c32)c(C(F)(F)F)n1]

TABLE B-continued

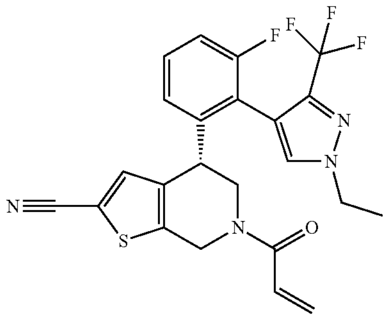 [SMILES: C=CC(=O)N1Cc2sc(C#N)cc2[C@H](c2cccc(F)c2-c2cn(CC)nc2C(F)(F)F)C1]

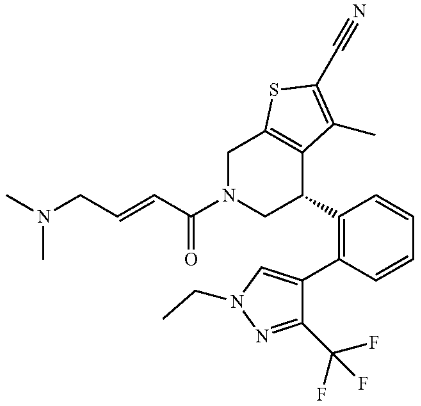 [SMILES: CCn1cc(-c2ccccc2[C@@H]2CN(C(=O)/C=C/CN(C)C)Cc3sc(C#N)c(C)c32)c(C(F)(F)F)n1]

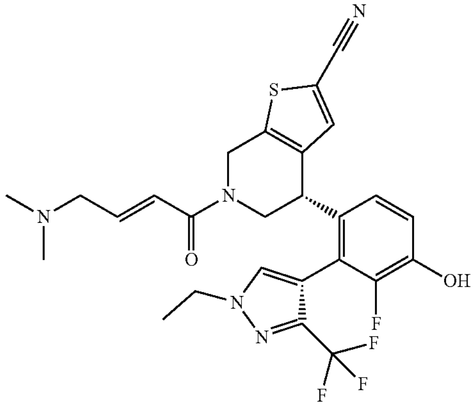

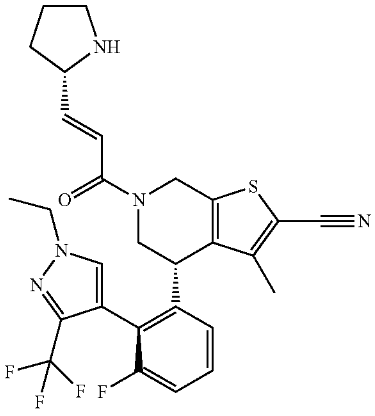

TABLE B-continued

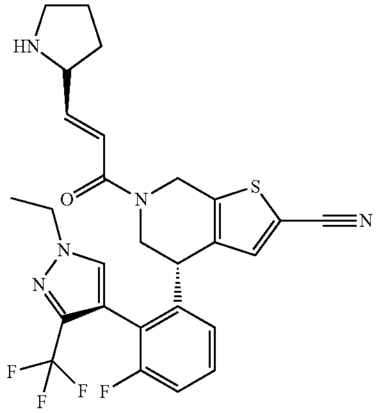

Method of Inhibition

In embodiments, the compounds of Formulas I-V covalently bind to an E1 cysteine amino acid corresponding to Cys30 of Uba2 subunit 2.

In embodiments, the method includes allowing the compound to covalently bind an E1 enzyme. In embodiments, the method includes allowing the compound to covalently bind an E1 cysteine amino acid corresponding to Cys30 of Uba2 subunit 2.

In some embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2.

In an aspect is provided a pharmaceutical composition including a compound described herein, or pharmaceutically acceptable salt thereof, and a pharmaceutically acceptable excipient.

In an aspect is provided a method of treating cancer, the method including administering to a subject in need thereof an effective amount of a compound described herein.

In an aspect is provided a method of inhibiting cell proliferation, the method including contacting the cell with a compound described herein.

Definitions

The abbreviations used herein have their conventional meaning within the chemical and biological arts. The chemical structures and formulae set forth herein are constructed according to the standard rules of chemical valency known in the chemical arts.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Preferred alkyl substituents are $C_1$-$C_6$alkyl. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. The term "alkylene," by itself or as part of another substituent, means, unless otherwise stated, a divalent radical derived from an alkyl, as exemplified, but not limited by, $—CH_2CH_2CH_2CH_2—$.

An unsaturated alkyl group is one having one or more double bonds or triple bonds referred to as "alkenyl" or "alkynyl" groups, respectively. Preferred alkenyl substituents are $C_2$-$C_6$ alkenyl and preferred alkynyl substituents are $C_2$-$C_6$ alkynyl. Examples of alkenyl or alkynyl groups include, but are not limited to, ethenyl, vinyl, 2-propenyl, butenyl, crotyl, 2-isopentenyl, 2-(butadienyl), 2,4-pentadienyl, 3-(1,4-pentadienyl), ethynyl, 1-propynyl, 3-propynyl, and 3-butynyl.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —ON. Up to two or three heteroatoms may be consecutive, such as, for example, $—CH_2—NH—OCH_3$ and $—CH_2—O—Si(CH_3)_3$. Heteroalkyl also includes terms such as alkoxy, and alkylamino.

An alkoxy is an alkyl attached to the remainder of the molecule via an oxygen linker (—O—). Preferred alkoxy substituents include $C_{1-4}$ alkoxy. Examples of alkoxy groups include, but are not limited to methoxy, ethoxy and propoxy. Preferred alkylamino substituents include mono substituted $C_{1-4}$ alkylamino and disubstituted alkylamino. Examples of alkylamino groups include, but are not limited to methylamino, dimethylamino and diethylamino.

Anther subgroup of heteroalkyl includes "alkoxyalkyl" where an alkyl group is substituted with an alkoxy group, as defined above. Preferred alkoxyalkyl substituents include $C_{1-4}$ alkoxy- $C_{1-4}$ alkyl. Examples of alkoxyalkyl groups include, but are not limited to methoxymethyl, ethoxymethyl and methoxyethyl.

As described above, heteroalkyl groups, as used herein, include those groups that are attached to the remainder of the molecule through a heteroatom, such as —C(O)R', —C(O)NR', —NR'R", —OR', —SR', and/or $—SO_2R'$.

The term "cycloalkyl" by itself or in combination with other terms, mean, unless otherwise stated, cyclic versions of "alkyl". Cycloalkyl are not fully aromatic rings. Preferred cycloalkyl substituents include $C_3$-$C_6$ cycloalkyl. A "cycloalkylene" alone or as part of another substituent, means a divalent radical derived from a cycloalkyl. For example, a cycloalkyl group having 3 to 8 ring members may be referred to as a ($C_3$-$C_4$)cycloalkyl, a cycloalkyl group having 3 to 7 ring members may be referred to as a ($C_3$-$C_7$)cycloalkyl and a cycloakyl group having 4 to 7 ring members may be referred to as a ($C_4$-$C_7$)cycloalkyl. In certain embodiments, the cycloalkyl group can be a ($C_3$-$C_{10}$)cycloalkyl; a ($C_3$-$C_8$)cycloalkyl, a ($C_3$-$C_7$)cycloalkyl, a ($C_3$-$C_6$)cycloalkyl, or a $C_4$-$C_7$)cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups.

The term "cycloalkenyl" by itself or in combination with other terms, mean, unless otherwise stated, cyclic versions of "alkenyl". Cycloalkenyl are not fully aromatic rings. Preferred cycloalkenyl substituents include $C_4$-$C_6$ cycloalkenyl. For example, a cycloalkenyl group having 4 to 8 ring members may be referred to as a ($C_4$-$C_8$)cycoalkenyl, a cycloalkenyl group having 3 to 7 ring members may be referred to as a ($C_3$-$C_7$)cycloakenyl and a cycloalkenyl group having 4 to 6 ring members may be referred to as a ($C_4$-$C_6$)cycloalkenyl.

The term "heterocycloalkyl" by itself or in combination with other terms, mean, unless otherwise stated, cyclic versions of "heteroalkyl". Heterocycloalkyl rings are not fully aromatic. Heterocycloalkyl is also referred by the term heterocyclyl. Preferred heterocyclyl substituents include $C_3$-$C_7$ oxygen or nitrogen containing rings, or both nitrogen and oxygen atms. Additionally, for heterocycloalkyl, a heteroatom can occupy the position at which the heterocycle is attached to the remainder of the molecule. A "heterocycloalkylene," alone or as part of another substituent, means a divalent radical derived from heterocycloalkyl. "Heterocyclyl" refers to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring. In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (═O) or oxide (—O—) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2 (3H)-only, 7H-purin-8(9H)-only, imidazolidin-2-only, 1H-imidazol-2(3H)-only, 1,1-dioxo-1-thiomorpholinyl, and the like.

The terms "halo" or "halogen," by themselves or as part of another substituent, mean, unless otherwise stated, a fluorine, chlorine, bromine, or iodine atom.

The term "haloalkyl" is meant to include monohaloalkyl and polyhaloalkyl. For example, the term "$C_1$-$C_3$-haloalkyl" includes, but is not limited to, fluoromethyl, difluoromethyl, trifluoromethyl, 2,2,2-trifluoroethyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. "Heteroaryl" refers to a monovalent heteroaromatic group derived by the removal of one hydrogen atom from a single atom of a parent heteroaromatic ring system. Heteroaryl groups typically include 5- to 14-membered; but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms; 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, ail three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When yen the total number of S and O atoms in the heteroaryl group exceeds 1, those heteroatoms are not adjacent to one another. In certain embodiments, the total number of S and 0 atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

An "arylene" and a "heteroarylene," alone or as part of another substituent, mean a divalent radical derived from an aryl and heteroaryl, respectively.

The term "carbonyl" refers to the radical —C(O) which may also be referred to as —C(═O) group.

The term "carboxy" refers to the radical —C(O) OH which may also be referred to as —C(═O)OH.

The term "cyano" refers to the radical —CN.

The term "amino" refers to the radical —$NH_2$.

The term "aminocarbonyl" refers to the radical—CO—$NH_2$. Aminocarbonyl radicals may be substituted with one or two alkyl groups to form "alkylaminocarbonyl" groups.

The term "alkylcarbonyl" refers to the radical alkyl-CO—.

The terms "hydroxyl" and "hydroxy" refers to the radical —OH.

The term "oxo," as used herein, means an oxygen that is double bonded to a carbon atom.

Each of the above terms (e.g., "alkyl," "heteroalkyl," "cycloalkyl," "heterocycloalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', —halogen, —SiR'R"R'", —OC(O)R', —C(O) R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R", —ONR'R", —NR'C(O)NR"NR"R", —CN, —$NO_2$, —NR'SO$_2$R", —NR'C(O)

R", —NR'C(O)—OR", —NR'OR", in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Such substituted alkyl groups include hydroxyalkyl; carboxyalkyl, alkoxycarbonylalkyl, cyanoalkyl, aminocarbonylalkyl, alkylaminocarbonylalkyl, alkylaminoalkyl, alkylcarbonylaminoalkyl, cycloalkylalkyl, aralkyl, heteroarylalkyl and heterocyclylalkyl; wherein the heterocyclyl, heteroaryl, aryl, cycloalkyl, hydroxyl; carboxyl, alkoxy, cyano, aminocarbonyl, alkylaminocarbonyl, alkylamino, and alkylcarbonylamino groups are defined above.

Similarly, alkenyl and alkynyl groups can be specifically substituted to form halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, heterocyclyl- substituted $C_2$-$C_6$ alkynyl, cycloalkyl- substituted $C_2$-$C_6$ alkenyl, oxygen-containing heterocyclyl- substituted $C_2$-$C_6$ alkenyl, oxygen-containing heterocyclyl- substituted $C_2$-$C_6$ alkynyl, nitrogen-containing heterocyclyl- substituted $C_2$-$C_6$ alkenyl, and cycloalkyl- substituted $C_2$-$C_6$ alkynyl groups; where the amino, halo, dialkylamino, alkylamino, alkoxy, cycloalkyl, oxygen-containing heterocyclyl, and nitrogen-containing heterocyclyl radicals are defined elsewhere.

The term "alkylsufonyl" refers to the radical alkyl-$SO_2$—; where alkyl is defined elsewhere.

Substituted amino groups include "alkylcarbonylamino," "alkylsulfonylamino," "alkylaminocarbonylamino" and "alkylsulfonylamino"; wherein the amino radical is substituted, preferably with one substituent selected from alkylcarbonyl, alkylsulfonyl, alkylaminocarbonyl, defined elsewhere.

Similar to the substituents described for the alkyl radical, substituents for the aryl and heteroaryl groups are varied and are selected from, for example: —OR', —NR'R", —SR',-halogen, —SiR'R"R'", —OC(O) R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", NR—C(NR'R")=NR'", —S(O) R', —$S(O)_2$R', —$S(O)_2$NR'R", —NR$SO_2$R', —NR'NR"R'", —ONR'R", —NR'C(O)NR"NR'"R"", —CN, —$NO_2$, —R', —$N_3$, —CH$(Ph)_2$, fluoro ($C_1$-$C_4$)alkoxy, fluoro ($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), Boron (B), and silicon (Si).

A "substituent group," as used herein, means a group selected from the following moieties: (A) halogen, oxo, cyano, —$CCl_3$, —$CBr_3$, —$CF_3$, —$Cl_3$, —$CHCl_2$, —$CHBr_2$, $—CHF_2$, $—CHI_2$, $—CH_2Cl$, $—CH_2Br$, $—CH_2F$, $—CH_2I$, —OH, $—NH_2$, —COOH, $—CONH_2$, $—NO_2$, —SH, $—SO_3H$, $—SO_4H$, $—SO_2NH_2$, $—NHNH_2$, $—ONH_2$, —NHOH, $—NHC(O)NHNH_2$, $—NHC(O)NH_2$, $—NHSO_2H$, —NHC(O)H, —NHC(O)OH, $—OCCl_3$, $—OCF_3$, $—OCBr_3$, $—OCl_3$, $—OCHCl_2$, $—OCHBr_2$, $—OCHI_2$, $—OCHF_2$, $—OCH_2Cl$, $—OCH_2Br$, $—OCH_2F$, $—OCH_2I$, $—N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halo, haloalkyl cyano, hydroxyl, amino, carboxyl, amnocarbonyl, nitro, aminosulfonyl, haloalkoxy, cycloalkyl, heterocyclyl, aryl, or heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_3$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_3$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_3$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule. As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, IN, 1972).

Unless otherwise stated, structures depicted herein are also meant to include compounds which differ only in the presence of one or more isotopically enriched atoms. For example, compounds having the present structures except for the replacement of a hydrogen by a deuterium [D] or tritium, or the replacement of a carbon by $^{13}C$- or $^{14}C$-enriched carbon are within the scope of this is selected from invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (XV)), a Roman alphabetic symbol may be used to distinguish each appearance of that particular R group.

The term "pharmaceutically acceptable salts" is meant to include salts of the active compounds that are prepared with relatively nontoxic acids or bases, depending on the particular substituents found on the compounds described herein. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, mono hydrogen phosphoric, di hydrogen phosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including acute lymphoblastic lymphoma, non-Hodgkin's lymphomas (e.g., Burkitt's, Small Cell, and Large Cell lymphomas (e.g., diffuse large B-cell lymphoma (DLBCL)), Hodgkin's lymphoma, leukemia (including AML, ALL, and CML), or multiple myeloma. As used herein, the term "cancer" refers to all types of cancer, neoplasm or malignant tumors found in mammals (e.g. humans), including leukemia, carcinomas and sarcomas. The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease) means that the disease (e.g. cancer) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term “signaling pathway” as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

The present invention comprises a method of treating cancer with a therapeutically effective amount of a compound of any of Formulas I-V. In some embodiments the cancer is selected from acute myeloid leukemia, large B-cell lymphoma, lung squamous cell carcinoma, pancreatic adenosarcoma, esophageal carcinoma, cervical squamous cell carcinoma, endocervical adenosarcoma, stomach adenocarcinomathymoma, renal cell carcinoma, head and neck squamous cell carcinoma, bladder carcinoma, ovarian cystadenocarcinoma and mesothelioma.

In certain embodiments, a compound of any of Formulas I-V is administered at a rate approximately equal to the half-life of an E1 enzyme.

The present invention comprises a method of treating cancer with a therapeutically-effective amount of a compound of any of Formulas I-V.

The present invention comprises a method of inhibiting E1 with a therapeutically-effective amount of a compound of any of Formulas I-V.

In embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2.

In a certain embodiment, the method includes allowing the compound to covalently bind an E1 enzyme.

In embodiments, the method includes allowing the compound to covalently bind an E1 cysteine amino acid corresponding to Cys30 of Uba2 subunit 2.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2.

General Synthetic Schemes

The compounds of this invention can be synthesized according to the procedures described in WO2020/191151 and PCT/US21/14653. In addition, the compounds of this invention can be synthesized according to the following procedure of Scheme I, wherein the substituents are as defined for Formulas I-V, above, except where further noted.

The following abbreviations are used:

RT room temperature
DCM, $CH_2Cl_2$ dichloromethane
DIEA, DIPEA diisopropylethylamine, Hunig’s base
TEA, $Et_3N$ triethylamine
DMF dimethylformamide
DMSO dimethylsulfoxide
$K_2CO_3$ potassium carbonate
AcCN, ACN, $CH_3CN$ acetonitrile
TFA trifluoroacetic acid
TFAA trifluoroacetic acid anhydride
HCl hydrochloric acid
HOAc, AcOH acetic acid
THF tetrahydrofuran
DMP 2,2-dimethoxypropane
$CDCl_3$ Deuterated chloroform
EA, EtOAc ethyl acetate
$Na_2SO_4$ sodium sulfate
LiHMDS Lithium bis(trimethylsilyl)amide
DMA dimethylacetamide
mg milligram
g gram
ml milliliter h hour
min minutes
$Et_2O$ ethyl ether
$MgSO_4$ magnesium sulfate
$NH_4Cl$ ammonium chloride
$H_2O$ water
$NaHCO_3$ sodium bicarbonate
$Na_2CO_3$ sodium carbonate
MeOH methanol
Boc tert-butyloxycarbonyl
$Boc_2O$ BOC anhydride, di-tert-butyl dicarbonate
NaOH sodium hydroxide
CuI copper iodide
LiOH lithium hydroxide
LiCl lithium chloride
MsCl mesyl chloride
HCHO formaldehyde
NBS N-bromosuccinimide
$NH_3$ ammonia
EtOH ethanol
DBU 1,8-Diazabicycloundec-7-ene
$Cs_2CO_3$ cesium carbonate
$H_2$ hydrogen
iPOH, IPA Isopropanol
HATU 2-(7-Aza-1H-benzotriazole-1-yl)-1,1,3,3-tetramethyluronium hexafluorophosphate
KOAc potassium acetate
$Pd(PPh_3)Cl_2$ bis(triphenylphosphine) palladium dichloride
Ar argon
$Ag_2O$ silver oxide
FA formic acid
$B_2Pin_2$ Bis(pinacolato)diboron
$Pd(dppf)Cl_2$ 1,1'-Bis(diphenylphosphino)ferrocene]dichloropalladium(II)
TMSCN Trimethylsilyl cyanide
$ZnI_2$ zinc iodide
LAH, $LiALH_4$ lithium aluminum hydride
PE petroleum ether
$NaBH_4$ sodium borohydride
$AlCl_3$ aluminum trichloride
$K_3PO_4$ potassium phosphate
$Pd(Pcy_3)_2Cl_2$ Choro((tricyclohexylphosphine)-2-(2'-aminobiphenyl)]palladium (II)
$NaNO_2$ sodium nitrite
KI potassium iodide
KOH potassium hydroxide
$Na_2S_2O_3$ sodium thiosulfate $NH_4Cl$ ammonium chloride Scheme I

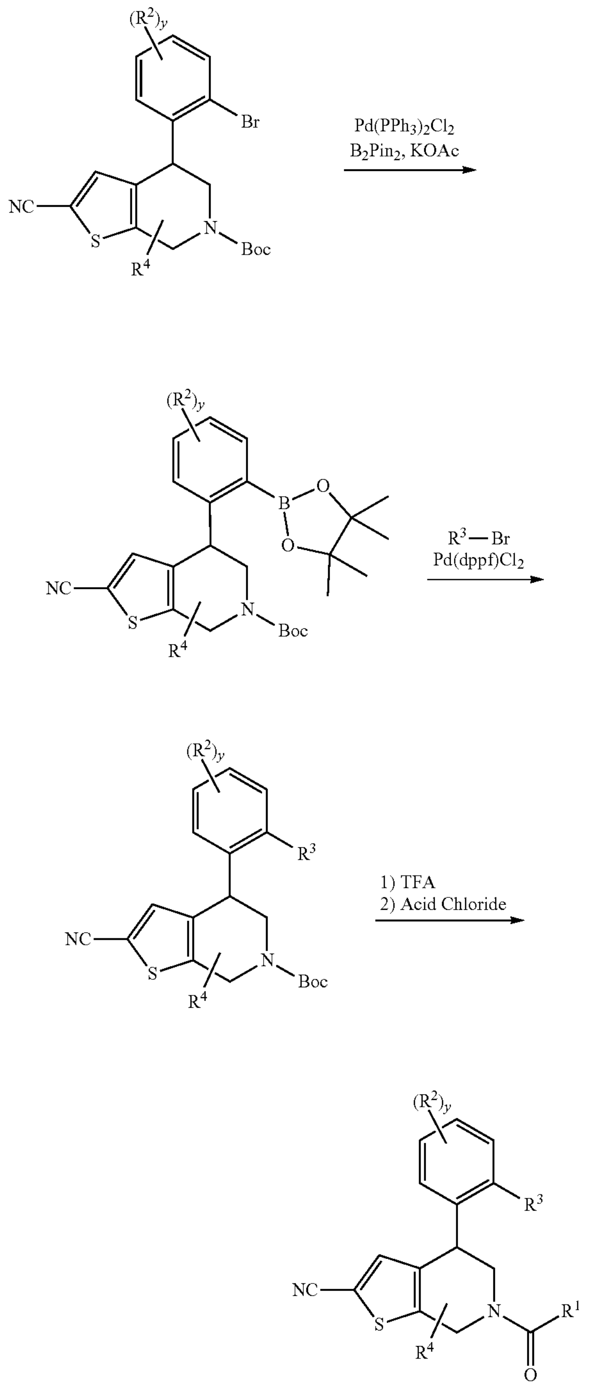

The cyano compounds of the invention can be synthesized according to Scheme I. In step A, the bromo compound is converted to the boronic ester such as in the presence of $Pd(PPh_3)_2Cl_2$. Coupling with the halide, such as in the presence of $Pd(dppf)Cl_2$ gives the substituted phenyl compound. The substituted phenyl compound is deprotected and acylated, such as with an acid chloride to provide the desired compounds of Formulas I-V.

Scheme II

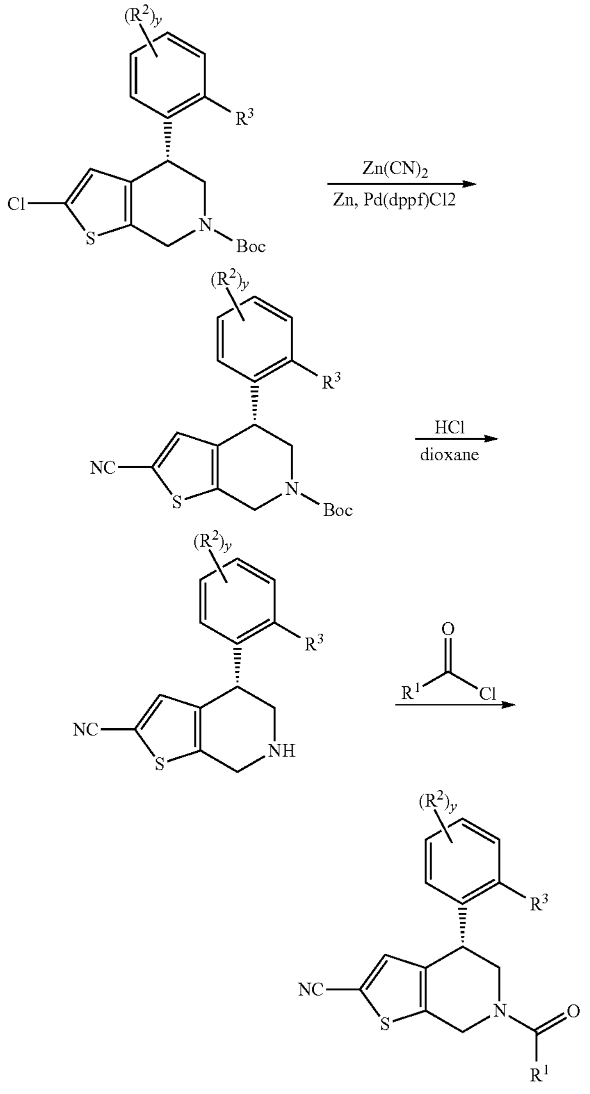

The cyano compounds of the invention can be synthesized from the chloro starting materials according to Scheme II. In step A, the chloro compound is converted to the cyano compound such as in the presence of Zn and $Pd(dppf)Cl_2$. The protected tetrahydro-thieno[2,3-c]pyridines are deprotected and acylated, such as with an acid chloride, to provide the desired compounds of Formulas I-V.

Scheme III

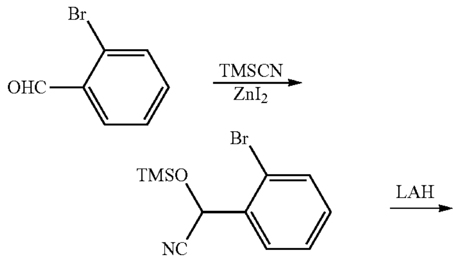

-continued

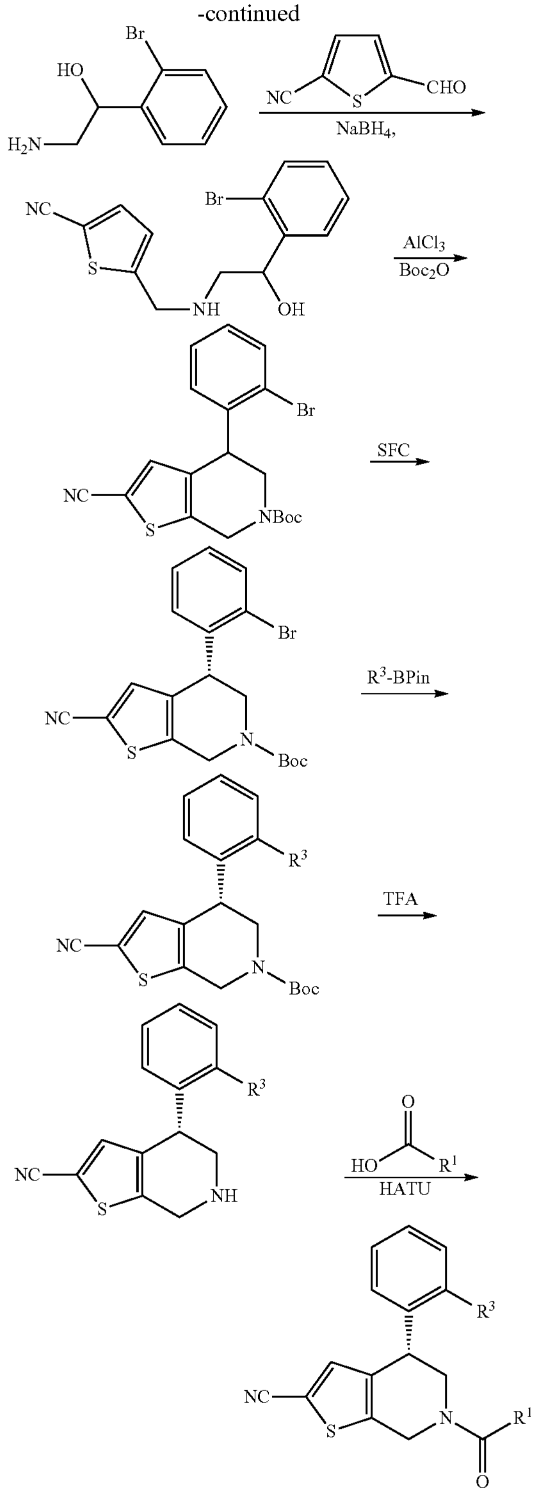

The 6-cyano compounds of the invention can also be synthesized according to Scheme III. In step A, 2-bromobenzaldehyde is treated with TMSCN and $ZnI_2$ to yield the ((trimethylsilyl)oxy)acetonitrile. Reduction of the protected phenoxy acetonitrile, such as with LAH provide the aminoalcohol. Coupling of the aminoalcohol with of 5-formylthiophene-2-carbonitrile, such as in the presence of $NaBH_4$ provides the substituted thiphenes. Cyclization of the aminoalcohol thiophenes, such as in the presence of $AlCl_3$ and protection with $Boc_2O$ yields the protected tetrydrothienylpyridines. Purification of the mixture, such as by SFC provides the respective isomers. Coupling with PinB substituted groups provides the substituted compounds. Deprotection, such as with TFA, followed by treatment with an acid or acid chloride, provides the desired compounds of Formula I-V.

Scheme IV

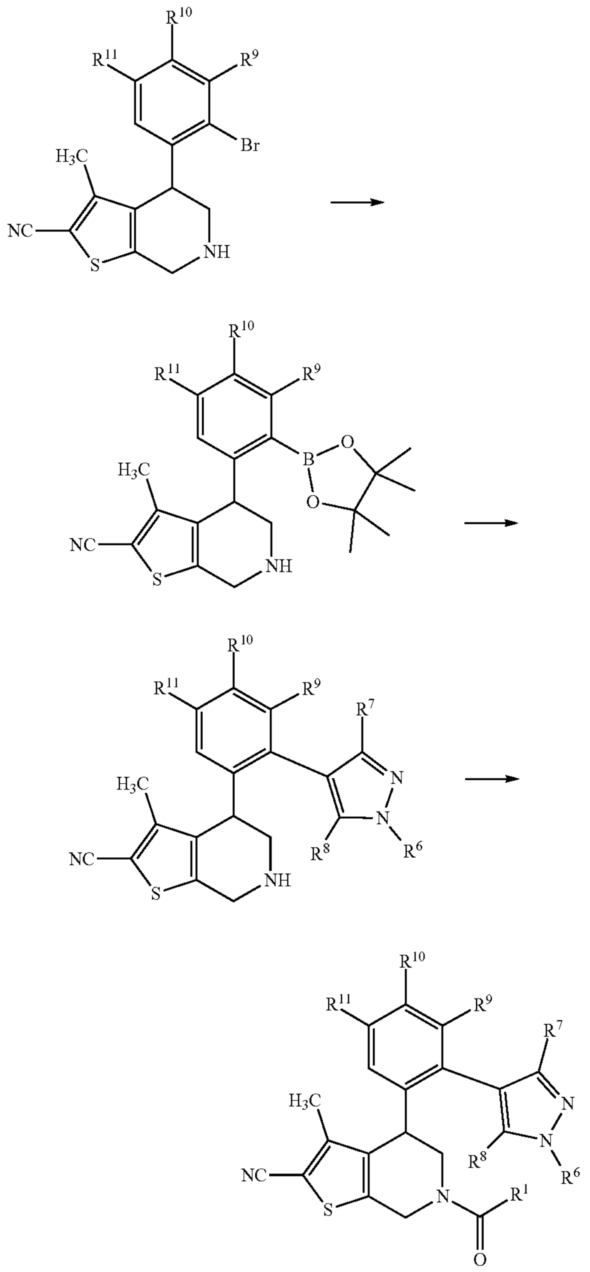

The 5-methyl compounds of the invention can also be synthesized according to Scheme IV. In step A, the bromo compound is converted to the boronic ester such as in the presence of $Pd(PPh_3)_2Cl_2$. acid chloride, to provide the desired compounds of Formula I-V.

Scheme V

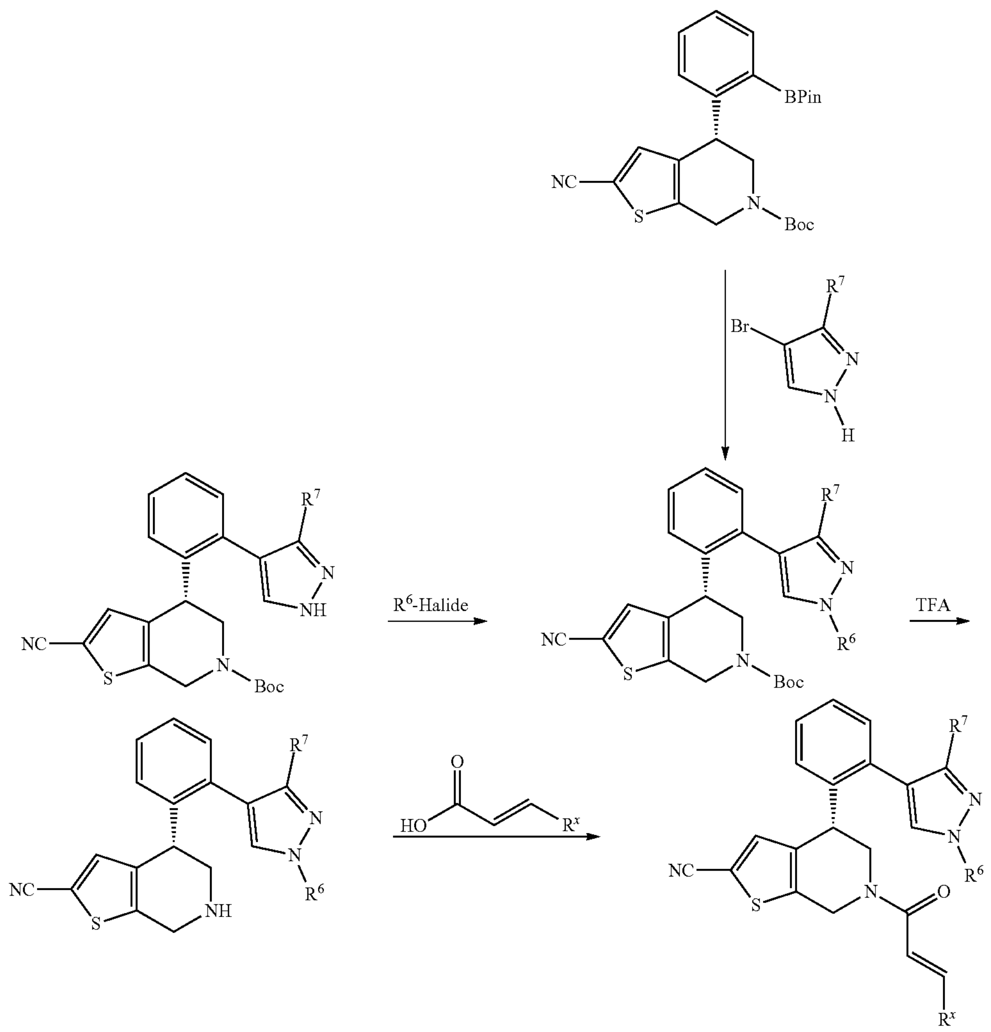

Additional compounds synthesized via general scheme V. In step A, boronic intermediates are coupled with hetoaryl rings such as substituted pyrazoles. The pyrazoles can be further modifies, such as by coupling with halides at the secondary amine. After deprotection, such as with treatment with TFA. Followed by reaction with substituted acrylic acids provides the desired compounds of Formula I-V.

The following examples contain detailed descriptions of the methods of preparation of compounds of the disclosure. These detailed descriptions fall within the scope, and serve to exemplify, the above described General Synthetic Procedure which form part of the invention. These detailed descriptions are presented for illustrative purposes only and are not intended as a restriction on the scope of the invention. All parts are by weight and temperatures are in Degrees centigrade unless otherwise indicated.

General Methods $^1$HNMR experiments were run on Bruker Avance III 400, at 25° C.

Preparative Methods:

CP Preparative Pre-HPLC

Method A: Mobile Phase: A: Water (10 mM $NH_4HCO_3$) B: ACN

Gradient: 25%-55% B within 9 min, stop at 17 min

Flow Rate: 30 ml/min

Column: Xtimate Prep C18 10 μm 21.2×250 mm

Column Temperature: 40C

Detection: UV (214 nm, 254 nm)

Method B: Mobile Phase: A: Water (0.2% FA) B: ACN

Gradient: 25%-55% B within 9 min, stop at 17 min

Flow Rate: 30 ml/min

Column: Boston Prep C18 10 μm 21.2×250 mm

Column Temperature: 40° C.

Detection: UV (214 nm, 254 nm)

Method C: Mobile Phase: A: Water (0.1% TFA) B: ACN

Gradient: 25%-55% B within 9 min, stop at 17 min

Flow Rate: 30 ml/min

Column: Boston Prep C18 10 μm 21.2×250 mm

Column Temperature: 40° C.

Detection: UV (214 nm, 254 nm)

LCMS Experiments:

All CP LCMS experiments were run on Agilent 1200, with a column temperature of 40° C., monitoring UV absorption at 214 nm and scanning a mass range from 100-1000. Individual conditions vary slightly as described in the methods below:

LCMS CP Method A (014): Column: Xbridge SB—C18 4.6*50 MM, 3.5 um; Mobile Phase: A: Water (0.1% TFA), B: ACN (0.1% TFA); Gradient: 5% B increase to 95% B over 1.8 min, stop at 3 min. Flow Rate: 1.8 mL/min LCMS CP Method B (026): Column: XBridge C18, 4.6*50 mm, 3.5 um; Mobile Phase: A: Water (0.05% TFA), B: ACN (0.05% TFA); Gradient: 5% B increase to 95% B over 1.7 min, stop at 3 min. Flow Rate: 2.0 mL/min LCMS CP Method C (025): Column: XBridge C18 50*4.6 mm, 3.5 um; Mobile Phase: A: $H_2O$ ($10mMNH_4HCO_3$), B: MeCN; Gradient: 5%-95% B in 1.3 min, 95% B for 2.95 min, back to 5% B within 0.05 min; Flow Rate: 2.0 mL/min LCMS CP Method D (028): Column: X-Bridge C18, 4.6*50 mm, 3.5 um; Mobile phase: A 10 mM $NH_4HCO_3$ in water B ACN; Gradient: 5% increase to 95% B within 1.4 min, 95% B for 1.6 min; Flow Rate: 2.0 ml/min LCMS CP Method E (008): Column: XBridge SB—C18, 4.6*50 mm, 3.5 um; Mobile Phase: A: Water ($10mNH_4HCO_3$), B: ACN; Gradient: 5% increase to 95% B within 1.4 min, 95% B for 2.9 min, back to 5% B within 0.05 min; Flow Rate: 2.0 ml/min LCMS CP Method F (051): Column: XBridge C18, 4.6*150 mm, 3.5 um; Mobile Phase: A: Water ($10mMNH_4HCO_3$) B: ACN; Gradient: 5% increase to 95% B within 9.5 min, 95% B for 5 min; Flow Rate: 1.0 ml/min LCMS CP Method G (054): Column: XBridge C18, 4.6*50 mm, 3.5 um; Mobile Phase: A: Water ($10mMNH_4HCO_3$) B: ACN; Gradient: 5% increase to 95% B within 1.4 min, 95% B for 1.7 min; Flow Rate: 2.0 ml/min Example 1

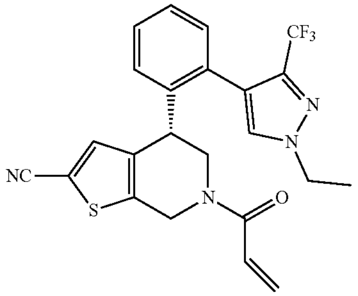 [SMILES: C=CC(=O)N1Cc2sc(C#N)cc2[C@H](c2ccccc2-c2cn(CC)nc2C(F)(F)F)C1]

(S)-6-Acryloyl-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of tert-butyl (S)-2-chloro-4-(2-(1-ethyl-3-(trifluoromethyl)-1H-pyrazol-4-yl)phenyl)-4,7-dihydrothieno[2,3-c]pyridine-6(5H)-carboxylate (200 mg, 0.391 mmol) in DMA (5 mL) at RT were added $Zn(CN)_2$ (90.8 mg, 0.783 mmol), Zn (10.2 mg, 0.156 mmol) and $Pd(dppf)Cl_2$ (28.6 mg, 0.0391 mmol). The reaction mixture was heated to 140° C. and stirred under microwave for 10 h. Once cooled to RT, water (10 mL) was added and the mixture was extracted with EA (3×10 mL). The combined organic layers were washed with water (3×10 mL), dried over anhydrous $Na_2SO_4$, filtered and concentrated in vacuum to give a residue. The residue was purified by silica gel chromatography (PE: EA=3:1) to give tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate as a yellow oil (150 mg, 76.3% yield). LCMS: $(M+23)^+$= 525.0; Retention time=2.25 min. LCMS CP Method A.

Step 2: To a solution of tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (Step 1, 150 mg, 0.307 mmol) in 1,4-dioxane (0.5 mL) was added HCl/dioxane (4M, 2 mL) at RT. The mixture was stirred at RT for 20 min. The pH value of the reaction mixture was adjusted to 9 with $NaHCO_3$ and the mixture was extracted with DCM (3×10 mL). The combined organic layers were dried over $Na_2SO_4$, filtered and concentrated under reduced pressure to give crude (S)-4-(2-(1-ethyl-3-(trifluoromethyl)-1H-pyrazol-4-yl)phenyl)-4,5,6,7-tetrahydrothieno[2,3-c]pyridine-2-carbonitrile (110 mg, 91.5% yield) as a yellow oil. LCMS: (M+1)+=402.9; Retention time=1.45 min. LCMS CP Method C.

Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (Step 2, 110 mg, 0.274 mmol) in 1,4-dioxane (2 mL) was added NaOH (10 M, 1 mL) at RT. The mixture was cooled to 0° C. with ice-water bath and acryloyl chloride (36.9 mg, 0.41 mmol) was added. The mixture was stirred at RT for 20 min. The reaction mixture was diluted with water (20 mL) and extracted with DCM (3×10 mL). The combined organic layers were dried over anhydrous $Na_2SO_4$, filtered and concentrated under reduced pressure to give a residue which was purified by Prep-HPLC (Method A). (S)-6-Acryloyl-4-(2-(1-ethyl-3-(trifluoromethyl)-1H-pyrazol-4-yl)phenyl)-4,5,6,7-tetrahydrothieno[2,3-c]pyridine-2-carbonitrile (50.0 mg, 40.0% yield) was isolated as a white solid. $^1$H NMR (400 MHz, DMSO) δ 8.30 (s, 1H), 7.34-7.22 (m, 4H), 6.81-6.79 (m, 1H), 6.23-6.16 (m, 1H), 5.94-5.90 (m, 1H), 5.52-5.49 (m, 1H), 4.94 (m, 1H), 4.29-4.24 (m, 2H), 4.07 (m, 1H), 3.91-3.87 (m, 1H), 3.59-3.53 (m, 1H), 1.46 (t, J=7.2 Hz, 3H) LCMS: $(M+H)^+$=456.9, purity=100% (254 nm); Retention time=1.63 min. LCMS CP Method D.

Example 2

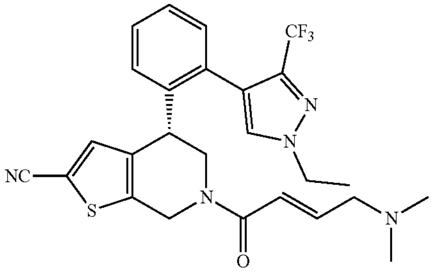 [SMILES: CCn1cc(-c2ccccc2[C@@H]2CN(C(=O)/C=C/CN(C)C)Cc3sc(C#N)cc32)c(C(F)(F)F)n1]

(S,E)-6-(4-(Dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of 2-bromobenzaldehyde (184 g, 1.0 mol) in anhydrous THF (500 mL) were added TMSCN (198 g, 2.0 mol) and $ZnI_2$ (63.8 g, 0.2 mol) under ice-salt bath. The reaction was stirred at RT overnight, then filtered. The filtrate was diluted with EA (2×500 mL) and washed with saturated $NH_4Cl$ (2×500 mL) followed by brine (2×500 mL). The organic phase was dried over $Na_2SO_4$, filtered and concentrated to give crude 2-(2-bromophenyl)-2-((trimethylsilyl)oxy)acetonitrile (283 g, 100%) as a yellow oil (PE: EA=10:1, Rf=0.7) which was used directly in the next step without further purification.

Step 2: To a suspension of 2-(2-bromophenyl)-2-((trimethylsilyl)oxy)acetonitrile (Step 1, 283 g, 1.0 mol) in THF (1000 mL) was added LAH (1M, 1200 mL) under ice-salt bath. The reaction was stirred at RT overnight and quenched with $Na_2SO_4 \cdot 10H_2O$. Filtered and concentrated to give a residue which was purified by column chromatography (silica gel, DCM:MeOH=10:1, Rf=0.4) to give 2-amino-1-(2-bromophenyl)ethan-1-ol (120 g 55%) as a yellow solid.

Step 3: To a stirred mixture of 5-formylthiophene-2-carbonitrile (8 g, 58.4 mol) in MeOH (200 mL) was added 2-amino-1-(2-bromophenyl)ethan-1-ol (Step 2, 13.18 g, 61.32 mol) and the suspension was stirred at RT overnight. The resulting thick slurry was cooled to 0° C. and $NaBH_4$ (4.44 g, 116.8 mol) was added in portions over 0.5 h. Then the cooling bath was removed and the mixture was stirred at RT for 3 h. The reaction was quenched with a mixed solution of cold water and saturated $NaHCO_3$ (aq) (1:1, ~300 mL total). The resulting solid was collected, washed with water and dried under reduced pressure to give 5-(((2-(2-bromophenyl)-2-hydroxyethyl)amino)methyl)thiophene-2-carbonitrile (16.9 g, 86% yield) as an off-white solid which was used directly in the next step reaction without further purification. LCMS: (M+H)+=337.1; Retention time=1.353 min. LCMS OP Method B.

Step 4: To a suspension of 5-(((2-(2-bromophenyl)-2-hydroxyethyl)amino)methyl)thiophene-2-carbonitrile (Step 3, 16.9 g, 50.3 mmol) in DCM (500 mL) was added solid $AlCl_3$ (20.07 g, 150.9 mmol) and the mixture was stirred at RT for 1 h, then more $AlCl_3$ (13.38 g, 100.6 mmol) was added and the resulting reaction was stirred at RT overnight. The mixture was diluted with DCM (200 mL) and quenched with water-ice mixture (~500 mL). The resulting mixture was neutralized with 10N NaOH (aq., to pH~10) and the resulting mixture was vigorously stirred at RT for 30 min. The separated aqueous layer was extracted with DCM (300 mL×3). The combined organic layers were washed with brine, dried over $Na_2SO_4$, filtered and concentrated. The residue was redissolved in DCM (200 mL) and $Boc_2O$ (22.0 g, 100.6 mmol) was added. The reaction mixture was stirred at RT overnight. Water (200 ml) was added and the aqueous layer was extracted with DCM (3×100 mL). The combined organic layers were washed with brine, dried over $Na_2SO_4$, filtered and concentrated. The residue was triturated in mixed solution of MeOH and PE, The resulting solid was collected, washed with PE and dried under reduced pressure to provide tert-butyl 4-(2-bromophenyl)-2-cyano-4,7-dihydrothieno[2,3-c]pyridine-6(5H)-carboxylate (15.0 g, 71% overall yield for two steps) as a white solid. LCMS: $(M-56+H)^+$=363.0; Retention time=1.976 min. LCMS CP Method B Step 5: The enantiomers were separated from 12.4 g of racemate [in 330 mL MeOH] by chiral SFC [SFC-150 (Thar, Waters), column—IG 20*250 mm, 10 um (Daicel), 35° C., mobile phase—$CO_2$/MeOH[0.2% $NH_3$ (7M in MeOH)]=65/35, flow rate 110 mL/min, back pressure—100 bar, detection 214 nm] to give peak 1 (tert-butyl (S)-4-(2-bromophenyl)-2-cyano-4,7-dihydrothieno[2,3-c]pyridine-6(5H)-carboxylate, 5.6 g, retention time=1.132 min) and peak 2 (tert-butyl (R)-4-(2-bromophenyl)-2-cyano-4,7-dihydrothieno[2,3-c]pyridine-6(5H)-carboxylate, 5.6 g, retention time=1.845 min) both as white solids.

Step 6: A mixture of tert-butyl (R)-4-(2-bromophenyl)-2-cyano-4,7-dihydrothieno[2,3-c]pyridine-6(5H)-carboxylate (step 5, 5.0 g, 11.96 mmol), 1-ethyl-4-(4,4,5,5-tetramethyl-1,3,2-dioxaborolan-2-yl)-3-(trifluoromethyl)-1H-pyrazole (3.82 g, 13.16 mmol), $K_3PO_4$ (5.07 g, 23.92 mmol), Pd(dppf)$C_{1-2}$ (875 mg, 1.196 mml), dioxane (45 ml) and $H_2O$ (9 ml) was heated to 100° C. and stirred under microwave for 2 h. The reaction mixture was cooled to RT and water (100 ml) was added. The resulting mixture was extracted with DCM (3×100 mL) and the combined organic phases were washed with brine, dried over $Na_2SO_4$ and concentrated. The residue was purified by chromatography ($SiO_2$, PE: EA=10:1-5:1) to afford tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (4.86 g, 81% yield) as a yellow solid. LCMS: $(M-56+H)^+$=447.0; Retention time=1.809 min. LCMS CP Method B Step 7: To a solution of tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (Step 6, 4.86 g, 9.7 mmol) in DCM (60 ml) was added TFA (6 ml) and the reaction was stirred at RT for 2 h. The mixture was concentrated and the residue was neutralized to pH=8-9 with a saturated solution of $NaHCO_3$. The mixture was extracted with DCM (3×80 ml) and the combined organic phases were washed with brine, dried over $Na_2SO_4$ and concentrated to afford crude (S)-4-(2-(1-ethyl-3-(trifluoromethyl)-1H-pyrazol-4-yl)phenyl)-4,5,6,7-tetrahydrothieno[2,3-c]pyridine-2-carbonitrile (3.9 g, 100% yield) which was used in the next step without further purification. LCMS: (M+H)+=403.2; Retention time=1.532 min. LCMS CP Method A Step 8: A mixture of (S)-4-(2-(1-ethyl-3-(trifluoromethyl)-1H-pyrazol-4-yl)phenyl)-4,5,6,7-tetrahydrothieno[2,3-c]pyridine-2-carbonitrile (Step 7, 3.9 g, 9.7 mmol), (E)-4-(dimethylamino)but-2-enoic acid hydrogen chloride (2.42 g, 14.55 mmol), HATU (5.53 g, 14.55 mmol), DIPEA (3.75 g, 29.1 mmol) and DCM (150 ml) was stirred at RT overnight. Water (100 ml) was added and the separated organic phase was washed with brine, dried over $Na_2SO_4$ and concentrated. The residue was purified by column chromatography (5% MeOH in DCM with 7M $NH_3$) and Prep-HPLC (Method A) to afford (S,E)-6-(4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (3.1 g, 60.2%) as a pale-yellow solid. $^1H$ NMR (400 MHz, DMSO) δ 8.29 (s, 1H), 7.41-7.22 (m, 4H), 6.97-6.75 (m, 1H), 6.62-6.44 (m, 1H), 5.88 (d, J=15.2 Hz, 1H), 5.15-4.79 (m, 2H), 4.30-4.16 (m, 3H), 3.96-3.77 (m, 1H), 3.62-3.57 (m, 1H), 3.02-2.76 (m, 2H), 2.13-1.94 (m, 6H), 1.45 (t, J=7.2 Hz, 3H). LCMS: (M+H)+=514.2, purity=100% (214 nm); Retention time=1.939 min. LCMS CP Method C.

Example 3

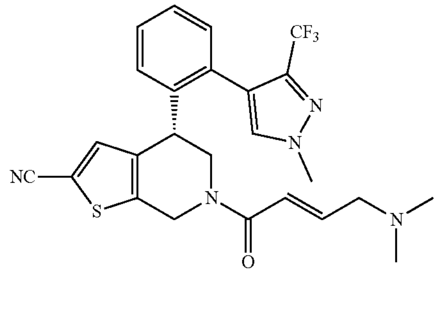 [SMILES: CN(C)C/C=C/C(=O)N1Cc2sc(C#N)cc2[C@H](c2ccccc2-c2cn(C)nc2C(F)(F)F)C1]

(S,E)-6-(4-(Dimethylamino)but-2-enoyl)-4-(2-(1-methyl-3-(trifluoromethyl)-1H-pyrazol-4-yl)phenyl)-4,5,6,7-tetrahydrothieno[2,3-c]pyridine-2-carbonitrile Step 1: To a suspension of 4-bromo-3-(trifluoromethyl)-1H-pyrazole (2.14 g, 0.01 mol) and $K_2CO_3$ (2.76 g, 0.02 mol) in DMF (40 mL) was added MeI (2.1 g, 0.015 mol). The reaction was stirred at RT overnight. The mixture was diluted with EA (60 mL) and washed with water (2×40 mL) followed by brine (40 mL). The organic phase was dried over $Na_2SO_4$, filtered and concentrated to give crude 4-bromo-1-methyl-3-(trifluoromethyl)-1H-pyrazole (2.4 g, 100%) as a brown oil which was used in the next step reaction without further purification. LCMS: $(M+H)^+$ =230.9; Retention time=1.78 min. LCMS CP Method A.

Step 2: A mixture of 4-bromo-1-methyl-3-(trifluoromethyl)-1H-pyrazole (Step 1, 258 mg, 1.1 mmol), (S)-tert butyl 2-chloro-4-(2-(4,4,5,5-tetramethyl-1,3,2-dioxaborolan-2-yl)phenyl)-4,5-dihydrothieno[2,3-c]pyridine-6(7H)-carboxylate (475 mg, 1 mmol), $K_3PO_4$ (530 mg, 2.5 mmol), Pd(dppf)$Cl_2$ (80 mg, 0.1 mml), dioxane (4 mL) and $H_2O$ (1 mL) was heated to 100° C. under microwave for 2 h. The mixture was filtered and the filtrate was concentrated in vacuo to give a residue which was purified by Prep-HPLC (Method A) to give Pert-butyl (S)-2-chloro-4-(2-(1-methyl-3-(trifluoromethyl)-1H-pyrazol-4-yl)phenyl)-4,7-dihydrothieno[2,3-c]pyridine-6(5H)-carboxylate (320 mg, 64% yield) as a brown solid. LCMS: $(M-56+H)^+$=441.9, Retention time=2.389 min. LCMS CP Method A Step 3: A mixture of tert-butyl (S)-2-chloro-4-(2-(1-methyl-3-(trifluoromethyl)-1H-pyrazol-4-yl)phenyl)-4,7-dihydrothieno[2,3-c]pyridine-6(5H)-carboxylate (Step 2, 500 mg, 1 mmol), Zn (26 mg, 0.4 mmol), $Zn(CN)_2$ (234 mg, 2 mmol), Pd(dppf)$Cl_2$ (73 mg, 0.1 mml) and DMA (8 ml) was heated to 140° C. under microwave overnight. The mixture was filtered and the filtrate was concentrated in vacuum to give a residue which was purified by Prep-HPLC (Method A) to give tert-butyl (S)-2-cyano-4-(2-(1-methyl-3-(trifluoromethyl)-1H-pyrazol-4-yl)phenyl)-4,7-dihydrothieno[2,3-c]pyridine-6(5H)-carboxylate (365 mg, 75% yield) as a brown solid. LCMS: (M−56+H)+=433.1, Retention time=1.94 min. LCMS CP Method B Step 4: To a solution of tert-butyl (S)-2-cyano-4-(2-(1-methyl-3-(trifluoromethyl)-1H-pyrazol-4-yl)phenyl)-4,7-dihydrothieno[2,3-c]pyridine-6(5H)-carboxylate (488 mg, 1 mmol) in DCM (5 mL) at RT was added TFA (1 mL) and the mixture was stirred for 1 h. The mixture was concentrated and water (10 mL) was added to the residue. The mixture was extracted with DCM (3×20 mL) and the combined organic layers were neutralized with saturated $NaHCO_3$ to pH=8-9, and dried over anhydrous $Na_2SO_4$, filtered and concentrated in vacuum to give (S)-4-(2-(1-methyl-3-(trifluoromethyl)-1H-pyrazol-4-yl)phenyl)-4,5,6,7-tetrahydrothieno[2,3-c]pyridine-2-carbonitrile as a yellow solid (320 mg, 82% yield) which was used in the next step reaction without further purification. LCMS: $(M+1, M+23)^+$= 388.9, 410.9; Retention time=1.44 min. LCMS CP Method A Step 5: To a solution of (S)-4-(2-(1-methyl-3-(trifluoromethyl)-1H-pyrazol-4-yl)phenyl)-4,5,6,7-tetrahydrothieno[2,3-c]pyridine-2-carbonitrile (step 4, 194 mg, 0.5 mmol) in DMF (6 mL) were added (E)-4-(dimethylamino)but-2-enoic acid hydrochloride (91 mg, 0.55 mmol), HATU (285 mg, 0.75 mmol), and DIEA (200 mg, 1.5 mmol) at RT. The mixture was stirred at RT overnight. The reaction was quenched by adding water (10 mL) and the mixture was extracted with EA (3×20 mL). The combined organic layers were washed with brine (20 mL), dried over $Na_2SO_4$, filtered and concentrated to give a residue which was purified by Prep-HPLC (Method A) to give (S,E)-6-(4-(dimethylamino)but-2-enoyl)-4-(2-(1-methyl-3-(trifluoromethyl)-1H-pyrazol-4-yl)phenyl)-4,5,6,7-tetrahydrothieno[2,3-c]pyridine-2-carbonitrile (105 mg, 42% yield, free base) as a brown solid. $^1$H NMR (400 MHz, DMSO-$d_6$) δ 8.23 (s, 1H), 7.40-7.23 (m, 4H), 6.95-6.75 (m, 1H), 6.62-6.42 (m, 1H), 5.89-4.78 (m, 3H), 4.16 (s, 1H), 3.98 (s, 3H), 3.98-3.57 (m, 2H), 3.05-2.81 (m, 2H), 2.16-2.03 (m, 6H). LCMS: (M+1, M+23)+=500.0, 522.0, Retention time=1.69 min. LCMS CP Method C.

Example 4

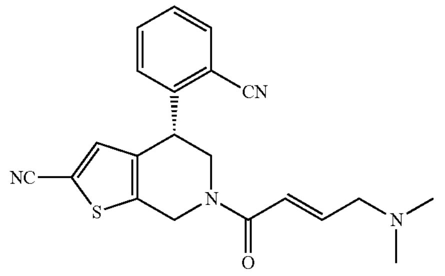 [SMILES: CN(C)C/C=C/C(=O)N1Cc2sc(C#N)cc2[C@H](c2ccccc2C#N)C1]

(S,E)-4-(2-Cyanophenyl)-6-(4-(dimethylamino)but-2-enoyl)-4,5,6,7-tetrahydrothieno[2,3-c]pyridine-2-carbonitrile Step 1: A mixture of tert-butyl (R)-4-(2-bromophenyl)-2-chloro-4,7-dihydrothieno[2,3-c]pyridine-6(5H)-carboxylate (150 mg, 0.35 mmol), $Zn(CN)_2$ (82 mg, 0.70 mmol), Zn (10 mg, 0.14 mmol), Pd(dppf)$C_{1-2}$ (128 mg, 0.18 mml) and DMA (8 ml) was heated to 140° C. under microwave overnight. The mixture was filtered and concentrated under reduced pressure to give a residue which was purified by Prep-HPLC (Method B) to give tert-butyl (S)-2-cyano-4-(2-cyanophenyl)-4,7-dihydrothieno[2,3-c]pyridine-6(5H)-carboxylate (40 mg, 31% yield) as a yellow solid. LCMS: $(M\text{-}Boc+H)^+$=266.0; Retention time=2.03 min. LCMS CP Method A Step 2: To a solution of tert-butyl (S)-2-cyano-4-(2-cyanophenyl)-4,7-dihydrothieno[2,3-c]pyridine-6(5H)-carboxylate (step 1, 40 mg, 0.11 mmol) in dioxane (1 mL) was added at RT HCl/dioxane (4M, 5 mL), then the mixture was stirred at RT for 20 min. The mixture was diluted with DCM (10 mL) and washed with $NaHCO_3$ (20 mL). The organic layer was dried over anhydrous $Na_2SO_4$, filtered and concentrated under reduced pressure to give crude (S)-4-(2-cyanophenyl)-4,5,6,7-tetrahydrothieno[2,3-c]pyridine-2-carbonitrile (50 mg) as a yellow oil which was used in the next step reaction without further purification. LCMS: $(M+H)^+$=266.0; Retention time=1.17 min. LCMS CP Method A Step 3: To a solution of (S)-4-(2-cyanophenyl)-4,5,6,7-tetrahydrothieno[2,3-c]pyridine-2-carbonitrile(50 mg, crude, ca. 0.19 mmol) in DMF (3 mL) were added (E)-4-(dimethylamino)but-2-enoic acid hydrochloride (35 mg, 0.21 mmol), HATU (110 mg, 029 mmol), and DIEA (74 mg, 0.57 mmol) at RT. The mixture was stirred at RT overnight and then concentrated. The residue was purified by Prep-HPLC (Method A) to give (S,E)-4-(2-cyanophenyl)-6-(4-(dimethylamino)but-2-enoyl)-4,5,6,7-tetrahydrothieno[2,3-c]pyridine-2-carbonitrile (19 mg, 0.05 mmol, 27% yield) as a white solid. 1H NMR (400 MHz, DMSO) δ 7.90 (d, J=7.6 Hz, 1H), 7.70-7.50 (m, 2H), 7.46 (t, J=7.6 Hz, 1H), 7.05-6.75 (m, 1H), 6.62-6.22 (m, 1H), 6.04 (d, J=15.3 Hz, 1H), 5.35-5.10 (m, 1H), 4.77-4.43 (m, 2H), 4.03 (dd, J=36.5, 12.1

Hz, 2H), 3.07-2.60 (m, 3H), 2.07 (d, J=52.4 Hz, 6H). LCMS: $(M+H)^+$=376.9, purity=100% (254 nm); Retention time=1.369 min. LCMS CP Method D Example 5

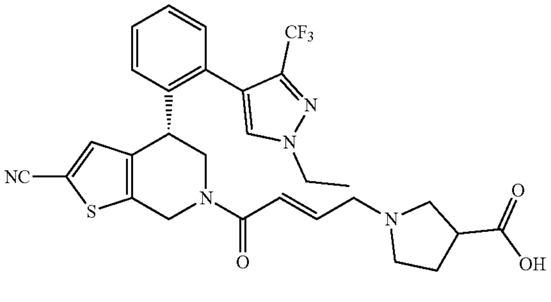 [SMILES: CCn1cc(-c2ccccc2[C@@H]2CN(C(=O)/C=C/CN3CCC(C(=O)O)C3)Cc3sc(C#N)cc32)c(C(F)(F)F)n1]

1-((E)-4-((S)-2-Cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)pyrrolidine-3-carboxylic acid Step 1: To a solution of methyl (E)-4-bromobut-2-enoate (0.171 g, 0.965 mmol) in DMF (3 mL) were added $K_2CO_3$ (0.363 g, 2.63 mmol) and tert-butyl pyrrolidine-3-carboxylate (0.150 g, 0.877 mmol) at RT. The reaction was heated to 50° C. and stirred for 2 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (PE: EA=3:1) to give tert-butyl (E)-1-(4-methoxy-4-oxobut-2-en-1-yl)pyrrolidine-3-carboxylate (0.120 g, 50.8% yield) as a yellow oil. LCMS: $(M+H)^+$=270.1, Retention time=1.17 min. LCMS CP method A Step 2: To a solution of tert-butyl (E)-1-(4-methoxy-4-oxobut-2-en-1-yl)pyrrolidine-3-carboxylate (step 1, 0.120 g, 0.408 mmol) in a mixed solvent THF:$H_2O$ (3:1, 3 mL) was added LiOH*$H_2O$ (0.0515 g, 1.22 mmol) at RT and the reaction was stirred for 3 h. The mixture was acidified with aqueous HCl (1 M) to pH=5-6 and the mixture was concentrated in vacuum to give a crude (E)-4-(3-(tert-butoxycarbonyl)pyrrolidin-1-yl)but-2-enoic acid (0.320 g, >99% yield) as a yellow oil. LCMS: $(M+H)^+$=256.1, Retention time=1.28 min. LCMS CP method G.

Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (0.100 g, 0.248 mmol) in DMF (5 mL) were added (E)-4-(3-(tert-butoxycarbonyl)pyrrolidin-1-yl)but-2-enoic acid (step 2, 0.0697 g, 0.273 mmol), HATU (0.142 g, 0.373 mmol) and DIEA (0.0963 g, 0.746 mmol) at RT. The reaction was stirred for 1 h. The mixture was diluted with water (20 mL) and extracted with EA (3×10 mL). The combined organic layers were dried over anhydrous $Na_2SO_4$, filtered and concentrated in vacuum give a residue which was purified by silica gel chromatography (PE:EA=3:1) to give tert-butyl 1-((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl) pyrrolidine-3-carboxylate (0.0800 g, 50.3% yield) as a yellow oil. LCMS: $(M+H)^+$=468.1, purity=100% (214 nm), Retention time=1.86 min. LCMS CP method G.

Step 4: To a solution of tert-butyl1-((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)pyrrolidine-3-carboxylate (Step 3, 0.0800 g, 0.125 mmol) in DCM (2 mL) was added TFA (2 mL) at RT. The mixture was stirred at RT for 2 h. The mixture was concentrated in vacuum to give a residue which was purified by Prep-HPLC (Method B) to give 1-((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl) pyrrolidine-3-carboxylic acid (0.0129 g, 17.6% yield) as a white solid. $^1H$ NMR (400 MHz, DMSO): δ 8.28 (s, 1H), 7.37-7.25 (m, 4H), 6.51 (s, 1H), 6.51-6.47 (m, 1H), 5.13-5.06 (m, 1H), 5.13-4.80 (m, 2H), 4.31- 4.26 (m, 2H), 4.14 (s, 1H), 3.82-3.79 (m, 1H), 3.64-3.59 (m, 2H), 3.14-3.01 (m, 4H), 2.51-2.31 (m, 2H), 2.03- 1.93 (m, 2H), 1.47 (t, J=7.2 Hz, 3H). LCMS: $(M+H)^+$=583.9, purity=100% (214 nm), Retention time=1.26 min. LCMS CP method D.

Example 6

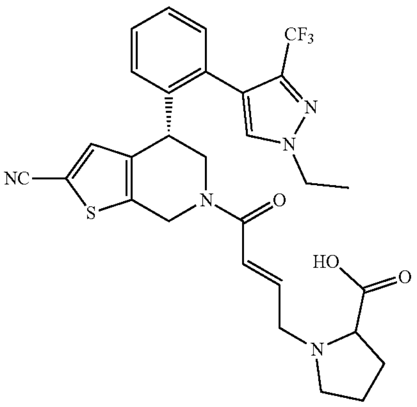 [SMILES: CCn1cc(-c2ccccc2[C@@H]2CN(C(=O)/C=C/CN3CCCC3C(=O)O)Cc3sc(C#N)cc32)c(C(F)(F)F)n1]

Step 1: To a solution of methyl (E)-4-bromobut-2-enoate (0.312 g, 0.643 mmol) in N,N-DMF (3 mL) were added $K_2CO_3$ (0.242 g, 1.75 mmol) and (rac)-tert-butyl prolinate (0.100 g, 0.584 mmol) at RT. The reaction was heated to 50° C. and stirred for 2 h. The mixture was diluted with water (20 mL) and extracted with EA (3×20 mL). The combined organic layers were washed with brine (50 mL), dried over anhydrous $Na_2SO_4$, filtered and concentrated and the residue was purified by silica gel chromatography (PE: EA=10:1) to give tert-butyl (E)-1-(4-methoxy-4-oxobut-2-en-1-yl)pyrrolidine-3-carboxylate (0.110 g, 0.408 mmol, 69% yield) as a yellow oil. LCMS: (M+H)+=270.0, Retention time=1.76 min. LCMS CP method G.

Step 2: To a solution of tert-butyl (E)-(4-methoxy-4-oxobut-2-en-1-yl)prolinate (step 1, 0.110 g, 0.408 mmol) in a mixed solvent THF: $H_2O$ (3:1, 3 mL) was added LiOH·$H_2O$ (0.0515 g, 1.22 mmol) at RT and the reaction was stirred at the same temperature overnight. The mixture was acidified with aqueous HCl (1 M) to pH=5-6 and the mixture was concentrated in vacuum to give crude (E)-4-(2-(tert-butoxycarbonyl)pyrrolidin-1-yl)but-2-enoic acid (0.0800 g, 0.313 mmol, 76% yield) as a yellow oil. LCMS: $(M+H)^+$=256.0, Retention time=1.23 min. LCMS CP method G Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (0.0400 g, 0.0995 mmol) in DMF (5 mL) were added (E)-4-(2-(tert-butoxycarbonyl) pyrrolidin-1-yl)but-2-enoic acid (Step 2, 0.0279 g, 0.109 mmol), HATU (0.0567 g, 0.149 mmol) and DIEA (0.0385 g, 0.0298 mmol) at RT. The reaction was stirred for 1 h. The mixture was diluted with water (20 mL) and extracted with EA (3×10 mL). The combined organic layers were dried over anhydrous $Na_2SO_4$, filtered and concentrated in vacuum to give a residue which was purified by silica gel chromatography (PE: EA=3:1) to give tert-butyl ((E)-4-((S)-2-cyano-4-(2-(1-ethyl-3-(trifluoromethyl)-1H-pyrazol-4-yl) phenyl)-4,7-dihydrothieno[2,3-c]pyridin-6(5H)-yl)-4-oxobut-2-en-1-yl)prolinate (0.0560 g, 0.0876 mmol, 88.1% yield) as a yellow oil. LCMS: $(M+H)^+$=270.0, purity=100% (214 nm), Retention time=1.76 min. LCMS CP method G.

Step 4: To a solution of tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)prolinate (step 3, 0.0560 g, 0.0876 mmol) in DCM (2 mL) was added TFA (2 mL) at RT. The mixture was stirred at RT for 2 h. The mixture was concentrated in vacuum to give a residue which was purified by Prep-HPLC (Method B) to give ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)proline (FA salt, 29.3 mg, 53.2% yield) as a white solid. LCMS: $(M+H)^+$=584.2, purity=100% (214 nm), Retention time=1.54 min. LCMS CP method B. $^1$H NMR (400 MHz, DMSO): δ 8.33-8.14 (m, 1H), 7.33-7.23 (m, 4H), 6.77-6.50 (m, 2H), 6.03-5.99 (m, 1H), 5.11-5.03 (m, 1H), 4.85-4.81 (m, 1H), 4.31-4.27 (m, 2H), 4.12 (m, 1H), 3.84- 3.81 (m, 1H), 3.65-3.56 (m, 2H), 3.41-3.35 (m, 2H), 2.94-2.92 (m, 1H), 2.36-1.99 (m, 3H), 1.84-1.70 (m, 3H), 1.68-1.48 (m, 3H).

Example 7

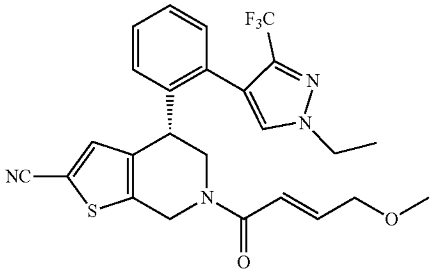 [SMILES: CCn1cc(-c2ccccc2[C@@H]2CN(C(=O)/C=C/COC)Cc3sc(C#N)cc32)c(C(F)(F)F)n1]

(S,E)-4-(2-(1-Ethyl-3-(trifluoromethyl)-1H-pyrazol-4-yl)phenyl)-6-(4-methoxybut-2-enoyl)-4,5,6,7-tetrahydrothieno[2,3-c]pyridine-2-carbonitrile To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (60 mg, 0.15 mmol), DIPEA (40 mg, 0.3 mmol) and (E)-4-methoxybut-2-enoic acid (26 mg, 0.22 mmol) in DMF (5 ml) was added HATU (85 mg, 0.22 mmol) and the reaction mixture was stirred at RT for 2 h. Water (30 ml) was added and the mixture was extracted with EA (3×20 ml). The combined organic phases were washed with brine, dried over $Na_2SO_4$, filtered and concentrated to give the residue which was purified by Prep-HPLC (Method A) to afford (S,E)-4-(2-(1-ethyl-3-(trifluoromethyl)-1H-pyrazol-4-yl)phenyl)-6-(4-methoxybut-2-enoyl)-4,5,6,7-tetrahydrothieno[2,3-c]pyridine-2-carbonitrile (25.6 mg, 34% yield, free base)) as a yellow solid. LCMS: $(M+H)^+$=501.2; Retention time=1.78 min. LCMS CP Method A $^1$H NMR (400 MHz, DMSO) δ: 8.25-8.20 (m, 1H), 7.36-7.21 (m, 4H), 6.91-6.77 (m, 1H), 6.64-6.47 (m, 1H), 6.00 (d, J=15.2 Hz, 1H), 5.15-4.85 (m, 2H), 4.27 (dd, J=14.8, 7.6 Hz, 2H), 4.20-4.05 (m, 2H), 3.88-3.80 (m, 2H), 3.60-3.45 (m, 1H), 3.29 (s, 1H), 3.18 (s, 2H), 1.45 (t, J=7.2 Hz, 3H).

Example 8

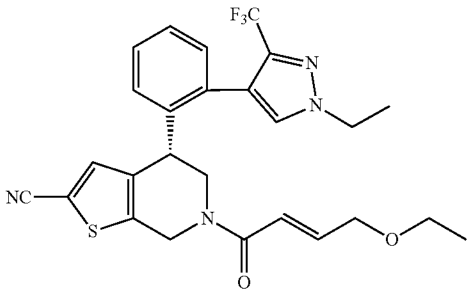 [SMILES: CCOC/C=C/C(=O)N1Cc2sc(C#N)cc2[C@H](c2ccccc2-c2cn(CC)nc2C(F)(F)F)C1]

(S,E)-6-(4-Ethoxybut-2-enoyl)-4-(2-(1-ethyl-3-(trifluoromethyl)-1H-pyrazol-4-yl)phenyl)-4,5,6,7 tetrahydrothieno[2,3-c]pyridine-2-carbonitrile Step 1: A solution of (E)-methyl 4-bromobut-2-enoate (2 g, 11.2 mmol), $Ag_2O$ (5.18 g, 22.3 mmol) in EtOH (20 ml) was stirred at 60° C. for 16 h and then cooled. The mixture was filtered and the filtrate was concentrated to give a residue which was purified by chromatography ($SiO_2$, PE: EA=5:1) to afford (E)-methyl 4-ethoxybut-2-enoate (470 mg, 29% yield) as a yellow liquid. LCMS: $(M+H)^+$=145.2; Retention time=1.41 min. LCMS CP Method B Step 2: To a mixture of (E)-methyl 4-ethoxybut-2-enoate (Step 1, 470 mg, 3.26 mmol), THE (8 ml and $H_2O$ (4 ml) was added $LiOH·H_2O$ (274 mg, 6.53 mmol) and the mixture was stirred at RT for 1.5 h. The pH was adjusted to 5-6 with HCl (1 N). The solution was concentrated in vacuum to afford (E)-4-ethoxybut-2-enoic acid (423 mg, 100% yield) as a white solid. LCMS: (M+Na)+=153.2; Retention time=1.17 min. LCMS CP Method B Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (65 mg, 0.5 mmol) and (E)-4-ethoxybut-2-enoic acid (Step 2, 65 mg, 0.5 mmol) in DMF (5 ml) was added HATU (143 mg, 0.375 mmol) and the reaction was stirred at RT for 2 h. Water (30 ml) was added and the mixture was extracted with EA (3×30 ml). The combined organic phases were washed with brine, dried over $Na_2SO_4$ filtered and concentrated to afford a residue. The residue was purified by Prep-HPLC (Method A) to afford (S,E)-6-(4-ethoxybut-2-enoyl)-4-(2-(1-ethyl-3-(trifluoromethyl)-1H-pyrazol-4-yl)phenyl)-4,5,6,7 tetrahydrothieno[2,3-c]pyridine-2-carbonitrile (26.7 mg, 21% yield) as a yellow solid. LCMS: $(M+H)^+$=515.0; Retention time=2.08 min. LCMS CP Method C $^1$H NMR (400 MHz, DMSO) δ: 8.25-8.22 (m, 1H), 7.36-7.25 (m, 4H), 6.90-6.76 (m, 1H), 6.63-6.48 (m, 1H), 5.98 (d, J=15.2 Hz, 1H), 5.07-4.80 (m, 2H), 4.27 (dd, J=14.4, 7.2 Hz, 2H), 4.11-3.91 (m, 3H), 3.80 (dd, J=14.0, 4.8 Hz, 1H), 3.64-3.61 (m, 1H), 3.48-3.46 (m, 1H), 3.36-3.35 (m, 1H), 1.45 (t, J=7.6 Hz, 3H), 1.16-1.07 (m, 3H).

Example 9

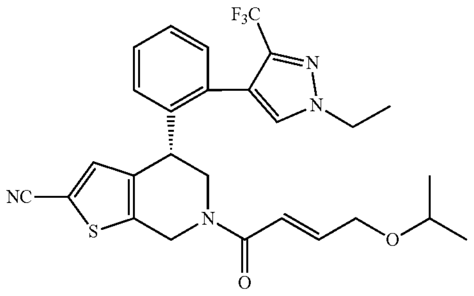 [SMILES: CCn1cc(-c2ccccc2[C@@H]2CN(C(=O)/C=C/COC(C)C)Cc3sc(C#N)cc32)c(C(F)(F)F)n1]

(S,E)-4-(2-(1-Ethyl-3-(trifluoromethyl)-1H-pyrazol-4-yl)phenyl)-6-(4-isopropoxybut-2-enoyl)-4,5,6,7-tetrahydrothieno[2,3-c]pyridine-2-carbonitrile Step 1: A solution of (E)-methyl 4-bromobut-2-enoate (2 g, 11.2 mmol), $Ag_2O$ (5.18 g, 22.3 mmol) in IPA (20 ml) was stirred at 60° C. for 16 h. After cooled to RT, the mixture was filtered and concentrated to give a residue which was purified by chromatography (PE: EA=5:1) to afford (E)-methyl 4-isopropoxybut-2-enoate (960 mg, 54% yield) as a yellow liquid. LCMS: $(M+H)^+$=159.1; Retention time=1.52 min. LCMS CP Method B Step 2: To a mixture of (E)-methyl 4-isopropoxybut-2-enoate (Step 1, 470 mg, 3.26 mmol), THE (8 ml) and $H_2O$ (4 ml) was added $LiOH{\cdot}H_2O$ (514 mg, 12.2 mmol) and the mixture was stirred at RT for 1.5 h. The pH was adjusted to 5-6 with HCl (1 N). The solution was concentrated in vacuum to afford (E)-4-isopropoxybut-2-enoic acid (900 mg, 102% yield) as a white solid. LCMS: (M+Na)+=167.2; Retention time=1.28 min. LCMS CP Method B Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (65 mg, 0.5 mmol), and (E)-4-isopropoxybut-2-enoic acid (step 2, 72 mg, 0.5 mmol) in DMF (5 ml) was added HATU (143 mg, 0.375 mmol) and the reaction was stirred at RT for 2 h. Water (30 ml) was added and the mixture was extracted with EA (3×30 ml). The combined organic phases were washed with brine, dried over $Na_2SO_4$ and concentrated to give a residue which was purified by Prep-HPLC (Method A) to afford (S,E)-4-(2-(1-ethyl-3-(trifluoromethyl)-1H-pyrazol-4-yl)phenyl)-6-(4-isopropoxybut-2-enoyl)-4,5,6,7-tetrahydrothieno[2,3-c]pyridine-2-carbonitrile (53.0 mg, 40% yield, free base) as a yellow solid. LCMS: $(M+H)^+$ =529.2; Retention time=2.16 min. LCMS CP Method A. $^1H$ NMR (400 MHz, DMSO) δ: 8.25-8.22 (m, 1H), 7.37-7.25 (m, 4H), 6.90-6.76 (m, 1H), 6.63-6.48 (m, 1H), 5.96 (d, J=16.0 Hz, 1H), 5.08-4.77 (m, 2H), 4.27 (dd, J=14.8, 7.2 Hz, 2H), 4.10-3.91 (m, 3H), 3.92-3.60 (m, 2H), 3.48-3.47 (m, 1H), 1.45 (t, J=7.6 Hz, 3H), 1.10-1.00 (m, 6H).

Example 10

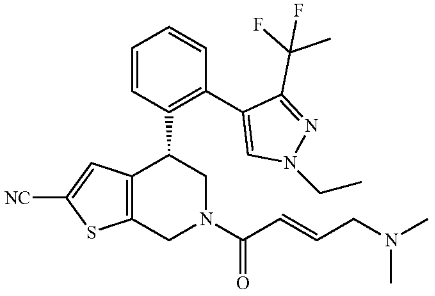 [SMILES: CCn1cc(-c2ccccc2[C@@H]2CN(C(=O)/C=C/CN(C)C)Cc3sc(C#N)cc32)c(C(C)(F)F)n1]

Step 1: A mixture of 1-(1H-pyrazol-3-yl)ethan-1-one (1.1 g, 10 mmol) in DAST (15 mL) was stirred at 4500 for 3 h. After cooled to RT, the reaction mixture was poured into ice-water and the pH was adjusted to 7-8 with a saturated solution of $NaHCO_3$. The resulting mixture was extracted with DCM (3×50 mL) and the combined organic phases were washed with brine, dried over $Na_2SO_4$ filtered and concentrated. The residue was purified by Prep-HPLC (0.2% FA) to afford 3-(1,1-difluoroethyl)-1H-pyrazole (300 mg, 22.7% yield) as a colorless oil. LCMS: $(M+H)^+$=133.1, Retention time=1.268 min. LCMS CP method B Step 2: To a mixture of 3-(1,1-difluoroethyl)-1H-pyrazole (step 1, 300 mg, 22.7 mmol), $K_2CO_3$ (626 mg, 4.54 mmol) and DMF (15 mL) was add iodoethane (531 mg, 3.41 mg) and the mixture was stirred at RT overnight. Water (75 mL) was added and the mixture was extracted with EA (3×30 mL). The combined organic phases were washed with brine, dried over $Na_2SO_4$, filtered and concentrated. The residue was purified by Prep-HPLC (0.2% FA) to afford 3-(1,1-difluoroethyl)-1-ethyl-1H-pyrazole (180 mg, 50% yield) as a yellow oil. LCMS: $(M+H)^+$=161.2, Retention time=1.486 min. LCMS CP method B Step 3: To a solution of 3-(1,1-difluoroethyl)-1-ethyl-1H-pyrazole (step 2, 180 mg, 1.125 mmol) in $CH_3CN$ (5 mL) was added NBS (240 mg, 1.35 mmol) and the mixture was stirred at RT overnight. Water (15 mL) was added and the mixture was extracted with EA (3×15 mL). The combined organic phases were washed with brine, dried over $Na_2SO_4$, filtered and concentrated. The residue was purified by a flash chromatography (PE: EA=5:1) to afford 4-bromo-3-(1,1-difluoroethyl)-1-ethyl-1H-pyrazole (150 mg, 56% yield) as a yellow oil. $^1H$ NMR (400 MHz, $CDCl_3$) δ 7.44 (s, 1H), 4.15 (q, J=7.6 Hz, 14.8 Hz, 2H), 2.04 (t, J=18.8 Hz, 3H), 1.48 (t, J=7.2 Hz, 3H).

Step 4: A mixture of tert-butyl (S)-2-cyano-4-(2-(4,4,5,5-tetramethyl-1,3,2-dioxaborolan-2-yl)phenyl)-4,7-dihydrothieno[2,3-c]pyridine-6(5H)-carboxylate (46.6 mg, 0.1 mmol), 4-bromo-3-(1,1-difluoroethyl)-1-ethyl-1H-pyrazole (step 3, 26.2 mg, 0.11 mmol), $K_3PO_4$ (42 mg, 0.2 mmol), $Pd(dppf)Cl_2$ (14.6 mg, 0.02 mmol), dioxane (2.5 ml) and $H_2O$ (0.5 ml) was stirred at 110° C. under microwave for 4 h. After cooled to RT, water (15 ml) was added and the mixture was extracted with DCM (3×15 mL). The combined organic phases were washed with brine, dried over $Na_2SO_4$, filtered and concentrated. The residue was purified by Prep-HPLC (Method B) to afford tert-butyl (S)-2-cyano-4-(2-(3-(1,1-difluoroethyl)-1-ethyl-1H-pyrazol-4-yl)phenyl)-4,7-dihydrothieno[2,3-c]pyridine-6(5H)-carboxylate (35 mg, 70% yield) as a black solid. LCMS: $(M+Na)^+$=521.2, Retention time=1.953 min. LCMS CP method B Step 5: To a solution of afford tert-butyl (S)-2-cyano-4-(2-(3-(1,1-difluoroethyl)-1-ethyl-1H-pyrazol-4-yl)phenyl)-4,7-dihydrothieno[2,3-c]pyridine-6(5H)-carboxylate (step 4, 35 mg, 0.06 mmol) in DCM (2 ml) was added TFA (0.4 ml) and the mixture was stirred at RT for 1 h. The mixture was concentrated to afford crude (S)-4-(2-(3-(1,1-difluoroethyl)-1-ethyl-1H-pyrazol-4-yl)phenyl)-4,5,6,7-tetrahydrothieno[2,3-c]pyridine-2-carbonitrile (24 mg, 100% yield) as a brown oil. LCMS: $(M+H)^+$=399.1, Retention time=1.489 min. LCMS CP method B Step 6: A mixture of (S)-4-(2-(3-(1,1-difluoroethyl)-1-ethyl-1H-pyrazol-4-yl)phenyl)-4,5,6,7-tetrahydrothieno[2,3-c]pyridine-2-carbonitrile (step 5, 24 mg, 0.06 mmol), (E)-4-(dimethylamino)but-2-enoic acid hydrogen chloride (15 mg, 0.09 mmol), HATU (34 mg, 0.09 mmol), DIPEA (23 mg, 0.18 mmol) and DCM (3 ml) was stirred at RT for 1 h. Water (5 mL) was added and the mixture was extracted with EA (3×10 mL). The combined organic layers were dried over $Na_2SO_4$, filtered and concentrated to give a residue which was purified by Prep-HPLC (Method A) to afford (S,E)-4-(2-(3-(1,1-difluoroethyl)-1-ethyl-1H-pyrazol-4-yl)phenyl)-6-(4-(dimethylamino)but-2-enoyl)-4,5,6,7-tetrahydrothieno[2,3-c]pyridine-2-carbonitrile (15 mg, 49.1% yield) as a white solid. $^1$H NMR (400 MHz, DMSO) δ 8.13-8.01 (m, 1H), 7.36-7.16 (m, 3H), 6.93-6.45 (m, 2H), 5.93 (d, J=15.6 Hz, 1H), 5.11-4.80 (m, 2H), 4.32-4.18 (m, 3H), 3.99-3.79 (m, 1H), 3.63-3.59 (m, 1H), 3.03-2.79 (m, 2H), 2.15-1.87 (m, 9H), 1.44 (t, J=7.2 Hz, 3H). LCMS: $(M+H)^+$=510.1, Retention time=1.773 min. LCMS CP method C Example 11

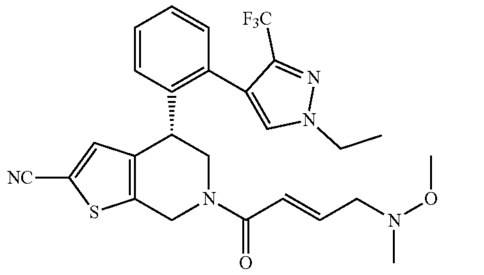 [SMILES: CCn1cc(-c2ccccc2[C@@H]2CN(C(=O)/C=C/CN(C)OC)Cc3sc(C#N)cc32)c(C(F)(F)F)n1]

(S,E)-4-(2-(1-Ethyl-3-(trifluoromethyl)-1H-pyrazol-4-yl)phenyl)-6-(4-(methoxy(methyl)amino)but-2-enoyl)-4,5,6,7-tetrahydrothieno[2,3-c]pyridine-2-carbonitrile Step 1: To a solution of methyl (E)-4-bromobut-2-enoate (1.01 g, 5.67 mmol) in DMF (3 mL) were added $K_2CO_3$ (2.134 g, 15.46 mmol) and N,O-dimethylhydroxylamine (0.500 g, 5.15 mmol) at RT. The mixture was heated to 50° C. and stirred for 2 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (PE: EA=10:1) to give methyl (E)-4-(methoxy(methyl)amino)but-2-enoate (0.200 g, 24.4% yield) as a yellow oil. LCMS: $(M+H)^+$=160.1, Retention time=1.55 min. LCMS CP method G Step 2: To a solution of methyl (E)-4-(methoxy(methyl)amino)but-2-enoate (step 1, 0.200 g, 1.26 mmol) in THE: $H_2O$ (3:1, 3 mL) was added $LiOH \cdot H_2O$ (0.158 g, 3.77 mmol) at RT and the mixture was stirred for 3 h. The mixture was acidified with aqueous HCl (1 M) to pH=5~6 and the mixture was concentrated in vacuum to give (E)-4-(methoxy(methyl)amino)but-2-enoic acid (0.110 g, 60.0% yield) as a yellow oil. LCMS: $(M+H)^+$=146.1, Retention time=0.86 min. LCMS CP method A Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (0.0500 g, 0.124 mmol) in DMF (5 mL) were added (E)-4-(methoxy(methyl)amino)but-2-enoic acid (step 2, 0.0361 g, 0.248 mmol), HATU (0.0567 g, 0.149 mmol) and DIEA (0.0385 g, 0.298 mmol) at RT. The reaction mixture was stirred for 1 h. Then the mixture was diluted with water (20 mL) and extracted with EA (3×10 mL). The combined organic layers were dried over anhydrous $Na_2SO_4$, filtered and concentrated in vacuum to give a residue which was purified by Prep-HPLC (Method A) To give (S,E)-4-(2-(1-ethyl-3-(trifluoromethyl)-1H-pyrazol-4-yl)phenyl)-6-(4-(methoxy(methyl)amino)but-2-enoyl)-4,5,6,7-tetrahydrothieno[2,3-c]pyridine-2-carbonitrile (0.0542 g, 82.4% yield) as a white solid. LCMS: $(M+H)^+$=530.0, purity=100% (214 nm), Retention time=1.62 min. LCMS CP method D $^1$H NMR (400 MHz, DMSO): δ 8.31-8.21 (m, 1H), 7.37-7.26 (m, 4H), 6.80-6.66 (m, 1H), 6.56-6.52 (m, 1H), 5.95-5.91 (m, 1H), 5.02-4.86 (m, 2H), 4.30-4.25 (m, 2H), 4.14 (m, 1H), 3.85-3.81 (m, 1H), 3.60-3.55 (m, 1H), 3.38-3.32 (m, 4H), 3.27-3.21 (m, 1H), 2.51-2.42 (m, 3H), 1.46 (t, J=7.2 Hz, 3H).

Example 12

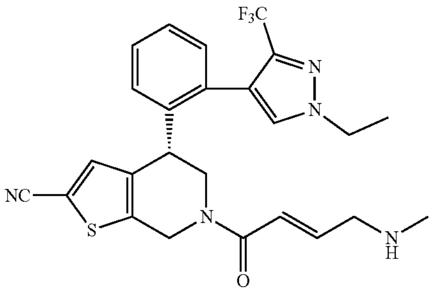 [SMILES: CCn1cc(-c2ccccc2[C@@H]2CN(C(=O)/C=C/CNC)Cc3sc(C#N)cc32)c(C(F)(F)F)n1]

(S,E)-4-(2-(1-Ethyl-3-(trifluoromethyl)-1H-pyrazol-4-yl)phenyl)-6-(4-(methylamino)but-2-enoyl)-4,5,6,7-tetrahydrothieno[2,3-c]pyridine-2-carbonitrile Step 1: To a solution of methyl (E)-4-bromobut-2-enoate (2.00 g, 11.23 mmol) in THF (20 mL) was added dropwaise $MeNH_2$ (2 M of THF, 5.62 mL) at RT and the mixture was stirred for 2 h. The mixture was concentrated to give a residue which was purified by silica gel chromatography to give methyl (E)-4-(methylamino)but-2-enoate (0.450 g, 15.4% yield) as a yellow oil. LCMS: $(M+H)^+$=130.1, Retention time=0.44 min. LCMS CP method A Step 2: To a solution of methyl (E)-4-(methylamino)but-2-enoate (0.450 g, 1 mmol) in) in DCM (5 mL) were added $E_3N$ (1.05 g, 10.46 mmol) and $Boc_2O$ (0.836 g, 3.83 mmol) at RT. The mixture was stirred for 2 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography to give tert-butyl methyl (E)-4-((tert-butoxycarbonyl)(methyl)amino)but-2-enoate (0.320 g, 40.1% yield) as a yellow oil.

Step 3: To a solution of tert-butyl methyl (E)-4-((tert-butoxycarbonyl)(methyl)amino)-but-2-enoate (step 2, 0.320 g, 1.39 mmol) in a mixed solvent of THF: $H_2O$ (3:1, 3 mL) was added LiOH*$H_2O$ (0.0515 g, 1.22 mmol) at RT and the mixture was stirred for 3 h. The mixture was acidified with aqueous HCl (1 M) to pH=5-6 and the mixture was concentrated in vacuum to give a crude (E)-4-((tert-butoxycarbonyl)(methyl)amino)but-2-enoic acid (0.450 g, crude) as a yellow oil. LCMS: $(M-Boc+H)^+$=116.1, Retention time=1.18 min. LCMS CP method G Step 4: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (0.240 g, 0.597 mmol) in DMF (5 mL) were added (E)-4-((tert-butoxycarbonyl)(methyl)amino)but-2-enoic acid (step 3, 0.256 g, 1.194 mmol), HATU (0.340 g, 0.896 mmol) and DIEA (0.231 g, 1.79 mmol) at RT. The mixture was stirred for 1 h. The mixture was diluted with water (20 mL) and extracted with EA (3×10 mL). The combined organic layers were dried over anhydrous $Na_2SO_4$, filtered and concentrated in vacuum to give a residue which was purified by silica gel chromatography (DCM: MeOH=30:1) to give tert-butyl (S,E)-(4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)(methyl)carbamate (0.190 g, 62.6% yield) as a yellow oil. LCMS: (M-Boc+H)+=500.0, Retention time=1.66 min. LCMS CP method D Step 5: To a solution of tert-butyl (S,E)-(4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)(methyl)carbamate (step 4, 0.190 g, 0.374 mmol) in DCM (2 mL) was added TFA (2 mL) at RT. The mixture was stirred at RT for 2 h. The mixture was concentrated in vacuum to give a residue which was purified by Prep-HPLC (Method C) to give (S,E)-4-(2-(1-ethyl-3-(trifluoromethyl)-1H-pyrazol-4-yl)phenyl)-6-(4-(methylamino)but-2-enoyl)-4,5,6,7-tetrahydrothieno[2,3-c]pyridine-2-carbonitrile TFA salt (29.5 mg, 12.9% yield) as a white solid. LCMS: $(M+H)^+$ =500.1, purity=100% (214 nm), Retention time=1.53 min. LCMS CP method B. $^1H$ NMR (400 MHz, DMSO): δ 8.64-8.62 (m, 1H), 8.30-78.21 (m, 1H), 7.34-7.25 (m, 4H), 6.82-6.21 (m, 3H), 5.06-4.90 (m, 2H), 4.31-4.25 (m, 2H), 4.15-3.70 (m, 4H), 3.78-3.35 (m, 2H), 2.57-2.45 (m, 3H), 1.49-1.45 (t, 3H).

Example 13

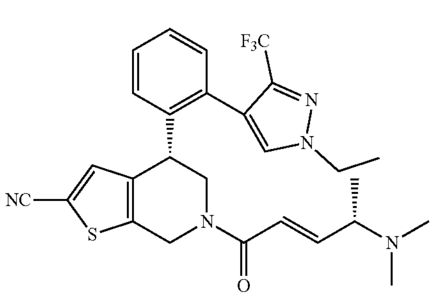 [SMILES: CCn1cc(-c2ccccc2[C@@H]2CN(C(=O)/C=C/[C@H](C)N(C)C)Cc3sc(C#N)cc32)c(C(F)(F)F)n1]

(S)-6-((S,E)-4-(dimethylamino)pent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of tert-butyl (S)-(1-hydroxypropan-2-yl)carbamate (1000 mg, 5.71 mmol) in DCM (5 mL) was added DMP (3000 mg, 6.85 mmol). The reaction mixture was stirred at the RT for 2 h. The mixture was washed with $H_2O$ (100 mL) and extracted with DCM (20 mL×3). The organic layer was concentrated to give a residue which was purified by silica gel chromatography to give tert-butyl (S)-(1-oxopropan-2-yl)carbamate (476 mg, 36.4% yield) as a white solid.

Step 2: To a solution of tert-butyl (S)-(1-oxopropan-2-yl) carbamate (step 1, 573 mg, 3.97 mmol) in MeCN (5 mL) were added methyl 2-(dimethoxyphosphoryl)acetate (663 mg, 3.84 mmol) LiCl (168 mg, 3.97 mmol) and DIPEA (513 mg, 3.97 mmol) and the mixture was stirred at RT for 2 h. The mixture was extracted with DCM (50 mL×3) and the combined organic layers were concentrated to give a residue which was purified by silica gel chromatography (PE: EA=5:1) to give methyl (S,E)-4-((tert-butoxycarbonyl) amino)pent-2-enoate (718 mg, 81.65% yield) as a transparent oil. LCMS: $(M+Na)^+$=252.1, Retention time=1.721 min. LCMS CP method A Step 3: To a solution of methyl (S,E)-4-((tert-butoxycarbonyl)amino)pent-2-enoate (step 2, 550.1 mg, 2.40 mmol) in DCM (8 mL) was added TFA (1.5 mL,Wt 99%) and the mixture was stirred at the RT for 2 h. The pH was adjusted to 6-7 with saturated $NaHCO_3$ aqueous solution and the mixture was extracted with DCM (3×20 mL). The combined organic layers were concentrated to give methyl (S,E)-4-aminopent-2-enoate (301 mg, 2.33 mmol, 98.0% yield) as a transparent oil which was used directly in the next step without further purification. LCMS: $(M+H)^+$=130.1, Retention time=1.048 min. LCMS CP method G Step 4: To a solution of methyl (S,E)-4-aminopent-2-enoate (step 3, 500 mg, 3.87 mmol) in MeOH (2 mL) were added HCHO (232.60 mg, 7.75 mmol), $NaBH_3CN$ (482 mg, 7.75 mmol) and AcOH (0.6156 mg, 0.0103 mmol). The mixture was stirred at RT for 2 h. The reaction was quenched with saturated $NaHCO_3$ aqueous solution and the mixture was extracted with EA (3×20 mL). The combined organic layers were washed with brine (50 mL), dried over anhydrous $Na_2SO_4$, filtered and concentrated to give a residue which was purified by silica gel chromatography (PE EA=10:1) to give methyl (S,E)-4-(dimethylamino)pent-2-enoate (400 mg, 66% yield) as a transparent oil. LCMS: $(M+H)^+$=158.1, Retention time=1.341 min. LCMS CP method F Step 5: To a solution of methyl (S,E)-4-(dimethylamino) pent-2-enoate (step 4, 208 mg, 1.22 mmol) in a mixed solvent of THE (10 ml) and $H_2O$ (2 mL) was added NaOH (159 mg, 3.97 mmol). The mixture was stirred at RT for 2 h. The reaction was neutralized to pH 6~7 with HCl (5 mL, 1 M in water) and extracted with DCM (20 mL×3). The aqueous phase was concentrated in vacuum to give a residue which was dissolved in DCM. The solution was dried over $Na_2SO_4$, filtered and concentrated to give (S,E)-4-(dimethylamino)pent-2-enoic acid (171 mg, 98.0% yield) as a yellow oil. LCMS: $(M+H)^+$=144.1, Retention time=0.36 min. LCMS CP method F Step 6: To a solution of (S,E)-4-(dimethylamino)pent-2-enoic acid (step 5, 30 mg, 0.17 mmol) in DCM (3 mL) were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (60 mg, 0.149 mmol) HATU (85 mg, 0.223 mmol) and DIPEA (58 mg, 0.447 mmol) and the mixture was stirred at RT for 2 h. The mixture was concentrated and purified by Prep-HPLC (Method A) to give a ((S)-6-((S,E)-4-(dimethylamino)pent-2-enoyl)-4-(2-(1-ethyl-3-(trifluoromethyl)-1H-pyrazol-4-yl)phenyl)-4,5,6,7-tetrahydrothieno[2,3-c] pyridine-2-carbonitrile (28.6 mg, 30.17% yield) as a white solid. LCMS: $(M+H)^+$=528.1, purity=95.43% (214 nm), Retention time=1.801 min. LCMS CP method C $^1H$ NMR (400 MHz, DMSO-$d_6$) δ 8.19 (s, 1H), 7.43-7.25 (m, 4H), 6.72-6.57 (m, 1H), 6.51-6.46 (m, 1H), 5.77-5.73 (d, J=14.8 Hz, 1H), 5.16-5.12 (m, 1H), 4.76-4.71 (m, 1H), 4.29-3.75 (m, 4H), 3.63-3.60 (m, 1H), 2.81 (s, 1H), 2.32-1.98 (m, 6H), 1.48-1.31 (m, 3H), 1.08-0.87 (m, 3H).

Example 14

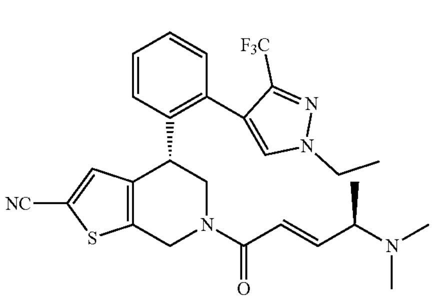 [SMILES: CCn1cc(-c2ccccc2[C@@H]2CN(C(=O)/C=C/[C@@H](C)N(C)C)Cc3sc(C#N)cc32)c(C(F)(F)F)n1]

(S)-6-((R,E)-4-(dimethylamino)pent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: A solution of (R)-tert-butyl 1-hydroxypropan-2-ylcarbamate (2 g, 11.4 mmol) and Dess-Martin Periodinane (7.27 g, 17.1 mmol) in DCM (25 ml) was stirred at RT for 2 h. Water (40 ml) was added and the mixture was extracted with DCM (3×40 ml). The combined organic phases were washed with brine, dried over $Na_2SO_4$ and concentrated to afford the residue. The residue was purified by flash chromatography (PE: EA=5:1) to afford (R)-tert-butyl 1-oxopropan-2-ylcarbamate (1.44 g, 73% yield) as a yellow oil. $^1H$ NMR (400 MHz, $CDCl_3$) δ: 9.56 (s, 1H), 5.10 (s, 1H), 4.26-4.22 (m, 1H), 1.46 (s, 9H), 1.3-1.305 (m, 3H).

Step 2: To a solution (R)-tert-butyl 1-oxopropan-2-ylcarbamate (Step 1, 1.44 g, 8.32 mmol) and LiCl (420 mg, 9.98 mmol) in ACN (20 ml) were added DIPEA (1.29 g, 9.98 mmoL) and methyl 2-(dimethoxyphosphoryl)acetate (1.67 g, 9.16 mmol) and the mixture was stirred at 25° C. for 2 h. The mixture was concentrated and the residue was purified by flash chromatography (PE:EA=85:15) to afford (R,E)-methyl 4-(tert-butoxycarbonylamino)pent-2-enoate (1.52 g, 80% yield) as a yellow liquid. LCMS: $(M-56+H)^+$=174.1; Retention time=1.61 min. LCMS CP Method C Step 3: A solution of (R,E)-methyl 4-(tert-butoxycarbonylamino)pent-2-enoate (step 2, 1 g, 4.37 mmol) in DCM (10 ml) and TFA (2 ml) was stirred at RT for 1.5 h and then concentrated to afford (R,E)-methyl 4-aminopent-2-enoate (560 mg, 100% yield) as a yellow solid. LCMS: $(M-16)^+$=113.2; Retention time=0.47 min. LCMS CP Method A Step 4: To a solution of (R,E)-methyl 4-aminopent-2-enoate (560 mg, 4.34 mmol), formaldehyde (0.4M in water) (651 mg, 8.68 mmol) and acetic acid (a drop) in MeOH (10 ml) was added $NaBH_3CN$ (547 mg, 8.68 mmol) and the mixture was stirred at RT for 1 h. Water (20 ml) was added and the mixture was extracted with DCM (3×20 ml). The combined organic phases were washed with brine, dried over $Na_2SO_4$ and concentrated to afford the residue which was purified by Prep-TLC (DCM: MeOH=10:1) to afford (R,E)-methyl 4-(dimethylamino)pent-2-enoate (494 mg, 72% yield) as a yellow solid. LCMS: $(M+H)^+$=158.1; Retention time=1.24 min. LCMS CP Method C Step 5: To a solution of (R,E)-methyl 4-(dimethylamino) pent-2-enoate (step 4, 494 mg, 3.15 mmol) in mixed THE (5 ml) and $H_2O$ (5 ml) was added $LiOH{\cdot}H_2O$ (265 mg, 6.3 mmol) and the mixture was stirred at RT for 1.5 h. The pH was adjusted to 5-6 with HCl (1 N) and the solution was concentrated in vacuum to afford (R,E)-4-(dimethylamino) pent-2-enoic acid (450 mg, 100% yield) as a white solid. LCMS: $(M+H)^+$=144.2; Retention time=0.44 min. LCMS CP Method A Step 6: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.24 mmol), DIPEA (62 mg, 0.48 mmol), and (R,E)-4-(dimethylamino)pent-2-enoic acid (step 5, 69 mg, 0.48 mmol) in DMF (4 ml) was added HATU (137 mg, 0.36 mmol) and the mixture was stirred at RT for 2 h. Water (50 ml) was added and the mixture was extracted with EA (3×40 ml). The combined organic phases were washed with brine, dried over $Na_2SO_4$ and concentrated to give a residue which was purified by Prep-HPLC (Method A) to afford (S)-6-((R,E)-4-(dimethylamino)pent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (58.4 mg, 46% yield, free base) as a yellow solid. LCMS: $(M+H)^+$=528.1; Retention time=1.78 min. LCMS CP Method C $^1H$ NMR (400 MHz, DMSO) δ: 8.29 (s, 1H), 7.40-7.25 (m, 4H), 6.97-6.76 (m, 1H), 6.60-6.47 (m, 1H), 5.84 (d, J=15.6 Hz, 1H), 5.12-4.77 (m, 2H), 4.27 (dd, J=14.4, 7.2 Hz, 2H), 4.15 (s, 1H), 3.97-3.60 (m, 2H), 2.90 (s, 1H), 2.21-1.99 (m, 6H), 1.46 (t, J=7.2 Hz, 3H), 1.15-0.99 (m, 3H).

Example 15

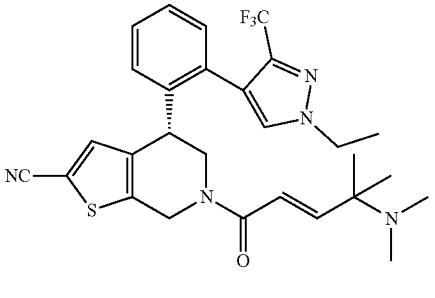 [SMILES: CCn1cc(-c2ccccc2[C@@H]2CN(C(=O)/C=C/C(C)(C)N(C)C)Cc3sc(C#N)cc32)c(C(F)(F)F)n1]

(S,E)-6-(4-(Dimethylamino)-4-methylpent-2-enoyl)-4-(2-(1-ethyl-3-(trifluoromethyl)-1H-pyrazol-4-yl) phenyl)-4,5,6,7-tetrahydrothieno[2,3-c]pyridine-2-carbonitrile Step 1: To a solution of ethyl 2-(diethoxyphosphoryl) acetate (658 mg, 2.93 mmol) in ACN (5 mL) were added tert-butyl (2-methyl-1-oxopropan-2-yl)carbamate (500 mg, 2.67 mmol), LiCl (136 mg, 3.20 mmol) and DIPEA (414 mg, 3.2 mmoL). The mixture was stirred at RT for 1 h. Then water (10 mL) was added and the mixture was extracted with DCM (3×20 mL). The combined organic layers were dried over $Na_2SO_4$, filtered and concentrated to give a residue which was purified by silica gel chromatography (PE: EA=15:1) to give ethyl (E)-4-((tert-butoxycarbonyl)amino)-4-methylpent-2-enoate (700 mg, 2.72 mmo, 92.30% yield) as a transparent oil. LCMS: (M 100)+=158, Retention time=1.857 min. LCMS CP method G Step 2: To a solution of ethyl (E)-4-((tert-butoxycarbonyl) amino)-4-methylpent-2-enoate (step 1, 700 mg, 2.72 mmol) in DCM (7 mL) was added TFA (1.5 mL, Wt 99%) and the mixture was stirred at RT for 2 h. The mixture was concentrated and the residue was dissolved in DCM (10 mL). The pH was adjusted to 6~7 with sat.$NaHCO_3$ and The mixture was extracted with DCM (3×20 mL). The combined organic layers were concentrated to give ethyl (E)-4-amino-4-methylpent-2-enoate (393 mg, 2.5 mmol, 92.0% yield) as a transparent oil which was used directly in the next step without further purification. LCMS: $(M+H)^+$=158, Retention time=1.366 min. LCMS CP method G Step 3: To a solution of ethyl (E)-4-amino-4-methylpent-2-enoate (step 2, 90 mg, 0.513 mmol) in MeOH (2 mL) were added HCHO (93 mg, 1.146 mmol), $NaBH_3CN$ (72 mg, 1.146 mmol) and AcOH (0.6156 mg, 0.0103 mmol) and the mixture was stirred at RT for 2 h. Then saturated $NaHCO_3$ aqueous solution (10 mL) was added and the mixture was extracted with EA (20 mL×3). The combined organic layers were washed with brine (50 mL), dried over anhydrous $Na_2SO_4$, filtered and concentrated to give a residue which was purified by silica gel chromatography (PE: EA=10:1) to give ethyl (E)-4-(dimethylamino)-4-methylpent-2-enoate (23 mg, 1.0.124 mmol, 39.0% yield) as a transparent oil. LCMS: $(M+H)^+$=186.1, Retention time=1.586 min. LCMS CP method G Step 4: To a solution of ethyl (E)-4-(dimethylamino)-4-methylpent-2-enoate (step 3, 50 mg, 0.269 mmol) in $H_2O$ (2 mL) was added NaOH (53.7 mg, 1.34 mmol) and the mixture was stirred at RT for 2 h. The pH was adjusted to 6~7 with HCl (4 mL, 1 mol/L) and extracted with DCM (3×20 mL). The aqueous phase was concentrated in vacuum to give a residue. The residue was redissolved in DCM (3×20 mL) and filtered. The filtrate was concentrated to give (E)-4-(dimethylamino)-4-methylpent-2-enoic acid (40 mg, 0.255 mmol 94.7% yield) as a yellow oil. LCMS: $(M+H)^+$= 158.1, Retention time=0.37 min. LCMS CP method G Step 5: To a solution of (E)-4-(dimethylamino)-4-methylpent-2-enoic acid (Step 4, 40 mg, 0.255 mmol) in DCM (3 mL) were added (S)-4-(2-(1-ethyl-3-(trifluoromethyl)-1H-pyrazol-4-yl)phenyl)-4,5,6,7-tetrahydrothieno[2,3-c]pyridine-2-carbonitrile-methane (50 mg, 0.124 mmol), HATU (70.89 mg, 0.186 mmol) and DIPEA (48.6 mg, 0.372 mmol) and the mixture was stirred at RT for 2 h. The mixture was concentrated and the residue was purified by Prep-HPLC (Method A) to give (S,E)-6-(4-(dimethylamino)-4-methylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (9.7 mg, 14.44% yield) as a white solid. LCMS: $(M+H)^+$=542, purity=100% (214 nm), Retention time=1.643 min. LCMS CP method E, $^1$H NMR (400 MHz, DMSO-$d_6$) δ 8.26 (s, 1H), 7.43-7.24 (m, 4H), 6.73-6.56 (m, 2H), 5.72-5.68(d, J=18 Hz 1H), 5.23-5.19 (m, 1H), 4.72-4.67 (d, J=20 Hz, 1H), 4.29-4.24 (m, 2H), 4.14 (s, 1H), 3.73-3.71 (m, 1H), 2.13-2.01 (m, 6H), 1.47-1.44 (m, 3H), 0.93-0.89 (m, 6H).

Example 16

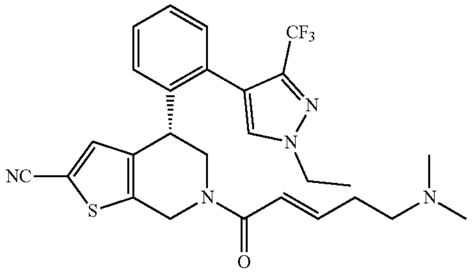 [SMILES: CCn1cc(-c2ccccc2[C@@H]2CN(C(=O)/C=C/CCN(C)C)Cc3sc(C#N)cc32)c(C(F)(F)F)n1]

S, E)-6-(5-(Dimethylamino)pent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of methyl 2-(dimethoxyphosphoryl) acetate (500 mg, 2.7 mmol) and LiCl (140 mg, 3.24 mmol) in $CH_3CN$ (10 ml) were added DIPEA (420 mg, 3.24 mmol) and tert-butyl methyl (3-oxopropyl)carbamate (570 mg, 3 mmol) and the resulting reaction mixture was stirred at 25° C. for 2 h. Then concentrated and the residue was purified by flash chromatography (PE:EA=85:15) to afford (E)-methyl 5-(tert-butoxycarbonyl(methyl)amino)pent-2-enoate (390 mg, 59% yield) as a yellow liquid. $^1$H NMR (400 MHz, $CDCl_3$) δ: 6.95-6.91 (m, 1H), 5.89-5.84 (m, 1H), 3.73 (s, 3H), 3.35 (t, J=6.8 Hz, 2H), 2.85 (s, 3H), 2.42 (d, J=6.4 Hz, 2H), 1.45 (s, 9H). Purify=100%

Step 2: To a solution of (E)-methyl 5-(tert-butoxycarbonyl (methyl)amino)pent-2-enoate (423 mg, 1.74 mmol) in DCM (5 ml) was added TFA (1 ml) and the resulting reaction mixture was stirred at RT for 1 h. Then the mixture was concentrated to give (E)-methyl 5-(methylamino)pent-2-enoate (250 mg, 100% yield) as a yellow solid which was used directly in the next step reaction without further purification. LCMS: $(M+H)^+$=144.1; Retention time=0.48 min. LCMS CP Method A Step 3: To a solution of (E)-methyl 5-(methylamino)pent-2-enoate (200 mg, 1.4 mmol), formaldehyde (0.4M in water) (210 mg, 2.8 mmol) and acetic acid (a drop) in MeOH (5 ml) was added $NaBH_3CN$ (176 mg, 2.8 mmol) and the reaction mixture was stirred at RT for 1 h. Water (20 ml) was added and the mixture was extracted with DCM (3×20 ml), the combined organic phases were washed with brine, dried over $Na_2SO_4$, filtered and concentrated to give a residue which was purified by flash column chromatography (DCM: MeOH=9:1) to afford (E)-methyl 5-(dimethylamino)pent-2-enoate (179 mg, 82% yield) as a yellow solid. LCMS: $(M+H)^+$=158.1; Retention time=1.15 min. LCMS CP Method C Step 4: To a mixture of (E)-methyl 5-(dimethylamino) pent-2-enoate (224 mg, 1.43 mmol), THE (4 ml) and $H_2O$ (4 ml) was added $LiOH{\cdot}H_2O$ (120 mg, 2.86 mmol) and the reaction mixture was stirred at room for 1.5 h. The pH of the solution was adjusted to 5-6 with HCl (1 N) and the solution was concentrated in vacuum to afford (E)-5-(dimethylamino)pent-2-enoic acid (200 mg, 100% yield) as a white solid. LCMS: $(M+H)^+$=144.2; Retention time=0.48 min. LCMS CP Method A Step 5: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (65 mg, 0.5 mmol), and (E)-5-(dimethylamino)pent-2-enoic acid (72 mg, 0.5 mmol) in DMF (4 ml) was added HATU (143 mg, 0.375 mmol) and the reaction mixture was stirred at RT for 2 h. Water (50 ml) was added and the mixture was extracted with EA (3×40 ml). The combined organic phases were washed with brine, dried over $Na_2SO_4$, filtered and concentrated to give a residue which was purified by Prep-HPLC (Method A) to afford (S,E)-6-(5-(dimethylamino)pent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (25.2 mg, 19% yield, free base) as a yellow solid. LCMS: $(M+H)^+$=528.2; Retention time=1.55 min. LCMS CP Method A. $^1H$ NMR (400 MHz, DMSO) δ: 8.31-8.19 (m, 1H), 7.39-7.26 (m, 4H), 6.91-6.78 (m, 1H), 6.60-6.53 (m, 1H), 5.78 (d, J=14.8 Hz, 1H), 4.94-4.88 (m, 2H), 4.27 (dd, J=14.4, 7.2 Hz, 2H), 4.13 (s, 1H), 3.95-3.79 (m, 1H), 3.55 (s, 1H), 3.30 (s, 1H), 2.36-2.32 (m, 1H), 2.21-2.06 (m, 8H), 1.46 (t, J=7.2 Hz, 3H).

Example 17

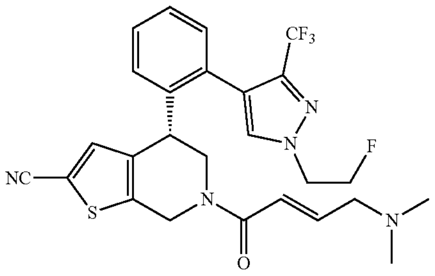 [SMILES: CN(C)C/C=C/C(=O)N1Cc2sc(C#N)cc2[C@H](c2ccccc2-c2cn(CCF)nc2C(F)(F)F)C1]

(S,E)-6-(4-(dimethylamino)but-2-enoyl)-4-(2-(1-(2-fluoroethyl)-3-(trifluoromethyl)-1H-pyrazol-4-yl)phenyl)-4,5,6,7-tetrahydrothieno[2,3-c]pyridine-2-carbonitrile Step 1: To a 50-mL round-bottomed flask were added tert-butyl (R)-4-(2-bromophenyl)-2-cyano-4,7-dihydrothieno[2,3-c]pyridine-6(5H)-carboxylate (200 mg, 0.48 mmol), 1-(2-fluoroethyl)-4-(4,4,5,5-tetramethyl-1,3,2-dioxaborolan-2-yl)-3-(trifluoromethyl)-1H-pyrazole (221 mg, 0.72 mmol), $K_3PO_4$ (304 mg, 1.43 mmol), Pd(dppf)$Cl_2$ (70 mg, 0.095 mmol), 1,4-dioxane (4 mL) and water (1 mL). The reaction mixture was stirred at 100° C. for 24 h then cooled to RT, and $H_2O$ (20 mL) was added. The mixture was extracted with EtOAc (2×10 mL). The organic extracts were washed with saturated NaCl (2* 20 mL), dried over $Na_2SO_4$ filtered and concentrated to give a residue which was purified by flash column chromatography (silica)(EtOAc/Hexane=20:1) to provide tert-butyl (S)-2-cyano-4-(2-(1-(2-fluoroethyl)-3-(trifluoromethyl)-1H-pyrazol-4-yl)phenyl)-4,7-dihydrothieno[2,3-c]pyridine-6(5H)-carboxylate (140 mg, 0.27 mmol, 56.3% yield) as a yellow solid. LCMS: $(M-56+H)^+$=465; Retention time=2.224 min. LCMS CP Method A Step 2: To a 50-mL round-bottomed flask were added tert-butyl (S)-2-cyano-4-(2-(1-(2-fluoroethyl)-3-(trifluoromethyl)-1H-pyrazol-4-yl)phenyl)-4,7-dihydrothieno[2,3-c]pyridine-6(5H)-carboxylate (Step 1, 140 mg, 0.27 mmol), TFA (307 mg, 2.7 mmol) and DCM (3 mL). The mixture was stirred at RT for 2 h. then concentrated and the residue was redissolved in DCM. $H_2O$ (10 mL) was added and the mixture was extracted with DCM (2×10 mL). The combined organic extracts were washed with saturated NaCl (2×10 mL) aqueous solution, dried over $Na_2SO_4$, filtered and concentrated to give (S)-4-(2-(1-(2-fluoroethyl)-3-(trifluoromethyl)-1H-pyrazol-4-yl)phenyl)-4,5,6,7-tetrahydrothieno[2,3-c]pyridine-2-carbonitrile TFA salt (110 mg, 96.5% yield) as a yellow oil which was used directly in the next step reaction without further purification.

Step 3: To a 50-mL round-bottomed flask were added (S)-4-(2-(1-(2-fluoroethyl)-3-(trifluoromethyl)-1H-pyrazol-4-yl)phenyl)-4,5,6,7-tetrahydrothieno[2,3-c]pyridine-2-carbonitrile (step 2, 100 mg, 0.26 mmol), DIPEA (92.1 mg, 0.71 mmol), (E)-4-(dimethylamino)but-2-enoic acid hydrochloride (60 mg, 0.36 mmol), HATU (135.7 mg, 0.36 mmol) and DMF (2 mL). The mixture was stirred at RT for 1 h. $H_2O$ (10 mL) was added and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (Method A) to provide (S,E)-6-(4-(dimethylamino)but-2-enoyl)-4-(2-(1-(2-fluoroethyl)-3-(trifluoromethyl)-1H-pyrazol-4-yl)phenyl)-4,5,6,7-tetrahydrothieno[2,3-c]pyridine-2-carbonitrile (82.7 mg, 0.16 mmol, 65.4% yield) as a white solid. LCMS: $(M+H)^+$=532; Retention time=1.522 min. LCMS CP Method D. $^1H$ NMR (400 MHz, DMSO) δ 8.36-8.15 (m, 1H), 7.54-7.16 (m, 4H), 7.00-6.70 (m, 1H), 6.64-6.35 (m, 1H), 5.87 (d, J=15.0 Hz, 1H), 5.08 (d, J=17.6 Hz, 1H), 4.98-4.89 (m, 1H), 4.86-4.67 (m, 2H), 4.59 (dd, J=27.7, 2.3 Hz, 2H), 4.15 (s, 1H), 3.84-3.50 (m, 2H), 3.06-2.72 (m, 2H), 2.09 (d, J=48.6 Hz, 6H).

Example 18

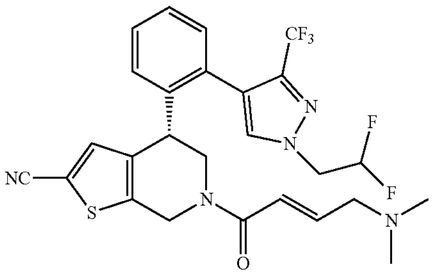 [SMILES: CN(C)C/C=C/C(=O)N1Cc2sc(C#N)cc2[C@H](c2ccccc2-c2cn(CC(F)F)nc2C(F)(F)F)C1]

(S,E)-4-(2-(1-(2,2-difluoroethyl)-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile Step 1: A mixture of (R)-tert-butyl 4-(2-bromophenyl)-2-cyano-4,5-dihydrothieno[2,3-c]pyridine-6(7H)-carboxylate (300 mg, 0.72 mmoL), 3-(trifluoromethyl)-1H-pyrazol-4-ylboronic acid (156 mg, 0.864 mmol), $K_3PO_4$ (306 mg, 1.14 mmol) and Pd(dppf)$Cl_2$ (108 mg, 0.114 mmol) in dioxane/water(4:1) (5 ml) was stirred at 100° C. for 2 h under microwave. The mixture was concentrated under reduced pressure and purified by flash column chromatography (DCM: MeOH=97: 3) to afford (S)-tert-butyl 2-cyano-4-(2-(3-(trifluoromethyl)-1H-pyrazol-4-yl)phenyl)-4,5-dihydrothieno[2,3-c]pyridine-6(7H)-carboxylate (334 mg, 98% yield) as a yellow solid. LCMS: $(M-56+H)^+$=419.0; Retention time=2.12 min. LCMS CP Method A Step 2: To a suspension of (S)-tert-butyl 2-cyano-4-(2-(3-(trifluoromethyl)-1H-pyrazol-4-yl)phenyl)-4,5-dihydrothieno[2,3-c]pyridine-6(7H)-carboxylate (step 1, 140 mg, 0.3 mmol) and $K_2CO_3$ (70 mg, 0.36 mmol) in DMF (5 ml) was added 1,1-difluoro-2-iodoethane (58 mg, 0.36 mmol). The mixture was heated to 60° C. and stirred for 2 h. Water (20 ml) was added and the mixture was extracted with EA (20 ml×3). The combined organic phases were washed with brine, dried over $Na_2SO_4$, filtered and concentrated to give a residue which was purified by flash column chromatography (DCM: MeOH=95: 5) to afford (S)-tert-butyl 2-cyano-4-(2-(1-(2,2-difluoroethyl)-3-(trifluoromethyl)-1H-pyrazol-4-yl)phenyl)-4,5-dihydrothieno[2,3-c]pyridine-6(7H)-carboxylate (118 mg, 78% yield) as a yellow solid. LCMS: $(M-56+H)^+$=483.1; Retention time=2.24 min. LCMS CP Method A Step 3: A mixture of (S)-tert-butyl 2-cyano-4-(2-(1-(2,2-difluoroethyl)-3-(trifluoromethyl)-1H-pyrazol-4-yl)phenyl)-4,5-dihydrothieno[2,3-c]pyridine-6(7H)-carboxylate (step 2, 160 mg, 0.3 mmol), DCM (5 ml) and TFA (1 ml) was stirred at RT for 1 h. The mixture was concentrated under reduced pressure to afford (S)-4-(2-(1-(2,2-difluoroethyl)-3-(trifluoromethyl)-1H-pyrazol-4-yl)phenyl)-4,5,6,7-tetrahydrothieno[2,3-c]pyridine-2-carbonitrile (TFA salt, 130 mg, 79% yield) as a yellow solid. LCMS: $(M+H)^+$=439.0; Retention time=1.54 min. LCMS CP Method A Step 4: To a solution of (S)-4-(2-(1-(2,2-difluoroethyl)-3-(trifluoromethyl)-1H-pyrazol-4-yl)phenyl)-4,5,6,7-tetrahydrothieno[2,3-c]pyridine-2-carbonitrile (step 3, 130 mg, 0.3 mmol), DIPEA (77 mg, 0.6 mmol) and (E)-4-(dimethylamino)but-2-enoic acid (74 mg, 0.45 mmol) in DMF(5 ml) was added HATU (171 mg, 0.45 mmol) and the mixture was stirred at RT for 2 h. Water (50 ml) was added and the mixture was extracted with EA (40 ml×3). The combined organic phases were washed with brine, dried over $Na_2SO_4$, filtered and concentrated to give a residue which was purified by Prep-HPLC (Method A) to afford (S,E)-4-(2-(1-(2,2-difluoroethyl)-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile (60.8 mg, 37% yield) as a yellow solid. LCMS: $(M+H)^+$=550.2; Retention time=1.56 min. LCMS CP Method A. $^1H$ NMR (400 MHz, DMSO) δ: 8.35-8.26 (m, 1H), 7.43-7.26 (m, 4H), 6.94-6.75 (m, 1H), 6.62-6.42 (m, 2H), 5.86 (d, J=14.8 Hz, 1H), 5.08 (d, J=17.6 Hz, 1H), 4.81 (t, J=14.8 Hz, 3H), 4.12 (s, 1H), 3.91-3.74 (m, 1H), 3.62-3.42 (m, 1H), 3.03-2.78 (m, 2H), 2.14-2.02 (m, 6H).

Example 19

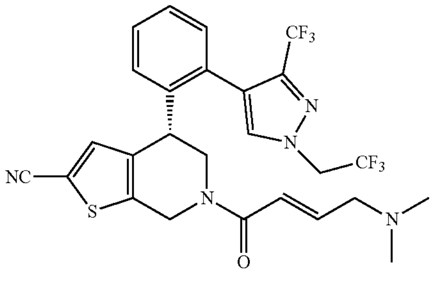 [SMILES: CN(C)C/C=C/C(=O)N1Cc2sc(C#N)cc2[C@H](c2ccccc2-c2cn(CC(F)(F)F)nc2C(F)(F)F)C1]

(S,E)-6-(4-(Dimethylamino)but-2-enoyl)-4-(2-(1-(2,2,2-trifluoroethyl)-3-(trifluoromethyl)-1H-pyrazol-4-yl)phenyl)-4,5,6,7-tetrahydrothieno[2,3-c]pyridine-2-carbonitrile Step 1: To a suspension of (S)-tert-butyl 2-cyano-4-(2-(3-(trifluoromethyl)-1H-pyrazol-4-yl)phenyl)-4,5-dihydrothieno[2,3-c]pyridine-6(7H)-carboxylate (150 mg, 0.316 mmol) and $K_2CO_3$ (133 mg, 0.632 mmol) in DMF (5 ml) was added 1,1,1-trifluoro-2-iodoethane (87 mg, 0.632 mmol). The reaction was heated to 60° C. and stirred for 16 h. Water (50 ml) was added and the mixture was extracted with EA (40 ml×3). The combined organic phases were washed with brine, dried over $Na_2SO_4$, filtered and concentrated to give a residue which was purified by flash column chromatography (DCM: MeOH=95:5) to afford (S)-tert-butyl 2-cyano-4-(2-(1-(2,2,2-trifluoroethyl)-3-(trifluoromethyl)-1H-pyrazol-4-yl)phenyl)-4,5-dihydrothieno[2,3-c]pyridine-6(7H)-carboxylate (90 mg, 54% yield) as a yellow solid. LCMS: $(M-56+H)^+$=501.1; Retention time=2.33 min. LCMS CP Method C Step 2: A mixture of (S)-tert-butyl 2-cyano-4-(2-(1-(2,2,2-trifluoroethyl)-3-(trifluoromethyl)-1H-pyrazol-4-yl)phenyl)-4,5-dihydrothieno[2,3-c]pyridine-6(7H)-carboxylate (step 1, 120 mg, 0.216 mmol), DCM (5 ml) and TFA (1 ml) was stirred at RT for 1 h. Then the mixture was concentrated under reduced pressure to afford (S)-4-(2-(1-(2,2,2-trifluoroethyl)-3-(trifluoromethyl)-1H-pyrazol-4-yl)phenyl)-4,5,6,7-tetrahydrothieno[2,3-c]pyridine-2-carbonitrile (98 mg, 80 yield) as a yellow solid which was used directly in the next step reaction without further purification. LCMS: $(M+H)^+$=457.0; Retention time=1.62 min. LCMS CP Method A Step 3: To a solution of (S)-4-(2-(1-(2,2,2-trifluoroethyl)-3-(trifluoromethyl)-1H-pyrazol-4-yl)phenyl)-4,5,6,7-tetrahydrothieno[2,3-c]pyridine-2-carbonitrile (step 2, 98 mg, 0.2 mmol), DIPEA (55 mg, 0.43 mmol) and (E)-4-(dimethylamino)but-2-enoic acid hydrochloride (49.8 mg, 0.3 mmol) in DMF (5 ml) was added HATU (114 mg, 0.3 mmol) and the mixture was stirred at RT for 2 h. Water (50 ml) was added and the mixture was extracted with EA (40 ml×3). The combined organic phases were washed with brine, dried over $Na_2SO_4$, filtered and concentrated to give a residue which was purified by Prep-HPLC (Method A) to afford (S,E)-6-(4-(dimethylamino)but-2-enoyl)-4-(2-(1-(2,2,2-trifluoroethyl)-3-(trifluoromethyl)-1H-pyrazol-4-yl)phenyl)-4,5,6,7-tetrahydrothieno[2,3-c]pyridine-2-carbonitrile (59.1 mg, 52% yield) as a yellow solid. LCMS: $(M+H)^+$=568.0; Retention time=1.62 min. LCMS CP Method A. $^1H$ NMR (400 MHz, DMSO) δ: 8.44-8.33 (m, 1H), 7.44-7.28 (m, 4H), 6.97-6.77 (m, 1H), 6.61-6.43 (m, 1H), 5.87 (d, J=15.6 Hz, 1H), 5.38-5.33 (m, 2H), 5.08-4.79 (m, 2H), 4.08 (s, 1H), 3.92-3.75 (m, 2H), 3.02-2.77 (m, 2H), 2.14-2.01 (m, 6H).

Example 20

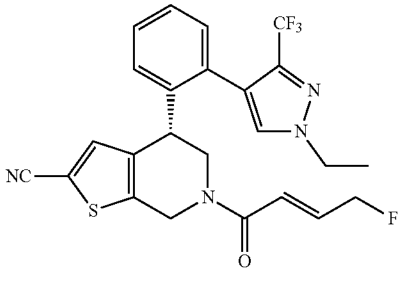 [SMILES: CCn1cc(-c2ccccc2[C@@H]2CN(C(=O)/C=C/CF)Cc3sc(C#N)cc32)c(C(F)(F)F)n1]

(S,E)-4-(2-(1-ethyl-3-(trifluoromethyl)-1H-pyrazol-4-yl)phenyl)-6-(4-fluorobut-2-enoyl)-4,5,6,7-tetrahydrothieno[2,3-c]pyridine-2-carbonitrile Step 1: To a solution of methyl (E)-4-bromobut-2-enoate (2 g, 11.2 mmol) in McCN (30 mL) was added AgF (2.14 g, 16.8 mol) with ice-salt bath. The mixture was stirred at RT for 3 h then filtered. The filtrate was concentrated and the resulting residue was dissolved in EA (30 mL). The solution was washed with saturated $NH_4Cl$ (2×50 mL) followed by brine (2×50 mL). The organic phase was dried over $Na_2SO_4$, filtered and concentrated to give a residue which was purified by flash column chromatography (EtOAc/Hexane=1:10) to provide methyl (E)-4-fluorobut-2-enoate (800 mg, 60% yield) as a brown oil.

Step 2: To a solution of methyl (E)-4-fluorobut-2-enoate (step 1, 500 mg, 4.2 mmol) in THE/$H_2O$=1:1 (2 mL) was added $LiOH{\cdot}H_2O$ (356 mg, 8.5 mmol) and the mixture was stirred at 45° C. for 2 h. 1 N HCl (20 mL) was added and the mixture was extracted with EA (2×20 mL). The combined organic extracts were washed with saturated NaCl aqueous solution (2×20 mL), dried over $Na_2SO_4$, filtered and concentrated to provide (E)-4-fluorobut-2-enoic acid (300 mg, 68.1% yield) as a white solid which was used directly in the next step reaction without further purification.

Step 3: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.24 mmol), DIPEA (93 mg, 0.72 mmol), (E)-4-fluorobut-2-enoic acid (step 2, 50 mg, 0.48 mmol), HATU (136.8 mg, 0.36 mmol) and DMF (2 mL). The mixture was stirred at RT for 1 h. $H_2O$ (10 mL) was added and the mixture was extracted with EA (2×10 mL). The combined organic extracts were washed with saturated NaCl aqueous solution (2×10 mL), and dried over $Na_2SO_4$. The mixture was filtered and the filtrate was concentrated to give a residue which was purified by Prep-HPLC (Method A) to give (S,E)-4-(2-(1-ethyl-3-(trifluoromethyl)-1H-pyrazol-4-yl)phenyl)-6-(4-fluorobut-2-enoyl)-4,5,6,7-tetrahydrothieno[2,3-c]pyridine-2-carbonitrile (38.4 mg, 32.8% yield) as a white solid. LCMS: $(M+H)^+$=489; Retention time=2.010 min. LCMS CP Method C. $^1H$ NMR (400 MHz, DMSO) δ 8.23 (d, J=22.0 Hz, 1H), 7.34-6.98 (m, 4H), 6.96-6.55 (m, 2H), 6.55-6.06 (m, 1H), 5.17-4.88 (m, 4H), 4.29-4.27 (m, 2H), 4.11-3.85 (m, 2H), 3.59 (dd, J=14.0, 6.6 Hz, 1H), 1.45 (t, J=7.2 Hz, 3H).

Example 21

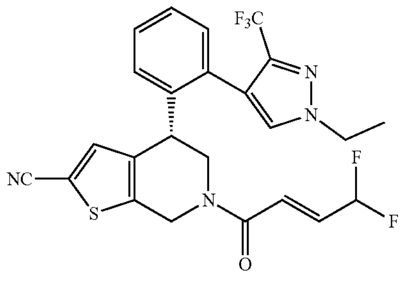 [SMILES: CCn1cc(-c2ccccc2[C@@H]2CN(C(=O)/C=C/C(F)F)Cc3sc(C#N)cc32)c(C(F)(F)F)n1]

(S,E)-6-(4,4-difluorobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 250-mL round-bottomed flask were added ethyl 4,4-difluoro-3-oxobutanoate (4 g, 24.1 mmol), $NaBH_4$ (1.37 g, 36.2 mmol) and MeOH (60 mL). The mixture was stirred at RT for 3 h. The mixture was filtered and concentrated to give crude ethyl 4,4-difluoro-3-hydroxybutanoate (4 g, 23.8 mmol, 98.8% yield) as a white solid which was used directly in the next step reaction without further purification.

Step 2: To a 50-mL round-bottomed flask were added ethyl 4,4-difluoro-3-hydroxybutanoate (step 1, 1 g, 5.9 mmol), $Et_3N$ (0.7 g, 1.1 mmol), DCM (20 mL) and MsCl (1 g, 8.9 mmol). The reaction was stirred at 0° C. to about RT for 2 h. To the mixture at RT was added 1 N HCl (40 mL) and the mixture was extracted with DCM (2×20 mL). The combined organic extracts were washed with saturated NaCl aqueous solution (2×40 mL), dried over $Na_2SO_4$. filtered and concentrated to provide ethyl (E)-4,4-difluorobut-2-enoate (700 mg, 4.6 mmol, 78.4% yield) as a white solid, which was used directly in the next step reaction without further purification.

Step 3: To a 50-mL round-bottomed flask were added methyl ethyl (E)-4,4-difluorobut-2-enoate (step 2, 700 mg, 4.6 mmol) and a solution of $LiOH{\cdot}H_2O$ (392 mg, 9.3 mmol) in THE/$H_2O$=1:1 (4 mL). The mixture was stirred at RT for 2 h. To the mixture at RT was added 1 N HCl (40 mL) and the mixture was extracted with EA (2×20 mL). The combined organic extracts were washed with saturated NaCl aqueous solution (2×40 mL), dried over $Na_2SO_4$. Filtered and concentrated to provide ((E)-4,4-difluorobut-2-enoic acid (500 mg, 4.1 mmol, 70.2% yield) as a yellow oil which was used directly in the next step reaction without further purification.

Step 4: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4,4-difluorobut-2-enoic acid (step 3, 45.5 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (Method A) to provide (S,E)-6-(4,4-difluorobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (50.1 mg, 0.1 mmol, 39.8% yield) as a white solid. LCMS: $(M+H)^+$=507; Retention time=1.634 min. LCMS OP Method D. $^1H$ NMR (400 MHz, DMSO) δ 8.23 (d, J=20.1 Hz, 1H), 7.39-7.17 (m, 4H), 7.16-6.47 (m, 2H), 6.47-6.13 (m, 2H), 5.18-4.75 (m, 2H), 4.23-4.20 (m, 2H), 4.15 (s, 1H), 4.03-3.74 (m, 1H), 3.60 (dd, J=14.1, 6.0 Hz, 1H), 1.46 (t, J=7.3 Hz, 3H).

Example 22

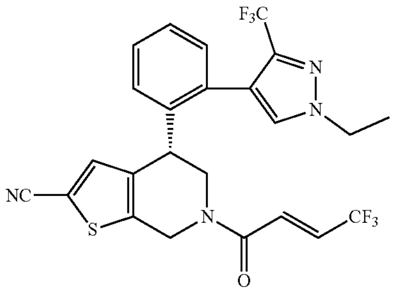 [SMILES: CCn1cc(-c2ccccc2[C@@H]2CN(C(=O)/C=C/C(F)(F)F)Cc3sc(C#N)cc32)c(C(F)(F)F)n1]

(S,E)-4-(2-(1-ethyl-3-(trifluoromethyl)-1H-pyrazol-4-yl)phenyl)-6-(4,4,4-trifluorobut-2-enoyl)-4,5,6,7-tetrahydrothieno[2,3-c]pyridine-2-carbonitrile Step 1: To a 50-mL round-bottomed flask were added methyl (E)-4,4,4-trifluorobut-2-enoate (100 mg, 0.65 mmol) and a solution of LiOH·$H_2O$ (55 mg, 1.3 mmol) in THE/$H_2O$ 1:1 (2 mL). The reaction was stirred at 45° C. for 2 h. To the mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4,4,4-trifluorobut-2-enoic acid (80 mg, 0.57 mmol, 88% yield) as a yellow oil which was used directly in the next step reaction without further purification.

Step 2: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4,4,4-trifluorobut-2-enoic acid (step 1, 51.8 mg, 0.37 mmol), HATU (141.8 mg, 0.37 mmol) and DMF (2 mL). The reaction mixture was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (Method A) to provide (S,E)-4-(2-(1-ethyl-3-(trifluoromethyl)-1H-pyrazol-4-yl)phenyl)-6-(4,4,4-trifluorobut-2-enoyl)-4,5,6,7-tetrahydrothieno[2,3-c]pyridine-2-carbonitrile (48.1 mg, 0.09 mmol, 36.9% yield) as a white solid. LCMS: $(M+H)^+$=525; Retention time=1.697 min. LCMS CP Method D. $^1H$ NMR (400 MHz, DMSO) δ 8.23 (d, J=15.7 Hz, 1H), 7.50-7.16 (m, 4H), 7.05-6.69 (m, 1H), 6.70-6.37 (m, 2H), 5.30-4.66 (m, 2H), 4.33-4.09 (m, 3H), 4.04- 3.76 (m, 1H), 3.64-3.41 (m, 1H), 1.46 (t, J=7.3 Hz, 3H).

Example 23

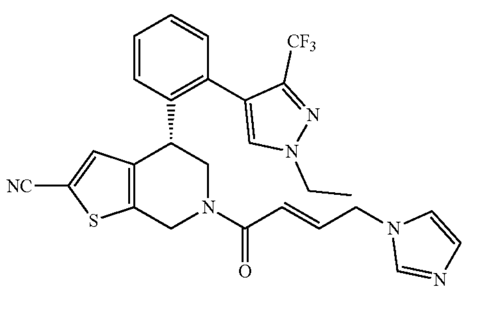 [SMILES: CCn1cc(-c2ccccc2[C@@H]2CN(C(=O)/C=C/Cn3ccnc3)Cc3sc(C#N)cc32)c(C(F)(F)F)n1]

(S,E)-6-(4-(1H-imidazol-1-yl)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of methyl (E)-4-bromobut-2-enoate (1.44 g, 8.08 mmol) in DMF (3 mL) were added $K_2CO_3$ (3.044 g, 22.0 mmol) and 1H-imidazole (0.500 g, 7.35 mmol) at RT. The mixture was heated to 50° C. and stirred for 2 h. The mixture was diluted with water (20 mL) and extracted with EA (20 mL×3). The combined organic layers were washed with brine (50 mL), dried over anhydrous $Na_2SO_4$, filtered and concentrated to give a residue which was purified by silica gel chromatography (PE: EA=5:1) to give methyl (E)-4-(1H-imidazol-1-yl)but-2-enoate (0.340 g, 2.04 mmol, 27.9% yield) as a yellow oil. LCMS: $(M+H)^+$=170.0, Retention time=1.39 min. LCMS CP method G Step 2: To a solution of methyl (E)-4-(1H-imidazol-1-yl) but-2-enoate (step 1, 0.340 g, 2.04 mmol) in mixed THF: $H_2O$ (3:1, 3 mL) was added LiOH·$H_2O$ (0.0258 g, 0.614 mmol) at RT and the mixture was stirred for 3 h. The mixture was acidified with aqueous HCl (1 M) to pH=5-6 and the mixture was concentrated in vacuum to give a (E) 4-(1H-imidazol-1-yl)but-2-enoic acid (0.150 g, 0.986 mmol, 48.2% yield) as a yellow oil. LCMS: $(M+H)^+$=153.1, Retention time=0.42 min. LCMS CP method A Step 3: A mixture of (S)-4-(2-(1-ethyl-3-(trifluoromethyl)-1H-pyrazol-4-yl)phenyl)-4,5,6,7-tetrahydrothieno[2,3-c]pyridine-2-carbonitrile (60 mg, 0.15 mmol), (E)-4-(1H-imidazol-1-yl)but-2-enoic acid (step 2, 68.4 mg, 0.45 mmol), HATU (85.5 mg, 0.225 mmol), DIPEA (58 mg, 0.45 mmol) and DCM (3 ml) was stirred at RT for 1 h. Water (10 ml) was added and the mixture was extracted with DCM (15 ml×3). The combined organic phases were washed with brine, dried over $Na_2SO_4$, filtered and concentrated. The residue was purified by Prep-HPLC (Method A) to afford (S,E)-6-(4-(1H-imidazol-1-yl)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (20.8 mg, 26% yield) as a white solid. $^1H$ NMR (400 MHz, DMSO) δ 8.33-8.19 (m, 1H), 7.88-7.77 (m, 1H), 7.55-7.49 (m, 1H), 7.46-7.26 (m, 4H), 7.01-6.67 (m, 3H), 6.04-5.80 (m, 1H), 5.03-4.86 (m, 2H), 4.31-4.06 (m, 3H), 4.05-3.75 (m, 1H), 3.56-3.38 (m, 1H), 2.85- 2.79 (m, 1H), 2.67-2.56 (m, 1H), 1.46 (t, J=7.2 Hz, 3H). LCMS: $(M+H)^+$=537.3, Retention time=1.541 min. LCMS CP method B Example 24

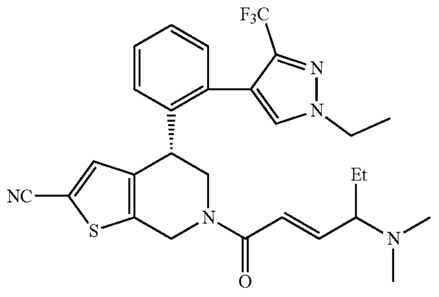 [SMILES: CCC(/C=C/C(=O)N1Cc2sc(C#N)cc2[C@H](c2ccccc2-c2cn(CC)nc2C(F)(F)F)C1)N(C)C]

Step 1: To a 500-mL round-bottomed flask were added 2-aminobutan-1-ol (10 g, 112 mmol), TEA (23 g, 225 mmol), $(Boc)_2O$ (73 g, 337 mmol) and DCM (100 mL). The reaction was stirred at 40° C. for 16 h. To the mixture at RT was added $H_2O$ (300 mL) and the mixture was extracted with EA (2×150 mL), The combined organic extracts were washed with saturated NaCl aqueous solution (2×300 mL), dried over $Na_2SO_4$. Filtered and concentrated to give a residue which was purified by flash column chromatography (silica): (EA/PE=1:1) to provide tert-butyl (1-hydroxybutan-2-yl)carbamate (6 g, 31.7 mmol, 28.2% yield) as a yellow oil. LCMS: $(M+Na)^+$=212; Retention time=1.428 min. LCMS CP Method A Step 2: To a 250-mL round-bottomed flask were added tert-butyl (1-hydroxybutan-2-yl)carbamate (step 1, 6 g, 31.7 mmol), DMP (16 g, 38 mmol) and DCM (100 mL). The reaction was stirred at RT for 1 h. To the mixture at RT was added $H_2O$ (400 mL) and the mixture was extracted with DCM (2×100 mL), The combined organic extracts were washed with saturated NaCl aqueous solution (2×200 mL), dried over $Na_2SO_4$, filtered and concentrated to provide tert-butyl (1-oxobutan-2-yl)carbamate (2.2 g, 11.7 mmol, 37.1% yield) as a colorless oil which was used directly in the next step reaction without further purification.

Step 3: To a 100-mL round-bottomed flask were added tert-butyl (1-oxobutan-2-yl)carbamate (step 2, 2.2 g, 11.7 mmol), LiCl (741 mg, 17.6 mmol), DIPEA (2.3 g, 17.6 mmol), ethyl 2-(diethoxyphosphoryl)acetate (5.6 g, 17.6 mmol) and $CH_3CN$ (50 mL). The reaction was stirred at RT for 4 h. To the mixture at RT was added $H_2O$ (100 mL) and the mixture was extracted with EA (2×50 mL), The combined organic extracts were washed with saturated NaCl aqueous solution (2×50 mL), dried over $Na_2SO_4$, filtered and concentrated to give a residue which was purified by flash column chromatography (silica, EA/PE=1:1) to provide ethyl (E)-4-((tert-butoxycarbonyl)amino)hex-2-enoate (2 g, 7.8 mmol, 66.1% yield) as a yellow solid. LCMS: $(M+Na)^+$=280; Retention time=1.704 min. LCMS CP Method B Step 4: To a 50-mL round-bottomed flask were added ethyl (E)-4-((tert-butoxycarbonyl)amino)hex-2-enoate (step 3, 1 g, 3.9 mmol) and a solution of $LiOH·H_2O$ (327 mg, 7.8 mmol) in THE/$H_2O$=1:1 (10 mL). The mixture was stirred at RT for 2 h. To the mixture at RT was added 1 N HCl (50 mL) and the mixture was extracted with EA (2×50 mL). The combined organic extracts were washed with saturated NaCl aqueous solution (2×50 mL), dried over $Na_2SO_4$, filtered and concentrated to give a residue which was purified by Prep-HPLC (Method B) to provide (E)-4-((tert-butoxycarbonyl)amino)hex-2-enoic acid (700 mg, 3.1 mmol, 78.6% yield) as a white solid. LCMS: $(M+Na)^+$=252; Retention time=1.463 min. LCMS CP Method B Step 5: To a 50-mL round-bottomed flask were added (E)-4-((tert-butoxycarbonyl)amino)hex-2-enoic acid (step 4, 110 mg, 0.72 mmol), DIPEA (190 mg, 1.8 mmol), (S)-4-(2-(1-ethyl-3-(trifluoromethyl)-1H-pyrazol-4-yl)phenyl)-4,5,6,7-tetrahydrothieno[2,3-c]pyridine-2-carbonitrile (240 mg, 0.6 mmol), HATU (280 mg, 0.9 mmol) and DMF (5 mL). The reaction was stirred at RT for 2 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (Method B) to provide tert-butyl ((E)-6-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-6-oxohex-4-en-3-yl)carbamate (180 mg, 0.29 mmol, 49.2% yield) as a yellow solid. LCMS: $(M-56+H)^+$=558; Retention time=1.890 min. LCMS CP Method B Step 6: To a 50-mL round-bottomed flask were added tert-butyl ((E)-6-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-6-oxohex-4-en-3-yl)carbamate (180 mg, 0.29 mmol), TFA (108 mg, 1.1 mmol) and DCM (2 mL). The mixture was stirred at RT for 2 h. The mixture was neutralized with saturated $NaHCO_3$ aqueous solution (20 mmol) at RT and the mixture was extracted with DCM (2×20 mL). The combined organic extracts were washed with saturated NaCl aqueous solution (2×20 mL), dried over $Na_2SO_4$, filtered and concentrated to provide (4S)-6-((E)-4-aminohex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (140 mg, 0.27 mmol, 92.9% yield) as a yellow oil. LCMS: $(M+H)^+$=514; Retention time=1.552 min. LCMS CP Method B Step 7: To a 50-mL round-bottomed flask were added (4S)-6-((E)-4-aminohex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (step 6, 140 mg, 0.27 mmol), formaldehyde (1 mL), $NaBH_3CN$ (26 mg, 0.4 mmol), HOAc (11 mg, 0.27 mmol) and MeOH (2 mL). The mixture was stirred at RT for 16 h. To the mixture at RT was added $H_2O$ (50 mL) and the mixture was extracted with DCM (2×50 mL). The combined organic extracts were washed with saturated NaCl aqueous solution (2×50 mL), dried over $Na_2SO_4$, filtered and concentrated to give a residue which was purified by Prep-HPLC (method B) to provide (4S)-6-((E)-4-(dimethylamino)hex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (62.1 mg, 0.47 mmol, 42.1% yield) as a white solid. LCMS: $(M+H)^+$=541; Retention time=1.584 min. LCMS CP Method B $^1H$ NMR (400 MHz, DMSO) δ 8.24 (d, J=32.0 Hz, 1H), 7.49-7.15 (m, 4H), 7.02-6.32 (m, 2H), 6.20-5.65 (m, 1H), 5.34-4.60 (m, 2H), 4.35-4.10 (m, 3H), 4.04-3.37 (m, 3H), 2.80-2.55 (m, 2H), 2.48-2.15 (m, 4H), 1.74-1.20 (m, 5H), 0.90-0.45 (m, 3H).

Example 25

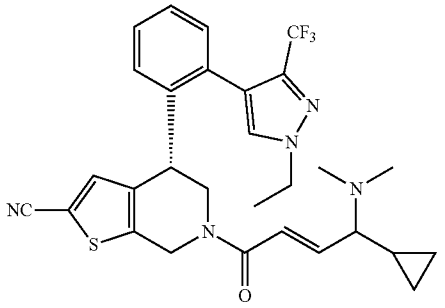 [SMILES: CCn1cc(-c2ccccc2[C@@H]2CN(C(=O)/C=C/C(C3CC3)N(C)C)Cc3sc(C#N)cc32)c(C(F)(F)F)n1]

Step 1: To a solution of 2-amino-2-cyclopropylethan-1-ol (0.500 g, 4.95 mmol) in DCM (10 mL) were added $(Boc)_2O$ (1.29 g, 5.94 mmol) and NaOH (0.594 g, 14.85 mmol) at RT. The mixture was stirred for 2 h. The mixture was diluted with water (20 mL) and extracted with DCM (3×20 mL). The combined organic layers were washed with brine (50 mL), dried over anhydrous $Na_2SO_4$, filtered and concentrated to give a residue which was purified by silica gel chromatography (DCM: MeOH=30:1) to give tert-butyl (1-cyclopropyl-2-hydroxyethyl)carbamate (0.750 g, 75.4% yield) as a yellow oil. LCMS: $(M-56+H)^+$=146.1, Retention time=1.51 min. LCMS CP method G Step 2: To a solution of tert-butyl (1-cyclopropyl-2-hydroxyethyl)carbamate (step 1, 0.260 g, 1.29 mmol) in DCM (5 mL) was added DMP (1.645 g, 3.88 mmol) at RT and the mixture was stirred for 2 h. The mixture was diluted with water (20 mL) and extracted with EA (3×10 mL). The combined organic layers were dried over anhydrous $Na_2SO_4$, filtered and concentrated in vacuum to give a residue which was purified by silica gel chromatography (PE:EA=100:1-1:1) to give a tert-butyl (1-cyclopropyl-2-oxoethyl)carbamate (0.200 g, 77.7% yield) as a white solid.

Step 3: To a solution of diethyl (S)-(2-(2-cyano-4-(2-(1-ethyl-3-(trifluoromethyl)-1H-pyrazol-4-( )phenyl)-4,7-dihydrothieno[2,3-c]pyridin-6(5H)-yl)-2-oxoethyl)phosphonate (0.200 g, 0.345 mmol) in ACN (5 mL) were added tert-butyl (1-cyclopropyl-2-oxoethyl)carbamate (step 2, 0.0823 g, 0.414 mmol), LiCl (0.0289 g, 0.689 mmol) and DIEA (0.0889 g, 0.689 mmol) at RT. The mixture was stirred for 3 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (DCM: MeOH=20:1) to give a tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-cyclopropyl-4-oxobut-2-en-1-yl)carbamate (0.200 g, 93% yield) as a yellow oil. LCMS: $(M-Boc+H)^+$=526.0, Retention time=2.08 min. LCMS CP method G Step 4: To a solution of tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-cyclopropyl-4-oxobut-2-en-1-yl)carbamate (step 3, 0.200 g, 0.32 mmol) in DCM (5 mL) was added TFA (5 mL) at RT. The resulting mixture was stirred at RT for 2 h. The pH was adjusted to 9 with $NaHCO_3$ and the mixture was extracted with DCM (10 mL×3). The combined organic layers were dried over $Na_2SO_4$, filtered and concentrated under reduced pressure to give (4S)-6-((E)-4-amino-4-cyclopropylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (0.160 g, 95% yield) as a yellow oil which was used directly in the next step reaction without further purification. LCMS: $(M+H)^+$=526.0, Retention time=1.87 min. LCMS CP method F Step 5: To a solution of (4S)-6-((E)-4-amino-4-cyclopropylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (Step 4, 0.160 g, 0.3 mmol) and HCHO aqueous solution (1 mL, excess) in MeOH (3 mL) was added $NaBH_3CN$ (0.0378 g, 0.6 mmol). The mixture was stirred at RT for 1 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by Prep-HPLC (Method A) to give (4S)-6-((E)-4-cyclopropyl-4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (0.0246 g, 14.82% yield) as a white solid. LCMS: $(M+H)^+$=554.3, purity=100% (214 nm), Retention time=1.61 min. LCMS CP method B. $^1$H NMR (400 MHz, DMSO): δ 8.28 (s, 1H), 7.46-7.26 (m, 4H), 6.78-6.54 (m, 2H), 5.79-5.71 (m, 1H), 5.20-4.71 (m, 2H), 4.29-4.20 (m, 3H), 3.83-3.57 (m, 2H), 3.33-3.29 (m, 1H), 2.26-2.08 (m, 6H), 1.49-1.45 (m, 3H), 0.73-0.03 (m, 5H).

Example 26

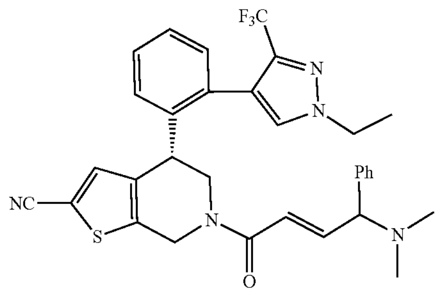

(4S)-6-((E)-4-(Dimethylamino)-4-phenylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 250-mL round-bottomed flask were added 2-amino-2-phenylethan-1-ol (10 g, 73 mmol), TEA (147 g, 146 mmol), $(Boc)_2O$ (47.7 g, 219 mmol) and DCM (100 mL). The reaction mixture was stirred at 40° C. for 16 h. To the reaction mixture at RT was added $H_2O$ (300 mL) and the mixture was extracted with EA (2×150 mL). The combined organic extracts were washed with saturated NaCl aqueous solution (2×200 mL), dried over $Na_2SO_4$, filtered and concentrated to give a residue which was purified by flash column chromatography (silica, EA/PE=1:2) to provide tert-butyl (2-hydroxy-1-phenylethyl)carbamate (6 g, 25.3 mmol, 34.7% yield) as a yellow oil. LCMS: $(M+Na)^+$=260; Retention time=1.495 min. LCMS CP Method B Step 2: To a 100-mL round-bottomed flask were added tert-butyl (2-hydroxy-1-phenylethyl)carbamate (1 g, 4.2 mmol), DMP (2.1 g, 5.1 mmol) and DCM (40 mL). The reaction mixture was stirred at RT for 1 h. To the reaction mixture at RT was added $H_2O$ (100 mL) and the mixture was extracted with DCM (2×50 mL), The combined organic extracts were washed with saturated NaCl aqueous solution (2×50 mL), dried over $Na_2SO_4$, filtered and concentrated to provide tert-butyl (2-oxo-1-phenylethyl)carbamate (650 mg, 2.8 mmol, 65.5% yield) as a colorless oil which was used directly in the next step reaction without further purification.

Step 3: To a 50-mL round-bottomed flask were added tert-butyl (2-oxo-1-phenylethyl)carbamate (650 mg, 2.8 mmol), LiCl (172 mg, 4.2 mmol), DIPEA (541 mg, 4.2 mmol), ethyl 2-(diethoxyphosphoryl)acetate (1.3 g, 4.2 mmol) and $CH_3CN$ (20 mL). The reaction mixture was stirred at RT for 4 h. LCMS and To the reaction mixture at RT was added $H_2O$ (50 mL) and the mixture was extracted with EA (2×50 mL), The combined organic extracts were washed with saturated NaCl aqueous solution (2×50 mL), dried over $Na_2SO_4$, filtered and concentrated to give a residue which was purified by flash column chromatography (silica, EA/PE=1:10) to provide ethyl (E)-4-((tert-butoxycarbonyl)amino)-5-phenylpent-2-enoate (590 mg, 1.9 mmol, 70.5% yield) as a yellow solid. LCMS: (M+Na)+=328; Retention time=1.764 min. LCMS CP Method B Step 4: To a 50-mL round-bottomed flask were added ethyl (E)-4-((tert-butoxycarbonyl)amino)-5-phenylpent-2-enoate (290 mg, 0.95 mmol), TFA (1.1 g, 9.5 mmol) and DCM (4 mL). The reaction mixture was stirred at RT for 1 h. To the reaction mixture at RT was added saturated $NaHCO_3$ aqueous solution (20 mL) and the mixture was extracted with DCM (2×20 mL). The combined organic extracts were washed with saturated NaCl aqueous solution (2×20 mL), dried over $Na_2SO_4$, filtered and concentrated to provide ethyl (E)-4-amino-4-phenylbut-2-enoate (180 mg, 0.89 mmol, 92.3% yield) as a yellow oil which was used directly in the next step reaction without further purification. LCMS: $(M+H)^+$=206; Retention time=1.238 min. LCMS CP Method B Step 5: To a 50-mL round-bottomed flask were added ethyl (E)-4-amino-4-phenylbut-2-enoate (180 mg, 0.89 mmol), formaldehyde (1 mL), $NaBH_3CN$ (82 mg, 1.3 mmol), HOAc (18 mg, 0.45 mmol) and MeOH (2 mL). The reaction mixture was stirred at RT for 16 h. To the reaction mixture at RT was added $H_2O$ (50 mL) and the mixture was extracted with EA (2×50 mL). The combined organic extracts were washed with saturated NaCl aqueous solution (2×50 mL), dried over $Na_2SO_4$, filtered, and concentrated to provide ethyl (E)-4-(dimethylamino)-4-phenylbut-2-enoate (120 mg, 0.52 mmol, 58.7% yield) as a yellow oil which was used directly in the next step reaction without further purification.

Step 6: To a 50-mL round-bottomed flask were added ethyl (E)-4-(dimethylamino)-4-phenylbut-2-enoate (120 mg, 0.52 mmol), $LiOH·H_2O$ (44 mg, 1.04 mmol) and mixed THE/$H_2O$=1:1 (2 mL). The reaction mixture was stirred at RT for 2 h. To the reaction mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4-(dimethylamino)-4-phenylbut-2-enoic acid (100 mg, 0.47 mmol, 60.5% yield) as a yellow solid which was used directly in the next step reaction without further purification. LCMS: $(M+H)^+$=206; Retention time=1.013 min. LCMS CP Method A Step 7: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4-(dimethylamino)-4-phenylbut-2-enoic acid (76 mg, 0.37 mmol), HATU (141.8 mg, 0.37 mmol) and DMF (2 mL). The reaction mixture was stirred at RT for 1 h. To the reaction mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method B) to provide (4S)-6-((E)-4-(dimethylamino)-4-phenylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (55.1 mg, 0.09 mmol, 36.7% yield) as a white solid. LCMS: $(M+H)^+$=604; Retention time=1.760 min. LCMS CP Method A. $^1H$ NMR (400 MHz, DMSO) δ 8.40-8.10 (m, 1H), 7.42 (d, J=5.6 Hz, 1H), 7.36-7.18 (m, 7H), 7.15 (d, J=6.9 Hz, 1H), 6.82-6.43 (m, 2H), 6.02-5.76 (m, 1H), 5.25-4.55 (m, 2H), 4.35-4.21 (m, 2H), 4.19 (s, 1H), 3.76 (d, J=13.9 Hz, 1H), 3.62 (d, J=15.2 Hz, 1H), 3.46 (d, J=4.8 Hz, 1H), 2.18-1.81 (m, 6H), 1.52-1.36 (m, 3H).

Example 27

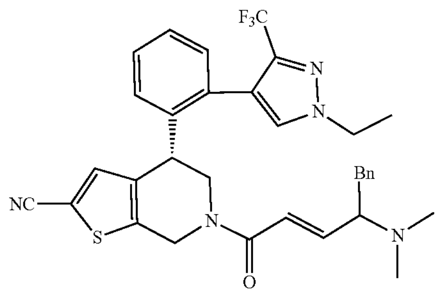 [SMILES: CCn1cc(-c2ccccc2[C@@H]2CN(C(=O)/C=C/C(c3ccccc3)N(C)C)Cc3sc(C#N)cc32)c(C(F)(F)F)n1]

(4S)-6-((E)-4-(dimethylamino)-5-phenylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 250-mL round-bottomed flask were added 2-amino-3-phenylpropan-1-ol (10 g, 66.2 mmol), TEA (13.4 g, 132 mmol), $(Boc)_2O$ (43.3 g, 199 mmol) and DCM (100 mL). The reaction mixture was stirred at 40° C. for 16 h. To the reaction mixture at RT was added $H_2O$ (300 mL) and the mixture was extracted with EA (2×150 mL). The combined organic extracts were washed with saturated NaCl aqueous solution (2×200 mL), dried over $Na_2SO_4$, filtered and concentrated to provide tert-butyl (1-hydroxy-3-phenylpropan-2-yl)carbamate (5.8 g, 23.1 mmol, 34.9% yield) as a yellow oil which was used directly in the next step reaction without further purification.

Step 2: To a 100-mL round-bottomed flask were added tert-butyl (1-hydroxy-3-phenylpropan-2-yl)carbamate (1 g, 4 mmol), DMP (2 g, 4.8 mmol) and DCM (40 mL). The reaction was stirred at RT for 1 h. To the mixture at RT was added $H_2O$ (100 mL) and the mixture was extracted with DCM (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:5) to provide tert-butyl (1-oxo-3-phenylpropan-2-yl)carbamate (600 mg, 2.4 mmol, 60.4% yield) as a colorless oil.

Step 3: To a 50-mL round-bottomed flask were added tert-butyl (1-oxo-3-phenylpropan-2-yl)carbamate (600 mg, 2.41 mmol), LiCl (151 mg, 3.61 mmol), DIPEA (466 mg, 3.61 mmol), ethyl 2-(diethoxyphosphoryl)acetate (809 mg, 3.61 mmol) and $CH_3CN$ (10 mL). The mixture was stirred at RT for 4 h. To the mixture at RT was added $H_2O$ (50 mL) and the mixture was extracted with EA (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:10) to provide ethyl (E)-4-((tert-butoxycarbonyl)amino)-5-phenylpent-2-enoate (550 mg, 1.7 mmol, 71.6% yield) as a yellow solid. LCMS: (M+Na)+=342; Retention time=1.787 min. LCMS CP Method B Step 4: To a 50-mL round-bottomed flask were added ethyl (E)-4-((tert-butoxycarbonyl)amino)-5-phenylpent-2-enoate (300 mg, 0.94 mmol), TFA (1.1 g, 9.4 mmol) and DCM (4 mL). The mixture was stirred at RT for 1 h. To the mixture at RT was added saturated $NaHCO_3$ aqueous solution (20 mL) and the mixture was extracted with DCM (2×20 mL). The combined organic extracts were washed with saturated NaCl aqueous solution (2×20 mL), dried over $Na_2SO_4$, filtered and concentrated to provide ethyl (E)-4-amino-5-phenylpent-2-enoate (150 mg, 0.68 mmol, 72.8% yield) as a yellow oil which was used directly in the next step reaction without further purification. LCMS: $(M+H)^+$=220; Retention time=1.272 min. LCMS CP Method D Step 5: To a 50-mL round-bottomed flask were added ethyl (E)-4-amino-5-phenylpent-2-enoate (150 mg, 0.68 mmol), formaldehyde (1 mL), $NaBH_3CN$ (63 mg, 1 mmol), HOAc (20 mg, 0.34 mmol) and MeOH (2 mL). The reaction was stirred at RT for 16 h. To the mixture at RT was added $H_2O$ (50 mL) and the mixture was extracted with EA (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:1) to provide ethyl (E)-4-(dimethylamino)-5-phenylpent-2-enoate (120 mg, 0.48 mmol, 70.9% yield) as a yellow oil. LCMS: $(M+H)^+$=248; Retention time=1.935 min. LCMS CP Method C Step 6: To a 50-mL round-bottomed flask were added ethyl (E)-4-(dimethylamino)-5-phenylpent-2-enoate (120 mg, 0.48 mmol), $LiOH·H_2O$ (40 mg, 0.96 mmol) and mixed THE/$H_2O$=1:1 (2 mL). The reaction was stirred at RT for 2 h. To the reaction mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4-(dimethylamino)-5-phenylpent-2-enoic acid (100 mg, 0.47 mmol, 60.5% yield) as a yellow solid which was used directly in the next step reaction without further purification. LCMS: $(M+H)^+$=220; Retention time=1.049 min. LCMS CP Method A Step 7: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4-(dimethylamino)-5-phenylpent-2-enoic acid (81 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method A) to provide (4S)-6-((E)-4-(dimethylamino)-5-phenylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (55.1 mg, 0.09 mmol, 36.7% yield) as a white solid. LCMS: $(M+H)^+$=604; Retention time=1.760 min. LCMS CP Method D $^1H$ NMR (400 MHz, DMSO) δ 8.19 (s, 1H), 7.50-7.30 (m, 1H), 7.30-7.19 (m, 5H), 7.11 (s, 3H), 7.00-6.73 (m, 1H), 6.53 (dd, J=15.1, 8.5 Hz, 1H), 5.70 (d, J=15.7 Hz, 1H), 4.90 (dd, J=49.3, 17.6 Hz, 2H), 4.25 (d, J=6.9 Hz, 2H), 4.13 (s, 1H), 3.99-3.58 (m, 1H), 3.44 (d, J=69.0 Hz, 1H), 3.31 (s, 1H), 3.11-2.56 (m, 2H), 2.16 (d, J=42.4 Hz, 6H), 1.45 (t, J=7.2 Hz, 3H).

Example 28

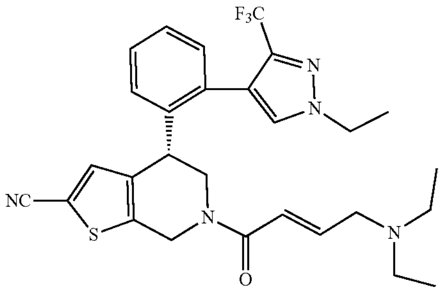 [SMILES: CCN(CC)C/C=C/C(=O)N1Cc2sc(C#N)cc2[C@H](c2ccccc2-c2cn(CC)nc2C(F)(F)F)C1]

(S,E)-6-(4-(Diethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 50-mL round-bottomed flask were added methyl (E)-4-bromobut-2-enoate (1 g, 5.6 mmol), $K_2CO_3$ (2.3 g, 16.9 mmol), DEA (492 mg, 6.7 mmol) and DMF (10 mL). The reaction was stirred at 60° C. for 16 h. To the mixture at RT was added $H_2O$ (100 mL) and the mixture was extracted with EA (2×50 mL). The combined organic extracts were washed with saturated NaCl aqueous solution (2×100 mL), dried over $Na_2SO_4$, filtered and concentrated to give a residue which was purified by flash column chromatography (silica, MeOH/DCM=1:10) to provide methyl (E)-4-(diethylamino)but-2-enoate (500 mg, 2.9 mmol, 52.0% yield) as a yellow solid. LCMS: $(M+H)^+$=172; Retention time=0.768 min. LCMS CP Method B Step 2: To a 50-mL round-bottomed flask were added methyl (E)-4-(diethylamino)but-2-enoate (500 mg, 2.9 mmol), $LiOH·H_2O$ (245 mg, 5.8 mmol) and mixed THE/$H_2O$=1:1 (2 mL). The reaction was stirred at 45° C. for 2 h. To the mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4-(diethylamino)but-2-enoic acid (400 mg, 2.5 mmol, 87.1% yield) as a yellow oil which was used directly in the next step reaction without further purification.

Step 3: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4-(diethylamino)but-2-enoic acid (58.6 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method A) to provide (S,E)-6-(4-(diethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (26.7 mg, 20.7% yield, free base) as a brown solid. LCMS: $(M+H)^+$=542; Retention time=1.682 min. LCMS CP Method E. $^1H$ NMR (400 MHz, DMSO) δ 8.29 (d, J=69.5 Hz, 1H), 7.44-7.16 (m, 4H), 7.05-6.55 (m, 2H), 6.43 (d, J=84.8 Hz, 1H), 5.29-4.66 (m, 2H), 4.28 (q, J=7.2 Hz, 2H), 4.14 (s, 1H), 4.04-3.72 (m, 2H), 3.69 (s, 2H), 3.25-2.60 (m, 4H), 1.47 (t, J=7.3 Hz, 3H), 1.33-0.91 (m, 6H).

Example 29

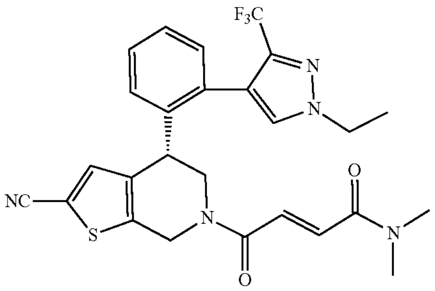 [SMILES: CCn1cc(-c2ccccc2[C@@H]2CN(C(=O)/C=C/C(=O)N(C)C)Cc3sc(C#N)cc32)c(C(F)(F)F)n1]

(S,E)-4-(2-cyano-4-(2-(1-ethyl-3-(trifluoromethyl)-1H-pyrazol-4-yl)phenyl)-4,7-dihydrothieno[2,3-c]pyridin-6(5H)- yl)-N, N-dimethyl-4-oxobut-2-enamide Step 1: To a solution of (E)-4-ethoxy-4-oxobut-2-enoic acid (500 mg, 3.5 mmol) in DMF (5 mL) were added dimethylamine (158 mg, 3.5 mmol) and HATU (4.00 g, 10.5 mmol). The reaction was stirred at RT for 30 min. The mixture was filtered and the filtrate was concentrated to give a residue which was purified by Prep-HPLC (method B) to give ethyl (E)-4-(dimethylamino)-4-oxobut-2-enoate (100 mg, 0.58 mmol, 16.71%) as a light-yellow oil. LCMS: $(M+H)^+$=171, purity=100% (214 nm), Retention time=1.22 min. LCMS CP method B Step 2: To a solution of ethyl (E)-4-(dimethylamino)-4-oxobut-2-enoate (100 mg, 0.58 mol) in THF/$H_2O$ (3 mL) was added LiOH·$H_2O$ (73 mg, 0.58 mmol). The reaction was stirred at 45° C. overnight. The mixture was neutralized with 1M HCl and concentrated to give (E)-4-(dimethylamino)-4-oxobut-2-enoic acid (170 mg, crude) as a light-yellow oil which was used directly in the next step without further purification. LCMS: $(M+H)^+$=143, purity=100% (214 nm), Retention time=1.26 min. LCMS CP method A Step 3: To a solution of ethyl (E)-4-(dimethylamino)-4-oxobut-2-enoate (170 mg, crude) in DMF (2 mL) was added (S)-4-(2-(1-ethyl-3-(trifluoromethyl)-1H-pyrazol-4-yl)phenyl)-4,5,6,7-tetrahydrothieno[2,3-c]pyridine-2-carbonitrile (40 mg, 0.1 mmol), HATU (57 mg, 0.15 mmol) and DIPEA (38 mg, 3.0 mmol). The mixture was stirred at RT for 2 h, then quenched with water (10 mL). The mixture was extracted with EA (3×20 mL). The combined organic layers were washed with brine (50 mL), dried over anhydrous $Na_2SO_4$, filtered and concentrated to give a residue which was purified by Prep-HPLC (method A) to give (S,E)-4-(2-cyano-4-(2-(1-ethyl-3-(trifluoromethyl)-1H-pyrazol-4-yl)phenyl)-4,7-dihydrothieno[2,3-c]pyridin-6(5H)-yl)-N,N-dimethyl-4-oxobut-2-enamide (2.8 mg, 5.3% yield, free base) as a white solid. LCMS: $(M+H)^+$=527, purity=100% (214 nm), Retention time=1.91 min. LCMS CP method A. $^1$H NMR (400 MHZ, DMSO) δ 8.23-8.21 (S, 1H), 7.33-7.22 (m, 5H), 6.92-6.73 (m, 2H), 5.12-4.84 (m, 2H), 4.30-4.25 (m, 2H), 4.09-3.66 (m, 2H), 3.67-3.31 (m, 1H), 3.05-2.88 (m, 6H), 1.48-1.43 (m, 3H).

Example 30

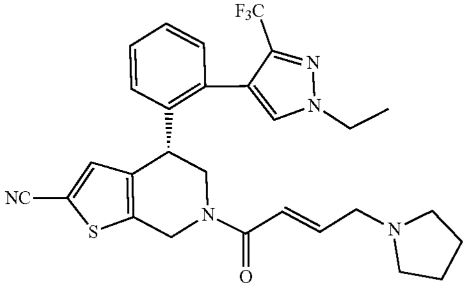 [SMILES: CCn1cc(-c2ccccc2[C@@H]2CN(C(=O)/C=C/CN3CCCC3)Cc3sc(C#N)cc32)c(C(F)(F)F)n1]

(S,E)-4-(2-(1-ethyl-3-(trifluoromethyl)-1H-pyrazol-4-yl)phenyl)-6-(4-(pyrrolidin-1-yl)but-2-enoyl)-4,5,6,7-tetrahydrothieno[2,3-c]pyridine-2-carbonitrile Step 1: To a solution of methyl (E)-4-bromobut-2-enoate (300 mg, 1.67 mmol) in DCM (5 mL) were added pyrrolidine (158 mg, 1.67 mmol) and $K_2CO_3$ (461 mg, 3.34 mmol). The reaction was stirred at RT for 30 min. The mixture was filtered and the filtrate was concentrated to give a residue which was purified by Prep-HPLC (method B) to give ethyl (E)-4-(pyrrolidin-1-yl)but-2-enoate (140 mg, 0.83 mmol, 49.70%) as a light yellow oil. LCMS: $(M+H)^+$=169, purity=100% (214 nm), Retention time=1.39 min. LCMS CP method G Step 2: To a solution of ethylmethyl (E)-4-(pyrrolidin-1-yl)but-2-enoate (step 1, 140 mg, 0.83 mmol) in THF/$H_2O$ (3 mL) was added LiOH·$H_2O$ (104 mg, 2.49 mmol). The reaction was stirred at 45° C. overnight. The mixture was neutralized with 1M HCl and concentrated in vacuum to give (E)-4-(pyrrolidin-1-yl)but-2-enoic acid (300 mg, crude) as a light yellow oil which was used directly in the next step without further purification. LCMS: $(M+H)^+$=155, purity=100% (214 nm), Retention time=0.52 min. LCMS CP method G Step 3: To a solution of (E)-4-(pyrrolidin-1-yl)but-2-enoic acid (step 2, 300 mg, crude) in DMF (2 mL) were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (40 mg, 0.099 mmol), HATU (57 mg, 0.15 mmol) and DIPEA (38 mg, 3.0 mmol). The reaction was stirred at RT for 2 h and then quenched with water (10 mL). The mixture was extracted with EA (3×20 mL). The combined organic layers were washed with brine (50 mL), dried over anhydrous $Na_2SO_4$, filtered and concentrated to give a residue which was purified by Prep-HPLC (method A) to give (S,E)-4-(2-(1-ethyl-3-(trifluoromethyl)-1H-pyrazol-4-yl)phenyl)-6-(4-(pyrrolidin-1-yl)but-2-enoyl)-4,5,6,7-tetrahydrothieno[2,3-c]pyridine-2-carbonitrile (12.6 mg, 23.61% yield) as a white solid. LCMS: $(M+H)^+$=539, purity=100% (214 nm), Retention time=1.59 min. LCMS CP method A $^1$HNMR (400 MHZ, DMSO) δ 8.29 (s, 1H), 7.39-7.27 (s, 4H), 6.97-6.49 (m, 2H), 5.94-5.93 (d, 4HZ, 1H), 5.11-4.81 (m, 2H), 4.28-4.14 (m, 3H), 3.90-3.61 (m, 2H), 3.34-3.27 (s, 2H), 3.03 (s, 1H), 2.31 (s, 3H), 1.65 (s, 4H), 1.48-1.44 (m, 3H).

Example 31

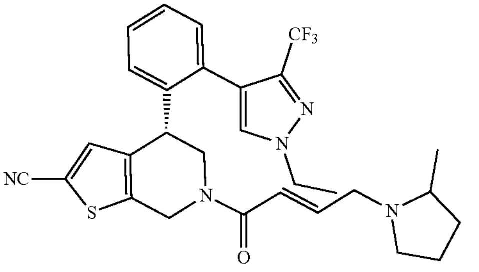 [SMILES: CCn1cc(-c2ccccc2[C@@H]2CN(C(=O)/C=C/CN3CCCC3C)Cc3sc(C#N)cc32)c(C(F)(F)F)n1]

(4S)-4-(2-(1-ethyl-3-(trifluoromethyl)-1H-pyrazol-4-yl)phenyl)-6-((E)-4-(2-methylpyrrolidin-1-yl)but-2-enoyl)-4,5,6,7-tetrahydrothieno[2,3-c]pyridine-2-carbonitrile Step 1: To a 50-mL round-bottomed flask were added methyl (E)-4-bromobut-2-enoate (1 g, 5.6 mmol), $K_2CO_3$ (2.3 g, 16.9 mmol), 2-methylpyrrolidine (569 mg, 6.7 mmol) and DMF (10 mL). The reaction was stirred at 60° C. for 16 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by flash column chromatography (silica, MeOH/DCM=1:10) to provide methyl (E)-4-(2-methylpyrrolidin-1-yl)but-2-enoate (400 mg, 2.2 mmol, 38.9% yield) as a yellow solid. LCMS: $(M+H)^+$=184; Retention time=0.825 min. LCMS CP Method B Step 2: To a 50-mL round-bottomed flask were added methyl (E)-4-(2-methylpyrrolidin-1-yl)but-2-enoate (step 1, 400 mg, 2.2 mmol), LiOH·$H_2O$ (183 mg, 4.4 mmol) and mixed THE/$H_2O$=1:1 (2 mL). The reaction was stirred at 45° C. for 2 h. To the mixture at RT was added 1 N HCl (10 mL) and the mixture was extracted with EA (2×10 mL). The combined organic extracts were washed with saturated NaCl aqueous solution (2×10 mL), dried over $Na_2SO_4$, filtered and concentrated to provide (E)-4-(2-methylpyrrolidin-1-yl) but-2-enoic acid (300 mg, 1.8 mmol, 54.1% yield) as a white solid which was used directly in the next step without further purification.

Step 3: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), methyl (E)-4-(2-methylpyrrolidin-1-yl)but-2-enoate (step 2, 62.5 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method B) to provide (4S)-4-(2-(1-ethyl-3-(trifluoromethyl)-1H-pyrazol-4-yl)phenyl)-6-((E)-4-(2-methylpyrrolidin-1-yl)but-2-enoyl)-4,5,6,7-tetrahydrothieno[2,3-c]pyridine-2-carbonitrile (38.1 mg, 0.07 mmol, 27.7% yield) as a white solid. LCMS: $(M+H)^+$=555; Retention time=1.604 min. LCMS CP Method A $^1H$ NMR (400 MHz, DMSO) δ 8.35-8.13 (m, 1H), 7.41-7.16 (m, 4H), 7.01-6.51 (m, 2H), 6.51-6.19 (m, 1H), 5.29-4.62 (m, 2H), 4.38-3.93 (m, 4H), 3.88-3.64 (m, 2H), 3.42-3.02 (m, 3H), 2.19 (d, J=7.9 Hz, 1H), 1.89 (s, 2H), 1.63-1.52 (m, 1H), 1.47 (td, J=7.3, 2.3 Hz, 3H), 1.37-1.24 (m, 1H).

Example 32

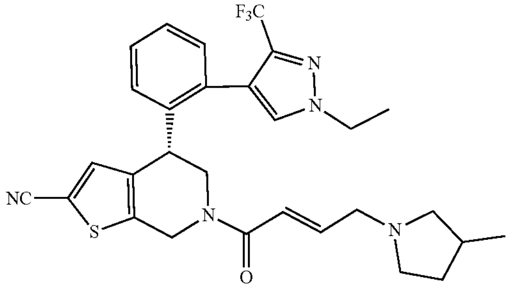 [SMILES: CCn1cc(-c2ccccc2[C@@H]2CN(C(=O)/C=C/CN3CCC(C)C3)Cc3sc(C#N)cc32)c(C(F)(F)F)n1]

4S)-4-(2-(1-ethyl-3-(trifluoromethyl)-1H-pyrazol-4-yl)phenyl)-6-((E)-4-(3-methylpyrrolidin-1-yl)but-2-enoyl)-4,5,6,7-tetrahydrothieno[2,3-c]pyridine-2-carbonitrile Step 1: To a suspension of (E)-methyl 4-bromobut-2-enoate (483 mg, 2.7 mmoL) and $K_2CO_3$ (1.02 g, 7.38 mmol) in THE (10 ml) was added 3-methylpyrrolidine hydrochloride (300 mg, 2.46 mmol) and the mixture was stirred at 35° C. for 1.5 h. The mixture was concentrated and purified by flash column chromatography (DCM: MeOH=95:5) to afford (E)-methyl 4-(3-methylpyrrolidin-1-yl)but-2-enoate (248 mg, 55% yield) as a yellow solid. LCMS: $(M+H)^+$=184.1; Retention time=1.33 min. LCMS CP Method E Step 2: To a mixture of (E)-methyl 4-(3-methylpyrrolidin-1-yl)but-2-enoate (330 mg, 1.8 mmol), THF (4 ml) and $H_2O$ (2 ml) was added LiOH·$H_2O$ (151 mg, 3.6 mmol) and the reaction was stirred at RT for 1.5 h. The pH of the solution was adjusted to 5-6 with HCl (1 N). The solution was concentrated in vacuum to afford (E)-4-(3-methylpyrrolidin-1-yl)but-2-enoic acid (300 mg, 100% yield) as a white solid. LCMS: $(M+H)^+$=170.0; Retention time=0.36 min. LCMS CP Method E Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (80 mg, 0.2 mmol), DIPEA (103 mg, 0.8 mmol) and (E)-4-(3-methylpyrrolidin-1-yl)but-2-enoic acid (step 2, 101 mg, 0.6 mmol) in DMF (5 ml) was added HATU (114 mg, 0.3 mmol) and the reaction was stirred at RT for 2 h. Water (30 ml) was added and the mixture was extracted with EA (3×20 ml). The combined organic phases were washed with brine, dried over $Na_2SO_4$, filtered and concentrated to afford a residue which was purified by Prep-HPLC (Method A) to afford (4S)-4-(2-(1-ethyl-3-(trifluoromethyl)-1H-pyrazol-4-yl)phenyl)-6-((E)-4-(3-methylpyrrolidin-1-yl)but-2-enoyl)-4,5,6,7-tetrahydrothieno[2,3-c]pyridine-2-carbonitrile (40.7 mg, 37% yield) as a yellow solid. LCMS: $(M+H)^+$=554.2; Retention time=1.62 min. LCMS CP Method A. $^1H$ NMR (400 MHz, DMSO) δ: 8.29-8.20 (m, 1H), 7.39-7.24 (m, 4H), 6.91-6.74 (m, 1H), 6.62-6.47 (m, 1H), 5.88 (d, J=14.8 Hz, 1H), 5.10-4.75 (m, 2H), 4.27 (dd, J=14.0, 6.8 Hz, 2H), 4.13-3.95 (m, 1H), 3.77-3.62 (m, 1 H), 3.31 (s, 1H), 3.21-2.96 (m, 2H), 2.65-2.56 (m, 1H), 2.43-2.28 (m, 2H), 2.11-1.83 (m, 3H), 1.46 (t, J=7.6 Hz, 3H), 1.24-1.22 (m, 1H), 0.95-0.93 (m, 3H).

Example 33

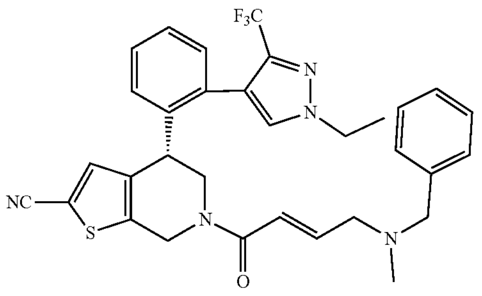 [SMILES: CCn1cc(-c2ccccc2[C@@H]2CN(C(=O)/C=C/CN(C)Cc3ccccc3)Cc3sc(C#N)cc32)c(C(F)(F)F)n1]

(S,E)-6-(4-(benzyl(methyl)amino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 50-mL round-bottomed flask were added methyl (E)-4-bromobut-2-enoate (1 g, 5.6 mmol), $K_2CO_3$ (2.3 g, 16.9 mmol), N-methyl-1-phenylmethanamine (811 mg, 6.7 mmol) and DMF (10 mL). The reaction was stirred at 60° C. for 16 h. To the reaction mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by flash column chromatography (silica, MeOH/DCM=1:10) to provide methyl (E)-4-(benzyl(methyl)amino)but-2-enoate (550 mg, 2.5 mmol, 44.7% yield) as a yellow solid. LCMS: $(M+H)^+$=220; Retention time=1.124 min. LCMS CP Method B Step 2: To a 50-mL round-bottomed flask were added methyl (E)-4-(benzyl(methyl)amino)but-2-enoate (step 1, 550 mg, 2.5 mmol), LiOH·$H_2O$ (211 mg, 5 mmol) and THE/$H_2O$=1:1 (2 mL). The reaction was stirred at 45° C. for 2 h. To the mixture at RT was added 1 N HCl (10 mL) and the mixture was extracted with EA (2×10 mL). The combined organic extracts were washed with saturated NaCl aqueous solution (2×10 mL), dried over $Na_2SO_4$. Filtered and concentrated to provide (E)-4-(benzyl(methyl)amino)but-2-enoic acid (300 mg, 1.5 mmol, 58.3% yield) as a white solid which was used directly in the next step reaction without further purification. LCMS: $(M+H)^+$=206; Retention time=1.055 min. LCMS CP Method B Step 3: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4-(benzyl(methyl)amino)but-2-enoic acid (step 2, 75.9 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (Method A) to provide (S,E)-6-(4-(benzyl(methyl)amino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (10.7 mg, 0.02 mmol, 7.8% yield) as a white solid. LCMS: $(M+H)^+$=590; Retention time=1.679 min. LCMS CP Method A. $^1H$ NMR (400 MHz, DMSO) δ 8.23 (d, J=28.7 Hz, 1H), 7.48-7.14 (m, 9H), 6.85-6.35 (m, 2H), 5.92 (d, J=15.3 Hz, 1H), 5.20-4.68 (m, 2H), 4.41-4.04 (m, 3H), 3.99-3.53 (m, 2H), 3.52-3.39 (m, 1H), 3.37 (d, J=3.4 Hz, 1H), 3.32 (s, 1H), 3.17-2.81 (m, 2H), 2.03 (d, J=58.7 Hz, 3H), 1.43 (t, J=7.2 Hz, 3H).

Example 34

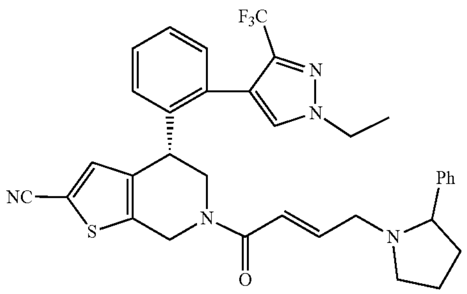 [SMILES: CCn1cc(-c2ccccc2[C@@H]2CN(C(=O)/C=C/CN3CCCC3c3ccccc3)Cc3sc(C#N)cc32)c(C(F)(F)F)n1]

(4S)-4-(2-(1-ethyl-3-(trifluoromethyl)-1H-pyrazol-4-yl)phenyl)-6-((E)-4-(2-phenylpyrrolidin-1-yl)but-2-enoyl)-4,5,6,7-tetrahydrothieno[2,3-c]pyridine-2-carbonitrile Step 1: To a solution of methyl (E)-4-bromobut-2-enoate (0.266 g, 1.49 mmol) in N,N-DMF (5 mL) were added $K_2CO_3$ (0.563 g, 4.08 mmol) and 2-phenylpyrrolidine (0.200 g, 0.1.36 mmol) at RT. The reaction was heated to 50° C. and stirred for 2 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (PE: EA=5:1) to give methyl (E)-4-(2-phenylpyrrolidin-1-yl)but-2-enoate (0.240 g, 72.0% yield) as a yellow oil. LCMS: $(M+H)^+$=246.1, Retention time=1.91 min. LCMS CP method G Step 2: To a solution of methyl (E)-4-(2-phenylpyrrolidin-1-yl)but-2-enoate (step 1, 0.240 g, 0.979 mmol) in THE: $H_2O$ (3:1, 3 mL) was added LiOH·$H_2O$ (0.123 g, 2.94 mmol) at RT and the reaction was stirred overnight. The mixture was acidified with aqueous HCl (1 M) to pH=5-6 and the mixture was concentrated in vacuum to give the crude (E)-4-(2-phenylpyrrolidin-1-yl)but-2-enoic acid (0.300 g, crude) as a yellow oil. LCMS: $(M+H)^+$=232.0, Retention time=1.15 min. LCMS CP method G Step 3: A mixture of (S)-4-(2-(1-ethyl-3-(trifluoromethyl)-1H-pyrazol-4-yl)phenyl)-4,5,6,7-tetrahydrothieno[2,3-c]pyridine-2-carbonitrile (80 mg, 0.2 mmol), (E)-4-(2-phenylpyrrolidin-1-yl)but-2-enoic acid (step 2, 139 mg, 0.6 mmol), HATU (114 mg, 0.3 mmol) and DIPEA (77 mg, 0.6 mmol) and DCM (5 ml) was stirred at RT for 1 h. Water (10 ml) was added and the mixture was extracted with DCM (3×15 ml). The combined organic phases were washed with brine, dried over $Na_2SO_4$, filtered and concentrated. The residue was purified by Prep-HPLC (Method A) to afford (4S)-4-(2-(1-ethyl-3-(trifluoromethyl)-1H-pyrazol-4-yl)phenyl)-6-((E)-4-(2-phenylpyrrolidin-1-yl)but-2-enoyl)-4,5,6,7-tetrahydrothieno[2,3-c]pyridine-2-carbonitrile (31.2 mg, 25% yield) as a white solid. $^1H$ NMR (400 MHz, DMSO) δ 8.26-8.19 (m, 1H), 7.43-7.24 (m, 9H), 6.97-6.73 (m, 1H), 6.57-6.47 (m, 1H), 5.87 (d, J=14.4 Hz, 1H), 5.17-5.06 (m, 1H), 4.79-4.68 (m, 1H), 4.27-4.13 (m, 3H), 3.78-3.58 (m, 2H), 3.28-3.07 (m, 2H), 2.95-2.85 (m, 1H), 2.63-2.55 (m, 1H), 2.11-1.98 (m, 2H), 1.80-1.68 (m, 2H), 1.56-1.38 (m, 4H). LCMS: $(M+H)^+$=616.1, Retention time=2.104 min. LCMS CP method F Example 35

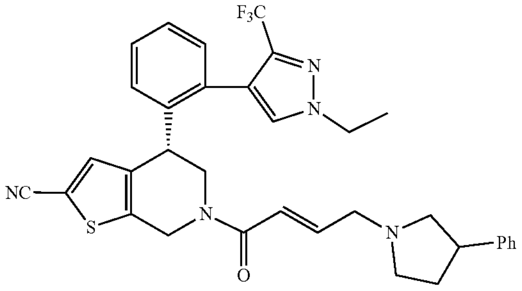 [SMILES: CCn1cc(-c2ccccc2[C@@H]2CN(C(=O)/C=C/CN3CCC(c4ccccc4)C3)Cc3sc(C#N)cc32)c(C(F)(F)F)n1]

(4S)-4-(2-(1-ethyl-3-(trifluoromethyl)-1H-pyrazol-4-yl)phenyl)-6-((E)-4-(3-phenylpyrrolidin-1-yl)but-2-enoyl)-4,5,6,7-tetrahydrothieno[2,3-c]pyridine-2-carbonitrile Step 1: To a suspension of (E)-methyl 4-bromobut-2-enoate (402 mg, 2.25 mmoL) and $K_2CO_3$ (746 mg, 6.12 mmol) in THF (5 ml) was added 3-phenylpyrrolidine (300 mg, 2.04 mmol) and the reaction was stirred at 35° C. for 1.5 h. The mixture was concentrated and the residue was purified by flash column chromatography (DCM: MeOH=97: 3) to afford (E)-methyl 4-(3-phenylpyrrolidin-1-yl)but-2-enoate (371 mg, 74% yield) as a yellow solid. LCMS: $(M+H)^+$ =246.1; Retention time=1.57 min. LCMS CP Method E Step 2: To a solution of (E)-methyl 4-(3-phenylpyrrolidin-1-yl)but-2-enoate (step 1, 495 mg, 2.02 mmol) in THF (8 ml) and $H_2O$ (4 ml) was added $LiOH \cdot H_2O$ (170 mg, 4.04 mmol) and the mixture was stirred at RT for 1.5 h. The pH of the solution was adjusted to 5-6 with HCl (1 N) and the solution was concentrated in vacuum to afford (E)-4-(4-methylpiperazin-1-yl)but-2-enoic acid (460 mg, 100% yield) as a white solid. LCMS: $(M+H)^+$=232.0; Retention time=1.00 min. LCMS CP Method D Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (80 mg, 0.2 mmol), DIPEA (103 mg, 0.8 mmol) and (E)-4-(3-phenylpyrrolidin-1-yl)but-2-enoic acid (step 2, 139 mg, 0.6 mmol) in DMF (5 ml) was added HATU (114 mg, 0.3 mmol) and the reaction was stirred at RT for 2 h. Water (30 ml) was added and the mixture was extracted with EA (3×20 ml). The combined organic phases were washed with brine, dried over $Na_2SO_4$, filtered and concentrated to afford a residue which was purified by Prep-HPLC ($NH_4HCO_3$ 0.1%) to afford (4S)-4-(2-(1-ethyl-3-(trifluoromethyl)-1H-pyrazol-4-yl)phenyl)-6-((E)-4-(3-phenylpyrrolidin-1-yl)but-2-enoyl)-4,5,6,7-tetrahydrothieno[2,3-c]pyridine-2-carbonitrile (52.5 mg, 43% yield) as a yellow solid. LCMS: $(M+H)^+$=616.2; Retention time=1.76 min. LCMS CP Method A. $^1H$ NMR (400 MHz, DMSO) δ: 8.28-8.18 (m, 1H), 7.38-7.17 (m, 9H), 6.74-6.52 (m, 2H), 5.92 (d, J=14.8 Hz, 1H), 5.11-4.75 (m, 2H), 4.28-4.13 (m, 3H), 3.95-3.60 (m, 2H), 3.28-3.23 (m, 2H), 3.10-3.04 (m, 2H), 3.00-2.57 (m, 2H), 2.29-2.27 (m, 2H), 1.70 (s, 1H), 1.47-1.42 (m, 3H).

Example 36

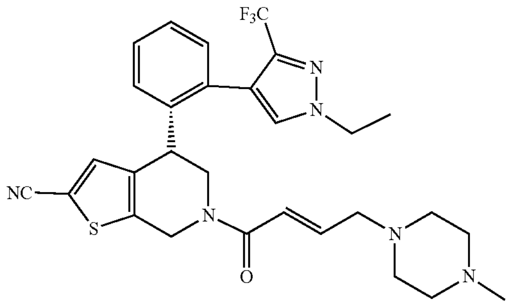

(S,E)-4-(2-(1-ethyl-3-(trifluoromethyl)-1H-pyrazol-4-yl)phenyl)-6-(4-(4-methyl piperazin-1-yl)but-2-enoyl)-4,5,6,7-tetrahydrothieno[2,3-c]pyridine-2-carbonitrile Step 1: To a suspension of (E)-methyl 4-bromobut-2-enoate (985 mg, 5.5 mmol) and $K_2CO_3$ (2.07 g, 15 mmol) in THF (15 ml) was added 1-methylpiperazine (500 mg, 5 mmol) and the reaction was stirred at 35° C. for 1.5 h. The mixture was concentrated and purified by flash column chromatography (DCM: MeOH=92: 8) to afford (E)-methyl 4-(4-methylpiperazin-1-yl)but-2-enoate (810 mg, 82% yield) as a yellow solid. LCMS: $(M+H)^+$=199.0; Retention time=0.97 min. LCMS CP Method D Step 2: To a mixture of (E)-methyl 4-(4-methylpiperazin-1-yl)but-2-enoate (step 1. 400 mg, 2.02 mmol) in THE (8 ml) and $H_2O$ (4 ml) was added $LiOH \cdot H_2O$ (170 mg, 4.04 mmol) and the reaction was stirred at RT for 1.5 h. The pH of the solution was adjusted to 5-6 with HCl (1N). The solution was concentrated in vacuum to afford (E)-4-(4-methylpiperazin-1-yl)but-2-enoic acid (371 mg, 100% yield) as a white solid. LCMS: $(M+H)^+$=185.1; Retention time=0.33 min. LCMS CP Method E Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (80 mg, 0.2 mmol), DIPEA (103 mg, 0.8 mmol) and (E)-4-(4-methylpiperazin-1-yl)but-2-enoic acid (step 2, 110 mg, 0.6 mmol) in DMF (5 ml) was added HATU (114 mg, 0.3 mmol) and the reaction was stirred at RT for 2 h. Water (30 ml) was added and the mixture was extracted with EA (3×20 ml). The combined organic phases were washed with brine, dried over $Na_2SO_4$, filtered and concentrated to give a residue which was purified by Prep-HPLC (Method B) to afford (S,E)-4-(2-(1-ethyl-3-(trifluoromethyl)-1H-pyrazol-4-yl)phenyl)-6-(4-(4-methylpiperazin-1-yl)but-2-enoyl)-4,5,6,7-tetrahydrothieno[2,3-c]pyridine-2-carbonitrile (11 mg, 8.9% yield) as a yellow solid. LCMS: $(M+H)^+$=569.3; Retention time=1.55 min. LCMS CP Method A. $^1H$ NMR (400 MHz, DMSO) δ: 8.30-8.14 (m, 1H), 7.40-7.25 (m, 4H), 6.91-6.72 (m, 1H), 6.46-6.42 (m, 1H), 5.88 (d, J=15.2 Hz, 1H), 5.14-4.73 (m, 2H), 4.27 (dd, J=14.0, 6.8 Hz, 2H), 4.15 (s, 1H), 3.76-3.62 (m, 2H), 3.09-2.83 (m, 5H), 2.40-2.27 (m, 8H), 1.46 (t, J=7.6 Hz, 3H).

Example 37

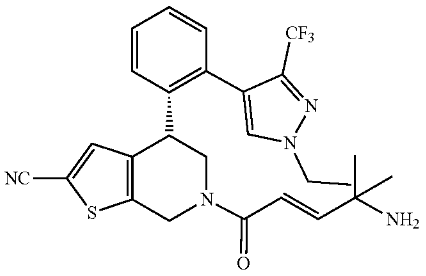

(S,E)-6-(4-amino-4-methylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (0.500 g, 1.24 mmol) in DMF (10 mL) were added 2-(diethoxyphosphoryl)acetic acid (0.292 g, 1.49 mmol), HATU (0.709 g, 1.87 mmol) and DIEA (0.481 g, 3.73 mmol) at RT. The reaction was stirred for 1 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (DCM: MeOH=20:1) to give diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (0.620 g, 1.07 mmol, 85.9% yield) as a brown oil. LCMS: $(M+H)^+$=581.0, Retention time=1.89 min. LCMS CP method G Step 2: To a solution of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (step 1, 0.620 g, 1.07 mmol) in ACN (15 mL) were added tert-butyl (2-methyl-1-oxopropan-2-yl)carbamate (0.219 g, 1.17 mmol), LiCl (0.0898 g, 2.14 mmol) and DIEA (0.276 g, 2.14 mmol) at RT. The reaction was stirred at RT for 2 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (DCM: MeOH=15:1) to give a tert-butyl (S,E)-(5-(2-cyano-4-(2-(1-ethyl-3-(trifluoromethyl)-1H-pyrazol-4-yl)phenyl)-4,7-dihydrothieno[2,3-c]pyridin-6(5H)-yl)-2-methyl-5-oxopent-3-en-2-yl)carbamate (0.580 g, 0.946 mmol, 80.2% yield) as a yellow oil. LCMS: $(M-56+H)^+$=558.0, Retention time=2.08 min. LCMS CP method G Step 3: To a solution of tert-butyl (S,E)-(5-(2-cyano-4-(2-(1-ethyl-3-(trifluoromethyl)-1H-pyrazol-4-yl)phenyl)-4,7-dihydrothieno[2,3-c]pyridin-6(5H)-yl)-2-methyl-5-oxopent-3-en-2-yl)carbamate (0.0400 g, 0.0653 mmol) in DCM (1 mL) was added TFA (1 mL) at RT. The resulting mixture was stirred at RT for 1 h. The mixture was concentrated in vacuum to give a residue which was purified by Prep-HPLC (method C) to give (S,E)-6-(4-amino-4-methylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (0.0232 g, 0.0452 mmol, 69.3% yield) as a white solid. LCMS: $(M+H)^+$=514.2, purity=100% (214 nm), Retention time=1.57 min. LCMS CP method B. $^1H$ NMR (400 MHz, DMSO): δ 8.21-8.08 (m, 1H), 7.35-7.26 (m, 4H), 6.99-6.65 (m, 2H), 5.99-5.96 (m, 1H), 5.18-4.80 (m, 2H), 4.29-4.25 (m, 3H), 3.99- 3.88 (m, 1H), 3.68-3.55 (m, 2H), 3.42-3.39 (m, 1H), 1.49-1.41 (m, 5H), 1.27-1.15 (m, 4H).

Example 38

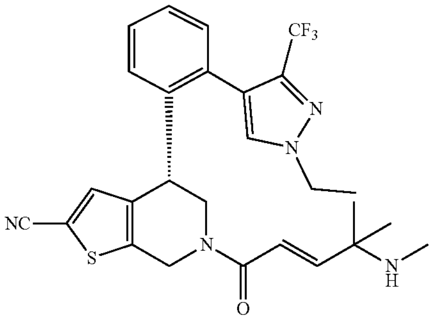 [SMILES: CCn1cc(-c2ccccc2[C@@H]2CN(C(=O)/C=C/C(C)(C)NC)Cc3sc(C#N)cc32)c(C(F)(F)F)n1]

(S,E)-4-(2-(1-ethyl-3-(trifluoromethyl)-1H-pyrazol-4-yl)phenyl)-6-(4-methyl-4-(methyl amino)pent-2-enoyl)-4,5,6,7-tetrahydrothieno[2,3-c]pyridine-2-carbonitrile Step 1: A mixture of (S)-diethyl 2-(2-cyano-4-(2-(1-ethyl-3-(trifluoromethyl)-1H-pyrazol-4-yl)phenyl)-4,5-dihydrothieno[2,3-c]pyridin-6(7H)-yl)-2-oxoethylphosphonate (580 mg, 1 mmol), tert-butyl 2-methyl-1-oxopropan-2-ylcarbamate (187 mg, 1 mmol), LiCl (42 mg, 1.0 mmol) and DIPEA (129 mg, 1 mml) in McCN (10 ml) was stirred at RT overnight. The mixture was filtered and concentrated in vacuum to give a residue which was purified by Prep-HPLC (Method A) to give (S,E)-tert-butyl 5-(2-cyano-4-(2-(1-ethyl-3-(trifluoromethyl)-1H-pyrazol-4-yl)phenyl)-4,5-dihydrothieno[2,3-c]pyridin-6(7H)-yl)-2-methyl-5-oxopent-3-en-2-ylcarbamate (520 mg, 85% yield) as a brown solid. LCMS: (M−55)+=558.1; Retention time=1.86 min. LCMS CP Method G Step 2: To a solution of (S,E)-tert-butyl 5-(2-cyano-4-(2-(1-ethyl-3-(trifluoromethyl)-1H-pyrazol-4-yl)phenyl)-4,5-dihydrothieno[2,3-c]pyridin-6(7H)-yl)-2-methyl-5-oxo-pent-3-en-2-ylcarbamate (306 mg, 0.5 mmol) in DCM (5 mL) at RT was added TFA (1 mL). The reaction was stirred for 1 h. The mixture was concentrated to give a residue which was diluted with water (10 mL). The mixture was extracted with DCM (3×20 mL), and the combined organic layers were neutralized with saturated $NaHCO_3$ to pH=8-9. The organic layer was dried over anhydrous $Na_2SO_4$, filtered and concentrated in vacuum to give (S,E)-6-(4-amino-4-methylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile as a yellow solid (260 mg, 100% yield) which was used directly in the next step reaction without further purification. LCMS: $(M-16, M+1)^+$=497.0, 514.0; Retention time=1.64 min. LCMS CP Method G Step 3: To a solution of (S,E)-6-(4-amino-4-methylpent-2-enoyl)-4-(2-(1-ethyl-3-(trifluoromethyl)-1H-pyrazol-4-yl) phenyl)-4,5,6,7-tetrahydrothieno[2,3-c]pyridine-2-carbonitrile (step 2, 128 mg, 0.25 mmol) in formic acid (1.2 mL) were added $NaBH_3CN$ (38 mg, 0.5 mmol) and formalin (0.04 ml, 0.5 mmol). The reaction was stirred 9000 overnight. The mixture was purified by Prep-HPLC (Method A) to give (S,E)-4-(2-(1-ethyl-3-(trifluoromethyl)-1H-pyrazol-4-yl)phenyl)-6-(4-methyl-4-(methylamino)pent-2-enoyl)-4,5,6,7-tetrahydrothieno[2,3-c]pyridine-2-carbonitrile (25 mg, 20% yield) as a brown solid. LCMS: $(M+1)^+$=528.1, Retention time=1.71 min. LCMS CP Method G. $^1H$ NMR (400 MHz, DMSO-$d_6$) δ 8.26 (s, 1H), 7.40-7.25 (m, 5H), 6.94-6.47 (m, 2H), 5.70-4.72 (m, 3H), 4.29-4.24 (m, 2H), 4.13-3.98 (m, 1H), 3.81-3.68 (m, 2H), 2.11-1.95 (m, 3H), 1.46 (t, 3H), 1.13-0.83 (m, 6H).

Example 39

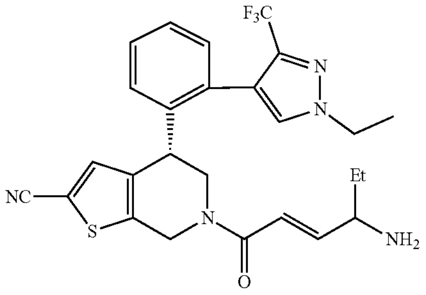 [SMILES: CCC(N)/C=C/C(=O)N1Cc2sc(C#N)cc2[C@H](c2ccccc2-c2cn(CC)nc2C(F)(F)F)C1]

(4S)-6-((E)-4-aminohex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 500-mL round-bottomed flask were added 2-aminobutan-1-ol (10 g, 112 mmol), TEA (23 g, 225 mmol), $(Boc)_2O$ (73 g, 337 mmol) and DCM (100 mL). The reaction was stirred at 40° C. for 16 h. To the mixture at RT was added $H_2O$ (300 mL) and the mixture was extracted with EA (2×150 mL). The combined organic extracts were washed with saturated NaCl aqueous solution (2×300 mL), dried over $Na_2SO_4$, filtered and concentrated to give a residue which was purified by flash column chromatography (silica, EA/PE=1:1) to provide tert-butyl (1-hydroxybutan-2-yl)carbamate (6 g, 31.7 mmol, 28.2% yield) as a yellow oil. LCMS: $(M+Na)^+$=212; Retention time=1.428 min. LCMS CP Method A Step 2: To a 250-mL round-bottomed flask were added tert-butyl (1-hydroxybutan-2-yl)carbamate (step 1, 6 g, 31.7 mmol), DMP (16 g, 38 mmol) and DCM (100 mL). The reaction was stirred at RT for 1 h. To the mixture at RT was added $H_2O$ (400 mL) and the mixture was extracted with DCM (2×100 mL). The combined organic extracts were washed with saturated NaCl aqueous solution (2×200 mL), dried over $Na_2SO_4$, filtered and concentrated to provide tert-butyl (1-oxobutan-2-yl)carbamate (2.2 g, 11.7 mmol, 37.1% yield) as a colorless oil which was used directly in the next step reaction without further purification.

Step 3: To a 100-mL round-bottomed flask were added tert-butyl (1-oxobutan-2-yl)carbamate (2.2 g, 11.7 mmol), LiCl (741 mg, 17.6 mmol), DIPEA (2.3 g, 17.6 mmol), ethyl 2-(diethoxyphosphoryl)acetate (5.6 g, 17.6 mmol) and $CH_3CN$ (50 mL). The reaction was stirred at RT for 4 h. To the mixture at RT was added $H_2O$ (100 mL) and the mixture was extracted with EA (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:10). to provide ethyl (E)-4-((tert-butoxycarbonyl)amino)hex-2-enoate (2 g, 7.8 mmol, 66.1% yield) as a yellow solid. LCMS: $(M+Na)^+$=280; Retention time=1.704 min. LCMS CP Method B Step 4: To a 50-mL round-bottomed flask were added ethyl (E)-4-((tert-butoxycarbonyl)amino)hex-2-enoate (step 3, 1 g, 3.9 mmol) and $LiOH \cdot H_2O$ (327 mg, 7.8 mmol) as a solution in THF/$H_2O$=1:1 (10 mL). The reaction was stirred at RT for 2 h. To the mixture at RT was added 1 N HCl (50 mL) and the mixture was extracted with EA (2×50 mL). The combined organic extracts were washed with saturated NaCl aqueous solution (2×50 mL), dried over $Na_2SO_4$, filtered and concentrated to give a residue which was purified by Prep-HPLC (method A) to provide (E)-4-((tert-butoxycarbonyl)amino)hex-2-enoic acid (700 mg, 3.1 mmol, 78.6% yield) as a white solid. LCMS: $(M+Na)^+$=252; Retention time=1.463 min. LCMS CP Method B Step 5: To a 50-mL round-bottomed flask were added (E)-4-((tert-butoxycarbonyl)-amino)hex-2-enoic acid (step 4, 55 mg, 0.24 mmol), DIPEA (94 mg, 0.73 mmol), (S)-4-(2-(1-ethyl-3-(trifluoromethyl)-1H-pyrazol-4-yl)phenyl)-4,5,6,7-tetrahydrothieno[2,3-c]pyridine-2-carbonitrile (118 mg, 0.15 mmol), HATU (139 mg, 0.37 mmol) and DMF (4 mL). The reaction was stirred at RT for 2 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method A) to provide tert-butyl ((E)-6-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-6-oxohex-4-en-3-yl)carbamate (70 mg, 0.11 mmol, 38.9% yield) as a yellow solid. LCMS: $(M-56+H)^+$=558; Retention time=1.890 min. LCMS CP Method B Step 6: To a 50-mL round-bottomed flask were added tert-butyl ((E)-6-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-6-oxohex-4-en-3-yl)carbamate (step 5, 70 mg, 0.11 mmol) and TFA (108 mg, 1.1 mmol) as a solution in DCM (2 mL). The reaction was stirred at RT for 2 h To the mixture at RT was added saturated $NaHCO_3$ aqueous solution (10 mL) and the mixture was extracted with DCM (2×10 mL). The combined organic extracts was washed with saturated NaCl aqueous solution (2×10 mL), dried over $Na_2SO_4$, filtered and concentrated to give a residue which was purified by Prep-HPLC (method A) to provide (4S)-6-((E)-4-aminohex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (16.6 mg, 0.03 mmol, 28.3% yield) as a white solid. LCMS: $(M+H)^+$=514; Retention time=1.559 min. LCMS CP Method B. $^1H$ NMR (400 MHz, DMSO) δ 8.40-8.10 (m, 1H), 8.00 (s, 2H), 7.63-7.12 (m, 4H), 7.01-6.67 (m, 1H), 6.55-5.96 (m, 1H), 5.44-4.48 (m, 2H), 4.40-4.05 (m, 3H), 4.00-3.40 (m, 3H), 3.25 (s, 1H), 1.81-1.18 (m, 5H), 0.97-0.45 (m, 3H).

Example 40

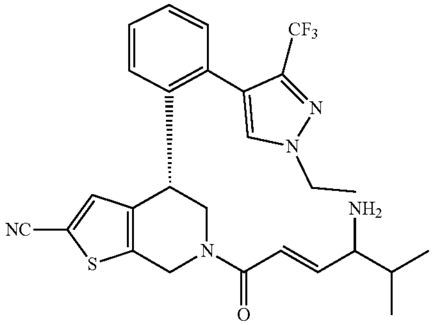 [SMILES: CCn1cc(-c2ccccc2[C@@H]2CN(C(=O)/C=C/C(N)C(C)C)Cc3sc(C#N)cc32)c(C(F)(F)F)n1]

(4S)-6-((E)-4-amino-5-methylhex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of 2-amino-3-methylbutan-1-ol (2 g, 19.42 mmol) and TEA (3.92 g, 38.84 mmol) in mixed DCM (20 ml) and $H_2O$ (4 ml) was added $(Boc)_2O$ (6.35 g, 29.13 mmol) at 0° C. and the reaction was stirred at RT for 16 h. Water (30 ml) was added and the mixture was extracted with DCM (30 ml×3). The combined organic phases were washed with brine, dried over $Na_2SO_4$, filtered and concentrated to afford tert-butyl 1-hydroxy-3-methylbutan-2-ylcarbamate (3 g, 76% yield) as a yellow oil. $^1H$ NMR (400 MHz, $CDCl_3$) δ: 4.65 (s, 1H), 5.89-5.84 (m, 1H), 3.73-3.69 (m, 1H), 3.63-3.59 (m, 1H), 3.43 (s, 1H), 1.86-1.81 (m, 1H), 1.45 (s, 9H), 0.97-0.91 (m, 6H). Purify=100%

Step 2: A solution of tert-butyl 1-hydroxy-3-methylbutan-2-ylcarbamate (step 1, 200 mg, 0.99 mmol) and DMP (627 mg, 1.48 mmol) in DCM (5 ml) was stirred at RT for 2 h. Water (20 ml) was added and the mixture was extracted with DCM (20 ml×3). The combined organic phases were washed with brine, dried over $Na_2SO_4$, filtered and concentrated to give a residue which was purified by flash (PE: EA=5: 1) to afford tert-butyl 3-methyl-1-oxobutan-2-ylcarbamate (150 mg, 75% yield) as a yellow oil. $^1H$ NMR (400 MHz, $CDCl_3$) δ: 9.65 (s, 1H), 5.10 (s, 1H), 4.27-4.24 (m, 1H), 2.32-2.27 (m, 1H), 1.46 (s, 9H), 1.03 (d, J=6.8 Hz, 3H), 0.95 (d, J=6.8 Hz, 3H). Purify=100%

Step 3: To a solution of (S)-diethyl 2-(2-cyano-4-(2-(1-ethyl-3-(trifluoromethyl)-1H-pyrazol-4-yl)phenyl)-4,5-dihydrothieno[2,3-c]pyridin-6(7H)-yl)-2-oxoethylphosphonate (340 mg, 0.58 mmol) and LiCl (29 mg, 0.7 mmol) in $CH_3CN$ (5 ml) at RT were added DIPEA (90 mg, 0.324 mmol) and tert-butyl 3-methyl-1-oxobutan-2-ylcarbamate (step 2, 150 mg, 0.75 mmol) and the mixture was stirred at 25° C. for 16 h. Filtered and concentrated. The residue was purified by Prep-TLC (DCM: MeOH=25:1) to afford tert-butyl (E)-6-((S)-2-cyano-4-(2-(1-ethyl-3-(trifluoromethyl)-1H-pyrazol-4-yl)phenyl)-4,5-dihydrothieno[2,3-c]pyridin-6(7H)-yl)-2-methyl-6-oxohex-4-en-3-ylcarbamate (340 mg, 93% yield) as a yellow solid. LCMS: $(M-55+H)^+$=572.3; Retention time=1.92 min. LCMS CP Method B Step 4: A solution of tert-butyl (E)-6-((S)-2-cyano-4-(2-(1-ethyl-3-(trifluoromethyl)-1H-pyrazol-4-yl)phenyl)-4,5-dihydrothieno[2,3-c]pyridin-6(7H)-yl)-2-methyl-6-oxohex-4-en-3-ylcarbamate (step 3, 340 mg, 0.54 mmol) in mixed DCM (5 ml) and TFA (1 ml) was stirred at RT for 1 h. The mixture was concentrated and purification of Prep-HPLC (Method B) to afford (4S)-6-((E)-4-amino-5-methylhex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (280 mg, 88% yield) as a yellow solid. LCMS: $(M+H)^+$=528.2; Retention time=1.60 min. LCMS CP Method A $^1H$ NMR (400 MHz, DMSO) δ: 8.32-8.31 (m, 1H), 7.30-7.25 (m, 4H), 6.95-6.80 (m, 1H), 6.57-6.51 (m, 1H), 5.92 (d, J=15.2 Hz, 1H), 5.16-4.94 (m, 2H), 4.30-4.25 (m, 2H), 4.10-3.89 (m, 3H), 3.62-3.57 (m, 2H), 3.00 (s, 1H), 1.65-1.557 (m, 1H), 1.47-1.43 (m, 3H), 0.82-0.74 (m, 6H).

Example 41

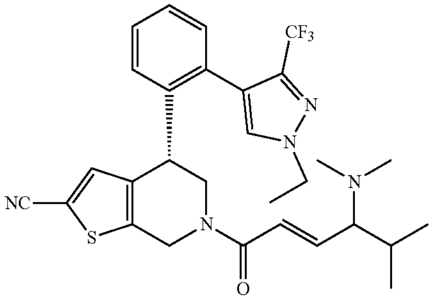 [SMILES: CCn1cc(-c2ccccc2[C@@H]2CN(C(=O)/C=C/C(C(C)C)N(C)C)Cc3sc(C#N)cc32)c(C(F)(F)F)n1]

(4S)-6-((E)-4-(dimethylamino)-5-methylhex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile To a solution of (4S)-6-((E)-4-amino-5-methylhex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (180 mg, 0.34 mmol), formaldehyde (0.4M in water) (103 mg, 1.37 mmol) and HOAc (a drop) in MeOH (5 ml) at RT was added $NaBH_3CN$ (86 mg, 1.37 mmol) and the mixture was stirred at RT for 1 h. LCMS indicated the product was formed. Water (15 ml) was added and the mixture was extracted with DCM (3×15 ml). The combined organic phases were washed with brine, dried over $Na_2SO_4$, filtered and concentrated to give a residue which was purified by Prep-HPLC ($NH_4HCO_3$ 0.1%) to afford (4S)-6-((E)-4-(dimethylamino)-5-methylhex-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (59.1 mg, 31% yield) as a yellow solid. LCMS: $(M+H)^+$=556.2; Retention time=2.02 min. LCMS CP Method C $^1H$ NMR (400 MHz, DMSO) δ: 8.28-8.15 (m, 1H), 7.48-7.26 (m, 4H), 6.95-6.75 (m, 1H), 6.47-6.40 (m, 1H), 5.67 (d, J=14.8 Hz, 1H), 5.20-4.70 (m, 2H), 4.30-4.22 (m, 3H), 3.80-3.64 (m, 2H), 2.14-1.75 (m, 8H), 1.46 (t, J=7.2 Hz, 3H), 0.88-0.82 (m, 3H), 0.74-0.64 (m, 3H).

Example 42

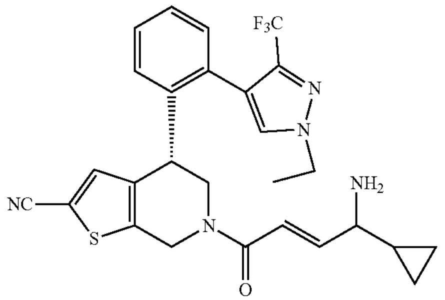 [SMILES: CCn1cc(-c2ccccc2[C@@H]2CN(C(=O)/C=C/C(N)C3CC3)Cc3sc(C#N)cc32)c(C(F)(F)F)n1]

(4S)-6-((E)-4-amino-4-cyclopropylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of 2-amino-2-cyclopropylethan-1-ol (0.500 g, 4.95 mmol) in DCM (10 mL) were added $(Boc)_2O$ (1.29 g, 5.94 mmol) and NaOH (0.594 g, 14.85 mmol) at RT. The reaction was stirred for 2 h. The mixture was diluted with water (20 mL) and extracted with DCM (3×20 mL). The combined organic layers were washed with brine (50 mL), dried over anhydrous $Na_2SO_4$, filtered and concentrated to give a residue which was purified by silica gel chromatography to give tert-butyl (1-cyclopropyl-2-hydroxyethyl)carbamate (0.750 g, 3.73 mmol, 75.4% yield) as a yellow oil. LCMS: $(M-56+H)^+$=146.1, Retention time=1.51 min. LCMS CP method C Step 2: To a solution of tert-butyl (1-cyclopropyl-2-hydroxyethyl)carbamate (step 1, 0.300 g, 1.49 mmol) in DCM (5 mL) was added DMP (1.89 g, 4.47 mmol) at RT and the reaction was stirred for 2 h. The mixture was diluted with water (20 mL) and extracted with EA (3×10 mL). The combined organic layers were dried over anhydrous $Na_2SO_4$, filtered and concentrated in vacuum to give a residue which was purified by silica gel chromatography (PE:EA=10:1 to 1:1) to give a tert-butyl (1-cyclopropyl-2-oxoethyl)carbamate (0.250 g, 1.25 mmol, 84.2% yield) as a white solid.

Step 3: To a solution of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (0.120 g, 0.207 mmol) in ACN (5 mL) were added tert-butyl (1-cyclopropyl-2-oxoethyl)carbamate (step 2, 0.0823 g, 0.414 mmol), LiCl (0.0173 g, 0.414 mmol) and DIEA (0.0534 g, 0.414 mmol) at RT. The reaction was stirred at same temperature for 3 h. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel chromatography (DCM:MeOH=30: 1) to give a tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-cyclopropyl-4-oxobut-2-en-1-yl)carbamate (130 mg, 99%) as a yellow oil. LCMS: $(M-56+H)^+$=570.0, Retention time=2.08 min. LCMS CP method G Step 4: To a solution of tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-cyclopropyl-4-oxobut-2-en-1-yl)carbamate (step 3, 0.130 g, 0.208 mmol) in DCM (4 mL) was added TFA (4 mL) at RT. The resulting mixture was stirred at RT for 2 h. The mixture was concentrated in vacuum to give a residue which was purified Prep-HPLC (method B) to give (4S)-6-((E)-4-amino-4-cyclopropylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (15.5 mg, 0.0295 mmol, 14.2% yield) as a yellow oil. LCMS: $(M+23)^+$=548.0, purity=100% (214 nm), Retention time=1.59 min. LCMS CP method B. $^1$H NMR (400 MHz, DMSO): δ 8.35-8.18 (m, 1H), 7.35-7.21 (m, 4H), 6.98-6.55 (m, 2H), 5.96-5.90 (m, 1H), 5.34-4.90 (m, 2H), 4.35- 4.28 (m, 2H), 4.22-3.60 (m, 4H), 2.68-2.58 (m, 2H), 1.51-1.41 (s, 3H), 0.88-0.64 (m, 1H), 0.44-0.01 (m, 4H).

Example 43

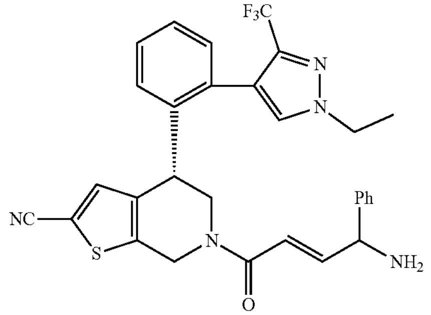 [SMILES: CCn1cc(-c2ccccc2[C@@H]2CN(C(=O)/C=C/C(N)c3ccccc3)Cc3sc(C#N)cc32)c(C(F)(F)F)n1]

(4S)-6-((E)-4-amino-4-cyclopropylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 250-mL round-bottomed flask were added 2-amino-2-phenylethan-1-ol (10 g, 73 mmol), TEA (147 g, 146 mmol), $(Boc)_2O$ (47.7 g, 219 mmol) and DCM (100 mL). The reaction was stirred at 40° C. for 16 h. To the mixture at RT was added $H_2O$ (300 mL) and the mixture was extracted with EA (2×150 mL). The combined organic extracts were washed with saturated NaCl aqueous solution (2×200 mL), dried over $Na_2SO_4$, filtered and concentrated to give a residue which was purified by flash column chromatography (silica, EA/PE=1:2) to provide tert-butyl (2-hydroxy-1-phenylethyl)carbamate (6 g, 25.3 mmol, 34.7% yield) as a yellow oil. LCMS: $(M+Na)^+$=260; Retention time=1.495 min. LCMS CP Method B Step 2: To a 100-mL round-bottomed flask were added tert-butyl (2-hydroxy-1-phenylethyl)carbamate (step 1, 1 g, 4.2 mmol), DMP (2.1 g, 5.1 mmol) and DCM (40 mL). The reaction was stirred at RT for 1 h. To the mixture at RT was added $H_2O$ (100 mL) and the mixture was extracted with DCM (2×50 mL). The combined organic extracts were washed with saturated NaCl aqueous solution (2×50 mL), dried over $Na_2SO_4$, filtered and concentrated to provide tert-butyl (2-oxo-1-phenylethyl)carbamate (650 mg, 2.8 mmol, 65.5% yield) as a colorless oil which was used directly in the next step without further purification.

Step 3: To a 50-mL round-bottomed flask were added tert-butyl (2-oxo-1-phenylethyl)carbamate (step 2, 650 mg, 2.8 mmol), LiCl (172 mg, 4.2 mmol), DIPEA (541 mg, 4.2 mmol), ethyl 2-(diethoxyphosphoryl)acetate (1.3 g, 4.2 mmol) and $CH_3CN$ (20 mL). The reaction was stirred at RT for 4 h. To the mixture at RT was added $H_2O$ (50 mL) and the mixture extracted with EA (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:10) to provide ethyl (E)-4-((tert-butoxycarbonyl)amino)-5-phenylpent-2-enoate (590 mg, 1.9 mmol, 70.5% yield) as a yellow solid. LCMS: $(M+Na)^+$=328; Retention time=1.764 min. LCMS CP Method B Step 4: To a 50-mL round-bottomed flask were added ethyl (E)-4-((tert-butoxycarbonyl)amino)-4-phenylbut-2-enoate (step 3, 200 mg, 0.66 mmol) and $LiOH·H_2O$ (55 mg, 1.3 mmol) as a solution in THE/$H_2O$=1:1 (2 mL). The reaction was stirred at RT for 2 h. To the mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4-((tert-butoxycarbonyl)amino)-4-phenylbut-2-enoic acid (150 mg, 0.54 mmol, 82.6% yield) as a yellow solid which was used directly in the next step reaction without further purification. LCMS: $(M+Na)^+$=300; Retention time=1.557 min. LCMS CP Method B Step 5: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (96.3 mg, 0.74 mmol), (E)-4-((tert-butoxycarbonyl)amino)-4-phenylbut-2-enoic acid (step 4, 102 mg, 0.37 mmol), HATU (141.8 mg, 0.37 mmol) and DMF (2 mL). The reaction was stirred at RT for 1 h. To the mixture at RT was added $H_2O$ (10 mL) and the mixture was extracted with EA (2×10 mL). The combined organic extracts were washed with saturated NaCl aqueous solution (2×10 mL), dried over $Na_2SO_4$, filtered and concentrated to give a residue which was purified by Prep-HPLC (method A) to provide tert-butyl ((E)-4-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-4-oxo-1-phenylbut-2-en-1-yl) carbamate (100 mg, 0.15 mmol, 57.8% yield) as a yellow solid. LCMS: $(M+H)^+$=662; Retention time=1.946 min. LCMS CP Method B Step 6: To a 50-mL round-bottomed flask were added tert-butyl ((E)-4-((S)-2-cyano-4-(2-(1-ethyl-3-(trifluoromethyl)-1H-pyrazol-4-yl)phenyl)-4,7-dihydrothieno[2,3-c] pyridin-6(5H)-yl)-4-oxo-1-phenylbut-2-en-1-yl)carbamate (step 5, 100 mg, 0.15 mmol) and TFA (147 mg, 1.5 mmol) as a solution in DCM (2 mL). The reaction was stirred at RT for 2 h. To the mixture at RT was added saturated $NaHCO_3$ aqueous solution (10 mL) and the mixture was extracted with DCM (2×10 mL), The combined organic extracts were washed with saturated NaCl aqueous solution (2×10 mL), dried over $Na_2SO_4$, filtered and concentrated to give a residue which was purified by Prep-HPLC (method A) to provide (4S)-6-((E)-4-amino-4-phenylbut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (54.4 mg, 0.10 mmol, 64.1% yield) as a white solid. LCMS: $(M+H)^+$=562; Retention time=1.864 min. LCMS OP Method B $^1H$ NMR (400 MHz, DMSO) δ 8.23 (d, J=65.9 Hz, 1H), 8.03-7.83 (m, 2H), 7.63 (t, J=7.3 Hz, 1H), 7.52 (t, J=7.6 Hz, 2H), 7.43-7.19 (m, 4H), 7.03-6.84 (m, 1H), 5.20-4.64 (m, 2H), 4.30-4.04 (m, 3H), 4.00-3.81 (m, 1H), 3.52 (dd, J=14.1, 7.9 Hz, 1H), 3.31 (s, 1H), 3.25-3.13 (m, 1H), 3.05-2.74 (m, 1H), 2.45-2.12 (m, 2H), 1.49-1.28 (m, 3H).

Example 43

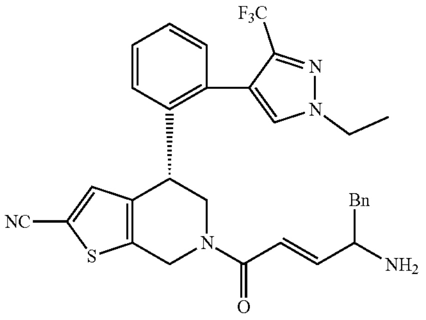 [SMILES: CCn1cc(-c2ccccc2[C@@H]2CN(C(=O)/C=C/C(N)Cc3ccccc3)Cc3sc(C#N)cc32)c(C(F)(F)F)n1]

(4S)-6-((E)-4-amino-5-phenylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a 250-mL round-bottomed flask were added 2-amino-3-phenylpropan-1-ol (10 g, 66.2 mmol), TEA (13.4 g, 132 mmol), $(Boc)_2O$ (43.3 g, 199 mmol) and DCM (100 mL). The reaction was stirred at 40° C. for 16 h. To the mixture at RT was added $H_2O$ (300 mL) and the mixture was extracted with EA (2×150 mL). The combined organic extracts were washed with saturated NaCl aqueous solution (2×200 mL), dried over $Na_2SO_4$, filtered and concentrated to provide tert-butyl (1-hydroxy-3-phenylpropan-2-yl)carbamate (5.8 g, 23.1 mmol, 34.9% yield) as a yellow oil which was used directly in the next step reaction without further purification.

Step 2: To a 100-mL round-bottomed flask were added tert-butyl (1-hydroxy-3-phenylpropan-2-yl)carbamate (step 1, 1 g, 4 mmol), DMP (2 g, 4.8 mmol) and DCM (40 mL). The reaction was stirred at RT for 1 h. To the mixture at RT was added $H_2O$ (100 mL) and the mixture was extracted with DCM (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1:5) to provide tert-butyl (1-oxo-3-phenylpropan-2-yl)carbamate (600 mg, 2.4 mmol, 60.4% yield) as a colorless oil.

Step 3: To a 50-mL round-bottomed flask were added tert-butyl (1-oxo-3-phenylpropan-2-yl)carbamate (step 2, 600 mg, 2.41 mmol), LiCl (151 mg, 3.61 mmol), DIPEA (466 mg, 3.61 mmol), ethyl 2-(diethoxyphosphoryl)acetate (809 mg, 3.61 mmol) and $CH_3CN$ (10 mL). The reaction was stirred at RT for 4 h. To the mixture at RT was added $H_2O$ (50 mL) and the mixture was extracted with EA (2×50 mL). The combined organic extracts were washed with saturated NaCl aqueous solution (2×50 mL), dried over $Na_2SO_4$, filtered and concentrated to give a residue which was purified by flash column chromatography (silica, EA/PE=1: 10) to provide ethyl (E)-4-((tert-butoxycarbonyl)amino)-5-phenylpent-2-enoate (550 mg, 1.7 mmol, 71.6% yield) as a yellow solid. LCMS: $(M+Na)^+$=342; Retention time=1.787 min. LCMS CP Method B Step 4: To a 50-mL round-bottomed flask were added ethyl (E)-4-((tert-butoxycarbonyl)amino)-4-phenylbut-2-enoate (step 3, 250 mg, 0.82 mmol) and $LiOH·H_2O$ (69 mg, 1.64 mmol) as a solution in THE/$H_2O$=1:1 (2 mL). The reaction was stirred at RT for 2 h. To the mixture at RT was added 1 N HCl (20 mL) and the mixture was extracted with EA (2×10 mL). The combined organic extracts were washed with saturated NaCl aqueous solution (2×20 mL), dried over $Na_2SO_4$, filtered and concentrated to provide (E)-4-((tert-butoxycarbonyl)amino)-4-phenylbut-2-enoic acid (200 mg, 0.69 mmol, 83.8% yield) as a yellow solid which was used in the next step reaction without further purification. LCMS: $(M+Na)^+$=300; Retention time=1.557 min. LCMS CP Method B Step 5: To a 50-mL round-bottomed flask were added (S)-4-(2-(1-ethyl-3-(trifluoromethyl)-1H-pyrazol-4-yl)phenyl)-4,5,6,7-tetrahydrothieno[2,3-c]pyridine-2-carbonitrile (200 mg, 0.5 mmol), DIPEA (193 mg, 1.5 mmol), (E)-4-((tert-butoxycarbonyl)amino)-5-phenylpent-2-enoic acid (step 4, 218 mg, 0.75 mmol), HATU (282 mg, 0.75 mmol) and DMF (4 mL). The reaction was stirred at RT for 1 h. To the mixture at RT was added $H_2O$ (10 mL) and the mixture extracted with EA (2×10 mL). The combined organic extracts were washed with saturated NaCl aqueous solution (2×10 mL), dried over $Na_2SO_4$, filtered and concentrated to give a residue which was purified by Prep-HPLC (method A) to provide tert-butyl ((E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-5-oxo-1-phenylpent-3-en-2-yl)carbamate (170 mg, 0.25 mmol, 50% yield) as a yellow solid. LCMS: $(M-100+H)^+$=576; Retention time=1.820 min. LCMS CP Method D.

Step 6: To a 50-mL round-bottomed flask were added tert-butyl ((E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-5-oxo-1-phenylpent-3-en-2-yl)carbamate (step 5, 170 mg, 0.25 mmol) and TFA (245 mg, 2.5 mmol) as a solution in DCM (2 mL). The reaction was stirred at RT for 2 h. To the mixture at RT was added saturated $NaHCO_3$ aqueous solution (10 mL) and the mixture was extracted with DCM (2×10 mL). The combined organic extracts were washed with saturated NaCl aqueous solution (2×10 mL), dried over $Na_2SO_4$, filtered and concentrated to give a residue which was purified by Prep-HPLC (method A) to provide (4S)-6-((E)-4-amino-5-phenylpent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (84.7 mg, 0.15 mmol, 58.4% yield) as a white solid. LCMS: $(M+H)^+$=576; Retention time=1.649 min. LCMS CP Method B $^1H$ NMR (400 MHz, DMSO) δ 8.24-8.13 (m, 1H), 7.73 (s, 2H), 7.45-7.10 (m, 9H), 6.85 (d, J=38.9 Hz, 1H), 6.55 (d, J=15.6 Hz, 0.5H), 6.51-6.36 (m, 1H), 5.95 (d, J=15.6 Hz, 0.5H), 5.02-4.67 (m, 2H), 4.27 (q, J=7.1 Hz, 2H), 4.15-3.85 (m, 2H), 3.84-3.63 (m, 1H), 3.60-3.40 (m, 1H), 3.09-2.61 (m, 2H), 1.46 (t, J=7.3 Hz, 3H).

Example 45

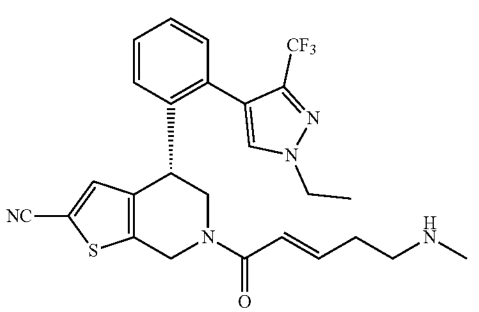 [SMILES: CCn1cc(-c2ccccc2[C@@H]2CN(C(=O)/C=C/CCNC)Cc3sc(C#N)cc32)c(C(F)(F)F)n1]

(S,E)-4-(2-(1-ethyl-3-(trifluoromethyl)-1H-pyrazol-4-yl)phenyl)-6-(5-(methylamino)pent-2-enoyl)-4,5,6,7-tetrahydrothieno[2,3-c]pyridine-2-carbonitrile Step 1: To a solution of tert-butyl methyl(3-oxopropyl) carbamate (450 mg, 2.41 mmol) and LiCl (121 mg, 2.89 mmol) in $CH_3CN$ (10 ml) were added DIPEA (373 mg, 2.89 mmol) and methyl 2-(dimethoxyphosphoryl)acetate (482 mg, 2.65 mmol) and the reaction was stirred at 25° C. for 2 h. The mixture was filtered, washed with DCM (3×10 ml). The filtrate was concentrated to give a residue which was purified by flash column chromatography (PE:DCM=1:1) to afford (E)-methyl 5-(tert-butoxycarbonyl(methyl)amino) pent-2-enoate (514 mg, 88% yield) as a yellow liquid. LCMS: $(M+Na)^+$=266.1; Retention time=1.83 min. LCMS CP Method A Step 2: To a solution of (E)-methyl 5-(tert-butoxycarbonyl (methyl)amino)pent-2-enoate (step 1, 514 mg, 2.12 mmol) in mixed THE (8 ml) and $H_2O$ (4 ml) was added LiOH·$H_2O$ (178 mg, 4.24 mmoL) at RT and the reaction mixture was heated to 40° C. and stirred for 1.5 h. The pH value of the solution was adjusted to 5-6 with HCl (1 N). The solution was concentrated in vacuum to afford (E)-5-(tert-butoxycarbonyl(methyl)amino)pent-2-enoic acid (480 mg, 99% yield) as a white solid. LCMS: $(M+Na)^+$=252.1; Retention time=1.54 min. LCMS CP Method A Step 3: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.25 mmol), DIPEA (65 mg, 0.5 mmol) and (E)-5-(tert-butoxycarbonyl(methyl) amino)pent-2-enoic acid (115 mg, 0.5 mmol) in DMF (4 ml) was added HATU (143 mg, 0.375 mmol) and the reaction was stirred at RT for 2 h. Water (50 ml) was added and the mixture was extracted with EA (40 ml×3). The combined organic phases were washed with brine, dried over $Na_2SO_4$, filtered and concentrated give a residue which was purified by Prep-TLC (DCM: MeOH=15: 1) to afford (S,E)-tert-butyl 5-(2-cyano-4-(2-(1-ethyl-3-(trifluoromethyl)-1H-pyrazol-4-yl)phenyl)-4,5-dihydrothieno[2,3-c]pyridin-6 (7H)-yl)-5-oxopent-3-enyl(methyl)carbamate (150 mg, 98% yield) as a yellow solid. LCMS: $(M-56+H)^+$=558.1; Retention time=2.11 min. LCMS CP Method C Step 4: To a solution of (S,E)-tert-butyl 5-(2-cyano-4-(2-(1-ethyl-3-(trifluoromethyl)-1H-pyrazol-4-yl)phenyl)-4,5-dihydrothieno[2,3-c]pyridin-6(7H)-yl)-5-oxopent-3-enyl (methyl)carbamate (150 mg, 0.245 mmol) in DCM (5 ml) was added TFA (1 ml) and the reaction was stirred at RT for 1 h. The mixture was concentrated and the residue was purified by Prep-HPLC (Method B) to afford (S,E)-4-(2-(1-ethyl-3-(trifluoromethyl)-1H-pyrazol-4-yl)phenyl)-6-(5-(methylamino)pent-2-enoyl)-4,5,6,7-tetrahydrothieno[2,3-c]pyridine-2-carbonitrile (41.6 mg, 30% yield) as a yellow solid. LCMS: $(M+H)^+$=514.2; Retention time=1.55 min. LCMS CP Method A $^1H$ NMR (400 MHz, DMSO) δ: 8.31 (s, 1H), 7.34-7.28 (m, 4H), 6.94-6.77 (m, 1H), 6.55-6.53 (m, 1H), 5.84 (d, J=14.8 Hz, 1H), 4.95-4.84 (m, 2H), 4.30-4.24 (m, 2H), 4.11 (s, 1H), 3.88-3.83 (m, 1H), 3.59-3.54 (m, 2H), 2.62-2.58 (m, 1H), 2.43-2.22 (m, 6H), 1.45 (t, J=7.6 Hz, 3H).

Example 46

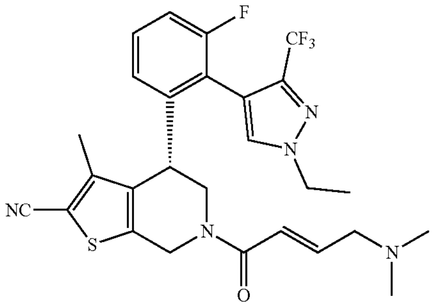 [SMILES: CCn1cc(-c2c(F)cccc2[C@@H]2CN(C(=O)/C=C/CN(C)C)Cc3sc(C#N)c(C)c32)c(C(F)(F)F)n1]

(S,E)-6-(4-(dimethylamino)but-2-enoyl)-4-(2-(1-ethyl-3-(trifluoromethyl)-1H-pyrazol-4-yl)-3-fluorophenyl)-3-methyl-4,5,6,7-tetrahydrothieno[2,3-c] pyridine-2-carbonitrile Step 1: To a solution of LDA (40 ml, 80 mmol, 2 M) in THF (150 ml) was added a solution of 3-methylthiophene-2-carbonitrile (4.92 g, 40 mmol) in THF (20 ml) dropwise at −78° C. and the mixture was stirred at 78° C. for 1 h. DMF (8.76 g, 120 mmol) was added dropwise and the resulting mixture was stirred for another 30 min. The reaction was quenched by adding a solution of 6.75 g of citric acid in $H_2O$ (40 mL), followed by addition of brine (200 ml). The mixture was extracted with EA (3×150 ml) and the combined organic phases were washed with brine, dried over $Na_2SO_4$, filtered and concentrated. The residue was purified by column chromatography (PE: EA=4:1) to afford 5-formyl-3-methylthiophene-2-carbonitrile (4.3 g, 71% yield) as a yellow solid. $^1$H NMR (400 MHz, DMSO) δ 9.98 (s, 1H), 8.01 (s, 1H), 2.45 (s, 3H).

Step 2: A mixture of 5-formyl-3-methylthiophene-2-carbonitrile (step 1, 4.3 g, 28.5 mmol) and 2-amino-1-(2-bromo-3-fluorophenyl)ethan-1-ol (7.97 g, 34.2 mmol) in MeOH (150 ml) was stirred at RT overnight. After cooling to 0° C., $NaBH_4$ (2.17 g, 57 mmol) was added slowly. The cooling bath was removed and the mixture was stirred at RT for 4 h. The reaction was quenched with a mixed solution of cold water and saturated $NaHCO_3$ (1:1, 500 ml total). The resulting solid was collected, washed with water and dried under reduced pressure to afford 5-(((2-(2-bromo-3-fluorophenyl)-2-hydroxyethyl)amino)methyl)-3-methylthiophene-2-carbonitrile (8.25 g, 79% yield) as a yellow solid. LCMS: $(M+H)^+$=369.0, Retention time=1.420 min. LCMS OP method B Step 3: To a suspension of 5-(((2-(2-bromo-3-fluorophenyl)-2-hydroxyethyl)amino)methyl)-3-methylthiophene-2-carbonitrile (step 2, 8.25 g, 22.4 mmol) in DCM (300 mL) was added solid $AlCl_3$ (8.94 g, 67.2 mmol) and the reaction was stirred at RT for 1 h. Another batch of $AlCl_3$ (5.96 g, 44.8 mmol) was added and the resulting mixture was stirred at RT overnight. The mixture was diluted with DCM (200 mL) and quenched with a water-ice mixture (~500 mL). The resulting mixture was neutralized with 10N NaOH (aq., to pH-10) and vigorously stirred at RT for 30 min. The separated aqueous layer was extracted with DCM (3×300 mL). The combined organic layers were washed with brine, dried over $Na_2SO_4$, filtered and concentrated. The residue was redissolved in DCM (150 mL) and $Boc_2O$ (7.65 g, 21.86 mmol) was added. The mixture was stirred at RT overnight. Water (200 ml) was added and the mixture was partitioned. The aqueous layer was extracted with DCM (3×100 mL) and the combined organic layers were washed with brine, dried over $Na_2SO_4$, filtered and concentrated. The residue was triturated in mixed solution of MeOH and PE, The resulting solid was collected, washed with PE and dried under reduced pressure to afford tert-butyl 4-(2-bromo-3-fluorophenyl)-2-cyano-3-methyl-4,7-dihydrothieno[2,3-c]pyridine-6(5H)-carboxylate (6.7 g, 66% overall yield for two steps) as a yellow solid. $^1$H NMR (400 MHz, DMSO) δ 7.35-7.24 (m, 2 H), 6.36-6.23 (m, 1H), 5.22 (d, J=18.0 Hz, 1H), 4.51-4.30 (m, 3H), 3.48-3.38 (m, 1H), 1.93 (s, 3H), 1.29-0.83 (m, 9H). LCMS: $(M-56+H)^+$=395.0; Retention time=2.000 min. LCMS CP Method B Step 4: The enantiomers were separated from 6.7 g of the racemate by chiral SFC [SFC-200 (Thar, Waters), column—IG 20*250 mm, 10 um (Daicel), 35° C., mobile phase—$CO_2$/MeOH[0.2% $NH_3$(7M in MeOH)]=85/15, flow rate 120 mL/min, back pressure—100 bar] to give tert-butyl (S)-2-cyano-4-(2-(1-ethyl-3-(trifluoromethyl)-1H-pyrazol-4-yl)-3-fluorophenyl)-3-methyl-4,7-dihydrothieno[2,3-c] pyridine-6(5H)-carboxylate (peak 2, 2.8 g, retention time=1.297 min) as a yellow solid. $^1$H NMR (400 MHz, DMSO) δ 7.35-7.24 (m, 2H), 6.36-6.23 (m, 1H), 5.22 (d, J=18.0 Hz, 1H), 4.51-4.30 (m, 3H), 3.48-3.38 (m, 1H), 1.93 (s, 3H), 1.29-0.83 (m, 9H). LCMS: $(M-56+H)^+$=395.0; Retention time=1.994 min. LCMS CP Method B Step 5: A mixture of tert-butyl (S)-2-cyano-4-(2-(1-ethyl-3-(trifluoromethyl)-1H-pyrazol-4-yl)-3-fluorophenyl)-3-methyl-4,7-dihydrothieno[2,3-c]pyridine-6(5H)-carboxylate (450 mg, 1.0 mmol), 1-ethyl-4-(4,4,5,5-tetramethyl-1,3,2-dioxaborolan-2-yl)-3-(trifluoromethyl)-1H-pyrazole (348 mg, 1.2 mmol), $K_3PO_4$ (424 mg, 2.0 mmol), Ruphos Pd G4 (170 mg, 0.2 mml), dioxane (5 ml) and $H_2O$ (1 ml) was heated to 100° C. and stirred under microwave for 2 h. The mixture was cooled to RT and water (30 ml) was added. The resulting mixture was extracted with DCM (3×30 ml). The combined organic phases were washed with brine, dried over $Na_2SO_4$, filtered and concentrated. The residue was purified by Prep-TLC (PE: EA=5:1) to afford tert-butyl (S)-2-cyano-4-(2-(1-ethyl-3-(trifluoromethyl)-1H-pyrazol-4-yl)-3-fluorophenyl)-3-methyl-4,7-dihydrothieno[2,3-c] pyridine-6(5H)-carboxylate (413 mg, 77% yield) as a yellow solid. LCMS: $(M-56+H)^+$=479.0; Retention time=1.965 min. LCMS CP Method B Step 6: To a solution of tert-butyl (S)-2-cyano-4-(2-(1-ethyl-3-(trifluoromethyl)-1H-pyrazol-4-yl)-3-fluorophenyl)-3-methyl-4,7-dihydrothieno[2,3-c]pyridine-6(5H)-carboxylate (step 5, 413 mg, 0.77 mmol) in DCM (5 mL) at RT was added TFA (1 mL). The reaction was stirred for 1 h then concentrated. The residue was dissolved in DCM and the pH value was adjusted to 7-8 with a saturated solution of $NaHCO_3$. The resulting mixture was extracted with DCM (3×30 ml). The combined organic phases were washed with brine, dried over $Na_2SO_4$, filtered and concentrated to afford (S)-4-(2-(1-ethyl-3-(trifluoromethyl)-1H-pyrazol-4-yl)-3-fluorophenyl)-3-methyl-4,5,6,7-tetrahydrothieno[2,3-c] pyridine-2-carbonitrile (320 mg, 96% yield) as a yellow solid which was used directly in the next step reaction without further purification. LCMS: $(M+H)^+$=435.0; Retention time=1.559 min. LCMS CP Method B Step 7: A mixture of (S)-4-(2-(1-ethyl-3-(trifluoromethyl)-1H-pyrazol-4-yl)-3-fluorophenyl)-3-methyl-4,5,6,7-tetrahydrothieno[2,3-c]pyridine-2-carbonitrile (step 6, 120 mg, 0.28 mmol), (E)-4-(dimethylamino)but-2-enoic acid (HCl salt, 93 mg, 0.56 mmol), HATU (160 mg, 0.42 mmol), DIPEA (108 mg, 0.84 mmol) and DCM (5 ml) was stirred at RT for 1 h. Water (30 ml) was added and the mixture was extracted with DCM (20 ml×3). The combined organic phases were washed with brine, dried over $Na_2SO_4$, filtered and concentrated. The residue was purified by Prep-HPLC (Method A) to afford (S,E)-6-(4-(dimethylamino)but-2-enoyl)-4-(2-(1-ethyl-3-(trifluoromethyl)-1H-pyrazol-4-yl)-3-fluorophenyl)-3-methyl-4,5,6,7-tetrahydrothieno[2,3-c]pyridine-2-carbonitrile (62.9 mg, 42.5% yield) as a white solid. $^1H$ NMR (400 MHz, DMSO) δ 8.43-8.16 (m, 1H), 7.32-7.11 (m, 2H), 6.66-6.06 (m, 3H), 5.62-5.37 (m, 1H), 4.44-4.27 (m, 3H), 4.23-3.93 (m, 1H), 3.72-3.58 (m, 1H), 3.03-2.67 (m, 2H), 2.14 (s, 1H), 2.08-1.99 (m, 6H), 1.78-1.72 (m, 2H), 1.53-1.46 (m, 3H). LCMS: $(M+H)^+$=546.1, purity=100% (214 nm); Retention time=1.812 min. LCMS CP Method C Example 47

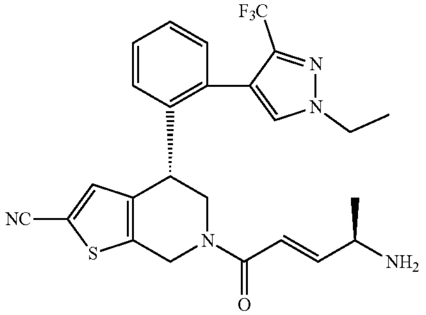 [SMILES: CCn1cc(-c2ccccc2[C@@H]2CN(C(=O)/C=C/[C@@H](C)N)Cc3sc(C#N)cc32)c(C(F)(F)F)n1]

(S)-6-((R,E)-4-aminopent-2-enoyl)-4-(2-(1-ethyl-3-(trifluoromethyl)-1H-pyrazol-4-yl)phenyl)-4, 5, 6,7-tetrahydrothieno[2,3-c]pyridine-2-carbonitrile Step 1: To a solution of (R,E)-methyl 4-(tert-butoxycarbonylamino)pent-2-enoate (520 mg, 2.27 mmol) in mixed THE (8 ml) and $H_2O$ (4 ml) was added LiOH·$H_2O$ (190 mg, 4.54 mmol) and the mixture was stirred at RT for 3 h. The pH value of the solution was adjusted to 5-6 with HCl (1N). The solution was concentrated in vacuum to afford (R,E)-4-(tert-butoxycarbonylamino)pent-2-enoic acid (469 mg, 100% yield) as a white solid. LCMS: $(M-56+H)^+$=160.0; Retention time=1.07 min. LCMS CP Method C Step 2: To a solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (130 mg, 0.32 mmol), DIPEA (83 mg, 0.64 mmol) and (R,E)-4-(tert-butoxycarbonylamino)pent-2-enoic acid (step 1, 138 mg, 0.64 mmol) in DMF (5 ml) was added HATU (182 mg, 0.48 mmol) and the mixture was stirred at RT for 2 h. Water (30 ml) was added and the mixture was extracted with EA (3×30 ml). The combined organic phases were washed with brine, dried over $Na_2SO_4$, filtered and concentrated to give a residue which was purified by Prep-TLC (DCM: MeOH=20: 1) without $NH_3$ to afford tert-butyl (R,E)-5-((S)-2-cyano-4-(2-(1-ethyl-3-(trifluoromethyl)-1H-pyrazol-4-yl)phenyl)-4,5-dihydrothieno[2,3-c]pyridin-6(7H)-yl)-5-oxopent-3-en-2-ylcarbamate (178 mg, 93% yield) as a yellow solid. LCMS: $(M-56+H)^+$=544.2; Retention time=2.17 min. LCMS CP Method A Step 3: To a solution of tert-butyl (R,E)-5-((S)-2-cyano-4-(2-(1-ethyl-3-(trifluoromethyl)-1H-pyrazol-4-yl)phenyl)-4,5-dihydrothieno[2,3-c]pyridin-6(7H)-yl)-5-oxopent-3-en-2-ylcarbamate (step 2, 178 mg, 0.3 mmol) in DCM (5 ml) was added TFA (1 ml) and the resulting mixture was stirred at RT for 1 h. The mixture was concentrated and the residue was purified by Prep-HPLC (Method B) to afford (S)-6-((R,E)-4-aminopent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (73.4 mg, 44.9% yield) as a yellow solid. LCMS: $(M+H)^+$=500.0; Retention time=1.55 min. LCMS CP Method A. $^1H$ NMR (400 MHz, DMSO) δ: 8.28 (s, 1H), 7.35-7.22 (m, 4H), 6.96-6.84 (m, 1H), 6.67-6.52 (m, 1H), 6.04 (d, J=14.8 Hz, 1H), 5.13 4.93 (m, 2H), 4.29-4.24 (m, 2H), 4.10-3.90 (m, 2H), 3.67-3.57 (m, 2H), 3.25-3.22 (m, 2H), 1.48-1.43 (m, 3H), 1.29-1.13 (m, 3H).

Example 48

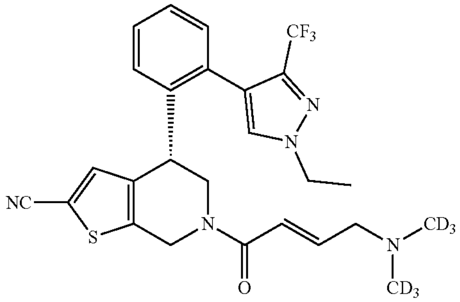 [SMILES: [2H]C([2H])([2H])N(C/C=C/C(=O)N1Cc2sc(C#N)cc2[C@H](c2ccccc2-c2cn(CC)nc2C(F)(F)F)C1)C([2H])([2H])[2H]]

(S,E)-6-(4-(bis(methyl-d3)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: To a solution of (S)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (210 mg, 0.5 mmol) in DMF (6 mL) were added (E)-4-(dimethylamino)but-2-enoic acid (71 mg, 0.55 mmol), HATU (285 mg, 0.75 mmol) and DIEA (200 mg, 1.5 mmol) at RT. The reaction was stirred at RT overnight then concentrated to give a residue which was purified by Prep-HPLC (Method A) to give tert-butyl (E)-4-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-4-oxobut-2-enylcarbamate (280 mg, 93% yield) as a brown solid. LCMS: $(M-55+H)^+$=547.8; Retention time=1.72 min. LCMS CP Method D Step 2: To a solution of tert-butyl (E)-4-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-4-oxobut-2-enylcarbamate (step 1, 280 mg, 0.46 mmol) in DCM (5 mL) at RT was added TFA (1 mL). The reaction was stirred for 1 h, then concentrated. Water (10 mL) was added and the mixture was extracted with DCM (3×20 mL). The combined organic layers were neutralized with saturated $NaHCO_3$ (pH=8-9), dried over anhydrous $Na_2SO_4$, filtered and concentrated under reduced pressure to give (S)-6-((E)-4-aminobut-2-enoyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (200 mg, 86% yield) as a yellow solid which was used directly in the next step reaction without further purification. LCMS: $(M+1, M+23)^+$= 504.0, 526.0; Retention time=1.57 min. LCMS CP Method A Step 3: To a solution of (S)-6-((E)-4-aminobut-2-enoyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (step 2, 126 mg, 0.25 mmol) and paraformaldehyde-$d_2$ (0.25 mL, 20% in $D_2O$) in MeOH-$d_4$ (2 mL) was added $NaBD_3CN$ (33 mg, 0.5 mmol). The reaction was stirred at RT overnight. The mixture was concentrated and the residue was purified by Prep-HPLC (Method A) to give (S,E)-6-(4-(bis(methyl-d3)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (86 mg, 64% yield) as a brown solid. LCMS: $(M+1)^+$=538.1, Retention time=1.42 min. LCMS CP Method A. $^1$H NMR (400 MHz, DMSO-$d_6$) δ 8.37-8.24 (m, 1H), 7.66-7.05 (m, 3H), 6.83-6.77 (m, 1H), 6.60-5.75 (m, 2H), 5.10-4.70 (m, 2H), 4.33-4.25 (m, 2H), 4.17- 3.93 (m, 1H), 3.74-3.52 (m, 2H), 3.05-2.67 (m, 2H), 1.51-1.43 (m, 3H).

Example 49

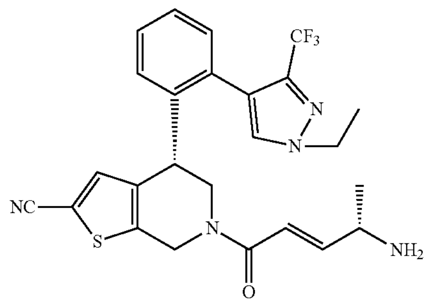 [SMILES: CCn1cc(-c2ccccc2[C@@H]2CN(C(=O)/C=C/[C@H](C)N)Cc3sc(C#N)cc32)c(C(F)(F)F)n1]

(S)-6-((S,E)-4-aminopent-2-enoyl)-4-(2-(1-ethyl-3-(trifluoromethyl)1H-pyrazol-4-yl)phenyl)-4,5,6,7-tetrahydrothieno[2,3-c]pyridine-2-carbonitrile Step 1: To a solution of tert-butyl (S)-(1-hydroxypropan-2-yl)carbamate (1000 mg, 5.71 mmol) in DCM (5 mL) was added DMP (3000 mg, 6.85 mmol). The reaction was stirred at the RT for 2 h. $H_2O$ (100 mL) was added and the mixture was extracted with DCM (3×20 mL). The combined organic layers was concentrated to give a residue which was purified by silica gel chromatography (PE:EA=5:1) to give a tert-butyl (S)-(1-oxopropan-2-yl)carbamate (476 mg, 2.078 mmol, 36.4% yield) as a white solid.

Step 2: To a solution of tert-butyl (S)-(1-oxopropan-2-yl) carbamate (step 1, 573 mg, 3.97 mmol) in ACN (5 mL) were added methyl 2-(dimethoxyphosphoryl)acetate (663 mg, 3.84 mmol) LiCl (168 mg, 3.97 mmol) and DIPEA (513 mg, 3.97 mmol). The reaction was stirred at the RT for 2 h. Water (20 mL) was added and the mixture was extracted with DCM (3×50 mL). The combined organic layers was concentrated to give a residue which was purified by silica gel column chromatography (DCM:MeOH=20:1) to give a methyl (S,E)-4-((tert-butoxycarbonyl)amino)pent-2-enoate (718 mg, 3.31 mmol, 81.65% yield) as a transparent oil. LCMS: $(M\text{-}Boc+H)^+$=500, purity=26.57% (214 nm), Retention time=2.044 min. LCMS CP method G Step 3: To a solution of tert-butyl ((S,E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-5-oxopent-3-en-2-yl)carbamate (60 mg, 0.10 mmol) in DCM (3 mL) was added TFA (0.5 mL, Wt 99%). The reaction was stirred at the RT for 2 h and then concentrated. The residue was purified by Prep-HPLC (Method B) to give a (S)-6-((S,E)-4-aminopent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (8.3 mg, 15.2% yield) as a white solid. LCMS: $(M+H)^+$=500.0, purity=100% (214 nm), Retention time=1.518 min. LCMS CP method B.

$^1$H NMR (400 MHz, DMSO-$d_6$) δ 8.29-8.27 (d, J=8.0 Hz, 1H), 7.43-7.25 (m, 4H), 6.72-6.57 (m, 1H), 6.51-6.46 (m, 4H), 5.87-5.86 (d, J=4.0 Hz, 1H), 5.16-5.12 (m, 1H), 4.17-4.09 (m, 4H), 3.98-3.75 (m, 1H), 3.53-3.49 (m, 1H), 1.48-1.31 (m, 3H), 1.08-0.87 (m, 3H).

Example 50

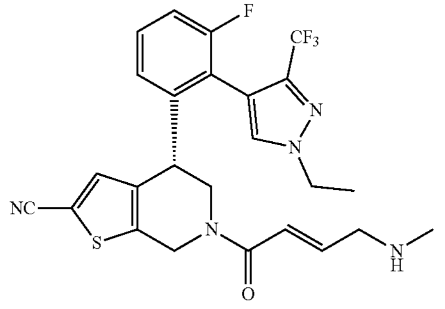 [SMILES: CCn1cc(-c2c(F)cccc2[C@@H]2CN(C(=O)/C=C/CNC)Cc3sc(C#N)cc32)c(C(F)(F)F)n1]

(S,E)-(4-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-4-oxobut-2-en-1-yl)(methyl)carbonitrile Step 1: A mixture of diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl) phosphonate (2.9 g, 4.85 mmol), tert-butyl methyl(2-oxoethyl)carbamate (1.26 g, 7.28 mmol), LiCl (244 mg, 5.82 mmol) and DIPEA (1.25 g, 9.7 mmol) in $CH_3CN$ (30 ml) was stirred at RT for 3 h. Water (50 ml) was added and the mixture was extracted with EA (3×50 ml). The combined organic phases were washed with brine, dried over $Na_2SO_4$, filtered and concentrated. The residue was purified by Prep-HPLC (10 Mm $NH_4HCO_3$) to afford tert-butyl (S,E)-(4-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-4-oxobut-2-en-1-yl)(methyl)carbamate (2.0 g, 67% yield) as a white solid. LCMS: $(M\text{–}Boc+H)^+$=518.2, Retention time=1.865 min. LCMS CP Method B Step 2: To a solution of tert-butyl (S,E)-(4-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-4-oxobut-2-en-1-yl)(methyl)carbamate (step 1, 2.0 g, 3.24 mmol) in DCM (25 mL) at RT were added TFA (2.5 mL). The reaction was stirred for 2 h and then concentrated to afford (S,E)-(4-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-4-oxobut-2-en-1-yl)(methyl)carbonitrile (1.958 g, 96% yield) as a white solid. $^1$H NMR (400 MHz, DMSO) δ 8.82-8.73 (m, 2H), 8.39-8.25 (m, 1H), 7.67-7.56 (m, 1H), 7.40-7.35 (m, 1H), 7.25-7.21 (m, 1H), 7.04-7.00 (m, 1H), 6.84-6.43 (m, 2H), 6.11-5.95 (m, 1H), 5.08-4.84 (m, 2H), 4.34-4.18 (m, 4H), 4.02-3.57 (m, 2H), 2.57 (s, 1H), 2.47-2.45 (m, 1H), 1.50-1.44 (m, 3H). LCMS: $(M+H)^+$= 518.2, Retention time=1.865 min. LCMS CP Method B Example 51

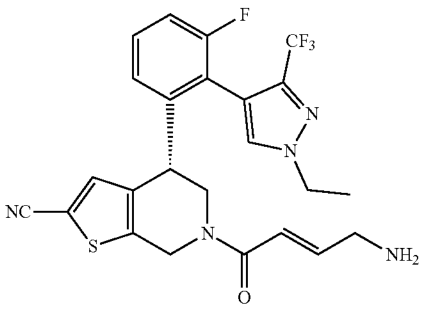 [SMILES: CCn1cc(-c2c(F)cccc2[C@@H]2CN(C(=O)/C=C/CN)Cc3sc(C#N)cc32)c(C(F)(F)F)n1]

(S)-6-((E)-4-aminobut-2-enoyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: To a solution of (E)-methyl 4-(tert-butoxycarbonylamino)but-2-enoate (840 mg, 3.9 mmoL) in mixed THE (10 ml) and $H_2O$ (10 ml) was added $LiOH{\cdot}H_2O$ (328 mg, 7.8 mmol) and the mixture was stirred at RT for 1.5 h. The pH value of the solution was adjusted to 5-6 with HCl (1 N) and the mixture was concentrated in vacuum to afford (E)-4-(tert-butoxycarbonylamino)but-2-enoic acid (780 mg, 100% yield) as a white solid which was used directly in the next step reaction without further purification. LCMS: $(M+Na)^+$= 224.1; Retention time=1.39 min. LCMS CP Method A Step 2: To a solution of (S)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (95 mg, 0.22 mmol), DIPEA (57 mg, 0.44 mmol) and (E)-4-(tert-butoxycarbonylamino)but-2-enoic acid (step 1, 88 mg, 0.44 mmol) in DMF (4 ml) was added HATU (125 mg, 0.33 mmol) and the reaction was stirred at RT for 2 h. Water (50 ml) was added and the mixture was extracted with EA (3×40 ml). The combined organic phases were washed with brine, dried over $Na_2SO_4$, filtered and concentrated to give a residue which was purified by Prep-TLC (DCM: MeOH=25:1) to afford tert-butyl (E)-4-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-4-oxobut-2-enylcarbamate (94 mg, 71% yield) as a yellow solid. LCMS: $(M-56+H)^+$=548.0; Retention time=2.13 min. LCMS CP Method A Step 3: To a solution of (E)-4-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-4-oxobut-2-enylcarbamate (step 2, 94 mg, 0.16 mmol) in DCM (5 ml) was added TFA (1 ml) and the mixture was stirred at RT for 1 h. The mixture was concentrated and the residue was purified by Prep-HPLC (Method B) to afford (S)-6-((E)-4-aminobut-2-enoyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (22.1 mg, 28% yield) as a yellow solid. LCMS: $(M+H)^+/(M+Na)$=504.1/526.0; Retention time=1.53 min. LCMS CP Method A $^1H$ NMR (400 MHz, DMSO) δ: 8.44-8.25 (m, 1H), 7.60-7.21 (m, 3H), 6.83-6.53 (m, 2H), 6.33-5.80 (m, 1H), 5.10-4.92 (m, 2H), 4.35-4.25 (m, 2H), 4.13-3.99 (m, 2H), 3.90-3.60 (m, 2H), 3.51-3.43 (m, 2H), 3.21- 3.19 (m, 1H), 1.49-1.43 (m, 3H).

Example 52

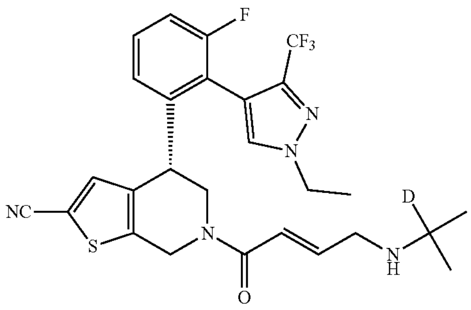 [SMILES: [2H]C(C)(C)NC/C=C/C(=O)N1Cc2sc(C#N)cc2[C@H](c2cccc(F)c2-c2cn(CC)nc2C(F)(F)F)C1]

(S,E)-4-(2-(1-ethyl-3-(trifluoromethyl)-1H-pyrazol-4-yl)-3-fluorophenyl)-6-(4-((propan-2-yl-2-d)amino)but-2-enoyl)-4,5,6,7-tetrahydrothieno[2,3-c]pyridine-2-carbonitrile Step 1: To a solution of $LiAlD_4$ (3 g, 72 mmol) in THF (60 ml) at 0° C. was added propan-2-one oxime (3.5 g, 48 mmol) dropwise. The mixture was heated to reflux and stirred for 4 h. The reaction was quenched by adding $Na_2SO_4$ decahydrate (6 g). The crude was purified by distillation (product fraction collected at 40-60-0C). HCl (37%) was added and the mixture was concentrated to afford crude propan-2-D-2-amine hydrochloride (2 g, 43% yield) as a colorless oil. $^1H$ NMR (400 MHz, $CDCl_3$) δ: 8.23 (s, 3H), 1.43 (s, 6H).

Step 2: To a suspension of propan-2-D-2-amine hydrochloride (step 1, 1 g, 10.4 mmoL) and $K_2CO_3$ (3.9 g, 28.5 mmol) in THF (20 ml) was added (E)-methyl 4-bromobut-2-enoate (1.7 g, 9.5 mmol) and the reaction was stirred at 35° C. for 2 h. The mixture was concentrated and the residue was purified by flash column chromatography (DCM: MeOH=97: 3) to afford methyl (E)-4-((propan-2-yl-2-d)amino)but-2-enoate (270 mg, 18% yield) as a yellow oil. LCMS: $(M+H)^+$=159.1; Retention time=1.15 min. LCMS CP Method C Step 3: To a solution of methyl (E)-4-((propan-2-yl-2-d)amino)but-2-enoate (step 2, 270 mg, 1.7 mmol) in mixed THF (8 ml) and $H_2O$ (4 ml) was added $LiOH{\cdot}H_2O$ (143 mg, 3.4 mmol) and the mixture was stirred at RT for 4 h. The pH value of the solution was adjusted to 5-6 with HCl (1 N). The mixture was concentrated in vacuum to afford (E)-4-((propan-2-yl-2-d)amino)but-2-enoic acid (246 mg, 100% yield) as a white solid. LCMS: $(M+H)^+$=145.3; Retention time=0.34 min. LCMS CP Method B Step 4: To a solution of (S)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (275 mg, 0.65 mmol), DIPEA (169 mg, 1.31 mmol) and (E)-4-((propan-2-yl-2-d)amino)but-2-enoic acid (step 3, 189 mg, 1.31 mmol) in DMF (4 ml) was added HATU (372 mg, 0.98 mmol) and the reaction was stirred at RT for 2 h. Water (50 ml) was added and the mixture was extracted with EA (40 ml×3). The combined organic phases were washed with brine, dried over $Na_2SO_4$, filtered and concentrated to give a residue which was purified by Prep-HPLC (Method A) to afford (S,E)-4-(2-(1-ethyl-3-(trifluoromethyl)-1H-pyrazol-4-yl)-3-fluorophenyl)-6-(4-((propan-2-yl-2-d)amino)but-2-enoyl)-

4,5,6,7-tetrahydrothieno[2,3-c]pyridine-2-carbonitrile (77.7 mg, 22% yield) as a yellow solid. LCMS: $(M+H)^+$=547.2; Retention time=1.78 min. LCMS CP Method C $^1$H NMR (400 MHz, DMSO) δ: 8.40-8.24 (m, 1H), 7.63-7.02 (m, 3H), 6.81-6.64 (m, 2H), 6.26-5.79 (m, 1H), 5.09-4.82 (m, 2H), 4.34-4.25 (m, 2H), 4.15-3.89 (m, 1H), 3.74-3.51 (m, 2H), 3.17 (s, 1H), 1.47-1.43 (m, 3H), 1.25-1.03 (m, 2H), 0.98-0.83 (m, 6H).

Example 53

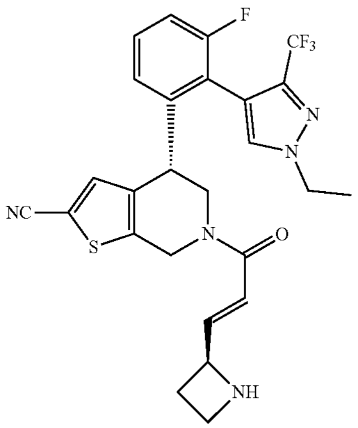 [SMILES: CCn1cc(-c2c(F)cccc2[C@@H]2CN(C(=O)/C=C/[C@@H]3CCN3)Cc3sc(C#N)cc32)c(C(F)(F)F)n1]

(S)-6-((E)-3-((S)-azetidin-2-yl)acryloyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: A solution of (S)-tert-butyl 2-(hydroxymethyl) azetidine-1-carboxylate (900 mg, 4.8 mmol) and DMP (3.05 g, 7.2 mmol) in DCM (20 ml) was stirred at RT for 2 h. Water (30 ml) was added and the mixture was extracted with DCM (30 ml×3). The combined organic phases were washed with brine, dried over $Na_2SO_4$, filtered and concentrated to give a residue which was purified by flash column chromatography (PE: EA=5:1) to afford (S)-tert-butyl 2-formylazetidine-1-carboxylate (468 mg, 52% yield) as a yellow oil. $^1$H NMR (400 MHz, $CDCl_3$) δ: 9.79 (s, 1H), 4.59 (s, 1H), 3.99-3.91 (m, 2H), 2.44-2.25 (m, 2H), 1.44 (s, 9H). Purify=100%

Step 2: To a solution of diethyl 2-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-2-oxoethylphosphonate (120 mg, 0.2 mmol) and LiCl (10 mg, 0.24 mmol) in $CH_3CN$ (5 ml) were added DIPEA (31 mg, 0.24 mmol) and (S)-tert-butyl 2-formylazetidine-1-carboxylate (step 1, 74 mg, 0.4 mmol). The reaction was stirred at 25° C. for 2 h, then concentrated. The residue was purified by flash column chromatography (DCM: MeOH=97: 3) to afford (S)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)azetidine-1-carboxylate (118 mg, 94% yield) as a yellow liquid. LCMS: $(M+Na)^+$=652.2; Retention time=2.20 min. LCMS CP Method A Step 3: To a solution of (S)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)azetidine-1-carboxylate (step 2, 118 mg, 0.19 mmol) in DCM (5 ml) was added TFA (1 ml) and the mixture was stirred at RT for 1 h. The mixture was concentrated and the residue was purified by Prep-HPLC (Method B) to afford (S)-6-((E)-3-((S)-azetidin-2-yl)acryloyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (45.3 mg, 41.5% yield) as a yellow solid. LCMS: $(M+H)^+$=530.1; Retention time=1.58 min. LCMS CP Method A $^1$H NMR (400 MHz, DMSO) δ: 8.66 (s, 1H), 8.35-8.26 (m, 1H), 7.67-7.04 (m, 3H), 6.84-6.49 (m, 2H), 6.34-5.84 (m, 1H), 5.21-4.96 (m, 2H), 4.79-4.68 (m, 1H), 4.32-4.19 (m, 3H), 4.00-3.83 (m, 2H), 3.79-3.45 (m, 2H), 2.49-2.40 (m, 1H), 2.14-2.08 (m, 1H), 1.51-1.44 (m, 3H).

Example 54

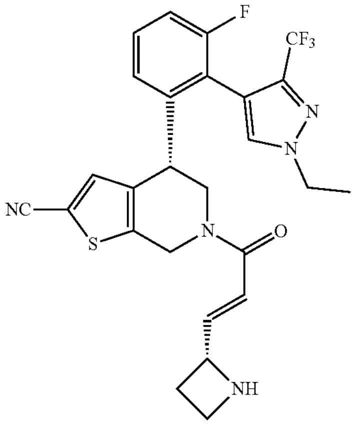 [SMILES: CCn1cc(-c2c(F)cccc2[C@@H]2CN(C(=O)/C=C/[C@H]3CCN3)Cc3sc(C#N)cc32)c(C(F)(F)F)n1]

(S)-6-((E)-3-((R)-azetidin-2-yl)acryloyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: A solution of (R)-tert-butyl 2-(hydroxymethyl) azetidine-1-carboxylate (200 mg, 1.07 mmol) and Dess-Martin (544 mg, 1.28 mmol) in DCM (10 ml) was stirred at RT for 2 h. Water (20 ml) was added and the mixture was extracted with DCM (20 ml×3). The combined organic phases were washed with brine, dried over $Na_2SO_4$, filtered and concentrated to give a residue which was purified by flash column chromatography (PE: EA=5: 1) to afford (R)-tert-butyl 2-formylazetidine-1-carboxylate (158 mg, 80% yield) as a yellow oil. $^1$H NMR (400 MHz, $CDCl_3$) δ: 9.79 (s, 1H), 4.59 (s, 1H), 3.99-3.91 (m, 2H), 2.42-2.24 (m, 2H), 1.44 (s, 9H).

Step 2: To a solution of diethyl 2-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-2-oxoethylphosphonate (129 mg, 0.22 mmol) and LiCl (11 mg, 0.264 mmol) in $CH_3CN$ (5 ml) were added DIPEA (34 mg, 0.264 mmol) and (R)-tert-butyl 2-formylazetidine-1-carboxylate (step 1, 81 mg, 0.44 mmol) and the reaction was stirred at 25° C. for 2 h. The mixture was concentrated and the residue was purified by flash column chromatography (DCM: MeOH=97: 3) to afford (R)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)azetidine-1-carboxylate (130 mg, 94% yield) as a yellow liquid. LCMS: $(M-100)^+=529.1$; Retention time=2.20 min. LCMS CP Method A Step 3: To a solution of (R)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)azetidine-1-carboxylate (130 mg, 0.21 mmol) in DCM (5 ml) was added TFA (1 ml) and the mixture was stirred at RT for 1 h. The mixture was concentrated and the residue was purified by Prep-HPLC (Mtanod B) to afford (S)-6-((E)-3-((R)-azetidin-2-yl)acryloyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (44.7 mg, 40% yield) as a yellow solid. LCMS: $(M-100)^+=530.0$; Retention time=1.55 min. LCMS CP Method A $^1H$ NMR (400 MHz, DMSO) δ: 8.45 (s, 1H), 8.35-8.25 (m, 1H), 7.60-7.01 (m, 3H), 6.84-6.57 (m, 2H), 6.42-5.95 (m, 1H), 5.04-4.73 (m, 3H), 4.30-4.25 (m, 2H), 4.10-3.88 (m, 2H), 3.78-3.69 (m, 3H), 2.33-2.20 (m, 1H), 1.52-1.43 (m, 3H).

Example 55

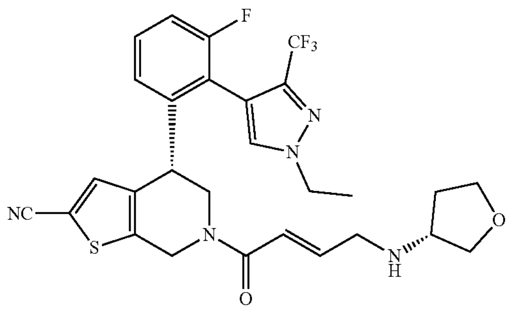 [SMILES: CCn1cc(-c2c(F)cccc2[C@@H]2CN(C(=O)/C=C/CN[C@@H]3CCOC3)Cc3sc(C#N)cc32)c(C(F)(F)F)n1]

(S)-4-(2-(1-ethyl-3-(trifluoromethyl)-1H-pyrazol-4-yl)-3-fluorophenyl)-6-((E)-4-(((R)-tetrahydrofuran-3-yl)amino)but-2-enoyl)-4,5,6,7-tetrahydrothieno[2,3-c]pyridine-2-carbonitrile Step 1: To a solution of methyl (E)-4-bromobut-2-enoate (226 mg, 1.26 mmol) in MeCN (5 mL) were added $K_2CO_3$ (317 mg, 2.296 mmol) and (R)-tetrahydrofuran-3-amine (100 mg, 1.15 mmol). The reaction was stirred at the RT for 2 h. The mixture was filtered and the filtrate was concentrated to give a residue which was purified by silica gel chromatography (DCM:MeOH=20:1) to give a methyl (R,E)-4-((tetrahydrofuran-3-yl)amino)but-2-enoate (100 mg, 42.0% yield) as a white solid. LCMS: $(M\text{-Boc}+H)^+=186.1$, Retention time=1.00 min. LCMS CP method D Step 2: To a solution of methyl (R,E)-4-((tetrahydrofuran-3-yl)amino)but-2-enoate (step 1, 249 mg, 1.345 mmol) in $H_2O$ (4 mL) was added NaOH (161.20 mg, 4.03 mmol). The reaction was stirred at RT for 2 h. The mixture was neutralized to pH 6-7 with HCl (4 mL, 1 mol/L) and extracted with DCM (3×30 mL). The aqueous phase was concentrated in vacuum to give a residue which was redissolved in DCM (60 mL). The solution was filtered and the filtrate was concentrated to give (R,E)-4-((tetrahydrofuran-3-yl)amino)but-2-enoic acid (181 mg, 1.06 mmol, 78.70% yield) as a yellow oil which was used directly in the next step reaction without further purification. LCMS: $(M+H)^+=172.1$, Retention time=0.32 min. LCMS CP method D Step 3: To a solution of (R,E)-4-((tetrahydrofuran-3-yl)amino)but-2-enoic acid (37 mg, 0.25 mmol) in DMF (3 mL) were added (S)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (60 mg, 0.14 mmol), HATU (82.0 mg, 0.22 mmol) and DIPEA (28 mg, 0.22 mmol). The reaction was stirred at RT for 2 h. Water (10 mL) was added and the mixture was extracted with EA (15 mL×3). The combined organic layers were concentrated and the residue was purified by Prep-HPLC (Method B) to give (S)-4-(2-(1-ethyl-3-(trifluoromethyl)-1H-pyrazol-4-yl)-3-fluorophenyl)-6-((E)-4-(((R)-tetrahydrofuran-3-yl)amino)but-2-enoyl)-4,5,6,7-tetrahydrothieno[2,3-c]pyridine-2-carbonitrile (18.5 mg, 17.5% yield) as a white solid. LCMS: $(M+H)^+=378.2$, purity=100% (214 nm), Retention time=1.606 min. LCMS CP method A $^1H$ NMR (400 MHz, DMSO-$d_6$) δ 8.18-8.15 (m, 1H), 7.33-7.02 (m, 3H), 6.92-6.27 (m, 2H), 6.14-5.89 (m, 1H), 5.06-4.90 (m, 2H), 4.16-4.12 (m, 2H), 4.09-3.94 (m, 2H), 3.91-3.31 (m, 5H), 0.3.27-3.3.25 (m, 2H), 3.13-3.19 (m, 1H) 1.98 (brs, 1H), 1.63 (brs, 1H) 1.23-1.19 (m, 3H)

Example 56

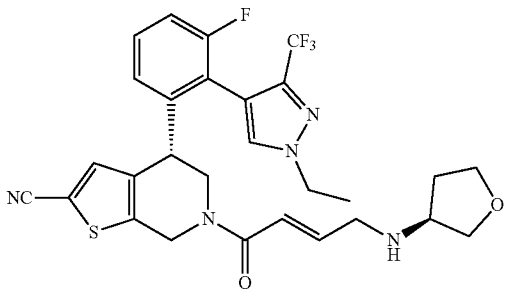 [SMILES: CCn1cc(-c2c(F)cccc2[C@@H]2CN(C(=O)/C=C/CN[C@H]3CCOC3)Cc3sc(C#N)cc32)c(C(F)(F)F)n1]

(S)-4-(2-(1-ethyl-3-(trifluoromethyl)-1H-pyrazol-4-yl)-3-fluorophenyl)-6-((E)-4-(((S)-tetrahydrofuran-3-yl)amino)but-2-enoyl)-4,5,6,7-tetrahydrothieno[2,3-c]pyridine-2-carbonitrile Step 1: To a solution of (S)-tetrahydrofuran-3-amine (0.200 g, 2.29 mmol) in DCM (5 mL) were added $K_2CO_3$ (0.952 g, 6.89 mmol) and methyl (E)-4-bromobut-2-enoate (0.368 g, 2.07 mmol) at RT. The reaction was heated to 50° C. and stirred overnight. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel column chromatography (PE:EA=3:1, 0.1% TEA involved) to give methyl (S,E)-4-((tetrahydrofuran-3-yl)amino)but-2-enoate (0.120 g, 0.648 mmol, 28.2% yield) as a yellow oil. LCMS: $(M+H)^+=186.1$, Retention time=1.22 min. LCMS CP method G Step 2: To a solution of methyl (S,E)-4-((tetrahydrofuran-3-yl)amino)but-2-enoate (0.120 g, 0.648 mmol) in mixed THF:$H_2O$ (3:1, 3 mL) was added LiOH·$H_2O$ (0.0817 g, 1.95 mmol) at RT and the reaction was stirred for 3 h. The mixture was acidified with aqueous HCl (1 M) to pH=5-6 and the mixture was concentrated in vacuum to give crude (S,E)-4-((tetrahydrofuran-3-yl)amino)but-2-enoic acid (0.230 g, crude) as a yellow oil. LCMS: $(M+H)^+=172.1$, Retention time=0.39 min. LCMS CP method G Step 3: To a solution of (S)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (0.0700 g, 0.167 mmol) in DMF (2 mL) were added (S,E)-4-((tetrahydrofuran-3-yl)amino)but-2-enoic acid (step 2, 0.0855 g, 0.500 mmol), HATU (0.0950 g, 0.250 mmol) and DIEA (0.0645 g, 0.500 mmol) at RT. The reaction was stirred for 1 h. The mixture was diluted with water (20 mL) and extracted with EA (3×20 mL). The combined organic layers were dried over anhydrous $Na_2SO_4$, filtered and concentrated under reduced pressure to give a residue which was purified by Prep-HPLC (method C) to give (S)-4-(2-(1-ethyl-3-(trifluoromethyl)-1H-pyrazol-4-yl)-3-fluorophenyl)-6-((E)-4-(((S)-tetrahydrofuran-3-yl)amino)but-2-enoyl)-4,5,6,7-tetrahydrothieno[2,3-c]pyridine-2-carbonitrile (23.8 mg, 0.0415 mmol, 17.5% yield) as a white solid. LCMS: $(M+H)^+$=574.0, purity=100% (214 nm), Retention time=1.81 min. LCMS CP method G $^1$H NMR (400 MHz, DMSO): δ 8.39-8.33 (m, 1H), 7.42-7.01 (m, 3H), 6.83-6.55 (m, 2H), 6.26-5.75 (m, 1H), 5.09-4.80 (m, 2H), 4.36-4.26 (m, 2H), 4.16-3.88 (m, 2H), 3.75-3.61 (m, 4H), 3.56-3.39 (m, 3H), 3.29-3.15 (m, 2H), 1.98- 1.57 (m, 2H), 1.48-1.45 (m, 3H).

Example 57

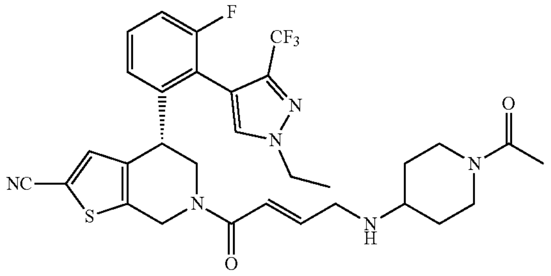 [SMILES: CCn1cc(-c2c(F)cccc2[C@@H]2CN(C(=O)/C=C/CNC3CCN(C(C)=O)CC3)Cc3sc(C#N)cc32)c(C(F)(F)F)n1]

(S,E)-6-(4-((1-acetylpiperidin-4-yl)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: To a solution of methyl (E)-4-bromobut-2-enoate (200 mg, 1.117 mmol) in MeCN (5 mL) were added $K_2CO_3$ (308 mg, 2.23 mmol) and 1-(4-aminopiperidin-1-yl)ethan-1-one (167 mg, 1.17 mmol). The reaction was stirred at the RT for 2 h. The mixture was filtered and the filtrate was concentrated to give a residue which was purified by silica gel chromatography (DCM:MeOH=20:1) to give a methyl (E)-4-((1-acetylpiperidin-4-yl)amino)but-2-enoate (114 mg, 45.10% yield) as a white solid. LCMS: $(M+H)^+$=241.1, Retention time=1.072 min. LCMS CP method D Step 2: To a solution of methyl (E)-4-((1-acetylpiperidin-4-yl)amino)but-2-enoate (step 1, 110 mg, 0.46 mmol) in $H_2O$ (2 mL) was added NaOH (56 mg, 1.37 mmol). The reaction was stirred at RT for 2 h, then neutralized to pH 6-7 with HCl (2 mL, 1 mol/L). The mixture was extracted with DCM (3×20 mL). The aqueous phase was concentrated in vacuum to give a residue which was redissolved in DCM (60 mL). The solution was filtered and the filtrate was concentrated to give (E)-4-((1-acetylpiperidin-4-yl)amino)but-2-enoic acid (66 mg, 68.0% yield) as a yellow oil which was used in the next step without further purification. LCMS: $(M+H)^+$=227.1, Retention time=0.387 min. LCMS CP method F Step 3: To a solution of (E)-4-((1-acetylpiperidin-4-yl)amino)but-2-enoic acid (step 2, 50 mg, 0.22 mmol) in DMF (3 mL) were added (S)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (62 mg, 0.15 mmol), HATU (84 mg, 0.22 mmol) and DIPEA (49.24 mg, 0.44 mmol). The mixture was stirred at RT for 2 h, then water (10 mL) was added. The mixture was extracted with EA (3×15 mL). The combined organic layers were concentrated and purified by Prep-HPLC (Method B) to give (S,E)-6-(4-((1-acetylpiperidin-4-yl)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (10.7 mg, 6.6% yield) as a white solid. LCMS: $(M+H)^+$=629.3, purity=100% (214 nm), Retention time=1.57 min. LCMS CP method B, $^1$H NMR (400 MHz, DMSO-$d_6$) δ 8.18 8.15 (m, 1H), 7.31-7.02 (m, 3H), 6.85-6.27 (m, 2H), 6.11-5.87 (m, 1H), 5.06-4.87 (m, 2H), 4.16-4.12 (m, 2H), 4.09-3.94 (m, 2H), 3.97-3.91 (m, 1H), 3.87-3.84 (m, 2H) 3.17-3.01 (m, 3H), 2.87-2.81 (m, 1H)1.98 (s, 3H), 1.63 (m, 3H), 1.27-1.22 (m, 3H), 1.14-0.99 (m, 3H).

Example 58

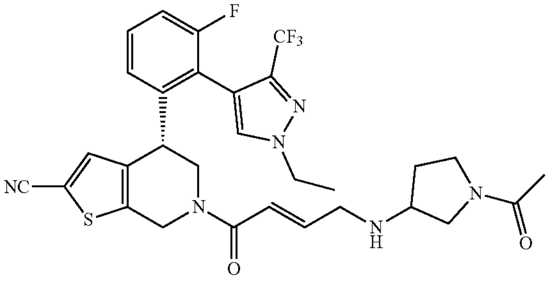 [SMILES: CCn1cc(-c2c(F)cccc2[C@@H]2CN(C(=O)/C=C/CNC3CCN(C(C)=O)C3)Cc3sc(C#N)cc32)c(C(F)(F)F)n1]

(4S)-6-((E)-4-((1-acetylpyrrolidin-3-yl)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: To a solution of 1-(3-aminocyclopentyl)ethan-1-one (0.700 g, 5.47 mmol) in DCM (20 mL) were added $K_2CO_3$ (2.059 g, 14.9 mmol) and methyl (E)-4-bromobut-2-enoate (0.885 g, 4.97 mmol) at RT. The reaction was heated to 50° C. and stirred overnight. The mixture was diluted with water (20 mL) and extracted with EA (3×20 mL). The combined organic layers were washed with brine (50 mL), dried over anhydrous $Na_2SO_4$, filtered and concentrated to give a residue which was purified by silica gel column chromatography to give methyl (E)-4-((3-acetylcyclopentyl)amino)but-2-enoate (0.295 g, 1.31 mmol, 23.9% yield) as a yellow oil. LCMS: $(M+H)^+$=227.1, Retention time=1.19 min. LCMS CP method G Step 2: To a solution of methyl (E)-4-((3-acetylcyclopentyl)amino)but-2-enoate (step 1, 0.295 g, 1.31 mmol) in mixed THF: $H_2O$ (5:1, 5 mL) was added $LiOH \cdot H_2O$ (0.165 g, 3.92 mmol) at RT and the reaction was stirred for 3 h. The mixture was acidified with aqueous HCl (1 M) to pH=5-6 and the mixture was concentrated in vacuum to give crude (E)-4-((3-acetylcyclopentyl)amino)but-2-enoic acid (0.350 g, crude) as a yellow oil which was used in the next step reaction without further purification. LCMS: $(M+H)^+$=213.1, Retention time=0.40 min. LCMS CP method G Step 3: To a solution of (S)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (0.100 g, 0.238 mmol) in DMF (5 mL) were added (E)-4-((3-acetylcyclopentyl)amino)but-2-enoic acid (0.151 g, 0.714 mmol), HATU (0.135 g, 0.357 mmol) and DIEA (0.0921 g, 0.714 mmol) at RT. The reaction was stirred for 1 h. The mixture was diluted with water (20 mL) and extracted with EA (3×20 mL). The combined organic layers were dried over anhydrous $Na_2SO_4$, filtered and concentrated in vacuum give a residue which was purified by Prep-HPLC (method C) to give (4S)-6-((E)-4-((1-acetylpyrrolidin-3-yl)amino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (0.0304 g, 0.0495 mmol, 20.8% yield) as a white solid. LCMS: $(M+H)^+$=614.9, purity=100% (214 nm), Retention time=1.42 min. LCMS CP method D $^1$H NMR (400 MHz, DMSO): δ 8.37-8.25 (m, 1H), 7.63-7.03 (m, 3H), 6.83-6.57 (m, 2H), 6.23-5.77 (m, 1H), 5.09-4.79 (m, 2H), 4.35-4.26 (m, 2H), 4.15- 3.73 (m, 3H), 3.55-3.49 (m, 3H), 3.27-2.99 (m, 5H), 1.95-1.91 (s, 5H), 1.48-1.42 (m, 3H).

Various intermediate compounds were prepared similar to that described above.

tert-Butyl (S)-2-cyano-4-(3-fluoro-2-(1-methyl-3-(trifluoromethyl)-1H-pyrazol-4-yl)phenyl)-4,7-dihydrothieno[2,3-c]pyridine-6(5H)-carboxylate. A mixture of tert-butyl (R)-4-(2-bromo-3-fluorophenyl)-2-cyano-4,7-dihydrothieno[2,3-c]pyridine-6(5H)-carboxylate (300 mg, 0.69 mmol), (1-methyl-3-(trifluoromethyl)-1H-pyrazol-4-yl)boronic acid (160 mg, 0.83 mmol), and $K_2CO_3$ (290 mg, 2.1 mmol) in dioxane-water (5:1, 3.5 mL) was deoxygenated with bubbling argon gas for 10 min, then $Pd(PPh_3)_4$ (80 mg, 0.069 mmol) was added. The mixture was stirred vigorously at 80° C. overnight. After cooling to RT, the mixture was diluted with EA (30 mL), washed with brine (3×30 mL), dried over anhydrous $MgSO_4$, filtered, and concentrated in vacuo. The crude residue was purified by flash chromatography ($SiO_2$, 0→20% EA in hexanes) to give the compound as a light-yellow foam (260 mg, 75%). MS (ESI) m/z 451.1 $[M-tBu+H]^+$.

Diethyl (S)-(2-(2-cyano-4-(3-fluoro-2-(1-methyl-3-(trifluoromethyl)-1H-pyrazol-4-yl)phenyl)-4,7-dihydrothieno[2,3-c]pyridin-6(5H)-yl)-2-oxoethyl)phosphonate. A solution of tert-butyl (S)-2-cyano-4-(3-fluoro-2-(1-methyl-3-(trifluoromethyl)-1H-pyrazol-4-yl)phenyl)-4,7-dihydrothieno[2,3-c]pyridine-6(5H)-carboxylate (160 mg, 0.32 mmol) in DCM (500 μL) was treated with TFA (500 μL). After 2 h, the solution was concentrated in vacuo and the residue was dissolved in DCM (1 mL). In a separate vial, a solution of 2-(diethoxyphosphoryl)acetic acid (188 μL, 1.17 mmol) and TEA (308 μL, 2.21 mmol) in DCM (1 mL) was added HATU (420 mg, 1.10 mmol) and the mixture was stirred at RT for 30 min, then cooled to 0° C. This active ester solution was added to the amine solution dropwise at 0° C. After the addition was complete, the entire solution was warmed to RT and stirred for 3 days. The mixture was diluted with DCM and washed with 2 M citric acid solution. The separated aqueous layer was extracted with DCM and the combined organic layers were washed with saturated aq $NaHCO_3$, brine, dried over $Na_2SO_4$, and concentrated in vacuo. The crude residue was purified by flash chromatography ($SiO_2$, 100% EA isocratic to 0→8% MeOH in DCM gradient) to give the compound as an orange oil (176 mg, 95%). MS (ESI) m/z 584.9 [M+H]+.

Diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate. tert-Butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (200 mg, 0.39 mmol) was dissolved in DCM (1 mL) and TFA (1 mL) was added to the mixture and stirred for 2 h. The mixture was concentrated in vacuo, suspended in THE (2 mL), and concentrated in vacuo. The residue was then suspended in DCM (4 mL). 2-(Diethoxyphosphoryl)acetic acid (0.080 mL, 0.49 mmol), $Et_3N$ (0.22 mL, 1.6 mmol) and HATU (0.23 g, 0.60 mmol) were added to the mixture and stirred at RT for 16 h. The mixture was ashed with 1 M citric acid (5 mL) and extracted with DCM (5 mL). The organic layer was washed with sat. aq. $NaHCO_3$ (5 mL), separated, dried over $MgSO_4$, filtered, and concentrated in vacuo. The residue was purified by a flash column chromatography ($SiO_2$, 0→100% EA in hexanes) to yield the compound as a fluffy off-white solid (0.22 g, 94%). MS (ESI) m/z 580.6 $[M]^+$.

Diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate. The compound was synthesized analogously as described above from tert-butyl (S)-2-cyano-4-(2-(1-ethyl-3-(trifluoromethyl)-1H-pyrazol-4-yl)-3-fluorophenyl)-4,7-dihydrothieno[2,3-c]pyridine-6(5H)-carboxylate and isolated a purple solid (96%). MS (ESI) m/z 589.9 $[M+H]^+$.

(S,E)-6-(4-Bromobut-2-enoyl)-4-(2-(1-ethyl-3-(trifluoromethyl)-1H pyrazol-4-yl)phenyl)-4,5,6,7-tetrahydrothieno[2,3-c]pyridine-2-carbonitrile and (S,E)-6-(4-chlorobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile. A solution of tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (240 mg, 0.48 mmol) in DCM (1 mL) was treated with TFA (1 mL) and maintained at RT for 1 h, then concentrated in vacuo to afford crude (S)-4-(2-(1-ethyl-3-(trifluoromethyl)-1H-pyrazol-4-yl)phenyl)-4,5,6,7-tetrahydrothieno[2,3-c]pyridine-2-carbonitrile which was used in the next step without purification, assuming theoretical yield.

A solution of (E)-4-bromobut-2-enoic acid (120 mg, 0.71 mmol) in DCM (0.55 mL) was sequentially treated with oxalyl chloride solution (0.41 mL, 2 M in DCM) and DMF (~1 drop, catalytic). The resulting mixture was maintained at RT for 4 h, then concentrated in vacuo to give a crude mixture of (E)-4-bromobut-2-enoyl chloride and (E)-4-chlorobut-2-enoyl chloride which was used in the next step without purification, assuming theoretical yield.

A solution of crude (S)-4-(2-(1-ethyl-3-(trifluoromethyl)-1H-pyrazol-4-yl)phenyl)-4,5,6,7-tetrahydrothieno[2,3-c]pyridine-2-carbonitrile in DCM (0.50 mL) was treated with DIPEA (250 μL, 1.43 mmol) and cooled to 0° C. in an ice-water bath. A solution of the crude mixture of (E)-4-bromobut-2-enoyl chloride and (E)-4-chlorobut-2-enoyl chloride in DCM (0.50 mL) was added dropwise. After 5 min, the reaction was quenched with sat. aq. $NaHCO_3$ (10 mL) and diluted with DCM (10 mL). The layers were partitioned and the aqueous phase was extracted with DCM (2×10 mL). The combined organic extracts were dried over anhydrous $MgSO_4$, filtered, and concentrated in vacuo. The filtrate was purified by flash column chromatography ($SiO_2$, 0→50→100% EA in hexanes) to give the compounds as a salmon-colored foam (230 mg, 88-96% yield).

tert-Butyl 4,4,4-trifluoro-3-oxo-2-(triphenyl-$\lambda^5$-phosphaneylidene)butanoate. A stirred solution of (tert-butoxycarbonylmethyl)triphenylphosphonium bromide (919 mg, 2 mmol) in DCM (3 mL) was cooled to 0° C. then $Et_3N$ (697 μL, 5 mmol) was added. To the resulting slurry was added TFAA (306 μL, 2.2 mmol) dropwise, and the mixture was warmed to RT overnight. The solvents were removed in vacuo and the residue was dissolved in MeOH, then water was added. The resulting precipitate was filtered, washed with water, and dried in vacuo overnight. The compound was recovered as a white powder (866 mg, 92%). MS (ESI) m/z 472.9 $[M+H]^+$.

tert-Butyl (Z)-4,4,4-trifluoro-3-methylbut-2-enoate. To a solution of tert-butyl 4,4,4-trifluoro-3-oxo-2-(triphenyl-$\lambda^5$-phosphaneylidene)butanoate (862 mg, 1.82 mmol) in THF (10 mL), cooled to 0° C., was added methylmagnesium iodide (763 μL, 2.87 M in $Et_2O$, 2.19 mmol) dropwise and the mixture was stirred at 0° C. for 1 h. The mixture was treated with AcOH (418 μL, 7.3 mmol) at 0° C. and warmed to RT. The resulting mixture was diluted with EA, washed subsequently with water, saturated aqueous $NaHCO_3$, and dried over $Na_2SO_4$, and filtered. The filtrate was concentrated and purified with flash chromatography($SiO_2$, 0→100% EA in hexanes gradient) to yield the compound as a clear oil.

(Z)-4,4,4-Trifluoro-3-methylbut-2-enoic acid. tert-Butyl (Z)-4,4,4-trifluoro-3-methylbut-2-enoate was dissolved in DCM (1 mL) and the resulting solution was treated with TFA (1 mL) overnight. Removal of the solvents in vacuo yielded the compound as an off-white crystalline solid (102 mg, 36% over 2 steps). MS (ESI) m/z 152.9 $[M H]^-$ Ethyl (E)-4-(ethylamino)but-2-enoate. A solution of ethylamine (2 M in THF, 1.5 mL) in THF (3.5 mL) was treated with $K_2CO_3$ (280 mg, 2.0 mmol) and ethyl (E)-4-bromobut-2-enoate (140 μL, 1.0 mmol). The resulting mixture was stirred at RT for 18 h then concentrated in vacuo. The resulting ethyl (E)-4-(ethylamino)but-2-enoate was decanted into a 100 mL round-bottom flask using DCM (5 mL) and carried into the next step without purification, assuming theoretical yield.

Ethyl (E)-4-((tert-butoxycarbonyl)(ethyl)amino)but-2-enoate. A solution of crude ethyl (E)-4-(ethylamino)but-2-enoate in DCM (5 mL) was sequentially treated with DIPEA (520 μL, 3.0 mmol) and $Boc_2O$ (460 μL, 2.0 mmol). The resulting mixture was maintained at RT for 18 h, then diluted with DCM (10 mL) and washed with brine (20 mL). The organic phase was dried over anhydrous $MgSO_4$, filtered, and concentrated in vacuo. The resulting residue was purified by flash column chromatography ($SiO_2$, 0→20% EA in hexanes) to yield the compound as a clear oil (130 mg, 50% yield over two steps).

(E)-4-((tert-Butoxycarbonyl)(ethyl)amino)but-2-enoic acid. A mixture of ethyl (E)-4-((tert-butoxycarbonyl)(ethyl)amino)but-2-enoate (130 mg, 0.50 mmol) and $LiOH{\cdot}H_2O$ (63 mg, 1.5 mmol) stirred in THF-$H_2O$ (5:1, 1 mL total) at 45° C. for 18 h. After cooling to RT, the mixture was filtered through a 0.45 μm nylon syringe tip filter, concentrated in vacuo, redissolved in MeCN—$H_2O$ (1:1, 10 mL total) and concentrated by lyophilization to afford compound as a white solid which was used in the next step without purification, assuming theoretical yield.

(E)-4-((tert-Butoxycarbonyl)(tert-butyl)amino)but-2-enoic acid. Crude compound was synthesized analogously as described above from tert-butylamine and isolated as a white solid.

(E)-4-((tert-Butoxycarbonyl)(cyclopropyl)amino)but-2-enoic acid. Crude compound was synthesized analogously as described above from cyclopropylamine and isolated as a white solid.

(E)-4-((tert-Butoxycarbonyl)(butyl)amino)but-2-enoic acid. Crude compound was synthesized analogously as described above from n-butylamine and isolated as a white solid.

(E)-4-((tert-Butoxycarbonyl)(isobutyl)amino)but-2-enoic acid. Crude compound was synthesized analogously as described above from 2-methylpropan-1-amine and isolated as a white solid.

(E)-4-((tert-Butoxycarbonyl)(isopropyl)amino)but-2-enoic acid. Crude compound was synthesized analogously as described above from propan-2-amine and isolated as a sticky clear residue.

tert-Butyl (E)-3-(3-methoxy-3-oxoprop-1-en-1-yl)azetidine-1-carboxylate. A mixture of methyl 2-(dimethoxyphosphoryl)acetate (0.12 mL, 0.72 mmol) and DBU (0.16 mL, 1.1 mmol) in THF (4.5 mL) was stirred at RT for 20 min, then a solution of tert-butyl 3-formylazetidine-1-carboxylate (200 mg, 1.1 mmol) in THF (2 mL) was added. The resulting yellow-orange solution was maintained at RT for 18 h, then concentrated in vacuo. The resulting residue was dissolved in EA (30 mL), sequentially washed with sat. aq. $NaHCO_3$ (30 mL), water (30 mL), and brine (30 mL), dried over anhydrous $MgSO_4$, filtered, and concentrated in vacuo. The resulting residue was purified by flash column chromatography ($SiO_2$, 0→20% EA in hexanes) to yield the compound as a clear oil (150 mg, 85%).

(E)-3-(1-(tert-Butoxycarbonyl)azetidin-3-yl)acrylic acid. A mixture of tert-butyl (E)-3-(3-methoxy-3-oxoprop-1-en-1-yl)azetidine-1-carboxylate (150 mg, 0.61 mmol) and $LiOH{\cdot}H_2O$ (77 mg, 1.8 mmol) was stirred in THF-$H_2O$ (5:1, 1.2 mL total) at 45° C. for 3 h. After cooling to RT, the mixture was filtered through a 0.45 μm nylon syringe tip filter, concentrated in vacuo, redissolved in MeCN—$H_2O$ (1:1, 10 mL total) and concentrated by lyophilization to afford crude compound as a sticky white residue which was used in the next step without purification, assuming theoretical yield.

(E)-3-(1-((tert-Butoxycarbonyl)amino)cyclopropyl)acrylic acid. Crude compound was synthesized analogously as described above from tert-butyl (1-formylcyclopropyl)carbamate and isolated as a white solid.

(E)-3-(1-((tert-Butoxycarbonyl)amino)cyclopentyl)acrylic acid. Crude compound was synthesized analogously as described above from tert-butyl (1-formylcyclopentyl)carbamate and isolated as a white solid.

tert-Butyl (2S,4R)-2-(methoxy(methyl)carbamoyl)-4-methylpyrrolidine-1-carboxylate. A mixture of (2S,4R)-1-(tert-butoxycarbonyl)-4-methylpyrrolidine-2-carboxylic acid (100 mg, 0.44 mmol), HATU (250 mg, 0.65 mmol), and $Et_3N$ (0.24 mL, 1.7 mmol) in DCM (1 mL) was stirred at RT for 10 min, then cooled to 0° C. in an ice-water bath. N,O-Dimethylhydroxylamine hydrochloride (64 mg, 0.65 mmol) was added and the resulting mixture was slowly warmed to RT, then stirred at RT for 16 h. The mixture was diluted with DCM (20 mL) and sequentially washed with sat. aq. $NH_4Cl$ solution (20 mL) and sat. aq. $NaHCO_3$ solution (20 mL). The organic phase was dried over anhydrous $MgSO_4$, filtered, and concentrated in vacuo. The resulting residue was purified by flash column chromatography ($SiO_2$, 0→50% EA in hexanes) to give the compound as a light-yellow oil (140 mg, quant.).

tert-Butyl (2S,4R)-2-formyl-4-methylpyrrolidine-1-carboxylate. A solution of tert-butyl (2S,4R)-2-(methoxy(methyl)carbamoyl)-4-methylpyrrolidine-1-carboxylate (61 mg) in THE (2 mL) was cooled to 0° C., then DIBAL solution (1 M in THF, 0.27 mL, 0.27 mmol) was added dropwise. After 3 h, the reaction was quenched using the Fieser method. The filtrate was concentrated in vacuo to give a crude light-yellow oil which was used directly in the next step without purification, assuming theoretical yield.

tert-Butyl (S)-6-formyl-5-azaspiro[2.4]heptane-5-carboxylate. The compound was synthesized analogously as described above from (S)-5-(tert-butoxycarbonyl)-5-azaspiro[2.4]heptane-6-carboxylic acid and isolated as a crude light-yellow oil.

tert-Butyl (1S,3S,5S)-3-formyl-2-azabicyclo[3.1.0]hexane-2-carboxylate. The compound was synthesized analogously as described above from (1 S,3S,5S)-2-(tert-butoxycarbonyl)-2-azabicyclo[3.1.0]hexane-3-carboxylic acid and isolated as a crude light-yellow oil.

tert-Butyl (2S,4S)-2-formyl-4-methoxypyrrolidine-1-carboxylate. The compound was synthesized analogously as described above from (2S,4S)-1-(tert-butoxycarbonyl)-4-methoxypyrrolidine-2-carboxylic acid and isolated as a crude light-yellow oil.

tert-Butyl (2S,4R)-2-formyl-4-methoxypyrrolidine-1-carboxylate. The compound was synthesized analogously as described above from (2S,4R)-1-(tert-butoxycarbonyl)-4-methoxypyrrolidine-2-carboxylic acid and isolated as a crude light-yellow oil tert-Butyl (2S,4R)-4-fluoro-2-formylpyrrolidine-1-carboxylate. The compound was synthesized analogously as described above from (2S,4R)-1-(tert-butoxycarbonyl)-4-fluoropyrrolidine-2-carboxylic acid and isolated as a crude (light-yellow oil).

tert-Butyl (2S,4S)-4-fluoro-2-formylpyrrolidine-1-carboxylate. The compound was synthesized analogously as described above from (2S,4S)-1-(tert-butoxycarbonyl)-4-fluoropyrrolidine-2-carboxylic acid and isolated as a crude (light-yellow oil).

tert-Butyl (R)-5-(methoxy(methyl)carbamoyl)-2,2-dimethylpyrrolidine-1-carboxylate. To a stirred mixture of (R)-1-(tert-butoxycarbonyl)-5,5-dimethylpyrrolidine-2-carboxylic acid (0.10 g, 0.41 mmol) DCM (4 mL) was added N,O-dimethylhydroxylamine hydrochloride (0.06 g, 0.62 mmol), 1-ethyl-3-(3-dimethylaminopropyl)carbodiimide (0.16 g, 0.82 mmol), and $Et_3N$ (0.29 mL, 0.82 mmol) and was stirred at RT for 16 h. The mixture was diluted with DCM (10 mL), washed with sat. $NH_4Cl_{(aq)}$ (10 mL). The organic layers were separated, washed with sat. $NaHCO_{3(aq)}$ (10 mL), and extracted with DCM (3×5 mL). The organic layers were combined, dried over $MgSO_4$, and concentrated in vacuo. The residue was purified by a flash column chromatography ($SiO_2$, 0→100% EA in hexanes then 0→10% MeOH in EA) to yield the compound as a white solid (0.0292 g, 25%). MS (ESI) m/z 187.1 $[M-Boc+H]^+$.

tert-Butyl (S)-5-(methoxy(methyl)carbamoyl)-2,2-dimethylpyrrolidine-1-carboxylate. The compound was synthesized analogously as described above from (S)-1-(tert-butoxycarbonyl)-5,5-dimethylpyrrolidine-2-carboxylic acid and isolated a white solid (41%). MS (ESI) m/z 187.1 $[M-Boc+H]^+$.

tert-Butyl (2S,4S)-2-(methoxy(methyl)carbamoyl)-4-methylpyrrolidine-1-carboxylate. The compound was synthesized analogously as described above from (2S,4S)-1-(tert-butoxycarbonyl)-4-methylpyrrolidine-2-carboxylic acid and isolated a white solid (11%). MS (ESI) m/z 173.1 $[M-Boc+H]^+$.

tert-Butyl (2R,4R)-2-(methoxy(methyl)carbamoyl)-4-methylpyrrolidine-1-carboxylate. The compound was synthesized analogously as described above from (2R,4R)-1-(tert-butoxycarbonyl)-4-methyl pyrrolidine-2-carboxylic acid and isolated a white solid (82%). MS (ESI) m/z 173.1 $[M-Boc+H]^+$.

tert-Butyl (R)-2-(methoxy(methyl)carbamoyl)-4,4-dimethylpyrrolidine-1-carboxylate. The compound was synthesized analogously as described above from (R)-1-(tert-butoxycarbonyl)-4,4-dimethylpyrrolidine-2-carboxylic acid and isolated a yellow oil (95%). MS (ESI) m/z 187.0 $[M-Boc+H]^+$.

tert-Butyl (S)-2-(methoxy(methyl)carbamoyl)-4,4-dimethylpyrrolidine-1-carboxylate. The compound was synthesized analogously as described above from (S)-1-(tert-butoxycarbonyl)-4,4-dimethylpyrrolidine-2-carboxylic acid and isolated a yellow oil (80%). MS (ESI) m/z 187.1 $[M-Boc+H]^+$.

tert-Butyl (S)-(1-hydroxy-3-methoxypropan-2-yl)(methyl)carbamate. To a mixture of N-(tert-butoxycarbonyl)-O-methyl-D-serine (300 mg, 1.37 mmol) in THF (14 mL) at RT was added LAH (2 M in THF, 2.05 mL, 4.11 mmol) and heated to 60° C. After 2 h, additional LAH (2 M in THF, 2.05 mL, 4.11 mmol) was added and the mixture was stirred for 16 h. The mixture was cooled to 0° C. and diluted with THF (10 mL) The reaction was quenched by the Fieser method. An addition of water (1 mL per g of LAH) was made then 15% NaOH (1 mL per g of LAH) and finally water (3 mL per g of LAH). The mixture was dried over $MgSO_4$, filtered, and concentrated in vacuo. The residue was suspended in DCM (14 mL), and $Boc_2O$ (0.38 mL, 1.64 mmol), and $Et_3N$ (0.38 mL, 2.74 mmol) were added. The mixture was stirred at RT for 72 h. The mixture was diluted with DCM (10 mL), washed with washed with sat. $NH_4Cl_{(aq)}$ (10 mL). The organic layers were separated, washed with sat. $NaHCO_{3(aq)}$ (10 mL), and extracted with DCM (3×5 mL). The organic layers were combined, dried over $MgSO_4$, and concentrated in vacuo. The residue was purified by a flash column chromatography ($SiO_2$, 0→100% EA in hexanes) to yield the compound as a colorless oil (0.0812 g, 27% over 2 steps). MS (ESI) m/z 164.1 $[M-t-Bu+H]^+$.

tert-Butyl (R)-(1-hydroxy-3-methoxypropan-2-yl)(methyl)carbamate. The compound was synthesized analogously as described above from N-(tert-butoxycarbonyl)-O-methyl-L-serine and isolated a colorless oil (15%, over 2 steps). MS (ESI) m/z 164.1 $[M-t-Bu+H]^+$.

tert-butyl (1R,3S,5R)-3-(methoxy(methyl)carbamoyl)-2-azabicyclo[3.1.0]hexane-2-carboxylate. The compound was synthesized analogously as described above from (1R,3S,5R)-2-(tert-butoxycarbonyl)-2-azabicyclo[3.1.0]hexane-3-carboxylic acid and isolated a yellow oil (quant.). MS (ESI) m/z 171.1 $[M-Boc+H]^+$.

tert-butyl (2S,5R)-2-(methoxy(methyl)carbamoyl)-5-methylpyrrolidine-1-carboxylate. The compound was synthesized analogously as described above from (2S,5R)-1-(tert-butoxycarbonyl)-5-methylpyrrolidine-2-carboxylic acid and isolated a yellow oil (quant.). MS (ESI) m/z 173.1 $[M-Boc+H]^+$.

Example 59

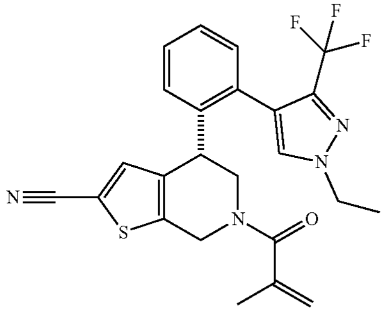

(S)-4-(2-(1-Ethyl-3-(trifluoromethyl)-1H-pyrazol-4-yl)phenyl)-6-methacryloyl-4,5,6,7-tetrahydrothieno[2,3-c]pyridine-2-carbonitrile To a stirred mixture of tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate (30.0 mg, 59.0 mmol) in DCM (0.5 mL) was added TFA (0.5 mL) and the mixture was stirred at RT for 2 h. The mixture was concentrated in vacuo and dissolved in THE (2 mL). The suspension was concentrated in vacuo. The crude material was dissolved in DCM (1 mL). Methacrylic acid (6.00 mg, 71.6 μmol), DIPEA (42.0 μL, 0.24 mmol), and HATU were added to the mixture and stirred at RT for 16 h. The mixture was diluted with EA (10 mL), washed with 1 M citric $acid_{(aq)}$ (10 mL), separated, then washed with saturated $NaHCO_{3(aq)}$ (10 mL). The organic layer was dried over $MgSO_4$, filtered, and concentrated in vacuo. The residue was purified by a flash column chromatography ($SiO_2$, 0→100% EA in hexanes) to yield the compound as an off-white solid (0.0264 g, 95%). MS (ESI) m/z 470.9 $[M]^+$.

Example 60

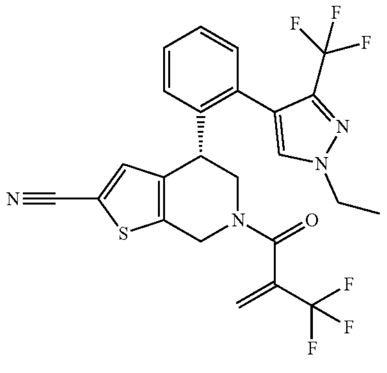 [SMILES: C=C(C(=O)N1Cc2sc(C#N)cc2[C@H](c2ccccc2-c2cn(CC)nc2C(F)(F)F)C1)C(F)(F)F]

(S)-4-(2-(1-Ethyl-3-(trifluoromethyl)-1H pyrazol-4-yl)phenyl)-6-(2-(trifluoromethyl)acryloyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2- carbonitrile and 2-(trifluoromethyl)acrylic acid, and isolated as colorless oil (49%). MS (ESI) m/z 525.2 $[M+H]^+$.

Example 61

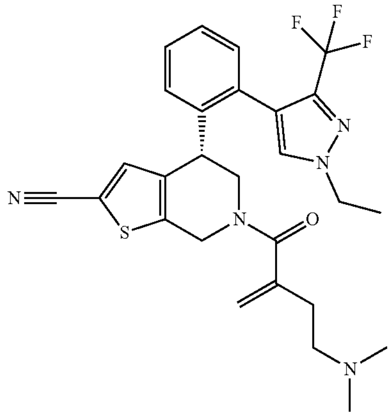 [SMILES: C=C(CCN(C)C)C(=O)N1Cc2sc(C#N)cc2[C@H](c2ccccc2-c2cn(CC)nc2C(F)(F)F)C1]

(S)-6-(4-(Dimechylamino)-2-methylenebutanoyl)-4-(2-(1-ethyl-3-(rifluoromethyl)-1H-pyrazol-4-yl)phenyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-(dimethylamino)-2-methylenebutanoic acid hydrochloride, and isolated as colorless oil (FA salt, 3%). MS (ESI) m/z 525.2 $[M+H]^+$.

Example 62

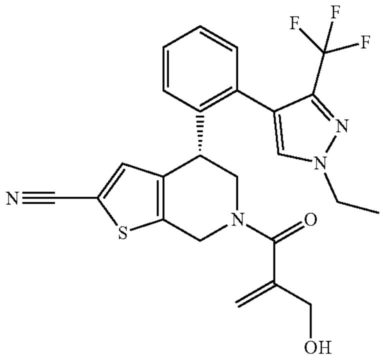 [SMILES: C=C(CO)C(=O)N1Cc2sc(C#N)cc2[C@H](c2ccccc2-c2cn(CC)nc2C(F)(F)F)C1]

(S)-4-(2-(1-Ethyl-3-(trifluoromethyl)-1H pyrazol-4-yl)phenyl)-6-(2-(hydroxymethyl)acryloyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 2-(hydroxymethyl)acrylic acid, and isolated as colorless oil (5%). MS (ESI) m/z 487.2 $[M+H]^+$.

Example 63

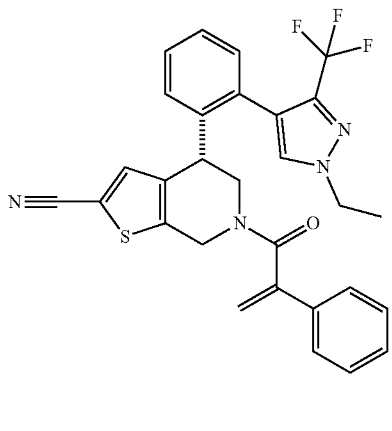

(S)-4-(2-(1-Ethyl-3-(trifluoromethyl)-1H pyrazol-4-yl)phenyl)-6-(2-phenylacryloyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 2-phenylacrylic acid, and isolated as white solid (95%). MS (ESI) m/z 533.2 $[M+H]^+$.

Example 64

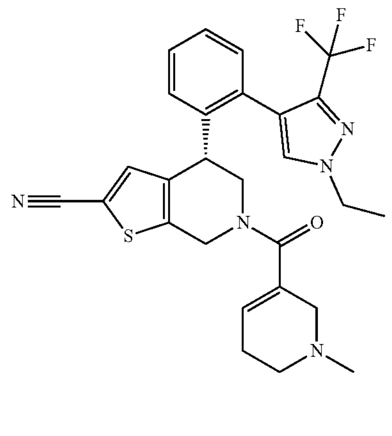 [SMILES: CCn1cc(-c2ccccc2[C@@H]2CN(C(=O)C3=CCCN(C)C3)Cc3sc(C#N)cc32)c(C(F)(F)F)n1]

(S)-4-(2-(1-Ethyl-3-(trifluoromethyl)-1H-pyrazol-4-yl)phenyl)-6-(1-methyl-1,2,5,6-tetrahydropyridine-3-carbonyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 1-methyl-1,2,5,6-tetrahydro-3-pyridinecarboxylic acid and isolated as sticky yellow solid (60%). MS (ESI) m/z 526.3 $[M+H]^+$.

Example 65

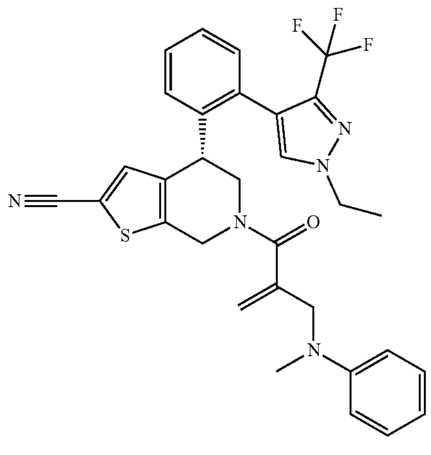 [SMILES: C=C(CN(C)c1ccccc1)C(=O)N1Cc2sc(C#N)cc2[C@H](c2ccccc2-c2cn(CC)nc2C(F)(F)F)C1]

(S)-4-(2-(1-Ethyl-3-(trifluoromethyl)-1H pyrazol-4-yl)phenyl)-6-(2-((methyl(phenyl)amino)methyl)acryloyl)-4,5,6,7-tetrahydrothieno[2,3-c]pyridine-2-carbonitrile 2-(Bromomethyl)acryloyl chloride. To a stirred mixture of 2-(bromomethyl)acrylic acid (100 mg, 0.61 mmol) in DCM (6 mL) at 0° C. was added a solution of $SOCl_2$ in DCM (2M, 0.91 mL, 1.82 mmol). The mixture was warmed to RT and stirred for 4 h. The mixture was concentrated in vacuo. The crude material was used directly in the following reaction (S)-6-(2-(Bromomethyl)acryloyl)-4-(2-(1-ethyl-3-(trifluoromethyl)-1H-pyrazol-4-yl)phenyl)-4,5,6,7-tetrahydrothieno[2,3-c]pyridine-2-carbonitrile. To a stirred mixture of (S)-4-(2-(1-ethyl-3-(trifluoromethyl)-1H-pyrazol-4-yl)phenyl)-4,5,6,7-tetrahydrothieno[2,3-c]pyridine-2-carbonitrile (100 mg, 0.19 mmol) in DCM (1 mL) was added TFA (1 mL) and the mixture was stirred at RT for 2 h. The mixture was concentrated in vacuo, suspended in THF (2 mL), and concentrated in vacuo. The crude was suspended in DCM (1 mL) and DIPEA (0.15 mL, 0.79 mmol) was added. At RT, 2-(bromomethyl)acryloyl chloride was dissolved in DCM (1 mL), and slowly added to the mixture, and the mixture was stirred at RT for 1 h. The mixture was diluted with DCM (10 mL), washed with 1 M citric $acid_{(aq)}$ (10 mL), separated, then washed with saturated $NaHCO_{3(aq)}$ (10 mL). The organic layer was dried over $MgSO_4$, filtered, and concentrated in vacuo. The residue was purified by a flash column chromatography ($SiO_2$, 0→100% EA in hexanes) to yield the compound as an off-white solid (0.023 g, 21%). MS (ESI) m/z 550.8 $[M+H]^+$.

(S)-4-(2-(1-Ethyl-3-(trifluoromethyl)-1H-pyrazol-4-yl)phenyl)-6-(2-((methyl(phenyl)amino)methyl)acryloyl)-4,5,6,7-tetrahydrothieno[2,3-c]pyridine-2-carbonitrile. To a stirred mixture of N-methylaniline (5.00 μL, 47.0 μmol) in THF (0.5 mL) at RT was added NaH (60 wt % dispersion in mineral oil, 1.90 mg, 47.0 μmol) and stirred for 30 min. (S)-6-(2-(bromomethyl)acryloyl)-4-(2-(1-ethyl-3-(trifluoromethyl)-1H-pyrazol-4-yl)phenyl)-4,5,6,7-tetrahydrothieno[2,3-c]pyridine-2-carbonitrile (21.0 mg, 37.0 μmol) was dissolved in THF (0.5 mL) and added to the mixture. The mixture was stirred at RT for 16 h. The mixture was diluted with EA (10 mL), and washed with saturated $NaHCO_{3(aq)}$ (10 mL). The organic layer was dried over $MgSO_4$, filtered, and concentrated in vacuo. The residue was purified by a flash column chromatography ($SiO_2$, 0→100% EA in hexanes) and further purified by HPLC purification (Agilent Prep-Cm column (50×21.2 mm, 5 mm); eluent A=$H_2O$ (0.1% FA), B=ACN (0.1% FA), 5→95% B over 19 min @ 25 mL/min) to yield the compound as a yellow oil (0.0053 g, 20%). MS (ESI) m/z 576.3 $[M+1]^+$.

Example 66

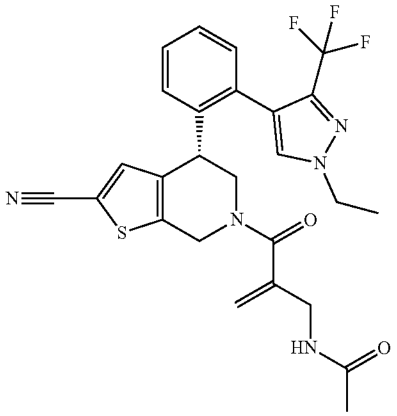 [SMILES: C=C(CNC(C)=O)C(=O)N1Cc2sc(C#N)cc2[C@H](c2ccccc2-c2cn(CC)nc2C(F)(F)F)C1]

(S)—N-(2-(2-Cyano-4-(2-(1-ethyl-3-(trifluoromethyl)-1H pyrazol-4-yl)phenyl)-4,5,6,7-tetrahydrothieno[2,3-c]pyridine-6-carbonyl) all yl) acetamide To a stirred mixture of acetamide (20.0 mg, 0.34 mmol) in THF (1 mL) at RT was added NaH (60 wt % dispersion in mineral oil, 15.0 mg, 0.37 mmol) and the mixture was stirred for 30 min. tert-Butyl 2-(bromomethyl)acrylate (58.0 μL, 0.34 mmol) was dissolved in THF (1 mL) and slowly added to the mixture and the mixture was stirred at RT for 2 h. The mixture was diluted with DCM (5 mL) and washed with $H_2O$ (5 mL). The aqueous layer was extracted with DCM (5 mL×3), and the organic layers were combined, dried over $MgSO_4$, and concentrated in vacuo. The crude compound was dissolved in DCM (1 mL), and (S)-4-(2-(1-ethyl-3-(trifluoromethyl)-1H-pyrazol-4-yl)phenyl)-4,5,6,7-tetrahydrothieno[2,3-c]pyridine-2-carbonitrile (30.0 mg, 59.6 μmol), and TFA (1 mL) were added to the mixture and stirred for 2 h. The mixture was concentrated in vacuo, suspended in THF (2 mL), and concentrated in vacuo. The mixture was suspended in DCM (2 mL). HATU (34.0 mg, 89.0 μmol) and DIPEA (42.0 μL, 0.24 mmol) were added to the mixture and the mixture was stirred at RT for 16 h. The mixture was diluted with DCM (10 mL), washed with washed with sat. $NH_4Cl_{(aq)}$ (10 mL), the organic layers were separated then washed with sat. $NaHCO_{3(aq)}$ (10 mL), extracted with DCM (5 mL×3). The organic layers were combined, dried over $MgSO_4$, and concentrated in vacuo. The residue was purified by a flash column chromatography ($SiO_2$, 0→100% EA in hexanes then 0→10% MeOH in EA) to yield the target compound as a yellow oil (0.032 g, 10%). MS (ESI) m/z 528.2 $[M+H]^+$.

Example 67

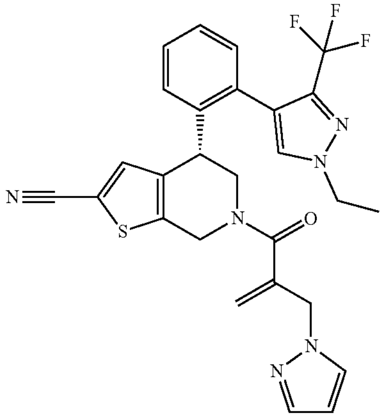 [SMILES: C=C(Cn1cccn1)C(=O)N1Cc2sc(C#N)cc2[C@H](c2ccccc2-c2cn(CC)nc2C(F)(F)F)C1]

(S)-6-(2-((1H-Pyrazol-1-yl)methyl)acryloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was made analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile, tert-butyl 2-(bromomethyl)acrylate and 1H-pyrazole, and isolated as yellow oil (14%). MS (ESI) m/z 537.3 $[M+H]^+$.

Example 68

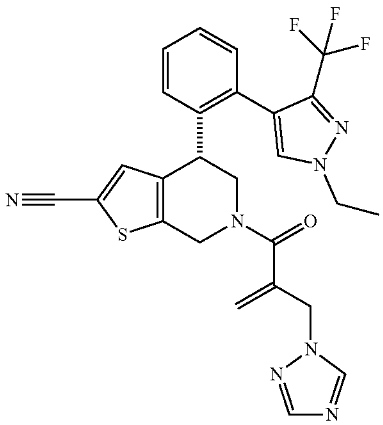

(S)-6-(2-((1H-1,2,4-Triazol-1-yl)methyl)acryloyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile, tert-butyl2-(bromomethyl)acrylate and 1H-1,2,4-triazole, and isolated as yellow oil (21%). MS (ESI) m/z 538.2 $[M+H]^+$.

Example 69

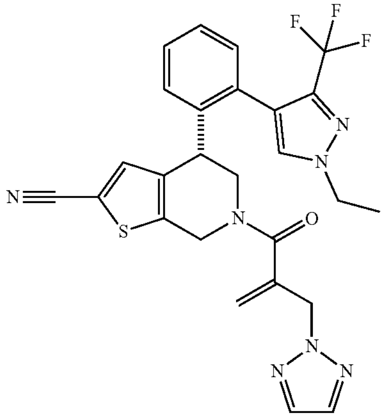

(S)-6-(2-((2H-1,2,3-Triazol-2-yl)methyl) acryloyl)-4-(2-(1-ethyl-3-(trifluoromethyl)-1H-pyrazol-4-yl) phenyl)-4,5,6,7-tetrahydrothieno[2,3-c]pyridine-2-carbonitrile The compound was synthesized analogously as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile, tert-butyl2-(bromomethyl)acrylate and 2H-1,2,3-triazole, and isolated as yellow oil (6%). MS (ESI) m/z 538.2 $[M+H]^+$.

Example 70

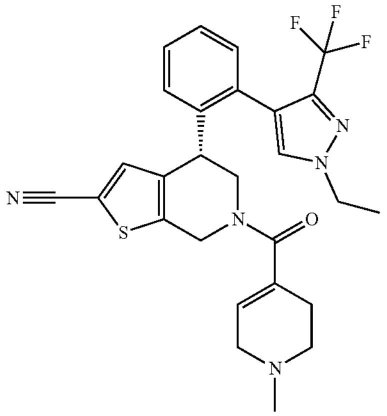 [SMILES: CCn1cc(-c2ccccc2[C@@H]2CN(C(=O)C3=CCN(C)CC3)Cc3sc(C#N)cc32)c(C(F)(F)F)n1]

(S)-4-(2-(1-ethyl-3-(trifluoromethyl)-1H-pyrazol-4-yl)phenyl)-6-(1-methyl-1, 2, 3, 6-tetrahydropyridine-4-carbonyl)-4,5,6,7-tetrahydrothieno[2,3-c] pyridine-2-carbonitrile Methyl 1-methyl-1,2,3,6-tetrahydropyridine-4-carboxylate (100 mg, 0.64 mmol) was stirred in conc. HCl (2 mL) 50° C. for 16 h. The mixture was concentrated in vacuo and used without further purification. (S)-4-(2-(1-Ethyl-3-(trifluoromethyl)-1H-pyrazol-4-yl)phenyl)-4,5,6,7-tetrahydrothieno[2,3-c]pyridine-2-carbonitrile (30.0 mg, 59.6 µmol) was dissolved in DCM (1 mL) and TFA (1 mL) was added to the mixture and stirred for 2 h. The mixture was concentrated in vacuo, suspended in THE (2 mL), and concentrated in vacuo. The mixture was suspended in DCM (2 mL). The crude acid, HATU (34.0 mg, 89.0 µmol) and DIPEA (42.0 µL, 0.24 mmol) were added to the mixture and stirred at RT for 16 h. The mixture was diluted with DCM (5 mL) and washed with $H_2O$ (5 mL). The aqueous layer was extracted with DCM (5 mL×3). The combined organic layers were dried over $MgSO_4$, filtered, and concentrated in vacuo. The crude product was purified by HPLC (Agilent Prep-018 column (50×21.2 mm, 5 µm); eluent A=$H_2O$ (0.1% FA), B=ACN in $H_2O$ (0.1% FA), 5→95% B over 19 min @ 25 mL/min) to yield the compound as a yellow oil (0.0512 g, 98%). MS (ESI) m/z 526.2 $[M+H]^+$.

Example 71

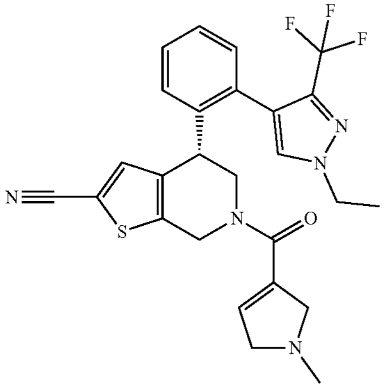 [SMILES: CCn1cc(-c2ccccc2[C@@H]2CN(C(=O)C3=CCN(C)C3)Cc3sc(C#N)cc32)c(C(F)(F)F)n1]

(S)-4-(2-(1-Ethyl-3-(trifluoromethyl)-1H pyrazol-4-yl)phenyl)-6-(1-methyl-2,5-dihydro-1H pyrrole-3-carbonyl)-4,5,6,7-tetrahydrothieno[2,3-c]pyridine-2-carbonitrile tert-Butyl (S)-3-(2-cyano-4-(2-(1-ethyl-3-(trifluoromethyl)-1H pyrazol-4-yl)phenyl)-4,5,6,7-tetrahydrothieno[2,3-c]pyridine-6-carbonyl)-2,5-dihydro-1H-pyrrole-1-carboxylate. (S)-4-(2-(1-Ethyl-3-(trifluoromethyl)-1H-pyrazol-4-yl)phenyl)-4,5,6,7-tetrahydrothieno[2,3-c]pyridine-2-carbonitrile (50.0 mg, 99.0 µmol) was dissolved in DCM (1 mL) and TFA (1 mL) was added to the mixture and stirred for 2 h. The mixture was concentrated in vacuo, suspended in THF (2 mL), and concentrated in vacuo. The mixture was suspended in DCM (2 mL). 1-(tert-Butoxycarbonyl)-2,5-dihydro-1H-pyrrole-3-carboxylic acid (25.0 mg, 119 µmol), HATU (57.0 mg, 149 µmol) and DIPEA (0.54 mL, 0.39 mmol) were added and the mixture was stirred at RT for 16 h. The mixture was diluted with DCM (5 mL), washed with 1 M citric $acid_{(aq)}$ (10 mL), separated, and washed with saturated $NaHCO_{3(aq)}$ (10 mL). The organic layer was dried over $MgSO_4$, filtered, and concentrated in vacuo. The residue was purified by a flash column chromatography ($SiO_2$, 0→100% EA in hexanes) to yield the compound as yellow oil (0.0563 g, 95%). MS (ESI) m/z 497.9 [M-Boc]+.

(S)-4-(2-(1-Ethyl-3-(trifluoromethyl)-1H-pyrazol-4-yl) phenyl)-6-(1-methyl-2,5-dihydro-1H-pyrrole-3-carbonyl)-4,5,6,7-tetrahydrothieno[2,3-c]pyridine-2-carbonitrile. tert-Butyl (S)-3-(2-cyano-4-(2-(1-ethyl-3-(trifluoromethyl)-1H-pyrazol-4-yl)phenyl)-4,5,6,7-tetrahydrothieno[2,3-c]

pyridine-6-carbonyl)-2,5-dihydro-1H-pyrrole-1-carboxylate (56.0 mg, 94.0 μmol) was dissolved in DCM (1 mL) and TFA (1 mL) was added to the mixture and stirred for 2 h. The mixture was concentrated in vacuo, suspended in THF (2 mL), and concentrated in vacuo. The crude mixture was then suspended in DCM (1 mL). Paraformaldehyde (3.00 mg, 112 μmol), and sodium triacetoxyborohydride (40.0 mg, 0.19 mmol) was added to the mixture and stirred at RT for 16 h. The mixture was diluted with DCM (10 mL) and washed with saturated $NaHCO_{3(aq)}$ (10 mL). The organic layer was then dried over $MgSO_4$, filtered, and concentrated in vacuo. The residue was then purified by HPLC purification (Agilent Prep-C18 column (50×21.2 mm, 5 μm); eluent A=$H_2O$ (0.1% FA), B=ACN in $H_2O$ (0.1% FA), 5→95% B over 19 min @ 25 mL/min to yield (S)-4-(2-(1-Ethyl-3-(trifluoromethyl)-1H-pyrazol-4-yl)phenyl)-6-(1-methyl-2,5-dihydro-1H-pyrrole-3-carbonyl)-4,5,6,7-tetrahydrothieno[2,3-c]pyridine-2-carbonitrile as a sticky yellow solid 0.0173 g, 36%). MS (ESI) m/z 512.2 $[M+H]^+$.

Example 72

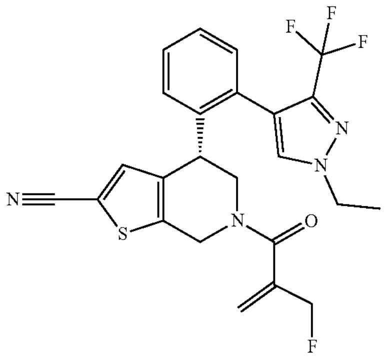 [SMILES: C=C(CF)C(=O)N1Cc2sc(C#N)cc2[C@H](c2ccccc2-c2cn(CC)nc2C(F)(F)F)C1]

(S)-4-(2-(1-Ethyl-3-(trifluoromethyl)-1H-pyrazol-4-yl)phenyl)-6-(2-(fluoromethyl)acryloyl)-4,5,6,7-tetrahydrothieno[2,3-c]pyridine-2-carbonitrile tert-Butyl 2-(bromomethyl)acrylate (50.0 mg, 226 μmol) and AgF (34.0 mg, 0.27 mmol) were dissolved in MeCN (2 mL) and stirred at RT for 16 h in the dark. The mixture was diluted with DCM (10 mL) and washed with saturated $NaHCO_{3(aq)}$ (10 mL). The organic layer was dried over $MgSO_4$, filtered over Celite®, and concentrated in vacuo. The residue was suspended in DCM (1 mL). (S)-4-(2-(1-Ethyl-3-(trifluoromethyl)-1H-pyrazol-4-yl)phenyl)-4,5,6,7-tetrahydrothieno[2,3-c]pyridine-2-carbonitrile (30.0 mg, 59.6 μmol) and TFA (1 mL) were added and the mixture was stirred at RT for 2 h. The mixture was concentrated in vacuo, suspended in THF (2 mL), and concentrated in vacuo. The crude mixture was suspended in DCM (1 mL). HATU (34.0 mg, 89.0 μmol), $Et_3N$ (0.32 mL, 0.24 mmol) were added to the mixture and stirred at RT for 16 h. The mixture was diluted with DCM (10 mL), washed with 1 M citric $acid_{(aq)}$ (10 mL), separated, and washed with saturated $NaHCO_{3(aq)}$ (10 mL). The organic layer was dried over $MgSO_4$, filtered, and concentrated in vacuo. The residue was purified by HPLC purification (Agilent Prep-C18 column (50×21.2 mm, 5 μm); eluent A=$H_2O$ (0.1% FA), B=ACN in $H_2O$ (0.1% FA), 5→95% B over 19 min @ 25 mL/min to yield the compound as an off-white solid (0.0080 g, 28%). MS (ESI) m/z 488.2 [M]+.

Various intermediate compounds were prepared similar to that described above.

tert-Butyl (S)-4-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethyloxazolidine-3-carboxylate. To a stirred mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (50.0 mg, 86.0 μmol) in THE (1 mL) at 0° C. was added NaH (60 wt % dispersion in mineral oil, 4.00 mg, 103 μmol) and stirred at 0° C. for 15 min. (R)-Garner's Aldehyde (0.030 mL, 0.13 mmol) was added to the mixture dropwise and stirred for 10 min at 0° C. then warmed to RT and stirred for 3 h. The mixture was diluted with DCM (5 mL) washed with sat. aq. $NaHCO_3$ (5 mL) and extracted with DCM (3 mL×3). The organic layer was separated, dried over $MgSO_4$, filtered, and concentrated in vacuo. The residue was purified by a flash column chromatography ($SiO_2$, 0→100% EA in hexanes) to yield the compound as a sticky yellow solid (0.0336 g, 60%). MS (ESI) m/z 656.0 $[M+H]^+$.

tert-Butyl (R)-4-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethyloxazolidine-3-carboxylate was synthesized analogously as described above from diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H-yl)-2-oxoethyl)phosphonate, and (S)-Garner's Aldehyde, and isolated a sticky yellow solid (81%). MS (ESI) m/z 656.0 $[M+H]^+$.

di-tert-Butyl 2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)piperazine-1,4-dicarboxylate was synthesized analogously as described above from diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H-yl)-2-oxoethyl)phosphonate, and di-tert-butyl 2-formylpiperazine-1,4-dicarboxylate, and isolated a yellow oil (80%). MS (ESI) m/z 741.0 $[M+H]^+$.

tert-Butyl 3-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)morpholine-4-carboxylate was synthesized analogously as described above from diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H-yl)-2-oxoethyl)phosphonate, and tert-butyl 3-formylmorpholine-4-carboxylate, and isolated a yellow oil (76%). MS (ESI) m/z 741.0 $[M+H]^+$.

tert-Butyl ((E)-5-((S)-2-cyano-4-(2-(1-ethyl-3-(trifluoromethyl)-1H pyrazol-4-yl)phenyl)-4,7-dihydrothieno[2,3-c]pyridin-6(5H)-yl)-5-oxopent-3-en-2-yl)(methyl)carbamate. To a stirred mixture of tert-butyl (1-hydroxypropan-2-yl)(methyl)carbamate (100 mg, 0.53 mmol) in DCM (5 mL) at 0° C., Dess-Martin Periodinane (269 mg, 0.63 mmol) was added. The mixture was warmed to RT and stirred for 3 h. The mixture was diluted with DCM (10 mL), washed with sat. aq. $NaHCO_3$ (10 mL) and extracted with DCM (3×3 mL). The organic layer was separated, dried over $MgSO_4$, filtered, and concentrated in vacuo. The residue was suspended in THF (1 mL) and used in the next reaction. To a stirred mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (50.0 mg, 86.0 μmol) in THF (1 mL) at 0° C. was added NaH (60 wt % dispersion in mineral oil, 4.00 mg, 103 μmol) and stirred at 0° C. for 15 min. The crude aldehyde was added to the mixture slowly at 0° C. The mixture was warmed to RT and stirred for 3 h. The mixture was diluted with DCM (10 mL), washed with sat. aq. $NaHCO_3$ (10 mL) and extracted with DCM (3 mL×3). The organic layer was separated, dried over $MgSO_4$, filtered, and concentrated in vacuo. The residue was purified by a flash column chromatography ($SiO_2$, 0→100% EA in hexanes then 0→10% MeOH in EA) to yield the target compound as a sticky yellow solid (0.0949 g, 89%). MS (ESI) m/z 614.0 $[M+H]^+$.

tert-Butyl ((S,E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-5-oxopent-3-en-2-yl)(methyl)carbamate was synthesized analogously as described above from diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate, and Pert butyl (S)-(1-hydroxypropan-2-yl)(methyl)carbamate, and isolated a white solid (44%). MS (ESI) m/z 614.0 $[M+H]^+$.

tert-Butyl ((R,E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-5-oxopent-3-en-2-yl)(methyl)carbamate was synthesized analogously as described above from diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate, and Pert butyl (R)-(1-hydroxypropan-2-yl)(methyl)carbamate, and isolated a yellow oil (70%). MS (ESI) m/z 636.3 $[M+Na]^+$.

tert-Butyl ((R,E)-5-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-5-oxopent-3-en-2-yl)(methyl)carbamate was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate, Pert butyl (R)-(1-hydroxypropan-2-yl)(methyl)carbamate, and isolated a yellow oil (72%). MS (ESI) m/z 632.0 $[M+H]^+$.

tert-Butyl ((S,E)-5-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-5-oxopent-3-en-2-yl)(methyl)carbamate was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate, and Pert butyl (S)-(1-hydroxypropan-2-yl)(methyl)carbamate, and isolated a yellow oil (69%). MS (ESI) m/z 632.0 $[M+H]^+$.

tert-Butyl (S,E)-(4-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-4-oxobut-2-en-1-yl)(methyl)carbamate was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-2-oxoethyl)phosphonate, and tert-butyl (2-hydroxyethyl)(methyl)carbamate, and isolated a yellow oil (85%). MS (ESI) m/z 618.0 $[M+H]^+$.

tert-Butyl (R)-5-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethylpyrrolidine-1-carboxylate. To a mixture of tert-butyl (R)-5-(methoxy(methyl)carbamoyl)-2,2-dimethylpyrrolidine-1-carboxylate (0.03 g, 0.10 mmol) in THF (1 mL) at 0° C. was added DIBAL (1 M in THF, 0.12 mL, 0.12 mmol) and stirred at 0° C. for 3 h. The mixture was diluted with THF (5 mL) then quenched by the Fieser method. An addition of water (1 mL per g of DIBAL) was made then 15% NaOH (1 mL per g of DIBAL) and finally water (3 mL per g of DIBAL). The mixture was dried with $MgSO_4$, filtered, and concentrated in vacuo. The crude aldehyde was dissolved in THF (1 mL) and used in the next reaction. To a stirred mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H-yl)-2-oxoethyl)phosphonate (50.0 mg, 86.0 μmol) in THF (1 mL) at 0° C. was added NaH (60 wt % dispersion in mineral oil, 4.00 mg, 103 μmol) and stirred at 0° C. for 15 min. The crude aldehyde was then added to the mixture slowly at 0° C. The mixture was warmed to RT and stirred for 3 h. The mixture was diluted with DCM (10 mL), washed with sat. aq. $NaHCO_3$ (10 mL) and extracted with DCM (3 mL×3). The organic layer was separated, dried over $MgSO_4$, filtered, and concentrated in vacuo. The residue was purified by a flash column chromatography ($SiO_2$, 0→100% EA in hexanes) to yield the compound as white solid (0.0161 g, 19%). MS (ESI) m/z 654.0 $[M+H]^+$.

tert-Butyl (S)-5-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethyl-pyrrolidine-1-carboxylate was synthesized analogously as described above from tert-butyl (S)-5-(methoxy(methyl)carbamoyl)-2,2-dimethylpyrrolidine-1-carboxylate and isolated a yellow oil (88%). MS (ESI) m/z 676.0 $[M+Na]^+$.

tert-Butyl (2S,4S)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-4-methylpyrrolidine-1-carboxylate was synthesized analogously as described above from tert-butyl (2S,4S)-2-(methoxy(methyl)carbamoyl)-4-methylpyrrolidine-1-carboxylate and isolated a yellow oil (73%). MS (ESI) m/z 663.0 $[M+Na]^+$.

tert-Butyl (2R,4R)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-4-methylpyrrolidine-1-carboxylate was synthesized analogously as described above from tert-butyl (2R,4R)-2-(methoxy(methyl)carbamoyl)-4-methylpyrrolidine-1-carboxylate and isolated a colorless oil (quant.). MS (ESI) m/z 640.0 $[M+H]^+$.

tert-Butyl (R)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-4,4-dimethylpyrrolidine-1-carboxylate was synthesized analogously as described above from tert-butyl (R)-2-(methoxy(methyl)carbamoyl)-4,4-dimethylpyrrolidine-1-carboxylate and isolated a colorless oil (73%). MS (ESI) m/z 654.0 $[M+H]^+$.

tert-Butyl (S)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-4,4-dimethylpyrrolidine-1-carboxylate was synthesized analogously as described above from tert-butyl (S)-2-(methoxy(methyl)carbamoyl)-4,4-dimethylpyrrolidine-1-carboxylate and isolated a colorless oil (quant.). MS (ESI) m/z 654.0 $[M+H]^+$.

tert-Butyl ((S,E)-5-((S)-2-cyano-4-(2-(1-ethyl-3-(trifluoromethyl)-1H pyrazol-4-yl)phenyl)-4,7-dihydrothieno[2,3-c]pyridin-6(5H)-yl)-1-methoxy-5-oxopent-3-en-2-yl)(methyl)carbamate. To a mixture of DMSO (68 μL, 0.95 mmol) in DCM (7) at −78° C. was added $(COCl)_2$ (2M in DCM, 0.48 mL, 0.95 mmol) and the reaction was stirred at −78° C. for 30 min. tert-Butyl (R)-(1-hydroxy-3-methoxypropan-2-yl)(methyl)carbamate (0.10 mL, 0.87 mmol) was dissolved in DCM (2 mL) and added slowly at −78° C. and the mixture was stirred for 45 min. $Et_3N$ (0.15 mL, 1.04 mmol) was added and the mixture was stirred at −78° C. for 1 h. The mixture was concentrated in vacuo. The crude aldehyde was dissolved in THF (1 mL) and used in the next reaction.

To a stirred mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (50.0 mg, 86.0 μmol) in THF (1 mL) at 0° C. was added NaH (60 wt % dispersion in mineral oil, 4.00 mg, 103 μmol) and stirred at 0° C. for 15 min. The crude aldehyde was added to the mixture slowly at 0° C. The mixture was warmed to RT and stirred for 3 h. The mixture was diluted with DCM (10 mL), washed with sat. aq. $NaHCO_3$ (10 mL) and extracted with DCM (3 mL×3). The organic layer was separated, dried over $MgSO_4$, filtered, and concentrated in vacuo. The residue was purified by a flash column chromatography ($SiO_2$, 0→100% EA in hexanes) to yield the compound as a purple oil (0.0648 g, 74%). MS (ESI) m/z 644.0 $[M+H]^+$.

tert-Butyl ((R,E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-methoxy-5-oxopent-3-en-2-yl)(methyl)carbamate was synthesized analogously as described above from tert-butyl (R)-(1-hydroxy-3-methoxypropan-2-yl)(methyl)carbamate and isolated a yellow oil (quant.). MS (ESI) m/z 644.0 $[M+H]^+$.

Example 73

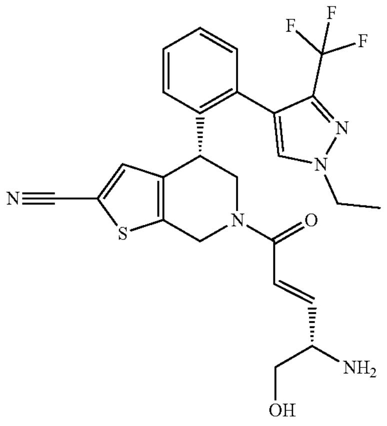 [SMILES: CCn1cc(-c2ccccc2[C@@H]2CN(C(=O)/C=C/[C@H](N)CO)Cc3sc(C#N)cc32)c(C(F)(F)F)n1]

(S)-6-((S,E)-4-Amino-5-hydroxypent-2-enoyl)-4-(2-(1-ethyl-3-(trifluoromethyl)-1H pyrazol-4-yl)phenyl)-4,5,6,7-tetrahydrothieno[2,3-c]pyridine-2-carbonitrile To a mixture of tert-butyl (S)-4-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethyloxazolidine-3-carboxylate (33.6 mg, 51.2 μmol), in DCM (1 mL) at RT, was added TFA (1 mL) and the reaction was stirred at RT for 2 h. The mixture was concentrated in vacuo, suspended in THF (2 mL), and concentrated in vacuo. The residue was purified by HPLC purification (Agilent Prep-Cis column (50×21.2 mm, 5 μm); eluent A=$H_2O$ (0.1% FA), B=ACN in $H_2O$ (0.1% FA), 5→95% B over 19 min @ 25 mL/min) to yield the compound as a white solid (FA salt, 0.020 g, 76%). MS (ESI) m/z 516.2 $[M+H]^+$.

Various intermediate compounds were prepared similar to that described above.

tert-Butyl (1R,3S,5R)-3-((E)-3-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-3-oxoprop-1-en-1-yl)-2-azabicyclo[3.1.0]hexane-2-carboxylate was synthesized analogously as described above from tert-butyl (1R,3S,5R)-3-(methoxy(methyl)carbamoyl)-2-azabicyclo[3.1.0]hexane-2-carboxylate and isolated a yellow oil (81%). MS (ESI) m/z 656.0 $[M+H]^+$.

tert-Butyl (2S,5R)-2-((E)-3-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-3-oxoprop-1-en-1-yl)-5-methylpyrrolidine-1-carboxylate was synthesized analogously as described above from tert-butyl (2S,5R)-2-(methoxy(methyl)carbamoyl)-5-methylpyrrolidine-1-carboxylate and isolated a yellow oil (23%). MS (ESI) m/z 658.7 $[M+H]^+$.

Example 74

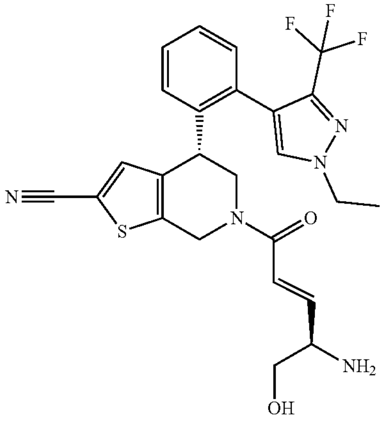 [SMILES: CCn1cc(-c2ccccc2[C@@H]2CN(C(=O)/C=C/[C@@H](N)CO)Cc3sc(C#N)cc32)c(C(F)(F)F)n1]

(S)-6-((R,E)-4-Amino-5-hydroxypent-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from tert-butyl (R)-4-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethyloxazolidine-3-carboxylate and isolated a white solid (FA salt, 71%). MS (ESI) m/z 516.2 $[M+H]^+$.

Example 75

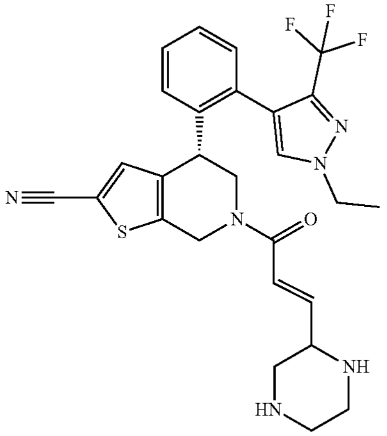 [SMILES: CCn1cc(-c2ccccc2[C@@H]2CN(C(=O)/C=C/C3CNCCN3)Cc3sc(C#N)cc32)c(C(F)(F)F)n1]

(4S)-4-(2-(1-Ethyl-3-(trifluoromethyl)-1H-pyrazol-4-yl)phenyl)-6-((E)-3-(piperazin-2-yl)acryloyl)-4,5,6,7-tetrahydrothieno[2,3-c]pyridine-2-carbonitrile The compound was synthesized analogously as described above from di-tert-butyl 2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H-yl)-3-oxoprop-1-en-1-yl) piperazine-1,4-dicarboxylate and isolated a white solid (FA salt, 71%). MS (ESI) m/z 541.3 $[M+H]^+$.

Example 76

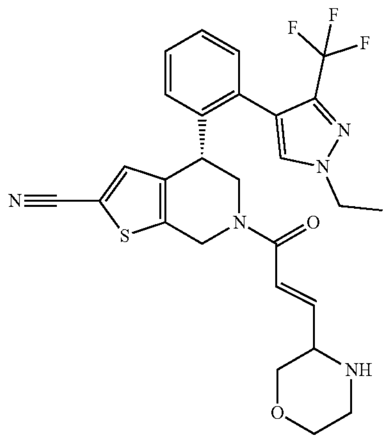 [SMILES: CCn1cc(-c2ccccc2[C@@H]2CN(C(=O)/C=C/C3COCCN3)Cc3sc(C#N)cc32)c(C(F)(F)F)n1]

(4S)-4-(2-(1-Ethyl-3-(trifluoromethyl)-1H-pyrazol-4-yl)phenyl)-6-((E)-3-(morpholin-3-yl)acryloyl)-4,5,6,7-tetrahydrothieno[2,3-c]pyridine-2-carbonitrile The compound was synthesized analogously as described above from tert-butyl 3-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)morpholine-4-carboxylate and isolated an off-white solid (FA salt, 67%). MS (ESI) m/z 542.3 $[M+H]^+$.

Example 77

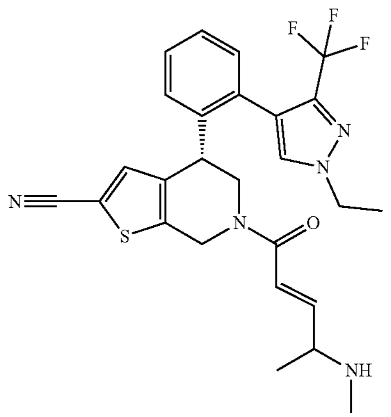 [SMILES: CCn1cc(-c2ccccc2[C@@H]2CN(C(=O)/C=C/C(C)NC)Cc3sc(C#N)cc32)c(C(F)(F)F)n1]

(4S)-4-(2-(1-Ethyl-3-(trifluoromethyl)-1H pyrazol-4-yl)phenyl)-6-((E)-4-(methylamino)pent-2-enoyl)-4,5,6,7-tetrahydrothieno[2,3-c]pyridine-2-carbonitrile The compound was synthesized analogously as described above from tert-butyl ((E)-5-((S)-2-cyano-4-(2-(1-ethyl-3-(trifluoromethyl)-1H-pyrazol-4-yl)phenyl)-4,7-dihydrothieno[2,3-c]pyridin-6(5H-yl)-5-oxopent-3-en-2-yl)(methyl) carbamate and isolated a white solid (FA salt, 13%). MS (ESI) m/z 514.3 $[M+H]^+$.

Example 78

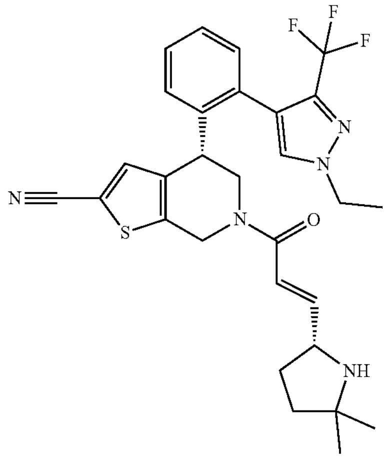 [SMILES: CCn1cc(-c2ccccc2[C@@H]2CN(C(=O)/C=C/[C@H]3CCC(C)(C)N3)Cc3sc(C#N)cc32)c(C(F)(F)F)n1]

(S)-6-((E)-3-((R)-5,5-Dimethylpyrrolidin-2-yl)acryloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above from tert-butyl (R)-5-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-2,2-dimethylpyrrolidine-1-carboxylate and isolated a white solid (FA salt, 66%). MS (ESI) m/z 554.3 $[M+H]^+$.

Example 79

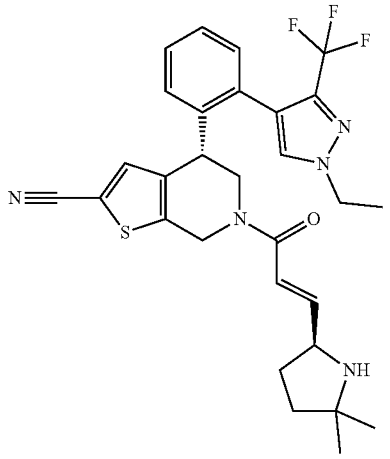 [SMILES: CCn1cc(-c2ccccc2[C@@H]2CN(C(=O)/C=C/[C@@H]3CCC(C)(C)N3)Cc3sc(C#N)cc32)c(C(F)(F)F)n1]

(S)-6-((E)-3-((S)-5,5-Dimethylpyrrolidin-2-yl)acryloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above from tert-butyl (S)-5-((E)-3-((S)-2-cyano-4-(2-(1-ethyl-3-(trifluoromethyl)-1H-pyrazol-4-yl)phenyl)-4,7-dihydrothieno[2,3-c]pyridin-6(5h)-yl)-3-oxoprop-1-en-1-yl)-2,2-dimethylpyrrolidine-1-carboxylate and isolated a white solid (FA salt, 27%). MS (ESI) m/z 554.3 [M+H]$^+$.

Example 80

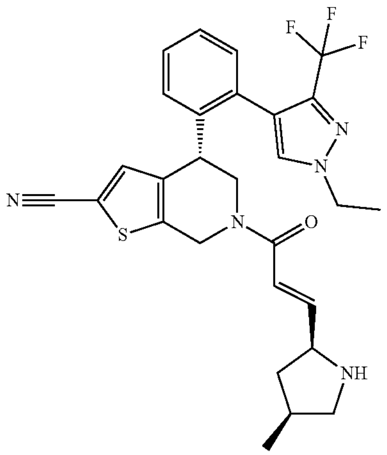 [SMILES: CCn1cc(-c2ccccc2[C@@H]2CN(C(=O)/C=C/[C@@H]3C[C@H](C)CN3)Cc3sc(C#N)cc32)c(C(F)(F)F)n1]

(S)-4-(2-(1-Ethyl-3-(trifluoromethyl)-1H pyrazol-4-yl)phenyl)-6-((E)-3-((2S,4S)-4-methylpyrrolidin-2-yl)acryloyl)-4,5,6,7-tetrahydrothieno[2,3-c]pyridine-2-carbonitrile The compound was synthesized analogously as described above from tert-butyl (2S,4S)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H-yl)-3-oxoprop-1-en-1-yl)-4-methylpyrrolidine-1-carboxylate and isolated a white solid (FA salt, 25%). MS (ESI) m/z 540.3 [M+H]$^+$.

Example 81

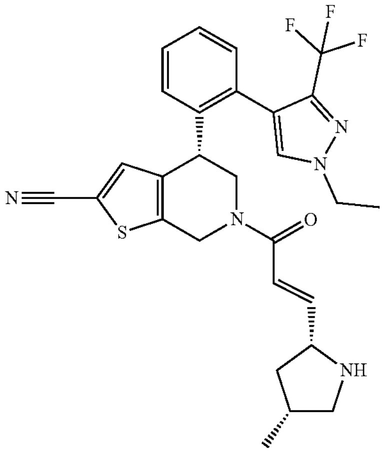 [SMILES: CCn1cc(-c2ccccc2[C@@H]2CN(C(=O)/C=C/[C@H]3C[C@@H](C)CN3)Cc3sc(C#N)cc32)c(C(F)(F)F)n1]

(S)-4-(2-(1-Ethyl-3-(trifluoromethyl)-1H-pyrazol-4-yl)phenyl)-6-((E)-3-((2R,4R)-4-methylpyrrolidin-2-yl)acryloyl)-4,5,6,7-tetrahydrothieno[2,3-c]pyridine-2-carbonitrile The compound was synthesized analogously as described above from tert-butyl (2R,4R)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H-yl)-3-oxoprop-1-en-1-yl)-4-methylpyrrolidine-1-carboxylate and isolated a white solid (FA salt, 49%). MS (ESI) m/z 540.3 [M+H]$^+$.

Example 82

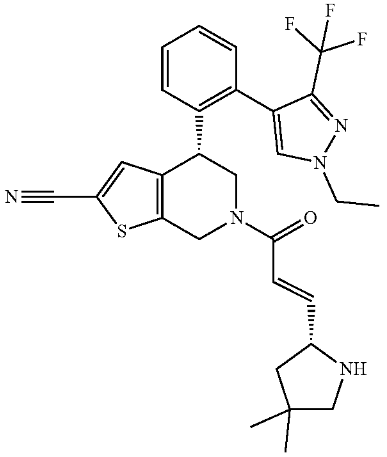 [SMILES: CCn1cc(-c2ccccc2[C@@H]2CN(C(=O)/C=C/[C@H]3CC(C)(C)CN3)Cc3sc(C#N)cc32)c(C(F)(F)F)n1]

(S)-6-((E)-3-((R)-4,4-Dimethylpyrrolidin-2-yl)acryloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above from tert-butyl (R)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5h)-yl)-3-oxoprop-1-en-1-yl)-4,4-dimethylpyrrolidine-1-carboxylate and isolated a white solid (FA salt, 80%). MS (ESI) m/z 554.3 $[M+H]^+$.

Example 83

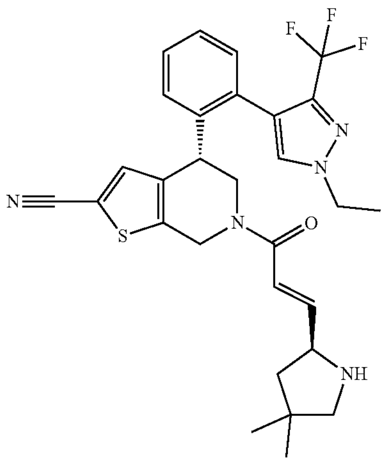 [SMILES: CCn1cc(-c2ccccc2[C@@H]2CN(C(=O)/C=C/[C@@H]3CC(C)(C)CN3)Cc3sc(C#N)cc32)c(C(F)(F)F)n1]

(S)-6-((E)-3-((S)-4,4-Dimethylpyrrolidin-2-yl)acryloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above from tert-butyl (S)-2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)-4,4-dimethylpyrrolidine-1-carboxylate and isolated a white solid (FA salt, 53%). MS (ESI) m/z 554.3 $[M+H]^+$.

Example 84

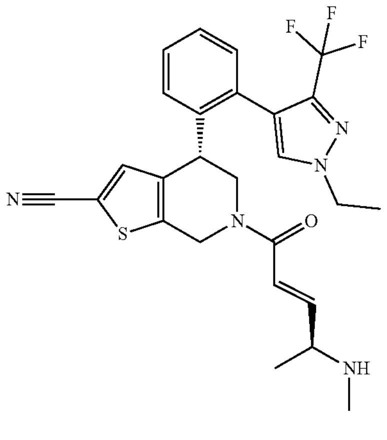 [SMILES: CCn1cc(-c2ccccc2[C@@H]2CN(C(=O)/C=C/[C@H](C)NC)Cc3sc(C#N)cc32)c(C(F)(F)F)n1]

(S)-4-(2-(1-Ethyl-3-(trifluoromethyl)-1H pyrazol-4-yl)phenyl)-6-((S,E)-4-(methylamino)pent-2-enoyl)-4,5,6,7-tetrahydrothieno[2,3-c]pyridine-2-carbonitrile The compound was synthesized analogously as described above from tert-butyl ((S,E)-5-((S)-2-cyano-4-(2-(1-ethyl-3-(trifluoromethyl)-1H-pyrazol-4-yl)phenyl)-4,7-dihydrothieno[2,3-c]pyridin-6(5H-yl)-5-oxopent-3-en-2-yl)(methyl) carbamate and isolated a white solid (FA salt, 55%). MS (ESI) m/z 514.2 $[M+H]^+$.

Example 85

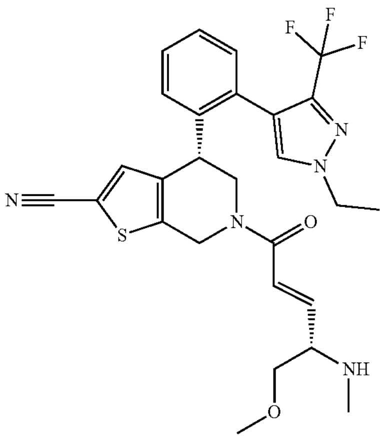 [SMILES: CCn1cc(-c2ccccc2[C@@H]2CN(C(=O)/C=C/[C@@H](COC)NC)Cc3sc(C#N)cc32)c(C(F)(F)F)n1]

(S)-4-(2-(1-Ethyl-3-(trifluoromethyl)-1H-pyrazol-4-yl)phenyl)-6-((S,E)-5-methoxy-4-(methylamino) pent-2-enoyl)-4,5,6,7-tetrahydrothieno[2,3-c]pyridine-2-carbonitrile The compound was synthesized analogously as described above from tert-butyl ((S,E)-5-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-1-methoxy-5-oxopent-3-en-2-yl)(methyl)carbamate and isolated a white solid (FA salt, 33%). MS (ESI) m/z 544.3 $[M+H]^+$.

Example 86

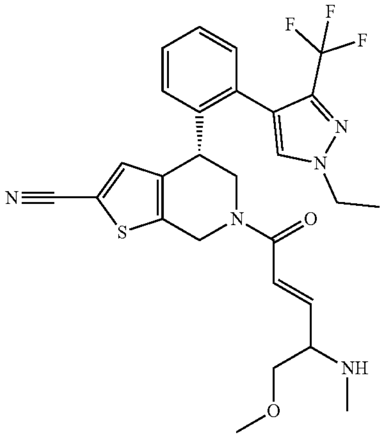 [SMILES: CCn1cc(-c2ccccc2[C@@H]2CN(C(=O)/C=C/C(COC)NC)Cc3sc(C#N)cc32)c(C(F)(F)F)n1]

(S)-4-(2-(1-Ethyl-3-(trifluoromethyl)-1H-pyrazol-4-yl)phenyl)-6-((R,E)-5-methoxy-4-(methylamino) pent-2-enoyl)-4,5,6,7-tetrahydrothieno[2,3-c]pyridine-2-carbonitrile The compound was synthesized analogously as described above from tert-butyl ((R,E)-5-((S)-2-cyano-4-(2-(1-ethyl- 3-(trifluoromethyl)-1H-pyrazol-4-yl)phenyl)-4,7-dihydrothieno[2,3-c]pyridin-6(5H)-yl)-1-methoxy-5-oxopent-3-en-2-yl)(methyl)carbamate and isolated a white solid (FA salt, 16%). MS (ESI) m/z 544.3 [M+H]+.

Example 87

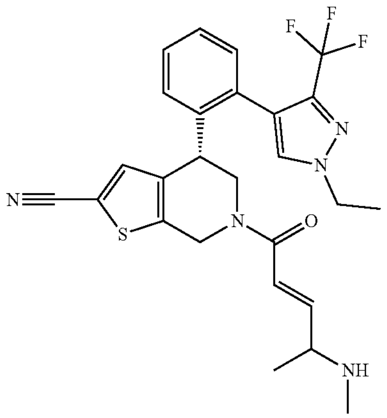 [SMILES: CCn1cc(-c2ccccc2[C@@H]2CN(C(=O)/C=C/C(C)NC)Cc3sc(C#N)cc32)c(C(F)(F)F)n1]

(S)-4-(2-(1-Ethyl-3-(trifluoromethyl)-1H-pyrazol-4-yl)phenyl)-6-((R,E)-4-(methylamino)pent-2-enoyl)-4,5,6,7-tetrahydrothieno[2,3-c]pyridine-2-carbonitrile The compound was synthesized analogously as described above from tert-butyl ((R,E)-5-((S)-2-cyano-4-(2-(1-ethyl-3-(trifluoromethyl)-1H-pyrazol-4-yl)phenyl)-4,7-dihydrothieno[2,3-c]pyridin-6(5H-yl)-5-oxopent-3-en-2-yl)(methyl)carbamate and isolated a white solid (FA salt, 52%). MS (ESI) m/z 514.3 [M+H]+.

Example 88

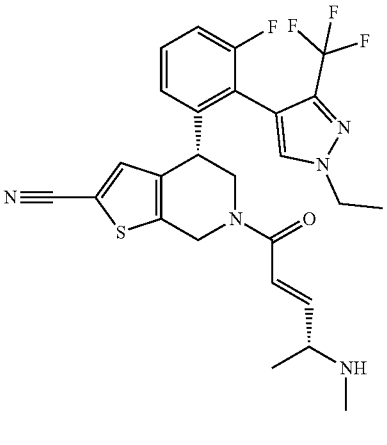 [SMILES: CCn1cc(-c2c(F)cccc2[C@@H]2CN(C(=O)/C=C/[C@@H](C)NC)Cc3sc(C#N)cc32)c(C(F)(F)F)n1]

(S)-4-(2-(1-Ethyl-3-(trifluoromethyl)-1H pyrazol-4-yl)-3-fluorophenyl)-6-((R,E)-4-(methylamino)pent-2-enoyl)-4,5,6,7-tetrahydrothieno[2,3-c]pyridine-2-carbonitrile The compound was synthesized analogously as described above from tert-butyl ((R,E)-5-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-5-oxopent-3-en-2-yl)(methyl)carbamate and isolated a white solid (FA salt, 29%). MS (ESI) m/z 532.2 [M+H]+.

Example 89

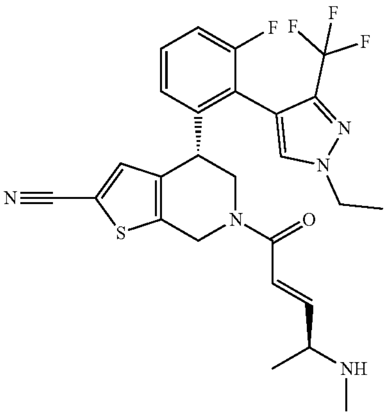 [SMILES: CCn1cc(-c2c(F)cccc2[C@@H]2CN(C(=O)/C=C/[C@H](C)NC)Cc3sc(C#N)cc32)c(C(F)(F)F)n1]

(S)-4-(2-(1-Ethyl-3-(trifluoromethyl)-1H pyrazol-4-yl)-3-fluorophenyl)-6-((S,E)-4-(methylamino)pent-2-enoyl)-4,5,6,7-tetrahydrothieno[2,3-c]pyridine-2-carbonitrile The compound was synthesized analogously as described above from tert-butyl ((S,E)-5-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-5-oxopent-3-en-2-yl)(methyl)carbamate and isolated a white solid (FA salt, 62%). MS (ESI) m/z 532.2 [M+H]+.

Example 90

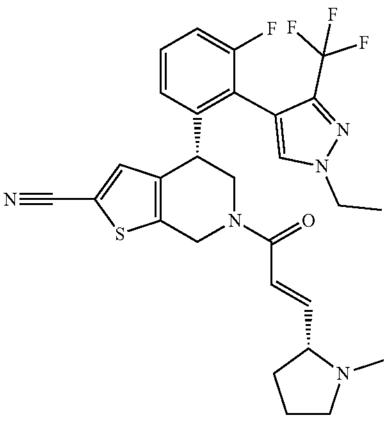 [SMILES: CCn1cc(-c2c(F)cccc2[C@@H]2CN(C(=O)/C=C/[C@H]3CCCN3C)Cc3sc(C#N)cc32)c(C(F)(F)F)n1]

(S)-4-(2-(1-Ethyl-3-(trifluoromethyl)-1H-pyrazol-4-yl)phenyl)-6-((E)-3-((R)-1-methylpyrrolidin-2-yl)acryloyl)-4,5,6,7-tetrahydrothieno[2,3-c]pyridine-2-carbonitrile To a mixture of DMSO (68 μL, 0.95 mmol) in DCM (7 mL) at −78° C. was added $(COCl)_2$ (2M in DCM, 0.48 mL, 0.95 mmol) and the reaction was stirred at −78° C. for 30 min. (R)-(1-methylpyrrolidin-2-yl)methanol (0.10 mL, 0.87 mmol) was dissolved in DCM (2 mL) then added to the mixture slowly at −78° C. and stirred for 45 min. $Et_3N$ (0.15 mL, 1.04 mmol) was added to the mixture and stirred at −78° C. for another 1 h. The resulting mixture was concentrated in vacuo. The crude aldehyde was dissolved in THE (1 mL) and used in the next reaction.

To a stirred mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl)phosphonate (50.0 mg, 86.0 μmol) in THE (1 mL) at 0° C. was added NaH (60 wt % dispersion in mineral oil, 4.00 mg, 103 μmol) and stirred at 0° C. for 15 min. The crude aldehyde was added to the mixture slowly at 0° C. The mixture was warmed to RT and stirred for 3 h. The mixture was diluted with DCM (10 mL), washed with sat. aq. $NaHCO_3$ (10 mL) and extracted with DCM (3×3 mL). The organic layer was separated, dried over $MgSO_4$, filtered, and concentrated in vacuo. The residue was purified by a flash column chromatography ($SiO_2$, 0→100% EA in hexanes) to yield the target compound as a white solid (FA salt, 0.058 g, 74%). MS (ESI) m/z 540.3 $[M+H]^+$.

Example 91

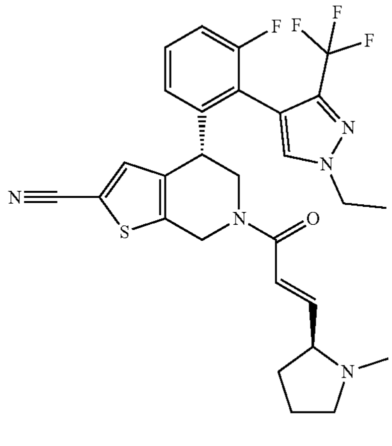 [SMILES: CCn1cc(-c2c(F)cccc2[C@@H]2CN(C(=O)/C=C/[C@@H]3CCCN3C)Cc3sc(C#N)cc32)c(C(F)(F)F)n1]

(S,E)-4-(2-(1-Ethyl-3-(trifluoromethyl)-1H-pyrazol-4-yl)-3-fluorophenyl)-6-(4-(methylamino)but-2-enoyl)-4,5,6,7-tetrahydrothieno[2,3-c]pyridine-2-carbonitrile The compound was synthesized analogously as described from (S)-(1-methylpyrrolidin-2-yl)methanol and isolated as an off-white solid (FA salt, 58%). MS (ESI) m/z 540.3 $[M+H]^+$.

Example 92

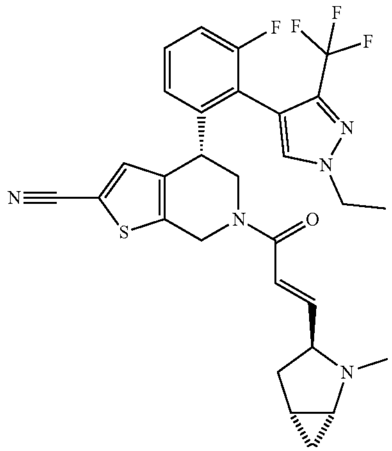

(S)-6-((E)-3-((1R,3S,5R)-2-azabicyclo[3.1.0]hexan-3-yl)acryloyl)-4-(2-(1-ethyl-3-(trifluoromethyl)-1H pyrazol- 4-yl)-3-fluorophenyl)-4,5,6,7-tetrahydrothieno[2,3-c]pyridine-2-carbonitrile The compound was synthesized analogously as described above from tert-butyl (1R,3S,5R)-3-((E)-3-((S)-2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-3-oxoprop-1-en-1-yl)-2-azabicyclo[3.1.0]hexane-2-carboxylate and isolated a white solid (TFA salt, 32%). MS (ESI) m/z 556.3 $[M+H]^+$.

Example 93

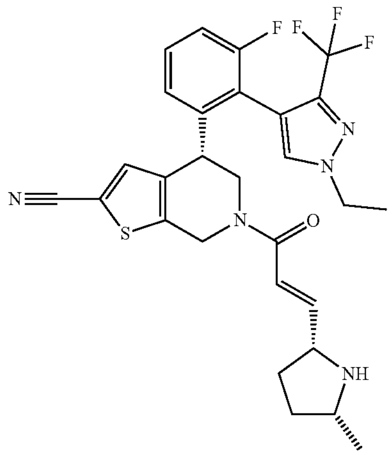 [SMILES: CCn1cc(-c2c(F)cccc2[C@@H]2CN(C(=O)/C=C/[C@H]3CC[C@@H](C)N3)Cc3sc(C#N)cc32)c(C(F)(F)F)n1]

(S)-4-(2-(1-ethyl-3-(trifluoromethyl)-1H pyrazol-4-yl)-3-fluorophenyl)-6-((E)-3-((2S,5R)-5-methylpyrrolidin-2-yl) acryloyl)-4,5,6,7-tetrahydrothieno[2,3-c]pyridine-2-carbonitrile The compound was synthesized analogously as described above from tert-butyl (2S,5R)-2-((E)-3-((S)-2-cyano-4-(2-

(1-ethyl-3-(trifluoromethyl)-1H-pyrazol-4-yl)-3-fluorophenyl)-4,7-dihydrothieno[2,3-c]pyridin-6(5H)-yl)-3-oxoprop-1-en-1-yl)-5-methylpyrrolidine-1-carboxylate and isolated a white solid (TFA salt, 14%). MS (ESI) m/z 558.3 [M+H]+.

Example 94

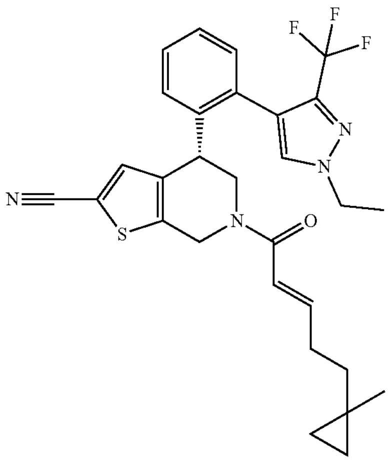 [SMILES: CCn1cc(-c2ccccc2[C@@H]2CN(C(=O)/C=C/CCC3(C)CC3)Cc3sc(C#N)cc32)c(C(F)(F)F)n1]

(S,E)-4-(2-(1-Ethyl-3-(trifluoromethyl)-1H pyrazol-4-yl)phenyl)-6-(4-((1-methylcyclopropyl)amino)but-2-enoyl)-4,5,6,7-tetrahydrothieno[2,3-c]pyridine-2-carbonitrile A solution of a mixture of (S,E)-6-(4-bromobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile and (S,E)-6-(4-chlorobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (40 mg, 0.073 mmol) in ACN (0.73 mL) was sequentially treated with $Na_2CO_3$ (43 mg, 0.40 mmol) and 1-methylcyclopropanamine, HCl salt (16 mg, 0.15 mmol), then heated at 60° C. for 4 h. After cooling to RT, the mixture was filtered through a 0.22 μm nylon syringe tip filter and the filtrate was concentrated in vacuo. The residue was dissolved in MeOH and purified by RP-HPLC (AgilentPrep-018 column (50×21.2 mm, 5 μm); eluent A=$H_2O$ (+0.1% FA), B=MeCN (+0.1% FA), 10→35→95% B over 19 min @ 25 mL/min) to yield the compound as a white solid (FA salt, 19 mg, 46%). MS (ESI) m/z 540.3 [M+H]+.

Example 95

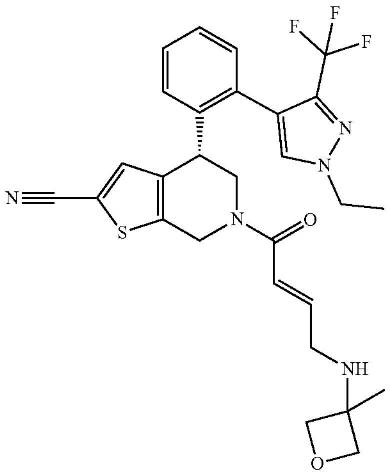 [SMILES: CCn1cc(-c2ccccc2[C@@H]2CN(C(=O)/C=C/CNC3(C)COC3)Cc3sc(C#N)cc32)c(C(F)(F)F)n1]

(S,E)-4-(2-(1-Ethyl-3-(trifluoromethyl)-1H-pyrazol-4-yl)phenyl)-6-(4-((3-methyloxetan-3-yl)amino)but-2-enoyl)-4,5,6,7-tetrahydrothieno[2,3-c]pyridine-2-carbonitrile The compound was synthesized analogously as described above from 3-methyloxetan-3-amine and isolated as a white solid (56%). MS (ESI) m/z 556.3 [M+H]+.

Example 96

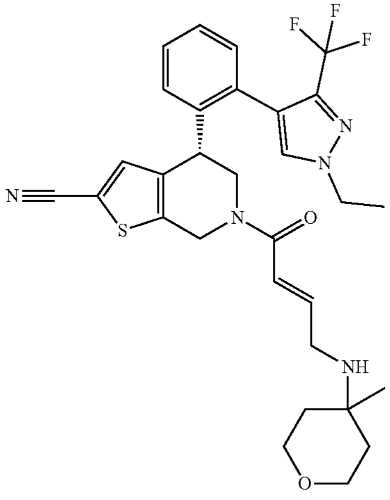 [SMILES: CCn1cc(-c2ccccc2[C@@H]2CN(C(=O)/C=C/CNC3(C)CCOCC3)Cc3sc(C#N)cc32)c(C(F)(F)F)n1]

(S,E)-4-(2-(1-Ethyl-3-(trifluoromethyl)-1H-pyrazol-4-yl)phenyl)-6-(4-((4-methyltetrahydro-2H pyran-4-yl)amino)but-2-enoyl)-4,5,6,7-tetrahydrothieno[2,3-c]pyridine-2-carbonitrile The compound was synthesized analogously as described above from 4-methyltetra-hydro-2H-pyran-4-amine, HCl salt and isolated as a white solid (FA salt, 69%). MS (ESI) m/z 584.3 [M+H]+.

Example 97

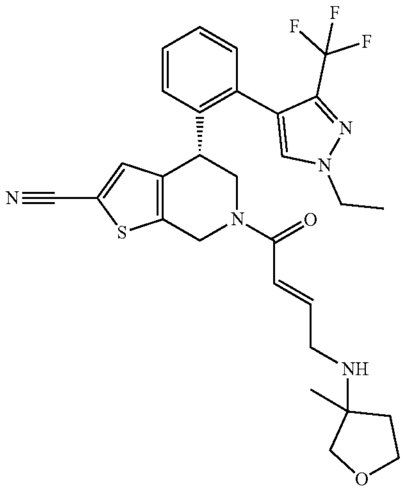 [SMILES: CCn1cc(-c2ccccc2[C@@H]2CN(C(=O)/C=C/CNC3(C)CCOC3)Cc3sc(C#N)cc32)c(C(F)(F)F)n1]

(4S)-4-(2-(1-Ethyl-3-(trifluoromethyl)-1H-pyrazol-4-yl)phenyl)-6-((E)-4-((3-methyltetrahydrofuran-3-yl)amino)but-2-enoyl)-4,5,6,7-tetrahydrothieno[2,3-c]pyridine-2-carbonitrile The compound was synthesized analogously as described above from 3-amino-3-methyl-tetrahydrofuran and isolated as a white solid (FA salt, 63%). MS (ESI) m/z 570.3 $[M+H]^+$.

Example 98

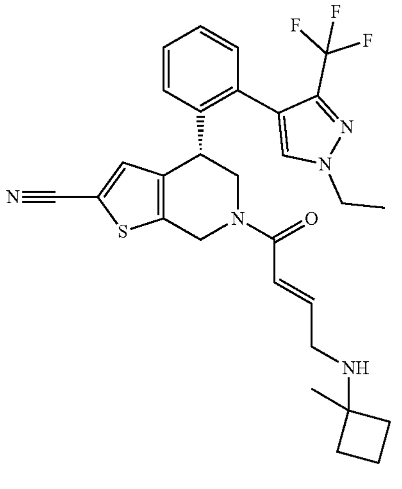 [SMILES: CCn1cc(-c2ccccc2[C@@H]2CN(C(=O)/C=C/CNC3(C)CCC3)Cc3sc(C#N)cc32)c(C(F)(F)F)n1]

(S,E)-4-(2-(1-Ethyl-3-(trifluoromethyl)-1H pyrazol-4-yl)phenyl)-6-(4-((3-methylazetidin-3-yl)amino) but-2-enoyl)-4,5,6,7-tetrahydrothieno[2,3-c]pyridine-2-carbonitrile tert-Butyl (S,E)-3-((4-(2-cyano-4-(2-(1-ethyl-3-(trifluoromethyl)-1H-pyrazol-4-yl)phenyl-4,7-dihydrothieno[2,3-c]pyridin-6(5H-yl)-4-oxobut-2-en-1-yl)amino)-3-methylazetidine-1-carboxylate was synthesized analogously as described above from tert-butyl 3-amino-3-methylazetidine-1-carboxylate and isolated by flash column chromatography ($SiO_2$, 0→100% (10% MeOH in EA) in hexanes) as a dark brown oil (91%). MS (ESI) m/z 555.3 $[M-Boc+H]^+$.

A solution of tert-butyl (S,E)-3-((4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl) amino)-3-methylazetidine-1-carboxylate (80 mg, 0.12 mmol) in DCM (1 mL) was treated with TFA (1 mL) and stirred for 1 h. The mixture was concentrated in vacuo. The resulting residue was dissolved in MeOH and filtered through a 0.22 μm nylon syringe tip filter and purified by RP-HPLC (Agilent Prep-Cm column (50×21.2 mm, 5 μm); eluent A=$H_2O$ (+0.1% FA), B=MeCN (+0.1% FA), 10→35→95% B over 19 min @ 25 mL/min) to yield the compound as a white solid (FA-TFA salt, 47 mg, 60%). MS (ESI) m/z 555.3 $[M+H]^+$.

Example 99

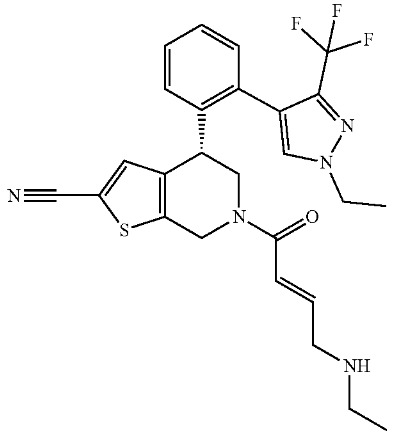 [SMILES: CCNC/C=C/C(=O)N1Cc2sc(C#N)cc2[C@H](c2ccccc2-c2cn(CC)nc2C(F)(F)F)C1]

(S,E)-4-(2-(1-Ethyl-3-(trifluoromethyl)-1H-pyrazol-4-yl)phenyl)-6-(4-(ethylamino)but-2-enoyl)-4,5,6,7-tetrahydrothieno[2,3-c]pyridine-2-carbonitrile Step 1. tert-Butyl (S,E)-(4-(2-cyano-4-(2-(1-ethyl-3-(trifluoromethyl)-1H-pyrazol-4-yl)phenyl)-4,7-dihydrothieno [2,3-c]pyridin-6(5H)-yl)-4-oxobut-2-en-1-yl)(ethyl)carbamate. A solution of tert-butyl (S)-2-cyano-4-(2-(1-ethyl-3-(trifluoromethyl)-1H-pyrazol-4-yl)phenyl)-4,7-dihydrothieno[2,3-c]pyridine-6(5H)-carboxylate in DCM (0.50 mL) was treated with TFA (0.50 mL) and stirred at RT. After 1 h, the mixture was concentrated in vacuo, dissolved in DMF (0.60 mL) and treated with DIPEA (44 μL, 0.25 mmol). In a separate vial, HATU (95 mg, 0.25 mmol), crude (E)-4-((tert-butoxycarbonyl)(ethyl)amino)but-2-enoic acid (60 mg, 0.12 mmol), and DIPEA (44 μL, 0.25 mmol) were stirred in DMF (0.20 mL) at RT for 40 min, then cooled to 0° C. in an ice-water bath. The amine mixture was slowly added, and the combination was slowly warmed to RT and stirred at RT for 18 h. Additional DIPEA (90 μL, 0.50 mmol) and HATU (90 mg, 0.24 mmol) were added. After 3.5 h, the mixture was diluted with EA (10 mL) and sat. aq. LiCl soln (10 mL). The layers were partitioned, and the organic phase was washed with sat. aq. LiCl soln (2×10 mL), then dried over anhydrous $MgSO_4$, filtered, and concentrated in vacuo.

The resulting golden oil was purified by flash column chromatography ($SiO_2$, 0→100% EA in hexanes) to give the compound as an impure brown oil that was used in the next step without additional purification, assuming theoretical yield.

Step 2. (S,E)-4-(2-(1-Ethyl-3-(trifluoromethyl)-1H-pyrazol-4-yl)phenyl)-6-(4-(ethylamino)but-2-enoyl)-4,5,6,7-tetrahydrothieno[2,3-c]pyridine-2-carbonitrile. A solution of tert-butyl (S,E)-(4-(2-cyano-4-(2-(1-ethyl-3-(trifluoromethyl)-1H-pyrazol-4-yl)phenyl)-4,7-dihydro-thieno[2,3-c]pyridin-6(5H)-yl)-4-oxobut-2-en-1-yl)(ethyl)carbamate (74 mg, 0.12 mmol) in DCM (1 mL) was treated with TFA (1 mL). After 4 h, the mixture was concentrated in vacuo, dissolved in MeOH, filtered through a 0.22 μm nylon syringe tip filter, and purified by RP-HPLC (Agilent Prep-C18 column (50×21.2 mm, 5 μm); eluent A=$H_2O$ (+0.1% FA), B=MeCN (+0.1% FA), 10→35→95% B over 19 min @ 25 mL/min) to yield the compound as an off-white solid (FA salt, 14 mg, 22%). MS (ESI) m/z 514.3 $[M+H]^+$.

Example 100

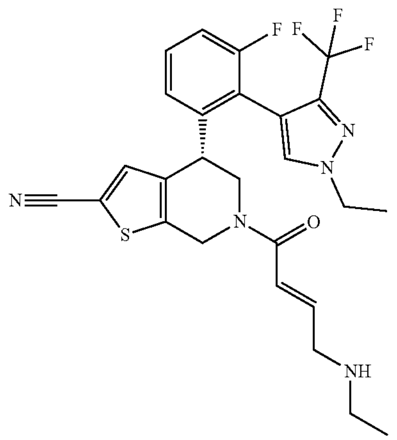 [SMILES: CCNC/C=C/C(=O)N1Cc2sc(C#N)cc2[C@H](c2cccc(F)c2-c2cn(CC)nc2C(F)(F)F)C1]

(S,E)-4-(2-(1-Ethyl-3-(trifluoromethyl)-1H-pyrazol-4-yl)-3-fluorophenyl)-6-(4-(ethylamino)but-2-enoyl)-4,5,6,7-tetrahydrothieno[2,3-c]pyridine-2-carbonitrile The compound was synthesized analogously as described above from tert-butyl (S)-2-cyano-4-(2-(1-ethyl-3-(trifluoromethyl)-1H-pyrazol-4-yl)-3-fluorophenyl)-4,7-dihydrothieno[2,3-c]pyridine-6(5H)-carboxylate and isolated as a beige solid (FA-TFA salt, 14 mg, 24%). MS (ESI) m/z 532.2 $[M+H]^+$.

Example 101

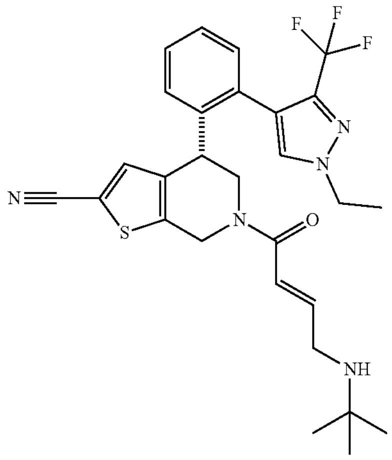 [SMILES: CCn1cc(-c2ccccc2[C@@H]2CN(C(=O)/C=C/CNC(C)(C)C)Cc3sc(C#N)cc32)c(C(F)(F)F)n1]

(S,E)-6-(4-(tert-Butylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from crude (E)-4-((tert-butoxycarbonyl)(tert-butyl)amino)but-2-enoic acid and isolated as a white solid (FA salt, 29 mg, 36%). MS (ESI) m/z 542.3 $[M+H]^+$.

Example 102

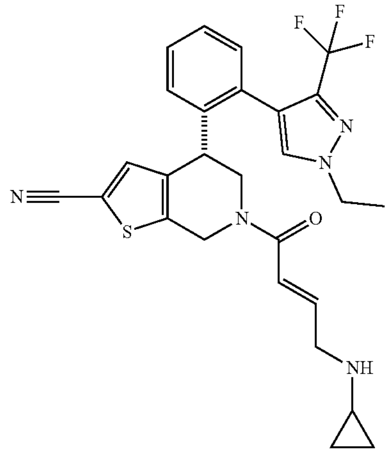 [SMILES: CCn1cc(-c2ccccc2[C@@H]2CN(C(=O)/C=C/CNC3CC3)Cc3sc(C#N)cc32)c(C(F)(F)F)n1]

(S,E)-6-(4-(Cyclopropylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from (E)-4-((tert-butoxycarbonyl)(cyclopropyl)amino)but-2-enoic acid and isolated as an off-white solid (45 mg, 54%). MS (ESI) m/z 526.3 $[M+H]^+$.

Example 103

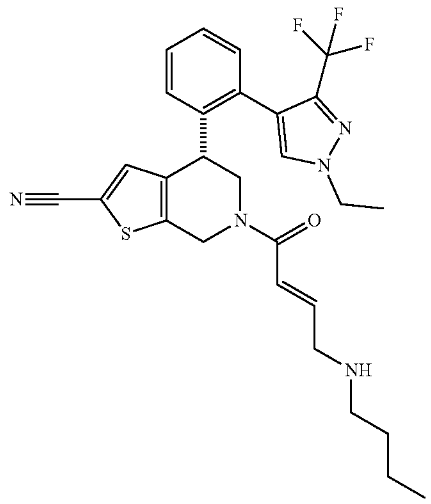 [SMILES: CCCCNC/C=C/C(=O)N1Cc2sc(C#N)cc2[C@H](c2ccccc2-c2cn(CC)nc2C(F)(F)F)C1]

(S,E)-6-(4-(Butylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from crude (E)-4-((tert-butoxycarbonyl)(butyl)amino)but-2-enoic acid and isolated as an off-white solid (FA salt, 9.8 mg, 30%). MS (ESI) m/z 542.3 $[M+H]^+$.

Example 104

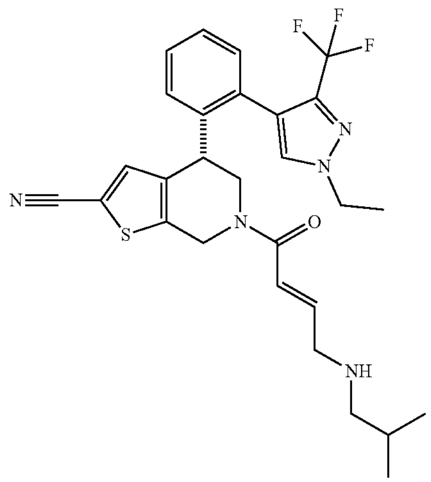 [SMILES: CCn1cc(-c2ccccc2[C@@H]2CN(C(=O)/C=C/CNCC(C)C)Cc3sc(C#N)cc32)c(C(F)(F)F)n1]

(S,E)-4-(2-(1-Ethyl-3-(trifluoromethyl)-1H-pyrazol-4-yl)phenyl-6-(4-(isobutylamino)but-2-enoyl)-4,5,6,7-tetrahydrothieno[2,3-c]pyridine-2-carbonitrile The compound was synthesized analogously as described above from crude (E)-4-((tert-butoxycarbonyl)(isobutyl)amino)but-2-enoic acid and isolated as an off-white solid (FA salt, 6.4 mg, 17%). MS (ESI) m/z 542.3 $[M+H]^+$.

Example 105

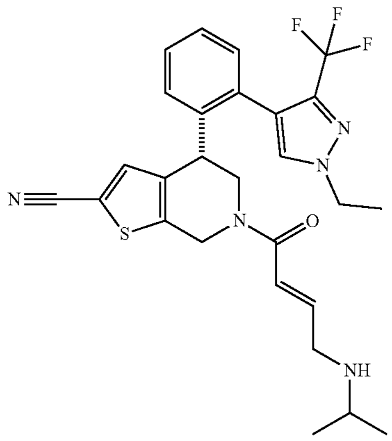 [SMILES: CCn1cc(-c2ccccc2[C@@H]2CN(C(=O)/C=C/CNC(C)C)Cc3sc(C#N)cc32)c(C(F)(F)F)n1]

(S,E)-4-(2-(1-Ethyl-3-(trifluoromethyl)-1H-pyrazol-4-yl)phenyl)-6-(4-(isopropylamino)but-2-enoyl)-4,5,6,7-tetrahydrothieno[2,3-c]pyridine-2-carbonitrile The compound was synthesized analogously as described above from crude (E)-4-((tert-butoxycarbonyl)(isopropyl)amino)but-2-enoic acid and isolated as a white solid (FA salt, 90 mg, 65%). MS (ESI) m/z 528.3 $[M+H]^+$.

Example 106

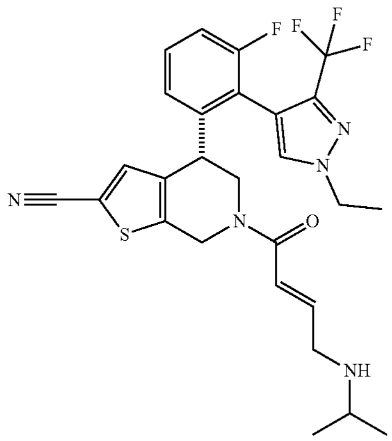 [SMILES: CCn1cc(-c2c(F)cccc2[C@@H]2CN(C(=O)/C=C/CNC(C)C)Cc3sc(C#N)cc32)c(C(F)(F)F)n1]

(S,E)-4-(2-(1-Ethyl-3-(trifluoromethyl)-1H pyrazol-4-yl)-3-fluorophenyl)-6-(4-(isopropylamino)but-2-enoyl)-4,5,6,7-tetrahydrothieno[2,3-c]pyridine-2-carbonitrile The compound was synthesized analogously as described above from crude (E)-4-((tert-butoxycarbonyl)(isopropyl)amino)but-2-enoic acid and tert-butyl (S)-2-cyano-4-(2-(1-ethyl-3-(trifluoromethyl)-1H-pyrazol-4-yl)-3-fluorophenyl)-4,7-dihydrothieno[2,3-c]pyridine-6(5H)-carboxylate and isolated as an off-white solid (FA-TFA salt, 66 mg, 42%). MS (ESI) m/z 546.3 $[M+H]^+$.

Example 107

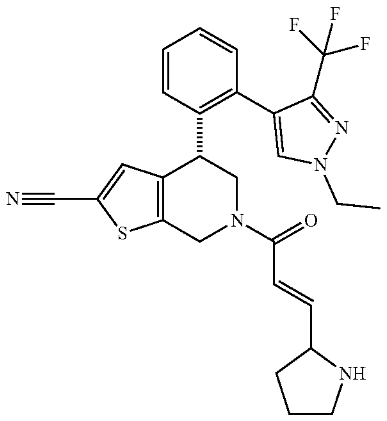 [SMILES: CCn1cc(-c2ccccc2[C@@H]2CN(C(=O)/C=C/C3CCCN3)Cc3sc(C#N)cc32)c(C(F)(F)F)n1]

(4S)-4-(2-(1-Ethyl-3-(trifluoromethyl)-1H-pyrazol-4-yl)phenyl)-6-((E)-3-(pyrrolidin-2-yl)acryloyl)-4,5,6,7-tetrahydrothieno[2,3-c]pyridine-2-carbonitrile The compound was synthesized analogously as described above from (E)-3-(1-(tert-butoxycarbonyl)pyrrolidin-2-yl) acrylic acid and isolated as a white solid (FA salt, 77 mg, 80%). MS (ESI) m/z 526.2 [M+H]$^+$.

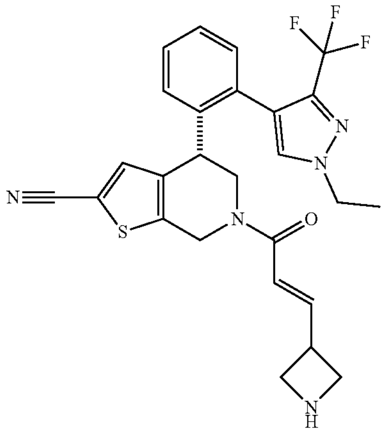 [SMILES: CCn1cc(-c2ccccc2[C@@H]2CN(C(=O)/C=C/C3CNC3)Cc3sc(C#N)cc32)c(C(F)(F)F)n1]

(S,E)-6-(3-(Azetidin-3-yl)acryloyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from (E)-3-(1-(tert-butoxycarbonyl)azetidin-3-yl) acrylic acid and isolated as a white solid (FA salt, 18 mg, 64%). MS (ESI) m/z 512.3 [M+H]$^+$.

Example 109

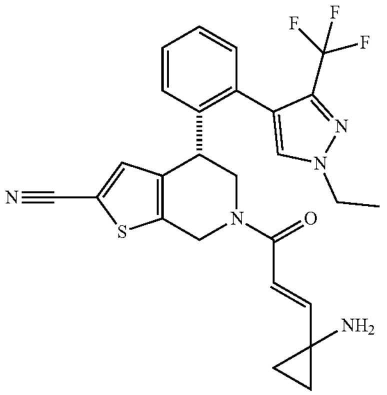 [SMILES: CCn1cc(-c2ccccc2[C@@H]2CN(C(=O)/C=C/C3(N)CC3)Cc3sc(C#N)cc32)c(C(F)(F)F)n1]

(S,E)-6-(3-(1-Aminocyclopropyl)acryloyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from (E)-3-(1-((tert-butoxycarbonyl)amino)cyclopropyl)acrylic acid and isolated as a white solid (FA salt, 110 mg, 79%). MS (ESI) m/z 512.2 [M+H]$^+$.

Example 110

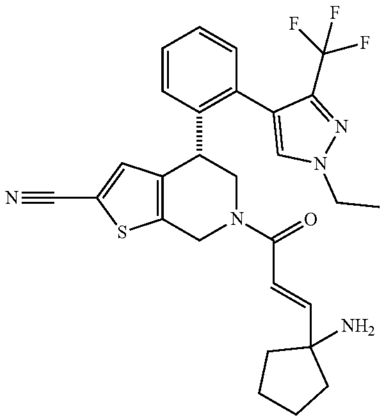 [SMILES: CCn1cc(-c2ccccc2[C@@H]2CN(C(=O)/C=C/C3(N)CCCC3)Cc3sc(C#N)cc32)c(C(F)(F)F)n1]

(S,E)-6-(3-(1-Aminocyclopentyl)acryloyl) 4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above from (E)-3-(1-((tert-butoxycarbonyl)amino)cyclopentyl)acrylic acid and isolated as an off-white solid (FA salt, 170 mg, 84%). MS (ESI) m/z 540.3 [M+H]$^+$.

Example 111

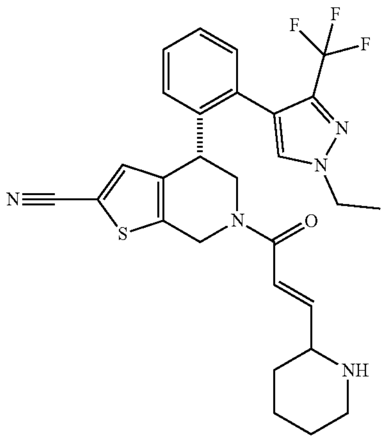 [SMILES: CCn1cc(-c2ccccc2[C@@H]2CN(C(=O)/C=C/C3CCCCN3)Cc3sc(C#N)cc32)c(C(F)(F)F)n1]

(4S)-4-(2-(1-Ethyl-3-(trifluoromethyl)-1H pyrazol-4-yl)phenyl)-6-((E)-3-(piperidin-2-yl)acryloyl)-4,5,6,7-tetrahydrothieno[2,3-c]pyridine-2-carbonitrile Step 1. tert-Butyl 2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)piperidine-1-carboxylate. A mixture of diethyl (S)-(2-(2-cyano-4-(2-(1-ethyl-3-(trifluoromethyl)-1H-pyrazol-4-yl)phenyl)-4,7-dihydrothieno[2,3-c]pyridin-6(5H)-yl)-2-oxoethyl) phosphonate (50 mg, 0.086 mmol) and LiCl (7.3 mg, 0.17 mmol) in MeCN (0.60 mL) was treated with DIPEA (30 μL, 0.17 mmol). After 10 min, tert-butyl 2-formylpiperidine-1-carboxylate (24 mg, 0.11 mmol) was added, and the resulting mixture was stirred at RT for 2 h. The mixture was concentrated in vacuo, dissolved in EtOAc (10 mL) and washed with sat. aq. $NH_4Cl$ (10 mL). The layers were partitioned, and the organic phase was sequentially washed with sat. aq. $NaHCO_3$ (10 mL) and brine, then dried over anhydrous $MgSO_4$, filtered, and concentrated in vacuo. The resulting residue was purified by flash column chromatography ($SiO_2$, 0→50→100% EA in hexanes) to give the compound as a yellow oil (55 mg, quant.).

Step 2. (4S)-4-(2-(1-Ethyl-3-(trifluoromethyl)-1H pyrazol-4-yl)phenyl)-6-((E)-3-(piperidin-2-yl)acryloyl)-4,5,6,7-tetrahydrothieno[2,3-c]pyridine-2-carbonitrile. A solution of tert-butyl 2-((E)-3-((S)-2-cyano-4-(2-(1-ethyl-3-(trifluoromethyl)-1H-pyrazol-4-yl)phenyl)-4,7-dihydrothieno[2,3-c]pyridin-6(5H)-yl)-3-oxoprop-1-en-1-yl)piperidine-1-carboxylate (55 mg, 0.086 mmol) in DCM (1 mL) was treated with TFA (1 mL) and maintained at RT. After 30 min, the mixture was concentrated in vacuo, dissolved in MeOH, filtered through a 0.22 μm nylon syringe tip filter, and purified by RP-HPLC (Agilent Prep-C18 column (50×21.2 mm, 5 μm); eluent A=$H_2O$ (+0.1% FA), B=MeCN (+0.1% FA), 10→35→95% B over 19 min @ 25 mL/min) to yield the compound as a white solid (FA salt, 38.3 mg, 76% yield). MS (ESI) m/z 540.3 $[M+H]^+$.

Example 112

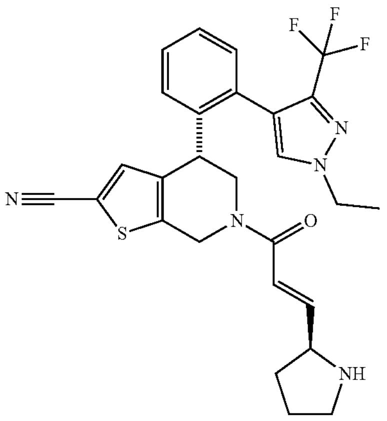 [SMILES: CCn1cc(-c2ccccc2[C@@H]2CN(C(=O)/C=C/[C@@H]3CCCN3)Cc3sc(C#N)cc32)c(C(F)(F)F)n1]

(S)-4-(2-(1-Ethyl-3-(trifluoromethyl)-1 'S)-pyrrolidin-2-yl)acryloyl)-4,5,6,7-tetrahydrothieno[2,3-c]pyridine-2-carbonitrile The compound was synthesized analogously as described above from tert-butyl (S)-2-formylpyrrolidine-1-carboxylate and isolated as a white solid (FA salt, 57 mg, 90%). MS (ESI) m/z 526.3 $[M+H]^+$.

Example 113

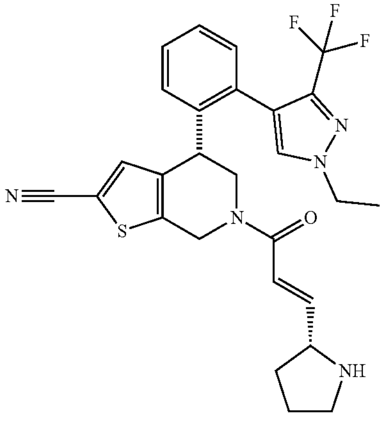 [SMILES: CCn1cc(-c2ccccc2[C@@H]2CN(C(=O)/C=C/[C@H]3CCCN3)Cc3sc(C#N)cc32)c(C(F)(F)F)n1]

(S)-4-(2-(1-Ethyl-3-(trifluoromethyl)-1H-pyrazol-4-yl)phenyl)-6-((E)-3-((R)-pyrrolidin-2-yl)acryloyl)-4,5,6,7-tetrahydrothieno[2,3-c]pyridine-2-carbonitrile The compound was synthesized analogously as described above from tert-butyl (R)-2-formylpyrrolidine-1-carboxylate and isolated as an off-white solid (FA salt, 58 mg, 92%). MS (ESI) m/z 526.3 $[M+H]^+$.

Example 114

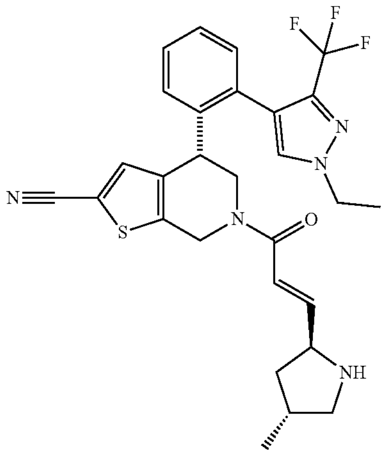 [SMILES: CCn1cc(-c2ccccc2[C@@H]2CN(C(=O)/C=C/[C@@H]3C[C@@H](C)CN3)Cc3sc(C#N)cc32)c(C(F)(F)F)n1]

(S)-4-(2-(1-Ethyl-3-(trifluoromethyl)-1H-pyrazol-4-yl)phenyl)-6-((E)-3-((2S,4R)-4-methylpyrrolidin-2-yl)acryloyl)-4,5,6,7-tetrahydrothieno[2,3-c]pyridine-2-carbonitrile The compound was synthesized analogously as described above from tert-butyl (2S,4R)-2-formyl-4-methylpyrrolidine-1-carboxylate and isolated as a white solid (16 mg, 60%). MS (ESI) m/z 540.3 $[M+H]^+$.

Example 115

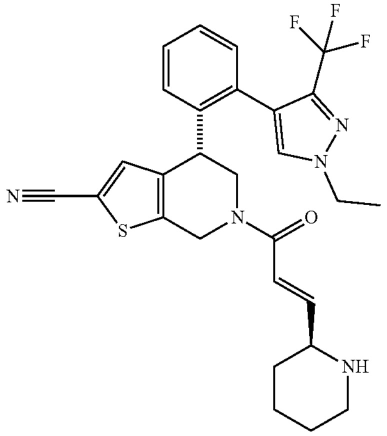 [SMILES: CCn1cc(-c2ccccc2[C@@H]2CN(C(=O)/C=C/[C@@H]3CCCCN3)Cc3sc(C#N)cc32)c(C(F)(F)F)n1]

(S)-4-(2-(1-Ethyl-3-(trifluoromethyl)-1H pyrazol-4-yl) phenyl)-6-((E)-3-((S)-piperidin-2-yl)acryloyl)-4,5,6,7-tetrahydrothieno[2,3-c]pyridine-2-carbonitrile The compound was synthesized analogously as described above from tert-butyl (S)-2-formylpiperidine-1-carboxylate and isolated as a white solid (FA-TFA salt, 110 mg, 79%). MS (ESI) m/z 540.3 $[M+H]^+$.

Example 116

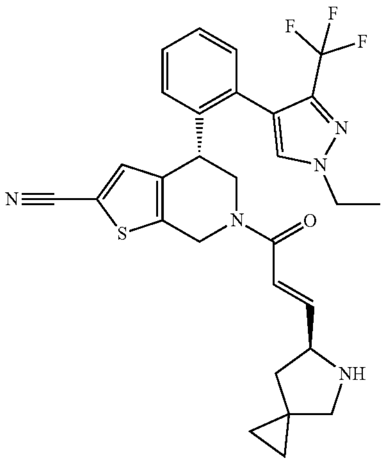 [SMILES: CCn1cc(-c2ccccc2[C@@H]2CN(C(=O)/C=C/[C@@H]3CC4(CC4)CN3)Cc3sc(C#N)cc32)c(C(F)(F)F)n1]

(S)-6-((E)-3-((S)—S-Azaspiro[2.4]heptan-6-yl)acryloyl)-4-(2-(1-ethyl-3-(trifluoromethyl)-1H pyrazol-4-yl) phenyl)-4,5,6,7-tetrahydrothieno[2,3-c]pyridine-2-carbonitrile The compound was synthesized analogously as described above from tert-butyl (S)-6-formyl-5-azaspiro[2.4]heptane-5-carboxylate and isolated as a white solid (FA salt, 29 mg, 53%). MS (ESI) m/z 552.3 $[M+H]^+$.

Example 117

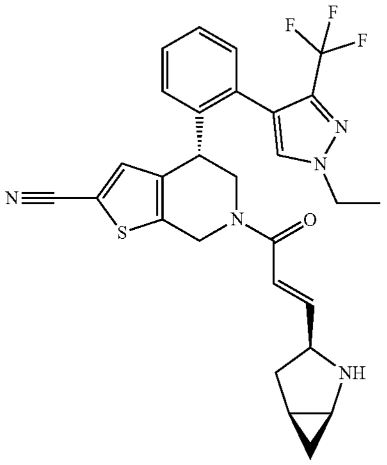 [SMILES: CCn1cc(-c2ccccc2[C@@H]2CN(C(=O)/C=C/[C@@H]3C[C@@H]4C[C@@H]4N3)Cc3sc(C#N)cc32)c(C(F)(F)F)n1]

(S)-6-((E)-3-((1S,3S,5S)-2-Azabicyclo[3.1.0]hexan-3-yl)acryloyl)-4-(2-(1-ethyl-3-(trifluoromethyl)-1H pyrazol- 4-yl)phenyl)-4,5,6,7-tetrahydrothieno[2,3-c]pyridine-2-carbonitrile The compound was synthesized analogously as described above from tert-butyl (1 S,3S,5S)-3-formyl-2-azabicyclo[3.1.0]hexane-2-carboxylate and isolated as a white solid (FA-TFA salt, 16 mg, 16%). MS (ESI) m/z 538.2 $[M+H]^+$.

Example 118

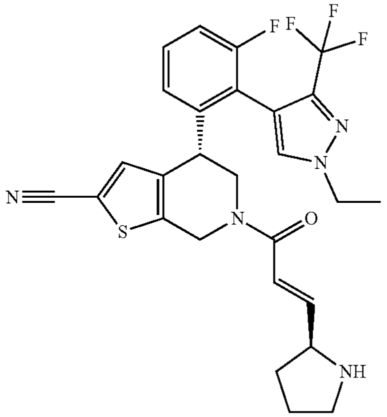 [SMILES: CCn1cc(-c2c(F)cccc2[C@@H]2CN(C(=O)/C=C/[C@@H]3CCCN3)Cc3sc(C#N)cc32)c(C(F)(F)F)n1]

(S)-4-(2-(1-Ethyl-3-(trifluoromethyl)-1H-pyrazol-4-yl)-3-fluorophenyl)-6-((E)-3-((S) pyrrolidin-2-yl)acryloyl)-4,5,6,7-tetrahydrothieno[2,3-c]pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-2-oxoethyl)phosphonate and tert-butyl (S)-2-formylpyrrolidine-1-carboxylate and isolated as a white solid (350 mg, 65%). MS (ESI) m/z 544.3 $[M+H]^+$.

Example 119

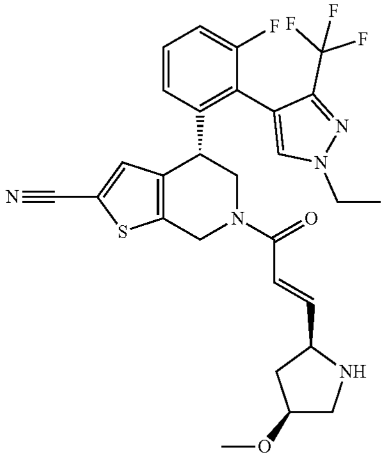

(S)-4-(2-(1-Ethyl-3-(trifluoromethyl)-1H pyrazol-4-yl)-3-fluorophenyl)-6-((E)-3-((2S,4S)-4-methoxy-pyrrolidin-2-yl) acryloyl)-4,5,6,7-tetrahydrothieno[2,3-c]pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-2-oxoethyl)phosphonate and tert-butyl (2S,4S)-2-formyl-4-methoxypyrrolidine-1-carboxylate and isolated as a white solid (TFA salt, 10 mg, 23%). MS (ESI) m/z 574.3 $[M+H]^+$.

Example 120

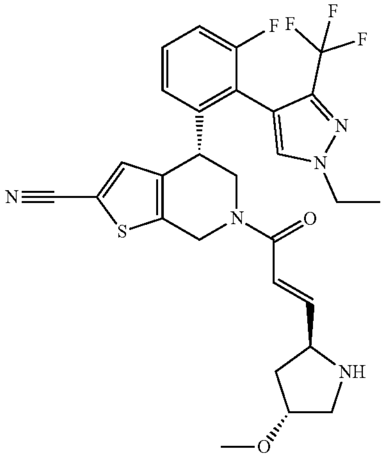 [SMILES: CCn1cc(-c2c(F)cccc2[C@@H]2CN(C(=O)/C=C/[C@@H]3C[C@@H](OC)CN3)Cc3sc(C#N)cc32)c(C(F)(F)F)n1]

(S)-4-(2-(1-Ethyl-3-(trifluoromethyl)-1H pyrazol-4-yl)-3-fluorophenyl)-6-((E)-3-((2S,4R)-4-methoxy-pyrrolidin-2-yl)acryloyl)-4,5,6,7-tetrahydrothieno[2,3-c]pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate and tert-butyl (2S,4R)-2-formyl-4-methoxypyrrolidine-1-carboxylate and isolated as a white solid (FA-TFA salt, 21 mg, 32%). MS (ESI) m/z 574.3 $[M+H]^+$.

Example 121

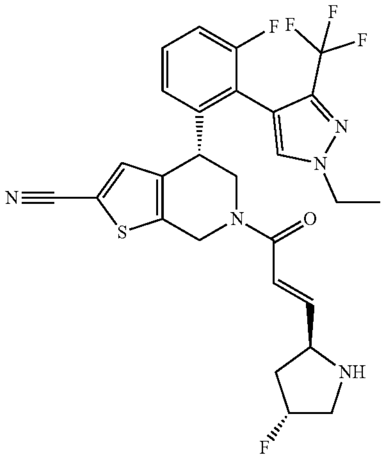 [SMILES: CCn1cc(-c2c(F)cccc2[C@@H]2CN(C(=O)/C=C/[C@@H]3C[C@@H](F)CN3)Cc3sc(C#N)cc32)c(C(F)(F)F)n1]

(S)-4-(2-(1-Ethyl-3-(trifluoromethyl)-1H pyrazol-4-yl)-3-fluorophenyl)-6-((E)-3-((2S,4R)-4-fluoropyrrolidin-2-yl) acryloyl)-4,5,6,7-tetrahydrothieno[2,3-c]pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate and tert-butyl (2S,4R)-4-fluoro-2-formylpyrrolidine-1-carboxylate and isolated as a white solid (FA-TFA salt, 16 mg, 8%). MS (ESI) m/z 562.2 [M+H]+.

Example 122

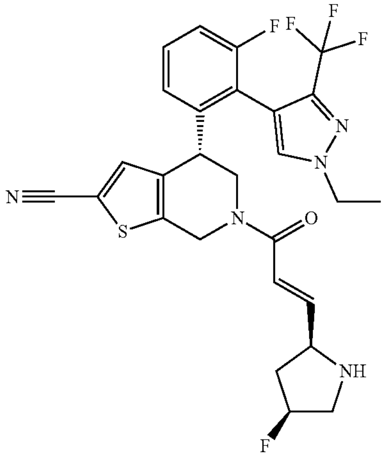 [SMILES: CCn1cc(-c2c(F)cccc2[C@@H]2CN(C(=O)/C=C/[C@@H]3C[C@H](F)CN3)Cc3sc(C#N)cc32)c(C(F)(F)F)n1]

(S)-4-(2-(1-Ethyl-3-(trifluoromethyl)-1H pyrazol-4-yl)-3-fluorophenyl)-6-((E)-3-((2S,4S)-4-fluoropyrrolidin-2-yl) acryloyl)-4,5,6,7-tetrahydrothieno[2,3-c] pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H)-yl)-2-oxoethyl)phosphonate and tert-butyl (2S,4S)-4-fluoro-2-formylpyrrolidine-1-carboxylate and isolated as a white solid (FA-TFA salt, 14 mg, 7%). MS (ESI) m/z 562.3 [M+H]+.

Example 123

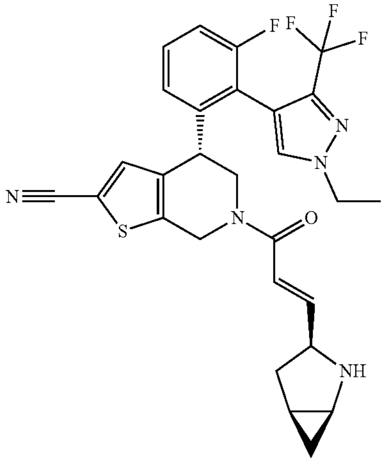 [SMILES: CCn1cc(-c2c(F)cccc2[C@@H]2CN(C(=O)/C=C/[C@@H]3C[C@@H]4C[C@@H]4N3)Cc3sc(C#N)cc32)c(C(F)(F)F)n1]

(S)-6-((E)-3-((1S,3S,5S)-2-Azabicyclo[3.1.0]hexan-3-yl)acryloyl)-4-(2-(1-ethyl-3-(trifluoromethyl)-1H pyrazol- 4-yl)-3-fluorophenyl)-4,5,6 7-tetrahydrothieno[2,3-c]pyridine-2-carbonitrile The compound was synthesized analogously as described above from diethyl (S)-(2-(2-cyano-4-(2-(1-ethyl-3-(trifluoromethyl)-1H-pyrazol-4-yl)-3-fluorophenyl)-4,7-dihydrothieno[2,3-c]pyridin-6(5H-yl)-2-oxoethyl)phosphonate and tert-butyl (1 S,3S,5S)-3-formyl-2-azabicyclo[3.1.0]hexane-2-carboxylate and isolated as a white solid (FA-TFA salt, 18 mg, 10%). MS (ESI) m/z 556.2 [M+H]+.

Example 124

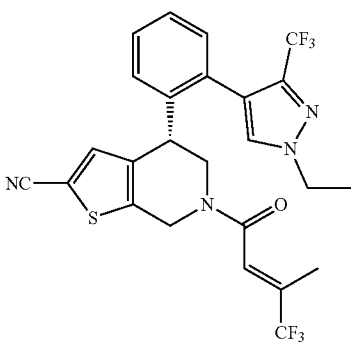 [SMILES: CCn1cc(-c2ccccc2[C@@H]2CN(C(=O)/C=C(\C)C(F)(F)F)Cc3sc(C#N)cc32)c(C(F)(F)F)n1]

(S,E)-4-(2-(1-ethyl-3-(trifluoromethyl)-1H-pyrazol-4-yl)phenyl)-6-(4,4,4-trifluoro-3-methylbut-2-enoyl)-4,5,6,7-tetrahydrothieno[2,3-c]pyridine-2-carbonitrile The compound was synthesized analogously to the general scheme, from (E)-4,4,4-trifluoro-3-methylbut-2-enoic acid, and isolated as an amorphous white solid (19 mg, 72% over 2 steps). MS (ESI) m/z 539.2 [M+H]+.

Example 125

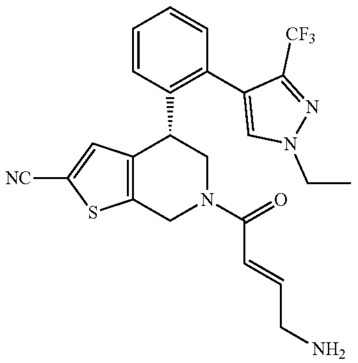 [SMILES: CCn1cc(-c2ccccc2[C@@H]2CN(C(=O)/C=C/CN)Cc3sc(C#N)cc32)c(C(F)(F)F)n1]

(S,E)-6-(4-Aminobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1. tert-Butyl (S,E)-(4-(2-cyano-4-(2-(1-ethyl-3-(trifluoromethyl)-1H-pyrazol-4-yl)phenyl)-4,7-dihydrothieno

[2,3-c]pyridin-6(5H)-yl)-4-oxobut-2-en-1-yl)carbamate. The compound was synthesized analogously to that above, from (E)-4-((tert-butoxycarbonyl)amino)but-2-enoic acid, and isolated as a solid (29 mg, quant.). MS (ESI) m/z 529.9 [M-tBu+H]+.

Step 2. (S,E)-6-(4-Aminobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile. The compound was synthesized analogously to that above, from tert-butyl (E)-(4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)carbamate, and isolated as an amorphous white solid (FA salt, 29 mg, 92%). MS (ESI) m/z 486.2 [M+H]+.

Example 126

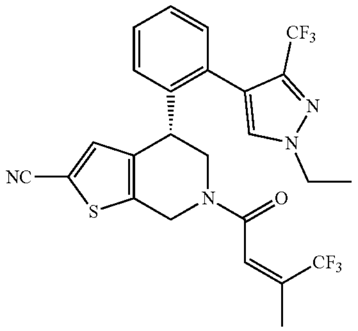 [SMILES: CCn1cc(-c2ccccc2[C@@H]2CN(C(=O)/C=C(/C)C(F)(F)F)Cc3sc(C#N)cc32)c(C(F)(F)F)n1]

(S,Z)-4-(2-(1-Ethyl-3-(trifluoromethyl)-1H-pyrazol-4-yl)phenyl)-6-(4,4,4-trifluoro-3-methylbut-2-enoyl)-4,5,6,7-tetrahydrothieno[2,3-c]pyridine-2-carbonitrile The compound was synthesized analogously to the general scheme, from (Z)-4,4,4-trifluoro-3-methylbut-2-enoic acid, and isolated as an amorphous light orange solid (20 mg, 74% over 2 steps). MS (ESI) m/z 539.2 [M+H]+.

Example 127

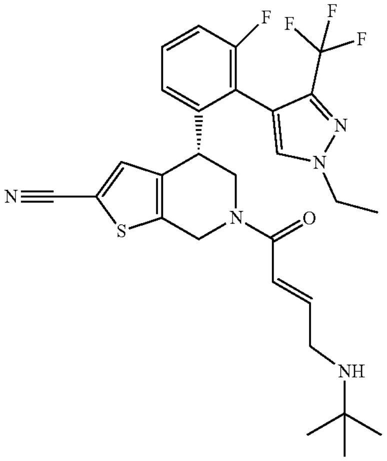 [SMILES: CCn1cc(-c2c(F)cccc2[C@@H]2CN(C(=O)/C=C/CNC(C)(C)C)Cc3sc(C#N)cc32)c(C(F)(F)F)n1]

(S,E)-6-(4-(tert-butylamino)but-2-enoyl)-4-(2-(1-ethyl-3-(trifluoromethyl)-1H pyrazol-4-yl)-3-fluorophenyl)-4,5,6,7-tetrahydrothieno[2,3-c]pyridine-2-carbonitrile Step 1. (S,E)-6-(4-Bromobut-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile and (S,E)-6-(4-chlorobut-2-enoyl)-4-(2-(1-ethyl-3-(trifluoromethyl)-1H pyrazol-4-yl)-3-fluorophenyl)-4,5,6,7-tetrahydrothieno[2,3-c]pyridine-2-carbonitrile. A solution of tert-butyl (S)-2-cyano-4-(2-(1-ethyl-3-(trifluoromethyl)-1H-pyrazol-4-yl)-3-fluorophenyl)-4,7-dihydrothieno[2,3-c]pyridine-6(5H)-carboxylate (104 mg, 0.2 mmol) in DCM (1 mL) was treated with TFA (1 mL). Separately, a solution of (E)-4-bromobut-2-enoic acid (50 mg, 0.3 mmol) was treated with oxalyl chloride (225 µL, 2 M in DCM, 0.45 mmol) and cat. DMF (1 drop) at 0° C., and the mixture was warmed to RT over 2 h. The solvents and excess oxalyl chloride were removed in vacuo, and the residue was dissolved in DCM. After 2 h, TFA and DCM were removed in vacuo. The residue was dissolved in DCM, $Et_3N$ (56 µL, 0.4 mmol) was added, and the mixture was cooled to 0° C. Acid chloride solution was added dropwise, and the mixture was warmed to RT. After 2 h, the mixture was diluted with DCM, washed with saturated $NH_4Cl_{(aq)}$, and brine, dried over $Na_2SO_4$, and concentrated in vacuo. The residue was purified by flash chromatography (04100% EA in hexanes gradient) and recovered the bromide intermediate contaminated slightly with chloride as a brown-green oily solid (90 mg, 86%). MS (ESI) m/z 566.8, 568.8 [M+H]+ (Bromide); 522.8 [M+H]+ (Chloride).

Step 2. (S,E)-6-(4-(tert-butylamino)but-2-enoyl)-4-(2-(1-ethyl-3-(trifluoromethyl)-1H pyrazol-4-yl)-3-fluorophenyl)-4,5,6,7-tetrahydrothieno[2,3-c]pyridine-2-carbonitrile. To a solution of (S,E)-6-(4-bromobut-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile and (S,E)-6-(4-chlorobut-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (90 mg, 0.16-0.17 mmol) in MeCN (1 mL) was added $K_2CO_3$ (47 mg, 0.34 mmol) and tert-butylamine (26 µL, 0.25 mmol) at RT and monitored by LC-MS until reaction completion. The mixture was diluted with DCM, washed with saturated $NH_4Cl_{(aq)}$, brine, dried over $Na_2SO_4$, and concentrated. Purified residue by reverse phase prep-HPLC (10→45% MeCN/$H_2O$ gradient) and recovered the compound as an amorphous white solid (FA-TFA salt; 40 mg, 45%). MS (ESI) m/z 560.3 [M+H]+.

Example 128

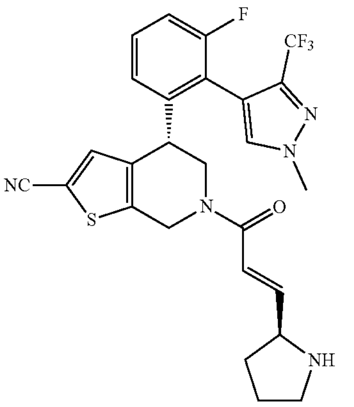 [SMILES: Cn1cc(-c2c(F)cccc2[C@@H]2CN(C(=O)/C=C/[C@@H]3CCCN3)Cc3sc(C#N)cc32)c(C(F)(F)F)n1]

(S)-4-(3-Fluoro-2-(1-methyl-3-(trifluoromethyl)-1H-pyrazol-4-yl)phenyl)-6-((E)-3-((S) pyrrolidin-2-yl) acryloyl)-4,5,6,7-tetrahydrothieno[2,3-c]pyridine-2-carbonitrile Step 1. tert-Butyl (S)-2-((E)-3-((S)-2-cyano-4-(3-fluoro-2-(1-methyl-3-(trifluoromethyl)-1H-pyrazol-4-yl)phenyl)-4,7-dihydrothieno[2,3-c]pyridin-6(5H)-yl)-3-oxoprop-1-en-1-yl)pyrrolidine-1-carboxylate. A solution of diethyl (S)-(2-(2-cyano-4-(3-fluoro-2-(1-methyl-3-(trifluoromethyl)-1H-pyrazol-4-yl)phenyl)-4,7-dihydrothieno[2,3-c]pyridin-6(5H)-yl)-2-oxoethyl)phosphonate (88 mg, 0.15 mmol) in THE (1 mL) was cooled to 0° C. and treated with NaH (7 mg, 60% dispersion in oil, 0.18 mmol) and stored for 30 min at 0° C. N-Boc-L-prolinal (31 µL, 0.165 mmol) was added and the mixture was warmed to RT. After 3 h, the mixture was diluted with EA, washed saturated $NH_4Cl_{(aq)}$, dried over $Na_2SO_4$, and concentrated in vacuo. Purification of the residue by a flash chromatography ($SiO_2$, 50→80% EA in hexanes gradient) recovered the compound as a light-yellow opaque oil (52 mg, 54%). MS (ESI) m/z 529.9 $[M+H]^+$.

Step 2. (S)-4-(3-Fluoro-2-(1-methyl-3-(trifluoromethyl)-1H-pyrazol-4-yl)phenyl)-6-((E)-3-((S) pyrrolidin-2-yl)acryloyl)-4,5,6,7-tetrahydrothieno[2,3-c]pyridine-2-carbonitrile. The compound was synthesized analogously to that above, from tert-butyl (S)-2-((E)-3-((S)-2-cyano-4-(3-fluoro-2-(1-methyl-3-(trifluoromethyl)-1H-pyrazol-4-yl)phenyl)-4,7-dihydrothieno[2,3-c]pyridin-6(5H)-yl)-3-oxoprop-1-en-1-yl) pyrrolidine-1-carboxylate, and isolated as an amorphous white solid (FA-TFA salt; 26 mg, 49%). MS (ESI) m/z 530.2 $[M+H]^+$.

Example 129

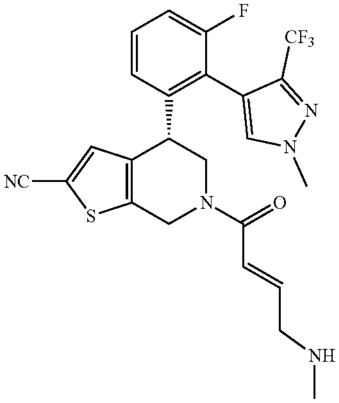 [SMILES: CNC/C=C/C(=O)N1Cc2sc(C#N)cc2[C@H](c2cccc(F)c2-c2cn(C)nc2C(F)(F)F)C1]

(S,E)-4-(3-Fluoro-2-(1-methyl-3-(trifluoromethyl)-1H pyrazol-4-yl)phenyl)-6-(4-(methylamino)but-2-enoyl)-4,5,6,7-tetrahydrothieno[2,3-c]pyridine-2-carbonitrile Step 1. t-Butyl (S,E)-(4-(2-cyano-4-(3-fluoro-2-(1-methyl-3-(trifluoromethyl)-1H pyrazol-4-yl)phenyl)-4,7-dihydrothieno[2,3-c]pyridin-6(5H)-yl)-4-oxobut-2-en-1-yl) (methyl)carbamate. The compound was synthesized analogously to that above, from tert-butyl methyl(2-oxoethyl)carbamate, and isolated as an opaque yellow semi solid (43 mg, 47%). MS (ESI) m/z 503.9 $[M-Boc+H]^+$.

Step 2. The compound was synthesized analogously to that above, from tert-butyl (S,E)-(4-(2-cyano-4-(3-fluoro-2-(1-methyl-3-(trifluoromethyl)-1H-pyrazol-4-yl)phenyl)-4,7-dihydrothieno[2,3-c]pyridin-6(5H)-yl)-4-oxobut-2-en-1-yl)(methyl)carbamate, and isolated as an amorphous white solid (FA-TFA salt; 24 mg, 56%). MS (ESI) m/z 504.2 $[M+H]^+$.

Example 130

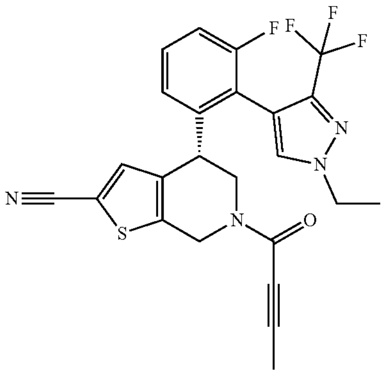 [SMILES: CC#CC(=O)N1Cc2sc(C#N)cc2[C@H](c2cccc(F)c2-c2cn(CC)nc2C(F)(F)F)C1]

(S)-6-(But-2-ynoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and but-2-ynoic acid, and isolated as a pale-yellow solid (57%). MS (ESI) m/z 469.2 $[M+H]^+$.

Example 131

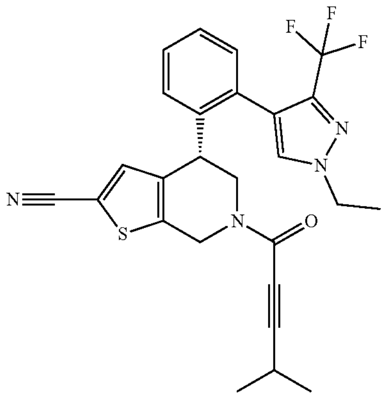 [SMILES: CCn1cc(-c2ccccc2[C@@H]2CN(C(=O)C#CC(C)C)Cc3sc(C#N)cc32)c(C(F)(F)F)n1]

(S)-4-(2-(1-Ethyl-3-(trifluoromethyl)-1H pyrazol-4-yl)phenyl)-6-(4-methylpent-2-ynoyl)-4,5,6,7-tetrahydrothieno[2,3-c]pyridine-2-carbonitrile The compound was synthesized analogous; y as described above from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-methylpent-2-ynoic acid, as a pale-yellow solid (57%). MS (ESI) m/z 497.2 $[M+H]^+$.

Example 132

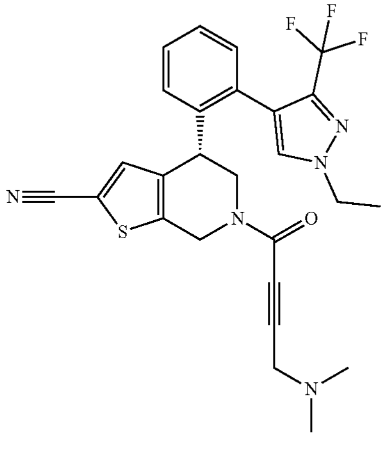 [SMILES: CCn1cc(-c2ccccc2[C@@H]2CN(C(=O)C#CCN(C)C)Cc3sc(C#N)cc32)c(C(F)(F)F)n1]

(S)-6-(4-(Dimethylamino)but-2-ynoyl)-4-(2-(1-ethyl-3-(trifluoromethyl)-1H-pyrazol-4-yl)phenyl)-4,5,6,7-tetrahydrothieno[2,3-c]pyridine-2-carbonitrile To a stirred solution of (S)-tert-butyl 4-(2-bromophenyl)-2-cyano-4,7-dihydrothieno[2,3-c]pyridine-6(5H)-carboxylate (45 mg, 0.089 mmol) in DCM (1 mL) was added TFA (1 mL) slowly at 0° C., and the mixture was stirred for 30 min and concentrated. The dark brown crude (S)-4-(2-(1-ethyl-3-(trifluoromethyl)-1H-pyrazol-4-yl)phenyl)-4,5,6,7-tetrahydrothieno[2,3-c]pyridine-2-carbonitrile TFA salt was dissolved in DMF (1 mL) and cooled to 0° C., to which DIEA (0.15 mL) was added followed by HATU (41 mg, 0.107 mmol) and 4-(dimethylamino)but-2-ynoic acid (15 mg, 0.116 mmol) was added subsequently. The resulting brown solution was stirred for 30 min then diluted with saturated $NH_4Cl_{(aq)}$ and water (2 mL each). The mixture was extracted with EA (5 mL×3) and organic phases were washed with brine, dried over $Na_2SO_4$, filtered, and the solvent was removed in vacuo. The residue was purified by a flash column chromatography ($SiO_2$, 0→2→5% MeOH in DCM w/$NH_3$) to yield the compound as a pale-brown solid (37.3 mg, 82%). MS (ESI) m/z 512.2 $[M+H]^+$.

Example 133 and Example 134

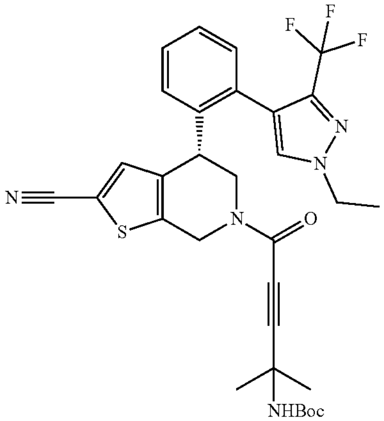

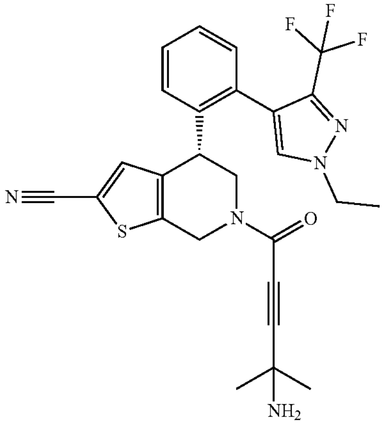

tert-Butyl (S)-(5-(2-cyano-4-(2-(1-ethyl-3-(trifluoromethyl)-1H pyrazol-4-yl)phenyl)-4,7-dihydrothieno[2,3-c]pyridin-6(5H)-yl)-2-methyl-5-oxopent-3-yn-2-yl)carbamate (133) and (S)-6-(4-Amino-4-methylpent-2-ynoyl)-4-(2-(1-ethyl-3-(trifluoromethyl)-1H-pyrazol-4-yl)phenyl)-4,5,6,7-tetrahydrothieno[2,3-c]pyridine-2-carbonitrile (134)

The initial amide-coupling product was prepared analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-((tert-butoxycarbonyl)amino)-4-methylpent-2-ynoic acid, and isolated as a light-yellow sticky oil. MS (ESI) m/z 634.3

[M+Na]$^+$. The material was dissolved in DCM and treated with TFA (1 mL each) at 0° C. and the solution was stirred for 30 min and concentrated. Flash column chromatographic purification with the residue ($SiO_2$, 0→2→5% MeOH in DCM w/$NH_3$) provided the free amine (S)-6-(4-amino-4-methylpent-2-ynoyl)-4-(2-(1-ethyl-3-(trifluoromethyl)-1H-pyrazol-4-yl)phenyl)-4,5,6,7-tetrahydrothieno[2,3-c]pyridine-2-carbonitrile as a white solid (40%). MS (ESI) m/z 512.2 [M+H]$^+$.

Example 135

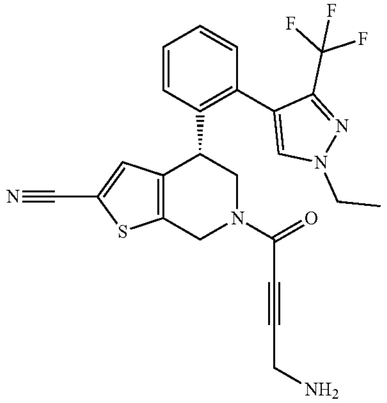 [SMILES: CCn1cc(-c2ccccc2[C@@H]2CN(C(=O)C#CCN)Cc3sc(C#N)cc32)c(C(F)(F)F)n1]

(S)-6-(4-Aminobut-2-ynoyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-((tert-butoxycarbonyl)amino)but-2-ynoic acid, and isolated as a white solid (2 FA salt, 33%). MS (ESI) m/z 484.2 [M+H]$^+$.

Example 136

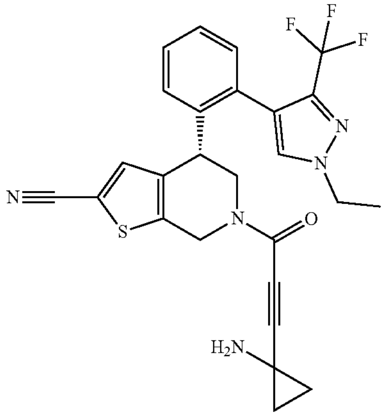 [SMILES: CCn1cc(-c2ccccc2[C@@H]2CN(C(=O)C#CC3(N)CC3)Cc3sc(C#N)cc32)c(C(F)(F)F)n1]

(S)-6-(3-(1-Aminocyclopropyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 3-(1-((tert-butoxycarbonyl)amino)cyclopropyl)propiolic acid, and isolated as a white solid (26%). MS (ESI) m/z 510.2 [M+H]$^+$.

Example 137

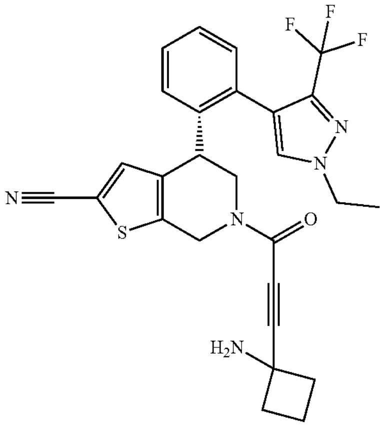

(S)-6-(3-(1-Aminocyclobutyl)propioloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above, from (S)-6-(3-(1-aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile and 3-(1-((tert-butoxycarbonyl)amino)cyclobutyl)-propiolic acid, and isolated as a pale-brown solid (31%). MS (ESI) m/z 524.2 [M+H]$^+$.

Example 138

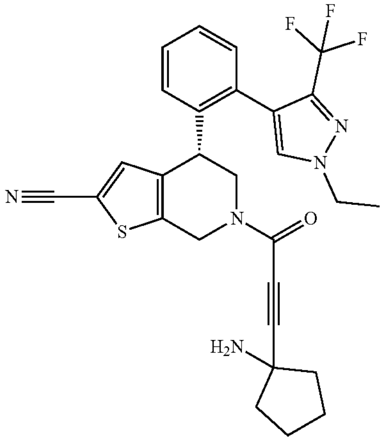 [SMILES: CCn1cc(-c2ccccc2[C@@H]2CN(C(=O)C#CC3(N)CCCC3)Cc3sc(C#N)cc32)c(C(F)(F)F)n1]

(S)-6-(3-(1-Aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above, from (S)-6-(3-(1-aminocyclopentyl)propioloyl)-4-

(2-(1-ethyl-3-(trifluoromethyl)-1H-pyrazol-4-yl)phenyl)-4,5,6,7-tetrahydrothieno[2,3-c]pyridine-2-carbonitrile and 3-(1-((tert-butoxycarbonyl)amino)cyclopentyl)-propiolic acid, and isolated as an off-white solid (41%). MS (ESI) m/z 538.3 [M+H]$^+$.

Example 139

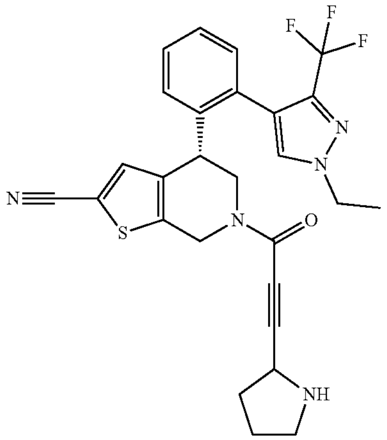 [SMILES: CCn1cc(-c2ccccc2[C@@H]2CN(C(=O)C#CC3CCCN3)Cc3sc(C#N)cc32)c(C(F)(F)F)n1]

(4S)-4-(2-(1-Ethyl-3-(trifluoromethyl)-1H pyrazol-4-yl)phenyl)-6-(3-(pyrrolidin-2-yl)propioloyl)-4,5,6,7-tetrahydrothieno[2,3-c]pyridine-2-carbonitrile The compound was synthesized analogously as described above, from (S)-6-(3-(1-aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile and (rac)-3-(1-(tert-butoxycarbonyl)pyrrolidin-2-yl)propiolic acid, and isolated as a pale-brown solid (55%). MS (ESI) m/z 524.2 [M+H]$^+$.

Example 140

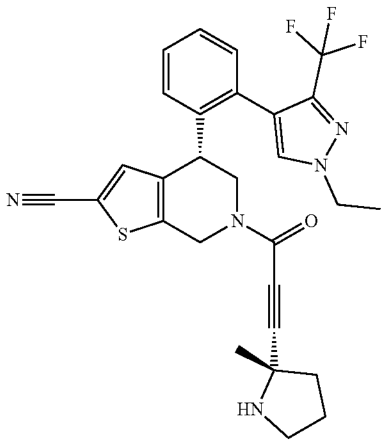

(S)-4-(2-(1-Ethyl-3-(trifluoromethyl)-1H-pyrazol-4-yl)phenyl)-6-(3-((S)-2-methylpyrrolidin-2-yl)propioloyl)-4,5,6,7-tetrahydrothieno[2,3-c]pyridine-2-carbonitrile The compound was synthesized analogously as described above, from (S)-6-(3-(1-aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile and (S)-3-(1-(tert-butoxycarbonyl)-2-methyl-pyrrolidin-2-yl) propiolic acid, and isolated as an off-white solid (47%). MS (ESI) m/z 538.3 [M+H]$^+$.

Example 141

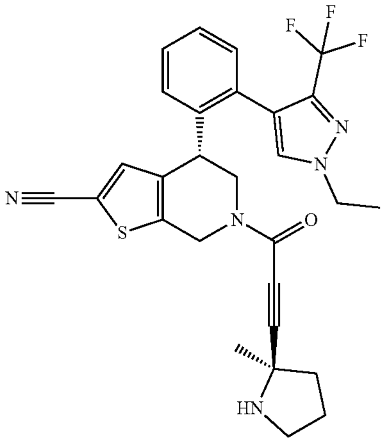 [SMILES: CCn1cc(-c2ccccc2[C@@H]2CN(C(=O)C#C[C@@]3(C)CCCN3)Cc3sc(C#N)cc32)c(C(F)(F)F)n1]

(S)-4-(2-(1-Ethyl-3-(trifluoromethyl)-1H pyrazol-4-yl)phenyl)-6-(3-((R)-2-methylpyrrolidin-2-yl)propioloyl)-4,5,6,7-tetrahydrothieno[2,3-c]pyridine-2-carbonitrile The compound was synthesized analogously as described above, from (S)-6-(3-(1-aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile and (R)-3-(1-(tert-butoxycarbonyl)-2-methyl-pyrrolidin-2-yl) propiolic acid, and isolated as an off-white solid (96%). MS (ESI) m/z 538.3 [M+H]$^+$.

Example 142

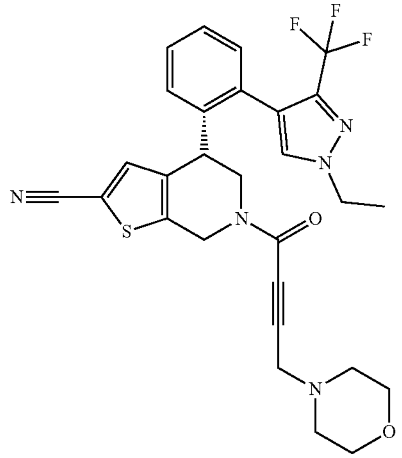

(S)-4-(2-(1-Ethyl-3-(trifluoromethyl)-1H-pyrazol-4-yl)phenyl)-6-(4-morpholinobut-2-ynoyl)-4,5,6,7-tetrahydrothieno[2,3-c]pyridine-2-carbonitrile The compound was synthesized analogously as described above, from (S)-6-(3-(1-aminocyclopentyl)propioloyl)-4-(2-(1-ethyl-3-(trifluoromethyl)-1H-pyrazol-4-yl)phenyl)-4,5,6,7-tetrahydrothieno[2,3-c]pyridine-2-carbonitrile and 4-morpholinobut-2-ynoic acid, and isolated as a pale-brown solid (23%). MS (ESI) m/z 554.3 $[M+H]^+$.

Example 143

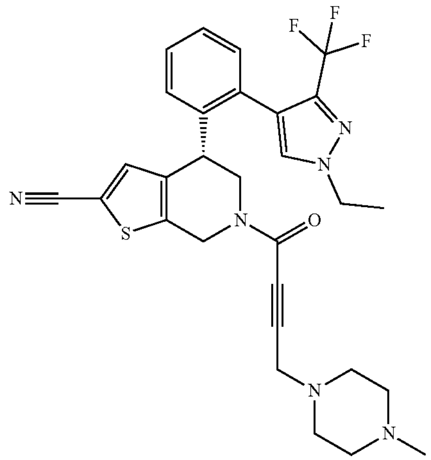 [SMILES: CCn1cc(-c2ccccc2[C@@H]2CN(C(=O)C#CCN3CCN(C)CC3)Cc3sc(C#N)cc32)c(C(F)(F)F)n1]

(S)-4-(2-(1-Ethyl-3-(trifluoromethyl)-1H pyrazol-4-yl)phenyl)-6-(4-(4-methylpiperazin-1-yl)but-2-ynoyl)-4,5,6,7-tetrahydrothieno[2,3-c]pyridine-2-carbonitrile To a stirred solution of (S)-4-(2-(1-ethyl-3-(trifluoromethyl)-1H-pyrazol-4-yl)phenyl)-4,5,6,7-tetrahydrothieno[2,3-c]pyridine-2-carbonitrile (40 mg, 0.099 mmol) in pyridine-DCM (1 mL each) was added lithium 4-(4-methylpiperazin-1-yl)but-2-ynoate (25 mg, 0.132 mol), pyridinium hydrogen bromide (27 mg, 0.168 mmol) at RT and the mixture was stirred for 10 min. The mixture was cooled to 0° C. then EDAC (25 mg, 0.132 mmol) was added. The solution was stirred at 0° C. for 2 h and quenched with water (5 mL). The separated aqueous layer was extracted with DCM (3×5 mL) and the combined organic phases were washed with 5% $CuSO_4·5H_2O$ aqueous solution and then brine. Filtration followed by concentration of the organic phase under a reduced pressure yielded a crude residue which was purified by a flash column chromatography ($SiO_2$, 0→2→45% MeOH in DCM w/$NH_3$) to yield the compound as a pale-brown solid (25.9 mg, 45%). MS (ESI) m/z 567.3 $[M+H]^+$.

Example 144

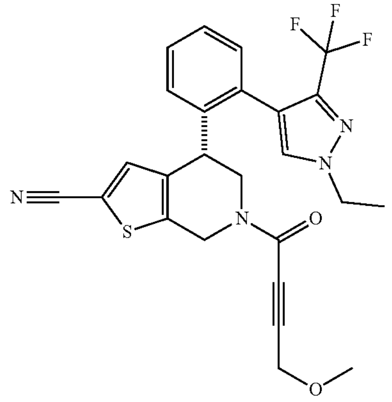 [SMILES: CCn1cc(-c2ccccc2[C@@H]2CN(C(=O)C#CCOC)Cc3sc(C#N)cc32)c(C(F)(F)F)n1]

(S)-4-(2-(1-Ethyl-3-(trifluoromethyl)-1H pyrazol-4-yl)phenyl)-6-(4-methoxybut-2-ynoyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-methoxybut-2-ynoic acid, and isolated as a white solid (57%). MS (ESI) m/z 499.2 $[M+H]^+$.

Example 145

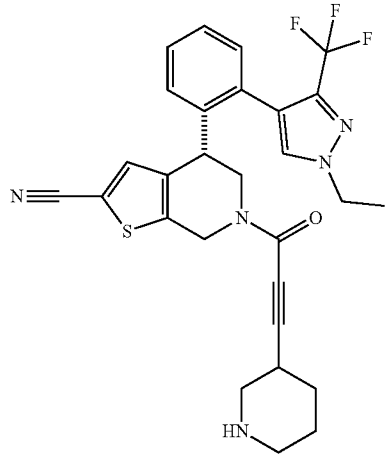 [SMILES: CCn1cc(-c2ccccc2[C@@H]2CN(C(=O)C#CC3CCCNC3)Cc3sc(C#N)cc32)c(C(F)(F)F)n1]

(4S)-4-(2-(1-Ethyl-3-(trifluoromethyl)-1H-pyrazol-4-yl)phenyl)-6-(3-(piperidin-3-yl)propioloyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and (rac)-3-(1-(tert-butoxycarbonyl)piperidin-3-yl)propiolic acid, and isolated as a pale-brown (58%). MS (ESI) m/z 538.3 $[M+H]^+$.

Example 146

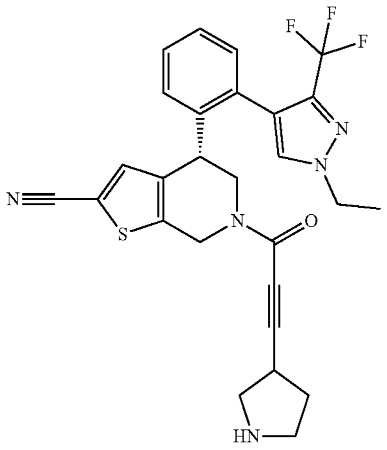 [SMILES: CCn1cc(-c2ccccc2[C@@H]2CN(C(=O)C#CC3CCNC3)Cc3sc(C#N)cc32)c(C(F)(F)F)n1]

(4S)-4-(2-(1-Ethyl-3-(trifluoromethyl)-1H pyrazol-4-yl)phenyl)-6-(3-(pyrrolidin-3-yl)propioloyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and (rac)-3-(1-(tert-butoxycarbonyl)pyrrolidin-3-yl)propiolic acid, and isolated as a pale-brown solid (60%). MS (ESI) m/z 524.2 $[M+H]^+$.

Example 147

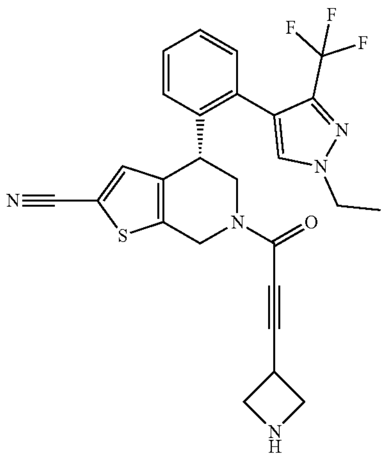 [SMILES: CCn1cc(-c2ccccc2[C@@H]2CN(C(=O)C#CC3CNC3)Cc3sc(C#N)cc32)c(C(F)(F)F)n1]

(S)-6-(3-(Azetidin-3-yl)propioloyl)-4-(2-(1-ethyl-3-(trifluoromethyl)-1H pyrazol-4-yl)phenyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 3-(1-(tert-butoxycarbonyl)azetidin-3-yl) propiolic acid, and isolated as a white solid (FA salt, 36%). MS (ESI) m/z 510.2 $[M+H]^+$.

Example 148

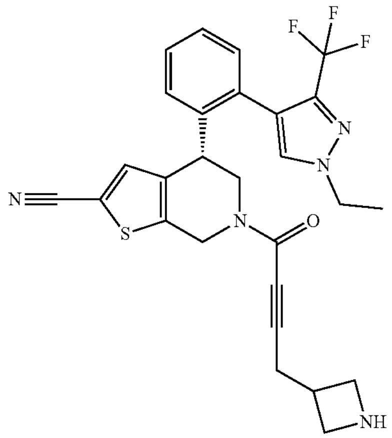 [SMILES: CCn1cc(-c2ccccc2[C@@H]2CN(C(=O)C#CCC3CNC3)Cc3sc(C#N)cc32)c(C(F)(F)F)n1]

(S)-6-(4-(Azetidin-3-yl)but-2-ynoyl)-4-(2-(1-ethyl-3-(trifluoromethyl)-1H-pyrazol-4-yl)phenyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-(1-(tert-butoxycarbonyl)azetidin-3-yl) but-2-ynoic acid, and isolated as a pale-brown solid (36%). MS (ESI) m/z 524.2 $[M+H]^+$.

Example 149

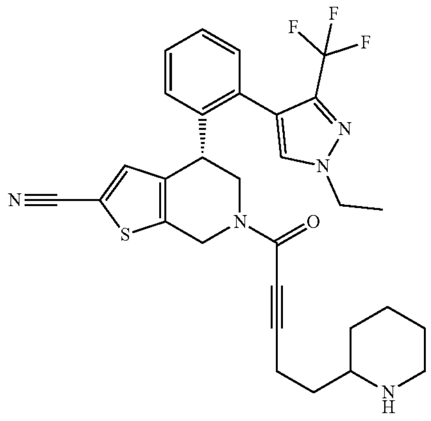 [SMILES: CCn1cc(-c2ccccc2[C@@H]2CN(C(=O)C#CCCC3CCCCN3)Cc3sc(C#N)cc32)c(C(F)(F)F)n1]

(4S)-4-(2-(1-Ethyl-3-(trifluoromethyl)-1H-pyrazol-4-yl)phenyl)-6-(5-(piperidin-2-yl)pent-2-ynoyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 5-(1-(tert-butoxycarbonyl)piperidin-2-yl) pent-2-ynoic acid, and isolated as a pale-yellow solid (9%). MS (ESI) m/z 566.3 $[M+H]^+$.

Example 150

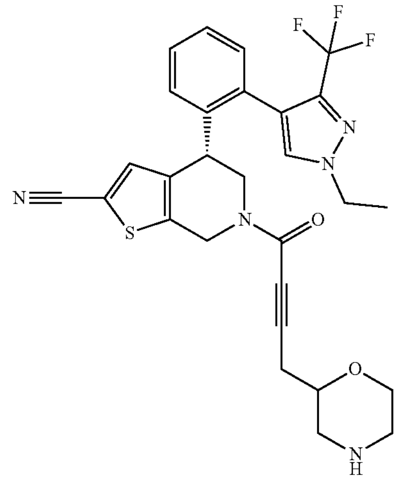 [SMILES: CCn1cc(-c2ccccc2[C@@H]2CN(C(=O)C#CCC3CNCCO3)Cc3sc(C#N)cc32)c(C(F)(F)F)n1]

(4S)-4-(2-(1-Ethyl-3-(trifluoromethyl)-1H-pyrazol-4-yl)phenyl)-6-(4-(morpholin-2-yl)but-2-ynoyl)-4,5,6,7-tetrahydrothieno[2,3-c]pyridine-2-carbonitrile The compound was synthesized analogously as described above, from (S)-4-(2-(1-ethyl-3-(trifluoromethyl)-1H-pyrazol-4-yl)phenyl)-4,5,6,7-tetrahydrothieno[2,3-c]pyridine-2-carbonitrile and 4-(4-(tert-butoxycarbonyl)morpholin-2-yl) but-2-ynoic acid, and isolated as a pale-brown solid (41%). MS (ESI) m/z 566.3 $[M+H]^+$.

Example 151

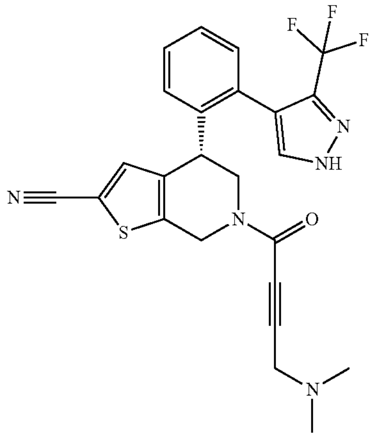 [SMILES: CN(C)CC#CC(=O)N1Cc2sc(C#N)cc2[C@H](c2ccccc2-c2c[nH]nc2C(F)(F)F)C1]

(S)-6-(4-(Dimethylamino)but-2-ynoyl)-4-(2-(3-(trifluoromethyl)-1H-pyrazol-4-yl)phenyl)-4,5,6,7-tetrahydrothieno[2,3-c]pyridine-2-carbonitrile Step 1. tert-Butyl (S)-2-cyano-4-(2-(3-(trifluoromethyl)-1H pyrazol-4-yl)phenyl)-4,7-dihydrothieno[2,3-c]pyridine-6(5H)-carboxylate. To a stirred mixture of tert-butyl (R)-4-(2-bromophenyl)-2-cyano-4,7-dihydrothieno[2,3-c] pyridine-6(5H)-carboxylate (1.0 g, 2.4 mmol), 4-(4,4,5,5-tetramethyl-1,3,2-dioxaborolan-2-yl)-3-(trifluoromethyl)-1H-pyrazole (0.943 g, 3.6 mmol), $Pd(dppf)Cl_2$ (0.176 g, 0.24 mmol), and $K_3PO_4$ (1.53 g, 7.2 mmol) in a sealable reaction vessel was added dioxane and water (5:1, 24 mL total) via syringe under nitrogen. The reaction vessel was screw-sealed and heated at 90° C. overnight. After cooling, the resulting dark mixture was filtered through a column of Celite®, washed with EA (3×20 mL), and the combined filtrates were concentrated in vacuo. The residue was purified by a flash column chromatography ($SiO_2$, 0→20→50% EA in hexanes) to yield the compound as a colorless oil (1.2 g, quantitative). MS (ESI) m/z 497.1 $[M+Na]^+$.

Step 2. (S)-6-(4-(Dimethylamino)but-2-ynoyl)-4-(2-(3-(trifluoromethyl)-1H pyrazol-4-yl)phenyl)-4,5,6,7-tetrahydrothieno[2,3-c]pyridine-2-carbonitrile. The compound was synthesized analogously as described above, from tert-butyl (S)-2-cyano-4-(2-(3-(trifluoromethyl)-1H-pyrazol-4-yl)phenyl)-4,7-dihydrothieno[2,3-c]pyridine-6(5H)-carboxylate, and 4-(dimethylamino)but-2-ynoic acid, and isolated as a pale-brown solid (36%). MS (ESI) m/z 484.2 $[M+H]^+$.

Example 152

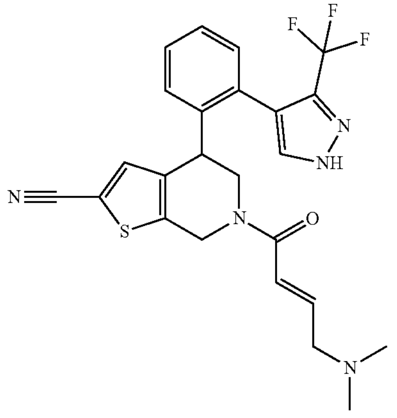 [SMILES: CN(C)C/C=C/C(=O)N1Cc2sc(C#N)cc2C(c2ccccc2-c2c[nH]nc2C(F)(F)F)C1]

(E)-6-(4-(Dimethylamino)but-2-enoyl)-4-(2-(3-(trifluoromethyl)-1H-pyrazol-4-yl)phenyl)-4,5,6,7-tetrahydrothieno[2,3-c]pyridine-2-carbonitrile Step 1. tert-Butyl 2-cyano-4-(2-(3-(trifluoromethyl)-1H-pyrazol-4-yl)phenyl)-4,7-dihydrothieno[2,3-c]pyridine-6(5H)-carboxylate. To a stirred mixture of tert-butyl 4-(2-bromophenyl)-2-cyano-4,7-dihydrothieno[2,3-c]pyridine-6(5H)-carboxylate (0.2 g, 0.48 mmol), 4-(4,4,5,5-tetramethyl-1,3,2-dioxaborolan-2-yl)-3-(trifluoromethyl)-1H-pyrazole (0.189 g, 0.72 mmol), $Pd(dppf)C_{1-2}$ (35 mg, 0.048 mmol), and $K_3PO_4$ (0.31 g, 2.4 mmol) in a sealable reaction vessel was added dioxane and water (5:1, 1.2 mL total) via syringe under nitrogen. The reaction vessel was screw-sealed and heated at 90° C. overnight. After cooling, the resulting dark mixture was filtered through a column of Celite®, washed with EA (3×2 mL), and the combined filtrates were concentrated in vacuo. The residue was purified by a flash column chromatography ($SiO_2$, 0→20→40% EA in hexanes) to yield the target compound as a colorless oil (0.22 g, 97%). MS (ESI) m/z 497.1 $[M+Na]^+$.

Step 2. (E)-6-(4-(Dimethylamino)but-2-enoyl)-4-(2-(3-(trifluoromethyl)-1H pyrazol-4-yl)phenyl)-4,5,6,7-tetrahydrothieno[2,3-c]pyridine-2-carbonitrile. To a stirred solution of tert-butyl 2-cyano-4-(2-(3-(trifluoromethyl)-1H-pyrazol-4-yl)phenyl)-4,7-dihydrothieno[2,3-c]pyridine-6(5H)-carboxylate (110 mg, 0.232 mmol) in DCM (2 mL) was added slowly TFA (2 mL) at 0° C. The reaction was stirred for 30 min and concentrated. The crude was dissolved in DMF (3 mL) and cooled to 0° C. DIEA (0.15 mL) was added to the mixture followed by HATU (106 mg, 0.278 mmol) and (E)-4-(dimethylamino)but-2-enoic acid HCl salt (50 mg, 0.30 mmol). The resulting brown solution was stirred for 30 min and then the mixture was diluted with saturated $NH_4Cl_{(aq)}$ and water (4 mL each). The mixture was extracted with EA (3×12 mL) and the combined organic phases were washed with brine, dried over $Na_2SO_4$, filtered, and the solvent was removed in vacuo. The residue was purified by a flash column chromatography ($SiO_2$, 0→→45% MeOH in DCM w/$NH_3$) to yield the compound as a pale-brown solid (43.7 mg, 39%). MS (ESI) m/z 486.2 $[M+H]^+$.

Example 153

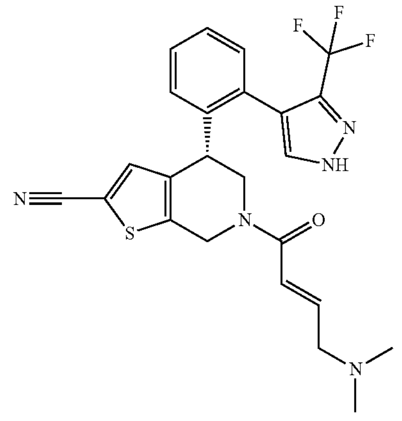

(S,E)-6-(4-(Dimethylamino)but-2-enoyl)-4-(2-(3-(trifluoromethyl)-1H-pyrazol-4-yl)phenyl)-4,5,6,7-tetrahydrothieno[2,3-c]pyridine-2-carbonitrile Step 1. tert-Butyl (S)-2-cyano-4-(2-(4,4,5,5-tetramethyl-1,3,2-dioxaborolan-2-yl)phenyl)-4,7-dihydrothieno[2,3-c]pyridine-6(5H)-carboxylate. To a degassed (5×) mixture of tert-butyl (R)-4-(2-bromophenyl)-2-cyano-4,7-dihydrothieno[2,3-c]pyridine-6(5H)-carboxylate (1 g, 2.4 mmol), $Pd(PPh_3)_2Cl_2$ (167 mg, 0.24 mmol), $B_2pin_2$ (727 mg, 2.9 mmol), and KOAc (468 mg, 4.8 mmol) was added dioxane. The suspension was degassed 2× with argon, and heated to 70° C. for 3 days. The mixture was cooled to RT then diluted with water, and extracted with EA. The combinedorganic phases were dried over $Na_2SO_4$, filtered, and concentrated in vacuo. Purification of the residue by flash chromatography ($SiO_2$, 10% EA in hexanes isocratic) gave the compound as a light orange foam (727 mg, 66%). MS (ESI) m/z 367.0 $[M-Boc+H]^+$.

Step 2. The chiral synthesis was carried out in a similar manner as described above, from optically pure (S)-tert-butyl 4-(2-bromophenyl)-2-cyano-4,7-dihydrothieno[2,3-c]pyridine-6(5H)-carboxylate, and the compound was isolated as a yellow solid (35%). MS (ESI) m/z 486.2 $[M+H]^+$.

Other substituted pyrazole intermediates are prepared as follows:

2-(2-(4-Bromo-3-(trifluoromethyl)-1H-pyrazol-1-yl)ethyl)pyridine. A suspension of 4-bromo-3-(trifluoromethyl)-1H-pyrazole (53.7 mg, 0.25 mmol), 2-(2-bromoethyl)pyridine hydrobromide (73.4 mg, 0.275 mmol), and $Cs_2CO_3$ (244 mg, 0.75 mmol) in DMF (1 mL) was heated to 90° C. overnight. After cooling to RT, the mixture was diluted with water, extracted with EA, washed with brine, dried over $Na_2SO_4$, filtered, and concentrated in vacuo. The residue was purified by flash chromatography ($SiO_2$, 0→100% EA in hexanes gradient) to provide the compound as a clear oil (31 mg, 39%). MS (ESI) m/z 319.8, 321.8 $[M+H]^+$.

4-(2-(4-Bromo-3-(trifluoromethyl)-1H-pyrazol-1-yl)ethyl)pyridine. The compound was synthesized analogously as described above from 4-(2-bromoethyl)pyridine hydrobromide, and isolated as a rose-colored crystalline solid (28 mg, 35%). MS (ESI) m/z 336.8, 338.8 $[M+H]^+$.

2-(4-Bromo-3-(trifluoromethyl)-1H-pyrazol-1-yl)-3-methoxypyridine. The compound was synthesized analogously as described above from 2-fluoro-3-methoxypyridine, and isolated as a white waxy solid (29 mg, 18%). MS (ESI) m/z 321.8, 323.8 $[M+H]^+$.

Example 154

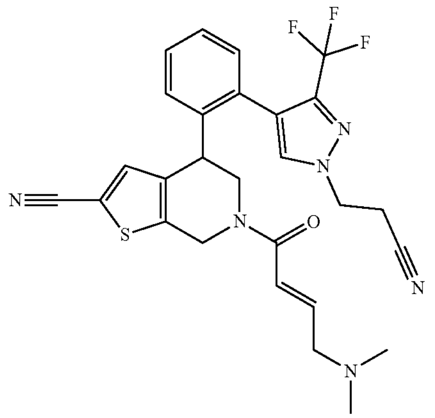 [SMILES: CN(C)C/C=C/C(=O)N1Cc2sc(C#N)cc2C(c2ccccc2-c2cn(CCC#N)nc2C(F)(F)F)C1]

(E)-4-(2-(1-(2-Cyanoethyl)-3-(trifluoromethyl)-1H pyrazol-4-yl)phenyl)-6-(4-(dimechylamino)but-2-enoyl)-4,5,6,7-tetrahydrothieno[2,3-c]pyridine-2-carbonitrile Step 1. tert-Butyl2-cyano-4-(2-(1-(2-cyanoethyl)-3-(trifluoromethyl)-1H-pyrazol-4 yl)phenyl)-4,7-dihydrothieno[2,3-c]pyridine-6(5H)-carboxylate. To a stirred solution of tert-butyl 2-cyano-4-(2-(3-(trifluoromethyl)-1H-pyrazol-4-yl)phenyl)-4,7-dihydrothieno[2,3-c]pyridine-6(5H)-carboxylate (110 mg, 0.232 mmol) in ACN (3 mL) was added DBU (70 μL, 0.47 mmol) followed by acrylonitrile (23 μL, 0.35 mmol) and the reaction was stirred at RT for 1 h. The mixture was concentrated to give crude tert-butyl 2-cyano-4-(2-(1-(2-cyanoethyl)-3-(trifluoromethyl)-1H- pyrazol-4-yl)phenyl)-4,7-dihydrothieno[2,3-c]pyridine-6(5H)-carboxylate as a brown residue.

Step 2. (E)-4-(2-(1-(2-Cyanoethyl)-3-(trifluoromethyl)-1H pyrazol-4-yl)phenyl)-6-(4-(dimethylamino)but-2-enoyl)-4,5,6,7-tetrahydrothieno[2,3-c]pyridine-2-carbonitrile. The compound was prepared via a similar sequence as described above, from tert-butyl 2-cyano-4-(2-(1-(2-cyanoethyl)-3-(trifluoromethyl)-1H-pyrazol-4-yl)phenyl)-4,7-dihydrothieno[2,3-c]pyridine-6(5H)-carboxylate, and isolated as a white solid (FA salt, 33%). MS (ESI) m/z 539.3 $[M+H]^+$.

Example 155

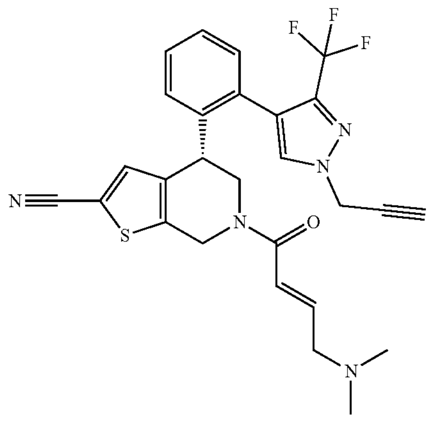 [SMILES: C#CCn1cc(-c2ccccc2[C@@H]2CN(C(=O)/C=C/CN(C)C)Cc3sc(C#N)cc32)c(C(F)(F)F)n1]

(S,E)-6-(4-(Dimethylamino)but-2-enoyl)-4-(2-(1-(prop-2-yn-1-yl)-3-(trifluoromethyl)-1H-pyrazol-4-yl)phenyl)-4,5,6,7-tetrahydrothieno[2,3-c]pyridine-2-carbonitrile Step 1. tert-Butyl (S)-2-cyano-4-(2-(1-(prop-2-yn-1-yl)-3-(trifluoromethyl)-1H pyrazol-4-yl)phenyl)-4,7-dihydrothieno[2,3-c]pyridine-6(5H)-carboxylate. This intermediate was synthesized analogously as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 3-bromoprop-1-yne, and was isolated as an oil and used in the next step without further purifications.

Step 2. (S,E)-6-(4-(Dimethylamino)but-2-enoyl)-4-(2-(1-(prop-2-yn-1-yl)-3-(trifluoromethyl)-1H pyrazol-4-yl)phenyl)-4,5,6,7-tetrahydrothieno[2,3-c]pyridine-2-carbonitrile. The compound was prepared in the same manner as described above, from tert-butyl (S)-2-cyano-4-(2-(1-(prop-2-yn-1-yl)-3-(trifluoromethyl)-1H-pyrazol-4-yl)phenyl)-4,7-dihydrothieno[2,3-c]pyridine-6(5H)-carboxylate, and isolated as a pale-yellow solid. MS (ESI) m/z 524.2 $[M+H]^+$.

Example 156

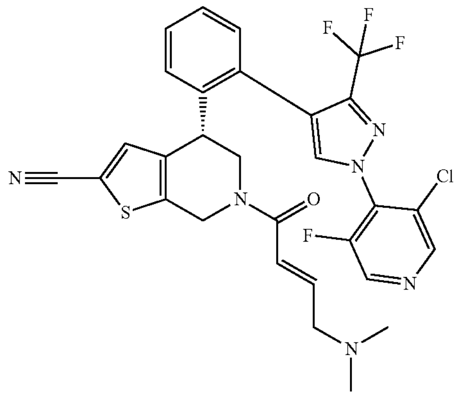 [SMILES: CN(C)C/C=C/C(=O)N1Cc2sc(C#N)cc2[C@H](c2ccccc2-c2cn(-c3c(F)cncc3Cl)nc2C(F)(F)F)C1]

(S,E)-4-(2-(1-(3-Chloro-5-fluoropyridin-4-yl)-3-(trifluoromethyl)-1H pyrazol-4-yl)phenyl)-6-(4-(dimethylamino)but-2-enoyl)-4,5,6,7-tetrahydrothieno[2,3-c]pyridine-2-carbonitrile Step 1. tert-Butyl (S)-4-(2-(1-(3-chloro-5-fluoropyridin-4-yl)-3-(trifluoromethyl)-1H-pyrazol-4-yl)phenyl)-2-cyano-4,7-dihydrothieno[2,3-c]pyridine-6(5H)-carboxylate. To a stirred suspension of (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate (64 mg, 0.135 mmol) and $Cs_2CO_3$ (88 mg, 0.27 mmol) in DMF (1 mL) was added 3-chloro-4,5-difluoropyridine (30 mg, 0.205 mmol) and the reaction was stirred at 70° C. overnight. After cooling, the mixture was diluted with saturated $NH_4Cl_{(aq)}$ and water (5 mL each). The mixture was extracted with EA(3×5 mL) and the organic phases were washed with brine, dried over $Na_2SO_4$, filtered, and the solvent was removed in vacuo to obtain a crude material, which was used directly in the next step without further purifications.

Step 2. (S,E)-4-(2-(1-(3-Chloro-5-fluoropyridin-4-yl)-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile. The compound was synthesized analogously as described previously, from crude tert-butyl (S)-4-(2-(1-(3-chloro-5-fluoropyridin-4-yl)-3-(trifluoromethyl)-1H-pyrazol-4-yl)phenyl)-2-cyano-4,7-dihydrothieno[2,3-c]pyridine-6(5H)-carboxylate, and was isolated as a white solid (8%). MS (ESI) m/z 615.2 $[M+H]^+$.

Example 157

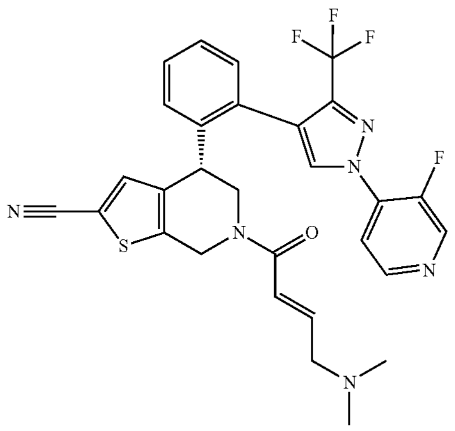 [SMILES: CN(C)C/C=C/C(=O)N1Cc2sc(C#N)cc2[C@H](c2ccccc2-c2cn(-c3ccncc3F)nc2C(F)(F)F)C1]

(S,E)-6-(4-(Dimethylamino)but-2-enoyl)-4-(2-(1-(3-fluoropyridin-4-yl)-3-(trifluoromethyl)-1H pyrazol-4-yl)phenyl)-4,5,6,7-tetrahydrothieno[2,3-c]pyridine-2-carbonitrile The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 3,4-difluoropyridine, and was isolated as a white powder (17%). MS (ESI) 581.3 $[M+H]^+$.

Example 158

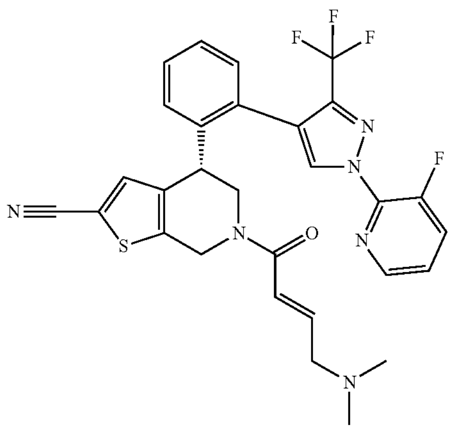 [SMILES: CN(C)C/C=C/C(=O)N1Cc2sc(C#N)cc2[C@H](c2ccccc2-c2cn(-c3ncccc3F)nc2C(F)(F)F)C1]

(S,E)-6-(4-(Dimethylamino)but-2-enoyl)-4-(2-(1-(3-fluoropyridin-2-yl)-3-(trifluoromethyl)-1H pyrazol-4-yl)phenyl)-4,5,6,7-tetrahydrothieno[2,3-c]pyridine-2-carbonitrile The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 2,3-difluoropyridine, and was isolated as a white powder (14%). MS (ESI) 581.3 $[M+H]^+$.

Example 159

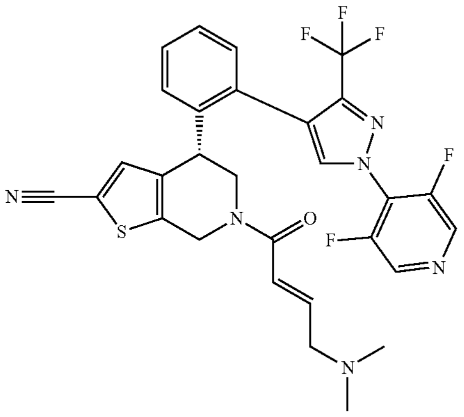 [SMILES: CN(C)C/C=C/C(=O)N1Cc2sc(C#N)cc2[C@H](c2ccccc2-c2cn(-c3c(F)cncc3F)nc2C(F)(F)F)C1]

(S,E)-4-(2-(1-(3,5-Difluoropyridin-4-yl)-3-(trifluoromethyl)-1H pyrazol-4-yl)phenyl)-6-(4-(dimethylamino)but-2-enoyl)-4,5,6,7-tetrahydrothieno[2,3-c]pyridine-2-carbonitrile The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 3,4,5-trifluoropyridine, and was isolated as an off-white powder (42%). MS (ESI) 599.3 $[M+H]^+$.

Example 160

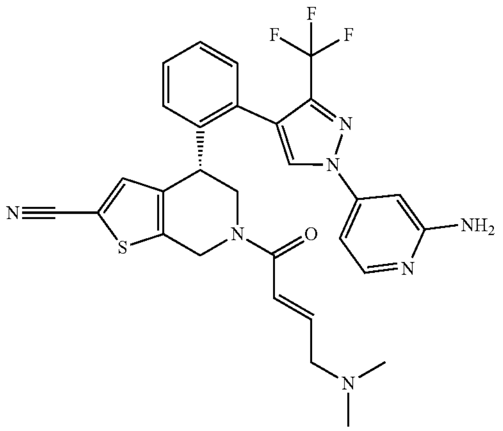 [SMILES: CN(C)C/C=C/C(=O)N1Cc2sc(C#N)cc2[C@H](c2ccccc2-c2cn(-c3ccnc(N)c3)nc2C(F)(F)F)C1]

(S,E)-4-(2-(1-(2-Aminopyridin-4-yl)-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and tert-butyl (4-fluoropyridin-2-yl)carbamate, and was isolated as a white solid (7%). MS (ESI) 578.3 $[M+H]^+$.

Example 161

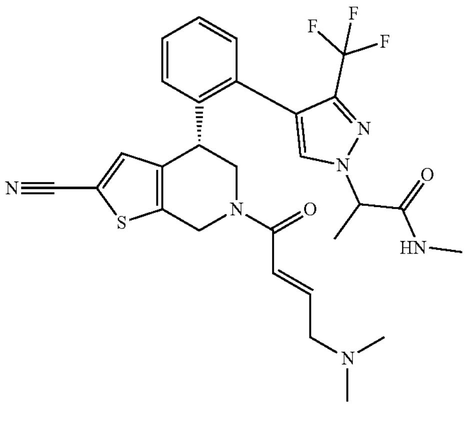 [SMILES: CNC(=O)C(C)n1cc(-c2ccccc2[C@@H]2CN(C(=O)/C=C/CN(C)C)Cc3sc(C#N)cc32)c(C(F)(F)F)n1]

2-(4-(2-((S)-2-Cyano-6-((E)-4-(dimethylamino)but-2-enoyl)-4,5,6,7-tetrahydrothieno[2,3-c]pyridin-4-yl)phenyl)-3-(trifluoromethyl)-1H-pyrazol-1-yl)-N-methylpropanamide The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 2-bromo-N-methylpropanamide, and was isolated as a pale-yellow solid (36%). MS (ESI) 571.3 $[M+H]^+$.

Example 162

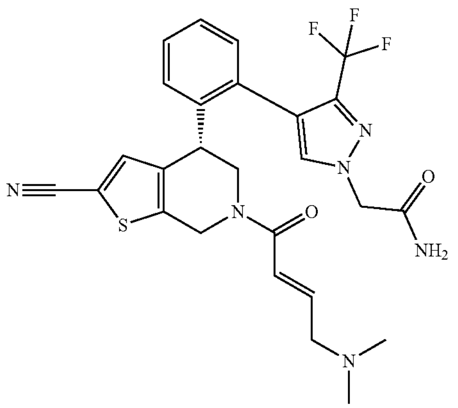 [SMILES: CN(C)C/C=C/C(=O)N1Cc2sc(C#N)cc2[C@H](c2ccccc2-c2cn(CC(N)=O)nc2C(F)(F)F)C1]

(S,E)-2-(4-(2-(2-Cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)acetamide The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 2-bromoacetamide, and was isolated as a pale-yellow solid (35%). MS (ESI) 543.3 $[M+H]^+$.

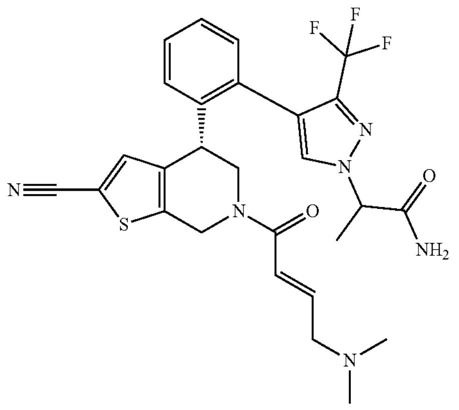 [SMILES: CC(C(N)=O)n1cc(-c2ccccc2[C@@H]2CN(C(=O)/C=C/CN(C)C)Cc3sc(C#N)cc32)c(C(F)(F)F)n1]

2-(4-(2-((S)-2-Cyano-6-((E)-4-(dimethylamino)but-2-enoyl)-4,5,6,7-tetrahydrothieno[2,3-c]pyridin-4-yl)phenyl)-3-(trifluoromethyl)-1H-pyrazol-1-yl)-N,N-dimethylpropanamide The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 2-bromopropanamide, and was isolated as a white solid (FA salt, 29%). MS (ESI) 557.3 $[M+H]^+$.

Example 164

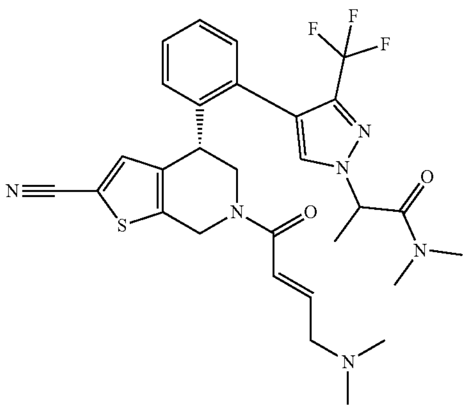 [SMILES: CC(C(=O)N(C)C)n1cc(-c2ccccc2[C@@H]2CN(C(=O)/C=C/CN(C)C)Cc3sc(C#N)cc32)c(C(F)(F)F)n1]

2-(4-(2-((S)-2-Cyano-6-((E)-4-(dimethylamino)but-2-enoyl)-4,5,6,7-tetrahydrothieno[2,3-c]pyridin-4-yl)phenyl)-3-(trifluoromethyl)-1H-pyrazol-1-yl)-N,N-dimethylpropanamide The compound was prepared in a similar sequence as described above, from (S)-tert-butyl 2-cyano-4-(2-(3-(trifluoromethyl)-1H-pyrazol-4-yl)phenyl)-4,7-dihydrothieno[2,3-c]pyridine-6(5H)-carboxylate and 2-bromo-N,N-dimethylpropanamide, and was isolated as a pale-brown solid (29%). MS (ESI) 585.3 $[M+H]^+$.

Example 165

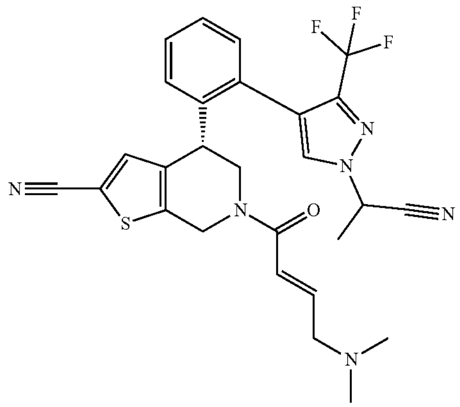 [SMILES: CC(C#N)n1cc(-c2ccccc2[C@@H]2CN(C(=O)/C=C/CN(C)C)Cc3sc(C#N)cc32)c(C(F)(F)F)n1]

(4S)-4-(2-(1-(1-Cyanoethyl)-3-(trifluoromethyl)-1H-pyrazol-4-yl)phenyl)-6-((E)-4-(dimethylamino) but-2-enoyl)-4,5,6,7-tetrahydrothieno[2,3-c]pyridine-2-carbonitrile The compound was prepared via a similar sequence as described above, from tert-butyl (S)-2-cyano-4-(2-(1-(prop-2-yn-1-yl)-3-(trifluoromethyl)-1H-pyrazol-4-yl)phenyl)-4,7-dihydrothieno[2,3-c]pyridine-6(5H)-carboxylate and 2-bromopropanenitrile, and was isolated as a white solid (FA salt, 22%). MS (ESI) 539.3 [M+H]$^+$.

Example 166

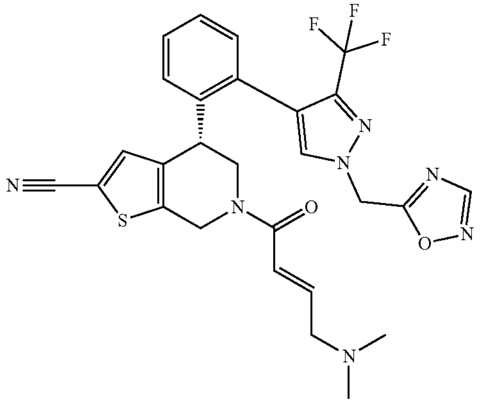 [SMILES: CN(C)C/C=C/C(=O)N1Cc2sc(C#N)cc2[C@H](c2ccccc2-c2cn(Cc3ncno3)nc2C(F)(F)F)C1]

(S,E)-4-(2-(1-((1,2,4-Oxadiazol-5-yl)methyl)-3-(trifluoromethyl)-1H pyrazol-4-yl)phenyl)-6-(4-(dimethylamino)but-2-enoyl)-4,5,6,7-tetrahydrothieno[2,3-c]pyridine-2-carbonitrile The compound was prepared via a similar sequence as described above, from tert-butyl (S)-2-cyano-4-(2-(1-(prop-2-yn-1-yl)-3-(trifluoromethyl)-1H-pyrazol-4-yl)phenyl)-4,7-dihydrothieno[2,3-c]pyridine-6(5H)-carboxylate and 5-(bromomethyl)-1,2,4-oxadiazole, and was isolated as a white solid (FA salt, 5%). MS (ESI) 568.3 [M+H]$^+$.

Example 167

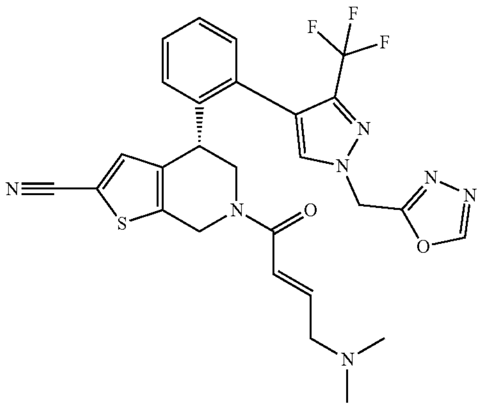 [SMILES: CN(C)C/C=C/C(=O)N1Cc2sc(C#N)cc2[C@H](c2ccccc2-c2cn(Cc3nnco3)nc2C(F)(F)F)C1]

(S,E)-4-(2-(1-((1,2,4-Oxadiazol-5-yl)methyl)-3-(trifluoromethyl)-1H pyrazol-4-yl)phenyl)-6-(4-(dimethylamino)but-2-enoyl)-4,5,6,7-tetrahydrothieno[2,3-c]pyridine-2-carbonitrile The compound was prepared via a similar sequence as described above, from tert-butyl (S)-2-cyano-4-(2-(1-(prop-2-yn-1-yl)-3-(trifluoromethyl)-1H-pyrazol-4-yl)phenyl)-4,7-dihydrothieno[2,3-c]pyridine-6(5H)-carboxylate and 2-(chloromethyl)-1,3,4-oxadiazole, and was isolated as a white solid (7%). MS (ESI) 568.3 [M+H]$^+$.

Example 168

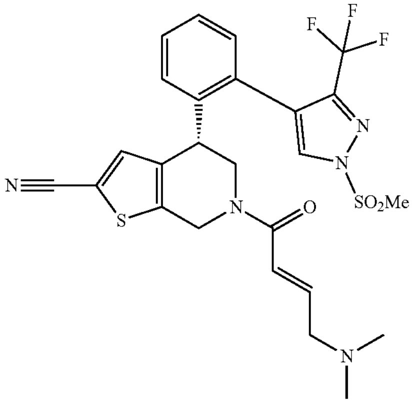 [SMILES: CN(C)C/C=C/C(=O)N1Cc2sc(C#N)cc2[C@H](c2ccccc2-c2cn(S(C)(=O)=O)nc2C(F)(F)F)C1]

(S,E)-6-(4-(Dimethylamino)but-2-enoyl)-4-(2-(1-(methylsulfonyl)-3-(trifluoromethyl)-1H pyrazol-4-yl)phenyl)-4,5,6,7-tetrahydrothieno[2,3-c]pyridine-2-carbonitrile The compound was prepared via a similar sequence as described above, from tert-butyl (S)-2-cyano-4-(2-(1-(prop-2-yn-1-yl)-3-(trifluoromethyl)-1H-pyrazol-4-yl)phenyl)-4,7-dihydrothieno[2,3-c]pyridine-6(5H)-carboxylate and methanesulfonyl chloride, and was isolated as a pale-brown solid (17%). MS (ESI) 564.2 [M+H]$^+$.

Example 169

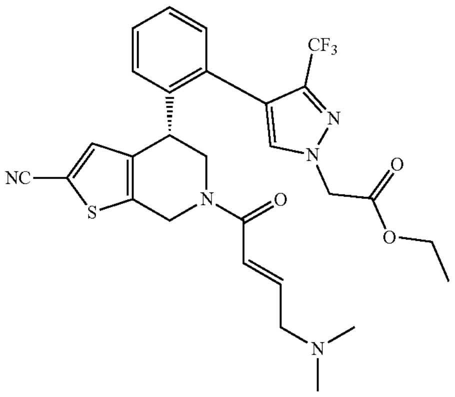 [SMILES: CCOC(=O)Cn1cc(-c2ccccc2[C@@H]2CN(C(=O)/C=C/CN(C)C)Cc3sc(C#N)cc32)c(C(F)(F)F)n1]

Ethyl (S,E)-2-(4-(2-(2-cyano-6-(4-(dimethylamino) but-2-enoyl)-4,5,6,7-tetrahydrothieno[2,3-c]pyridin-4-yl)phenyl)-3-(trifluoromethyl)-1H-pyrazol-1-yl) acetate Step 1. tert-Butyl (S)-2-cyano-4-(2-(1-(2-ethoxy-2-oxoethyl)-3-(trifluoromethyl)-1H pyrazol-4-yl)phenyl)-4,7-dihydrothieno[2,3-c]pyridine-6(5H)-carboxylate. The compound was synthesized analogously to the general scheme, from ethyl 2-bromoacetate, and was isolated as a viscous yellow oil (78 mg, 53%). MS (ESI) m/z 584.9 $[M+Na]^+$.

Step 2. Ethyl (S,E)-2-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)acetate. The compound was synthesized analogously to the general scheme, from tert-butyl 2-cyano-4-(2-(1-(2-ethoxy-2-oxoethyl)-3-(trifluoromethyl)-1H-pyrazol-4-yl)phenyl)-4,7-dihydrothieno[2,3-c]pyridine-6(5H)-carboxylate, and was isolated as an off-white to light orange solid (27 mg, 33% over 2 steps). MS (ESI) m/z 572.3 $[M+H]^+$.

Example 170

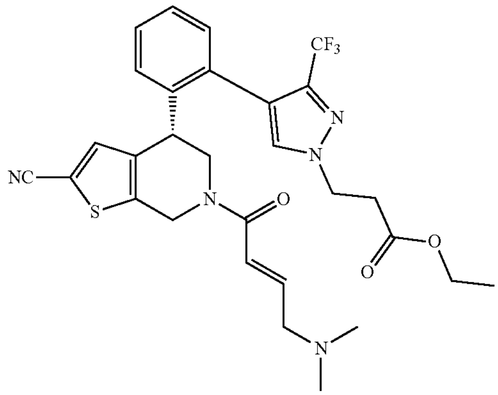 [SMILES: CCOC(=O)CCn1cc(-c2ccccc2[C@@H]2CN(C(=O)/C=C/CN(C)C)Cc3sc(C#N)cc32)c(C(F)(F)F)n1]

Ethyl (S,E)-3-(4-(2-(2-cyano-6-(4-(dimethylamino) but-2-enoyl)-4,5,6,7-tetrahydrothieno[2,3-c]pyridin-4-yl)phenyl)-3-(trifluoromethyl)-1H pyrazol-1-yl) propanoate Step 1. tert-Butyl (S)-2-cyano-4-(2-(1-(3-ethoxy-3-oxopropyl)-3-(trifluoromethyl)-1H pyrazol-4-yl)phenyl)-4,7-dihydrothieno[2,3-c]pyridine-6(5H)-carboxylate. The compound was synthesized analogously to the general scheme, from ethyl 3-bromopropanoate, and was isolated as a viscous yellow oil (88 mg, 58%). MS (ESI) m/z 575.0 $[M+H]^+$.

Step 2. Ethyl (S,E)-3-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)propanoate. The compound was synthesized analogously to the general scheme, from tert-butyl 2-cyano-4-(2-(1-(3-ethoxy-3-oxopropyl)-3-(trifluoromethyl)-1H-pyrazol-4-yl)phenyl)-4,7-dihydrothieno[2,3-c]pyridine-6(5H)-carboxylate, and was isolated as an off-white to beige solid (19 mg, 21% over 2 steps). MS (ESI) m/z 586.3 $[M+H]^+$.

Example 171

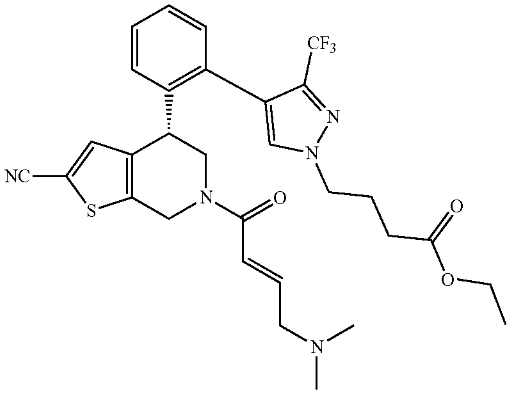 [SMILES: CCOC(=O)CCCn1cc(-c2ccccc2[C@@H]2CN(C(=O)/C=C/CN(C)C)Cc3sc(C#N)cc32)c(C(F)(F)F)n1]

Ethyl (S,E)-3-(4-(2-(2-cyano-6-(4-(dimethylamino) but-2-enoyl)-4,5,6,7-tetrahydrothieno[2,3-c]pyridin-4-yl)phenyl)-3-(trifluoromethyl)-1H pyrazol-1-yl) propanoate Step 1. tert-Butyl (S)-2-cyano-4-(2-(1-(4-ethoxy-4-oxobutyl)-3-(trifluoromethyl)-1H pyrazol-4-yl)phenyl)-4,7-dihydrothieno[2,3-c]pyridine-6(5H)-carboxylate. The compound was synthesized analogously to the general scheme, from ethyl 4-bromobutanoate, and was isolated as a viscous yellow oil (79 mg, 51%). MS (ESI) m/z 532.8 $[M-tBu+H]^+$.

Step 2. Ethyl (S,E)-3-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)propanoate. The compound was synthesized analogously to the general scheme, from tert-butyl (S)-2-cyano-4-(2-(1-(4-ethoxy-4-oxobutyl)-3-(trifluoromethyl)-1H-pyrazol-4-yl)phenyl)-4,7-dihydrothieno[2,3-c]pyridine-6(5H)-carboxylate, and was isolated as an off-white to beige solid (33 mg, 41% over 2 steps). MS (ESI) m/z 600.3 $[M+H]^+$.

Example 172

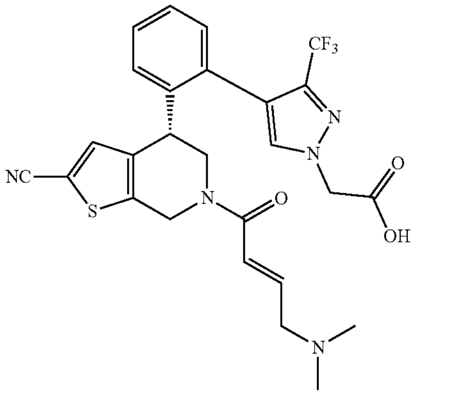 [SMILES: CN(C)C/C=C/C(=O)N1Cc2sc(C#N)cc2[C@H](c2ccccc2-c2cn(CC(=O)O)nc2C(F)(F)F)C1]

(S,E)-2-(4-(2-(2-Cyano-6-(4-(dimethylamino)but-2-enoyl)-4,5,6,7-tetrahydrothieno[2,3-c]pyridin-4-yl)phenyl)-3-(trifluoromethyl)-1H pyrazol-1-yl)acetic acid To a solution of ethyl (S,E)-2-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)acetate (22.2 mg, 0.04 mmol) in THF (500 μL) at RT was added LiOH·$H_2O$ (117 μL, 1 M in $H_2O$, 0.117 mmol). The mixture was stirred at RT and monitored by LC-MS until reaction completion. The volatiles were removed in vacuo, and the residue was dissolved in 1 N NaOH (250 μL) and MeOH (250 μL), filtered through a 0.45 μm membrane filter, and purified by reverse phase prep-HPLC (10→35% MeCN/$H_2O$ with 0.1% formic acid gradient). Compound was lyophilized overnight and recovered as an amorphous white solid (FA salt, 2.7 mg). MS (ESI) m/z 544.2 $[M+H]^+$.

Example 173

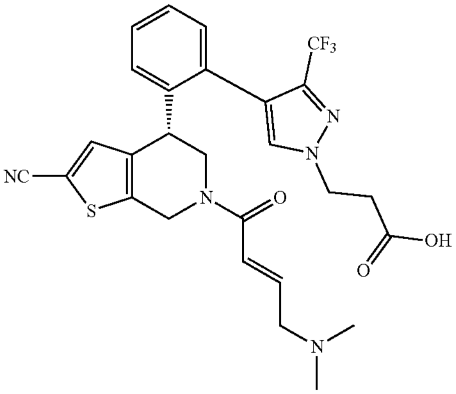 [SMILES: CN(C)C/C=C/C(=O)N1Cc2sc(C#N)cc2[C@H](c2ccccc2-c2cn(CCC(=O)O)nc2C(F)(F)F)C1]

(S,E)-3-(4-(2-(2-Cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)propanoic acid The compound was synthesized analogously to the general scheme from ethyl (S,E)-3-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)propanoate, and was isolated as an amorphous white solid (FA salt, 2.3 mg). MS (ESI) m/z 558.3 $[M+H]^+$.

Example 174

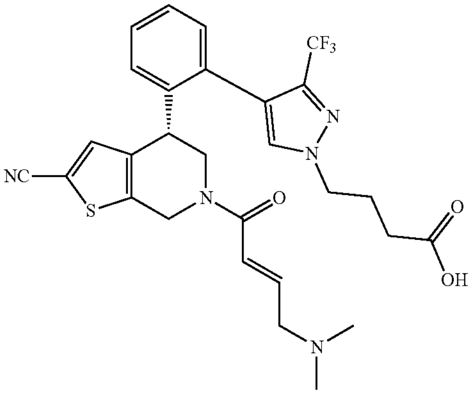 [SMILES: CN(C)C/C=C/C(=O)N1Cc2sc(C#N)cc2[C@H](c2ccccc2-c2cn(CCCC(=O)O)nc2C(F)(F)F)C1]

(S,E)-4-(4-(2-(2-Cyano-6-(4-(dimethylamino)but-2-enoyl)-4,5,6,7-tetrahydrothieno[2,3-c]pyridin-4-yl)phenyl)-3-(trifluoromethyl)-1H pyrazol-1-yl)butanoic acid The compound was synthesized analogously to the general scheme, from ethyl (S,E)-4-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)butanoate, and was isolated as an amorphous white solid (FA salt, 3.9 mg). MS (ESI) m/z 572.3 $[M+H]^+$.

Example 175

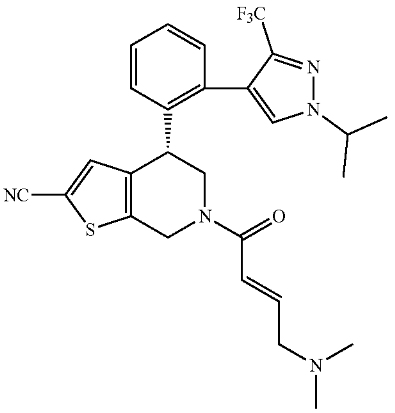 [SMILES: CC(C)n1cc(-c2ccccc2[C@@H]2CN(C(=O)/C=C/CN(C)C)Cc3sc(C#N)cc32)c(C(F)(F)F)n1]

Ethyl (S,E)-3-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H pyrazol-1-yl)propanoate Step 1. tert-Butyl (S)-2-cyano-4-(2-(1-isopropyl-3-(trifluoromethyl)-1H pyrazol-4-yl)phenyl)-4,7-dihydrothieno[2, 3-c]pyridine-6(5H)-carboxylate. The compound was synthesized analogously to the general scheme, from 4-bromo-1-isopropyl-3-(trifluoromethyl)-1H-pyrazole, and was isolated as a brown sticky solid (53 mg, quant.). MS (ESI) m/z 460.9 [M-tBu+H]$^+$.

Step 2. Ethyl (S,E)-3-(4-(2-(2-cyano-6-(4-(dimethylamino)but-2-enoyl)-4,5,6,7-tetrahydrothieno[2,3-c]pyridin-4-yl)phenyl)-3-(trifluoromethyl)-1H-pyrazol-1-yl)propanoate. The compound was synthesized analogously to the general scheme, from tert-butyl (S)-2-cyano-4-(2-(1-isopropyl-3-(trifluoromethyl)-1H-pyrazol-4-yl)phenyl)-4,7-dihydrothieno[2,3-c]pyridine-6(5H)-carboxylate, and isolated as a brown foam (33 mg, 61% over 2 steps). MS (ESI) m/z 528.3 [M+H]$^+$.

Example 176

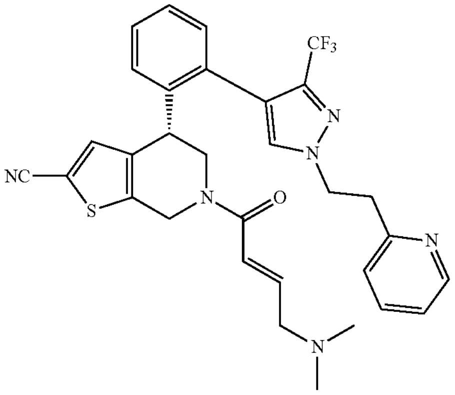 [SMILES: CN(C)C/C=C/C(=O)N1Cc2sc(C#N)cc2[C@H](c2ccccc2-c2cn(CCc3ccccn3)nc2C(F)(F)F)C1]

(S,E)-6-(4-(Dimethylamino)but-2-enoyl)-4-(2-(1-(2-(pyridin-2-yl)ethyl)-3-(trifluoromethyl)-1H pyrazol-4-yl)phenyl)-4,5,6,7-tetrahydrothieno[2,3-c]pyridine-2-carbonitrile Step 1. tert-Butyl (S)-2-cyano-4-(2-(1-(2-(pyridin-2-yl)ethyl)-3-(trifluoromethyl)-1H-pyrazol-4-yl)phenyl)-4,7-dihydrothieno[2,3-c]pyridine-6(5H)-carboxylate. tert-Butyl (S)-2-cyano-4-(2-(4,4,5,5-tetramethyl-1,3,2-dioxaborolan-2-yl)phenyl)-4,7-dihydrothieno[2,3-c]pyridine-6(5H)-carboxylate (50 mg, 1.1 eq.), 2-(2-(4-bromo-3-(trifluoromethyl)-1H-pyrazol-1-yl)ethyl)pyridine (31 mg, 1 eq.), Pd(dppf)$Cl_2$ (7 mg, 10 mol %), and $K_2CO_3$ (40 mg, 3 eq.) were degassed 5× with Ar. Dioxane (0.9 mL) and water (0.1 mL) were added, degassed 2× with Ar, and the reaction was heated to 80° C. and stirred overnight. The mixture was cooled to RT, diluted with EA, washed with saturated $NH_4Cl_{(aq)}$, dried over $Na_2SO_4$, and concentrated in vacuo. Purified residue by flash chromatography ($SiO_2$, 40% EA in hexanes isocratic) and recovered the compound as a brown sticky solid (20 mg, 35%). MS (ESI) m/z 580.0 [M+H]$^+$.

Step 2. (S,E)-6-(4-(Dimethylamino)but-2-enoyl)-4-(2-(1-(2-(pyridin-2-yl)ethyl)-3-(trifluoromethyl)-1H-pyrazol-4-yl)phenyl)-4,5,6,7-tetrahydrothieno[2,3-c]pyridine-2-carbonitrile. The compound was synthesized analogously to the general scheme, from tert-butyl (S)-2-cyano-4-(2-(1-(2-(pyridin-2-yl)ethyl)-3-(trifluoromethyl)-1H-pyrazol-4-yl)phenyl)-4,7-dihydrothieno[2,3-c]pyridine-6(5H)-carboxylate, and was isolated as an amorphous beige solid (12 mg, 61% over 2 steps). MS (ESI) m/z 591.3 [M+H]$^+$.

Example 177

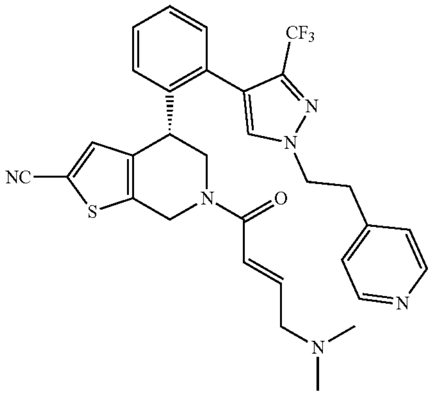 [SMILES: CN(C)C/C=C/C(=O)N1Cc2sc(C#N)cc2[C@H](c2ccccc2-c2cn(CCc3ccncc3)nc2C(F)(F)F)C1]

(S,E)-6-(4-(Dimethylamino)but-2-enoyl)-4-(2-(1-(2-(pyridin-4-yl)ethyl)-3-(trifluoromethyl)-1H pyrazol-4-yl)phenyl)-4,5,6,7-tetrahydrothieno[2,3-c]pyridine-2-carbonitrile Step 1. tert-Butyl (S)-2-cyano-4-(2-(1-(2-(pyridin-4-yl)ethyl)-3-(trifluoromethyl)-1H-pyrazol-4-yl)phenyl)-4,7-dihydrothieno[2,3-c]pyridine-6(5H)-carboxylate. The compound was synthesized analogously to the general scheme, from 4-(2-(4-bromo-3-(trifluoromethyl)-1H-pyrazol-1-yl)ethyl)pyridine, and isolated as a sticky brown solid (41 mg, 81%). MS (ESI) m/z 580.0 [M+H]$^+$.

Step 2. (S,E)-6-(4-(Dimethylamino)but-2-enoyl)-4-(2-(1-(2-(pyridin-2-yl)ethyl)-3-(trifluoromethyl)-1H-pyrazol-4-yl)phenyl)-4,5,6,7-tetrahydrothieno[2,3-c]pyridine-2-carbonitrile. The compound was synthesized analogously to the general scheme, from tert-butyl (S)-2-cyano-4-(2-(1-(2-(pyridin-2-yl)ethyl)-3-(trifluoromethyl)-1H-pyrazol-4-yl)phenyl)-4,7-dihydrothieno[2,3-c]pyridine-6(5H)-carboxylate, and was isolated as an amorphous beige solid (12 mg, 61% over 2 steps). MS (ESI) m/z 591.3 [M+H]$^+$.

Example 178

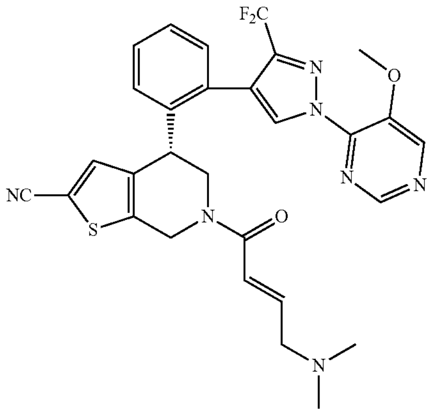

(S,E)-6-(4-(dimethylamino)but-2-enoyl)-4-(2-(1-(5-methoxypyrimidin-4-yl)-3-(trifluoromethyl)-1H pyrazol-4-yl)phenyl)-4,5,6,7-tetrahydrothieno[2,3-c] pyridine-2-carbonitrile Step 1. tert-Butyl (S)-2-cyano-4-(2-(1-(5-methoxypyrimidin-4-yl)-3-(trifluoromethyl)-1H-pyrazol-4-yl)phenyl)-4,7-dihydrothieno[2,3-c]pyridine-6(5H)-carboxylate. The compound was synthesized analogously to the general scheme, from 4-chloro-5-methoxypyrimidine, and was isolated as a clear oil (9 mg, 15%). MS (ESI) m/z 582.9 $[M+H]^+$.

Step 2. (S,E)-6-(4-(Dimethylamino)but-2-enoyl)-4-(2-(1-(5-methoxypyrimidin-4-yl)-3-(trifluoromethyl)-1H-pyrazol-4-yl)phenyl)-4,5,6,7-tetrahydrothieno[2,3-c]pyridine-2-carbonitrile. The compound was synthesized analogously to that above, from tert-butyl (S)-2-cyano-4-(2-(1-(5-methoxypyrimidin-4-yl)-3-(trifluoromethyl)-1H-pyrazol-4-yl)phenyl)-4,7-dihydrothieno[2,3-c]pyridine-6(5H)-carboxylate, and was isolated as a lyophilized white solid (0.5 FA salt, 4.6 mg, 51% over 2 steps). MS (ESI) m/z 594.3 $[M+H]^+$.

Example 179

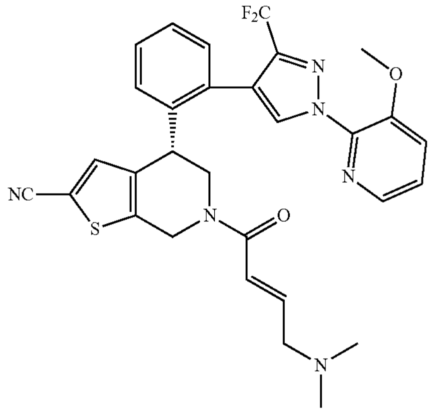

(S,E)-6-(4-(Dimethylamino)but-2-enoyl)-4-(2-(1-(5-methoxypyrimidin-4-yl)-3-(trifluoromethyl)-1H-pyrazol-4-yl)phenyl)-4,5,6,7-tetrahydrothieno[2,3-c] pyridine-2-carbonitrile Step 1. tert-butyl (S)-2-cyano-4-(2-(1-(3-methoxypyridin-2-yl)-3-(trifluoromethyl)-1H-pyrazol-4-yl)phenyl)-4,7-dihydrothieno[2,3-c]pyridine-6(5H)-carboxylate. The compound was synthesized analogously to the general scheme, from 2-(4-bromo-3-(trifluoromethyl)-1H-pyrazol-1-yl)-3-methoxypyridine, and was isolated as an opaque light-yellow waxy solid (42 mg, 90%). MS (ESI) m/z 581.9 $[M+H]^+$.

Step 2. (S,E)-6-(4-(Dimethylamino)but-2-enoyl)-4-(2-(1-(5-methoxypyrimidin-4-yl)-3-(trifluoromethyl)-1H-pyrazol-4-yl)phenyl)-4,5,6,7-tetrahydrothieno[2,3-c]pyridine-2-carbonitrile. The compound was synthesized analogously to the general scheme, from tert-butyl (S)-2-cyano-4-(2-(1-(3-methoxypyridin-2-yl)-3-(trifluoromethyl)-1H-pyrazol-4-yl) phenyl)-4,7-dihydrothieno[2,3-c]pyridine-6(5H)-carboxylate, and was isolated as a lyophilized white solid (0.33 FA salt, 19 mg, 43% over 2 steps). MS (ESI) m/z 593.3 $[M+H]^+$.

Other substituted pyrazole intermediates are prepared as follows:

4-(2-Bromo-4-fluorophenyl)-1-ethyl-3-(trifluoromethyl)-1H-pyrazole. The compound was synthesized analogously as described above from 2-bromo-4-fluoro-1-iodobenzene, and was isolated as a colorless oil (57%). MS (ESI) m/z 337.0 $[M+H]^+$.

4-(2-Bromocyclopent-1-en-1-yl)-1-ethyl-3-(trifluoromethyl)-1H pyrazole. The compound was synthesized analogously as described above from 1,2-di bromocyclopent-1-ene, and was isolated as a colorless liquid (35%). MS (ESI) m/z 309.0 $[M+H]^+$.

4-(2-Bromocyclohex-1-en-1-yl)-1-ethyl-3-(trifluoromethyl)-1H pyrazole. The compound was synthesized analogously as described above from 1,2-dibromocyclohex-1-ene, and was isolated as a light-purple solid (17%). MS (ESI) m/z 324.0 $[M+H]^+$.

4-(2-Bromo-4,6-difluorophenyl)-1-ethyl-3-(trifluoromethyl)-1H pyrazole. The compound was synthesized analogously as described above from 1-bromo-3,5-difluoro-2-iodobenzene, and isolated as a light-yellow solid (44%). MS (ESI) m/z 355.0 $[M+H]^+$.

4-(6-Bromo-2,3-difluorophenyl)-1-ethyl-3-(trifluoromethyl)-1H pyrazole. The compound was synthesized analogously as described above from 1-bromo-3,4-difluoro-2-iodobenzene, and isolated as a pale-yellow oil (23%). MS (ESI) m/z 355.0 $[M+H]^+$.

3-Bromo-2-(1-ethyl-3-(trifluoromethyl)-1H pyrazol-4-yl) benzonitrile. The compound was synthesized analogously as described above from 3-bromo-2-iodobenzonitrile, and isolated as a pale-yellow solid (40%). MS (ESI) m/z 344.0 $[M+H]^+$.

4-(6-Bromo-2-chloro-3-fluorophenyl)-1-ethyl-3-(trifluoromethyl)-1H-pyrazole. The compound was synthesized analogously as described above from 1-bromo-3-chloro-4-fluoro-2-iodobenzene, and isolated as an off-white solid (32%). MS (ESI) m/z 371.0 $[M+H]^+$.

4-(2-Bromo-6-chloro-4-fluorophenyl)-1-ethyl-3-(trifluoromethyl)-1H-pyrazole. The compound was synthesized analogously as described above from 1-bromo-3-chloro-5-fluoro-2-iodobenzene, and isolated as a pale-purple solid (23%). MS (ESI) m/z 371.0 $[M+H]^+$.

2-Bromo-3-fluoro-4-((4-methoxybenzyl)oxy)-1-nitrobenzene. To a stirred yellow solution of 2-bromo-3,4-difluoro-1-nitrobenzene (2.38 g, 0.01 mol) in ACN (6 mL) was added 4-methoxybenzylalcohol (1.38 g, 0.01 mol) followed by KOH (0.84 g, 0.015 mol) at RT. The resulting suspension was stirred at RT overnight. The dark suspension was quenched with cold water and a precipitate formed. The solid was collected by filtration, washed with more cold water, and dried under reduced pressure to give the desired 2-bromo-3-fluoro-4-((4-methoxybenzyl)oxy)-1-nitrobenzene as a light brown solid (3.3982 g, 96%). This was used directly in the next step without further purification.

1-Ethyl-4-(2-fluoro-3-((4-methoxybenzyl)oxy)-6-nitrophenyl)-3-(trifluoromethyl)-1H pyrazole. The compound was synthesized analogously as described above, from 2-bromo-3-fluoro-4-((4-methoxybenzyl)oxy)-1-nitrobenzene, and isolated as a pale-yellow solid (69%). MS (ESI) m/z 440.1 $[M+H]^+$.

2-(1-Ethyl-3-(trifluoromethyl)-1H pyrazol-4-yl)-3-fluoro-4-((4-methoxybenzyl)oxy)aniline. To a mixture of 2-bromo-3-fluoro-4-((4-methoxybenzyl)oxy)-1-nitrobenzene (0.98 g, 0.002 mol) in EtOH (12 mL) and water (2 mL) was added $NH_4Cl$ (0.36 g, 0.006 mol) and iron powder (0.38 g, 0.006 mol) and the mixture was heated to reflux for 3 h and then cooled. The resulting dark mixture was filtered through a column of Celite®, washed with EtOH (3×5 mL), and the combined filtrates were concentrated in vacuo. The residue was dissolved in EA (20 mL) and washed with brine. The separated organic phase was dried ($Na_2SO_4$), filtered, and concentrated to yield the desired aniline (0.81 g, 99%) as a yellow oil. MS (ESI) m/z 410.1 $[M+H]^+$. This crude material was used in the next step without further purification.

3-(1-Ethyl-3-(trifluoromethyl)-1H pyrazol-4-yl)-2-fluoro-4-iodophenol. To the crude aniline (0.81 g, 1.98 mmol) isolated from above was added 1.0N HCl (aq, 15 mL) and the suspension was added a solution of $NaNO_2$ (0.164 g, 2.38 mmol) in $H_2O$ (2 mL) slowly at 0° C. The resulting dark mixture was stirred for additional 1 h then a solution of KI (0.99 g, 5.94 mmol) in $H_2O$ (5 mL) was introduced. The mixture was warmed to RT and stirred for another 1 h. The sticky mixture was diluted with EA (50 mL) then quenched with saturated sodium thiosulfate (~20 mL). The separated aqueous layer was extracted with EA (3×50 mL) and the organic phases were washed with brine, dried over $Na_2SO_4$, filtered, and concentrated. The residue was purified by a flash column chromatography ($SiO_2$, 0→20→40% EA in hexanes) to yield a semi-pure material (contaminated with ~30% of 1-ethyl-4-(2-fluoro-6-iodo-3-((4-methoxybenzyl)oxy)phenyl)-3-(trifluoromethyl)-1H-pyrazole). The material was then treated with TFA (0.5 mL) in DCM (5 mL) at RT for 30 min and concentrated. The residue was dissolved in DCM (50 mL) and washed with saturated $NaHCO_{3(aq)}$ and brine. The separated organic layer was dried over $Na_2SO_4$, filtered, and concentrated to afford 3-(1-ethyl-3-(trifluoromethyl)-1H-pyrazol-4-yl)-2-fluoro-4-iodophenol as a pale-yellow solid (0.5258 g, 66%). MS (ESI) m/z 401.0 $[M+H]^+$.

4-Bromo-3-iodo-2-((4-methoxybenzyl)oxy)pyridine. To a solution of 4-bromo-2-chloro-3-iodopyridine (1.495 g, 4.7 mmol) in THF (15 mL) was added slowly potassium tert-butoxide (1.0 M in THF, 5.9 mL) at −10 00. The resulting heterogeneous mixture was stirred for 1 h before the mixture was diluted with EA and quenched with saturated $NH_4Cl$ aqueous solution (15 mL each). The separated aqueous layer was extracted with EA (3×15 mL) and the organic phases were washed with brine, dried over $Na_2SO_4$, filtered, and concentrated. The residue was purified by a flash column chromatography ($SiO_2$, 0→5→10% EA in hexanes) to yield the compound as a white crystalline solid (1.29 g, 66%). MS (ESI) m/z 419.9 $[M+H]^+$.

4-Bromo-3-(1-ethyl-3-(trifluoromethyl)-1H pyrazol-4-yl)-2-((4-methoxybenzyl)oxy)pyridine. The compound was synthesized analogously as described above from 4-bromo-3-iodo-2-((4-methoxybenzyl)oxy)pyridine, and isolated as a colorless sticky oil (64%, based on the recovered starting material). MS (ESI) m/z 456.1 $[M+H]^+$.

3-Bromo-2-(1-ethyl-3-(trifluoromethyl)-1H pyrazol-4-yl) phenol. The compound was synthesized analogously as described above from 3-bromo-2-iodophenol, and isolated as a yellow solid (36%). MS (ESI) m/z 336.1 $[M+H]^+$.

3-Bromo-2-(1-ethyl-3-(trifluoromethyl)-1H-pyrazol-4-yl)-6-methylphenol. In a sealable reaction vessel was charged paraformaldehyde (0.154 g, 5.1 mmol), magnesium (II) chloride (0.33 g, 3.4 mmol), followed by THF (10 mL) and $Et_3N$ (0.47 mL, 3.4 mmol). The suspension was stirred at RT for 30 min, then 3-bromo-2-(1-ethyl-3-(trifluoromethyl)-1H-pyrazol-4-yl)phenol (0.57 g, 1.7 mmol) in THF (5 mL) was introduced. The reaction vessel was screw-sealed and heated at 90° C. overnight then cooled. The mixture was diluted with ice-water and EA (10 mL each). The separated aqueous layer was extracted with EA (3×10 mL) and the organic phases were washed with brine, dried over $Na_2SO_4$, filtered, and concentrated. The crude bright yellow oil was used in the next reaction without further purification.

4-Bromo-3-(1-ethyl-3-(trifluoromethyl)-1H pyrazol-4-yl)-2-hydroxybenzaldehyde oxime. The crude aldehyde isolated above was added EtOH-THF (5 mL each) followed by solid $NH_4OH{\cdot}HCl$ (0.142 g, 2.0 mmol). The mixture was cooled 0° C. and a solution of NaOH (88 mg, 2.2 mmol) in water (5 mL) was slowly added. The mixture was warmed to RT and stirred overnight. The resulting suspension was added to water-ice mixture and stirred for 30 min. The precipitate was collected, washed with more water, and dried in vacuo to give a crude off-white solid which was used in the next reaction without further purification.

6-Bromo-7-(1-ethyl-3-(trifluoromethyl)-1H pyrazol-4-yl) benzo[d]isoxazole. To a solution of $PPh_3$ (0.54 g, 2.04 mmol) in DCM (10 mL) was added DDQ (0.46 g, 2.04 mmol) and the resulting dark mixture was stirred at RT for 2 min followed by introduction of a solution of crude 4-bromo-3-(1-ethyl-3-(trifluoromethyl)-1H-pyrazol-4-yl)-2-hydroxybenzaldehyde oxime in DCM (5 mL). The resulting brown solution was stirred at RT for 30 min and then concentrated. The residue was purified by a flash column chromatography ($SiO_2$, 0→20→40% EA in hexanes) to yield the compound as a white crystalline solid (0.3412 g, 56% in three steps). MS (ESI) m/z 361.1 $[M+H]^+$.

4-Bromo-3-(1-ethyl-3-(trifluoromethyl)-1H pyrazol-4-yl) aniline. To a stirred mixture of 4-bromo-3-iodoaniline (0.30 g, 1.09 mmol), (1-ethyl-3-(trifluoromethyl)-1H-pyrazol-4-yl)boronic acid (0.25 g, 1.19 mmol), Pd(dppf)$C_{1-2}$ (0.08 g, 0.11 mmol), and $K_2CO_3$ (0.46 g, 3.29 mmol) in a sealable reaction vessel was added dioxane and water (4:1, 11 mL total) via syringe under argon. The reaction vessel was screw-sealed and heated at 90° C. for 3 h. The mixture was cooled and diluted with EA (10 mL), washed with saturated $NaHCO_{3(aq)}$. The organic layer was dried over $MgSO_4$, filtered, and concentrated in vacuo. The residue was purified by a flash column chromatography ($SiO_2$, 0→100% EA in hexanes) to yield the compound as a brown solid (0.2762 g, 76%). MS (ESI) m/z 335.8 $[M+H]^+$.

5-Bromo-6-(1-ethyl-3-(trifluoromethyl)-1H pyrazol-4-yl) pyridin-2-amine. The compound was synthesized analogously as described above from 5-bromo-6-iodopyridin-2-amine, and isolated as a colorless oil (68%). MS (ESI) m/z 335.0 $[M+H]^+$.

(4-Bromo-3-(1-ethyl-3-(trifluoromethyl)-1H-pyrazol-4-yl)phenyl)methanol

Methyl 4-bromo-3-(1-ethyl-3-(trifluoromethyl)-1H pyrazol-4-yl)benzoate. The compound was synthesized analogously as described above from methyl 4-bromo-3-iodobenzoate, and isolated as a yellow solid (46%). MS (ESI) m/z 376.8 $[M]^+$.

(4-Bromo-3-(1-ethyl-3-(trifluoromethyl)-1H-pyrazol-4-yl)phenyl)methanol. To a stirred mixture of methyl 4-bromo-3-(1-ethyl-3-(trifluoromethyl)-1H-pyrazol-4-yl) benzoate (0.14 g, 0.37 mmol) in THF (4 mL) cooled to 0° C. was added $LiAlH_4$ (2.0 M in THF, 0.18 mL, 0.37 mmol) dropwise. The mixture was warmed to RT and stirred for 1 h. The reaction was quenched by the Fieser method. An addition of water (1 mL per g of $LiAlH_4$) was made then 15% NaOH (1 mL per g of $LiAlH_4$) and finally water (3 mL per g of $LiAlH_4$). The mixture was dried with $MgSO_4$, filtered, and concentrated in vacuo. The residue was purified by a flash column chromatography ($SiO_2$, 0→100% EA in hexanes) to yield the compound as a clear oil (79.2 mg, 61%). MS (ESI) m/z 350.8 [M+H]+.

3-Bromo-4-(1-ethyl-3-(trifluoromethyl)-1H pyrazol-4-yl) aniline. The compound was synthesized analogously as described above from 3-bromo-4-iodoaniline, and isolated as a colorless oil (42%). MS (ESI) m/z 335.7 $[M+H]^+$.

1'-Ethyl-2-methyl-3'-(trifluoromethyl)-1'H, 2H-3,4'-bipyrazole The titlecompound was synthesized analogously as described above from 5-bromo-1-methyl-1H-pyrazole, and isolated as a colorless oil (76%). MS (ESI) m/z 245.0 $[M+H]^+$.

4-Bromo-1'-ethyl-2-methyl-3'-(trifluoromethyl)-1'H, 2H-3,4'-bipyrazole. To a stirred mixture of 1'-ethyl-2-methyl-3'-(trifluoromethyl)-1'H, 2H-3,4'-bipyrazole (0.37 g, 1.32 mmol) in $CHCl_3$ (13 mL) at 0° C. was added $Br_2$ (67 μL, 1.32 mmol) to the reaction. The reaction was warmed to RT and stirred for 2 h. The mixture was washed with sat. sodium thiosulfate$_{(aq)}$, extracted with DCM (5 mL×3), and the organic layers were combined, dried over $MgSO_4$, filtered, and concentrated in vacuo. The residue was purified by a flash column chromatography ($SiO_2$, 0→100% EA in hexanes) to yield the compound as an off-white oil (0.3763 g, 88%). MS (ESI) m/z 324.8 $[M+H]^+$.

4-Bromo-3-(1-ethyl-3-(trifluoromethyl)-1H pyrazol-4-yl) thiophene-2-carbaldehyde. The compound was synthesized analogously as described from above 3,4-dibromothiophene-2-carbaldehyde, and isolated as a colorless oil (75%). MS (ESI) m/z 352.8 [M]+.

(4-Bromo-3-(1-ethyl-3-(trifluoromethyl)-1H pyrazol-4-yl)thiophen-2-yl)methanol. To a stirred mixture of 4-bromo-3-(1-ethyl-3-(trifluoromethyl)-1H-pyrazol-4-yl)thiophene-2-carbaldehyde (0.35 g, 0.99 mmol) in MeOH (10 mL) at RT was added $NaBH_4$ (37.0 mg, 0.99 mmol) and the mixture was stirred for 1 h. The mixture was diluted with DCM (10 mL), washed with water and separated. The organic layer was dried over $MgSO_4$, filtered, and concentrated in vacuo to yield the compound as a brown oil (0.3658 g, quant.). MS (ESI) m/z 355.0 $[M]^+$.

4-(4-Bromo-2-methylthiophen-3-yl)-1-ethyl-3-(trifluoromethyl)-1H-pyrazole. To a stirred mixture of (4-bromo-3-(1-ethyl-3-(trifluoromethyl)-1H-pyrazol-4-yl)thiophen-2-yl)methanol (0.32 g, 0.89 mmol) in TFA(6 mL) at RT was added $Et_3SiH$ (3 mL, 18.7 mmol) and stirred for 1 h. The mixture was diluted with DCM (10 mL) washed with sat. $NaHCO_{3(aq)}$ and separated. The organic layer was dried over $MgSO_4$, filtered, and concentrated in vacuo. The residue was purified by a flash column chromatography ($SiO_2$, 0→100% EA in hexanes) to yield the compound as a colorless oil (0.4247 g, 99%). MS (ESI) m/z 340.8 $[M+H]^+$.

2-(1-Ethyl-3-(trifluoromethyl)-1H pyrazol-4-yl)-3-methylaniline. To a stirred mixture of 2-iodo-3-methylaniline (0.50 g, 2.15 mmol), (1-ethyl-3-(trifluoromethyl)-1H-pyrazol-4-yl)boronic acid (0.54 g, 2.58 mmol), RuPhos Pd G3 (0.18 g, 0.22 mmol), and $K_2CO_3$ (0.89 g, 6.44 mmol) in a sealable reaction vessel was added dioxane and water (4:1, 9 mL total) via syringe under argon. The reaction vessel was screw-sealed and heated at 80° C. for 16 h. The mixture was cooled and diluted with EA (10 mL), washed with saturated $NaHCO_{3(aq)}$. The organic layer was dried over $MgSO_4$, filtered, and concentrated in vacuo. The residue was purified by a flash column chromatography ($SiO_2$, 0→100% EA in hexanes) to yield the compound as an off-white solid (0.3521 g, 61%). MS (ESI) m/z 270.0 $[M+H]^+$.

1-Ethyl-4-(2-iodo-6-methylphenyl)-3-(trifluoromethyl)-1H-pyrazole. To a stirred mixture of 2-(1-ethyl-3-(trifluoromethyl)-1H-pyrazol-4-yl)-3-methylaniline (0.32 g, 1.18 mmol) and p-TsOH hydrate (0.34 g, 1.77 mmol) in EtOH (5 mL) at 0° C. was added tert-butyl nitrite (0.21 mL, 1.77 mmol) and the reaction was stirred for 1 h at 0° C. Tetrabutylammonium iodide (0.65 g, 1.77 mmol) and a drop of water was added to the mixture. The mixture was heated to 70° C. and stirred for 3 h. The mixture was diluted with DCM (10 mL), washed with sat. $NaHCO_{3(aq)}$ (15 mL) and separated. The organic layer was dried over $MgSO_4$, filtered, and concentrated in vacuo. The residue was purified by a flash column chromatography ($SiO_2$, 0→100% EA in hexanes) to yield the compound as an orange oil (0.2915 g, 65%). MS (ESI) m/z 381.1 $[M+H]^+$.

3-Chloro-2-(1-ethyl-3-(trifluoromethyl)-1H pyrazol-4-yl) aniline. The compound was synthesized analogously as described above from 3-chloro-2-iodoaniline, and isolated as a colorless oil (74%). MS (ESI) m/z 289.9 [M]+.

4-(2-Chloro-6-iodophenyl)-1-ethyl-3-(trifluoromethyl)-1H-pyrazole. The compound was synthesized analogously as described above 3-chloro-2-(1-ethyl-3-(trifluoromethyl)-1H-pyrazol-4-yl)aniline, and isolated as a colorless oil (67%). MS (ESI) m/z 401.1 $[M+H]^+$.

tert-Butyl (3-bromo-2-fluoropyridin-4-yl)carbamate. To a stirred mixture of 3-bromo-2-fluoropyridin-4-amine (1.00 g, 5.24 mmol), $Et_3N$ (2.2 mL, 15.7 mmol) in DCM (52 mL) at RT was added $Boc_2O$ (2.4 mL, 10.5 mmol) and the reaction was stirred for 16 h. The mixture was washed with 1 M citric acid (50 mL). The organic layer was separated and washed with sat. $NaHCO_{3(aq)}$ (50 mL) and separated. The organic layer was, dried over $MgSO_4$, and concentrated in vacuo. The residue was purified by a flash column chromatography ($SiO_2$, 0→100% EA in hexanes) to yield the compound as a pale-yellow oil (1.3908 g, 91%). MS (ESI) m/z 292.8 $[M+H]^+$.

tert-Butyl (3-(1-ethyl-3-(trifluoromethyl)-1H pyrazol-4-yl)-2-fluoropyridin-4-yl)carbamate. The compound was synthesized analogously as described above from tert-butyl (3-bromo-2-fluoropyridin-4-yl)carbamate, and isolated as a yellow oil (25%). MS (ESI) m/z 375.0 $[M]^+$.

3-(1-Ethyl-3-(trifluoromethyl)-1H pyrazol-4-yl)-2-fluoro-4-iodopyridine. To a stirred mixture of tert-butyl (3-(1-ethyl-3-(trifluoromethyl)-1H-pyrazol-4-yl)-2-fluoropyridin-4-yl)carbamate (0.45 g, 1.20 mmol) in $H_2SO_4$ (15 mL) at 0° C. was added $NaNO_2$ (249 mg, 3.60 mmol) and stirred for 30 min at 0° C. KI (0.60 g, 3.60 mmol) was added to the mixture and the reaction was stirred for 3 h at 0° C. The mixture was diluted with DCM (25 mL), washed with sat. $NaHCO_{3(aq)}$ (50 mL) and extracted with DCM (25 mL×3) and separated. The organic layers were combined, dried over $MgSO_4$, and concentrated in vacuo. The residue was purified by a flash column chromatography ($SiO_2$, 0→100% EA in hexanes) to yield the target compound as a yellow oil (0.1778 g, 38%). MS (ESI) m/z 385.8 $[M]^+$.

4-Bromo-3-(1-ethyl-3-(trifluoromethyl)-1H-pyrazol-4 yl)phenol. A mixture of 4-bromo-3-iodophenol (300 mg, 1.0 mmol), (1-ethyl-3-(trifluoromethyl)-1H-pyrazol-4-yl)boronic acid (210 mg, 1.0 mmol), and $K_3PO_4$ (640 mg, 3.0 mmol) in dioxane-water (10:1, 10 mL total) was deoxygenated with bubbling argon gas for 10 min, then $Pd(dppf)Cl_2$ (73 mg, 0.10 mmol) was added. The resulting mixture stirred vigorously at 80° C. for 18 h. The mixture was filtered through Celite® and concentrated in vacuo. The resulting residue was purified by flash column chromatography ($SiO_2$, 0→60→100% EA in hexanes) to yield the compound as an off-white solid (0.19 g, 56%).

2-Bromo-3-(1-ethyl-3-(trifluoromethyl)-1H pyrazol-4-yl) phenol. The compound was synthesized analogously as described above from 2-bromo-3-iodophenol and isolated as an off-white solid (54%).

4-(2-Bromo-4-methoxyphenyl)-1-ethyl-3-(trifluoromethyl)-1H pyrazole. The compound was synthesized analogously as described above from 2-bromo-1-iodo-4-methoxybenzene and isolated as a red-purple oil (49%).

4-(2-Bromo-6-methoxyphenyl)-1-ethyl-3-(trifluoromethyl)-1H pyrazole. The compound was synthesized analogously as described above from 1-bromo-2-iodo-3-methoxybenzene and isolated as a tan solid (41%).

2-(1-Ethyl-3-(trifluoromethyl)-1H pyrazol-4-yl)-3-fluoroaniline. The compound was synthesized analogously as described above from 2-bromo-3-fluoroaniline and isolated as a dark orange oil (70%). MS (ESI) m/z 274.1 $[M+H]^+$.

3-Bromo-4-(1-ethyl-3-(trifluoromethyl)-1H pyrazol-4-yl) phenol. A solution of 4-(2-bromo-4-methoxyphenyl)-1-ethyl-3-(trifluoromethyl)-1H-pyrazole (280 mg, 0.81 mmol) in DCM (2.7 mL) was cooled to 0° C., then a solution of $BBr_3$ in DCM (1 M, 1.6 mL, 1.6 mmol) was added dropwise. After 2.5 h, the reaction was quenched by adding sat. aq. $Na_2S_2O_3$ (3 mL), followed by water (2 mL) and DCM (3 mL). The resulting mixture was stirred at RT for 30 min, then the layers were partitioned and the aqueous phase was extracted with DCM (2×5 mL). The combined organic extracts were washed with brine (20 mL), dried over anhydrous $MgSO_4$, filtered, and concentrated in vacuo. The resulting residue was purified by flash column chromatography ($SiO_2$, 0→60% EA in hexanes) to yield the compound as a peach-colored semi-solid (210 mg, 78%).

4-Bromo-3-iodo-N-methylbenzamide. To a stirred solution of 4-bromo-3-iodobenzoic acid (327 mg, 1 mmol) in DMF (5 mL) was added DIPEA (348 μL, 2 mmol) and HATU (399 mg, 1.05 mmol) and stirred at RT for 30 min. To the solution was added methylamine (525 μL, 2 M in THF, 1.05 mmol) and stirred for 1 h. The resulting solution was treated with water and extracted with EA (×3). The combined organic layers were washed with saturated $NH_4Cl_{(aq)}$, brine, dried over $Na_2SO_4$, and concentrated. The crude residue was purified by flash chromatography ($SiO_2$, 40% EA in hexanes isocratic) to yield the compound as a white solid (214 mg, 63%). MS (ESI) m/z 339.9, 341.9 $[M+H]^+$.

4-Bromo-3-(1-ethyl-3-(trifluoromethyl)-1H pyrazol-4-yl)-N-methylbenzamide. To a mixture of 4-bromo-3-iodo-N-methylbenzamide (214.4 mg, 0.63 mmol), (1-ethyl-3-(trifluoromethyl)-1H-pyrazol-4-yl)boronic acid (131.2 mg, 0.63 mmol), $Pd(dppf)C_{1-2}$ (46 mg, 0.063 mmol), and $K_2CO_3$ (174 mg, 1.26 mmol) (degassed 5×) was added dioxane (2.7 mL) and water (0.3 mL) subsequently. The suspension was degassed 2× with argon and heated to 80° C. overnight. The mixture was cooled to RT and diluted with EA. The combined organic layers were with saturated $NH_4Cl_{(aq)}$, dried over $Na_2SO_4$, filtered, and concentrated. The crude residue was purified by flash chromatography ($SiO_2$, 0→100% EA in hexanes gradient) to yield the compound as a beige solid (126 mg, 53%). MS (ESI) m/z 375.8, 377.8 $[M+H]^+$.

4-Bromo-3-(1-ethyl-3-(trifluoromethyl)-1H-pyrazol-4 yl)benzonitrile. The compound was synthesized analogously as described above from 4-bromo-3-iodobenzonitrile, and isolated as a light brown crystalline solid (157 mg, 45%). MS (ESI) m/z 343.8, 345.8 $[M+H]^+$.

4-(2-Bromo-5-methylphenyl)-1-ethyl-3-(trifluoromethyl)-1H-pyrazole. The compound was synthesized analogously as described above from 1-bromo-2-iodo-4-methylbenzene, and isolated as an off-white crystalline solid (175 mg, 53%). MS (ESI) m/z 332.8, 334.8 $[M+H]^+$.

4-(2-Bromo-5-fluorophenyl)-1-ethyl-3-(trifluoromethyl)-1H-pyrazole. The compound was synthesized analogously as described above from 1-bromo-4-fluoro-2-iodobenzene, and isolated as a light-yellow oil (183 mg, 54%). MS (ESI) m/z 336.8, 338.8 $[M+H]^+$.

4-(2-Bromo-5-chlorophenyl)-1-ethyl-3-(trifluoromethyl)-1H pyrazole. The compound was synthesized analogously as described above from 1-bromo-4-chloro-2-iodobenzene, and isolated as colorless crystalline solid (203 mg, 57%). MS (ESI) m/z 352.8, 354.8, 356.8 $[M+H]^+$.

Methyl 4-bromothieno[2,3-c]pyridine-2-carboxylate. A mixture of 3,5-dibromo-isonicotinaldehyde (30.00 g, 114 mmol), methyl 2-mercaptoacetate (13.25 g, 125 mmol) and cesium carbonate (74.00 g, 228 mmol) in THE (350 mL) was heated to 60° C. and stirred overnight. Cooling to RT, water (500 mL) was added, and the mixture was extracted with EA (400 mL×3). The combined organic phases were washed with brine, dried over $Na_2SO_4$, and concentrated. The residue was purified by column chromatography (PE: EA=5:1) to afford the molecule (23 g, 74% yield) as a white solid. MS (ESI) m/z 271.8 $[M+H]^+$.

4-Bromothieno[2,3-c]pyridine-2-carboxamide. A mixture of methyl 4-bromothieno[2,3-c]pyridine-2-carboxylate (18.00 g, 66.40 mmol) and a solution of $NH_3$ in MeOH (300 ml) was stirred at 75° C. overnight in a 500 mL of sealed tube. After cooled to RT, the mixture was concentrated to afford crude molecule (15.5 g, 91% yield) as a white solid which was used directly the next step without further purification. MS (ESI) m/z 256.8 $[M+H]^+$.

4-Bromothieno[2,3-c]pyridine-2-carbonitrile. A mixture of 4-bromothieno[2,3-c]pyridine-2-carboxamide (20 g, 78 mmol) and TFAA (300 ml) was stirred at 45° C. for 24 hrs. Cooling to RT, the mixture was concentrated and purified by column chromatography (DCM 100%) to afford the molecule (13 g, 70%) as a yellow solid. MS (ESI) m/z 240.9 $[M+2H]^+$. $^1$H-NMR (400 MHz, $CDCl_3$) δ 9.12 (s, 1H), 8.73 (s, 1H), 8.04 (s, 1H).

4-(Tributylstannyl)thieno[2,3-c]pyridine-2-carbonitrile. 4-Bromothieno[2,3-c]pyridine-2-carbonitrile (1.00 g, 4.18 mmol) and $Sn_2Bu_6$ (4.2 mL, 8.37 mmol, 2 equiv.) were suspended in dioxane (17 mL, 0.25 M) and deoxygenated with bubbling argon gas for 10 min. $Pd(dppf)C_{1-2}$ (0.31 g, 0.42 mmol, 10 mol %) was added to the suspension and the resulting mixture was stirred at 100° C. for 24 h. The mixture was cooled to RT, filtered over Celite®, and concentrated in vacuo. The crude material was purified by flash silica column chromatography (0420% EtOAc/hexanes) to give the compound (1.26 g, 67%) as a light-red oil. MS (ESI) m/z 451.1 $[M+H]^+$.

4-(2-(1-Ethyl-3-(trifluoromethyl)-1H-pyrazol-4-yl)-S-fluorophenyl)thieno[2,3-c]pyridine-2-carbonitrile. To a stirred mixture of 4-(2-bromo-4-fluorophenyl)-1-ethyl-3-(trifluoromethyl)-1H-pyrazole (0.337 g, 1.0 mmol), 4-(tributylstannyl)thieno[2,3-c]pyridine-2-carbonitrile (0.450 g, 1.0 mmol), $Pd(Cy_3P)_2Cl_2$(74 mg, 0.1 eq.), and copper (I) iodide (38 mg, 0.2 eq.) in a sealable reaction vessel was added dioxane (2.5 mL) via syringe under nitrogen. The reaction vessel was screw-sealed and heated at 100° C. overnight. After cooling, the resulting dark mixture was filtered through a column of Celite®, washed with EA (3×5 mL), and the combined filtrates were concentrated in vacuo. The residue was purified by a flash column chromatography ($SiO_2$, 0→20→40% EA in hexanes) to yield the compound as a white solid (100 mg, 24%). MS (ESI) m/z 417.1 $[M+H]^+$.

4-(2-(1-Ethyl-3-(trifluoromethyl)-1H-pyrazol-4-yl)cyclopenf-1-en-1-yl)thieno[2,3-c]pyridine-2-carbonitrile. The compound was synthesized analogously as described above, from 4-(2-bromocyclopent-1-en-1-yl)-1-ethyl-3-(trifluoromethyl)-1H-pyrazole, and isolated as pale-brown sticky oil (54%). MS (ESI) m/z 389.1 $[M+H]^+$.

4-(2-(1-Ethyl-3-(trifluoromethyl)-1H-pyrazol-4-yl)cyclohex-1-en-1-yl)thieno[2,3-c]pyridine-2-carbonitrile. The compound was synthesized analogously as described above, from 4-(2-bromocyclohex-1-en-1-yl)-1-ethyl-3-(trifluoromethyl)-1H-pyrazole, and isolated as a yellow foam (32%). MS (ESI) m/z 403.1 $[M+H]^+$.

4-(2-(1-Ethyl-3-(trifluoromethyl)-1H-pyrazol-4-yl)-3,5-difluorophenyl)thieno[2,3-c]pyridine-2-carbonitrile. The compound was synthesized analogously as described above, from 4-(2-bromo-4,6-difluorophenyl)-1-ethyl-3-(trifluoromethyl)-1H-pyrazole, and isolated as a brown solid (27%). MS (ESI) m/z 435.1 $[M+H]^+$.

4-(2-(1-Ethyl-3-(trifluoromethyl)-1H-pyrazol-4-yl)-3,4-difluorophenyl)thieno[2,3-c]pyridine-2-carbonitrile. The compound was synthesized analogously as described above, from 4-(6-bromo-2,3-difluorophenyl)-1-ethyl-3-(trifluoromethyl)-1H-pyrazole, and isolated as an off-white solid (51%). MS (ESI) m/z 435.1 $[M+H]^+$.

4-(3-Cyano-2-(1-ethyl-3-(trifluoromethyl)-1H-pyrazol-4-yl)phenyl)thieno[2,3-c]pyridine-2-carbonitrile. The compound was synthesized analogously as described above, from 3-bromo-2-(1-ethyl-3-(trifluoromethyl)-1H-pyrazol-4-yl)benzonitrile, and isolated as an off-white solid (59%). MS (ESI) m/z 424.1 $[M+H]^+$.

4-(3-Chloro-2-(1-ethyl-3-(trifluoromethyl)-1H pyrazol-4-yl)-5-fluorophenyl)thieno[2,3-c]pyridine-2-carbonitrile. The compound was synthesized analogously as described above, from 4-(2-bromo-6-chloro-4-fluorophenyl)-1-ethyl-3-(trifluoromethyl)-1H-pyrazole, and isolated as a pale-yellow sticky oil (16%). MS (ESI) m/z 451.0 $[M+H]^+$.

4-(3-Chloro-2-(1-ethyl-3-(trifluoromethyl)-1H pyrazol-4-yl)-4-fluorophenyl)thieno[2,3-c]pyridine-2-carbonitrile. The compound was synthesized analogously as described above, from 4-(6-bromo-2-chloro-3-fluorophenyl)-1-ethyl-3-(trifluoromethyl)-1H-pyrazole, and isolated as a white crystalline solid (26%). MS (ESI) m/z 451.0 $[M+H]^+$.

4-(2-(1-Ethyl-3-(trifluoromethyl)-1H-pyrazol-4-yl)-3-fluoro-4-hydroxyphenyl)-thieno[2,3-c]pyridine-2-carbonitrile. The compound was synthesized analogously as described above, from 3-(1-ethyl-3-(trifluoromethyl)-1H-pyrazol-4-yl)-2-fluoro-4-iodophenol, and isolated as a brown solid (25%). MS (ESI) m/z 433.1 $[M+H]^+$.

4-(3-(1-Ethyl-3-(trifluoromethyl)-1H-pyrazol-4-yl)-2-((4-methoxybenzyl)oxy)pyridin-4-yl)thieno[2,3-c]pyridine-2-carbonitrile. The compound was synthesized analogously as described above, from 4-bromo-3-(1-ethyl-3-(trifluoromethyl)-1H-pyrazol-4-yl)-2-((4-methoxybenzyl)-oxy)pyridine, and isolated as a pale-yellow film (41%). MS (ESI) m/z 536.1 $[M+H]^+$.

4-(7-(1-Ethyl-3-(trifluoromethyl)-1H-pyrazol-4-yl)benzo[d]isoxazol-6-yl)thieno[2,3-c]pyridine-2-carbonitrile. The compound was synthesized analogously as described above, from 6-bromo-7-(1-ethyl-3-(trifluoromethyl)-1H-pyrazol-4-yl)benzo[d]isoxazole, and isolated as a yellow thin film (41%, based on the recovered starting material). MS (ESI) m/z 440.1 $[M+H]^+$.

4-(4-Amino-2-(1-ethyl-3-(trifluoromethyl)-1H pyrazol-4-yl)phenyl)thieno[2,3-c]pyridine-2-carbonitrile. The compound was synthesized analogously as described above from tert-butyl (3-bromo-2-fluoropyridin-4-yl)carbamate, and isolated as a yellow oil (53%). MS (ESI) m/z 414.1 $[M+H]^+$.

4-(6-Amino-2-(1-ethyl-3-(trifluoromethyl)-1H pyrazol-4-yl)pyridin-3-yl)thieno[2,3-c]pyridine-2-carbonitrile. The compound was synthesized analogously as described above from 5-bromo-6-(1-ethyl-3-(trifluoromethyl)-1H-pyrazol-4-yl)pyridin-2-amine, and isolated as a yellow solid (73%). MS (ESI) m/z 414.9 $[M]^+$.

4-(2-(1-Ethyl-3-(trifluoromethyl)-1H-pyrazol-4-yl)-4-(hydroxymethyl)phenyl)thieno[2,3-c]pyridine-2-carbonitrile. The compound was synthesized analogously as described above from (4-bromo-3-(1-ethyl-3-(trifluoromethyl)-1H-pyrazol-4-yl)phenyl)methanol, and isolated as a white solid (65%). MS (ESI) m/z 428.9 $[M]^+$.

4-(5-Amino-2-(1-ethyl-3-(trifluoromethyl)-1H pyrazol-4-yl)phenyl)thieno[2,3-c]pyridine-2-carbonitrile. The compound was synthesized analogously as described above from 3-bromo-4-(1-ethyl-3-(trifluoromethyl)-1H-pyrazol-4-yl) aniline, and isolated as an orange solid (66%). MS (ESI) m/z 413.9 $[M]^+$.

4-(1'-Ethyl-2-methyl-3'-(trifluoromethyl)-1'H,2H-[3,4'-bipyrazol]-4-yl)thieno[2,3-c]pyridine-2-carbonitrile. The compound was synthesized analogously as described above from 4-bromo-1'-ethyl-2-methyl-3'-(trifluoromethyl)-1'H,2H-3,4'-bipyrazole, and isolated as an orange solid (20%). MS (ESI) m/z 402.9 $[M]^+$.

4-(4-(1-Ethyl-3-(trifluoromethyl)-1H-pyrazol-4-yl)-5-methylthiophen-3-yl)thieno[2,3-c]pyridine-2-carbonitrile. The compound was synthesized analogously as described above from 4-(4-bromo-2-methylthiophen-3-yl)-1-ethyl-3-(trifluoromethyl)-1H-pyrazole, and isolated as a yellow oil (32%). MS (ESI) m/z 418.7 $[M]^+$.

4-(2-(1-Ethyl-3-(trifluoromethyl)-1H-pyrazol-4-yl)-3-methylphenyl)thieno[2,3-c]pyridine-2-carbonitrile. The compound was synthesized analogously as described above from 1-ethyl-4-(2-iodo-6-methylphenyl)-3-(trifluoromethyl)-1H-pyrazole and isolated as orange foam (36%). MS (ESI) m/z 412.9 $[M]^+$.

4-(3-Chloro-2-(1-ethyl-3-(trifluoromethyl)-1H pyrazol-4-yl)phenyl)thieno[2,3-c]pyridine-2-carbonitrile. The compound was synthesized analogously as described above from 4-(2-chloro-6-iodophenyl)-1-ethyl-3-(trifluoromethyl)-1H-pyrazole and isolated as a yellow oil (33%). MS (ESI) m/z 432.8 $[M]^+$.

4-(3-(1-Ethyl-3-(trifluoromethyl)-1H-pyrazol-4-yl)-2-fluoropyridin-4-yl)thieno[2,3-c]pyridine-2-carbonitrile. The compound was synthesized analogously as described above from 3-(1-ethyl-3-(trifluoromethyl)-1H-pyrazol-4-yl)-2-fluoro-4-iodopyridine and isolated as a cream solid (36%). MS (ESI) m/z 417.9 $[M]^+$.

4-(2-(1-Ethyl-3-(trifluoromethyl)-1H-pyrazol-4-yl)-4-hydroxyphenyl)thieno[2,3-c]pyridine-2-carbonitrile. A mixture of 4-(tributylstannyl)thieno[2,3-c]pyridine-2-carbonitrile (230 mg, 0.50 mmol), 4-bromo-3-(1-ethyl-3-(trifluoromethyl)-1H-pyrazol-4-yl)phenol (190 mg, 0.56 mmol), and CuI (19 mg, 0.10 mmol) in dioxane (2.5 mL) was deoxygenated with bubbling argon gas for 10 min, then $Pd(Cy_3P)_2C_{1-2}$ (37 mg, 0.050 mmol) was added. The resulting mixture was heated at 100° C. for 24 h, stirring vigorously. After cooling to RT, the mixture was filtered through Celite® and concentrated in vacuo. The resulting residue was purified by flash column chromatography ($SiO_2$, 0→70→100% EA in hexanes) to yield the compound as a brown foam (86 mg, 41%). MS (ESI) m/z 415.1 $[M+H]^+$.

4-(2-(1-Ethyl-3-(trifluoromethyl)-1H-pyrazol-4-yl)-6-hydroxyphenyl)thieno[2,3-c]pyridine-2-carbonitrile. The compound was synthesized analogously as described above from 2-bromo-3-(1-ethyl-3-(trifluoromethyl)-1H-pyrazol-4-yl) phenol and isolated as a red-brown oil (19 mg, 11%). MS (ESI) m/z 415.1 $[M+H]^+$.

4-(2-(1-Ethyl-3-(trifluoromethyl)-1H-pyrazol-4-yl)-5-hydroxyphenyl)thieno[2,3-c]pyridine-2-carbonitrile. The compound was synthesized analogously as described above from 3-bromo-4-(1-ethyl-3-(trifluoromethyl)-1H-pyrazol-4-yl) phenol and isolated as a sticky orange oil (21%).

4-(2-(1-Ethyl-3-(trifluoromethyl)-1H-pyrazol-4-yl)-3-methoxyphenyl)thieno[2,3-c]pyridine-2-carbonitrile. The compound was synthesized analogously as described above from 4-(2-bromo-6-methoxyphenyl)-1-ethyl-3-(trifluoromethyl)-1H-pyrazole and isolated as a light-yellow foam (48%). MS (ESI) m/z 429.1 $[M+H]^+$.

4-(2-Chlorothiophen-3-yl)thieno[2,3-c]pyridine-2-carbonitrile. A mixture of 4-bromothieno[2,3-c]pyridine-2-carbonitrile (100 mg, 0.42 mmol), (2-chlorothiophen-3-yl)boronic acid (82 mg, 0.50 mmol), and $K_3PO_4$ (270 mg, 1.3 mmol) in dioxane (2.1 mL) was deoxygenated with bubbling argon gas for 10 min, then $Pd(dppf)Cl_2$ was added. The resulting mixture was stirred vigorously at 80° C. for 18 h. After cooling to RT, the mixture was filtered through Celite® and the filtrate was concentrated in vacuo. The resulting residue was purified by flash column chromatography ($SiO_2$, 0→70→100% EA in hexanes) to yield the compound as a tan solid (88 mg, 76%).

4-(2-Chlorothiophen-3-yl)-4,5,6,7-tetrahydrothieno[2,3-c]pyridine-2-carbonitrile. A solution of 4-(2-chlorothiophen-3-yl)thieno[2,3-c]pyridine-2-carbonitrile (88 mg, 0.32 mmol) and bromocresol green (~1 mg, catalytic) in DCM-MeOH (1:1, 4 mL total) was treated with an excess of sodium cyanoborohydride (≥5 equiv). The pH of the solution was kept acidic by slowly adding drops of TFA in portions. After the solution was kept constant yellow to orange in color for more than 30 min, the reaction was quenched carefully with sat. aq. $NaHCO_3$ (10 mL) and diluted with water (20 mL) and DCM (30 mL). The layers were partitioned, and the aqueous layer was washed with DCM (2×30 mL). The combined organic extracts were dried over anhydrous $MgSO_4$, filtered, and conc. in vacuo. The resulting film was carried directly into the next step without purification, assuming theoretical yield.

tert-Butyl4-(2-chlorothiophen-3-yl)-2-cyano-4,7-dihydrothieno[2,3-c]pyridine-6(5H)-carboxylate. A solution of crude 4-(2-chlorothiophen-3-yl)-4,5,6,7-tetrahydrothieno[2,3-c]pyridine-2-carbonitrile (89 mg, 0.32 mmol) and DIPEA (170 μL, 0.95 mmol) in DCM (5 mL) was treated with $Boc_2O$ and maintained at RT for 18 h. The reaction was diluted with DCM (15 mL) and sequentially washed with brine (20 mL). The aqueous phase was extracted with DCM (2×15 mL). The combined organic extracts were dried over anhydrous $MgSO_4$, filtered, and concentrated in vacuo. The resulting residue was purified by flash column chromatography ($SiO_2$, 0→20% EA in hexanes) to yield the compound as a light-yellow oil (110 mg, 93%).

tert-Butyl2-cyano-4-(2-(1-ethyl-3-(trifluoromethyl)-1H pyrazol-4-yl)thiophen-3-yl)-4,7-dihydrothieno[2,3-c]pyridine-6(5H)-carboxylate. A mixture of tert-butyl 4-(2-chlorothiophen-3-yl)-2-cyano-4,7-dihydrothieno[2,3-c]pyridine-6(5H)-carboxylate (110 mg, 0.29 mmol), (1-ethyl-3-(trifluoromethyl)-1H-pyrazol-4-yl)boronic acid (67 mg, 0.32 mmol), and $K_2CO_3$ (120 mg, 0.88 mmol) in dioxane (1.5 mL) was deoxygenated with bubbling argon gas for 10 min, then XPhos Pd G3 (25 mg, 0.029 mmol) was added. The resulting mixture was stirred vigorously at 80° C. for 18 h. After cooling to RT, the mixture was filtered through Celite®. The filtrate was concentrated in vacuo and then purified by flash column chromatography ($SiO_2$, 0→20% EA in hexanes) to yield the compound as a brown oil (14 mg, 9%).

N-(4-(2-Cyanothieno[2,3-c]pyridin-4-yl)-3-(1-ethyl-3-(trifluoromethyl)-1H-pyrazol-4-yl)phenyl)acetamide. To a stirred mixture of 4-(4-amino-2-(1-ethyl-3-(trifluoromethyl)-1H-pyrazol-4-yl)phenyl)thieno[2,3-c]pyridine-2-carbonitrile (53.0 mg, 0.13 mmol) in Pyr (1.2 mL) at 0° C. was added $Ac_2O$ (24.0 μL, 0.26 mmol). The mixture was warmed to RT and stirred for 2 h. The mixture was diluted with DCM (5 mL) then washed with sat. $NaHCO_{3(aq)}$ (50 mL) and separated. The organic layer was, dried over $MgSO_4$, and concentrated in vacuo. The residue was used in the next reaction without further purification.

N-(4-(2-Cyano-4,5,6,7-tetrahydrothieno[2,3-c]pyridin-4-yl)-3-(1-ethyl-3-(trifluoromethyl)-1H pyrazol-4-yl)phenyl) acetamide. To a stirred mixture of N-(4-(2-cyanothieno[2,3-c]pyridin-4-yl)-3-(1-ethyl-3-(trifluoromethyl)-1H-pyrazol-4-yl)phenyl)acetamide (49.0 mg, 0.11 mmol), bromocresol green (1.00 mg), and $NaBH_3CN$ (27.0 mg, 0.43 mmol) in DCM:MeOH (1:1, 1 mL) at RT, TFA was added dropwise to the mixture to maintain a yellow solution. The mixture was diluted with DCM (5 mL), then washed with sat. $NaHCO_{3(aq)}$ (10 mL), extracted with DCM (5 mL×3). The organic layers were combined, dried over $MgSO_4$, and concentrated in vacuo. The residue was purified by a flash column chromatography ($SiO_2$, 30→100% EA in hexanes with 1% $Et_3N$ then 0→10% MeOH in EA with 1% $Et_3N$) to yield the compound as a yellow oil (0.0346 g, 59%, over 2 steps). MS (ESI) m/z 459.9 $[M]^+$.

N-(4-(2-Cyanothieno[2,3-c]pyridin-4-yl)-3-(1-ethyl-3-(trifluoromethyl)-1H-pyrazol-4-yl)phenyl)methanesulfonamide. The compound was synthesized analogously as described above from 4-(4-amino-2-(1-ethyl-3-(trifluoromethyl)-1H-pyrazol-4-yl)phenyl)thieno[2,3-c]pyridine-2-carbonitrile and used in the next reaction without further purification.

N-(4-(2-Cyano-4,5,6,7-tetrahydrothieno[2,3-c]pyridin-4-yl)-3-(1-ethyl-3-(trifluoromethyl)-1H pyrazol-4-yl)phenyl) methanesulfonamide. The compound was synthesized analogously as described above from N-(4-(2-cyanothieno[2,3-c]pyridin-4-yl)-3-(1-ethyl-3-(trifluoromethyl)-1H-pyrazol-4-yl)phenyl)methanesulfonamide and isolated as a yellow oil (52%, over 2 steps). MS (ESI) m/z 495.9 $[M]^+$.

1-(4-(2-Cyanothieno[2,3-c]pyridin-4-yl)-3-(1-ethyl-3-(trifluoromethyl)-1H-pyrazol-4-yl)phenyl)-3-methylurea. The compound was synthesized analogously as described above from 4-(4-amino-2-(1-ethyl-3-(trifluoromethyl)-1H-pyrazol-4-yl)phenyl)thieno[2,3-c]pyridine-2-carbonitrile and used in the next reaction without further purification.

1-(4-(2-Cyano-4,5,6,7-tetrahydrothieno[2,3-c]pyridin-4-yl)-3-(1-ethyl-3-(trifluoromethyl)-1H pyrazol-4-yl)phenyl)-3-methylurea. The compound was synthesized analogously as described above from 1-(4-(2-cyanothieno[2,3-c]pyridin-4-yl)-3-(1-ethyl-3-(trifluoromethyl)-1H-pyrazol-4-yl)phenyl)-3-methylurea and isolated as a yellow oil (85%, over 2 steps). MS (ESI) m/z 474.9 $[M]^+$.

4-(4-Amino-2-(1-ethyl-3-(trifluoromethyl)-1H pyrazol-4-yl)phenyl)-4,5,6,7-tetrahydrothieno[2,3-c]pyridine-2-carbonitrile. The compound was synthesized analogously as described above from 4-(4-amino-2-(1-ethyl-3-(trifluoromethyl)-1H-pyrazol-4-yl)phenyl)thieno[2,3-c]pyridine-2-carbonitrile and isolated as yellow oil (35%). MS (ESI) m/z 417.9 $[M]^+$.

4-(6-Amino-2-(1-ethyl-3-(trifluoromethyl)-1H pyrazol-4-yl)pyridin-3-yl)-4,5,6,7-tetrahydrothieno[2,3-c]pyridine-2-carbonitrile. The compound was synthesized analogously as described above from 4-(6-amino-2-(1-ethyl-3-(trifluoromethyl)-1H-pyrazol-4-yl)pyridin-3-yl)thieno[2,3-c]pyridine-2-carbonitrile and isolated as yellow oil (44%). MS (ESI) m/z 418.9 $[M]^+$.

4-(2-(1-Ethyl-3-(trifluoromethyl)-1H-pyrazol-4-yl)-4-(hydroxymethyl)phenyl)-4,5,6,7-tetrahydrothieno[2,3-c]pyridine-2-carbonitrile. The compound was synthesized analogously as described above from 4-(2-(1-ethyl-3-(trifluoromethyl)-1H-pyrazol-4-yl)-4-(hydroxymethyl)phenyl)thieno[2,3-c]pyridine-2-carbonitrile and isolated as yellow oil (71%). MS (ESI) m/z 433.1 $[M+H]^+$.

4-(5-Amino-2-(1-ethyl-3-(trifluoromethyl)-1H pyrazol-4-yl)phenyl)-4,5,6,7-tetrahydrothieno[2,3-c]pyridine-2-carbonitrile. The compound was synthesized analogously as described above from 4-(5-amino-2-(1-ethyl-3-(trifluoromethyl)-1H-pyrazol-4-yl)phenyl)thieno[2,3-c]pyridine-2-carbonitrile and isolated as yellow oil (76%). MS (ESI) m/z 417.9 $[M]^+$.

Example 180

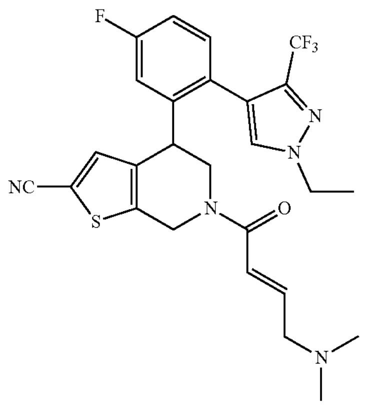 [SMILES: CCn1cc(-c2ccc(F)cc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-5-fluorophenyl)-4,5,6,7-tetrahydrothieno[2,3-c]pyridine-2-carbonitrile To a stirred mixture of 4-(2-(1-ethyl-3-(trifluoromethyl)-1H-pyrazol-4-yl)-5-fluorophenyl)thieno[2,3-c]pyridine-2-carbonitrile (100 mg, 0.243 mmol) In MeOH (5 mL) was added a couple of drops of saturated MeOH solution of bromobresol green. The mixture was treated with excess of sodium cyanoborohydride (5 eq.) periodically while keeping the pH of the solution acidic (with slow addition of 4 N HCl in dioxane in drops). After the reduction was completed and the solution was kept constant yellow to orange in color for 30 min, the reaction was quenched carefully with saturated $NaHCO_{3(aq)}$ and water (3 mL each), then diluted with EA (10 mL). The separated aqueous layer was extracted with EA (10 mL×3) and the organic phases were washed with brine, dried over $Na_2SO_4$, filtered, and finally concentrated. The crude material was redissolved in DMF (5 mL) and cooled to 0° C., to which DIEA (0.15 mL) was added followed by HATU (111 mg, 0.291 mmol) and (E)-4-(dimethylamino)but-2-enoic acid HCl salt (53 mg, 0.316 mmol) subsequentially. The resulting brown solution was stirred for 30 min then diluted with saturated $NH_4Cl_{(aq)}$ and water (5 mL each). The mixture was extracted with EA (15 mL×3) and the organic phases were washed with brine, dried over $Na_2SO_4$, filtered, and the solvent was removed in vacuo. The residue was purified by a flash column chromatography ($SiO_2$, 0→2→5% MeOH in DCM w/$NH_3$) to yield the compound as a pale-yellow solid (0.24 mg, 24%). MS (ESI) m/z 532.2 $[M+H]^+$.

Example 181

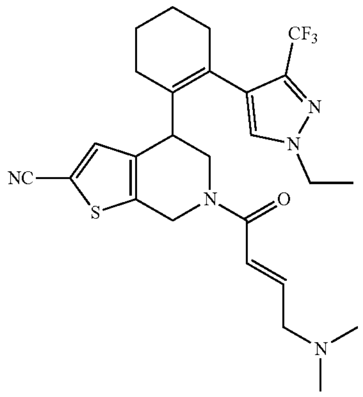 [SMILES: CCn1cc(C2=C(C3CN(C(=O)/C=C/CN(C)C)Cc4sc(C#N)cc43)CCCC2)c(C(F)(F)F)n1]

(E)-6-(4-(Dimethylamino)but-2-enoyl)-4-(2-(1-ethyl-3-(trifluoromethyl)-1H-pyrazol-4-yl)cyclohex-1-en-1-yl)-4,5,6,7-tetrahydrothieno[2,3-c]pyridine-2-carbonitrile The compound was synthesized analogously as described above, from 4-(2-(1-ethyl-3-(trifluoromethyl)-1H-pyrazol-4-yl)cyclohex-1-en-1-yl)thieno[2,3-c]pyridine-2-carbonitrile, as a pale-yellow foam (43%). MS (ESI) m/z 518.3 $[M+H]^+$.

Example 182

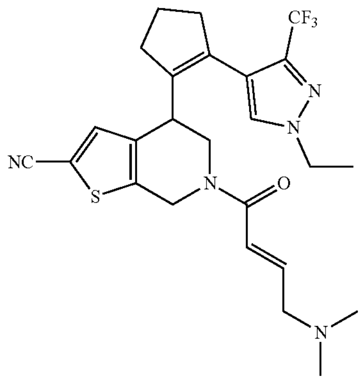 [SMILES: CCn1cc(C2=C(C3CN(C(=O)/C=C/CN(C)C)Cc4sc(C#N)cc43)CCC2)c(C(F)(F)F)n1]

(E)-6-(4-(Dimethylamino)but-2-enoyl)-4-(2-(1-ethyl-3-(trifluoromethyl)-1H-pyrazol-4-yl)cyclopent-1-en-1-yl)-4,5,6,7-tetrahydrothieno[2,3-c]pyridine-2-carbonitrile The compound was synthesized analogously as described above, from 4-(2-(1-ethyl-3-(trifluoromethyl)-1H-pyrazol-4-yl)cyclopent-1-en-1-yl)thieno[2,3-c]pyridine-2-carbonitrile, and isolated as a pale-yellow solid (56%). MS (ESI) m/z 504.2 $[M+H]^+$.

Example 183

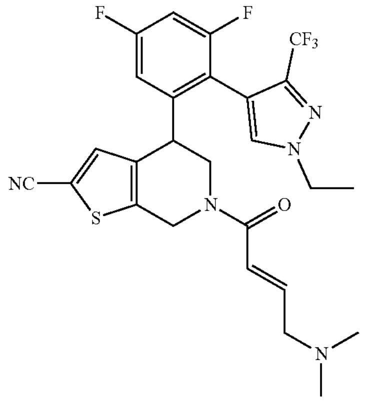 [SMILES: CCn1cc(-c2c(F)cc(F)cc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-3,5-difluorophenyl)-4,5,6,7-tetrahydrothieno[2,3-c]pyridine-2-carbonitrile The compound was synthesized analogously as described above, and from 4-(2-(1-ethyl-3-(trifluoromethyl)-1H-pyrazol-4-yl)-3,5-difluorophenyl)thieno[2,3-c]pyridine-2-carbonitrile, and isolated as a pale-yellow solid (26%). MS (ESI) m/z 550.2 $[M+H]^+$.

Example 184

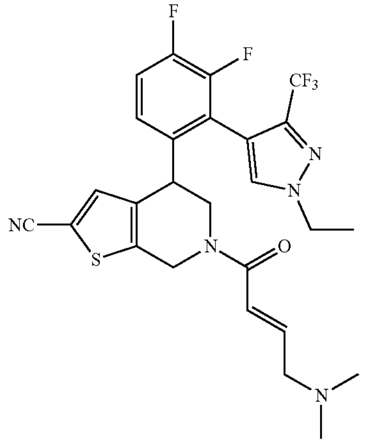 [SMILES: CCn1cc(-c2c(C3CN(C(=O)/C=C/CN(C)C)Cc4sc(C#N)cc43)ccc(F)c2F)c(C(F)(F)F)n1]

(E)-6-(4-(Dimethylamino)but-2-enoyl)-4-(2-(1-ethyl-3-(trifluoromethyl)-1H-pyrazol-4-yl)-3,4-difluorophenyl)-4,5,6,7-tetrahydrothieno[2,3-c]pyridine-2-carbonitrile The compound was synthesized analogously as described above, from 4-(2-(1-ethyl-3-(trifluoromethyl)-1H-pyrazol-4-yl)-3,4-difluorophenyl)thieno[2,3-c]pyridine-2-carbonitrile, and isolated as a pale-yellow solid (27%). MS (ESI) m/z 550.2 $[M+H]^+$.

Example 185

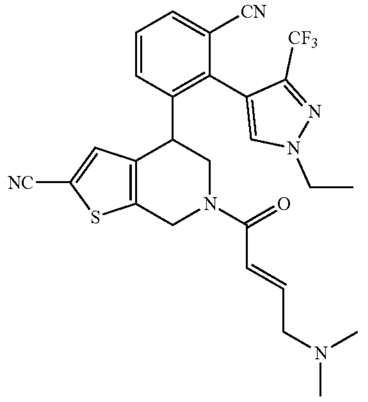 [SMILES: CCn1cc(-c2c(C#N)cccc2C2CN(C(=O)/C=C/CN(C)C)Cc3sc(C#N)cc32)c(C(F)(F)F)n1]

(E)-3-(6-(4-(Dimethylamino)but-2-enoyl)-2-isocyano-4,5,6,7-tetrahydrothieno[2,3-c]pyridin-4-yl)-2-(1-ethyl-3-(trifluoromethyl)-1H-pyrazol-4-yl)benzonitrile The compound was synthesized analogously as described above, from 4-(3-cyano-2-(1-ethyl-3-(trifluoromethyl)-1H-pyrazol-4-yl)phenyl)thieno[2,3-c]pyridine-2-carbonitrile, and isolated as an off-white solid (11%). MS (ESI) m/z 539.2 $[M+H]^+$.

Example 186

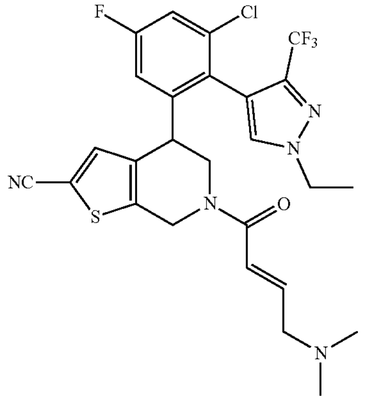 [SMILES: CCn1cc(-c2c(Cl)cc(F)cc2C2CN(C(=O)/C=C/CN(C)C)Cc3sc(C#N)cc32)c(C(F)(F)F)n1]

(E)-4-(3-Chloro-2-(1-ethyl-3-(trifluoromethyl)-1H-pyrazol-4-yl)-5-fluorophenyl)-6-(4-(dimethylamino)but-2-enoyl)-4,5,6,7-tetrahydrothieno[2,3-c]pyridine-2-carbonitrile The compound was synthesized analogously as described above, from 4-(3-chloro-2-(1-ethyl-3-(trifluoromethyl)-1H-pyrazol-4-yl)-5-fluorophenyl)thieno[2,3-c]pyridine-2-carbonitrile, and isolated as a pale-yellow solid (36%). MS (ESI) m/z 566.2 $[M+H]^+$.

Example 187

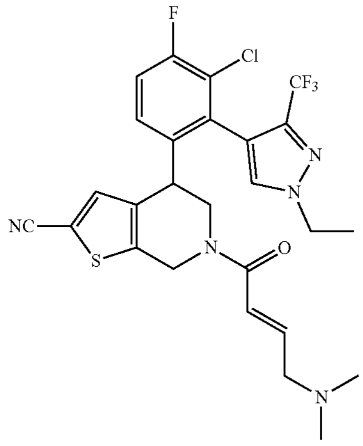 [SMILES: CCn1cc(-c2c(C3CN(C(=O)/C=C/CN(C)C)Cc4sc(C#N)cc43)ccc(F)c2Cl)c(C(F)(F)F)n1]

(E)-4-(3-Chloro-2-(1-ethyl-3-(trifluoromethyl)-1H-pyrazol-4-yl)-4-fluorophenyl)-6-(4-(dimethylamino)but-2-enoyl)-4,5,6,7-tetrahydrothieno[2,3-c]pyridine-2-carbonitrile The compound was synthesized analogously as described above, from 4-(3-chloro-2-(1-ethyl-3-(trifluoromethyl)-1H-pyrazol-4-yl)-4-fluorophenyl)thieno[2,3-c]pyridine-2-carbonitrile, and isolated as a pale-brown solid (25%). MS (ESI) m/z 566.2 $[M+H]^+$.

Example 188

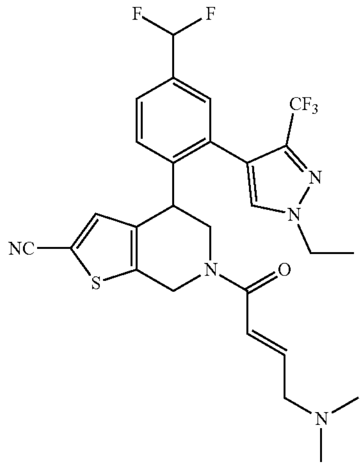 [SMILES: CCn1cc(-c2cc(C(F)F)ccc2C2CN(C(=O)/C=C/CN(C)C)Cc3sc(C#N)cc32)c(C(F)(F)F)n1]

(E)-4-(4-(Difluoromethyl)-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile The compound was synthesized analogously as described above, from 4-(4-(difluoromethyl)-2-(1-ethyl-3-(trifluoromethyl)-1H-pyrazol-4-yl)phenyl)thieno[2,3-c]pyridine-2-carbonitrile, and isolated as a pale-brown solid (54%). MS (ESI) m/z 564.2 $[M+H]^+$.

Example 189

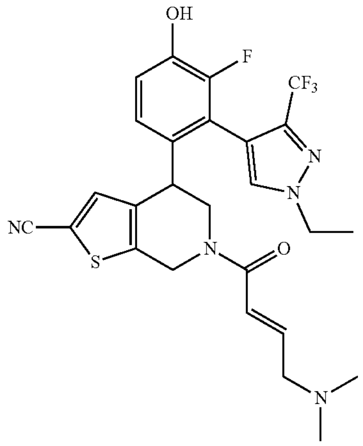 [SMILES: CCn1cc(-c2c(C3CN(C(=O)/C=C/CN(C)C)Cc4sc(C#N)cc43)ccc(O)c2F)c(C(F)(F)F)n1]

(E)-6-(4-(Dimethylamino)but-2-enoyl)-4-(2-(1-ethyl-3-(trifluoromethyl)-1H-pyrazol-4-yl)-3-fluoro-4-hydroxyphenyl)-4,5,6,7-tetrahydrothieno[2,3-c]pyridine-2-carbonitrile The compound was synthesized analogously as described above, from 4-(2-(1-ethyl-3-(trifluoromethyl)-1H-pyrazol-4-yl)-3-fluoro-4-hydroxyphenyl)thieno[2,3-c]pyridine-2-carbonitrile, and isolated as an off-white solid (38%). MS (ESI) m/z 548.2 $[M+H]^+$.

Example 190

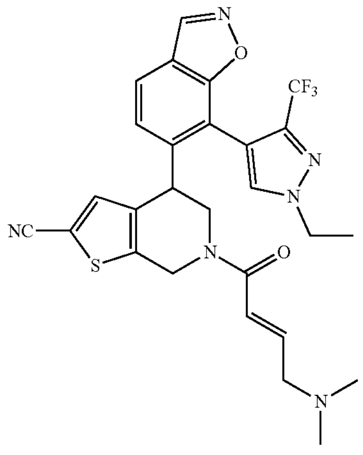 [SMILES: CCn1cc(-c2c(C3CN(C(=O)/C=C/CN(C)C)Cc4sc(C#N)cc43)ccc3cnoc23)c(C(F)(F)F)n1]

(E)-6-(4-(Dimethylamino)but-2-enoyl)-4-(7-(1-ethyl-3-(trifluoromethyl)-1H-pyrazol-4-yl)benzo[d]isoxazol-6-yl)-4,5,6,7-tetrahydrothieno[2,3-c]pyridine-2-carbonitrile The compound was synthesized analogously as described above from 4-(7-(1-ethyl-3-(trifluoromethyl)-1H-pyrazol-4-yl)benzo[d]isoxazol-6-yl)thieno[2,3-c]pyridine-2-carbonitrile. The residue was purified by a flash column chromatography ($SiO_2$, 0→5→10% MeOH in DCM w/$NH_3$)

followed by another HPLC purification (Agilent Prep-018 column (50×21.2 mm, 5 μm); eluent A=$H_2O$ (0.1% formic acid), B=ACN in $H_2O$ (0.1% FA), 5→95% B over 15 min @ 25 mL/min)) to yield the compound as a white solid (FA salt, 24%). MS (ESI) m/z 555.2 [M+H]$^+$.

Example 191

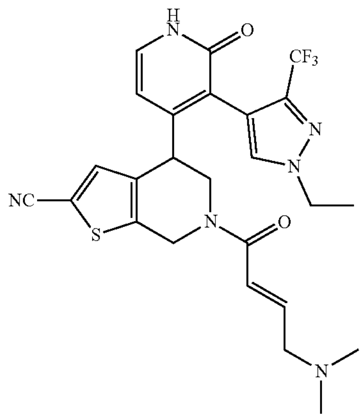 [SMILES: CCn1cc(-c2c(C3CN(C(=O)/C=C/CN(C)C)Cc4sc(C#N)cc43)cc[nH]c2=O)c(C(F)(F)F)n1]

(E)-6-(4-(Dimethylamino)but-2-enoyl)-4-(3-(1-ethyl-3-(trifluoromethyl)-1H pyrazol-4-yl)-2-oxo-1,2-dihydropyridin-4-yl)-4,5,6,7-tetrahydrothieno[2,3-c]pyridine-2-carbonitrile The compound was synthesized analogously as described above from 4-(3-(1-ethyl-3-(trifluoromethyl)-1H-pyrazol-4-yl)-2-((4-methoxybenzyl)oxy)pyridin-4-yl)thieno[2,3-c]pyridine-2-carbonitrile. The aqueous layer was concentrated, and the residue was subjected to a HPLC purification (Agilent Prep-018 column (50×21.2 mm, 5 μm); eluent A=$H_2O$ (0.1% formic acid), B=ACN in $H_2O$ (0.1% formic acid), 5→95% B over 15 min @ 25 mL/min)) to yield the compound as a white solid (FA salt, 22%). MS (ESI) m/z 531.2 [M+H]$^+$.

Example 192

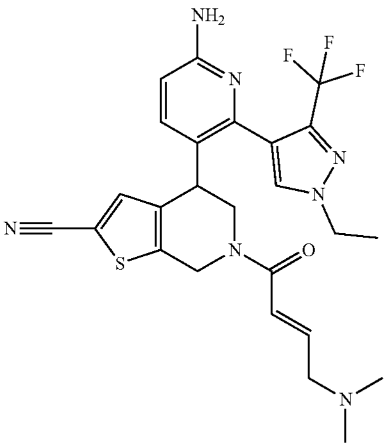 [SMILES: CCn1cc(-c2nc(N)ccc2C2CN(C(=O)/C=C/CN(C)C)Cc3sc(C#N)cc32)c(C(F)(F)F)n1]

(E)-4-(6-Amino-2-(1-ethyl-3-(trifluoromethyl)-1H-pyrazol-4-yl)pyridin-3-yl)-6-(4-(dimethylamino)but-2-enoyl)-4,5,6,7-tetrahydrothieno[2,3-c]pyridine-2-carbonitrile The compound was synthesized analogously as described above from 4-(6-amino-2-(1-ethyl-3-(trifluoromethyl)-1H-pyrazol-4-yl)pyridin-3-yl)-4,5,6,7-tetrahydrothieno[2,3-c]pyridine-2-carbonitrile and isolated as an off-white solid (35%). MS (ESI) m/z 530.3 [M+H]$^+$.

Example 193

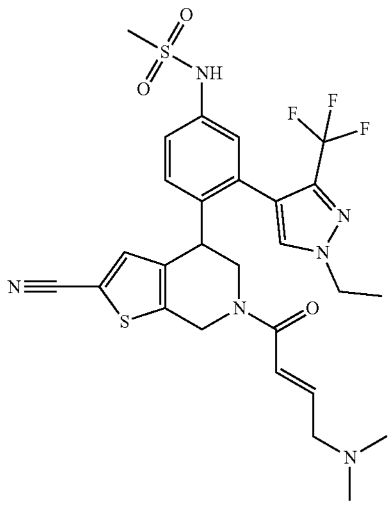 [SMILES: CCn1cc(-c2cc(NS(C)(=O)=O)ccc2C2CN(C(=O)/C=C/CN(C)C)Cc3sc(C#N)cc32)c(C(F)(F)F)n1]

(E)-N-(4-(2-Cyano-6-(4-(dimethylamino)but-2-enoyl)-4,5,6,7-tetrahydrothieno[2,3-c]pyridin-4-yl)-3-(1-ethyl-3-(trifluoromethyl)-1H-pyrazol-4-yl)phenyl)methanesulfonamide.

The compound was synthesized analogously as described above from N-(4-(2-cyano-4,5,6,7-tetrahydrothieno[2,3-c]pyridin-4-yl)-3-(1-ethyl-3-(trifluoromethyl)-1H-pyrazol-4-yl)phenyl)methanesulfonamide and isolated as a sticky yellow solid (FA salt, 7%). MS (ESI) m/z 607.3 [M+H]$^+$.

Example 194

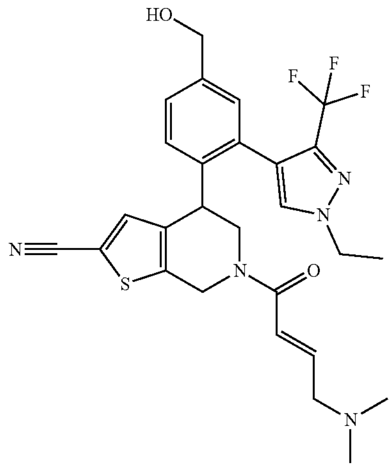 [SMILES: CCn1cc(-c2cc(CO)ccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-4-(hydroxymethyl)phenyl)-4,5,6,7-tetrahydrothieno[2,3-c]pyridine-2-carbonitrile The compound was synthesized analogously as described above from 4-(2-(1-ethyl-3-(trifluoromethyl)-1H-pyrazol-4-yl)-4-(hydroxymethyl)phenyl)-4,5,6,7-tetrahydrothieno[2,3-c]pyridine-2-carbonitrile and isolated as a yellow solid (FA salt, 79%). MS (ESI) m/z 544.3 $[M+H]^+$.

Example 195

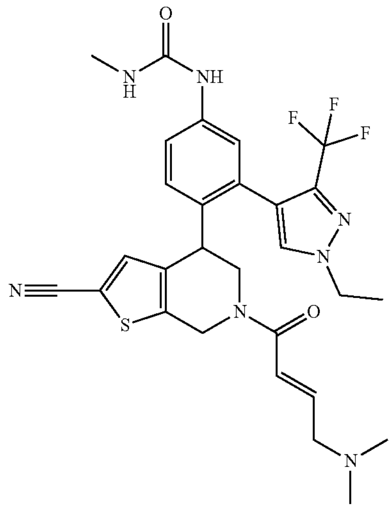 [SMILES: CCn1cc(-c2cc(NC(=O)NC)ccc2C2CN(C(=O)/C=C/CN(C)C)Cc3sc(C#N)cc32)c(C(F)(F)F)n1]

(E)-1-(4-(2-Cyano-6-(4-(dimethylamino)but-2-enoyl)-4,5,6,7-tetrahydrothieno[2,3-c]pyridin-4-yl)-3-(1-ethyl-3-(trifluoromethyl)-1H-pyrazol-4-yl)phenyl)-3-methylurea The compound was synthesized analogously as described above from 1-(4-(2-cyano-4,5,6,7-tetrahydrothieno[2,3-c]pyridin-4-yl)-3-(1-ethyl-3-(trifluoromethyl)-1H-pyrazol-4-yl)phenyl)-3-methylurea and isolated as a sticky off-white solid (FA salt, 59%). MS (ESI) m/z 586.3 $[M+H]^+$.

Example 196

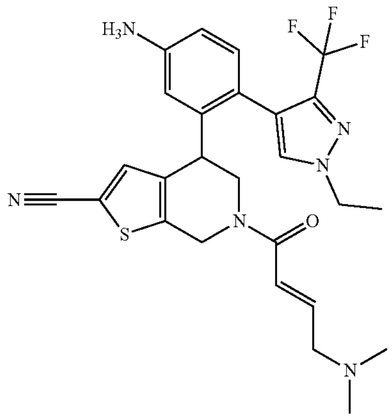 [SMILES: CCn1cc(-c2ccc(N)cc2C2CN(C(=O)/C=C/CN(C)C)Cc3sc(C#N)cc32)c(C(F)(F)F)n1]

(E)-4-(5-Amino-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile The compound was synthesized analogously as described above from 4-(5-amino-2-(1-ethyl-3-(trifluoromethyl)-1H-pyrazol-4-yl)phenyl)-4,5,6,7-tetrahydrothieno[2,3-c]pyridine-2-carbonitrile and isolated as an off-white solid (FA salt, 29%). MS (ESI) m/z 529.3 $[M+H]^+$.

Example 197

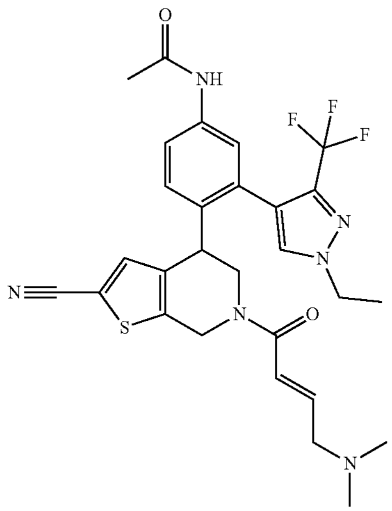 [SMILES: CCn1cc(-c2cc(NC(C)=O)ccc2C2CN(C(=O)/C=C/CN(C)C)Cc3sc(C#N)cc32)c(C(F)(F)F)n1]

(E)-N-(4-(2-Cyano-6-(4-(dimethylamino)but-2-enoyl)-4,5,6,7-tetrahydrothieno[2,3-c]pyridin-4-yl)-3-(1-ethyl-3-(trifluoromethyl)-1H-pyrazol-4-yl)phenyl)acetamide To a stirred mixture of (E)-4-(4-amino-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile (19.4 mg, 36.7 μmol) in pyridine (0.4 mL) at 0° C. was added $Ac_2O$ (7.00 μL, 73.4 μmol). The mixture was warmed to RT and stirred for 2 h. The mixture was diluted with DCM (5 mL) then washed with sat. $NaHCO_{3(aq)}$ (50 mL) and separated. The organic layer was dried over $MgSO_4$, and concentrated in vacuo. The residue purified by HPLC purification (Agilent Prep-C18 column (50×21.2 mm, 5 μm); eluent A=$H_2O$ (0.1% TFA), B=ACN in $H_2O$ (0.1% TFA), 5→95% B over 19 min @ 25 mL/min) to yield the compound as a clear oil (12.2 mg, TFA salt, 58%). MS (ESI) m/z 571.3 $[M+H]^+$.

Example 198

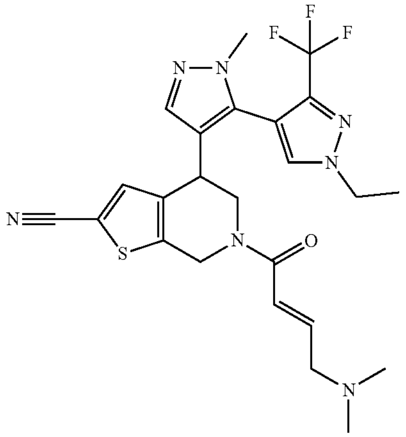 [SMILES: CCn1cc(-c2c(C3CN(C(=O)/C=C/CN(C)C)Cc4sc(C#N)cc43)cnn2C)c(C(F)(F)F)n1]

(E)-6-(4-(Dimethylamino)but-2-enoyl)-4-(1'-ethyl-2-methyl-3'-(trifluoromethyl)-1'H,2H-[3,4'-bipyrazol]-4-yl)- 4,5,6,7-tetrahydrothieno[2,3-c]pyridine-2-carbonitrile The compound was synthesized analogously as described above from 4-(1'-ethyl-2-methyl-3'-(trifluoromethyl)-1'H,2H-[3,4'-bipyrazol]-4-yl)thieno[2,3-c]pyridine-2-carbonitrile and isolated as a brown solid (FA salt, 28%). MS (ESI) m/z 518.2 $[M+H]^+$.

Example 199

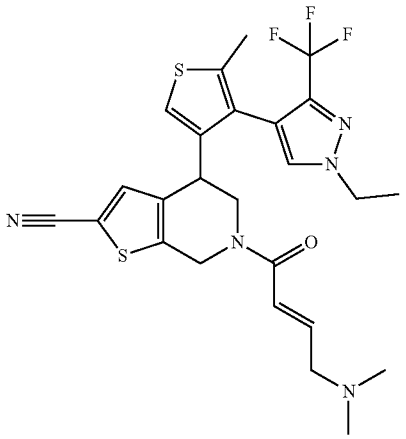 [SMILES: CCn1cc(-c2c(C3CN(C(=O)/C=C/CN(C)C)Cc4sc(C#N)cc43)csc2C)c(C(F)(F)F)n1]

(E)-6-(4-(Dimethylamino)but-2-enoyl)-4-(4-(1-ethyl-3-(trifluoromethyl)-1H-pyrazol-4-yl)-5-methylthiophen-3-yl)-4,5,6,7-tetrahydrothieno[2,3-c]pyridine-2-carbonitrile The compound was synthesized analogously as described above from 4-(4-(1-ethyl-3-(trifluoromethyl)-1H-pyrazol-4-yl)-5-methylthiophen-3-yl)thieno[2,3-c]pyridine-2-carbonitrile and isolated as an off-white solid (17%). MS (ESI) m/z 534.2 $[M+H]^+$.

Example 200

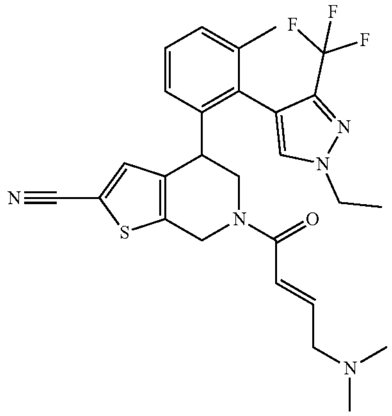 [SMILES: CCn1cc(-c2c(C)cccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-3-methylphenyl)-4,5,6,7-tetrahydrothieno[2,3-c]pyridine-2-carbonitrile The compound was synthesized analogously as described above from 4-(2-(1-ethyl-3-(trifluoromethyl)-1H-pyrazol-4-yl)-3-methylphenyl)thieno[2,3-c]pyridine-2-carbonitrile and isolated as an off-white (FA salt, 54%). MS (ESI) m/z 528.3 $[M+H]^+$.

Example 201

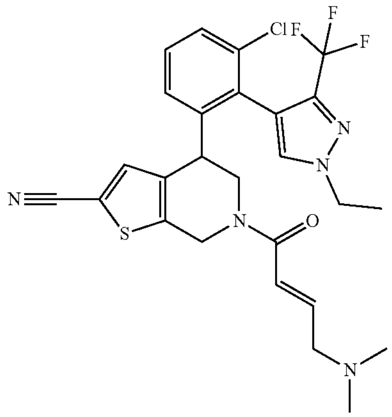 [SMILES: CCn1cc(-c2c(Cl)cccc2C2CN(C(=O)/C=C/CN(C)C)Cc3sc(C#N)cc32)c(C(F)(F)F)n1]

(E)-4-(3-Chloro-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile The compound was synthesized analogously as described above from 4-(3-chloro-2-(1-ethyl-3-(trifluoromethyl)-1H-pyrazol-4-yl)phenyl)thieno[2,3-c]pyridine-2-carbonitrile and isolated as an off-white solid (43%). MS (ESI) m/z 548.2 $[M+H]^+$.

Example 202

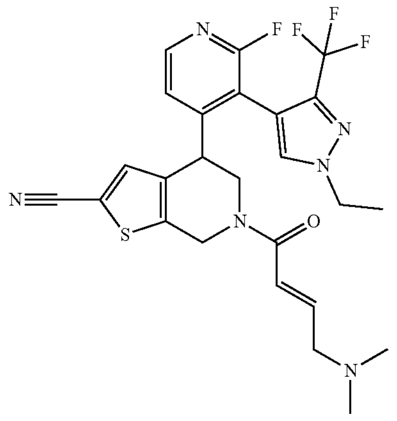 [SMILES: CCn1cc(-c2c(C3CN(C(=O)/C=C/CN(C)C)Cc4sc(C#N)cc43)ccnc2F)c(C(F)(F)F)n1]

(E)-6-(4-(Dimethylamino)but-2-enoyl)-4-(3-(1-ethyl-3-(trifluoromethyl)-1H-pyrazol-4-yl)-2-fluoropyridin-4-yl)-4,5,6,7-tetrahydrothieno[2,3-c]pyridine-2-carbonitrile The compound was synthesized analogously as described above from 4-(3-(1-ethyl-3-(trifluoromethyl)-1H-pyrazol-4-yl)-2-fluoropyridin-4-yl)thieno[2,3-c]pyridine-2-carbonitrile and isolated as a white solid (26%). MS (ESI) m/z 533.2 $[M+H]^+$.

Example 203

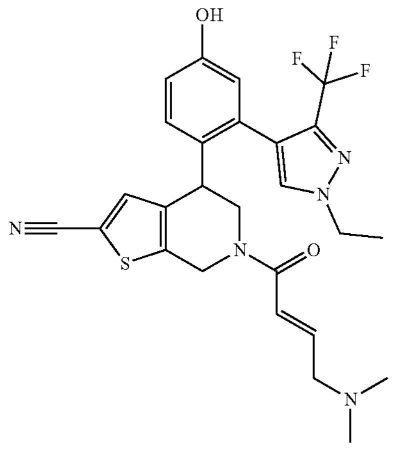 [SMILES: CCn1cc(-c2cc(O)ccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-4-hydroxyphenyl)-4,5,6,7-tetrahydrothieno[2,3-c]pyridine-2-carbonitrile 4-(2-(1-Ethyl-3-(trifluoromethyl)-1H-pyrazol-4-yl)-4-hydroxyphenyl)-4,5,6,7-tetrahydrothieno[2,3-c]pyridine-2-carbonitrile. A stirred mixture of 4-(2-(1-ethyl-3-(trifluoromethyl)-1H-pyrazol-4-yl)-4-hydroxyphenyl)thieno[2,3-c]pyridine-2-carbonitrile (86 mg, 0.21 mmol) and bromocresol green (~1 mg, catalytic) was treated with an excess of sodium cyanoborohydride (>5 equiv). The pH of the solution was kept acidic by slowly adding drops of TFA in portions. After the reduction was completed and the solution was kept constant yellow to orange in color for more than 30 min, the reaction was quenched carefully with sat. aq. $NaHCO_3$ (10 mL) and diluted with water (20 mL) and DCM (30 mL). The layers were partitioned and the aqueous layer was washed with DCM (2×30 mL). The combined organic extracts were dried over anhydrous $MgSO_4$, filtered, and conc. in vacuo. The resulting film was purified by flash column chromatography ($SiO_2$, 0→70→100% (10% MeOH in EA) in hexanes) to yield the target compound as an orange solid (51 mg, 59%).

(E)-6-(4-(Dimethylamino)but-2-enoyl)-4-(2-(1-ethyl-3-(trifluoromethyl)-1H pyrazol-4-yl)-4-hydroxyphenyl)-4,5,6,7-tetrahydrothieno[2,3-c]pyridine-2-carbonitrile. A mixture of (E)-4-(dimethylamino)but-2-enoic acid HCl salt (20 mg, 0.12 mmol), DIPEA (43 μL, 0.24 mmol), and HATU (47 mg, 0.12 mmol) in DMF (0.60 mL) was stirred at RT for 10 min, then was cooled to 0° C. in an ice-water bath. A solution of 4-(2-(1-ethyl-3-(trifluoromethyl)-1H-pyrazol-4-yl)-4-hydroxyphenyl)-4,5,6,7-tetrahydrothieno[2,3-c]pyridine-2-carbonitrile (51 mg, 0.12 mmol) and DIPEA (43 μL, 0.24 mmol) in DMF (0.60 mL) was slowly added dropwise and the resulting solution slowly warmed to RT and stirred for 18 h. Additional DIPEA (86 μL, 0.49 mmol) and (E)-4-(dimethylamino)but-2-enoic acid HCl salt (20 mg, 0.12 mmol) and HATU (47 mg, 0.12 mmol) in DMF (180 μL) were added. After 2 h, the mixture was diluted with EA (20 mL) and sat. aq. LiCl soln. (20 mL). The layers were partitioned and the aqueous layer was washed with EA (2×20 mL). The combined organic extracts were dried over anhydrous $MgSO_4$, filtered, and concentrated in vacuo then redissolved in MeOH and filtered through a 0.22 μm nylon syringe tip filter. The filtrate was purified by RP-HPLC (Agilent Prep-C18 column (50×21.2 mm, 5 μm); eluent A=$H_2O$ (+0.1% FA), B=MeCN (+0.1% FA), 5495% B over 19 min @ 25 mL/min) to yield the compound as an off-white solid (14 mg, 21%). MS (ESI) m/z 530.2 $[M+H]^+$.

Example 204

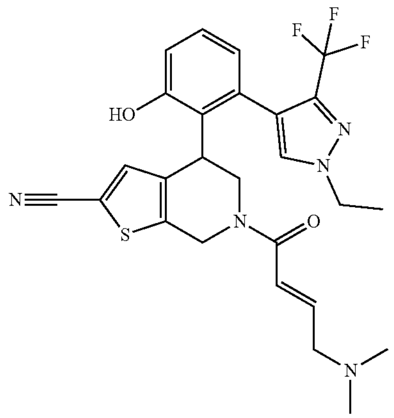 [SMILES: CCn1cc(-c2cccc(O)c2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-6-hydroxyphenyl)-4,5,6,7-tetrahydrothieno[2,3-c]pyridine-2-carbonitrile The compound was synthesized analogously as described above from 4-(2-(1-ethyl-3-(trifluoromethyl)-1H-pyrazol-4-yl)-6-hydroxyphenyl)thieno[2,3-c]pyridine-2-carbonitrile and 4-(2-(1-ethyl-3-(trifluoromethyl)-1H-pyrazol-4-yl)-6-hydroxyphenyl)-4,5,6,7-tetrahydrothieno[2,3-c]pyridine-2-carbonitrile and isolated as a white solid (FA salt, 31%). MS (ESI) m/z 530.2 $[M+H]^+$.

Example 205

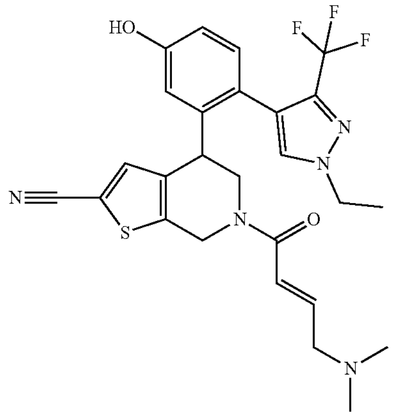 [SMILES: CCn1cc(-c2ccc(O)cc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-5-hydroxyphenyl)-4,5,6,7-tetrahydrothieno[2,3-c]pyridine-2-carbonitrile The compound was synthesized analogously as described above from 4-(2-(1-ethyl-3-(trifluoromethyl)-1H-pyrazol-4-yl)-5-hydroxyphenyl)thieno[2,3-c]pyridine-2-carbonitrile and 4-(2-(1-ethyl-3-(trifluoromethyl)-1H-pyrazol-4-yl)-5-hydroxyphenyl)-4,5,6,7-tetrahydrothieno[2,3-c]pyridine-2-carbonitrile and isolated as a white solid (FA salt, 42%). MS (ESI) m/z 530.2 $[M+H]^+$.

Example 206

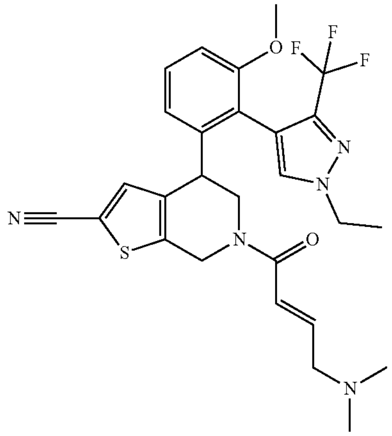 [SMILES: CCn1cc(-c2c(OC)cccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4-yl)-3-methoxyphenyl)-4,5,6,7-tetrahydrothieno[2,3-c]pyridine-2-carbonitrile The compound was synthesized analogously as described above from 4-(2-(1-ethyl-3-(trifluoromethyl)-1H-pyrazol-4-yl)-3-methoxyphenyl)thieno[2,3-c]pyridine-2-carbonitrile and 4-(2-(1-ethyl-3-(trifluoromethyl)-1H-pyrazol-4-yl)-3-methoxyphenyl)-4,5,6,7-tetrahydrothieno[2,3-c]pyridine-2-carbonitrile and isolated as a beige solid (32%). MS (ESI) m/z 544.3 $[M+H]^+$.

Example 207

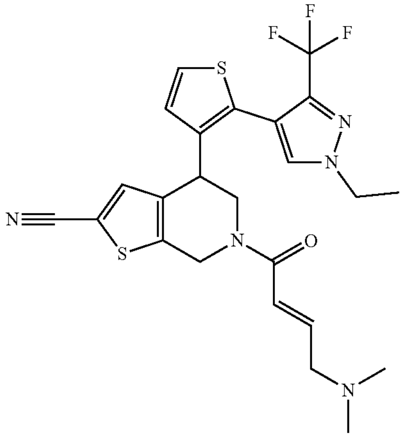 [SMILES: CCn1cc(-c2sccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H pyrazol-4-yl)thiophen-3-yl)-4,5,6,7-tetrahydrothieno[2,3-c]pyridine-2-carbonitrile A solution of tert-butyl 2-cyano-4-(2-(1-ethyl-3-(trifluoromethyl)-1H-pyrazol-4-yl)thiophen-3-yl)-4,7-dihydrothieno[2,3-c]pyridine-6(5H)-carboxylate (14 mg, 0.027 mmol) in DCM (1 mL) was treated with TFA (1 mL) and then maintained at RT for 10 min. The mixture was concentrated in vacuo, dissolved in DMF (0.80 mL) and treated with DIPEA (19 μL, 0.11 mmol). In a separate vial, HATU (21 mg, 0.054 mmol), (E)-4-(dimethylamino)but-2-enoic acid HCl salt (8.9 mg, 0.054 mmol) and DIPEA (19 μL, 0.11 mmol) stirred in DMF (0.20 mL) at RT for 15 min, then was cooled to 0° C. in an ice-water bath. The amine mixture was slowly added, and the reaction was stirred at 0° C. for 1 h, then was purified by RP-HPLC (Agilent Prep-018 column (50×21.2 mm, 5 μm); eluent A=$H_2O$ (+0.1% FA), B=MeCN (+0.1% FA), 10→35→95% B over 19 min @ 25 mL/min) to yield the compound as a sticky golden oil (7.9 mg, FA salt, 65%). MS (ESI) m/z 520.2 $[M+H]^+$.

Example 208

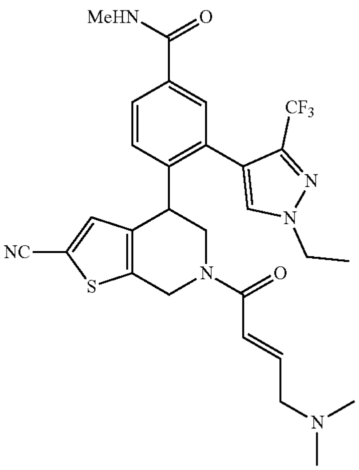 [SMILES: CCn1cc(-c2cc(C(=O)NC)ccc2C2CN(C(=O)/C=C/CN(C)C)Cc3sc(C#N)cc32)c(C(F)(F)F)n1]

(E)-4-(2-Cyano-6-(4-(dimethylamino)but-2-enoyl)-4,5,6,7-tetrahydrothieno[2,3-c]pyridin-4-yl)-3-(1-ethyl-3-(trifluoromethyl)-1H pyrazol-4-yl)-N-methylbenzamide Step 1. 4-(2-Cyanothieno[2,3-c]pyridin-4-yl)-3-(1-ethyl-3-(trifluoromethyl)-1H pyrazol-4-yl)-N-methylbenzamide. 4-Bromo-3-(1-ethyl-3-(trifluoromethyl)-1H-pyrazol-4-yl)-N-methylbenzamide (126 mg, 0.34 mmol), 4-(tributylstannyl)thieno[2,3-c]pyridine-2-carbonitrile (241 mg, 0.54 mmol), $Pd(CyP_3)_2Cl_2$ (35 mg, 0.034 mmol), and CuI (13 mg, 0.067 mmol) were degassed with Ar. Dioxane (2 mL) was added, resulting in a solution which was briefly degassed with Ar, then heated to 100° C. overnight. The mixture was cooled to RT, filtered solids through Celite®, washed with DCM, and concentrated in vacuo. The crude residue was purified by flash chromatography ($SiO_2$, 0→100% EA in hexanes gradient) resulting in the compound as a beige solid (99 mg, 65%). MS (ESI) m/z 455.9 $[M+H]^+$.

Step 2. 4-(2-Cyano-4,5,6,7-tetrahydrothieno[2,3-c]pyridin-4-yl)-3-(1-ethyl-3-(trifluoromethyl)-1H pyrazol-4-yl)-N-methylbenzamide. 4-(2-Cyanothieno[2,3-c]pyridin-4-yl)-3-(1-ethyl-3-(trifluoromethyl)-1H-pyrazol-4-yl)-N-methylbenzamide was dissolved in MeOH (2 mL). $NaBH_3CN$ (>5 eq.) and bromocresol green (2 mg) were added, resulting in a blue solution. TFA was added dropwise in small portions. The reaction was quenched carefully with saturated aqueous $NaHCO_3$, extracted 3× with EA, dried over $Na_2SO_4$, and concentrated in vacuo. The crude residue was purified by flash chromatography ($SiO_2$, 30→100% EA with 0.1% $Et_3N$ in hexanes, then 0→10% MeOH in EA with 0.1% $Et_3N$) and recovered the compound as a light-yellow sticky solid (87 mg, 87%). MS (ESI) m/z 459.9 $[M+H]^+$.

Step 3. (E)-4-(2-Cyano-6-(4-(dimethylamino)but-2-enoyl)-4,5,6,7-tetrahydrothieno[2,3-c]pyridin-4-yl)-3-(1-ethyl-3-(trifluoromethyl)-1H-pyrazol-4-yl)-N-methylbenzamide. The compound was synthesized analogously to the general scheme, from 4-(2-cyano-4,5,6,7-tetrahydrothieno[2,3-c]pyridin-4-yl)-3-(1-ethyl-3-(trifluoromethyl)-1H-pyrazol-4-yl)-N-methylbenzamide, and isolated as a beige solid (48 mg, 44%). MS (ESI) m/z 571.3 $[M+H]^+$.

Example 209

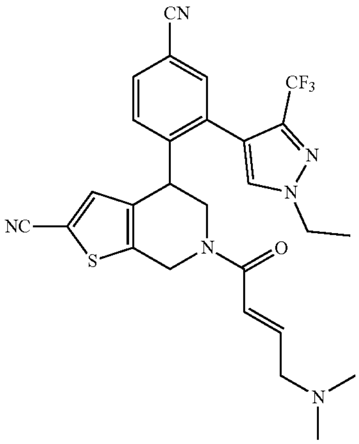 [SMILES: CCn1cc(-c2cc(C#N)ccc2C2CN(C(=O)/C=C/CN(C)C)Cc3sc(C#N)cc32)c(C(F)(F)F)n1]

(E)-4-(4-Cyano-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile Step 1. 4-(4-Cyano-2-(1-ethyl-3-(trifluoromethyl)-1H-pyrazol-4-yl)phenyl)thieno[2,3-c]pyridine-2-carbonitrile. The compound was synthesized analogously to the general scheme, from 4-bromo-3-(1-ethyl-3-(trifluoromethyl)-1H-pyrazol-4-yl)benzonitrile, and isolated as a cream-colored solid (145 mg, 75%). MS (ESI) m/z 423.9 $[M+H]^+$.

Step 2. 4-(4-Cyano-2-(1-ethyl-3-(trifluoromethyl)-1H-pyrazol-4-yl)phenyl)-4,5,6,7-tetrahydrothieno[2,3-c]pyridine-2-carbonitrile. The compound was synthesized analogously to the general scheme, from 4-(4-cyano-2-(1-ethyl-3-(trifluoromethyl)-1H-pyrazol-4-yl)phenyl)thieno[2,3-c]pyridine-2-carbonitrile, and isolated as a light-yellow solid (100 mg, 68%). MS (ESI) m/z 427.9 $[M+H]^+$.

Step 3. (E)-4-(4-Cyano-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile. The compound was synthesized analogously to the general scheme, from 4-(4-cyano-2-(1-ethyl-3-(trifluoromethyl)-1H-pyrazol-4-yl)phenyl)-4,5,6,7-tetrahydrothieno[2,3-c]pyridine-2-carbonitrile, and isolated as a light pink solid (68 mg, 54%). MS (ESI) m/z 539.3 $[M+H]^+$.

Example 210

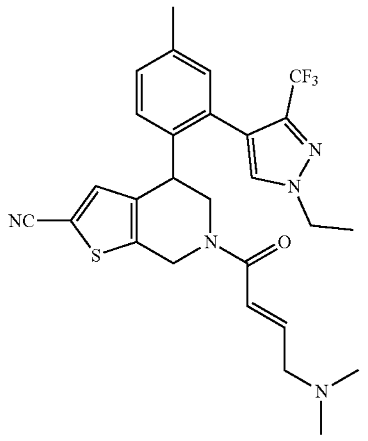 [SMILES: CCn1cc(-c2cc(C)ccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H pyrazol-4-yl)-4-methylphenyl)-4,5,6,7-tetrahydrothieno[2,3-c]pyridine-2-carbonitrile Step 1. 4-(2-(1-Ethyl-3-(trifluoromethyl)-1H pyrazol-4-yl)-4-methylphenyl)thieno[2,3-c]pyridine-2-carbonitrile. The compound was synthesized analogously to the general scheme, from 4-(2-bromo-5-methylphenyl)-1-ethyl-3-(trifluoromethyl)-1H-pyrazole, and isolated as an orange waxy solid (176 mg, 81%). MS (ESI) m/z 412.9 $[M+H]^+$.

Step 2. 4-(2-(1-Ethyl-3-(trifluoromethyl)-1H pyrazol-4-yl)-4-methylphenyl)-4,5,6,7-tetrahydrothieno[2,3-c]pyridine-2-carbonitrile. The compound was synthesized analogously to the general scheme, from 4-(2-(1-ethyl-3-(trifluoromethyl)-1H-pyrazol-4-yl)-4-methylphenyl)thieno[2,3-c]pyridine-2-carbonitrile, and isolated as a yellow solid (103 mg, 58%). MS (ESI) m/z 416.9 $[M+H]^+$.

Step 3. (E)-6-(4-(Dimethylamino)but-2-enoyl)-4-(2-(1-ethyl-3-(trifluoromethyl)-1H-pyrazol-4-yl)-4-methylphenyl)-4,5,6,7-tetrahydrothieno[2,3-c]pyridine-2-carbonitrile. The compound was synthesized analogously to the general scheme, from 4-(2-(1-ethyl-3-(trifluoromethyl)-1H-pyrazol-4-yl)-4-methylphenyl)-4,5,6,7-tetrahydrothieno[2,3-c]pyridine-2-carbonitrile, and isolated as a beige solid (98 mg, 75%). MS (ESI) m/z 528.3 $[M+H]^+$.

Example 211

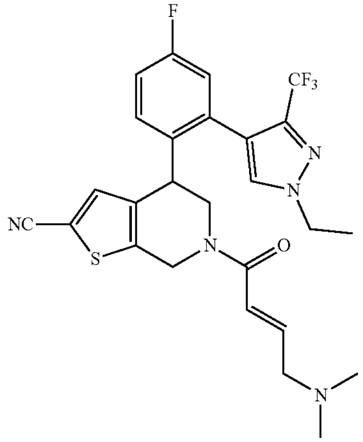 [SMILES: CCn1cc(-c2cc(F)ccc2C2CN(C(=O)/C=C/CN(C)C)Cc3sc(C#N)cc32)c(C(F)(F)F)n1]

(E)-6-(4-(Dimethylamino)but-2-enoyl)-4-(2-(1-ethyl-3-(trifluoromethyl)-1H-pyrazol-4 yl)-4-fluorophenyl)-4,5,6,7-tetrahydrothieno[2,3-c]pyridine-2-carbonitrile Step 1. 4-(2-(1-Ethyl-3-(trifluoromethyl)-1H pyrazol-4-yl)-4-fluorophenyl)thieno[2,3-c]pyridine-2-carbonitrile. The compound was synthesized analogously to the general scheme, from 4-(2-bromo-5-fluorophenyl)-1-ethyl-3-(trifluoromethyl)-1H-pyrazole, and isolated as an orange waxy solid (167 mg, 74%). MS (ESI) m/z 416.9 $[M+H]^+$.

Step 2. 4-(2-(1-Ethyl-3-(trifluoromethyl)-1H pyrazol-4-yl)-4-fluorophenyl)-4,5,6,7-tetrahydrothieno[2,3-c]pyridine-2-carbonitrile. The compound was synthesized analogously to the general scheme, from 4-(2-(1-ethyl-3-(trifluoromethyl)-1H-pyrazol-4-yl)-4-fluorophenyl)thieno[2,3-c]pyridine-2-carbonitrile, and isolated as a light-yellow solid (107 mg, 63%). MS (ESI) m/z 420.9 $[M+H]^+$.

Step 3. (E)-6-(4-(Dimethylamino)but-2-enoyl)-4-(2-(1-ethyl-3-(trifluoromethyl)-1H-pyrazol-4-yl)-4-fluorophenyl)-4,5,6,7-tetrahydrothieno[2,3-c]pyridine-2-carbonitrile. The compound was synthesized analogously to the general scheme, from 4-(2-(1-ethyl-3-(trifluoromethyl)-1H-pyrazol-4-yl)-4-fluorophenyl)-4,5,6,7-tetrahydrothieno[2,3-c]pyridine-2-carbonitrile, and isolated as a light yellow foamy solid (82 mg, 60%). MS (ESI) m/z 532.2 $[M+H]^+$.

Example 212

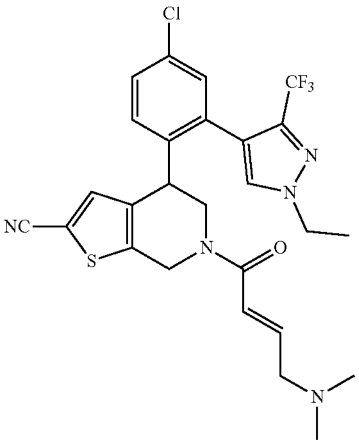 [SMILES: CCn1cc(-c2cc(Cl)ccc2C2CN(C(=O)/C=C/CN(C)C)Cc3sc(C#N)cc32)c(C(F)(F)F)n1]

(E)-4-(4-Chloro-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile Step 1. 4-(4-Chloro-2-(1-ethyl-3-(trifluoromethyl)-1H pyrazol-4-yl)phenyl)thieno[2,3-c]pyridine-2-carbonitrile. The compound was synthesized analogously to the general scheme, from 4-(2-bromo-5-chlorophenyl)-1-ethyl-3-(trifluoromethyl)-1H-pyrazole, and isolated as an orange waxy solid (159 mg, 64%). MS (ESI) m/z 432.8 $[M+H]^+$.

Step 2. 4-(4-Chloro-2-(1-ethyl-3-(trifluoromethyl)-1H pyrazol-4-yl)phenyl)-4,5,6,7-tetrahydrothieno[2,3-c]pyridine-2-carbonitrile. The compound was synthesized analogously to the general scheme, from 4-(4-chloro-2-(1-ethyl-3-(trifluoromethyl)-1H-pyrazol-4-yl)phenyl)thieno[2,3-c] pyridine-2-carbonitrile, and isolated as a white foam (115 mg, 72%). MS (ESI) m/z 437.1 $[M+H]^+$.

Step 3. (E)-4-(4-Chloro-2-(1-ethyl-3-(trifluoromethyl)-1H-pyrazol-4-yl)phenyl)-6-(4-(dimethylamino)but-2-enoyl)-4,5,6,7-tetrahydrothieno[2,3-c]pyridine-2-carbonitrile. The compound was synthesized analogously to the general scheme, from 4-(4-chloro-2-(1-ethyl-3-(trifluoromethyl)-1H-pyrazol-4-yl)phenyl)-4,5,6,7-tetrahydrothieno[2,3-c]pyridine-2-carbonitrile, and isolated as a beige solid (77 mg, 53%). MS (ESI) m/z 548.2 $[M+H]^+$.

Example 213

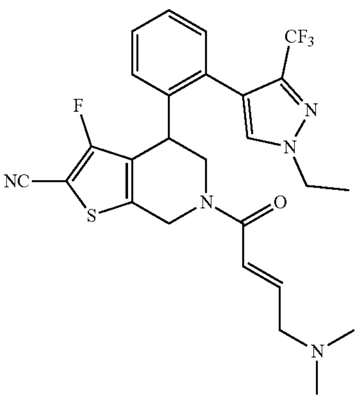 [SMILES: CCn1cc(-c2ccccc2C2CN(C(=O)/C=C/CN(C)C)Cc3sc(C#N)c(F)c32)c(C(F)(F)F)n1]

(E)-6-(4-(dimethylamino)but-2-enoyl)-4-(2-(1-ethyl-3-(trifluoromethyl)-1H pyrazol-4-yl)phenyl)-3-fluoro-4,5,6,7-tetrahydrothieno[2,3-c]pyridine-2-carbonitrile Step 1 Preparation of 3-fluorothiophene-2-carboxamide To a solution of 3-fluorothiophene-2-carboxylic acid (5 g, 34.2 mmol) in DCM (50 mL) were added 3 drops of DMF, followed by oxalyl chloride (25 mL, 2M in DCM, 51.3 mmol) dropwise at RT. Upon completion of addition, the solution was stirred for 3 h. Volatiles were removed in vacuo, then $NH_4OH$ (150 mL, 28-30% in $H_2O$, 150 mL) was added slowly and the reaction was stirred for 1 h at RT. The aqueous layer was extracted with DCM, and the organic phases were dried over $Na_2SO_4$, and concentrated in vacuo. The crude residue was purified by flash chromatography ($SiO_2$, 40% EA/hexanes isocratic), and the compound was recovered as a crystalline white solid (3.60 g, 72%). MS (ESI) m/z 146.0 $[M+H]^+$.

Step 2 Preparation of 3-fluorothiophene-2-carbonitrile. A solution of 3-fluorothiophene-2-carboxamide (1.45 g, 10 mmol) and pyridine (1.13 mL, 14 mmol) in THF (50 mL) was cooled to 0° C. Trifluoroacetic anhydride (1.67 mL, 12 mmol) was added dropwise, then the solution was warmed to RT. After 4 h, the mixture was diluted with DCM, washed twice with water, 1 M HCl, and brine (3×). The organic layer was dried over $Na_2SO_4$ and concentrated. The residue was purified by flash chromatography ($SiO_2$, 15% EA/hexanes isocratic). The compound was recovered as a light-yellow liquid, which darkens upon exposure to light (1.07 g, 84%).

Step 3 Preparation of 3-fluoro-5-formylthiophene-2-carbonitrile Anhydrous THF (100 mL) was cooled to −78° C. A solution of lithium diisopropylamide was added (1.88 M in THE/heptanes/ethylbenzene, 9.57 mL, 18 mmol) and stirred briefly at −78° C. A solution of 3-fluorothiophene-2-carbonitrile (1.76 g, 13.8 mmol) in THF (10 mL) was added dropwise, then stirred for 1 h at −78° C., until solution remained red. Anhydrous DMF (5.34 mL, 69.2 mmol) was added dropwise to the red solution, resulting in a brown solution which was stirred at −78° C. for 45 min. The reaction was quenched at −78° C. by addition of citric acid (2.6 g) in water (15 mL), resulting in a dark, teal-colored solution. Volatiles were removed in vacuo, then the mixture was diluted with brine and DCM. The aqueous layer was extracted 3 times with DCM, then washed combined organic layers twice with brine and concentrated the purple solution in vacuo. The residue was purified by flash chromatography ($SiO_2$, 0-12% EA/hexanes gradient). The compound was recovered as a light orange crystalline solid (798 mg, 37%).

Step 4 Preparation of 5-(((2-(2-bromophenyl)-2-hydroxyethyl)amino)methyl)-3-fluorothiophene-2-carbonitrile A suspension of 3-fluoro-5-formylthiophene-2-carbonitrile (798 mg, 5.14 mmol), 2-amino-1-(2-bromophenyl)ethan-1-ol (1.22 g, 5.66 mmol), and $Et_3N$ (789 μL, 5.66 mmol) in absolute EtOH (10 mL) was stirred at RT overnight. The suspension became clear, and then a light yellow precipitate formed. The mixture was diluted with MeOH (20 mL), glacial acetic acid (3 mL) was added, and the suspension was cooled to 0° C. To the suspension was added sodium cyanoborohydride (970 mg, 15.4 mmol) portionwise, then the reaction was stirred at 0° C. for 30 min. The reaction was quenched with saturated aq. $NaHCO_3$, extracted with EtOAc (3×), washed with brine, dried over $Na_2SO_4$, and concentrated in vacuo. The crude residue was purified by flash chromatography ($SiO_2$, 0-30% EA/hexanes gradient). The compound was recovered as a light-yellow waxy solid (393 mg). MS (ESI) m/z 354.9, 356.9 $[M+H]^+$ Step 5 Preparation of tert-butyl 4-(2-bromophenyl)-3-fluoro-2-cyano-4,7-dihydrothieno[2,3-c]pyridine-6(5H)-carboxylate To a solution of 5-(((2-(2-bromophenyl)-2-hydroxyethyl)amino)methyl)-3-fluorothiophene-2-carbonitrile (345 mg, 0.97 mmol) in DCE (50 mL) was added aluminum chloride (647 mg, 4.85 mmol), then heated to reflux for 2 h. Aluminum chloride (200 mg) was added and heated to reflux for 1 h. The mixture was diluted with DCM, washed with saturated Rochelle $salt_{(aq)}$, 1 M $K_2CO_3$, and brine, then dried over $MgSO_4$, filtered, and concentrated in vacuo. The residue was dissolved in DCM (10 mL), to which were added $Boc_2O$ (268 μL, 1.17 mmol) and $Et_3N$ (271 μL, 1.94 mmol). The solution was stirred overnight at RT. The solution was diluted with EtOAc, washed with water, saturated $NaHCO_{3(aq)}$, brine, dried over $Na_2SO_4$ and concentrated in vacuo. The crude residue was purified by flash chromatography ($SiO_2$, 0-15% EA/hexanes gradient). The compound was recovered as a yellow foam (302 mg, 71% over 2 steps). MS (ESI) m/z 380.8, 382.8 $[M-tBu+H]^+$ Step 6 Preparation of tert-butyl2-cyano-4-(2-(1-ethyl-3-(trifluoromethyl)-1H-pyrazol-4-yl)phenyl)-3-fluoro-4,7-dihydrothieno[2,3-c]pyridine-6(5H)-carboxylate The compound was prepared analogously to methods above, from tert-butyl 4-(2-bromophenyl)-3-fluoro-2-cyano-4,7-dihydrothieno[2,3-c]pyridine-6(5H)-carboxylate, and isolated as an orange-brown viscous oil (340 mg), which was contaminated with 19% tert-butyl 2-(1-ethyl-3-(trifluoromethyl)-1H-pyrazol-4-yl)-4-(2-(1-ethyl-3-(trifluoromethyl)-1H-pyrazol-4-yl)phenyl)-3-fluoro-4,7-dihydrothieno[2,3-c]pyridine-6(5H)-carboxylate by HPLC and was used without further purification. MS (ESI) m/z 464.9 $[M-tBu+H]^+$, 542.9 $[M+N_a]^+$ Step 7 Preparation of (E)-6-(4-(dimethylamino)but-2-enoyl)-4-(2-(1-ethyl-3-(trifluoromethyl)-1H-pyrazol-4-yl)phenyl)-3-fluoro-4,5,6,7-tetrahydrothieno[2,3-c]pyridine-2-carbonitrile The compound was prepared analogously to methods above, from tert-butyl 2-cyano-4-(2-(1-ethyl-3-(trifluoromethyl)-1H-pyrazol-4-yl)phenyl)-3-fluoro-4,7-dihydrothieno[2,3-c]pyridine-6(5H)-carboxylate and purified by 018 prep-HPLC (10-35% MeCN/$H_2O$ gradient with 0.1% FA), resulting in the compound as an off-white solid (186 mg, 54% over 2 steps). MS (ESI) m/z 532.2 $[M+H]^+$ Example 214

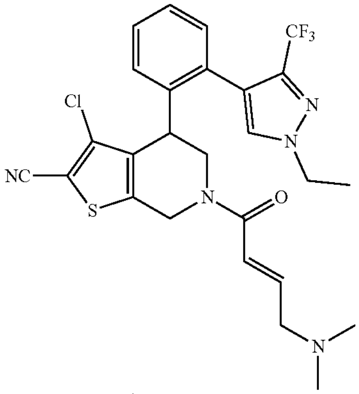

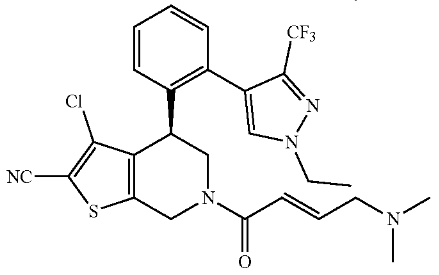

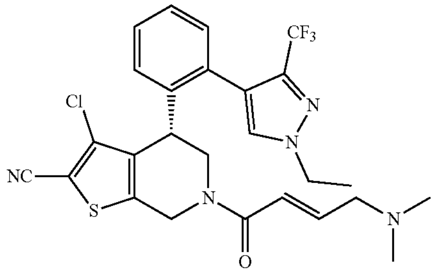

(E)-3-chloro-6-(4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1 Preparation of 3-chlorothiophene-2-carbonitrile A solution of 3-chlorothiophene-2-carboxamide (5 g, 30.9 mmol, 1 eq.) and pyridine (3.49 mL, 43.3 mmol) in THF (150 mL) was cooled to 0° C. TFAA (5.16 mL, 37.1 mmol) was added dropwise, then the solution warmed to RT. After 4 h, the mixture was diluted with DCM, washed twice with water, once with 1 M HCl, and brine (3×). The organic layer was dried over $Na_2SO_4$ and concentrated. The residue was purified by silica gel flash chromatography (20% EtOAc/hexanes). The compound was recovered as a white crystalline solid (3.69 g, 83%).

Step 2 Preparation of 3-chloro-5-formyl-thiophene-2-carbonitrile. Anhydrous THF (100 mL) was cooled to −78° C. A solution of lithium diisopropylamide was added (1.88 M in THE/heptanes/ethylbenzene, 9.6 mL, 18.1 mmol) and stirred briefly at −78° C. A solution of 3-chlorothiophene-2-carbonitrile (2 g, 13.9 mmol) in THF (8 mL) was added dropwise, and stirred for 45 min at −78° C. Anhydrous DMF (5.37 mL, 69.6 mmol) was added dropwise to the red solution, resulting in a brown solution which was stirred at −78° C. for 45 min. The reaction was quenched at −78° C. by addition of citric acid (2.6 g) in water (14 mL), resulting in a dark blue solution. Removed volatiles in vacuo, then diluted the mixture with brine and DCM. Extracted aqueous layer with DCM (3×), washed combined organic layers twice with brine and concentrated the purple solution in vacuo. Purified by silica gel flash chromatography (0-10% EtOAc/hexanes gradient). The compound was recovered as light orange to beige fine needles (1.39 g, 54%).

Step 3 Preparation of 5-(((2-(2-bromophenyl)-2-hydroxyethyl)amino)methyl)-3-chlorothiophene-2-carbonitrile A solution of 3-chloro-5-formyl-thiophene-2-carbonitrile (394 mg, 2.3 mmol, 1 eq.), 2-amino-1-(2-bromophenyl)ethan-1-ol (546 mg, 2.5 mmol, 1.1 eq.), and TEA (353 μL, 2.5 mmol, 1.1 eq.) in absolute EtOH (10 mL) was heated to reflux for 2 h. The reaction was cooled to 0° C., resulting in the formation of a precipitate. To the suspension was added sodium borohydride (261 mg, 6.9 mmol, 3 eq.) portionwise, then warmed to RT slowly. After 2 h, the reaction was quenched with saturated aq. $NaHCO_3$, extracted 3 times with EtOAc, washed with brine, dried over $Na_2SO_4$, and concentrated in vacuo. The crude residue was purified by silica gel flash chromatography (0-40% EtOAc/hexanes gradient), The compound was recovered as a light yellow solid (387 mg, 45% over 2 steps). MS (ESI) m/z 370.8, 372.7, 374.8 $[M+H]^+$ Step 4 Preparation of tert-butyl 4-(2-bromophenyl)-3-chloro-2-cyano-4,7-dihydrothieno[2,3-c]pyridine-6(5H)-carboxylate 5-(((2-(2-Bromophenyl)-2-hydroxyethyl)amino)methyl)-3-chlorothiophene-2-carbonitrile (372 mg, 1 mmol, 1 eq.) was suspended in DCM (10 mL) and cooled to 0° C. Aluminum chloride (400 mg, 3 mmol, 3 eq.) was added portionwise, then the mixture was warmed to RT slowly. After stirring over the weekend, the reaction was quenched with saturated aqueous $NaHCO_3$ and diluted with DCM. The organic layer was washed with 1 M Rochelle salt and brine, dried over $Na_2SO_4$, and concentrated in vacuo. The residue was redissolved in DCM (10 mL), to which were added $Boc_2O$ (276 μL, 1.2 mmol, 1.2 eq.) and TEA (279 μL, 2 mmol, 2 eq.). The solution was stirred overnight at RT. The solution was diluted with EtOAc, washed twice with water, once with saturated aq. $NaHCO_3$, and once with brine, then dried over $Na_2SO_4$ and concentrated in vacuo. The crude residue was purified by silica gel flash chromatography (0-15% EtOAc/hexanes gradient). The compound was recovered as a light yellow solid (249 mg, 55% over 2 steps). MS (ESI) m/z 396.7, 398.7, 400.7 $[M-tBu+H]^+$ Step 5 Preparation of (E)-3-chloro-6-(4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (E)-3-Chloro-6-(4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile was prepared from the BOG-protected intermediate via a process similar to that described above.

Step 6 Preparation of tert-butyl3-chloro-2-cyano-4-(2-(1-ethyl-3-(trifluoromethyl)-1H-pyrazol-4-yl)phenyl)-4,7-dihydrothieno[2,3-c]pyridine-6(5H)-carboxylate. tert-Butyl 4-(2-bromophenyl)-3-chloro-2-cyano-4,7-dihydrothieno[2,3-c]pyridine-6(5H)-carboxylate (240 mg, 0.53 mmol), (1-ethyl-3-(trifluoromethyl)-1H-pyrazol-4-yl)boronic acid (143 mg, 0.69 mmol), $Pd(dppf)Cl_2$ (39 mg, 0.053 mmol), and $K_2CO_3$ (146 mg, 1.06 mmol) were degassed with argon. Dioxane (2.7 mL) and water (0.3 mL) were added, degassed briefly with argon, and the mixture was heated to 80° C. overnight. The reaction was cooled to RT, diluted with EA, washed with saturated $NH_4Cl_{(aq)}$, brine, dried over $Na_2SO_4$, and concentrated in vacuo. The crude residue was purified by flash chromatography ($SiO_2$, 0-35% EA/hexanes gradient), resulting in the compound as a golden yellow foam (225 mg, 79%). MS (ESI) m/z 480.8, 482.8 $[M-tBu+H]^+$ Step 7 Preparation of (E)-3-chloro-6-(4-(dimethylamino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile A solution of tert-butyl 3-chloro-2-cyano-4-(2-(1-ethyl-3-(trifluoromethyl)-1H-pyrazol-4-yl)phenyl)-4,7-dihydrothieno[2,3-c]pyridine-6(5H)-carboxylate in DCM (3 mL) was treated with TFA (321 μL, 4.2 mmol) overnight. Volatiles were removed in vacuo and the residue was dissolved in DMF (3 mL). DIPEA (876 μL, 5 mmol), (E)-4-(dimethylamino)but-2-enoic acid hydrochloride (83 mg, 0.50 mmol), and HATU (191 mg, 0.50 mmol) were added sequentially and the solution was stirred for 6 h. The mixture was diluted with water, extracted with EA, washed with saturated $NaHCO_{3(aq)}$, brine, and dried over $Na_2SO_4$. The crude residue was purified by flash chromatography ($SiO_2$, 100% EA to 0-8% MeOH/DCM gradient), resulting in the compound as a brown foam (135 mg, 59%). MS (ESI) m/z 548.2 $[M+H]^+$ Step 8 Separation by chiral SFC. The (E)-3-chloro-6-(4-(di methyl amino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile enantiomers were separated from 129 mg of racemate by chiral SFC with a SFC-150 (Waters) eluting with $CO_2$/MeOH (0.2% Methanol Ammonia)=60/40 over an IG column 20*250 mm, 10 um (Daicel) at 35° C. [flow rate 10 100 ml/min with a back pressure of 100 bar, detection of 214 nm with a cycle time of 4.0 min) to give #1 (24.0 mg, retention time=1.486 min) and #2 (19.9 mg, retention time=2.164 min) both as white solids.

Example 215

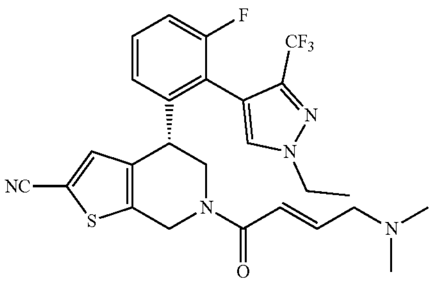 [SMILES: CCn1cc(-c2c(F)cccc2[C@@H]2CN(C(=O)/C=C/CN(C)C)Cc3sc(C#N)cc32)c(C(F)(F)F)n1]

(S,E)-6-(4-(dimethylamino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carb To a solution of (S)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile (210 mg, 0.5 mmol) in DMF (6 mL) were added (E)-4-(dimethylamino)but-2-enoic acid hydrochloride (91.0 mg, 0.55 mmol), HATU (272.0 mg, 0.715 mmol) and DIEA (194.0 mg, 1.5 mmol) at RT. The reaction was stirred overnight. The mixture was diluted with water (30 mL) and extracted with EA (3×15 mL). The combined organic layers were dried over anhydrous $Na_2SO_4$, filtered and concentrated under vacuum to give a residue which was purified by Prep-HPLC (Method A) to give (S,E)-6-(4-(dimethylamino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (88 mg, 0.165 mmol, 33.1% yield) as a brown solid. $^1$H NMR (400 MHz, DMSO-$d_6$) δ 8.33-8.22 (m, 1H), 7.60-7.07 (m, 3H), 6.67-5.83 (m, 3H), 5.23-4.78 (m, 2H), 4.33-4.25 (m, 2H), 4.19-3.93 (m, 2H), 3.52-3.05 (m, 3H), 2.44-2.19 (m, 6H), 1.51-1.44 (m, 3H), LCMS: $(M+H)^+$=532.1, Retention time=1.79 min. LCMS CP Method C HPLC: Retention time=9.108 min. LCMS CP Method F Example 216

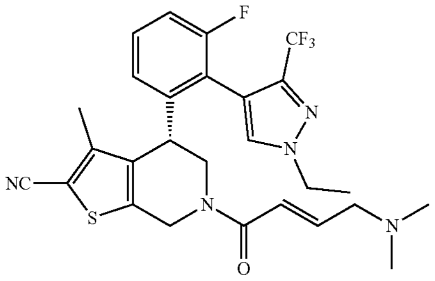 [SMILES: CCn1cc(-c2c(F)cccc2[C@@H]2CN(C(=O)/C=C/CN(C)C)Cc3sc(C#N)c(C)c32)c(C(F)(F)F)n1]

(S,E)-4-(3-fluoro-2-(1-methyl-3-(trifluoromethyl)-1H-pyrazol-4-yl)phenyl)-3-methyl-6-(4-(methylamino)but-2-enoyl)-4,5,6,7-tetrahydrothieno[2,3-c]pyridine-2-carbonitrile Step 1: To a solution of tert-butyl (R)-4-(2-bromo-3-fluorophenyl)-2-cyano-3-methyl-4,7-dihydrothieno[2,3-c]pyridine-6(5H)-carboxylate (200 mg, 0.444 mmol) in a mixed solution of 1,4-dioxane and $H_2O$ (10:1, 3 mL) were added 1-methyl-4-(4,4,5,5-tetramethyl-1,3,2-dioxaborolan-2-yl)-3-(trifluoromethyl)-1H-pyrazole (135 mg, 0.489 mmol), $K_3PO_4$ (188 mg, 0.889 mmol) and Ruphos Pd $G_4$(75.5 mg, 0.0889 mmol). The reaction was stirred at 100° C. for 1 h under microwave then cooled to RT. Water (10 mL) was added and the mixture was extracted with EA (3×10 mL). The combined organic layers were washed with saturated NaCl aqueous solution (20 mL×2), dried over $Na_2SO_4$, filtered and concentrated to give a residue which was purified by silica gel chromatography (PE: EA=3:1) to give a tert-butyl (S)-2-cyano-4-(3-fluoro-2-(1-methyl-3-(trifluoromethyl)-1H-pyrazol-4-yl)phenyl)-3-methyl-4,7-dihydrothieno[2,3-c]pyridine-6(5H)-carboxylate (220 mg, 95.2% yield) as a yellow oil. LCMS: $(M+Na)^+$=543.1, Retention time=1.92 min. LCMS CP method B Step 2: To a solution of tert-butyl (S)-2-cyano-4-(3-fluoro-2-(1-methyl-3-(trifluoromethyl)-1H-pyrazol-4-yl)phenyl)-3-methyl-4,7-dihydrothieno[2,3-c]pyridine-6(5H)-carboxylate (220 mg, 0.423 mmol) in DCM (5 mL) was added TFA (1 mL, Wt 99%) and the reaction was stirred at RT for 1 h. The pH was adjusted to 6-7 with saturated $NaHCO_3$ aqueous solution and the mixture was extracted with DCM (20 mL×3). The combined organic layers were concentrated to give the crude (S)-4-(3-fluoro-2-(1-methyl-3-(trifluoromethyl)-1H-pyrazol-4-yl)phenyl)-3-methyl-4,5,6,7-tetrahydrothieno[2,3-c]pyridine-2-carbonitrile (177 mg, 100% yield) as a yellow oil which was used directly in the next step reaction without further purification. LCMS: $(M+H)^+$=421.0, Retention time=1.54 min. LCMS CP method B Step 3: To a solution of (S)-4-(3-fluoro-2-(1-methyl-3-(trifluoromethyl)-1H-pyrazol-4-yl)phenyl)-3-methyl-4,5,6,7-tetrahydrothieno[2,3-c]pyridine-2-carbonitrile (177 mg, 0.42 mmol) in DCM (5 mL) were added 2-(diethoxyphosphoryl)acetic acid (123 mg, 0.63 mmol), HATU (239 mg, 0.63 mmol) and DIPEA (108 mg, 0.84 mmol). The resulting mixture was stirred at RT for 1 h then water (10 mL) was added. The mixture was extracted with DCM (15 mL×3). The combined organic layers were concentrated and the residue was purified by silica gel chromatography (DCM: MeOH=20:1) to give diethyl (S)-(2-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-2-oxoethyl)phosphonate (247 mg, 98% yield) as a yellow solid. LCMS: $(M+H)^+$=599.1, Retention time=1.94 min. LCMS CP method A Step 4: To a solution of diethyl(2-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-2-oxoethyl)phosphonate (100 mg, 0.167 mmol) in MeCN (3 mL) were added tert-butyl methyl(2-oxoethyl)carbamate (43.4 mg, 0.251 mmol), LiCl (14.04 mg, 0.334 mmol) and DIPEA (43.14 mg, 0.334 mmol) and the reaction was stirred at the RT for 2 h. Then water (10 mL) was added and the mixture was extracted with DCM (3×50 mL). The combined organic layers were concentrated to give a residue which was purified by Prep-HPLC (Method C) to give tert-butyl (S,E)-(4-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-4-oxobut-2-en-1-yl)(methyl)carbamate (50 mg, 48.5% yield) as a white solid. LCMS:$(M-Boc+1)^+$=518.0, Retention time=2.01 min. LCMS CP method G Step 5: To a solution of tert-butyl (S,E)-(4-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-4-oxobut-2-en-1-yl)(methyl)carbamate (50 mg, 0.0810 mmol) in DCM (5 mL) was added TFA (1 mL, Wt 99%) and the reaction was stirred at the RT for 1 h. The mixture was concentrated under reduced pressure to give (S,E)-4-(3-fluoro-2-(1-methyl-3-(trifluoromethyl)-1H-pyrazol-4-yl)phenyl)-3-methyl-6-(4-(methylamino)but-2-enoyl)-4,5,6,7-tetrahydrothieno[2,3-c]pyridine-2-carbonitrile (42.5 mg, 83.1% yield, TFA salt) as a white solid. LCMS:$(M+H)^+$=518.1, purity=100% (214 nm), Retention time=1.52 min. LCMS CP method B $^1$H NMR (400 MHz, DMSO) δ 8.81-8.57 (m, 2H), 8.43-8.12 (m, 1H), 7.34-7.15 (m, 2H), 6.52-6.28 (m, 2H), 5.75-5.51 (m, 1H), 5.40-4.77 (m, 1H), 4.54-4.16 (m, 1H), 4.07-3.99 (m, 3H), 3.90-3.68 (m, 3H), 3.65-3.36 (m, 2H), 2.68-2.58 (m, 1H), 2.40-2.34 (m, 2H), 2.02-1.76 (m, 3H).

Example 217

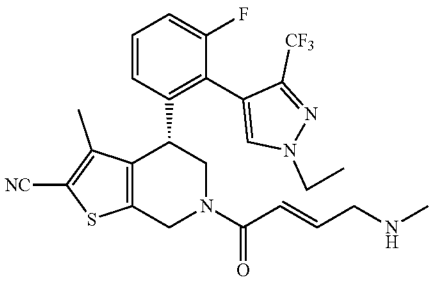 [SMILES: CCn1cc(-c2c(F)cccc2[C@@H]2CN(C(=O)/C=C/CNC)Cc3sc(C#N)c(C)c32)c(C(F)(F)F)n1]

(S,E)-4-(2-(1-ethyl-3-(trifluoromethyl)-1H-pyrazol-4-yl)-3-fluorophenyl)-3-methyl-6-(4-(methylamino)but-2-enoyl)-4,5,6,7-tetrahydrothieno[2,3-c]pyridine-2-carbonitrile Step 1: To a solution of diethyl (S)-(2-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-2-oxoethyl)phosphonate (130 mg, 0.212 mmol) in MeCN (3 mL) were added tert-butyl methyl(2-oxoethyl)carbamate (38.6 mg, 0.223 mmol), LiCl (10.6 mg, 0.255 mmol) and DIPEA (82.7 mg, 0.636 mmol) and the reaction was stirred at the RT for 2 h. The mixture was concentrated and the residue was added water (20 mL). The mixture was extracted with DCM (50 mL×3). The combined organic layers were concentrated to give a residue which was purified by Prep-HPLC (Method B) to afford tert-butyl (S,E)-(4-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-4-oxobut-2-en-1-yl)(methyl)carbamate (50 mg, 37.7% yield) as a white solid. LCMS: $(M+H)^+$=632.3, Retention time=1.899 min. LCMS CP method B Step 2: To a solution of tert-butyl (S,E)-(4-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-4-oxobut-2-en-1-yl)(methyl)carbamate (50 mg, 0.08 mmol) in DCM (5 mL) was added TFA (1 mL) and the reaction was stirred at the RT for 1 h. The mixture was concentrated under reduced pressure to give (S,E)-4-(2-(1-ethyl-3-(trifluoromethyl)-1H-pyrazol-4-yl)-3-fluorophenyl)-3-methyl-6-(4-(methylamino)but-2-enoyl)-4,5,6,7-tetrahydrothieno[2,3-c]pyridine-2-carbonitrile (47.7 mg, 92.5% yield, TFA salt) as a white solid LCMS:$(M+H)^+$=532.2, purity=100% (214 nm), Retention time=1.537 min. LCMS CP method B $^1$H NMR (400 MHz, DMSO) δ 8.72 (s, 2H), 8.57-8.95 (m, 1H), 7.57-6.74 (m, 2H), 6.77-6.18 (m, 2H), 5.65 (dd, J=69.7, 16.7 Hz, 1H), 5.50-4.71 (m, 1H), 4.48-4.33 (m, 3H), 4.24-3.55 (m, 5H), 2.58 (s, 1H), 2.40 (d, J=21.0 Hz, 2H), 2.08-1.76 (m, 3H), 1.59-1.39 (m, 3H).

Example 218

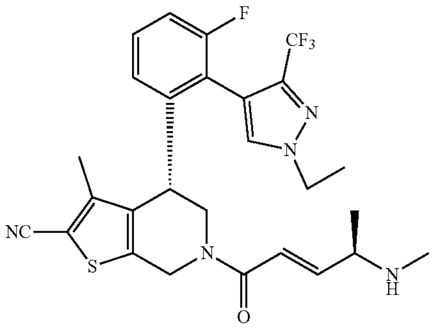 [SMILES: CCn1cc(-c2c(F)cccc2[C@@H]2CN(C(=O)/C=C/[C@@H](C)NC)Cc3sc(C#N)c(C)c32)c(C(F)(F)F)n1]

(S)-4-(2-(1-ethyl-3-(trifluoromethyl)-1H-pyrazol-4-yl)-3-fluorophenyl)-3-methyl-6-((R,E)-4-(methylamino)pent-2-enoyl)-4,5,6,7-tetrahydrothieno[2,3-c]pyridine-2-carbonitrile Step 1: To a solution of diethyl (S)-(2-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-2-oxoethyl)-phosphonate (150 mg, 0.245 mmol) in MeCN (3 mL) were added tert-butyl methyl(2-oxoethyl)-carbamate (63.6 mg, 0.367 mmol), LiCl (20.58 mg, 0.490 mmol) and DIPEA (63.2 mg, 0.490 mmol) and the reaction was stirred at the RT for 3 h. Then water (10 mL) was added and the mixture was extracted with DCM (3×20 mL). The combined organic layers were concentrated to give a residue which was purified by silica gel chromatography (DCM: MeOH=20:1) to give tert-butyl ((R,E)-5-((S)-2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-5-oxopent-3-en-2-yl)(methyl)carbamate (150 mg, 95% yield) as a yellow oil. LCMS: $(M+H)^+$=646.2, Retention time=1.95 min. LCMS CP method B Step 2: To a solution of tert-butyl ((R,E)-5-((S)-2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-5-oxopent-3-en-2-yl)(methyl)carbamate (150 mg, 0.232 mmol) in DCM (5 mL) was added TFA (1 mL, Wt 99%) and the reaction was stirred at the RT for 1 h. The mixture was concentrated under reduced pressure to give a residue which was purified by Prep-HPLC (Method C) to give (S)-4-(2-(1-ethyl-3-(trifluoromethyl)-1H-pyrazol-4-yl)-3-fluorophenyl)-3-methyl-6-((R,E)-4-(methylamino)pent-2-enoyl)-4,5,6,7-tetrahydrothieno[2,3-c]pyridine-2-carbonitrile (36.7 mg, 24% yield, TFA salt) as a white solid. LCMS: $(M+H)^+$=546.2, purity=100% (214 nm), Retention time=1.58 min. LCMS CP method B $^1$H NMR (400 MHz, DMSO) δ 8.76-8.68 (m, 2H), 8.45-8.18 (m, 1H), 7.32-6.84 (m, 2H), 6.55-6.22 (m, 2H), 5.78-5.19 (m, 1H), 4.42-4.25 (m, 3H), 4.23-3.92 (m, 2H), 3.84-3.71 (m, 3H), 3.39-3.36 (m, 1H), 2.43-2.32 (m, 3H), 2.02-1.72 (m, 3H), 1.54-1.44 (m, 3H), 1.35-0.98 (m, 3H).

Example 219

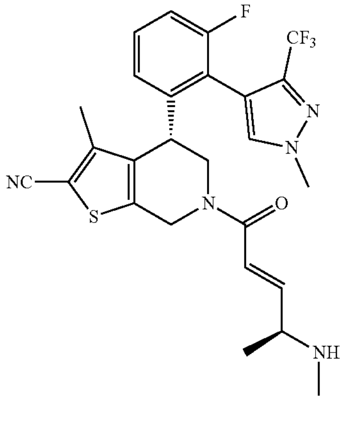 [SMILES: CN[C@@H](C)/C=C/C(=O)N1Cc2sc(C#N)c(C)c2[C@H](c2cccc(F)c2-c2cn(C)nc2C(F)(F)F)C1]

(S)-4-(3-fluoro-2-(1-methyl-3-(trifluoromethyl)-1H-pyrazol-4-yl)phenyl)-3-methyl-6-((S,E)-4-(methylamino)pent-2-enoyl)-4,5,6,7-tetrahydrothieno[2,3-c]pyridine-2-carbonitrile Step 1: To a solution of diethyl (S)-(2-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-2-oxoethyl)phosphonate (280 mg, 0.47 mmol) in MeCN (5 mL) were added tert-butyl (S)-methyl(1-oxopropan-2-yl)

carbamate (97 mg, 0.564 mmol), LiCl (30 mg, 0.705 mmol) and DIPEA (121 mg, 0.94 mmol) and the reaction was stirred at the RT for 3 h. Then water (10 mL) was added and the mixture was extracted with DCM (3×20 mL). The combined organic layers were concentrated to give a residue which was purified by silica gel chromatography (DCM: MeOH=20:1) to give tert-butyl ((S,E)-5-((S)-2-cyano-4-(3-fluoro-2-(1-methyl-3-(trifluoromethyl)-1H-pyrazol-4-yl) phenyl)-3-methyl-4,7-dihydrothieno[2,3-c]pyridin-6(5H)-yl)-5-oxopent-3-en-2-yl)(methyl)carbamate (280 mg, 88.4% yield) as a yellow oil. LCMS: $(M+H)^+$=632.3, Retention time=1.91 min. LCMS CP method B Step 2: To a solution of tert-butyl ((S,E)-5-((S)-2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-5-oxopent-3-en-2-yl)(methyl)carbamate (150 mg, 0.238 mmol) in DCM (3 mL) was added TFA (1 mL, Wt 99%) and the reaction was stirred at the RT for 1 h. The mixture was concentrated to give a residue which was purified by Prep-HPLC (Method C) to give (S)-4-(3-fluoro-2-(1-methyl-3-(trifluoromethyl)-1H-pyrazol-4-yl)phenyl)-3-methyl-6-((S,E)-4-(methylamino)pent-2-enoyl)-4,5,6,7-tetrahydrothieno[2,3-c]pyridine-2-carbonitrile (80.9 mg, 52.7% yield, TFA salt) as a white solid. LCMS:$(M+H)^+$=532.1, purity=100% (214 nm), Retention time=1.54 min. LCMS CP method B $^1H$ NMR (400 MHz, DMSO) δ 8.79-8.69 (m, 2H), 8.42-8.19 (m, 1H), 7.32-6.84 (m, 2H), 6.52-6.19 (m, 2H), 5.78-5.26 (m, 1H), 4.81-4.27 (m, 2H), 4.15-4.01 (m, 4H), 3.98-3.62 (m, 3H), 3.49-3.39 (m, 1H), 2.44-2.34 (m, 3H), 2.02-1.73 (m, 3H), 1.24-1.16 (m, 1H), 1.06-0.98 (m, 2H).

The following compounds were prepared by methods similar to the procedures described above:

| Compound | Structure | M + H |
|---|---|---|
| 220 | 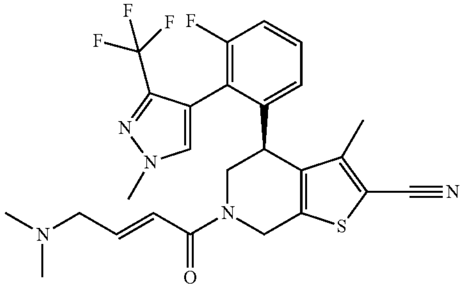 [SMILES: Cc1c(C#N)sc2c1[C@H](c1cccc(F)c1-c1cn(C)nc1C(F)(F)F)CN(C(=O)/C=C/CN(C)C)C2] | 532.3 |
| 221 | 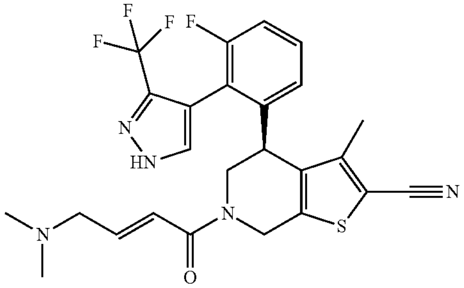 [SMILES: Cc1c(C#N)sc2c1[C@H](c1cccc(F)c1-c1c[nH]nc1C(F)(F)F)CN(C(=O)/C=C/CN(C)C)C2] | 517.9 |
| 222 | 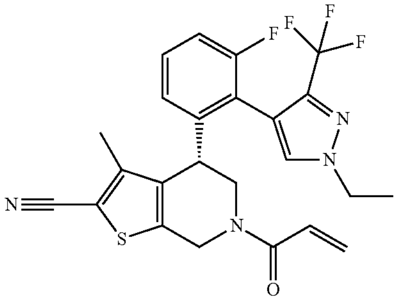 [SMILES: C=CC(=O)N1Cc2sc(C#N)c(C)c2[C@H](c2cccc(F)c2-c2cn(CC)nc2C(F)(F)F)C1] | 489.0 |

-continued
| Compound | Structure | M + H |
|---|---|---|
| 223 | 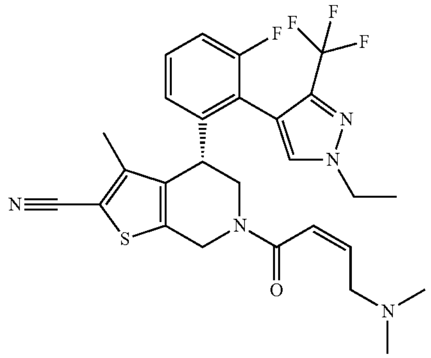 [SMILES: CCn1cc(-c2c(F)cccc2[C@@H]2CN(C(=O)/C=C\CN(C)C)Cc3sc(C#N)c(C)c32)c(C(F)(F)F)n1] | 546.0 |
| 224 | 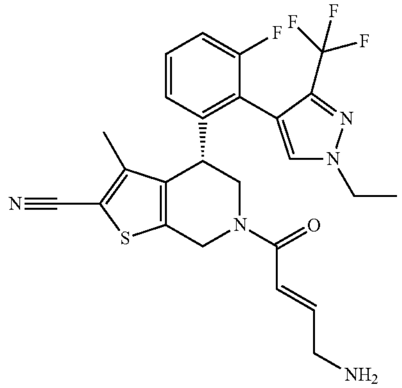 [SMILES: CCn1cc(-c2c(F)cccc2[C@@H]2CN(C(=O)/C=C/CN)Cc3sc(C#N)c(C)c32)c(C(F)(F)F)n1] | 518.2 |
| 225 | 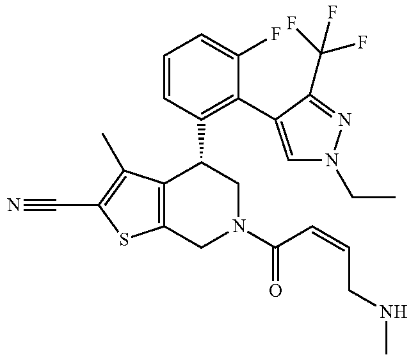 [SMILES: CCn1cc(-c2c(F)cccc2[C@@H]2CN(C(=O)/C=C\CNC)Cc3sc(C#N)c(C)c32)c(C(F)(F)F)n1] | 532.2 |
| 226 | 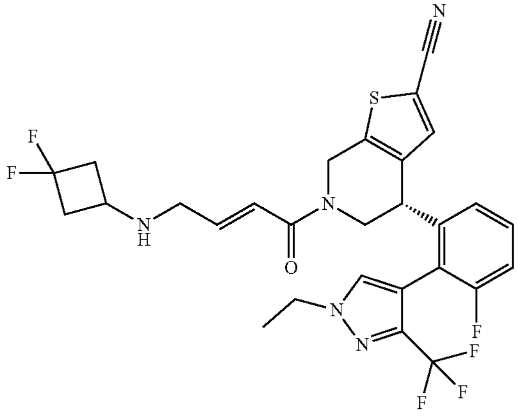 [SMILES: CCn1cc(-c2c(F)cccc2[C@@H]2CN(C(=O)/C=C/CNC3CC(F)(F)C3)Cc3sc(C#N)cc32)c(C(F)(F)F)n1] | 595.1 |

-continued
| Compound | Structure | M + H |
| --- | --- | --- |
| 227 | 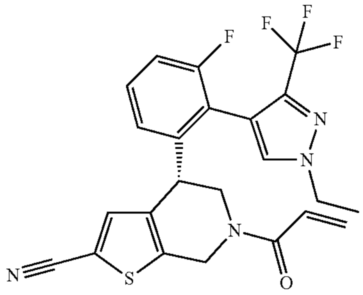 [SMILES: C=CC(=O)N1Cc2sc(C#N)cc2[C@H](c2cccc(F)c2-c2cn(CC)nc2C(F)(F)F)C1] | 475.2 |
| 228 | 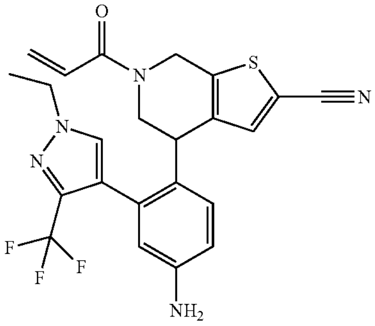 [SMILES: C=CC(=O)N1Cc2sc(C#N)cc2C(c2ccc(N)cc2-c2cn(CC)nc2C(F)(F)F)C1] | 472.2 |
| 229 | 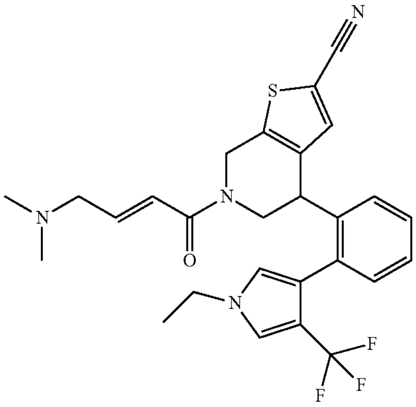 [SMILES: CCn1cc(-c2ccccc2C2CN(C(=O)/C=C/CN(C)C)Cc3sc(C#N)cc32)c(C(F)(F)F)c1] | 514.2 |
| 230 | 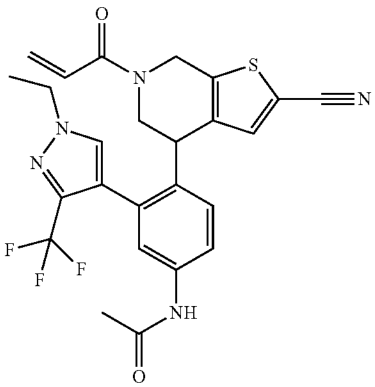 [SMILES: C=CC(=O)N1Cc2sc(C#N)cc2C(c2ccc(NC(C)=O)cc2-c2cn(CC)nc2C(F)(F)F)C1] | 514.2 |

-continued
| Compound | Structure | M + H |
|---|---|---|
| 231 | 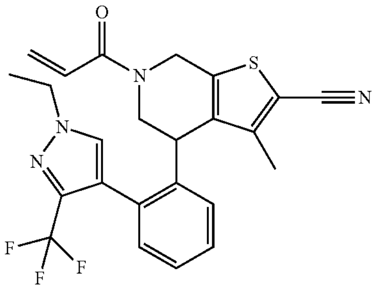 [SMILES: C=CC(=O)N1Cc2sc(C#N)c(C)c2C(c2ccccc2-c2cn(CC)nc2C(F)(F)F)C1] | 471.1 |
| 232 | 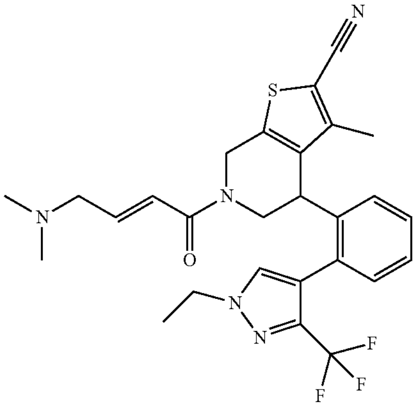 [SMILES: CCn1cc(-c2ccccc2C2CN(C(=O)/C=C/CN(C)C)Cc3sc(C#N)c(C)c32)c(C(F)(F)F)n1] | 528.3 |
| 233 | 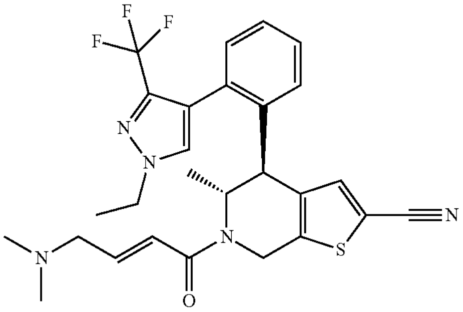 [SMILES: CCn1cc(-c2ccccc2[C@H]2c3cc(C#N)sc3CN(C(=O)/C=C/CN(C)C)[C@@H]2C)c(C(F)(F)F)n1] | 528.3 |
| 234 | 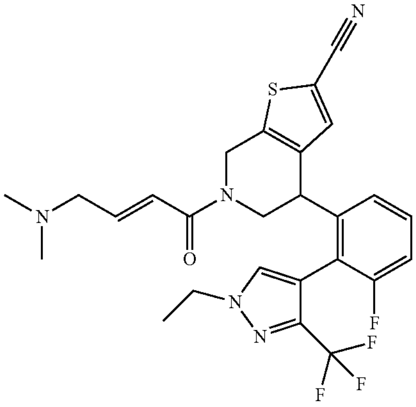 [SMILES: CCn1cc(-c2c(F)cccc2C2CN(C(=O)/C=C/CN(C)C)Cc3sc(C#N)cc32)c(C(F)(F)F)n1] | 532.2 |

-continued
| Compound | Structure | M + H |
|---|---|---|
| 235 | 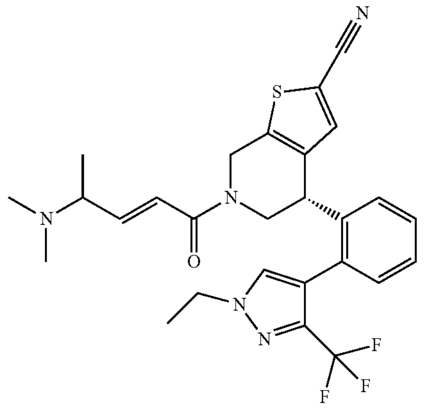 [SMILES: CCn1cc(-c2ccccc2[C@@H]2CN(C(=O)/C=C/C(C)N(C)C)Cc3sc(C#N)cc32)c(C(F)(F)F)n1] | 528 |
| 236 | 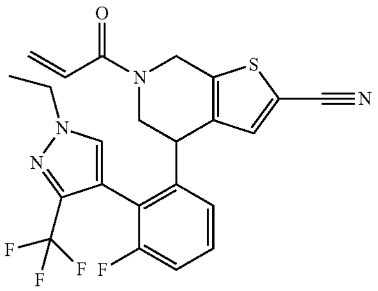 [SMILES: C=CC(=O)N1Cc2sc(C#N)cc2C(c2cccc(F)c2-c2cn(CC)nc2C(F)(F)F)C1] | 475.2 |
| 237 | 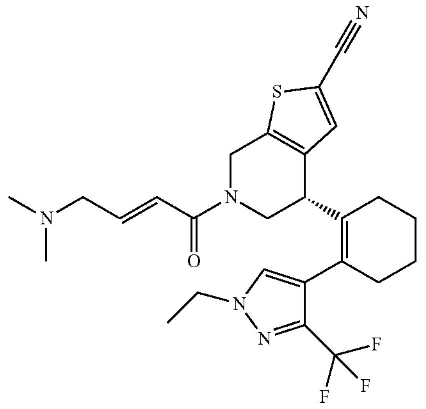 [SMILES: CCn1cc(C2=C([C@@H]3CN(C(=O)/C=C/CN(C)C)Cc4sc(C#N)cc43)CCCC2)c(C(F)(F)F)n1] | 518 |
| 238 | 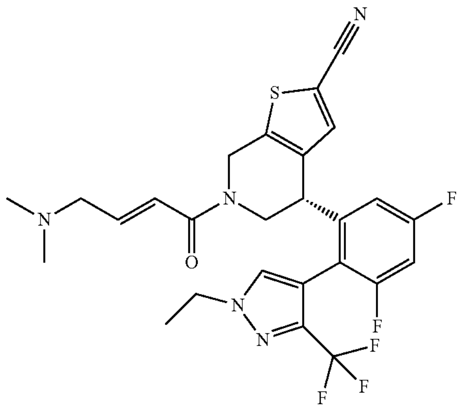 [SMILES: CCn1cc(-c2c(F)cc(F)cc2[C@@H]2CN(C(=O)/C=C/CN(C)C)Cc3sc(C#N)cc32)c(C(F)(F)F)n1] | 549.9 |

-continued
| Compound | Structure | M + H |
|---|---|---|
| 239 | 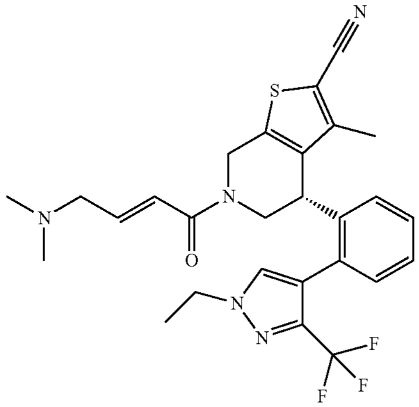 [SMILES: CCn1cc(-c2ccccc2[C@@H]2CN(C(=O)/C=C/CN(C)C)Cc3sc(C#N)c(C)c32)c(C(F)(F)F)n1] | 528 |
| 240 | 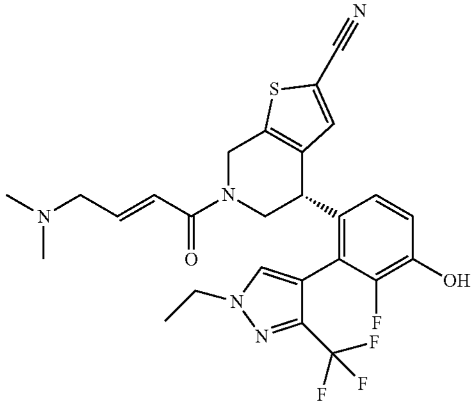 [SMILES: CCn1cc(-c2c([C@@H]3CN(C(=O)/C=C/CN(C)C)Cc4sc(C#N)cc43)ccc(O)c2F)c(C(F)(F)F)n1] | 548 |
| 241 | 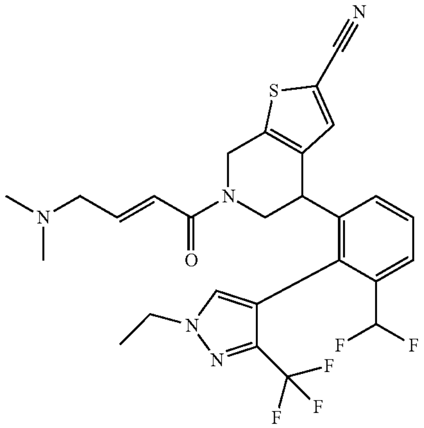 [SMILES: CCn1cc(-c2c(C(F)F)cccc2C2CN(C(=O)/C=C/CN(C)C)Cc3sc(C#N)cc32)c(C(F)(F)F)n1] | 564.3 |

-continued
| Compound | Structure | M + H |
|---|---|---|
| 242 | 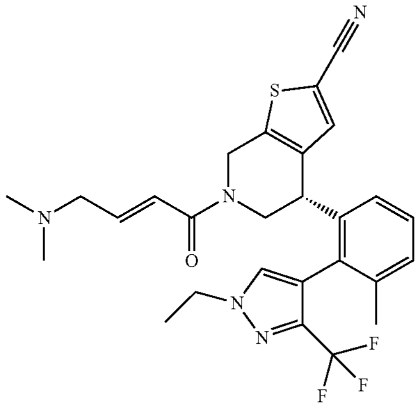 [SMILES: CCn1cc(-c2c(C)cccc2[C@@H]2CN(C(=O)/C=C/CN(C)C)Cc3sc(C#N)cc32)c(C(F)(F)F)n1] | 528.1 |
| 243 | 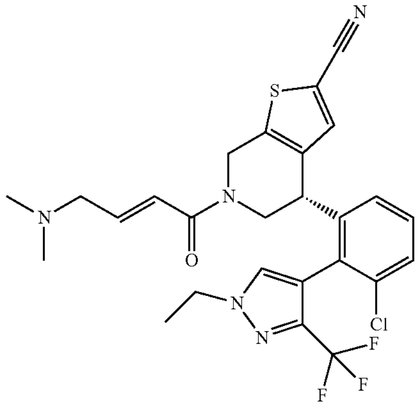 [SMILES: CCn1cc(-c2c(Cl)cccc2[C@@H]2CN(C(=O)/C=C/CN(C)C)Cc3sc(C#N)cc32)c(C(F)(F)F)n1] | 548 |
| 244 | 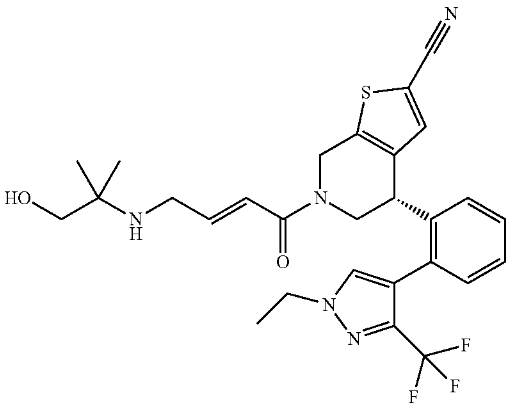 [SMILES: CCn1cc(-c2ccccc2[C@@H]2CN(C(=O)/C=C/CNC(C)(C)CO)Cc3sc(C#N)cc32)c(C(F)(F)F)n1] | 558.3 |

-continued

| Compound | Structure | M + H |
|---|---|---|
| 247 | 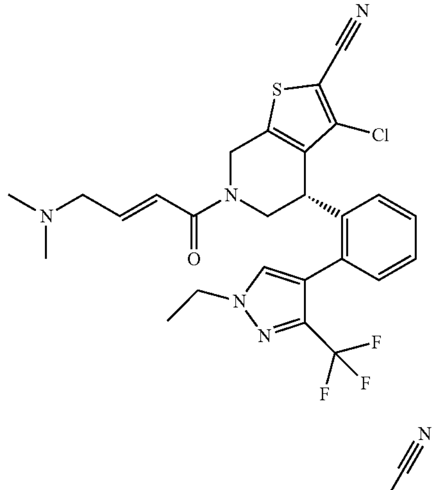 | 548 |
| 248 | 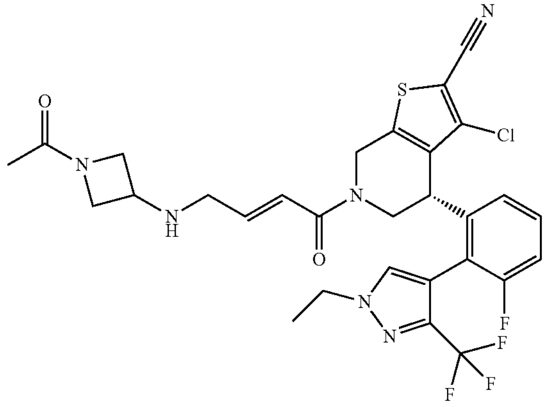 [SMILES: CCn1cc(-c2c(F)cccc2[C@@H]2CN(C(=O)/C=C/CNC3CN(C(C)=O)C3)Cc3sc(C#N)c(Cl)c32)c(C(F)(F)F)n1] | 601.1 |

Example 245

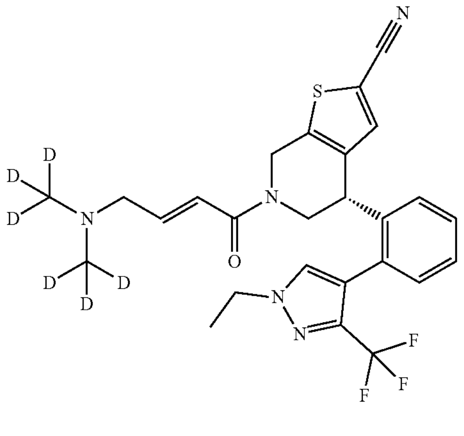 [SMILES: [2H]C([2H])([2H])N(C/C=C/C(=O)N1Cc2sc(C#N)cc2[C@H](c2ccccc2-c2cn(CC)nc2C(F)(F)F)C1)C([2H])([2H])[2H]]

(S,E)-6-(4-(bis(methyl-d3)amino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile Step 1: To a solution of methyl (E)-4-((tert-butoxycarbonyl)amino)but-2-enoate (1.3 g, 6.05 mmol) in THE (20 ml) and $H_2O$ (4 ml) was added LiOH (290 mg, 12.1 mmol) and the reaction was stirred at RT for 16 h. The pH was adjusted to 5-6 with 1 M HCl and the resulting mixture was extracted with DCM/MeOH (30 ml*3, 10/1). The combined organic phases were washed with brine, dried over $Na_2SO_4$, filtered and concentrated to afford (E)-4-((tert-butoxycarbonyl)amino)but-2-enoic acid (900 mg, 74%) as a colorless oil which was used directly in the next step reaction without further purification. LCMS:$(M+H)^+$=202.0, Retention time=1.32 min. LCMS CP method B Step 2: To a mixture of (E)-4-((tert-butoxycarbonyl)amino)but-2-enoic acid (step 1, 201 mg, 1 mmol), (S)-4-(2-(1-ethyl-3-(trifluoromethyl)-1H-pyrazol-4-yl)phenyl)-4,5,6,7-tetrahydrothieno[2,3-c]pyridine-2-carbonitrile (362 mg, 0.9 mmol) and HATU (410 mg, 1.08 mmol) in DMF (10 ml) was added DIPEA (348 mg, 2.7 mmol). The reaction was stirred at RT for 16 h. $H_2O$ (50 ml) was added and the mixture was extracted with EA (3×30 ml). The combined organic phases were washed with brine, dried over $Na_2SO_4$, filtered and concentrated. The residue was purified by com-flash (20% EA in PE) to afford tert-butyl (S,E)-(4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)carbamate (150 mg, 28%) as a yellow solid. LCMS: $(M+H)^+$=530.0, Retention time=1.72 min. LCMS CP method D Step 3: To a solution of tert-butyl (S,E)-(4-(2-cyano-4-(2-(1-ethyl-3-(trifluoromethyl)-1H-pyrazol-4-yl)phenyl)-4,7-dihydrothieno[2,3-c]pyridin-6(5H)-yl)-4-oxobut-2-en-1-yl)carbamate (Step 2, 150 mg, 0.26 mmol) in DCM (5 ml) was added TFA (0.5 ml). The reaction was stirred at RT for 1 h. The mixture was concentrated and the pH was adjusted to 8-9 with 1 M NaOH. The resulting mixture was extracted with DCM (3×30 ml) and the combined organic phases were washed with brine, dried over $Na_2SO_4$, filtered and concentrated to afford (S,E)-6-(4-aminobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (90 mg, 73%) as a yellow oil. LCMS: $(M+H)^+$=485.9, Retention time=1.52 min. LCMS CP method D Step 4: To a mixture of (S,E)-6-(4-aminobut-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (step 3, 90 mg, 0.16 mmol) and formaldehyde-d2 (256 mg, 1.6 mmol, 20% in $D_2O$) in MeOD (5 ml) was added NaBD4 (20 mg, 0.48 mmol). The reaction was stirred at RT for 16 h. $H_2O$ (20 ml) was added and the mixture was extracted with DCM (3×20 ml). The combined organic phases were washed with brine, dried over $Na_2SO_4$, filtered and concentrated. The residue was purified by Prep-HLPC (Method A) to afford (S,E)-6-(4-(bis(methyl-d3)amino)but-2-enoyl)-4-(2-(1-ethyl-3-(trifluoromethyl)-1H-pyrazol-4-yl)phenyl)-4,5,6,7-tetrahydrothieno[2,3-c]pyridine-2-carbonitrile (61.7 mg, 74%) as a white solid. LCMS:$(M+H)^+$=520.2, Retention time=1.45 min. LCMS CP method A 1H NMR (400 MHz, DMSO) δ: 8.29 (s, 1H), 7.40-7.24 (m, 4H), 7.01-6.75 (m, 1H), 6.62-6.45 (m, 1H), 5.88 (d, J=15.2 Hz, 1H), 5.08-4.79 (m, 2H), 4.30-4.25 (m, 2H), 4.16 (s, 1H), 3.98-3.57 (m, 2H), 3.05-2.81 (m, 2H), 1.46 (t, J=7.2 Hz, 3H).

Example 246

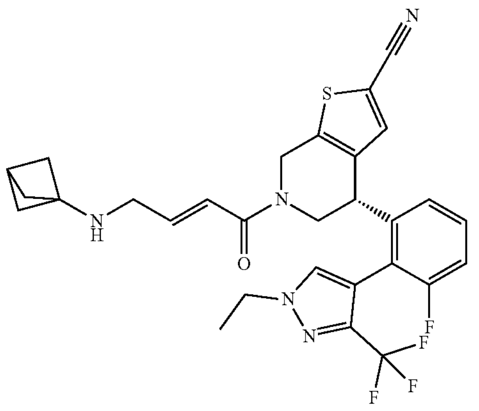 [SMILES: CCn1cc(-c2c(F)cccc2[C@@H]2CN(C(=O)/C=C/CNC34CC(C3)C4)Cc3sc(C#N)cc32)c(C(F)(F)F)n1]

(S,E)-6-(4-(bicyclo[1.1.1]pentan-1-ylamino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile Step 1: To a mixture of bicyclo[1.1.1]pentan-1-amine (112 mg, 1.35 mmol) and $K_2CO_3$ (310 mg, 2.25 mmol) in $CH_3CN$ was added methyl (E)-4-bromobut-2-enoate (200 mg, 1.125 mmol). The reaction was stirred at RT overnight. The mixture was filtered and the filtrates were concentrated. The residue was purified by com-flash (40% EA in PE) to afford methyl (E)-4-(bicyclo[1.1.1]pentan-1-ylamino)but-2-enoate (80 mg, 39%) as a white solid. LCMS:$(M+H)^+$=182.1, Retention time=1.48 min. LCMS CP method C.

Step 2: To a solution of methyl (E)-4-(bicyclo[1.1.1]pentan-1-ylamino)but-2-enoate (step 1, 80 mg, 0.44 mmol) in MeOH (4 ml) and $H_2O$ (1 ml) was added NaOH (35 ml, 0.88 mmol) and the reaction was stirred at RT for 2 h. The pH value was adjusted to 5-6 with 1 M HCl and the mixture was concentrated to afford (E)-4-(bicyclo[1.1.1]pentan-1-ylamino)but-2-enoic acid (73 mg, 100%) as a white solid which was used directly in the next step without further purification. LCMS: $(M+H)^+$=168.1, Retention time=0.36 min. LCMS CP method C Step 3: To a mixture of (E)-4-(bicyclo[1.1.1]pentan-1-ylamino)but-2-enoic acid step 2, (73 mg, 0.44 mmol), (S)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile (168 mg, 0.4 mmol) and HATU (167 mg, 0.44 mmol) in DMF (5 ml) was added DIPEA (155 mg, 1.2 mmol). The reaction was stirred at RT for 2h. $H_2O$ (25 ml) was added and the mixture was extracted with EA (3×20 ml). The combined organic phases were washed with brine, dried over $Na_2SO_4$, filtered and concentrated. The residue was purified by Prep-HLPC (Method C) to afford (S,E)-6-(4-(bicyclo[1.1.1]pentan-1-ylamino)but-2-enoyl)-4-(2-(1-ethyl-3-(trifluoromethyl)-1H-pyrazol-4-yl)-3-fluorophenyl)-4,5,6,7-tetrahydrothieno[2,3-c]pyridine-2-carbonitrile TFA salt (37.8 mg, 14%) as a white solid. LCMS: $(M+H)^+$=570.1, Retention time=1.62 min. LCMS CP method A 1H NMR (400 MHz, DMSO) δ: 9.66-9.57 (m, 2H), 8.42-8.25 (m, 1H), 7.62-7.22 (m, 3H), 7.05-6.43 (m, 2H), 6.04 (d, J=15.2 Hz, 1H), 5.11-4.88 (m, 2H), 4.38-3.97 (m, 4H), 3.92-3.72 (m, 3H), 2.68 (s, 1H), 2.01-1.95 (m, 6H), 1.50-1.44 (m, 3H).

Example 249

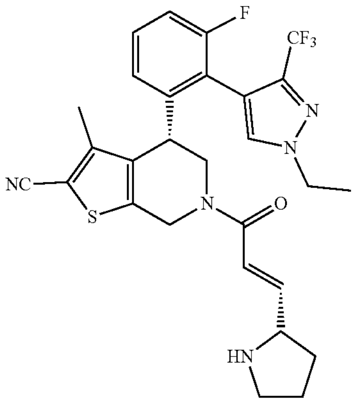

(S)-4-(2-(1-ethyl-3-(trifluoromethyl)-1H-pyrazol-4-yl)-3-fluorophenyl)-3-methyl-6-((E)-3-((S)-pyrrolidin-2-yl)acryloyl)-4,5,6,7-tetrahydrothieno[2,3-c]pyridine-2-carbonitrile Step 1: To a solution of tert-butyl (R)-4-(2-bromo-3-fluorophenyl)-2-cyano-3-methyl-4,7-dihydrothieno[2,3-c]pyridine-6(5H)-carboxylate (450 mg, 1.0 mmol) in 1,4-dioxane (5 mL) and water (1 ml) were added 1-ethyl-4-(4,4,5,5-tetramethyl-1,3,2-dioxaborolan-2-yl)-3-(trifluoromethyl)-1H-pyrazole (348 mg, 1.2 mmol), $K_3PO_4$ (412 mg, 2.0 mmol) and RuphosPdG4 (170 mg, 0.2 mmol). The reaction was stirred at 100° C. under microwave for 2 h. After cooling to RT, $H_2O$ (30 ml) was added and the mixture was extracted with DCM (20 mL×3). The combined organic layers were washed with brine, dried over $Na_2SO_4$, filtered and concentrated to give a residue which was purified by silica gel chromatography (PE:EA=5:1) to give tert-butyl(S)-2-cyano-4-(2-(1-ethyl-3-(trifluoromethyl)-1H-pyrazol-4-yl)-3-fluorophenyl)-3-methyl-4,7-dihydrothieno [2,3-c]pyridine-6(5H)-carboxylate (401 mg, 74%) as a yellow solid. LCMS: $(M+Na)^+$=557.2, Retention time=2.201 min. LCMS CP Method A Step 2: To a solution of tert-butyl (S)-2-cyano-4-(2-(1-ethyl-3-(trifluoromethyl)-1H-pyrazol-4-yl)-3-fluorophenyl)-3-methyl-4,7-dihydrothieno[2,3-c]pyridine-6(5H)-carboxylate (step 1, 401 mg, 0.74 mmol) in DCM (5 mL) was added TFA (1.0 mL). The reaction was stirred at RT for 2 h. The mixture was concentrated and the pH value was adjusted pH=8-9 with saturated aqueous solution of $NaHCO_3$. The mixture was extracted with DCM (20 mL×3). The combined organic layers were washed with brine, dried over $Na_2SO_4$, filtered and concentrated to afford (S)-4-(2-(1-ethyl-3-(trifluoromethyl)-1H-pyrazol-4-yl)-3-fluorophenyl)-3-methyl-4,5,6,7-tetrahydrothieno[2,3-c]pyridine-2-carbonitrile (303 mg, 97.2%) as a yellow oil. LCMS:$(M+H)^+$=435.1, Retention time=1.56 min. LCMS CP method A Step 3: To a solution of (S)-4-(2-(1-ethyl-3-(trifluoromethyl)-1H-pyrazol-4-yl)-3-fluorophenyl)-3-methyl-4,5,6,7-tetrahydrothieno[2,3-c]pyridine-2-carbonitrile (step 2, 303 mg, 0.70 mmol) in DCM (8 mL) were added 2-(diethoxyphosphoryl)acetic acid (164 mg, 0.84 mmol), HATU (433 mg, 1.14 mmol) and DIPEA (148 mg, 1.14 mmol). The reaction was stirred at RT for 2 h. $H_2O$ (10 mL) was added and the mixture was extracted with DCM (15 mL×3). The combined organic layers were washed with brine, dried over $Na_2SO_4$, filtered and concentrated. The residue was purified by silica gel chromatography (PE:EA=10:1) to afford diethyl (S)-(2-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-2-oxoethyl)phosphonate (410 mg, 95.7%) as a yellow solid. LCMS:$(M+H)^+$=613.2, Retention time=2.00 min. LCMS CP method A.

Step 4: To a mixture of diethyl (S)-(2-(2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-2-oxoethyl)phosphonate (130 mg, 0.212 mmol) in MeCN (3 mL) were added tert-butyl (S)-2-formylpyrrolidine-1-carboxylate (35 mg, 0.175 mmol), LiCl (8.5 mg, 0.2 mmol) and DIPEA (65 mg, 0.501 mmol) and the reaction was stirred at RT for 2 h. $H_2O$ (15 ml) was added and the mixture was extracted with DCM (30 mL×3). The combined organic layers were washed with brine, dried over $Na_2SO_4$, filtered and concentrated. The residue was purified by Prep-HPLC (Method C) to give tert-butyl (S)-2-((E)-3-((S)-2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-3-oxoprop-1-en-1-yl)pyrrolidine-1-carboxylate (121.8 mg, 87.26%) as a white solid. LCMS:$(M-Boc)^+$=558.1, Retention time=2.25 min. LCMS CP method A.

Step 5: To a solution of tert-butyl (S)-2-((E)-3-((S)-2-cyano-4-(2-(1-ethyl-3-(trifluoromethyl)-1H-pyrazol-4-yl)-3-fluorophenyl)-3-methyl-4,7-dihydrothieno[2,3-c]pyridin-6(5H)-yl)-3-oxoprop-1-en-1-yl)pyrrolidine-1-carboxylate (step 4, 50 mg, 0.08 mmol) in DCM (5 mL) was added TFA (0.5 mL). The reaction was stirred at RT for 2 h. The solvent was removed solvent in vacuum to give (S)-4-(2-(1-ethyl-3-(trifluoromethyl)-1H-pyrazol-4-yl)-3-fluorophenyl)-3-methyl-6-((E)-3-((S)-pyrrolidin-2-yl)acryloyl)-4,5,6,7-tetrahydrothieno[2,3-c]pyridine-2-carbonitrile TFA salt (124.4 mg, 100%) as a white solid. LCMS:$(M+H)^+$=558.0, Retention time=1.58 min. LCMS CP method B $^1H$ NMR (400 MHz, DMSO) δ 9.16-9.04 (m, 1H), 8.79-8.70 (m, 1H), 8.43-7.17 (m, 1H), 7.30-7.17 (m, 2H), 6.87-6.22 (m, 2H), 5.74-5.52 (m, 1H), 5.19-4.85 (m, 1H), 4.37-4.30 (m, 3H), 4.24-4.14 (m, 2H), 3.82-3.75 (m, 2H), 3.64-3.54 (m, 1H), 3.22-3.10 (m, 2H), 2.02-1.72 (m, 7H), 1.5-1.46 (m, 3H).

Example 250

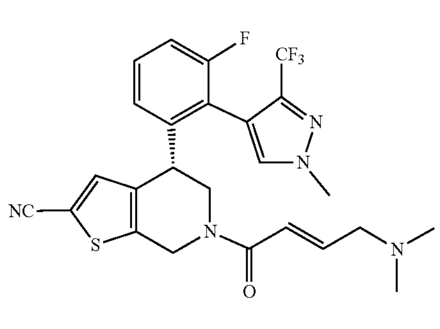 [SMILES: CN(C)C/C=C/C(=O)N1Cc2sc(C#N)cc2[C@H](c2cccc(F)c2-c2cn(C)nc2C(F)(F)F)C1]

Step 1: To a mixture of (R)-tert-butyl 4-(2-bromo-3-fluorophenyl)-2-cyano-4,5-dihydrothieno[2,3-c]pyridine-6 (7H)-carboxylate (460 mg, 1.05 mmol), 1-methyl-4-(4,4,5,5-tetramethyl-1,3,2-dioxaborolan-2-yl)-3-(trifluoromethyl)-1H-pyrazole (306 mg, 1.1 mmol) and $K_3PO_4$ (445 mg, 2.1 mmol) in dioxane (5 ml) and $H_2O$ (1 ml) was added RuPhos Pd G4 (179 mg, 0.21 mmol) and the mixture was stirred at 110° C. under microwave for 2 h. After the mixture was cooled to RT, $H_2O$ (20 ml) was added and the mixture was extracted with DCM (20 ml×3). The combined organic phases were washed with brine, dried over $Na_2SO_4$, filtered and concentrated. The residue was purified by Prep-TLC (PE: EA=5: 1) to afford (S)-tert-butyl 2-cyano-4-((S)-3-fluoro-2-(1-methyl-3-(trifluoromethyl)-1H-pyrazol-4-yl) phenyl)-4,5-dihydrothieno[2,3-c]pyridine-6(7H)-carboxylate (350 mg, 66%) as a yellow solid. LCMS: $(M+Na)^+$=529.0; Retention time=2.21 min. LCMS CP Method A.

Step 2: To a solution of (S)-tert-butyl 2-cyano-4-((S)-3-fluoro-2-(1-methyl-3-(trifluoromethyl)-1H-pyrazol-4-yl) phenyl)-4,5-dihydrothieno[2,3-c]pyridine-6(7H)-carboxylate (step 1, 350 mg, 0.69 mmol) in DCM (5 ml) was added TFA (1 ml) and the mixture was stirred at RT for 2 h. The mixture was concentrated and the pH value of the residue was adjusted to 8-9 with a saturated solution of $NaHCO_3$. The combined organic phases were washed with brine, dried over $Na_2SO_4$, filtered and concentrated to afford (S)-4-((S)-3-fluoro-2-(1-methyl-3-(trifluoromethyl)-1H-pyrazol-4-yl) phenyl)-4,5,6,7-tetrahydrothieno[2,3-c]pyridine-2-carbonitrile (260 mg, 93%) as a yellow solid. LCMS: $(M+H)^+$=407.1; Retention time=1.48 min. LCMS CP Method A.

Step 3: To mixture of (S)-4-((S)-3-fluoro-2-(1-methyl-3-(trifluoromethyl)-1H-pyrazol-4-yl)phenyl)-4,5,6,7-tetrahydrothieno[2,3-c]pyridine-2-carbonitrile (step 2, 140 mg, 0.345 mmol), (E)-4-(dimethylamino)but-2-enoic acid (54 mg, 0.414 mmol) and HATU (197 mg, 0.518 mmol) in DCM (5 ml) was added DIPEA (89 mg, 0.69 mmol) and the mixture was stirred at RT for 2 h. Water (20 ml) was added and the mixture was extracted with DCM (20 ml×3). The combined organic phases were washed with brine, dried over $Na_2SO_4$, filtered and concentrated. The residue was purified by Prep-HPLC (Method A) to afford (S)-6-((E)-4-(di methylamino)but-2-enoyl)-4-((S)-3-fluoro-2-(1-methyl-3-(trifluoromethyl)-1H-pyrazol-4-yl)phenyl)-4,5,6,7-tetrahydrothieno[2,3-c]pyridine-2-carbonitrile (100.1 mg, 56%) as a white solid. LCMS: $(M+H)^+$=517.9; Retention time=1.49 min. LCMS CP Method D $^1H$ NMR (400 MHz, DMSO) δ: 8.32-8.27 (m, 1H), 7.65-7.06 (m, 3H), 6.86-6.42 (m, 2H), 6.19-5.78 (m, 1H), 5.07-4.69 (m, 2H), 4.18 3.96 (m, 4H), 3.88-3.57 (m, 2H), 3.06-2.51 (m, 2H), 2.17-2.04 (m, 6H).

Example 251

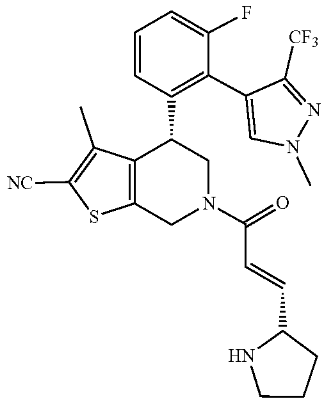

(S)-4-(3-fluoro-2-(1-methyl-3-(trifluoromethyl)-1H-pyrazol-4-yl)phenyl)-3-methyl-6-((E)-3-((S)-pyrrolidin-2-yl)acryloyl)-4,5,6,7-tetrahydrothieno[2,3-c]pyridine-2-carbonitrile Step 1: To a solution of tert-butyl 4-(2-bromo-3-fluorophenyl)-2-cyano-3-methyl-4,7-dihydrothieno[2,3-c]pyridine-6(5H)-carboxylate (450 mg, 1.0 mmol) in 1,4-dioxane (5 mL) and water (1 ml) were added 1-methyl-4-(4,4,5,5-tetramethyl-1,3,2-dioxaborolan-2-yl)-3-(trifluoromethyl)-1H-pyrazole (331.2 mg, 1.2 mmol), $K_3PO_4$ (412 mg, 2.0 mmol) and RuphosPd$G_4$ (170 mg, 0.2 mmol). The reaction was stirred at 100° C. under microwave for 2 h. After cooling to RT, $H_2O$ (20 ml) was added and the mixture was extracted with DCM (30 mL×3). The combined organic layers were washed with brine, dried over $Na_2SO_4$, filtered and concentrated. The residue was purified by silica gel chromatography (PE:EA=5:1) to afford tert-butyl 2-cyano-4-(3-fluoro-2-(1-methyl-3-(trifluoromethyl)-1H-pyrazol-4-yl)phenyl)-3-methyl-4,7-dihydrothieno[2,3-c]pyridine-6(5H)-carboxylate (401 mg, 76.9%) as a yellow solid. LCMS: $(M+Na)^+$=543.1, Retention time=2.25 min. LCMS CP Method A.

Step 2: To a solution of tert-butyl 2-cyano-4-(3-fluoro-2-(1-methyl-3-(trifluoromethyl)-1H-pyrazol-4-yl)phenyl)-3-methyl-4,7-dihydrothieno[2,3-c]pyridine-6(5H)-carboxylate (step 1, 401 mg, 0.77 mmol) in DCM (10 mL) was added TFA (2.0 mL) and the reaction was stirred at RT for 2 h. The mixture was concentrated and the pH value of the residue was adjusted to 8-9 with saturated solution of $NaHCO_3$. The mixture was extracted with DCM (20 mL×3). The combined organic layers were washed with brine, dried over $Na_2SO_4$, filtered and concentrated to afford 4-(3-fluoro-2-(1-methyl-3-(trifluoromethyl)-1H-pyrazol-4-yl)phenyl)-3-methyl-4,5,6,7-tetrahydrothieno[2,3-c]pyridine-2-carbonitrile (250 mg, 76.6%) as a yellow solid. LCMS:$(M+H)^+$=421.0, Retention time=1.532 min. LCMS CP method A.

Step 3: To a solution of 4-(3-fluoro-2-(1-methyl-3-(trifluoromethyl)-1H-pyrazol-4-yl)phenyl)-3-methyl-4,5,6,7-tetrahydrothieno[2,3-c]pyridine-2-carbonitrile (step 2, 250 mg, 0.59 mmol) in DCM (8 mL) were added 2-(diethoxyphosphoryl)acetic acid (128 mg, 0.65 mmol), HATU (336 mg, 0.885 mmol) and DIPEA (115 mg, 0.885 mmol). The reaction was stirred at RT for 2 h. $H_2O$ (20 mL) was added and the mixture was extracted with DCM (20 mL×3). The combined organic layers were washed with brine, dried over $Na_2SO_4$, filtered and concentrated. The residue was purified by silica gel chromatography (DCM:MeOH=30:1) to afford diethyl(2-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-2-oxoethyl)phosphonate (156 mg, 44.2%) as a yellow solid. LCMS:$(M+H)^+$=599.1, Retention time=1.93 min·LCMS CP method A.

Step 4: To a solution of diethyl(2-(2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-2-oxoethyl)phosphonate (step 3, 100 mg, 0.167 mmol) in MeCN (4 mL) were added tert-butyl (S)-2-formylpyrrolidine-1-carboxylate (35 mg, 0.175 mmol), LiCl (8.5 mg, 0.2 mmol) and DIPEA (65 mg, 0.501 mmol) and the mixture was stirred at RT for 2 h. $H_2O$ (20 mL) was added and the mixture was extracted with EA (20 mL×3). The combined organic layers were washed with brine, dried over $Na_2SO_4$, filtered and concentrated. The residue was purified by Prep-HPLC (Method C) to afford tert-butyl (S)-2-((E)-3-((S)-2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-3-oxoprop-1-en-1-yl)pyrrolidine-1-carboxylate (37 mg, 34.4%) as a white solid. LCMS:$(M\text{-}Boc+H)^+$=544.1, Retention time=2.20 min. LCMS CP method A.

Step 5: To a solution of tert-butyl (S)-2-((E)-3-((S)-2-cyano-4-(3-fluoro-2-(1-methyl-3-(trifluoromethyl)-1H-pyrazol-4-yl)phenyl)-3-methyl-4,7-dihydrothieno[2,3-c]pyridin-6(5H)-yl)-3-oxoprop-1-en-1-yl)pyrrolidine-1-carboxylate (37 mg, 0.057 mmol) in DCM (3 mL) was added TFA (0.5 mL) and the mixture was stirred at RT for 2 h. The mixture was concentrated to remove the solvent in vacuum to afford (S)-4-(3-fluoro-2-(1-methyl-3-(trifluoromethyl)-1H-pyrazol-4-yl)phenyl)-3-methyl-6-((E)-3-((S)-pyrrolidin-2-yl)acryloyl)-4,5,6,7-tetrahydrothieno[2,3-c]pyridine-2-carbonitrile (41.6 mg, 100%)(TFA salt) as a white solid. LCMS:$(M+H)^+$=544.2, Retention time=1.52 min. LCMS CP method B $^1H$ NMR (400 MHz, DMSO) δ 9.16-8.70 (m, 2H), 8.41-8.14 (m, 1H), 7.28-7.17 (m, 2H), 6.84-6.44 (m, 2H), 6.33-6.22 (m, 2H), 5.74-5.52 (m, 1H), 4.44-4.14 (m, 3H), 4.04-3.50 (m, 5H), 3.18-3.15 (m, 2H), 2.02-1.70 (m, 7H).

Example 252

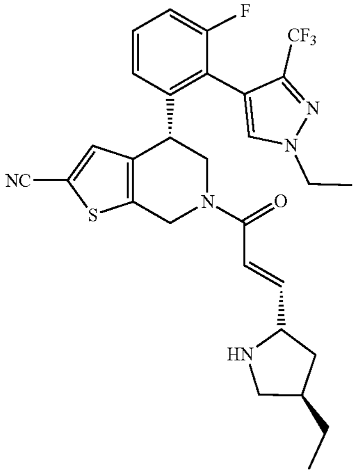

(S)-4-((S)-2-(1-ethyl-3-(trifluoromethyl)-1H-pyrazol-4-yl)-3-fluorophenyl)-6-((E)-3-((2S,4R)-4-ethylpyrrolidin-2-yl)acryloyl)-4,5,6,7-tetrahydrothieno[2,3-c]pyridine-2-carbonitrile Step 1: To a mixture of (2S,4R)-1-(tert-butoxycarbonyl)-4-ethylpyrrolidine-2-carboxylic acid (500 mg, 2.06 mmol), DIPEA (531 mg, 4.12 mmol) and O,N-dimethyl-hydroxylamine hydrochloride (404 mg, 4.12 mmol) in DCM (5 ml) was added HATU (1.17 g, 3.09 mmol) and the mixture was stirred at RT for 2 h. $H_2O$ (20 ml) was added and the mixture was extracted with DCM (3x20 ml). The combined organic phases were washed with brine, dried over $Na_2SO_4$, filtered and concentrated. The residue was purified by com-flash (PE: EA=3:1) to afford (2S,4R)-tert-butyl 4-ethyl-2-(methoxy(methyl)carbamoyl)pyrrolidine-1-carboxylate (450 mg, 76%) as a yellow oil. LCMS: $(M-Boc+H)^+$=187.2; Retention time=1.84 min. LCMS CP Method A Step 2: To a solution of (2S,4R)-tert-butyl 4-ethyl-2-(methoxy(methyl)carbamoyl)-pyrrolidine-1-carboxylate (100 mg, 0.35 mmol) in dry THF (5 ml) at 0° C. was added a solution of $LiAlH_4$ (1M in THF) (0.42 ml, 0.42 mmol) and the mixture was stirred at 0° C. for 1 h. The reaction was quenched with sat. solution of $NH_4Cl$ (aq), then $H_2O$ (10 ml) was added and the mixture was extracted with EA (3x15 ml). The combined organic phases were washed with brine, dried over $Na_2SO_4$, filtered and concentrated to afford a crude (2S,4R)-tert-butyl 4-ethyl-2-formylpyrrolidine-1-carboxylate (75 mg, 94%) as a yellow oil which was used directly in the next step without further purification. $^1H$ NMR (400 MHz, $CDCl_3$) δ: 9.62-9.54 (m, 1H), 4.13-4.11 (m, 1H), 3.72-3.66 (m, 1H), 3.10-2.95 (m, 1H), 2.16-2.00 (m, 2H), 1.80-1.77 (m, 2H), 1.48-1.36 (m, 10H), 1.25-0.90 (m, 3H).

Step 3: To a mixture of diethyl 2-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-2-oxoethylphosphonate (117 mg, 0.2 mmol) and LiCl (10 mg, 0.24 mmol) in MeCN (5 ml) were added DIPEA (52 mg, 0.4 mmol) and (2S,4R)-tert-butyl 4-ethyl-2-formyl-pyrrolidine-1-carboxylate (step 2, 68 mg, 0.3 mmol) and the reaction was stirred at RT for 16 hrs. The mixture was filtered and the filtrates were concentrated. The residue was purified by Prep-HPLC (Method C) to afford (2S,4R)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)-4-ethylpyrrolidine-1-carboxylate (57 mg, 42% yield) as a white solid. LCMS: $(M+H)^+$=672.3; Retention time=2.27 min. LCMS CP Method A Step 4: To a solution of (2S,4R)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)-4-ethylpyrrolidine-1-carboxylate (step 3, 36 mg, 0.054 mmol) in DCM (5 ml) was added TFA (0.5 ml) and the mixture was stirred at RT for 1 h. The mixture was concentrated in vacuum to afford (S)-4-((S)-2-(1-ethyl-3-(trifluoromethyl)-1H-pyrazol-4-yl)-3-fluorophenyl)-6-((E)-3-((2S,4R)-4-ethylpyrrolidin-2-yl)acryloyl)-4,5,6,7-tetrahydrothieno[2,3-c]pyridine-2-carbonitrile 2,2,2-trifluoroacetate (35 mg, 94%) as a white solid. LCMS: $(M+H)^+$=572.2; Retention time=1.61 min. LCMS CP Method B $^1H$ NMR (400 MHz, DMSO) δ: 9.24-9.14 (m, 1H), 8.82 (s, 1H), 8.37-8.24 (m, 1H), 7.70-7.05 (m, 3H), 6.81-6.47 (m, 2H), 6.40-6.36 (m, 1H), 5.33-4.91 (m, 1H), 4.66 (d, J=17.6 Hz, 1H), 4.34-4.25 (m, 3H), 3.98-3.53 (m, 3H), 2.81 (s, 1H), 2.31-1.57 (m, 3H), 1.49-1.23 (m, 5H), 0.90-0.83 (m, 3H).

Example 253

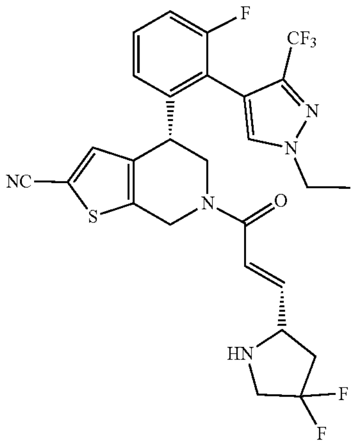

Step 1: To a solution of (S)-tert-butyl 4,4-difluoro-2-(hydroxymethyl)pyrrolidine-1-carboxylate (200 mg, 0.84 mmol) in DCM (15 ml) was added DMP (534 mg, 1.26 mmol) and the mixture was stirred at RT for 2 h. Water (20 ml) was added and the mixture was extracted with DCM (20 mlx3). The combined organic phases were washed with brine, dried over $Na_2SO_4$, filtered and concentrated. The residue was purified by com-flash (PE: EA=5: 1) to afford (S)-tert-butyl 4,4-difluoro-2-formylpyrrolidine-1-carboxylate (110 mg, 56% yield) as a yellow oil. $^1H$ NMR (400 MHz, DMSO) δ: 9.57 (d, J=26 Hz, 1H), 4.42-4.27 (m, 1H), 3.88-3.75 (m, 2H), 2.61-2.46 (m, 2H), 1.49-1.33 (m, 9H).

Step 2: To a mixture of diethyl 2-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-2-oxoethylphosphonate (117 mg, 0.2 mmol) and LiCl (10 mg, 0.24 mmol) in MeCN (5 ml) were added DIPEA (52 mg, 0.4 mmol) and (S)-tert-butyl 4,4-difluoro-2-formylpyrrolidine-1-carboxylate (94 mg, 0.4 mmol) and the mixture was stirred at RT for 16 h. The reaction mixture was filtered and the filtrates were concentrated. The residue was purified by Prep-HPLC(Method A) to afford (S)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c] pyridin-6(7H)-yl)-3-oxoprop-1-enyl)-4,4-difluoropyrrolidine-1-carboxylate (57 mg, 42%) as a white solid. LCMS: $(M-56+H)^+$=624.2; Retention time=2.10 min. LCMS CP Method C Step 3: To a solution of (S)-tert-butyl 2-((E)-3-((S)-2-cyano-4-((S)-2-(1-ethyl-3-(trifluoromethyl)-1H-pyrazol-4-yl)-3-fluorophenyl)-4,5-dihydrothieno[2,3-c]pyridin-6(7H)-yl)-3-oxoprop-1-enyl)-4,4-difluoropyrrolidine-1-carboxylate (57 mg, 0.084 mmol) in DCM (5 ml)) was added TFA (0.5 ml and the mixture was stirred at RT for 1 h. The mixture was concentrated in vacuum to afford (S)-6-((E)-3-((S)-4,4-difluoropyrrolidin-2-yl)acryloyl)-4-((S)-2-(1-ethyl-3-(trifluoromethyl)-1H-pyrazol-4-yl)-3-fluorophenyl)-4,5,6,7-tetrahydrothieno[2,3-c]pyridine-2-carbonitrile 2,2,2-trifluoroacetate (57.9 mg, 99% yield) as a white solid. LCMS: $(M+H)^+$=580.2; Retention time=1.59 min. LCMS CP Method B. $^1$H NMR (400 MHz, DMSO) δ: 8.36-8.25 (m, 1H), 7.66-7.21 (m, 3H), 7.03-6.52 (m, 3H), 6.36-5.92 (m, 1H), 5.16-4.75 (m, 2H), 4.39-4.19 (m, 3H), 4.08-3.95 (m, 2H), 3.78-3.73 (m, 1H), 3.56-3.42 (m, 3H), 2.33-2.01 (m, 1H), 1.50-1.45 (m, 3H).

Example 254

When incubating such compounds with the activating enzymes (E1) of ubiquitin, SUMO, Nedd8, Urm1, ISG15 or Atg7, it forms covalent adducts with the specific Cys residue as depicted below. For the compounds provided herein including embodiments thereof, a covalent adduct may be formed with a cysteine amino acid corresponding to a Cys residue from Uba1, Uba2, Uba3, Uba4, Uba7 or Atg7 as shown in the sequences below.

```
Uba1 (ubiquitin)
                                  SEQ ID NO: 1
LVGAGAIGCELLK

Uba2 (SUMO)
                                  SEQ ID NO: 2
WGAGGIGCELLK

Uba3 (Nedd8)
                                  SEQ ID NO: 3
VIGAGGLGCELLK

Uba4 (Urm1)
                                  SEQ ID NO: 4
IVGCGGLGCPLAQ

Uba7 (ISG15)
                                  SEQ ID NO: 5
LVGAGAIGCELLK

Atg7 (Atg8, Atg12)
                                  SEQ ID NO: 6
LLGAGTLGCNVAR
```

Compounds are evaluated for their inhibitory effect on activating enzymes (E1) of ubiquitin, SUMO, Nedd8, Urm1, ISG15 or Atg7 using previously reported methods and protocols. One example is in: Allosteric inhibition of ubiquitin-like modifications by a class of inhibitor of SUMO-activating enzyme. Cell Chemical Biology, 26,1-11, 2019. PMID: 28051857. The enzyme was preincubated with the compounds for 15 minutes.

Example 255

SAE High Throughput Biochemical Assay Protocol:

Assay buffer was prepared [50 mM HEPES, pH 7.5, 0.1% BSA and 10 mM MgCl2] as was the Stop Buffer [100 mM HEPES, pH 7.5, 0.05% Tween20, and 410 mM KF]. The 2× Reaction Buffer [80 nM SUMO-GST, 80 nM UBC9-His, 200 µM ATP and diluted in Assay Buffer] and Antibody Reaction Mix [13.34 nM anti-GSTXL665, 1.66 nM anti-His EuK and Diluted in Stop Buffer] were also prepared. Compounds were dissolved at 200× in DMSO in a 384-well plate. Serial dilutions were performed in DMSO for each compound, and then each concentration was diluted another 50-fold in Assay Buffer, to 4× the final concentration. 2.5 µL of each concentration was transferred into its own well in a 384-well plate. SAE1 was then diluted to 4× in Assay Buffer, and 2.5 µL of 4×SAE1 was mixed into each compound-containing well. After incubating for 15 minutes at RT, 5 µL of 2× Reaction Buffer was mixed into every well. Then after another 45 minutes at RT, 10 µL of Antibody Reaction Mix was added and mixed into every well. This plate was then read on an HTRF-compatible plate reader after 2 hours at RT, and again after sitting at RT overnight. [Final Component Concentrations: SAE1: 12.5 nM; SUMO-GST: 40 nM; UBC9-His: 40 nM; Anti-GST-XL665: 6.67 nM; Anti-His-EuK: 0.83 nM; and ATP: 100 µM] The IC50's are provided in Table 1. Alternatively, the compounds are tested at a single concentration of 25 micromolar and the percent of control is measured. The POC are also provided in Table 1 where appropriate.

Example 256

HCT-116 4 Hour Cell Assay

This protocol describes the procedures used to assess the effects of compounds of interest on sumoylation levels. Immunoblot of SUMO 2/3 conjugates are performed and IC50 curves are generated upon quantification of sumoylations bands. HCT-116 cells are seeded in a 12 well plate (500,000 cells/well). The following day the cells are treated with compounds of interest (resuspended in DMSO) for 4 hours (11 concentrations with a three-fold dilution; starting concentration 25 µM) Following 4 hours of incubation the cells are washed with ice cold PBS 1× and protein extraction is performed with RIPA buffer supplemented with phosphatases and proteases inhibitors, 25 mM of NEM and 50 units/mL of Benzonase. Samples undergo centrifugation at 13,000 RPM, 4° C., for 10 minutes and the supernatant is collected. Protein quantification is performed using BCA. Non-Reducing Laemmli Buffer is added to the samples. Samples are heated at 75° C. for 10 minutes, and are centrifuged for 3 minutes at 9000 RPM Nupage 4-12% Bis Tris gels and 1× MOPS buffer (Fisher Scientific)+1× NuPAGE Antioxidant (Invitrogen) are used to perform the SDS-PAGE gel electrophoresis (20 to 40 µg of proteins are loaded in the gels). Proteins are then transferred to PVDF membranes and the level of total proteins are measured by staining with Revert Total Protein Stain and the fluorescent bands are acquired using the LI-COR FC (700 nm for 1 min) Membranes are blocked for 5 minutes with Bio-Rad Blocking Buffer and are subsequently incubated over night at 4° C. with Anti-Sumo 2-3 mAb (MBL #M114-3, 1:1000 in Bio-Rad Blocking Buffer, 0.2% Tween 20) Membranes are washed with 1×TBS-T (3 times for 5 minutes) and sumoylation is detected using LI-cor IRDye 800CW Goat anti-Mouse IgG secondary antibody (1:10,000 dilution) upon 1 hour of incubation in blocking buffer with 0.2% Tween 20 and 0.01% SDS. After the incubation, the membranes are washed with 1×TBS-T (3 times for 5 minutes). To visualize the fluorescent bands the membranes are scanned with LI-COR FC (700 nm for 1 min and 800 nM for 2 mins). Sumoylation levels are quantified upon normalization with total protein levels, using the LI-COR Image Studio Lite 5.2 Software. The results are provided in the following Table 1.

TABLE 1

| Example | 15 min preincubation HTRF IC50 (μM) Ave | HCT-116 Western 4 h IC50 (μM) Ave |
|---|---|---|
| 1 | 0.21 | 0.20062 |
| 2 | 4.38 | 0.435 |
| 3 | 7.87 | 0.985 |
| 4 | >25 | |
| 5 | 10.31 | 14.08 |
| 6 | 7.43 | |
| 7 | 9.31 | 1.946 |
| 8 | 10.78 | |
| 10 | 13.43 | |
| 11 | >25 | |
| 12 | 3.33 | 0.353 |
| 13 | 6.22 | |
| 16 | 18.08 | |
| 17 | 2.47 | 0.26855 |
| 18 | 8.99 | |
| 19 | 6.12 | |
| 20 | 0.69 | 0.69195 |
| 21 | 0.15 | 0.1197 |
| 22 | 0.39 | 0.21415 |
| 24 | >25 | |
| 26 | 7.92 | |
| 28 | 8.43 | 0.33075 |
| 30 | 3.3 | 0.74555 |
| 31 | 10.23 | 0.91805 |
| 32 | 3.9 | 2.053 |
| 33 | 8.44 | |
| 35 | >25 | |
| 37 | >25 | |
| 38 | >25 | |
| 39 | 8.56 | |
| 42 | 8.39 | |
| 44 | 9.86 | |
| 45 | 23.17 | |
| 46 | 0.2 | 0.09525 |
| 47 | 3.37 | 2.718 |
| 48 | 1.12 | 0.19685 |
| 49 | 10.06 | |
| 50 | 0.51 | 0.157 |
| 51 | 1.29 | 0.5689 |
| 52 | 0.69 | 0.3077 |
| 53 | 0.34 | 0.1909 |
| 54 | 0.55 | 0.5703 |
| 55 | 1.66 | |
| 56 | 1.09 | |
| 57 | >25 | |
| 58 | 6.06 | |
| 60 | 1.36 | 2.593 |
| 62 | >25 | |
| 63 | >25 | |
| 73 | 21.91 | |
| 74 | 2.84 | 2.237 |
| 76 | 14.65 | |
| 77 | 9.55 | |
| 78 | 6 | |
| 79 | 1.77 | 0.32375 |
| 80 | 1.24 | 0.2119 |
| 81 | 2.69 | 0.3504 |
| 82 | 1.08 | 0.3567 |
| 83 | 0.76 | 0.309 |
| 84 | 2.79 | 0.5027 |
| 85 | >25 | |
| 86 | 9.1 | |
| 87 | 18.24 | |
| 88 | 2.7 | |
| 89 | 1.13 | 0.1453 |

TABLE 1-continued

| Example | 15 min preincubation HTRF IC50 (μM) Ave | HCT-116 Western 4 h IC50 (μM) Ave |
|---|---|---|
| 90 | 5.68 | 3.05 |
| 91 | 2.97 | 0.42625 |
| 92 | 0.4 | 0.4505 |
| 93 | 0.76 | 0.145 |
| 94 | 1.86 | 1.158 |
| 95 | 15.61 | |
| 96 | 2.92 | 2.79 |
| 97 | 2.76 | |
| 98 | >25 | |
| 99 | 2.83 | 0.5632 |
| 100 | 1.38 | 0.174 |
| 101 | 2.24 | 0.73245 |
| 102 | 1.74 | 0.6748 |
| 103 | 2.66 | 1.659 |
| 104 | 2.14 | 1.7785 |
| 105 | 2.42 | 0.61985 |
| 106 | 0.8 | 0.28265 |
| 107 | 2.07 | 0.2259 |
| 108 | 10.97 | |
| 109 | 26.54 | |
| 111 | 3.36 | 0.90925 |
| 112 | 0.76 | 0.2094 |
| 113 | 1.61 | 1.793 |
| 114 | 1.19 | 0.2616 |
| 115 | 1.95 | 0.6004 |
| 116 | 1.49 | 0.2021 |
| 117 | 1.16 | 0.427 |
| 118 | 0.29 | 0.113787 |
| 119 | 0.44 | 0.1206 |
| 120 | 0.31 | 0.38345 |
| 121 | 0.43 | 0.5771 |
| 122 | 0.12 | 0.06306 |
| 123 | 1.17 | 0.1785 |
| 125 | 1.23 | 0.5426 |
| 127 | 1.07 | 0.2249 |
| 128 | 0.75 | 0.06576 |
| 129 | 0.505 | 0.24855 |
| 132 | 0.18 | 0.5467 |
| 134 | 0.32 | 3.12 |
| 135 | 0.51 | 1.202 |
| 136 | 4.13 | 2.53 |
| 137 | 0.36 | |
| 138 | 0.5 | 2.69 |
| 139 | 0.07 | 0.9702 |
| 140 | 0.12 | 2.36 |
| 141 | 0.35 | 4.877 |
| 143 | 2.18 | |
| 144 | 0.54 | 0.7917 |
| 145 | 5.62 | |
| 146 | 1.92 | 0.50085 |
| 147 | 0.62 | 3.473 |
| 151 | 0.18 | 0.5869 |
| 152 | 10.38 | |
| 153 | 9.68 | |
| 154 | 7.34 | |
| 155 | 3.52 | 0.3212 |
| 156 | 2.91 | 0.34895 |
| 157 | 18.57 | |
| 158 | 6.37 | |
| 159 | 4.52 | 0.12775 |
| 160 | 24.39 | |
| 161 | 15.82 | |
| 162 | 11.56 | |
| 163 | 8.68 | |
| 164 | 10.9 | |
| 165 | 3.42 | 1.05565 |
| 166 | 19.9 | |
| 167 | 7.43 | |
| 168 | 18.83 | |
| 169 | 14.51 | |
| 170 | 10.22 | |
| 171 | 11.99 | |
| 172 | 21.08 | |
| 173 | 17.27 | |
| 174 | 12.49 | |

TABLE 1-continued

| Example | 15 min preincubation HTRF IC50 (μM) Ave | HCT-116 Western 4 h IC50 (μM) Ave |
|---|---|---|
| 175 | 3.05 | 0.32075 |
| 176 | 19.91 | |
| 177 | 6.3 | |
| 178 | 16.71 | 0.69 |
| 179 | 4.29 | 0.2764 |
| 180 | 5.29 | 1.15 |
| 181 | 3.16 | 0.87775 |
| 183 | 2.16 | 0.3213 |
| 184 | 8.37 | |
| 185 | 5.86 | |
| 186 | 6.37 | 2.13 |
| 187 | 8.1 | |
| 188 | 17.98 | |
| 189 | 1.67 | 0.46015 |
| 192 | >25 | |
| 193 | 9.08 | 8.85 |
| 194 | >25 | |
| 195 | 11.31 | |
| 196 | >25 | |
| 197 | 15.21 | |
| 198 | >25 | |
| 199 | 2.87 | 1.2585 |
| 200 | 2.28 | 0.8913 |
| 201 | 1.56 | 1.4635 |
| 202 | 24.91 | |
| 203 | 4.75 | 0.76675 |
| 204 | >25 | |
| 205 | >25 | |
| 207 | >25 | |
| 208 | >25 | |
| 210 | 19.69 | |
| 211 | 20.16 | |
| 212 | 11.72 | |
| 213 | 8.81 | |
| 214 | 3.97 | 0.35635 |
| 215 | 1.35 | 0.085615 |
| 216 | 0.18 | 0.10 |
| 217 | 0.13, 0.15 | 0.101125, 0.18 |
| 218 | 0.81 | |
| 219 | 1.01 | |
| 220 | 0.067 | 0.057315 |
| 221 | 0.347 | 0.13445 |
| 222 | 0.1 | 0.09741 |
| 223 | 0.052 | 0.04731 |
| 224 | 0.172 | 0.10618 |
| 225 | 0.034 | 0.2976 |
| 226 | 4.79 | 2.055 |
| 227 | 0.12 | 0.057 |
| 228 | 2.07 | |
| 229 | 4.12 | 0.4435 |
| 230 | 1.1 | 5.39 |
| 231 | 0.16 | 1.005 |
| 232 | 1.36 | 0.40235 |
| 233 | 4.82 | 0.9137 |
| 234 | 2.23 | 0.3389 |
| 235 | 4.15 | 0.28535 |
| 236 | 0.24 | 0.3564 |
| 237 | 2.64 | 0.897 |
| 238 | 1.79 | 0.8441 |
| 239 | 1.12 | 0.18655 |
| 240 | 0.81 | 0.187 |
| 241 | 5.52 | 0.4448 |
| 242 | 2.32 | 1.2865 |
| 243 | 1.17 | 0.5016 |
| 244 | 2.88 | 1.966 |
| 245 | 4.15 | 0.20685 |
| 246 | 1.65 | 0.4827 |
| 247 | 1.66 | 0.20035 |
| 248 | 0.97 | >25 |
| 249 | 0.14 | 0.1689 |
| 250 | 0.76 | 0.2634 |
| 251 | 0.11 | 0.08223 |
| 252 | 0.39 | 0.28795 |
| 253 | 2.92 | 0.9191 |

Example 257

PK Evaluation

The compounds of interest were evaluated for various PK parameters. Specifically CACO permeability/efflux and plasma protein binding (PPP) were determined. Stock solutions were prepared at 10 mM in DMSO for test and reference compounds. Aliquots of the stock solution were diluted to 500× of final concentration (0.5 mM) with DMSO, then further diluted upon the addition of bank PE3-buffer to 20× of final concentration (20 μM). Then test and reference compounds were prepared in plasma at 1 μM. For 0 hour incubation: 25 μL of the plasma spiked with test and reference compounds was transferred into a 96-well sample preparation plate, and then 25 μL blank PB-buffer was added. The samples were quenched by 200 μL of IS solution to prepare $[\text{Initial}]_{0h}$ samples. For 5 hours incubation: 100 μL of the plasma spiking with test and reference compounds was loaded on donor side, and 100 μL of blank PB-buffer were loaded on receiver side of the equilibrium dialysis device. Samples were incubated in an air-bath shaker (60 rpm) for 5 hours at 37° C. After 5 hours incubation, 25 μL of samples (from both the donor sides and receiver sides of the dialysis apparatus) was aspirated and added into new sample preparation plates, separately. 25 μL of blank PB-buffer was added to donor side samples and 25 μL of blank plasma was added to receiver side samples to balance the matrix. The samples were quenched with 200 μL of IS solution. The assay plate was shaken at the vibrator (Hangzhou Allsheng, MX100-4A) for 10 min (600 rpm) and then centrifuged at 5,594×g for 15 min (Thermo Multifugex 3R). An aliquot of the 50 μL supernatant was taken from each well and diluted by 50 μL distilled water, then analyzed by UPLC-MS/MS. The results are provided in the following Table 2.

Caco-2 cells were obtained from American Tissue Culture Collection (Rockville, MD). The cells were maintained in Modified Eagle's medium (MEM), containing 10% heat-inactivated fetal bovine serum (FBS), and 1% non-essential amino acids, in $CO_2$ at 37° C. Cells were seeded on polycarbonate filter inserts (Millipore, CAT #PSHT 010R5). The cells were cultured for 21-28 days prior to the permeability experiments. The Lucifer Yellow permeability was checked before and after the assay. Compounds were dissolved at 10 mM in 100% dimethyl sulfoxide (DMSO) and diluted for studies in Hanks Balanced Salt Solution (HBSS, Invitrogen, Cat #14025-092) with 25 mM HEPES, pH 7.4. Compounds were tested at 10 UM in both the apical-to-basolateral (A-B) and basolateral-to-apical (B-A) directions, incubations were conducted at 37° C. for 90 min. At the end of incubation, samples were diluted by assay buffer, and analyzed by LC-MS/MS. The concentrations of the compounds were quantified by standard curve. The results are provided in the following Table 3. The first comparator example (Comp. Ex. 1) is the chloro substituted thienodihydropyridine

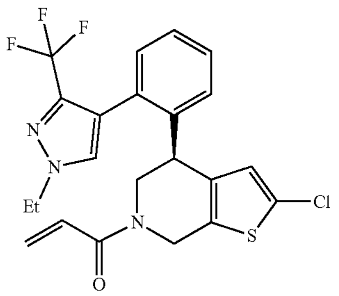 [SMILES: C=CC(=O)N1Cc2sc(Cl)cc2[C@H](c2ccccc2-c2cn(CC)nc2C(F)(F)F)C1]

and the second comparator example (Comp. Ex. 2) is

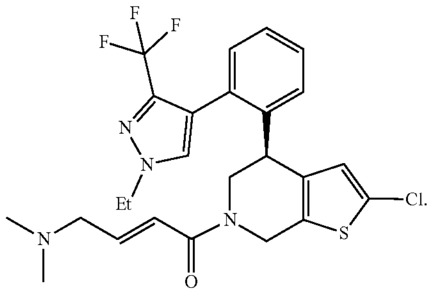 [SMILES: CCn1cc(-c2ccccc2[C@@H]2CN(C(=O)/C=C/CN(C)C)Cc3sc(Cl)cc32)c(C(F)(F)F)n1]

TABLE 2

| PPB % bound | | | | | |
|---|---|---|---|---|---|
| Example | Mouse | Rat | Human | Dog | Monkey |
| Comp. Ex. 1 | >99.9 | ND | 99.8 | ND | ND |
| Comp. Ex. 2 | >99.7 | ND | 99.2 | ND | ND |
| 1 | 98.4 | ND | ND | ND | ND |
| 2 | 98.4 | 95.6 | 95.3 | 98.3 | 88.4 |
| 12 | 96.5 | ND | 95.1 | ND | ND |
| 46 | 98.7 | 97.9 | 97.2 | 99.2 | 95.3 |
| 50 | 96.1 | 93.8 | 96.7 | 98.0 | 93.6 |
| 89 | 97.6 | ND | 97.1 | ND | ND |
| 118 | 98.6 | ND | 96.8 | ND | ND |
| 215 | 97.7 | ND | 96.0 | 98.0 | ND |
| 217 | 97.4 | 94.9 | 97.2 | 98.7 | ND |
| 222 | 99.5 | 99.6 | 99.2 | 99.9 | 99.1 |
| 227 | 97.9 | ND | ND | ND | ND |

ND—not determined

TABLE 3

| Caco-2 efflux | | | |
|---|---|---|---|
| Example | A-B | B-A | Efflux Ratio |
| Comp 1 | 1.9 | 2.9 | ND |
| Comp 2 | 2.6 | 2.4 | ND |
| 2 | 15 | 12 | 1 |
| 12 | 5 | 58 | 5 |
| 46 | 12.7 | 11.6 | 1 |
| 50 | 4 | 21 | 6 |
| 89 | 8 | 11 | |
| 118 | 4 | 21 | |
| 215 | 15 | 20 | 1 |
| 217 | 6 | 14 | 2 |
| 222 | 3.4 | 4.1 | 1 |

Example 258

Solubility Evaluation

The compounds of interest were evaluated for their solubility in various biological solutions. Specifically, aliquots (8 μL) of reference and test compound stock solutions (10 mM) were added into 792 μL of buffer (PBS, pH7.4, FaSSIF, pH 6.5, or FaSSGF, pH 1.6) respectively (Final DMSO conc.: 1%). Sample tubes were shaken for 1 hour (1000 rpm) at RT. The experiment was calibrated using 300 μM spiked solution (SS) in MeOH/CAN (4:1) by adding 6 μL of 10 mM compound stock solution in 194 μL MeOH/ACN(4:1) ranging from 60 μM to 0.02 μM. The samples were centrifuged (10 min-12000 rpm) to precipitate un-dissolved particles. The supernatants were transferred to a new tube or plate. Supernatants were diluted 10 times and 100 times with 100 mM buffer then analyzed by LC-MS/MS. The results are provided in the following Table 4. SGF=simulated gastric fluid, SIF=simulated intestinal fluid, PBS=phosphate buffered saline pH 7.4 Values are noted in μM.

TABLE 4

| Solubilities | | | |
|---|---|---|---|
| Example | SGF | SIF | PBS |
| Comp 1 | 20 | 11 | 0.5 |
| Comp 2 | 15 | 29 | 36 |
| 2 | | 72 | 67 |
| 46 | | >100 | 97 |
| 50 | | 28 | 30 |
| 118 | | 70 | 57 |
| 89 | | 90 | 78 |
| 222 | | 29 | 41 |

Embodiments

The following non-limiting embodiments provide illustrative examples of the invention, but do not limit the scope of the invention.

1. A compound of the structure of Formula I:

[I]

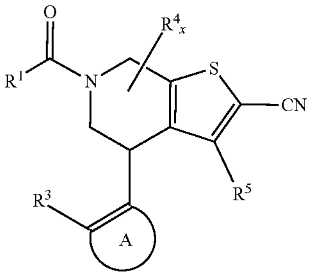

wherein ring A is selected from
- a) 5-7 membered cycloalkenyl,
- b) phenyl,
- c) 5- or 6-membered heteroaryl,
- d) 9-, 10- or 11-membered fused partially saturated heterocyclyl, and
- e) 9- or 10-membered fused heteroaryl;

wherein ring A is unsubstituted or substituted with one, two or three $R^2$ substituents;

$R^1$ is substituted or unsubstituted alkenyl or substituted or unsubstituted alkynyl;

each $R^2$ is independently selected from halo, alkoxy, hydroxy, amino, alkyl, haloalkyl, cyano, alkylcarbonylamino, alkylsulfonylamino, and alkylaminocarbonylamino;

$R^3$ is selected from substituted or unsubstituted nitrogen containing 5-membered heteroaryl, substituted or unsubstituted 5- or 6-membered cycloalkenyl, substituted or unsubstituted nitrogen containing 5- or 6-membered partially unsaturated heterocyclyl and substituted or unsubstituted nitrogen containing 6-10 membered heteroaryl;

each $R^4$ is independently selected from hydroxy and $C_1$-$C_3$ alkyl;

$R^5$ is selected from H, halo and $C_1$-$C_3$ alkyl; and x is 0, 1, or 2;

or an isomer or stereoisomer of any of the foregoing, or a mixture thereof or a pharmaceutically acceptable salt thereof.

2. The compound of embodiment 1, wherein at least one $R^2$ is selected from fluoro, chloro, $C_1$-$C_3$ alkoxy, hydroxy, amino, $C_1$-$C_3$ alkyl, $C_1$-$C_3$ haloalkyl, cyano, $C_1$-$C_3$ alkylcarbonylamino, $C_1$-$C_3$ alkylsulfonylamino, and $C_1$-$C_3$ alkylaminocarbonylamino; or an isomer or stereoisomer of any of the foregoing, or a mixture thereof or a pharmaceutically acceptable salt thereof.

3. The compound of embodiment 1, wherein at least one $R^2$ is selected from fluoro, chloro, methylcarbonylamino, hydroxy, methyl, difluoromethyl, methylsulfonylamino, methylaminocarbonylamino and cyano; or an isomer or stereoisomer of any of the foregoing, or a mixture thereof or a pharmaceutically acceptable salt thereof.

4. The compound of embodiment 1, wherein ring A is unsubstituted with $R^2$.

5. The compound of any one of embodiments 1-4, wherein ring A is selected from phenyl, thienyl, pyrazolyl, cyclopentenyl, cyclohexenyl, 4-pyridyl, and indolyl; or an isomer or stereoisomer of any of the foregoing, or a mixture thereof or a pharmaceutically acceptable salt thereof.

6. The compound of embodiment 5, wherein ring A is phenyl; or an isomer or stereoisomer of any of the foregoing, or a mixture thereof or a pharmaceutically acceptable salt thereof.

7. The compound of any one of embodiments 1-6, wherein $R^3$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or stereoisomer of any of the foregoing, or a mixture thereof or a pharmaceutically acceptable salt thereof.

8. The compound of embodiment 7, wherein $R^3$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or stereoisomer of any of the foregoing, or a mixture thereof or a pharmaceutically acceptable salt thereof.

9. The compound of embodiment 8, wherein $R^3$ is substituted 4-pyrazolyl; or an isomer or stereoisomer of any of the foregoing, or a mixture thereof or a pharmaceutically acceptable salt thereof.

10. The compound of embodiment 9, wherein $R^3$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-trifluoromethyl-pyrazol-4-yl, 1-methyl-3-difluoromethyl-pyrazol-4-yl, 1-butyl-3-trifluoromethyl-pyrazol-4-yl, 1-propynyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-(2-fluoroethyl)-3-trifluoromethyl-pyrazol-4-yl, 1-(2,2-difluoroethyl)-3-trifluoromethyl-pyrazol-4-yl, 1-(2,2,2-trifluoroethyl)-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[1-aminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-[1-(N-methylaminocarbonyl)ethyl]-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3-trifluoromethyl-pyrazol-4-yl, 1-cyanopropyl-3-trifluoromethyl-pyrazol-4-yl, 1-cyanoethyl-3-trifluoromethyl-pyrazol-4-yl, 2-cyanoethyl-3-trifluoromethyl-pyrazol-4-yl, cyanomethyl-3-trifluoromethyl-pyrazol-4-yl, 1-[N,N-dimethylaminocarbonylethyl]-3-trifluoromethyl-pyrazol-4-yl, 1-carboxypropyl-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethoxycarbonylmethyl-3-trifluoromethyl-pyrazol-4-yl, 1-ethoxycarbonylethyl-3-trifluoromethyl-pyrazol-4-yl, 1-ethoxycarbonylpropyl-3-trifluoromethyl-pyrazol-4-yl, 1-methylsulfonyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-[[1,3,4-oxadiazol-2-yl]methyl]-3-trifluoromethyl-pyrazol-4-yl, 1-[[1,2,4-oxadiazol-5-yl]methyl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-[3-chloro-5-fluoro-4-pyridyl]-3-trifluoromethyl-pyrazol-4-yl, 1-[2-amino-4-pyridyl]-3-trifluoromethyl-pyrazol-4-yl, 1-[3,5-difluoro-4-pyridyl]-3-trifluoromethyl-pyrazol-4-yl, 1-[3-fluoro-4-pyridyl]-3-trifluoromethyl-pyrazol-4-yl, 1-[3-fluoro-2-pyridyl]-3-trifluoromethyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl or 4-methyl-5-thiazolyl; or an isomer or stereoisomer of any of the foregoing, or a mixture thereof or a pharmaceutically acceptable salt thereof.

11. The compound of embodiment 8, wherein $R^3$ is selected from 5-pyrimidinyl, 2-methyl-5-pyrimidinyl, 4-methyl-5-pyrimidinyl, 4,6-dimethoxy-5-pyrimidinyl, 4,6-dimethyl-5-pyrimidinyl, 4-trifluoromethyl-5-pyrimidinyl, 4-pyrimidinyl, 2-methyl-4-pyrimidinyl, 4-methyl-6-pyrimidinyl, 2,4-dimethyl-6-pyrimidinyl, 3-pyridinyl, 2-pyridinyl, 4-methyl-2-pyridinyl, 2-trifluoromethyl-3-pyridinyl, 4-trifluoromethyl-3-pyridinyl, 2-methyl-3-pyridinyl, 2,5-dimethyl-3-pyridinyl, 2,6-dimethyl-3-pyridinyl, 2,4-dimethyl-3-pyridinyl, 2-ethyl-3-pyridinyl, 5-methyl-3-pyridinyl, 2-ethoxy-3-pyridinyl, 2-ethoxy-5-methyl-3-pyridinyl, 2-methoxy-3-pyridinyl, 2-methoxy-6-methyl-3-pyridinyl, 2-ethoxy-6-methyl-3-pyridinyl, 2-isopropoxy-3-pyridinyl, 2-(3-pentoxy)-3-pyridinyl, 2-methoxyethoxy-3-pyridinyl, 2-cyclopropoxy-3-pyridinyl, 2-cyclopentyloxy-3-pyridinyl, 2-cyclohexloxy-3-pyridinyl, 2-fluoro-3-pyridinyl, 2-chloro-3-pyridinyl, 2-phenyl-3-pyridinyl, 2-fluoro-3-methyl-5-pyridinyl, 2-fluoro-3-chloro-5-pyridinyl, 3-fluoro-5-pyridinyl, 3-chloro-5-pyridinyl, 2-chloro-4-methyl-5-pyridinyl, 2-methoxy-5-pyridinyl, 3-methoxy-5-pyridinyl, 2-ethoxy-5-pyridinyl, 3-ethoxy-5-pyridinyl, 3-trifluoromethyl-5-pyridinyl, 2-trifluoromethyl-3-pyridinyl, 3-ethyl-5-pyridinyl, 2,3-dimethyl-5-pyridinyl, 2-(2-hydroxymethylpyrrolidin-1-yl)-5-pyridinyl, 2-(morpholin-1-yl)-3-chloro-5-pyridinyl, 2-(dimethylaminoethoxy)-5-pyridinyl, 2-(2-dimethylaminomethylpyrrolidin-1-yl)-5-pyridinyl, 2-phenyl-5-pyridinyl, 2-methyl-6-pyridinyl, 2,4-dimethyl-6-pyridinyl or 2-ethyl-6-pyridinyl; or an isomer or stereoisomer of any of the foregoing, or a mixture thereof or a pharmaceutically acceptable salt thereof.

12. The compound of embodiment 11, wherein $R^3$ is 2-trifluoromethyl-3-pyridinyl; or an isomer or stereoisomer of any of the foregoing, or a mixture thereof or a pharmaceutically acceptable salt thereof.

13. The compound of any one of embodiments 1-12, wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl- substituted $C_2$-$C_6$ alkynyl; or an isomer or stereoisomer of any of the foregoing, or a mixture thereof or a pharmaceutically acceptable salt thereof.

14. The compound of embodiment 13, wherein $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-8 membered nitrogen-containing heterocyclyl-propynyl, substituted or unsubstituted 3-8 membered cycloalkyl-ethenyl, substituted or unsubstituted 3-8 membered cycloalkyl-propenyl, substituted or unsubstituted 3-8 membered nitrogen-containing heterocyclyl-ethynyl, substituted or unsubstituted 3-8 membered nitrogen-containing heterocyclyl-propynyl, substituted or unsubstituted 3-8 membered oxygen-containing heterocyclyl-ethenyl, substituted or unsubstituted 3-8 membered oxygen-containing heterocyclyl-propenyl, substituted or unsubstituted 3-8 membered nitrogen-containing heterocyclyl-ethenyl, substituted or unsubstituted 3-8 membered nitrogen-containing heterocyclyl-propenyl, substituted or unsubstituted 3-8 membered cycloalkyl-ethynyl, substituted or unsubstituted 3-8 membered cycloalkyl-propynyl, substituted or unsubstituted 3-8 membered cycloalkyl-ethynyl, and substituted or unsubstituted 3-8 membered cycloalkyl-propynyl; or an isomer or stereoisomer of any of the foregoing, or a mixture thereof or a pharmaceutically acceptable salt thereof.

15. The compound of embodiment 13, wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di(d1,d2,d3-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-(d2-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof or an isomer or stereoisomer of any of the foregoing, or a mixture thereof or a pharmaceutically acceptable salt thereof 16. The compound of any one of embodiments 1-16, wherein x is 0; or an isomer or stereoisomer of any of the foregoing, or a mixture thereof or a pharmaceutically acceptable salt thereof 17. The compound of any one of embodiments 1-16, wherein $R^5$ is H; or an isomer or stereoisomer of any of the foregoing, or a mixture thereof or a pharmaceutically acceptable salt thereof 18. The compound of embodiment 1 as recited in Table A, or a pharmaceutically acceptable salt thereof.
19. The compound of embodiment 1 selected from
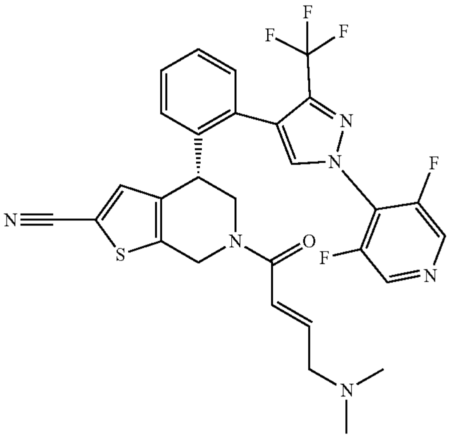
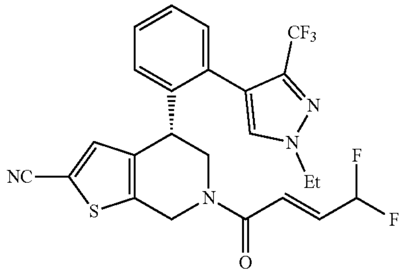
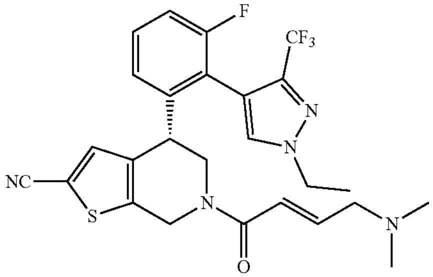
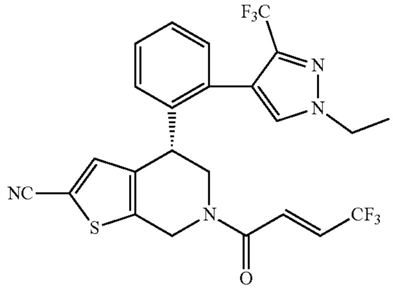
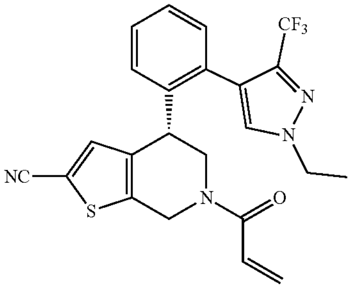
-continued
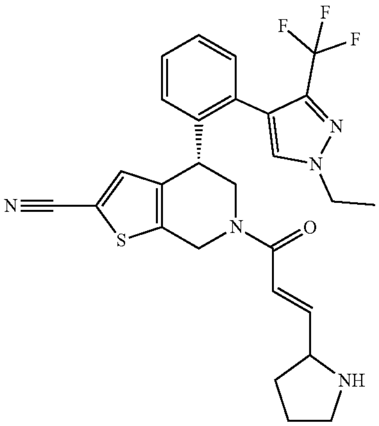
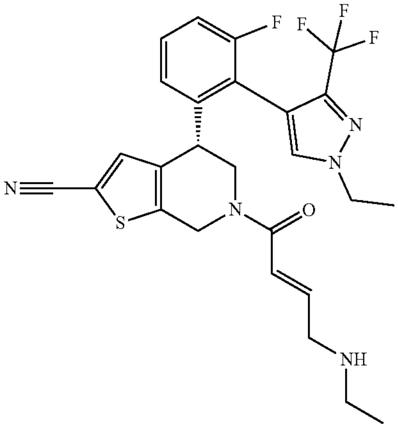
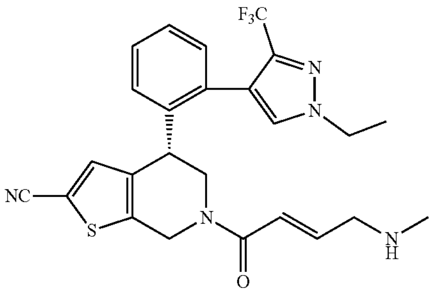
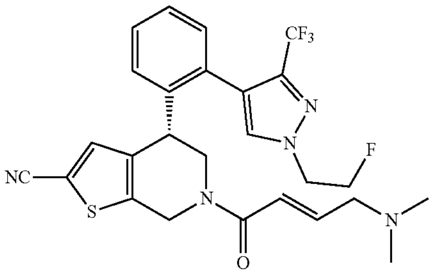

-continued
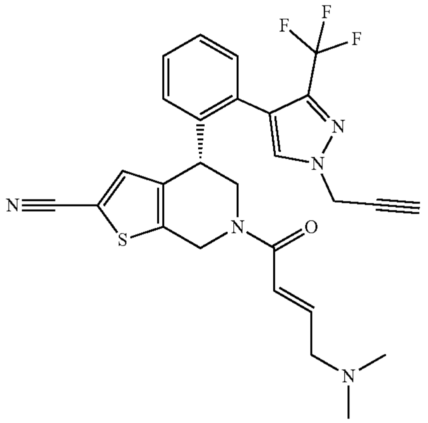
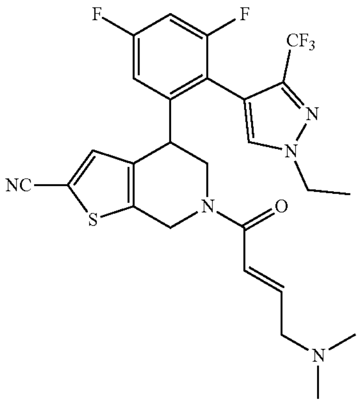
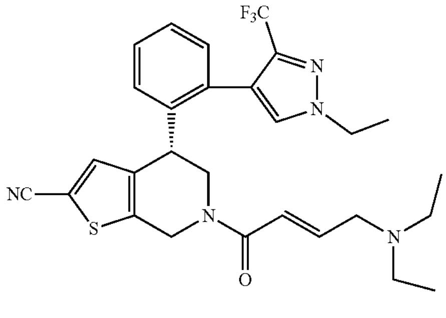
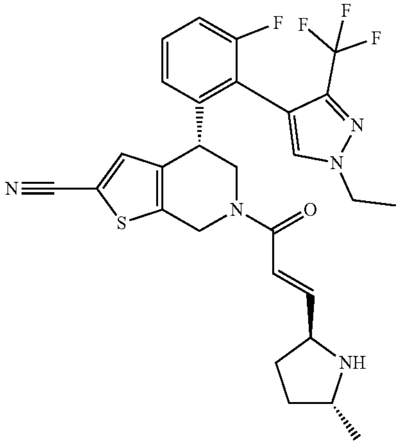
-continued
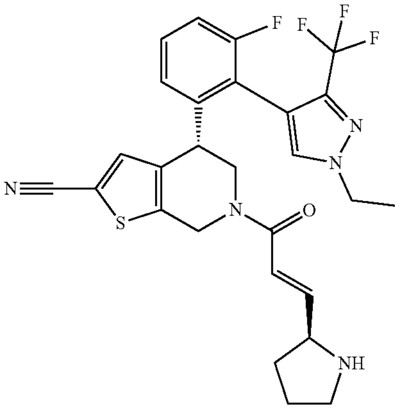
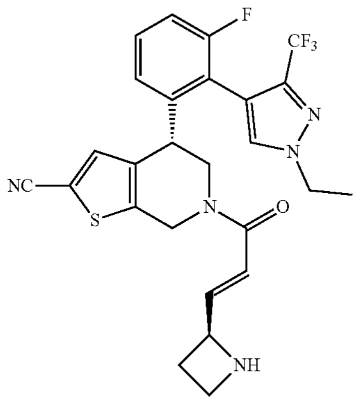
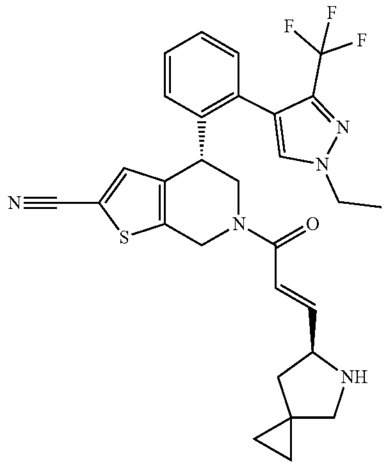
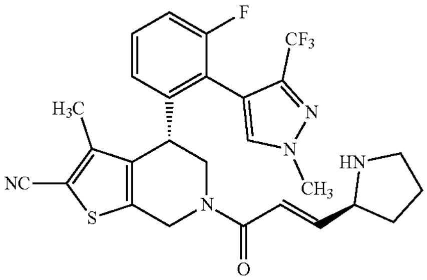

-continued
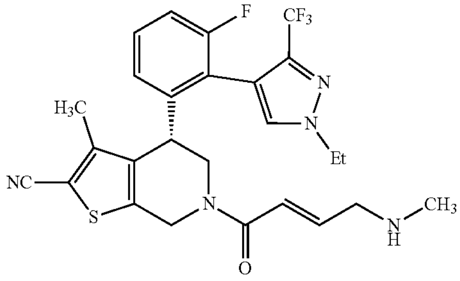
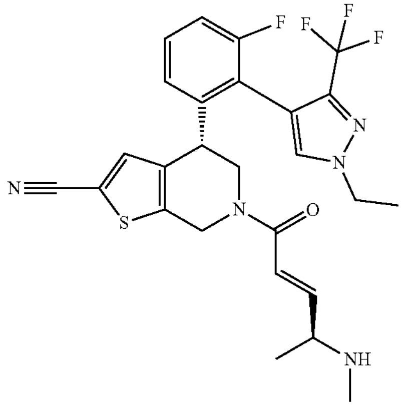
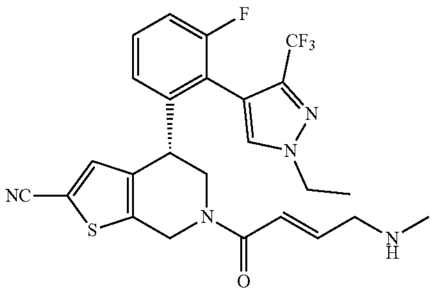
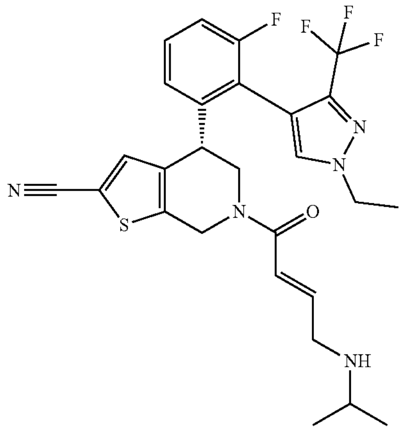
-continued
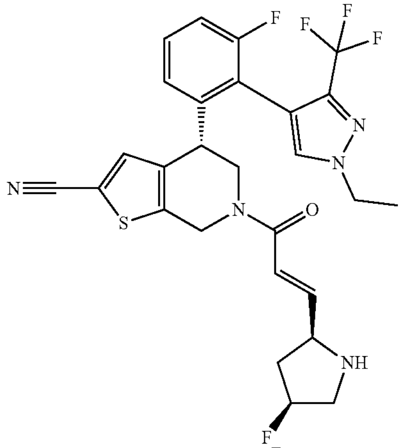
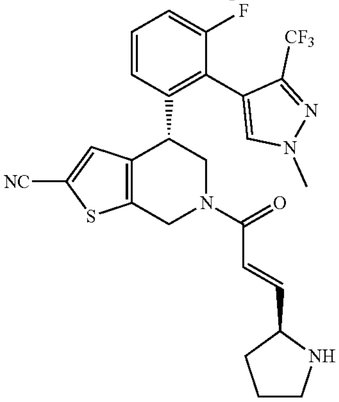
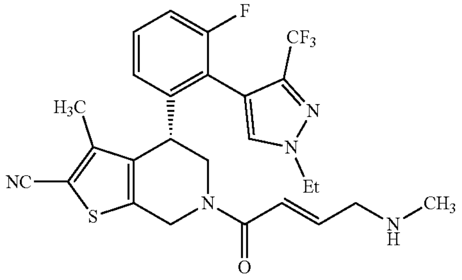
or a pharmaceutically
20. A compound of the structure of Formula II
[II]
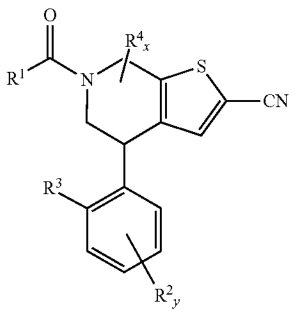
wherein
$R^1$ is substituted or unsubstituted $C_2$-$C_6$ alkenyl, or substituted or unsubstituted $C_2$-$C_6$ alkynyl;
each $R^2$ is independently selected from halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^3$ is selected from substituted or unsubstituted nitrogen containing 5-membered heteroaryl, substituted or unsubstituted nitrogen containing 5- or 6-membered partially unsaturated heterocyclyl and substituted or unsubstituted nitrogen containing 6-10 membered heteroaryl;

each $R^4$ is independently $C_1$-$C_3$ alkyl;

x is 0, 1, or 2; and y is 0, 1, or 2;

or an isomer or stereoisomer of any of the foregoing, or a mixture thereof or a pharmaceutically acceptable salt thereof.

21. The compound of embodiment 20, wherein $R^3$ is selected from substituted or unsubstituted nitrogen containing 5-membered heteroaryl selected from pyrazolyl, isoxazolyl, isothiazolyl, pyrrolyl, thiazolyl, triazolyl and imidazolyl; substituted or unsubstituted nitrogen containing 6-membered heteroaryl selected from pyridinyl, pyrimidinyl and pyrazinyl; substituted or unsubstituted nitrogen containing 5-membered partially unsaturated heterocyclyl selected from pyrrolinyl, and imidazolidinyl; and substituted or unsubstituted dihydropyridinyl; or an isomer or stereoisomer of any of the foregoing, or a mixture thereof or a pharmaceutically acceptable salt thereof.

22. The compound of embodiment 20, wherein $R^3$ is selected from substituted 5-pyrazolyl, substituted 4-pyrazolyl, substituted 1-pyrazolyl, substituted or unsubstituted 4-isoxazolyl, substituted or unsubstituted 4-isothiazolyl, substituted or unsubstituted 3-pyrrolyl, substituted or unsubstituted 5-thiazolyl, substituted or unsubstituted 5-imidazolyl, substituted or unsubstituted 1-imidazolyl, substituted or unsubstituted [1,2,4]triazol-5-yl, substituted or unsubstituted 3-pyridyl, and substituted or unsubstituted 5-pyrimidinyl; or an isomer or stereoisomer of any of the foregoing, or a mixture thereof or a pharmaceutically acceptable salt thereof.

23. The compound of embodiment 20, wherein $R^3$ is selected from 3-trifluoromethyl-pyrazol-4-yl, 1-isopropyl-3-trifluoromethyl-pyrazol-4-yl, 1-ethyl-3-trifluoromethyl-pyrazol-4-yl, 1-methyl-3-trifluoromethyl-pyrazol-4-yl, 1-methyl-3-difluoromethyl-pyrazol-4-yl, 1-butyl-3-trifluoromethyl-pyrazol-4-yl, 1-propynyl-3-trifluoromethyl-pyrazol-4-yl, 1-methoxymethyl-3-trifluoromethyl-pyrazol-4-yl, 1-propyl-3-trifluoromethyl-pyrazol-4-yl, 1,3-dimethyl-pyrazol-4-yl, 1,3,5-trimethyl-pyrazol-4-yl, 1-methyl-3-cyclopropyl-pyrazol-4-yl, 1-methyl-3-trifluoromethyl-pyrazol-4-yl, 1-ethyl-3-amino-pyrazol-4-yl, 1-ethyl-3-methoxy-pyrazol-4-yl, 1-hydroxyethyl-3-trifluoromethyl-pyrazol-4-yl, 1-[2-hydroxypropyl]-3-trifluoromethyl-pyrazol-4-yl, 1-[2-hydroxyisobutyl]-3-trifluoromethyl-pyrazol-4-yl, 1-methoxyethyl-3-trifluoromethyl-pyrazol-4-yl, 1-(2-fluoroethyl)-3-trifluoromethyl-pyrazol-4-yl, 1-(2,2-difluoroethyl)-3-trifluoromethyl-pyrazol-4-yl, 1-(2,2,2-trifluoroethyl)-3-trifluoromethyl-pyrazol-4-yl, 1-[N,N-dimethylaminoethyl]-3-trifluoromethyl-pyrazol-4-yl, 1-[N-methylaminocarbonylmethyl]-3-trifluoromethyl-pyrazol-4-yl, 1-[1-aminocarbonylethyl]-3-trifluoromethyl-pyrazol-4-yl, 1-[N,N-dimethylaminocarbonylmethyl]-3-trifluoromethyl-pyrazol-4-yl, 1-aminocarbonylmethyl-3-trifluoromethyl-pyrazol-4-yl, 1-[1-(N-methylaminocarbonyl)ethyl]-3-trifluoromethyl-pyrazol-4-yl, 1-methylcarbonylaminoethyl-3-trifluoromethyl-pyrazol-4-yl, 1-methylcarbonylaminobutyl-3-trifluoromethyl-pyrazol-4-yl, 1-aminocarbonylethyl-3-trifluoromethyl-pyrazol-4-yl, 1-aminocarbonylpropyl-3-trifluoromethyl-pyrazol-4-yl, 1-aminocarbonylisopropyl-3- trifluoromethyl-pyrazol-4-yl, 1-cyanopropyl-3-trifluoromethyl-pyrazol-4-yl, 1-cyanoethyl-3-trifluoromethyl-pyrazol-4-yl, 2-cyanoethyl-3-trifluoromethyl-pyrazol-4-yl, cyanomethyl-3-trifluoromethyl-pyrazol-4-yl, 1-[N,N-dimethylaminocarbonylethyl]-3-trifluoromethyl-pyrazol-4-yl, 1-carboxypropyl-3-trifluoromethyl-pyrazol-4-yl, 1-carboxyethyl-3-trifluoromethyl-pyrazol-4-yl, 1-carboxymethyl-3-trifluoromethyl-pyrazol-4-yl, 1-methoxycarbonylmethyl-3-trifluoromethyl-pyrazol-4-yl, 1-ethoxycarbonylmethyl-3-trifluoromethyl-pyrazol-4-yl, 1-ethoxycarbonylethyl-3-trifluoromethyl-pyrazol-4-yl, 1-ethoxycarbonylpropyl-3-trifluoromethyl-pyrazol-4-yl, 1-methylsulfonyl-3-trifluoromethyl-pyrazol-4-yl, 1-ethyl-3-carboxy-pyrazol-4-yl, 1-ethyl-5-carboxy-pyrazol-4-yl, 1-ethyl-3-methylaminocarbonyl-pyrazol-4-yl, 1-ethyl-3-[N,N-dimethylaminocarbonyl]-pyrazol-4-yl, 1-ethyl-5-methylaminocarbonyl-pyrazol-4-yl, 1-ethyl-5-[N,N-dimethylaminocarbonyl]-pyrazol-4-yl, 1-benzyl-3-methyl-pyrazol-4-yl, 1-(cyclopropylmethyl)-3-trifluoromethyl-pyrazol-4-yl, 1-cyclopropyl-3-trifluoromethyl-pyrazol-4-yl, 1-[1-methylazetidin-3-yl]-3-trifluoromethyl-pyrazol-4-yl, 1-[1-methylpyrrolidin-3-yl]-3-trifluoromethyl-pyrazol-4-yl, 1-[1-methylpiperidin-3-yl]-3-trifluoromethyl-pyrazol-4-yl, 1-[1-methylpiperidin-4-yl]-3-trifluoromethyl-pyrazol-4-yl, 1-[[1,3,4-oxadiazol-2-yl]methyl]-3-trifluoromethyl-pyrazol-4-yl, 1-[[1,2,4-oxadiazol-5-yl]methyl]-3-trifluoromethyl-pyrazol-4-yl, 1-(3-pyridinylmethyl)-3-methyl-pyrazol-4-yl, 1-(2-pyridinylmethyl)-3-methyl-pyrazol-4-yl, 1-[2-pyridyl]-3-methyl-pyrazol-4-yl, 1-[3-chloro-5-fluoro-4-pyridyl]-3-trifluoromethyl-pyrazol-4-yl, 1-[2-amino-4-pyridyl]-3-trifluoromethyl-pyrazol-4-yl, 1-[3,5-difluoro-4-pyridyl]-3-trifluoromethyl-pyrazol-4-yl, 1-[3-fluoro-4-pyridyl]-3-trifluoromethyl-pyrazol-4-yl, 1-[3-fluoro-2-pyridyl]-3-trifluoromethyl-pyrazol-4-yl, 1-methyl-5-pyrazolyl, 1-ethyl-5-trifluoromethylpyrazol-4-yl, 1,3-dimethyl-5-pyrazolyl, 1-methyl-3-cyclopropyl-pyrazol-5-yl, 1-methyl-4-pyrazolyl, 1-ethyl-3-methylpyrazol-4-yl, 1,5-dimethyl-4-pyrazolyl, 1,3,5-trimethyl-4-pyrazolyl, 1-methyl-3-pyrazolyl, 4-methyl-3-pyrazolyl, 1-methyl-[1,2,4]triazol-3-yl, 4-bromo-2-methyl-[1,2,4]triazol-5-yl, 4-bromo-2-ethyl-[1,2,4]triazol-5-yl, 1-methyl-[1,2,4]triazol-5-yl, 4-isothiazolyl, 4-methyl-2-oxazolyl, isoxazol-4-yl, 2,4-dimethylthiazol-5-yl, 3,5-dimethylisoxazol-4-yl, 2-methyl-5-thiazolyl or 4-methyl-5-thiazolyl; or an isomer or stereoisomer of any of the foregoing, or a mixture thereof or a pharmaceutically acceptable salt thereof.

24. The compound of any one of embodiments 20-23, wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-8 membered nitrogen-containing heterocyclyl- substituted $C_2$-$C_6$ alkynyl, substituted or unsubstituted 3-8 membered cycloalkyl-substituted $C_2$-$C_6$ alkenyl, substituted or unsubstituted 3-8 membered oxygen-containing heterocyclyl-substituted $C_2$-$C_6$ alkenyl, substituted or unsubstituted 3-8 membered oxygen-containing heterocyclyl-substituted $C_2$-$C_6$ alkynyl, substituted or unsubstituted 3-8 membered nitrogen-containing heterocyclyl-substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

25. The compound of embodiment 24, wherein $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

26. The compound of embodiment 24, wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di(d1,d2,d3-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-(d2-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

27. The compound of any one of embodiments 20-26, wherein y is 0; or an isomer or stereoisomer of any of the foregoing, or a mixture thereof or a pharmaceutically acceptable salt thereof.

28. The compound of any one of embodiments 20-26, wherein at least one $R^2$ is selected from fluoro, chloro, methylcarbonylamino, amino, hydroxy, methyl, difluoromethyl, methylsulfonylamino, and methylaminocarbonylamino and cyano; or an isomer or stereoisomer of any of the foregoing, or a mixture thereof or a pharmaceutically acceptable salt thereof.

29. The compound of any one of embodiments 20-28, wherein x is 0; or an isomer or stereoisomer of any of the foregoing, or a mixture thereof or a pharmaceutically acceptable salt thereof.

30. A compound of the structure of Formula III

III

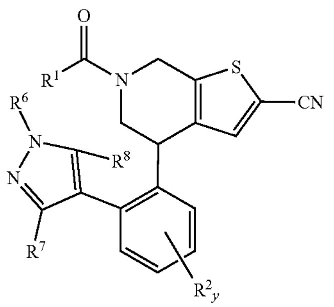

wherein $R^1$ is substituted or unsubstituted $C_2$-$C_6$ alkenyl, or substituted or unsubstituted $C_2$-$C_6$ alkynyl;

each $R^2$ is independently selected from halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

y is 0, 1, or 2;

$R^6$ is selected from H, $C_{1-6}$ alkyl, $C_{2-4}$ alkynyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, C1-6 alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, C1-6 alkylaminocarbonyl, and $C_{3-6}$ cycloalkyl; and $R^8$ is selected from H, carboxy, cyano, $C_{1-4}$ alkyl, $C_{1-3}$ haloalkyl, and $C_{1-6}$ alkylaminocarbonyl; or an isomer or stereoisomer of my of the foregoing, or a mixture thereof or a pharmaceutically acceptable salt thereof.

31. The compound of embodiment 30, wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl- substituted $C_2$-$C_6$ alkynyl; or an isomer or stereoisomer of any of the foregoing, or a mixture thereof or a pharmaceutically acceptable salt thereof.

32. The compound of embodiment 30, wherein $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

33. The compound of embodiment 30, wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di(d1,d2, d3-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (1-methylcarbonyl-azetidin-3-ylamino)propenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-(d2-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyloxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

34. The compound of any one of embodiments 30-34, wherein $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methyl aminocarbonylmethyl, aminocarbonylmethyl, aminocarbonylethyl, 1-aminocarbonylethyl, aminocarbonyl-1, 1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl]methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl; or an isomer or stereoisomer of any of the foregoing, or a mixture thereof or a pharmaceutically acceptable salt thereof.

35. The compound of any one of embodiments 30-34, wherein $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl; or an isomer or stereoisomer of any of the foregoing, or a mixture thereof or a pharmaceutically acceptable salt thereof.

36. The compound of any one of embodiments 30-35, wherein $R^8$ is selected from H, trifluoromethyl, methyl, ethyl, carboxy, cyano and methylaminocarbonyl; or an isomer or stereoisomer of any of the foregoing, or a mixture thereof or a pharmaceutically acceptable salt thereof.

37. The compound of any one of embodiments 30-36, wherein y is 0; or an isomer or stereoisomer of any of the foregoing, or a mixture thereof or a pharmaceutically acceptable salt thereof.

38. The compound of any one of embodiments 30-36, wherein at least one $R^2$ is selected from fluoro, methylcarbonylamino, chloro, amino, hydroxy, methyl, difluoromethyl, methylsulfonylamino-, and methylaminocarbonylamino- and cyano; or an isomer or stereoisomer of any of the foregoing, or a mixture thereof or a pharmaceutically acceptable salt thereof.

39. The compound of any one of embodiments 30-33 and 37-38, wherein $R^6$ is ethyl; $R^7$ is trifluoromethyl; and $R^8$ is H; or an isomer or stereoisomer of any of the foregoing, or a mixture thereof or a pharmaceutically acceptable salt thereof.

40. A compound of the structure of Formula IV or Formula V:

IV

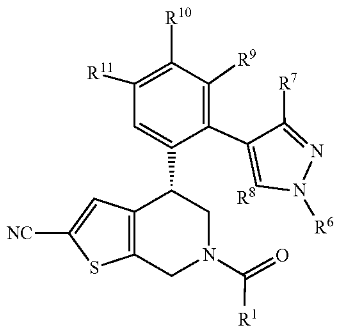

V

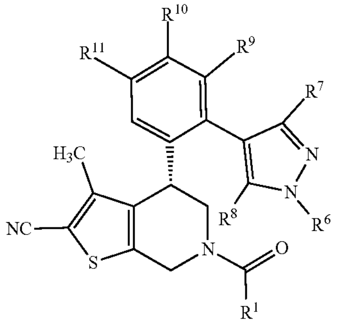

wherein $R^1$ is substituted or unsubstituted $C_2$-$C_6$ alkenyl, or substituted or unsubstituted $C_2$-$C_6$ alkynyl;

$R^6$ is selected from H, $C_{1-6}$ alkyl, $C_{2-4}$ alkynyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, C1-6 alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, C1-6 alkylaminocarbonyl, and $C_{3-6}$ cycloalkyl;

$R^8$ is selected from H, carboxy, cyano, $C_{1-4}$ alkyl, $C_{1-3}$ haloalkyl, and $C_{1-6}$ alkylaminocarbonyl;

$R^9$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^{10}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino; and $R^{11}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

or an isomer or stereoisomer of any of the foregoing, or a mixture thereof or a pharmaceutically acceptable salt thereof.

41. The compound of embodiment 40, wherein $R^1$ is selected from $C_2$-$C_6$ alkenyl, halo-substituted $C_2$-$C_6$ alkenyl; alkoxy substituted $C_2$-$C_6$ alkenyl; dialkylamino substituted $C_2$-$C_6$ alkenyl, alkylamino substituted $C_2$-$C_6$ alkenyl, amino substituted $C_2$-$C_6$ alkenyl, hydroxy substituted amino-$C_2$-$C_6$ alkenyl, phenyl substituted amino-$C_2$-$C_6$ alkenyl, amino substituted $C_2$-$C_6$ alkynyl, dialkylamino substituted $C_2$-$C_6$ alkynyl, alkylamino substituted $C_2$-$C_6$ alkynyl, alkoxy substituted $C_2$-$C_6$ alkynyl, substituted or unsubstituted 3-7 membered nitrogen-containing heterocyclyl- substituted $C_2$-$C_6$ alkynyl, substituted or unsubstituted 3-7 membered cycloalkyl- substituted $C_2$-$C_6$ alkenyl, substituted or unsubstituted 3-7 membered oxygen-containing heterocyclyl- substituted $C_2$-$C_6$ alkenyl, substituted or unsubstituted 3-7 membered oxygen-containing heterocyclyl- substituted $C_2$-$C_6$ alkynyl, substituted or unsubstituted 3-7 membered nitrogen-containing heterocyclyl- substituted $C_2$-$C_6$ alkenyl, and substituted or unsubstituted 3-7 membered cycloalkyl-substituted $C_2$-$C_6$ alkynyl; or an isomer or stereoisomer of any of the foregoing, or a mixture thereof or a pharmaceutically acceptable salt thereof.

42. The compound of embodiment 40, wherein $R^1$ is selected from ethenyl, fluoropropenyl, 3,3-difluoropropenyl, 3,3,3-trifluoropropenyl, 3,3,3-trifluoroprop-1-enyl, alkoxypropenyl, dialkylaminopropenyl, alkylaminopropenyl, aminopropenyl, 3-amino-4-hydroxy-butenyl, 3-amino-4-phenyl-butenyl, dialkylaminobutenyl, alkylaminobutenyl, aminobutenyl, dialkylaminopentenyl, alkylaminopentenyl, aminopentenyl, aminopropynyl, dialkylaminopropynyl, alkylaminopropynyl, methoxypropynyl, substituted or unsubstituted 3-7 membered nitrogen-containing heterocyclyl-propynyl, substituted or unsubstituted 3-7 membered cycloalkyl-ethenyl, substituted or unsubstituted 3-7 membered cycloalkyl-propenyl, substituted or unsubstituted 3-7 membered nitrogen-containing heterocyclyl-ethynyl, substituted or unsubstituted 3-7 membered nitrogen-containing heterocyclyl-propynyl, substituted or unsubstituted 3-7 membered oxygen-containing heterocyclyl-ethenyl, substituted or unsubstituted 3-7 membered oxygen-containing heterocyclyl-propenyl, substituted or unsubstituted 3-7 membered nitrogen-containing heterocyclyl-ethenyl, substituted or unsubstituted 3-7 membered nitrogen-containing heterocyclyl-propenyl, substituted or unsubstituted 3-7 membered cycloalkyl-ethynyl, substituted or unsubstituted 3-7 membered cycloalkyl-propynyl, substituted or unsubstituted 3-7 membered cycloalkyl-ethynyl, and substituted or unsubstituted 3-7 membered cycloalkyl-propynyl; or an isomer or stereoisomer of any of the foregoing, or a mixture thereof or a pharmaceutically acceptable salt thereof.

43. The compound of embodiment 40, wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di(d1,d2, d3-methyl)aminopropenyl, diethylaminopropenyl, 3-(N,N-dimethylamino)-3-phenyl-propenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-(d2-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyl-oxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo[3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-ylpropenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or an isomer or stereoisomer of any of the foregoing, or a mixture thereof or a pharmaceutically acceptable salt thereof.

44. The compound of any one of embodiments 40-43, wherein $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methyl aminocarbonylmethyl, aminocarbonylmethyl, aminocarbonylethyl, 1-aminocarbonylethyl, aminocarbonyl-1,1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl]methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl; or an isomer or stereoisomer of any of the foregoing, or a mixture thereof or a pharmaceutically acceptable salt thereof.

45. The compound of any one of embodiments 40-44, wherein $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl; or an isomer or stereoisomer of any of the foregoing, or a mixture thereof or a pharmaceutically acceptable salt thereof.

46. The compound of any one of embodiments 40-45, wherein $R^8$ is selected from H, trifluoromethyl, methyl, ethyl, carboxy, cyano and methylaminocarbonyl; or an isomer or stereoisomer of any of the foregoing, or a mixture thereof or a pharmaceutically acceptable salt thereof.

47. The compound of any one of embodiments 40-46, wherein $R^9$ is selected from H, fluoro, chloro, methyl, and cyano; or an isomer or stereoisomer of any of the foregoing, or a mixture thereof or a pharmaceutically acceptable salt thereof.

48. The compound of any one of embodiments 40-47, wherein $R^{10}$ is selected from H, fluoro, methylcarbonylamino, chloro, amino, hydroxy, methyl, difluoromethyl, methylsulfonylamino, and methylaminocarbonylamino; or an isomer or stereoisomer of any of the foregoing, or a mixture thereof or a pharmaceutically acceptable salt thereof.

49. The compound of any one of embodiments 40-48, wherein $R^{11}$ is H or fluoro; or an isomer or stereoisomer of any of the foregoing, or a mixture thereof or a pharmaceutically acceptable salt thereof.

50. The compound of any one of embodiments 40-43 and 47-49, wherein $R^6$ is ethyl; $R^7$ is trifluoromethyl; and $R^8$ is H; or an isomer or stereoisomer of any of the foregoing, or a mixture thereof or a pharmaceutically acceptable salt thereof.

51. The compound of any one of embodiments 40-43 and 47-49, wherein $R^6$ is methyl; $R^7$ is trifluoromethyl; and $R^8$ is H; or an isomer or stereoisomer of any of the foregoing, or a mixture thereof or a pharmaceutically acceptable salt thereof.

52. The compound of any one of embodiments 40-43 and 47-49, wherein $R^6$ is H; $R^7$ is trifluoromethyl; and $R^8$ is H; or an isomer or stereoisomer of any of the foregoing, or a mixture thereof or a pharmaceutically acceptable salt thereof.

53. The compound of any one of embodiments 40-43 and 47-49, wherein $R^6$ is 3,5-difluoropyridin-4-yl; $R^7$ is trifluoromethyl; and $R^8$ is H; or an isomer or stereoisomer of any of the foregoing, or a mixture thereof or a pharmaceutically acceptable salt thereof.

54. The compound of any one of embodiments 40 and 44-53, wherein $R^1$ is substituted ethenyl; or an isomer or stereoisomer of any of the foregoing, or a mixture thereof or a pharmaceutically acceptable salt thereof.

55. The compound of any one of embodiments 40 and 44-53, wherein $R^1$ is dimethylaminopropenyl; or an isomer or stereoisomer of any of the foregoing, or a mixture thereof or a pharmaceutically acceptable salt thereof.

56. The compound of any one of embodiments 40 and 44-53, wherein $R^1$ is methylaminopropenyl; or an isomer or stereoisomer of any of the foregoing, or a mixture thereof or a pharmaceutically acceptable salt thereof.

57. The compound of any one of embodiments 40 and 44-53, wherein $R^1$ is 3,3-difluoropropenyl; or an isomer or stereoisomer of any of the foregoing, or a mixture thereof or a pharmaceutically acceptable salt thereof.

58. The compound of any one of embodiments 40 and 44-53, wherein $R^1$ is 2-(azetin-2-yl)ethenyl; or an isomer or stereoisomer of any of the foregoing, or a mixture thereof or a pharmaceutically acceptable salt thereof.

59. The compound of any one of embodiments 40 and 44-53, wherein $R^1$ is 2-(2-methyl-pyrrolidiny-5-yl)ethenyl; or an isomer or stereoisomer of any of the foregoing, or a mixture thereof or a pharmaceutically acceptable salt thereof.

60. The compound of any one of embodiments 40 and 44-53, wherein $R^1$ is 3-(methylamino)butenyl; or an isomer or stereoisomer of any of the foregoing, or a mixture thereof or a pharmaceutically acceptable salt thereof.

61. The compound of any one of embodiments 40 and 44-53, wherein $R^1$ is ethylaminopropenyl; or an isomer or stereoisomer of any of the foregoing, or a mixture thereof or a pharmaceutically acceptable salt thereof.

62. The compound of any one of embodiments 40 and 44-53, wherein $R^1$ is 2-(3-methoxypyrrolidiny-5-yl)ethenyl; or an isomer or stereoisomer of any of the foregoing, or a mixture thereof or a pharmaceutically acceptable salt thereof.

63. The compound of any one of embodiments 40 and 44-53, wherein $R^1$ is 2-(3-fluoropyrrolidiny-5-yl)ethenyl; or an isomer or stereoisomer of any of the foregoing, or a mixture thereof or a pharmaceutically acceptable salt thereof.

64. The compound of any one of embodiments 40 and 44-53, wherein $R^1$ is 2-(pyrrolidiny-2-yl)ethenyl; or an isomer or stereoisomer of any of the foregoing, or a mixture thereof or a pharmaceutically acceptable salt thereof.

65. The compound of any one of embodiments 40 and 44-53, wherein $R^1$ is aminopropenyl; or an isomer or stereoisomer of any of the foregoing, or a mixture thereof or a pharmaceutically acceptable salt thereof.

66. The compound of any one of embodiments 40-65, wherein $R^9$ is fluoro; $R^{10}$ is H; and $R^{11}$ is H; or an isomer or stereoisomer of any of the foregoing, or a mixture thereof or a pharmaceutically acceptable salt thereof.

67. A compound of any of embodiments 1-66, wherein the compound has the formula:

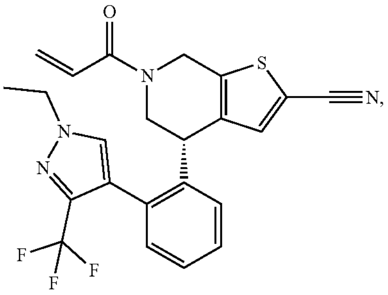

-continued

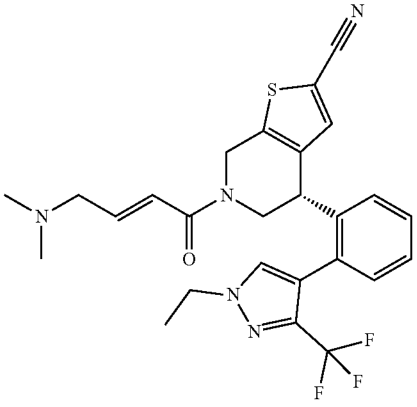

,

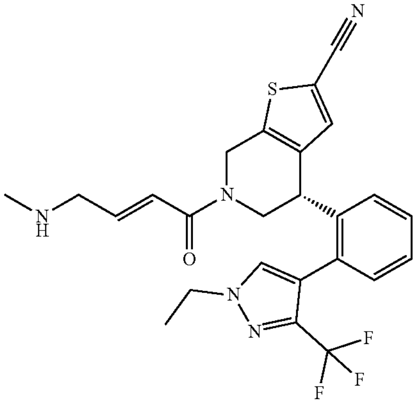

,

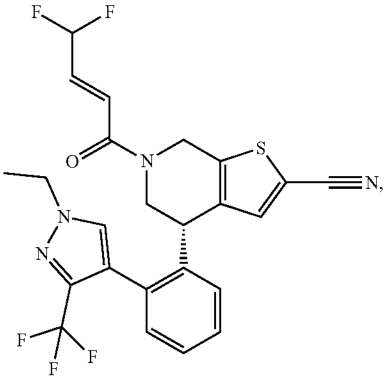

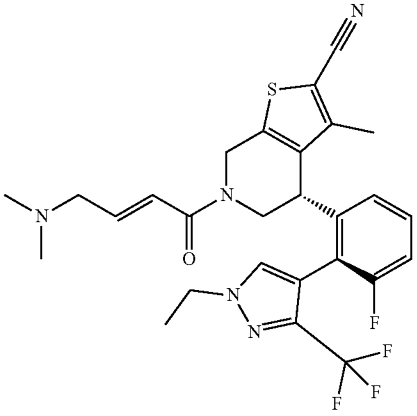

,

-continued
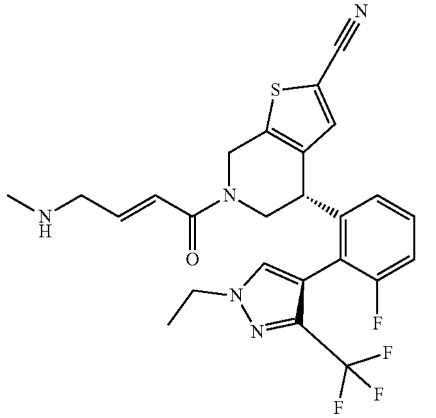
,
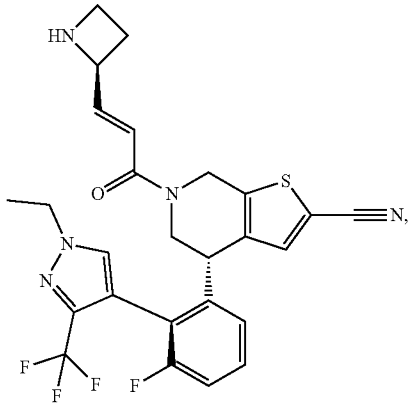
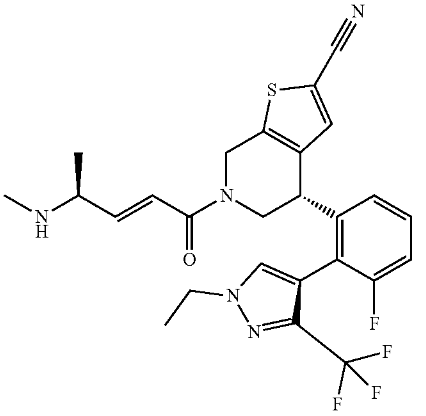
,
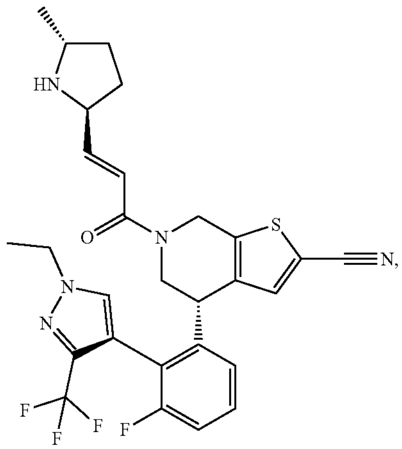
-continued
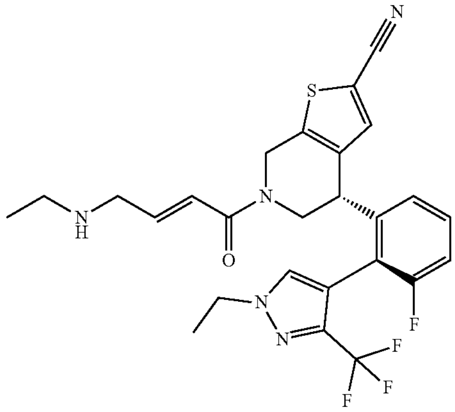
,
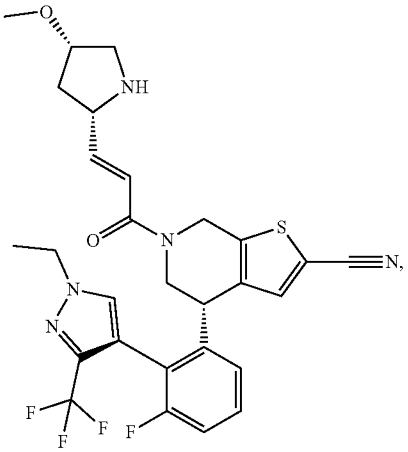
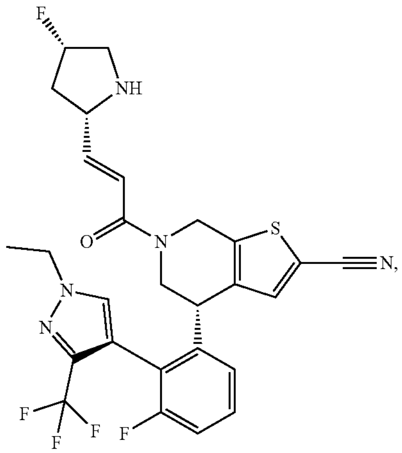
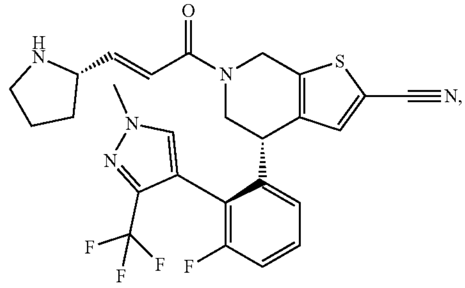

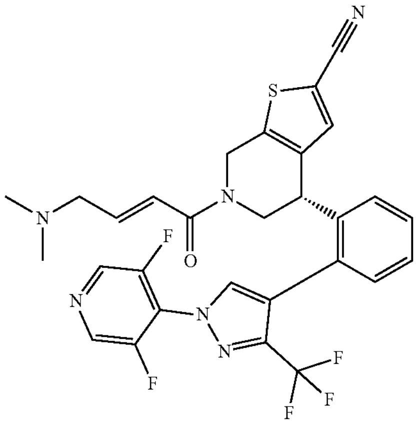
,
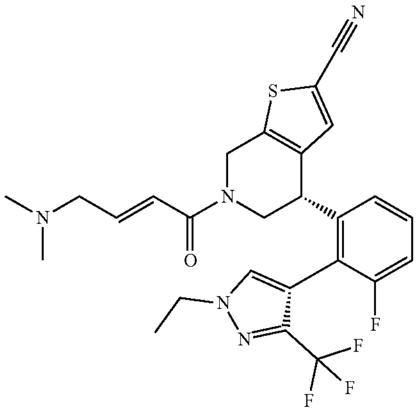
,
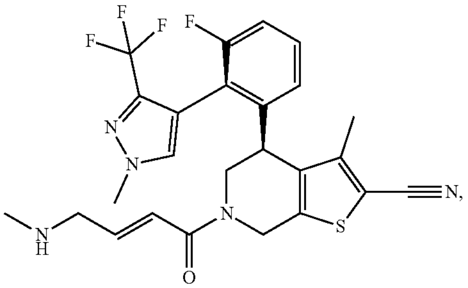
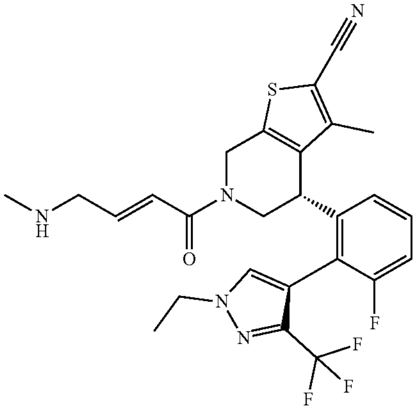
,
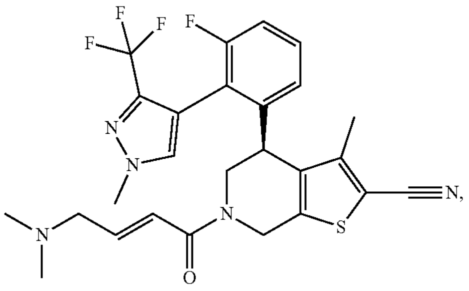
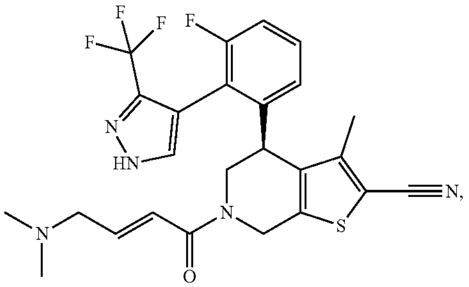
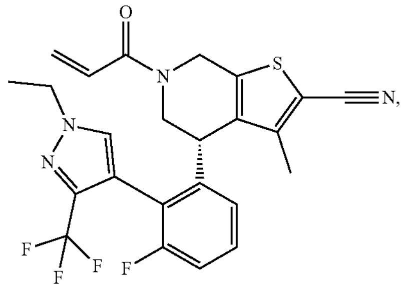
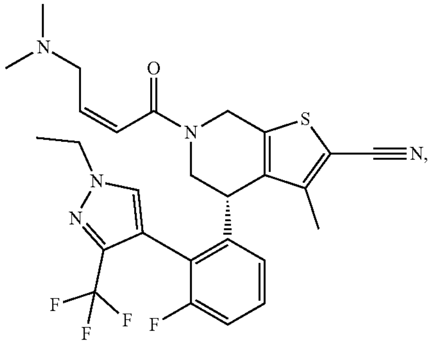
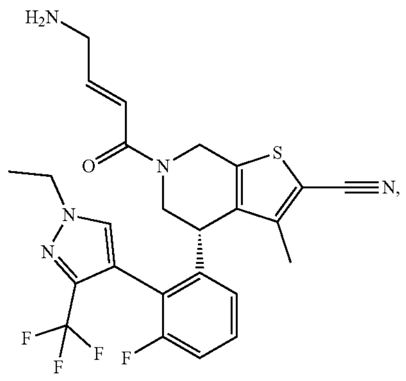

-continued

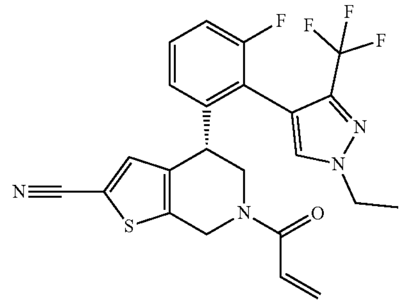

,

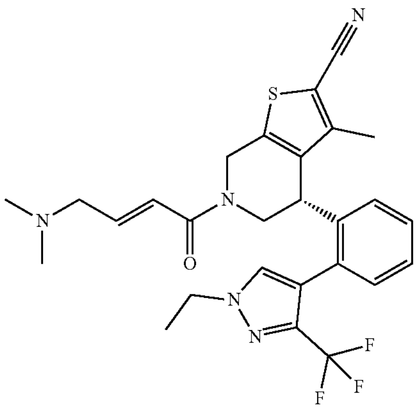

,

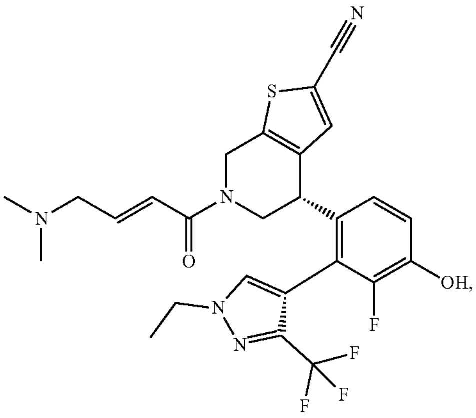

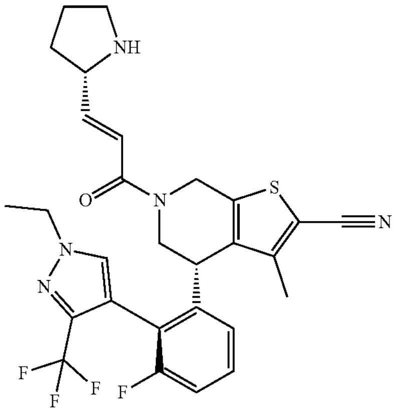

and

-continued

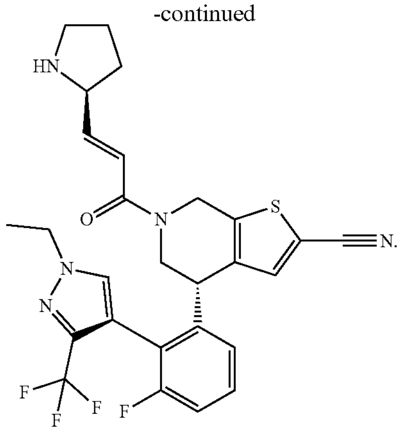

68. A pharmaceutical composition, comprising the compound of any one of embodiments 1-67 or an isomer or stereoisomer of the compound, or a mixture thereof or a pharmaceutically acceptable salt thereof and at least one carrier, excipient, or diluent.

69. A method of inhibiting E1 in a subject in need thereof, said method comprising administering to said subject a therapeutically effective amount of the compound of any one of embodiments 1-67 or the pharmaceutical composition according to embodiment 68.

70. A method of inhibiting cell proliferation in a subject in need thereof, said method comprising administering to said subject a therapeutically effective amount of the compound of any one of embodiments 1-67 or the pharmaceutical composition according to embodiment 68.

71. A method of treating cancer in a subject in need thereof, said method comprising administering to said subject a therapeutically effective amount of the compound of any one of embodiments 1-67 or the pharmaceutical composition according to embodiment 68.

72. The method of embodiment 71, wherein the cancer is selected from acute myeloid leukemia, large B-cell lymphoma, lung squamous cell carcinoma, pancreatic adenosarcoma, esophageal carcinoma, cervical squamous cell carcinoma, endocervical adenosarcoma, stomach adenocarcinomathymoma, renal cell carcinoma, head and neck squamous cell carcinoma, bladder carcinoma, ovarian cystadenocarcinoma, multiple myeloma, non-Hodgkin's lymphoma (NHL), and mesothelioma.

73. The method of embodiment 71, wherein the cancer is selected from head and neck squamous cell carcinoma (HNSCC), non-squamous non-small cell lung cancer (NSCLC), cervical cancer, colorectal cancer (CRC), cutaneous melanoma, squamous NSCLC, and small cell lung cancer.

74. Use of the compound of any one of embodiments 1-67, or the pharmaceutical composition according to embodiment 68, in the manufacture of a medicament for treating an E1 related disease.

75. The compound of any one of embodiments 1-67, or the composition according to embodiment 68, for use in treating an E1 related disease.

76. A medicament for treating an E1 related disease in a patient in need of such treatment, comprising administering to the patient a therapeutically effective amount of the compound of any one of embodiments 1-67, or the pharmaceutical composition according to embodiment 68.

77. The use of embodiment 74, wherein the E1 related disease is selected from acute myeloid leukemia, large B-cell lymphoma, lung squamous cell carcinoma, pancreatic adenosarcoma, esophageal carcinoma, cervical squamous cell carcinoma, endocervical adenosarcoma, stomach adenocarcinomathymoma, renal cell carcinoma, head and neck squamous cell carcinoma, bladder carcinoma, ovarian cystadenocarcinoma, multiple myeloma, non-Hodgkin's lymphoma (NHL), and mesothelioma.

78. The use of embodiment 74, wherein the E1 related disease is selected from head and neck squamous cell carcinoma (HNSCC), non-squamous non-small cell lung cancer (NSCLC), cervical cancer, colorectal cancer (CRC), cutaneous melanoma, squamous NSCLC, and small cell lung cancer.

79. The medicament of embodiment 76, wherein the E1 related disease is selected from acute myeloid leukemia, large B-cell lymphoma, lung squamous cell carcinoma, pancreatic adenosarcoma, esophageal carcinoma, cervical squamous cell carcinoma, endocervical adenosarcoma, stomach adenocarcinomathymoma, renal cell carcinoma, head and neck squamous cell carcinoma, bladder carcinoma, ovarian cystadenocarcinoma, multiple myeloma, non-Hodgkin's lymphoma (NHL), and mesothelioma.

80. The medicament of embodiment 76, wherein the E1 related disease is selected from head and neck squamous cell carcinoma (HNSCC), non-squamous non-small cell lung cancer (NSCLC), cervical cancer, colorectal cancer (CRC), cutaneous melanoma, squamous NSCLC, and small cell lung cancer.

81. The compound of embodiment 75, wherein the E1 related disease is selected from acute myeloid leukemia, large B-cell lymphoma, lung squamous cell carcinoma, pancreatic adenosarcoma, esophageal carcinoma, cervical squamous cell carcinoma, endocervical adenosarcoma, stomach adenocarcinomathymoma, renal cell carcinoma, head and neck squamous cell carcinoma, bladder carcinoma, ovarian cystadenocarcinoma, multiple myeloma, non-Hodgkin's lymphoma (NHL), and mesothelioma.

82. The compound of embodiment 75, wherein the E1 related disease is selected from head and neck squamous cell carcinoma (HNSCC), non-squamous non-small cell lung cancer (NSCLC), cervical cancer, colorectal cancer (CRC), cutaneous melanoma, squamous NSCLC, and small cell lung cancer.

83. The compound of any one of embodiments 1-67 having a plasma protein binding of less than about 99.5% in rat plasma or human plasma.

84. The compound of any one of embodiments 1-67 and 83 having a permeability in CACO-2 cells greater than about 3.0 ucm/s.

85. The compound of any one of embodiments 1-67, 83 and 84 having solubility in simulated gastric fluid greater than about 20 μM.

86. The compound of any one of embodiments 1-67 and 83-85 having solubility in simulated intestinal fluid greater than about 30 μM.

87. The compound of any one of embodiments 1-67 and 83-86 having solubility in phosphate buffered saline [pH 7.4] greater than about 40 μM.

88. The compound of any one of embodiments 1-67 and 83-87 having an 1050 in HCT-116 cells less than 0.2 μM.

What is claimed is:

1. A compound of the structure of Formula IV or Formula V:

IV

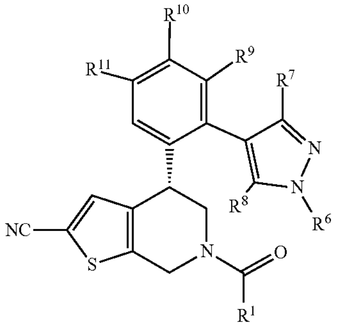

or

V

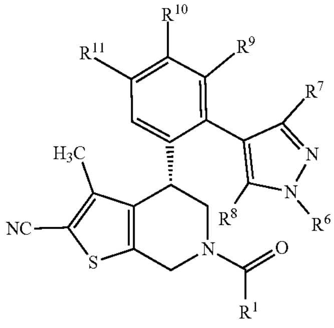

wherein $R^1$ is substituted or unsubstituted $C_2$-$C_6$ alkenyl, or substituted or unsubstituted $C_2$-$C_6$ alkynyl;

$R^6$ is selected from H, $C_{1-6}$ alkyl, $C_{2-4}$ alkynyl, $C_{1-6}$ hydroxyalkyl, $C_{1-6}$ alkoxyalkyl, $C_{1-6}$ alkylamino-$C_{1-6}$ alkyl, $C_{1-6}$ alkylaminocarbonyl-$C_{1-6}$ alkyl, aminocarbonyl-$C_{1-6}$ alkyl, $C_{1-6}$ alkoxycarbonyl-$C_{1-6}$ alkyl, carboxy-$C_{1-6}$ alkyl, $C_{1-6}$ alkylcarbonylamino-$C_{1-6}$ alkyl, $C_{1-6}$ cyanoalkyl, $C_{1-6}$ haloalkyl, $C_{1-6}$ alkylsulfonyl, $C_{3-6}$ cycloalkyl, $C_{3-6}$ cycloalkyl-$C_{1-6}$ alkyl, aryl-$C_{1-6}$ alkyl, substituted or unsubstituted 5 or 6 membered heteroaryl-$C_{1-6}$ alkyl, substituted or unsubstituted 5 or 6 membered heterocyclyl and substituted or unsubstituted 5 or 6 membered heteroaryl;

$R^7$ is selected from H, carboxy, amino, $C_{1-6}$ alkyl, $C_{1-3}$ haloalkyl, $C_{1-6}$ alkoxy, $C_{1-6}$ alkylamino, $C_{1-6}$ alkylaminocarbonyl, and $C_{3-6}$ cycloalkyl;

$R^8$ is selected from H, carboxy, cyano, $C_{1-4}$ alkyl, $C_{1-3}$ haloalkyl, and $C_{1-6}$ alkylaminocarbonyl;

$R^9$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

$R^{10}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino; and $R^{11}$ is selected from H, halo, hydroxy, $C_{1-3}$ alkyl, $C_{1-3}$ haloalkyl, cyano, amino, $C_{1-3}$ alkylcarbonylamino, $C_{1-3}$ alkylsulfonylamino, and $C_{1-3}$ alkylaminocarbonylamino;

or a pharmaceutically acceptable salt thereof.

2. The compound of claim 1, wherein $R^1$ is selected from ethenyl, fluoropropenyl, 3,3-difluoropropenyl, 3,3,3-trifluoropropenyl, 3,3,3-trifluoroprop-1-enyl, methoxypropenyl, ethoxypropenyl, aminopropenyl, 3-amino-butenyl, 3-methylamino-butenyl, 3-amino-4-hydroxy-butenyl, 3-methylamino-4-methoxy-butenyl, 3-amino-4-phenyl-butenyl, 3-amino-pentenyl, aminopropynyl, methoxypropynyl, dimethylaminopropenyl, di($d_1$,$d_2$,$d_3$-methyl)aminopropenyl, diethylaminopropenyl, 3-(N,N-dimethylamino)-3-phenylpropenyl, 3-(N,N-dimethylamino)-3-cyclopropyl-propenyl, (cyclopropylamino)propenyl, bicyclo[1.1.1]pent-1-ylamino, (1-methylcyclopropylamino)propenyl, (3-methyloxetan-3-yl)aminopropenyl, (3-methyltetrahydrofur-3-yl)aminopropenyl, (4-methyl-tetrahydropyran-4-yl)aminopropenyl, methylaminopropenyl, N-benzyl-N-methylaminopropenyl, N-(tert-butyl)aminopropenyl, N-sec-butylaminopropenyl, N-butylaminopropenyl, N-(isopropyl)aminopropenyl, N-($d_2$-isopropyl)aminopropenyl, ethylaminopropenyl, N-[3,3-difluorocyclobutyl]aminopropenyl, 1-hydroxymethyl-1-methyl-ethylaminopropenyl, 3-dimethylamino-butenyl, 3-(N-methylamino)-butenyl, methylaminobutenyl, N,N-dimethylaminobutenyl, piperidin-2-ylpropenyl, pyrrolidin-1-ylpropenyl, 3-methyl-oxetan-3-ylpropenyl, 4-methyl-tetrahydropyran-4-ylpropenyl, piperidin-2-ylethenyl, pyrrolidin-2-ylethenyl, azetidin-2-ylethenyl, morpholin-3-ylethenyl, 1-methylpyrrolidin-2-ylethenyl, 3-methylpyrrolidin-5-ylethenyl, 3-ethylpyrrolidin-5-ylethenyl, 2-methylpyrrolidin-5-ylethenyl, 2,2-dimethylpyrrolidin-5-ylethenyl, 3-methoxypyrrolidin-5-ylethenyl, 3-fluoropyrrolidin-5-ylethenyl, 3,3-difluoropyrrolidin-5-ylethenyl, 5-azaspiro[2.4]heptan-6-ylethenyl, 2-azabicyclo [3.1.0]hexan-3-ylethenyl, 3,3-dimethylpyrrolidin-5-ylethenyl, 3-methylpyrrolidin-1-ylpropenyl, 2-methylpyrrolidin-1-ylpropenyl, 1-methylcarbonylpyrrolidin-3-ylethenyl, 2-carboxypyrrolidin-1-ylpropenyl, 3-carboxypyrrolidin-1-ylpropenyl, tetrahydrofur-3-yl-propenyl, dimethylaminopropynyl, methylaminopropynyl, 2-amino-2-methylbutynyl, 2-(1-amino-cyclopropyl)-ethynyl, 2-(1-amino-cyclobutyl)-ethynyl, 2-(1-amino-cyclopentyl)-ethynyl, azetidin-2-ylethynyl, pyrrolidin-2-ylethynyl, pyrrolidin-3-ylethynyl, 2-methyl-pyrrolidin-2-ylethynyl, 4-methyl-piperazin-1-ylpropynyl, and piperidin-3-ylethynyl; or a pharmaceutically acceptable salt thereof.

3. The compound of claim 1, wherein $R^6$ is selected from H, ethyl, isopropyl, butyl, propyl, methyl, propynyl, 1-hydroxyethyl, 2-hydroxymethylethyl, 1-hydroxy-2,2-dimethylethyl, 2-hydroxypropyl, 2-hydroxy-2-methylpropyl, methoxymethyl, methoxyethyl, dimethylaminoethyl, carboxymethyl, carboxyethyl, carboxypropyl, methoxycarbonylmethyl, ethoxycarbonylmethyl, ethoxycarbonylethyl, ethoxycarbonylpropyl, dimethylaminocarbonylmethyl, dimethylaminocarbonyl-1-ethyl, methylaminocarbonyl-1-ethyl, methylaminocarbonylethyl, methylaminocarbonylmethyl, aminocarbonylmethyl, aminocarbonylethyl, 1-aminocarbonylethyl, aminocarbonyl-1,1-dimethylmethyl, methylcarbonylaminoethyl, 1-methylcarbonylamino-2,2-dimethylethyl, 2-cyano-2-methylethyl, cyanomethyl, 2-cyanoethyl, 1-cyanoethyl, 2-fluoroethyl, 2,2-difluoroethyl, 2,2,2-trifluoroethyl, methylsulfonyl, cyclopropyl, cyclopropylmethyl, benzyl, 4-pyridinylethyl, 2-pyridinylethyl, 3-pyridinylmethyl, 2-pyridinylmethyl, 4-oxazolylmethyl, 1,3,4-oxadiazol-2-yl]methyl, 1,2,4-oxadiazol-2-yl]methyl 1-methylazetidin-3-yl, 1-methylpyrrolidin-3-yl, 1-methylpiperidin-4-yl, 1-methylpiperidin-3-yl, 5-methoxypyrimidin-4-yl, 2-amino-4-pyridyl, 3-chloro-5-fluoro-4-pyridyl, 3,5-difluoro-4-pyridyl, 3-fluoro-2-pyridyl, 3-methoxy-2-pyridyl, 3-fluoro-4-pyridyl, 3-chloro-4-pyridyl, 4-pyridyl and 2-pyridyl; or a pharmaceutically acceptable salt thereof.

4. The compound of claim 1, wherein $R^7$ is selected from H, trifluoromethyl, difluoromethyl, 1,1-difluoroethyl, methyl, ethyl, methoxy, amino, dimethylamino, carboxy, methylaminocarbonyl, dimethylaminocarbonyl, and cyclopropyl; or a pharmaceutically acceptable salt thereof.

5. The compound of claim 1, wherein $R^8$ is selected from H, trifluoromethyl, methyl, ethyl, carboxy, cyano and methylaminocarbonyl; or a pharmaceutically acceptable salt thereof.

6. The compound of claim 1, wherein $R^9$ is selected from H, fluoro, chloro, methyl, and cyano; or or a pharmaceutically acceptable salt thereof.

7. The compound of claim 1, wherein $R^{10}$ is selected from H, fluoro, methylcarbonylamino, chloro, amino, hydroxy, methyl, difluoromethyl, methylsulfonylamino, and methylaminocarbonylamino; or a pharmaceutically acceptable salt thereof.

8. The compound of claim 1, wherein $R^{11}$ is H or fluoro; or a pharmaceutically acceptable salt thereof.

9. The compound of claim 1, wherein $R^6$ is ethyl; $R^7$ is trifluoromethyl; and $R^8$ is H; or $R^6$ is methyl; $R^7$ is trifluoromethyl; and $R^8$ is H; or $R^6$ is H; $R^7$ is trifluoromethyl; and $R^8$ is H; or $R^6$ is 3,5-difluoropyridin-4-yl; $R^7$ is trifluoromethyl; and $R^8$ is H;

or a pharmaceutically acceptable salt thereof.

10. The compound of claim 1, wherein $R^1$ is substituted ethenyl; or a pharmaceutically acceptable salt thereof.

11. The compound of claim 1, wherein $R^1$ is dimethylaminopropenyl; or a pharmaceutically acceptable salt thereof.

12. The compound of claim 1, wherein $R^9$ is fluoro; $R^{10}$ is H; and $R^{11}$ is H; or a pharmaceutically acceptable salt thereof.

13. The compound of claim 1, wherein the compound is a specific isomer selected from:

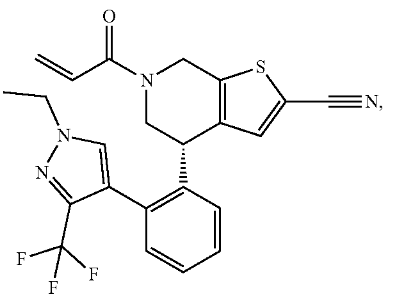

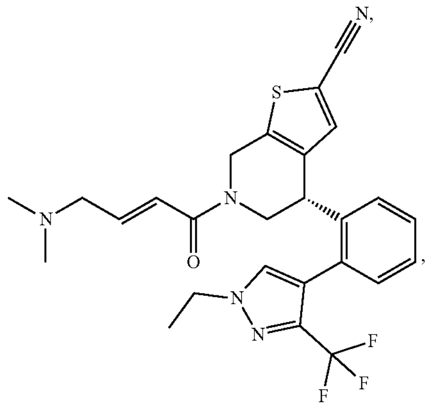

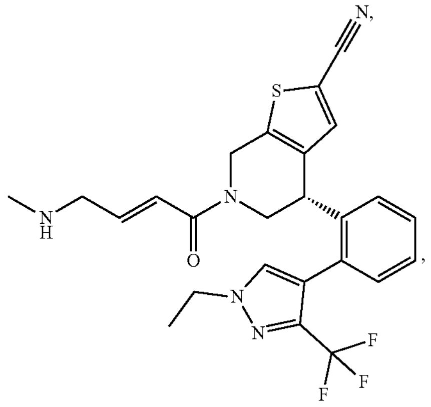

-continued
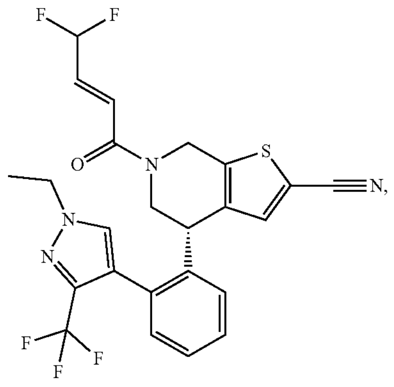
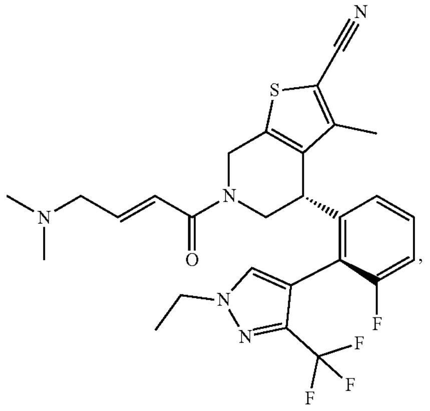
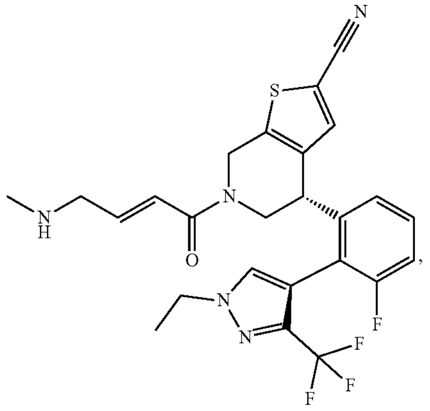
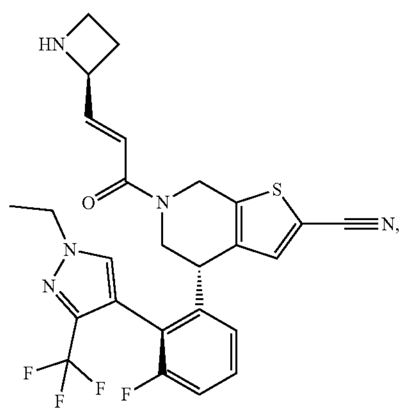
-continued
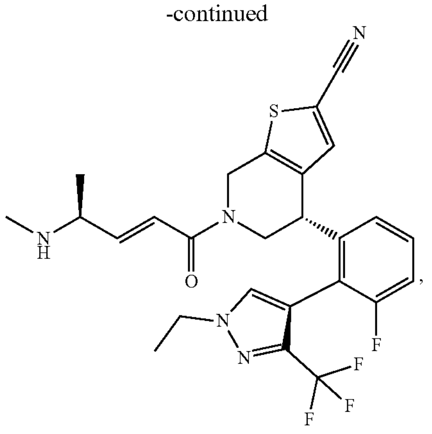
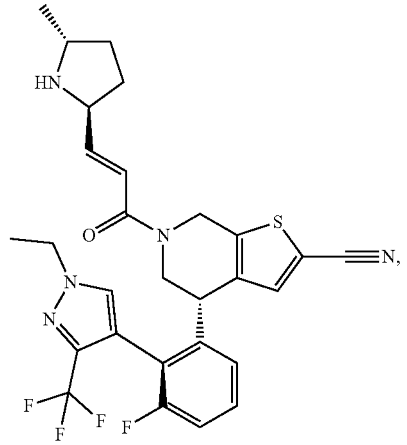
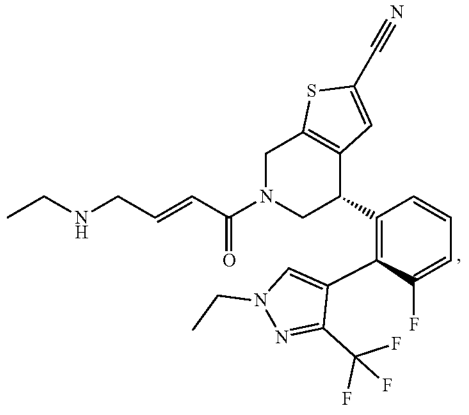
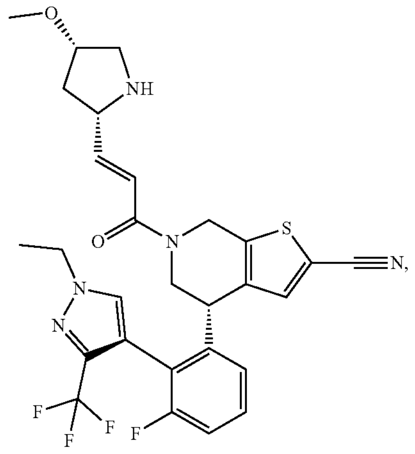

-continued
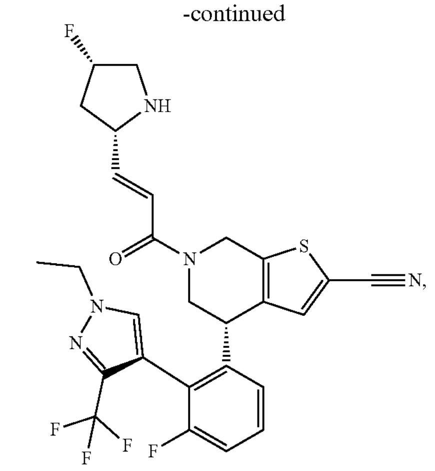
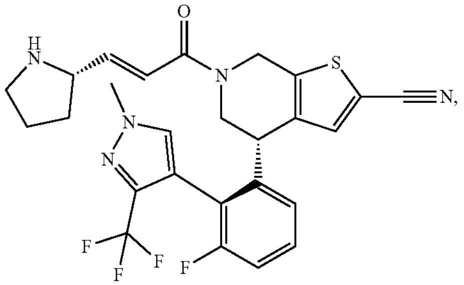
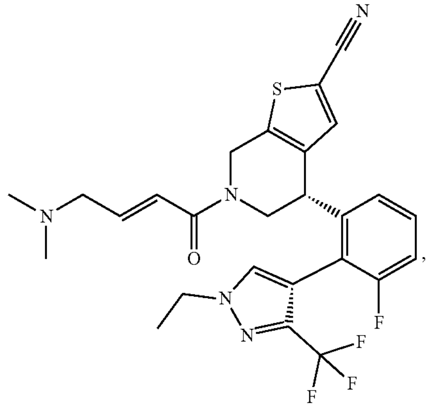
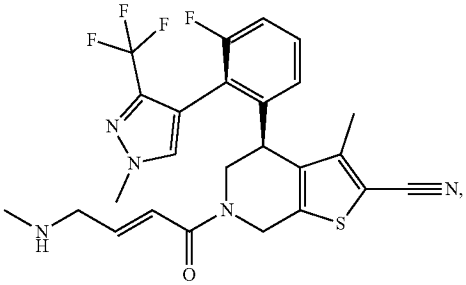
-continued
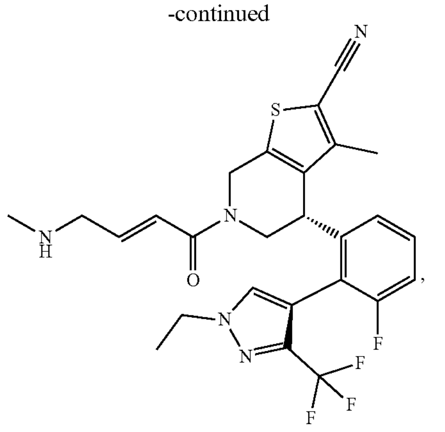
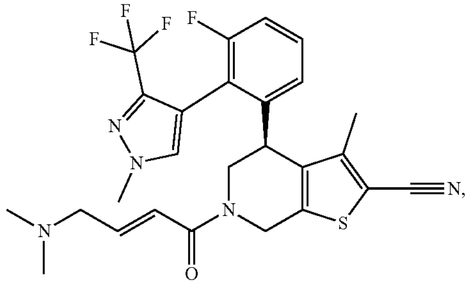
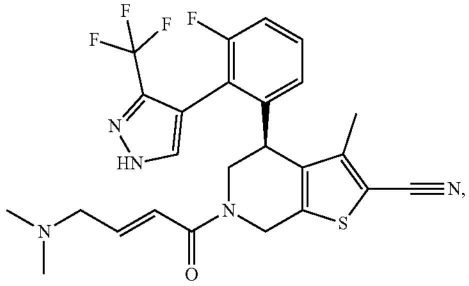
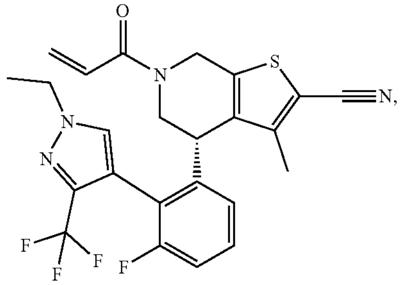
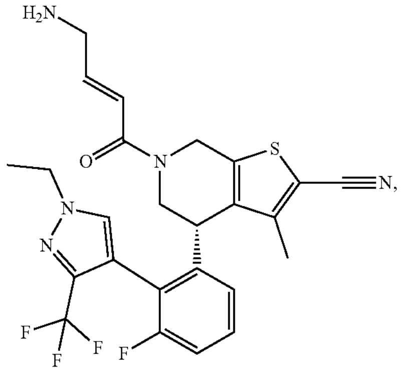

-continued
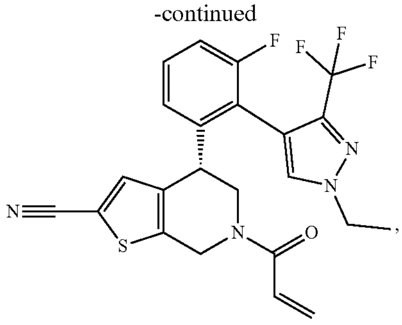
,
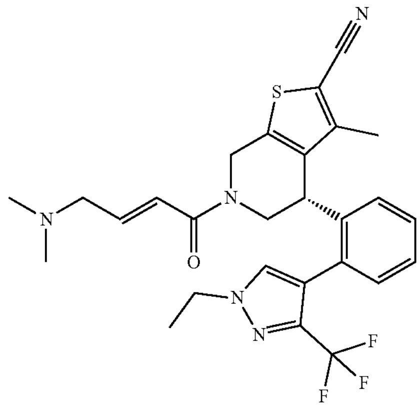
,
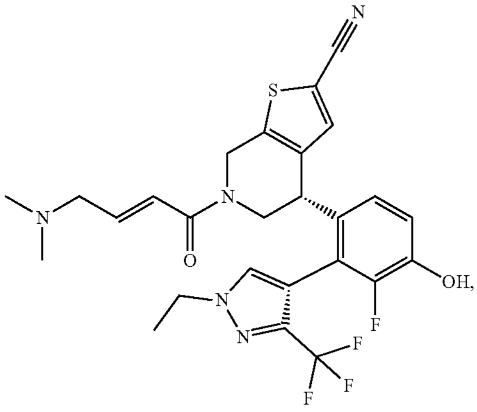
,
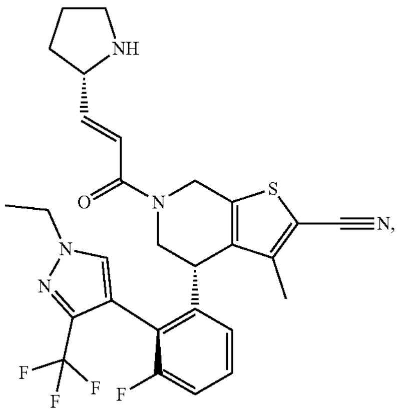
and
-continued
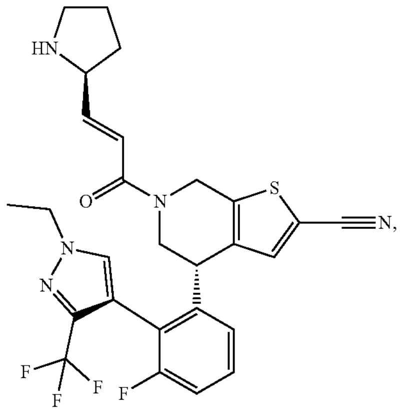
,
or is a specific isomer selected from the group consisting of
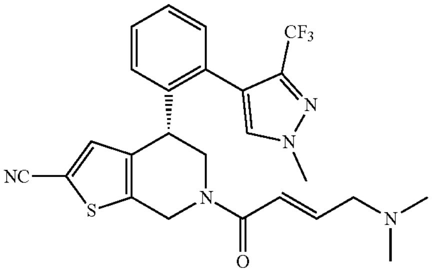
,
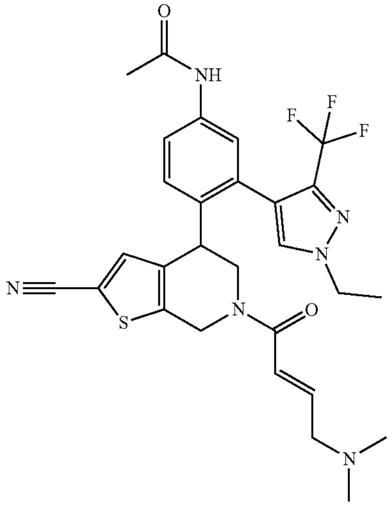
, -continued
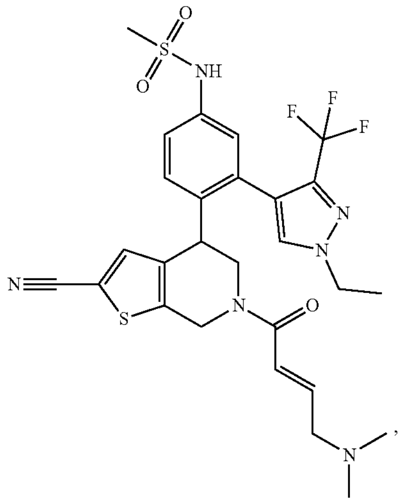
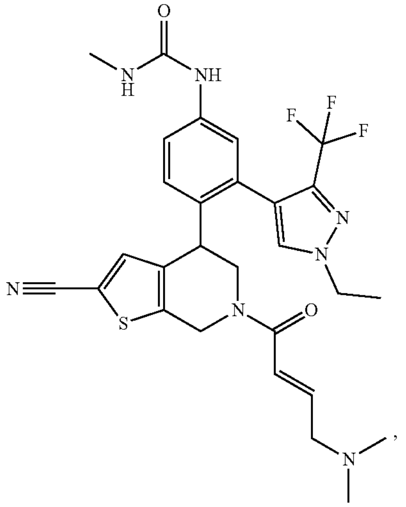
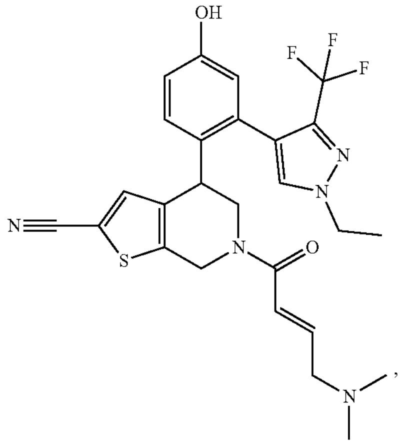
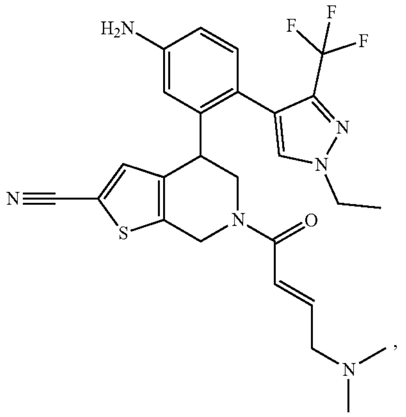
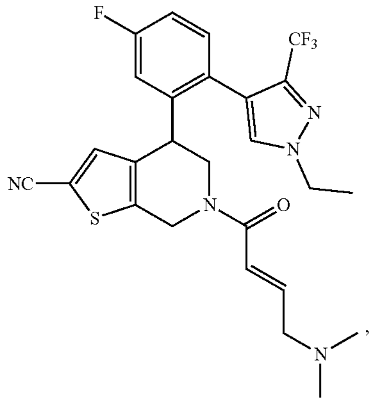
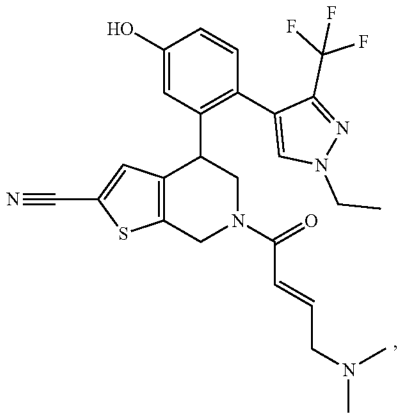

-continued
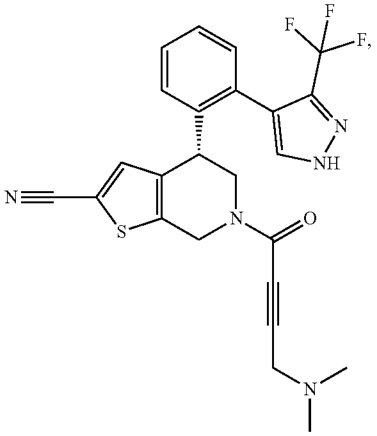
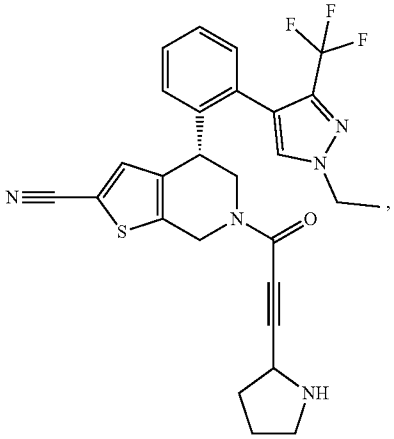
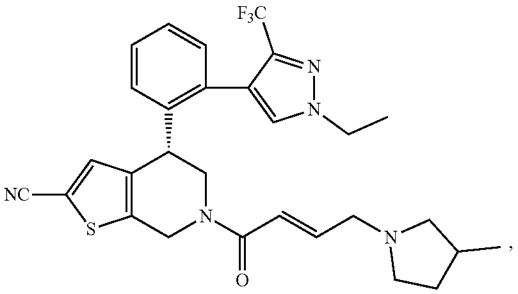
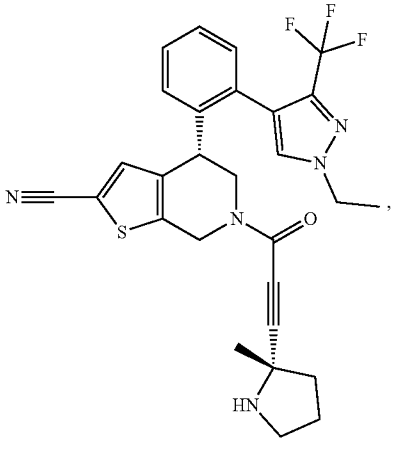
-continued
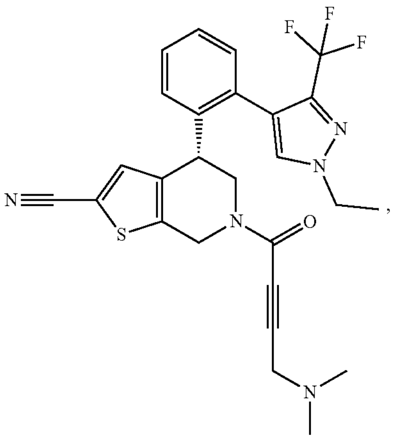
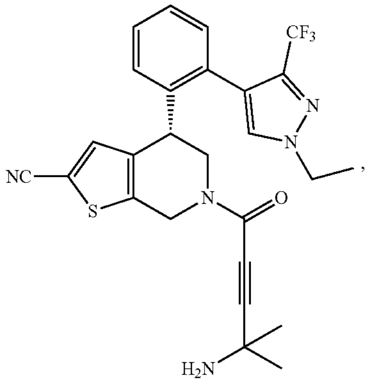
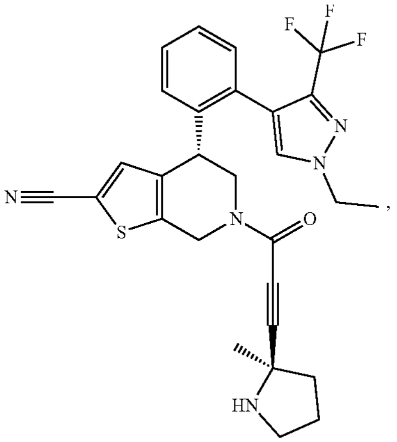
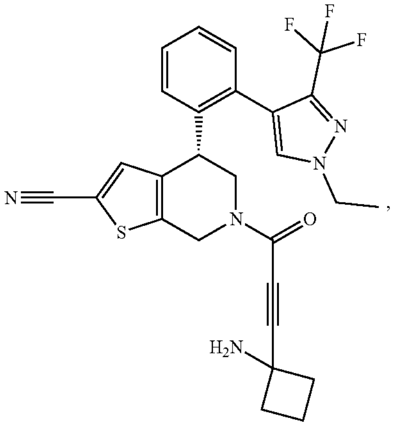

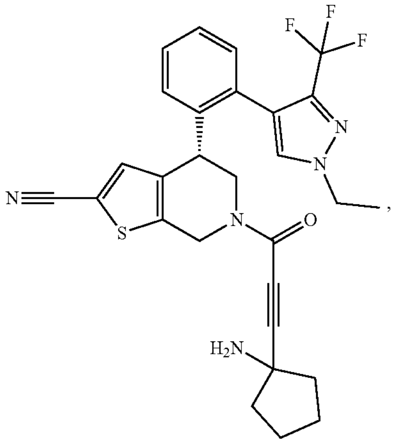
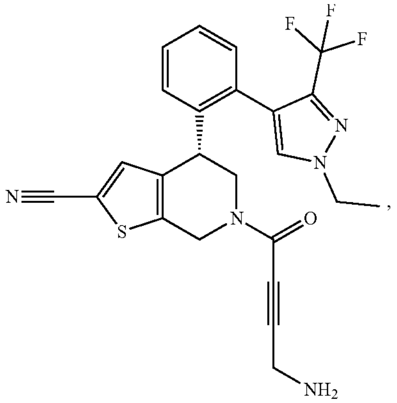
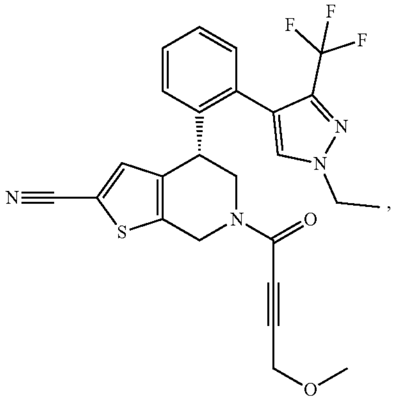
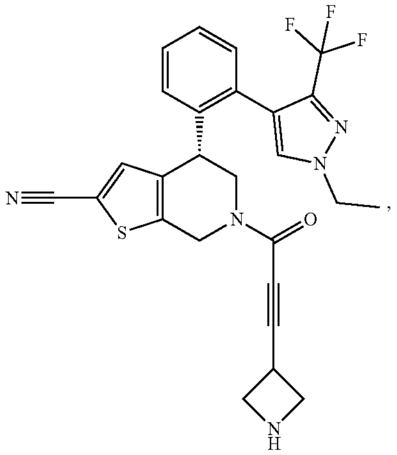
-continued
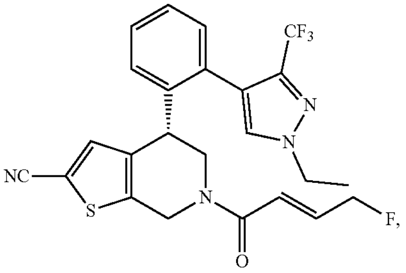
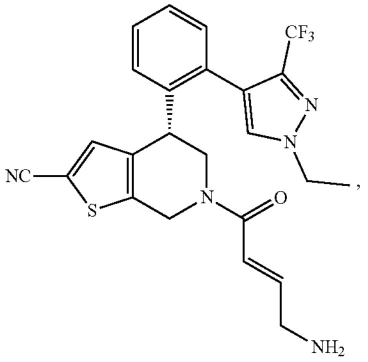
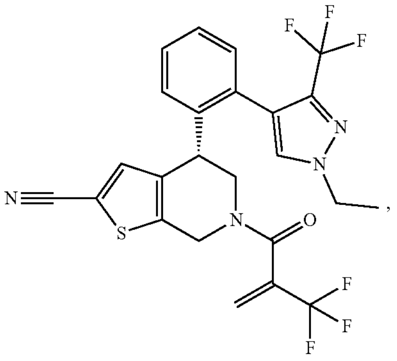
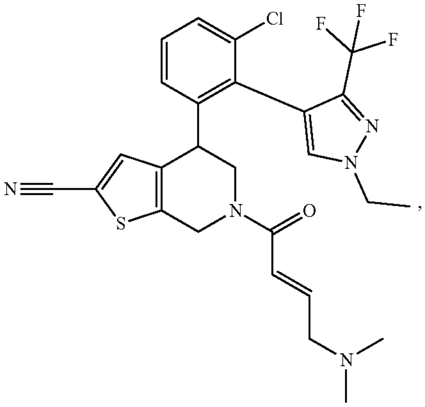

-continued
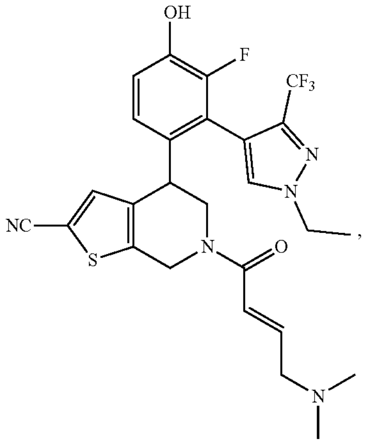
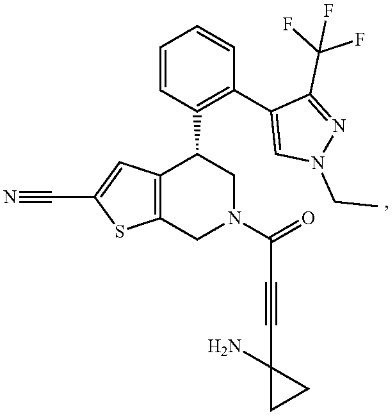
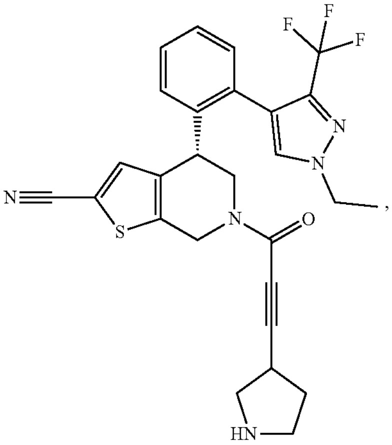
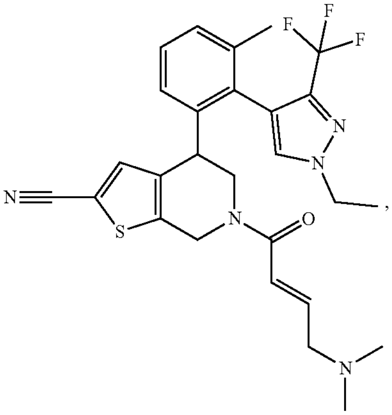
-continued
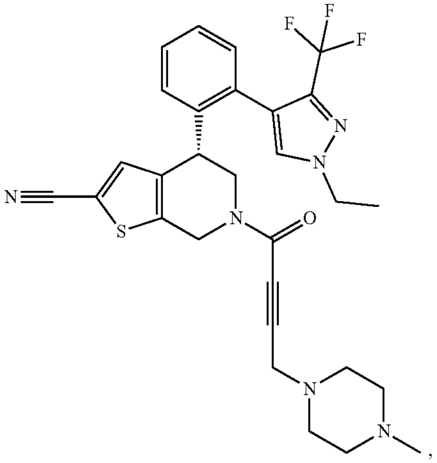
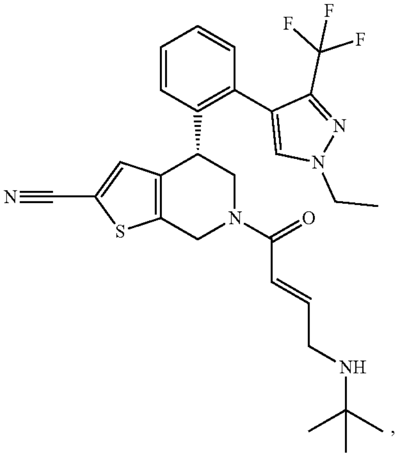
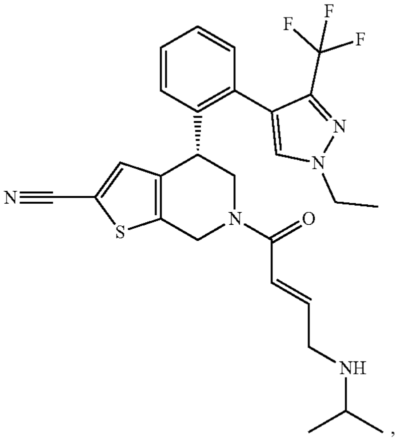

-continued
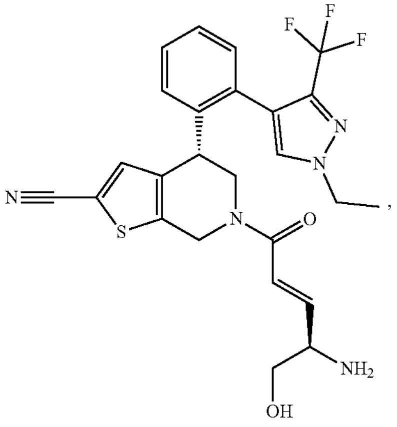
,
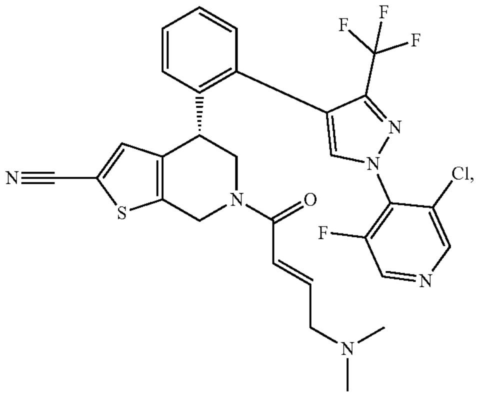
,
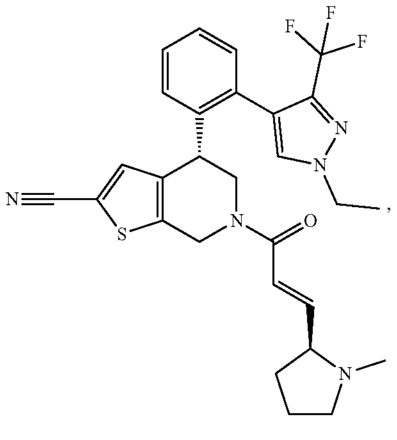
,
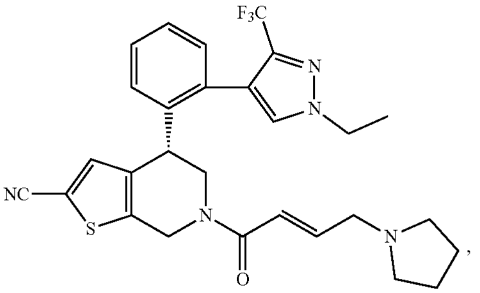
,
-continued
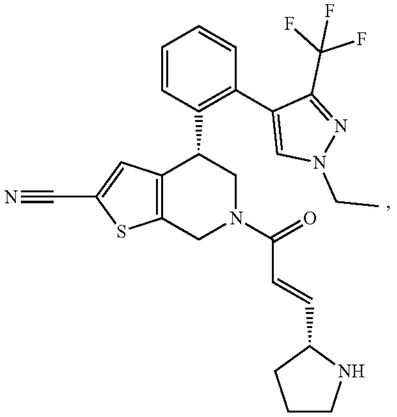
,
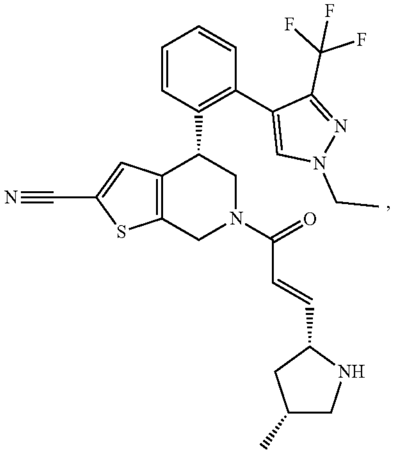
,
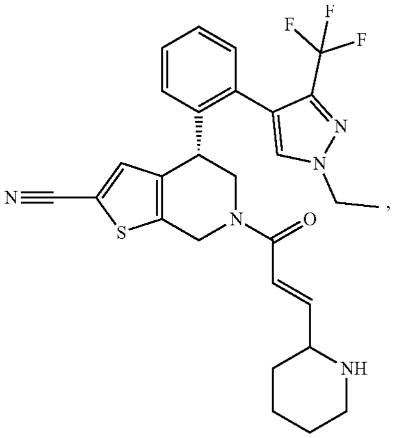
,
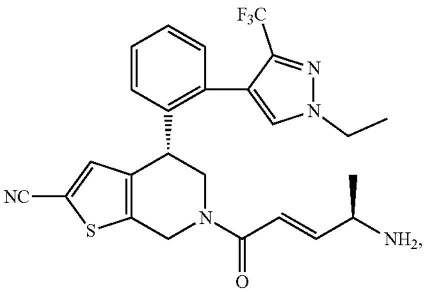
,

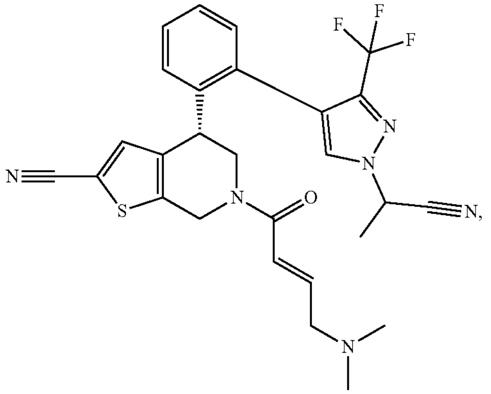
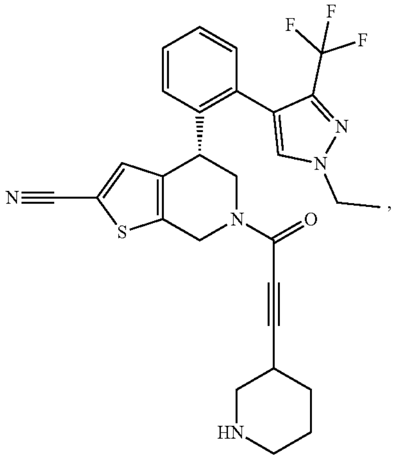
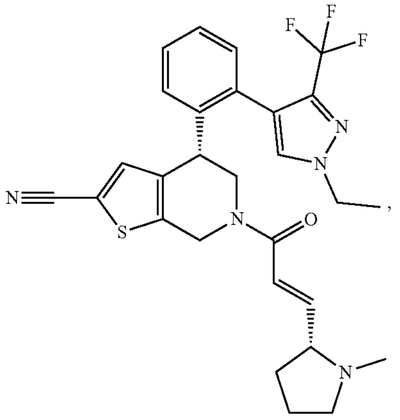
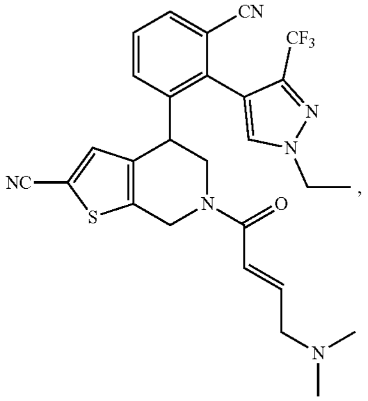
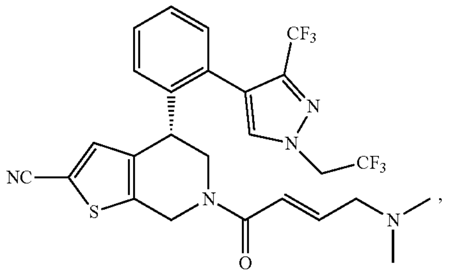
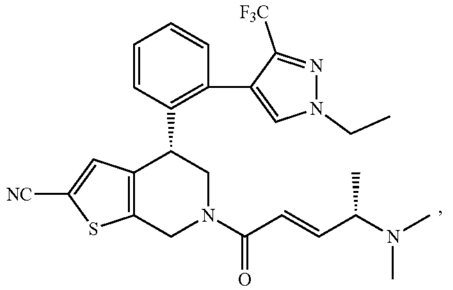
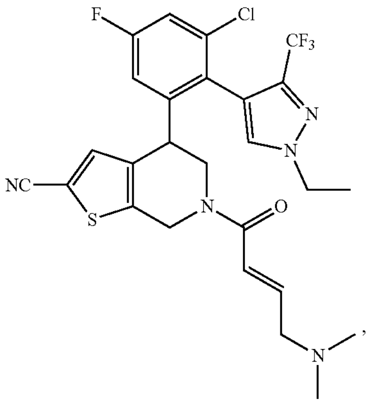
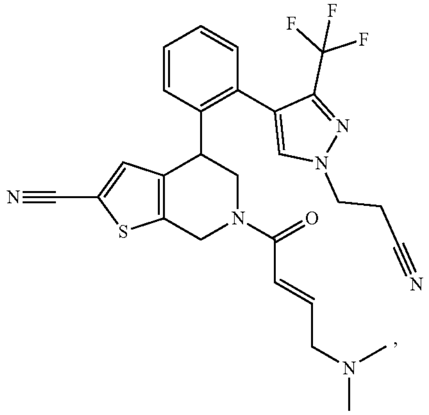
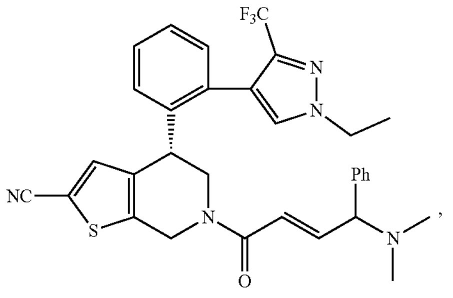

-continued
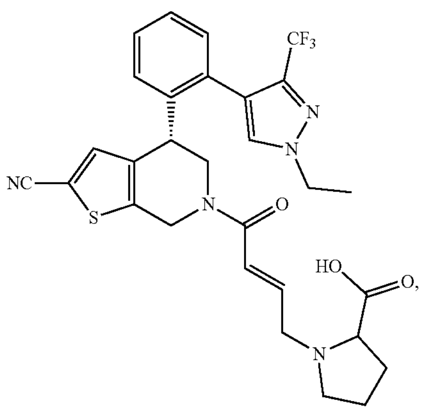
,
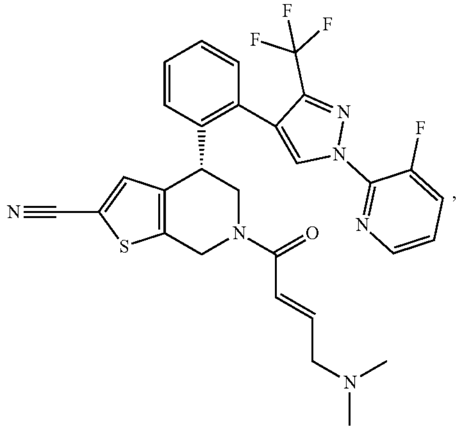
,
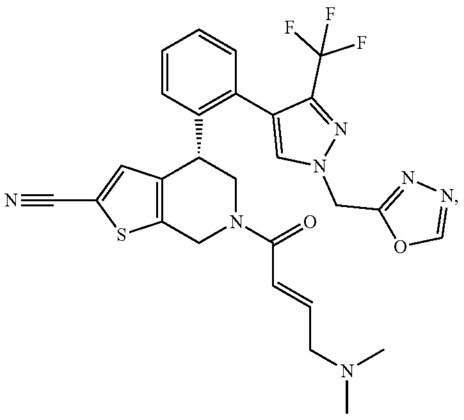
,
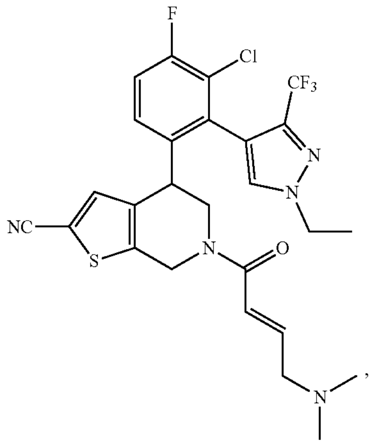
,
-continued
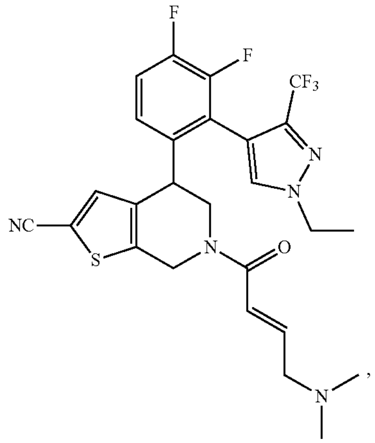
,
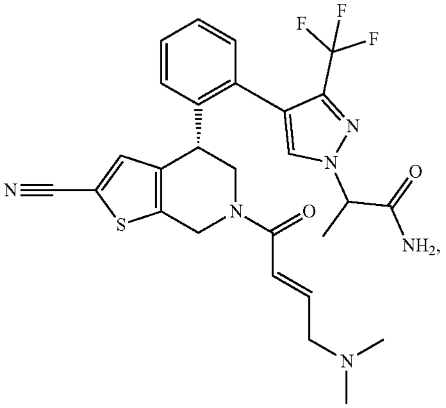
,
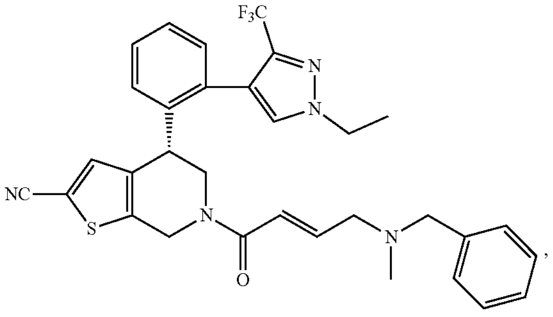
,
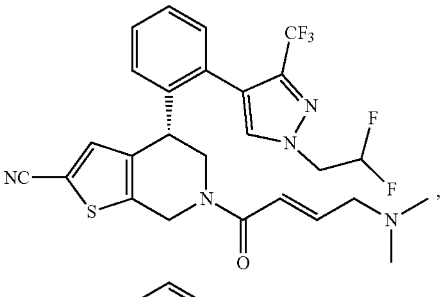
,
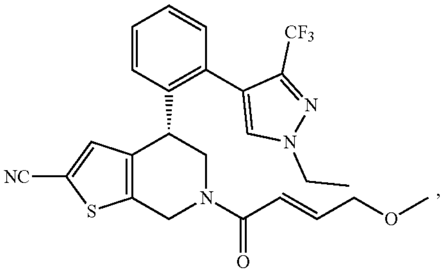
, -continued
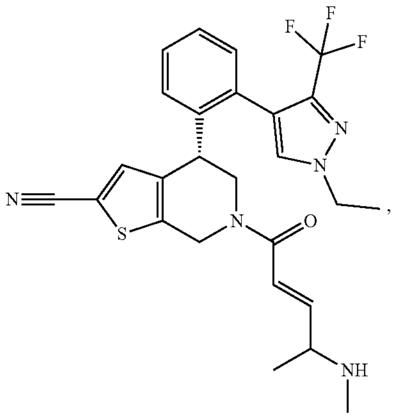
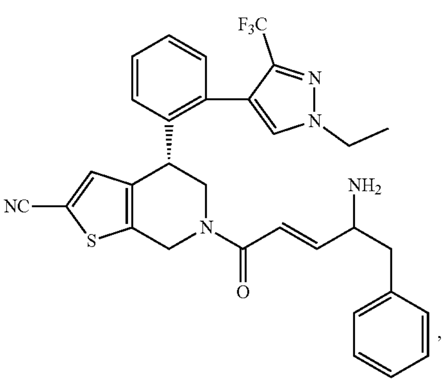
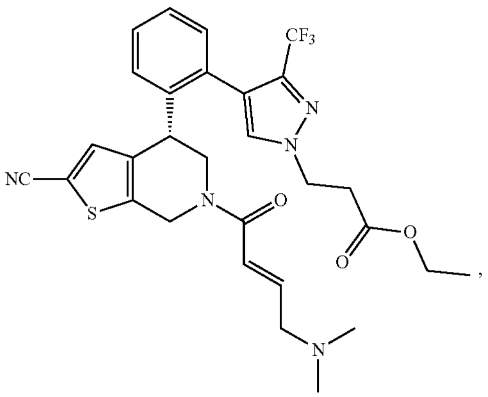
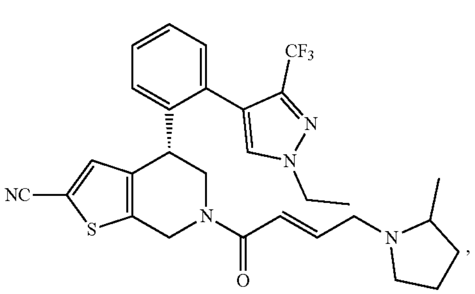
-continued
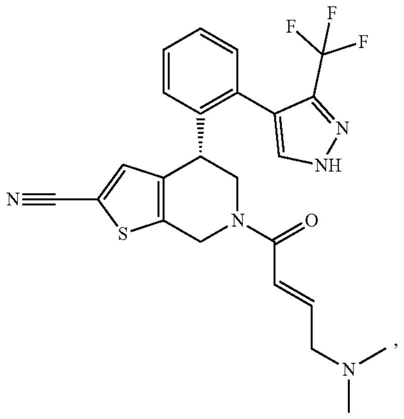
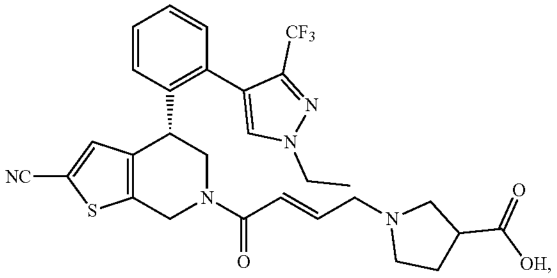
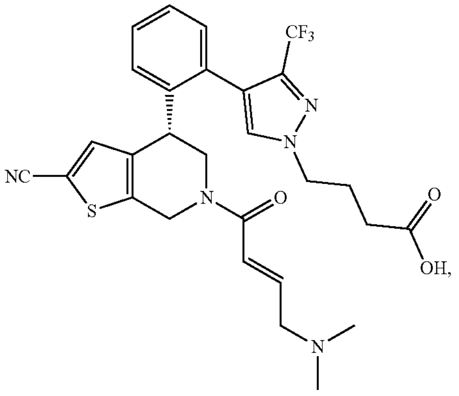
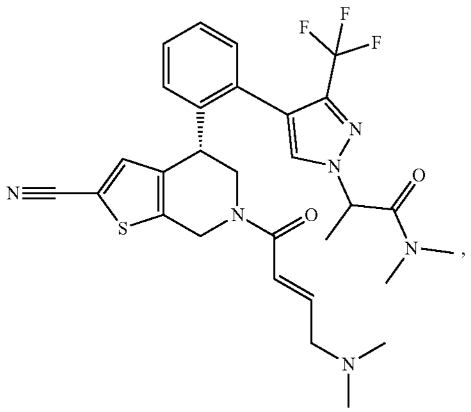

-continued
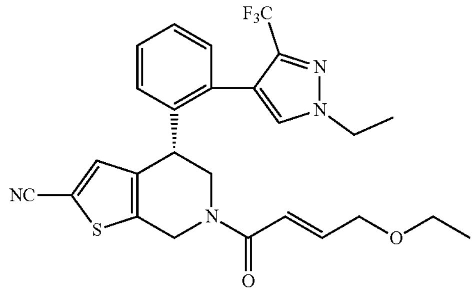
,
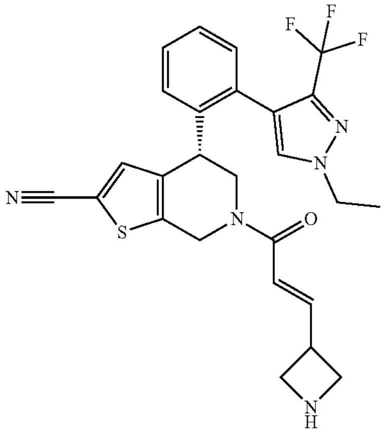
,
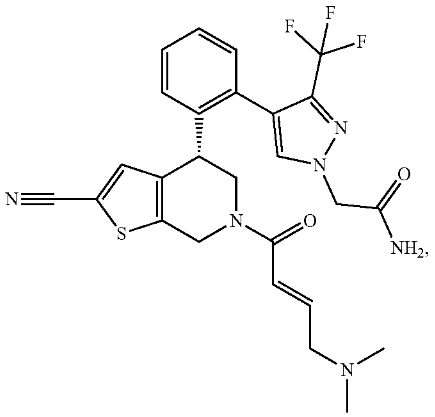
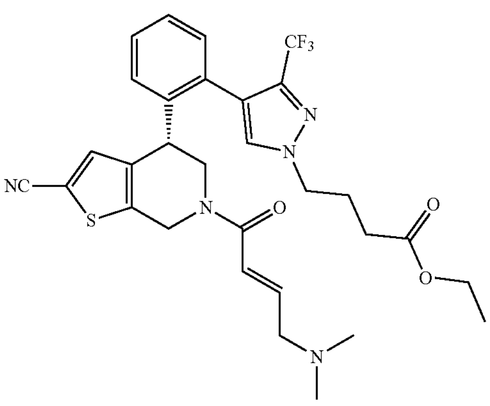
,
-continued
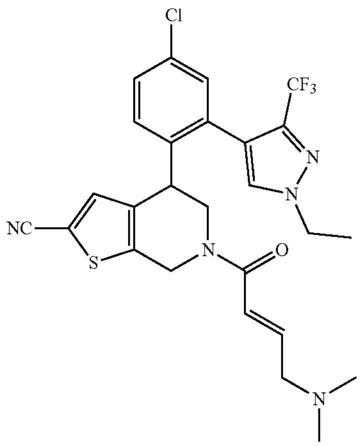
,
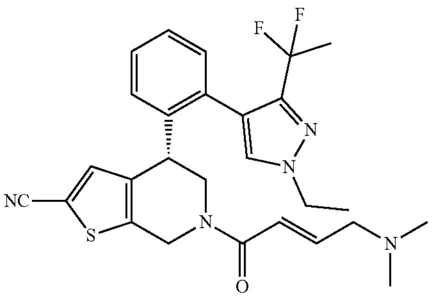
,
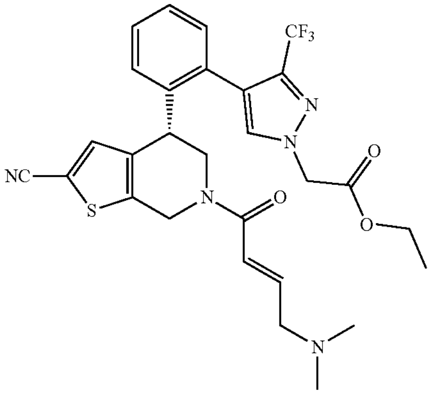
,
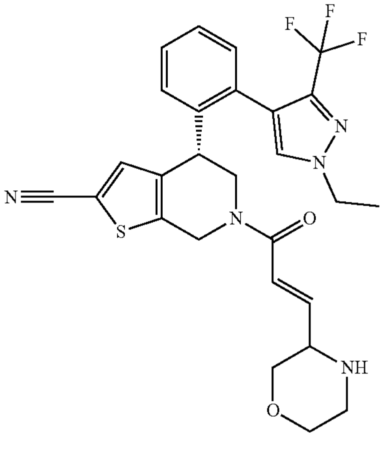
, -continued
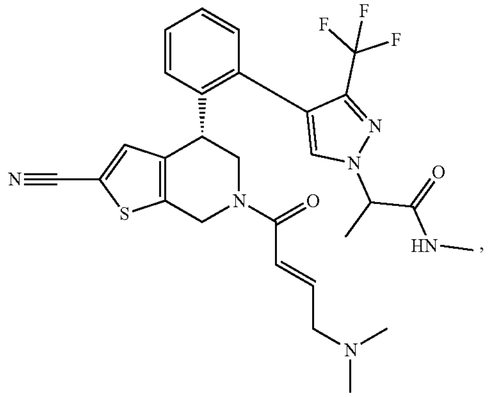
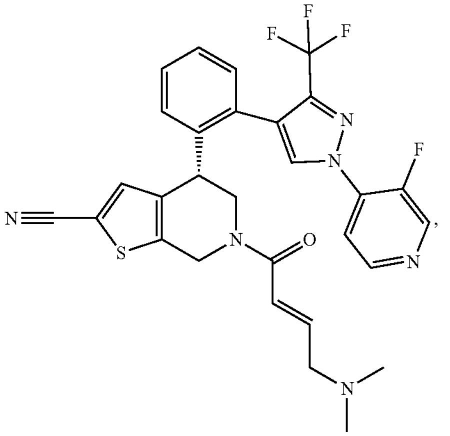
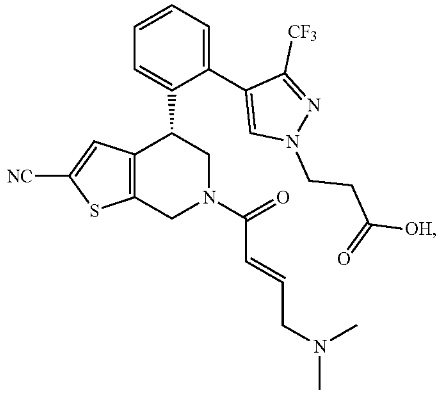
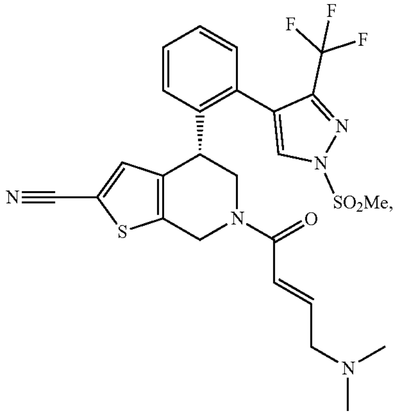
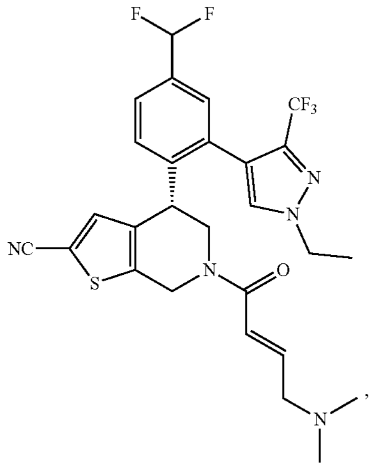
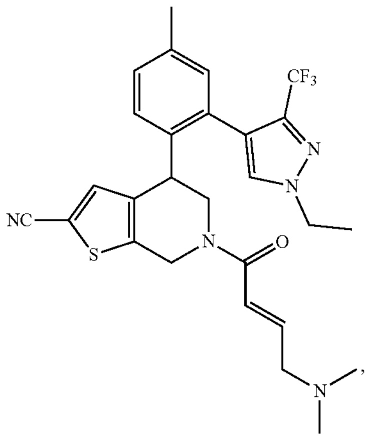
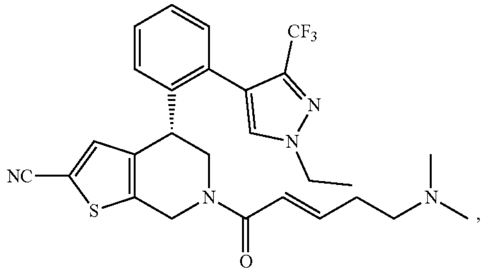
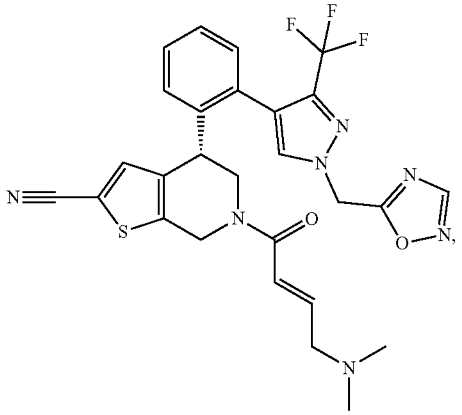

-continued
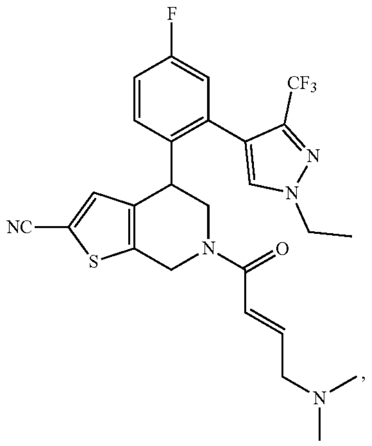
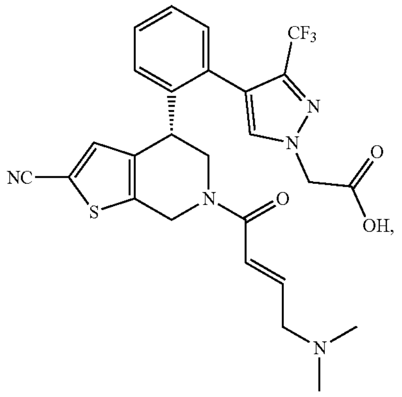
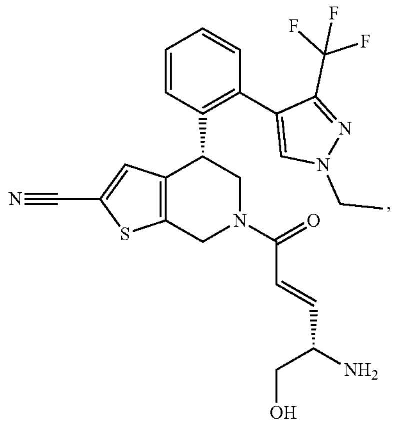
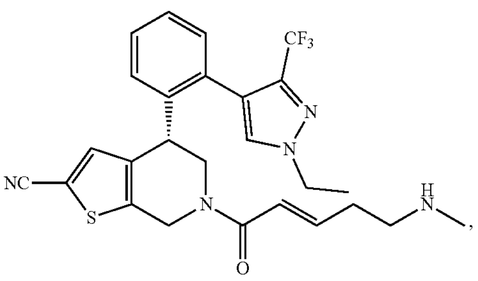
-continued
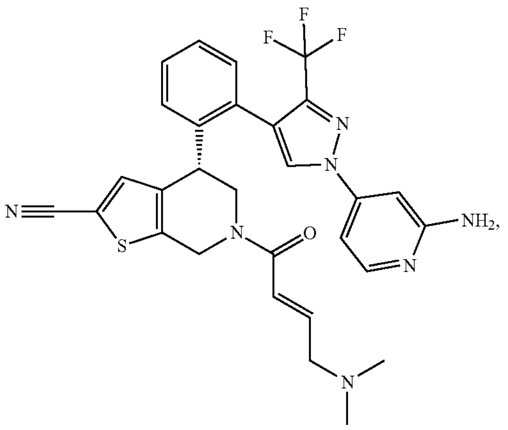
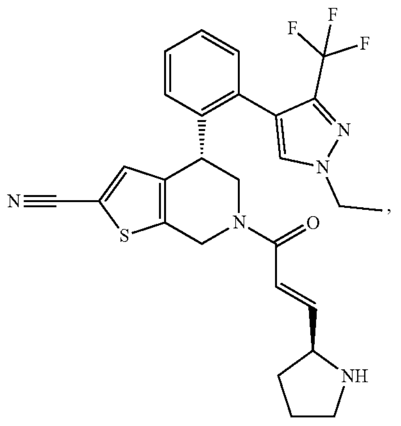
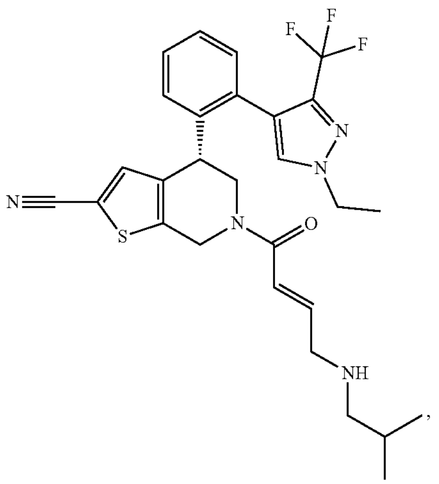

-continued
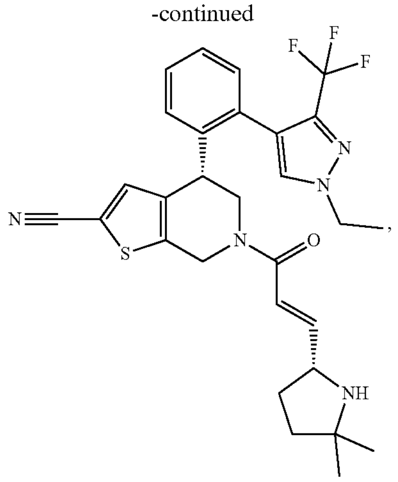
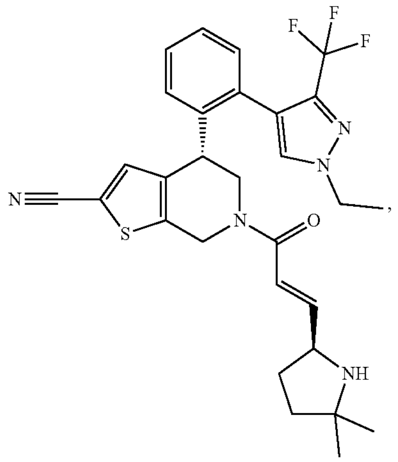
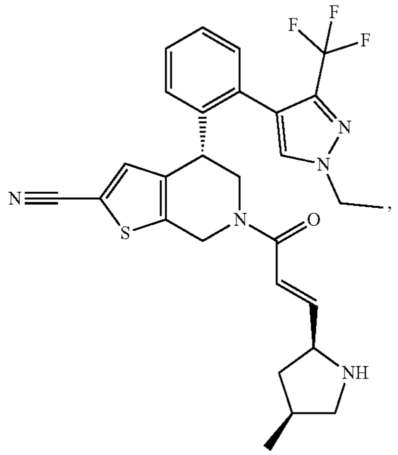
-continued
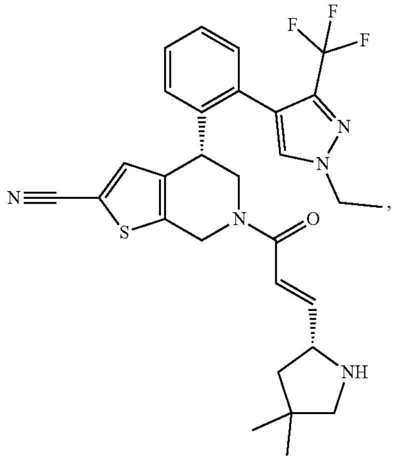
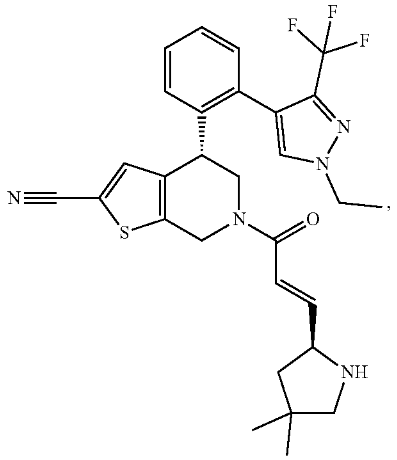
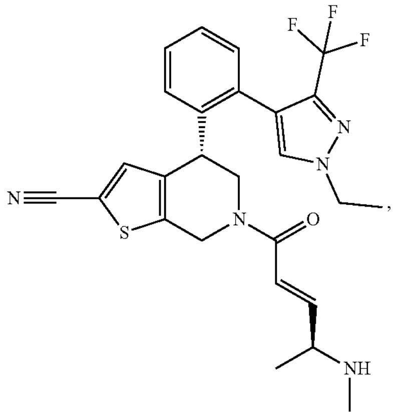

-continued
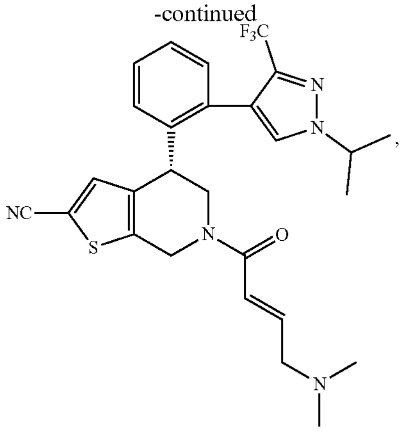
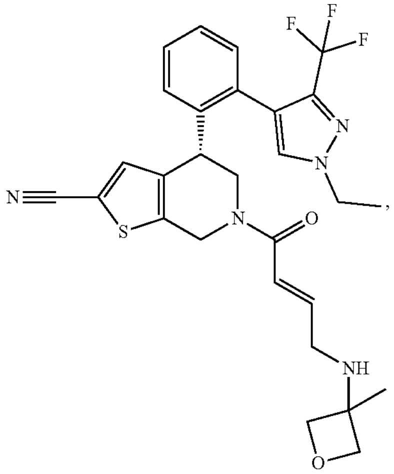
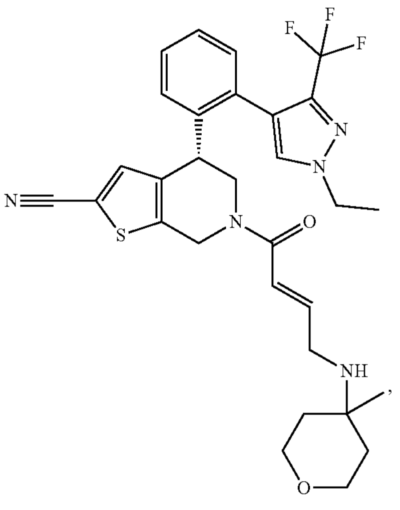
-continued
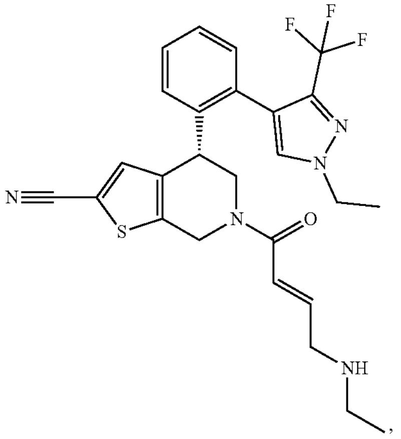
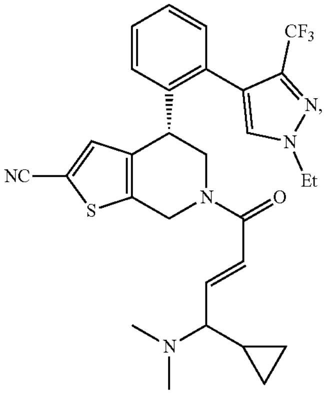
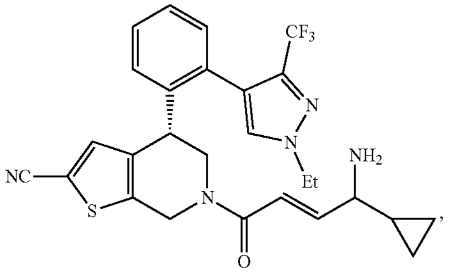
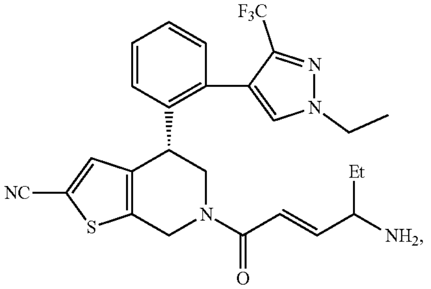
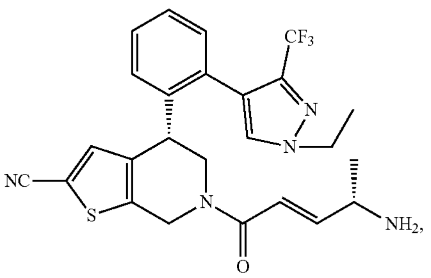

-continued
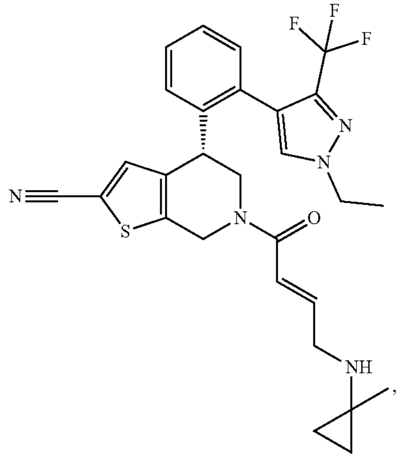
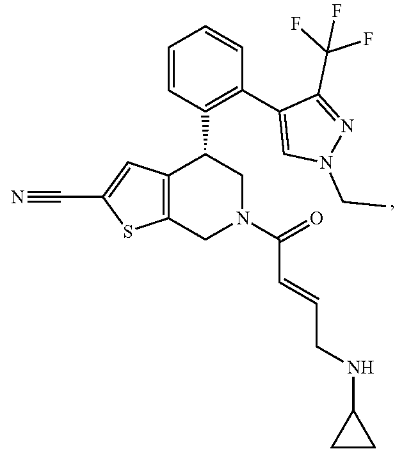
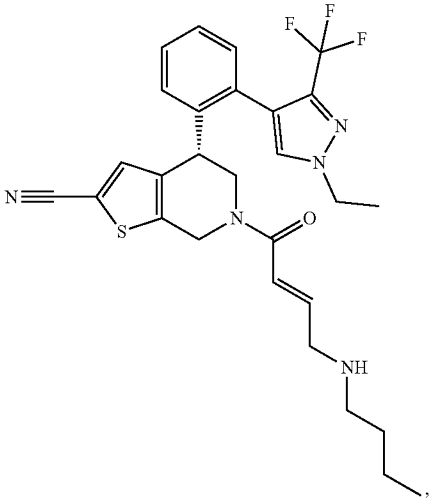
-continued
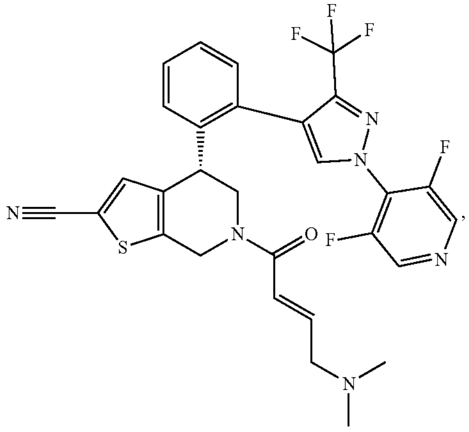
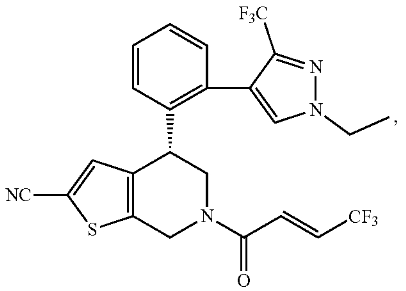
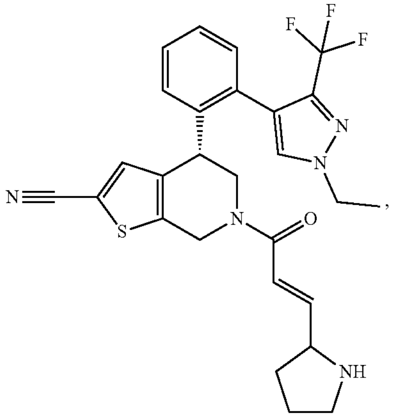
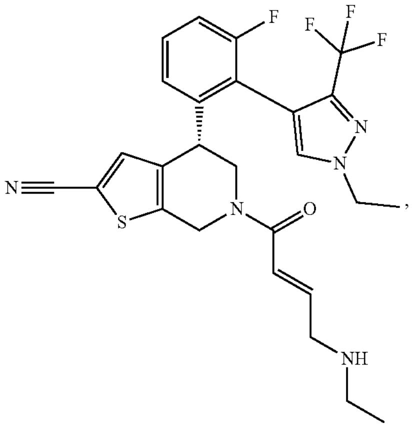

-continued
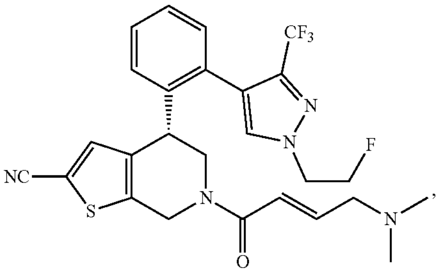
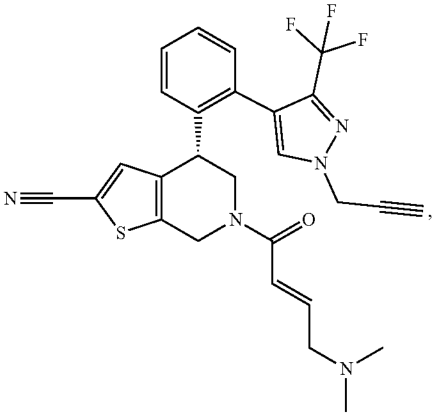
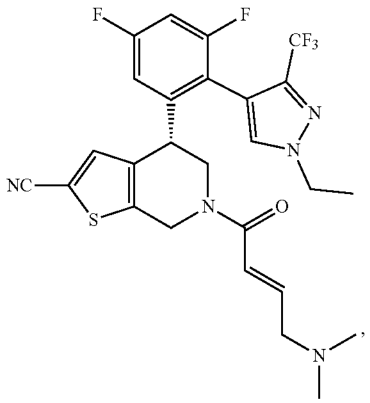
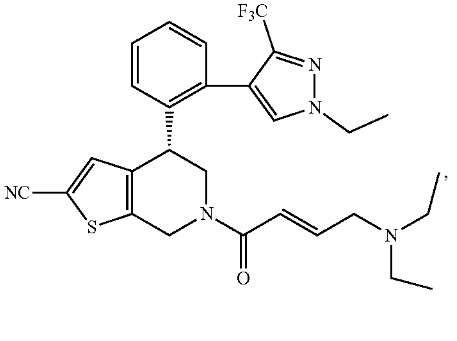
-continued
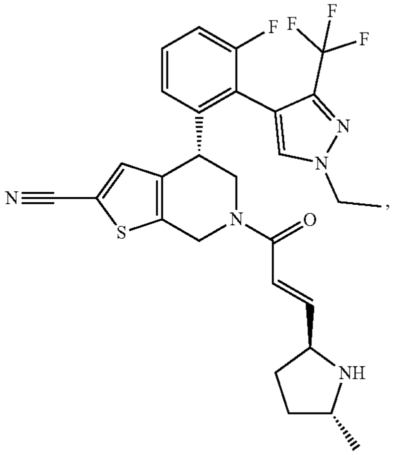
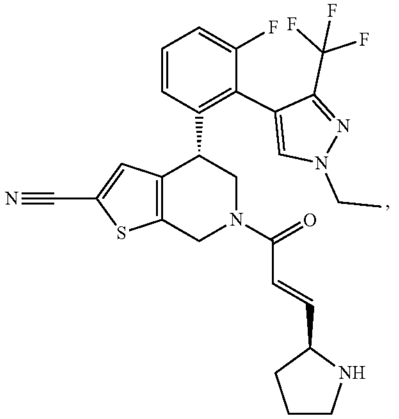
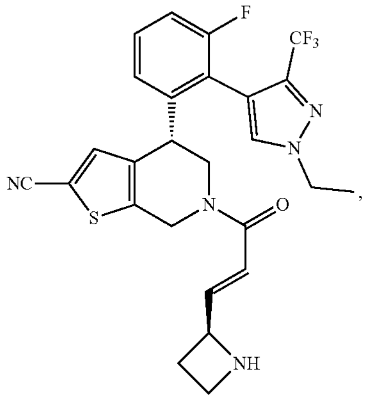
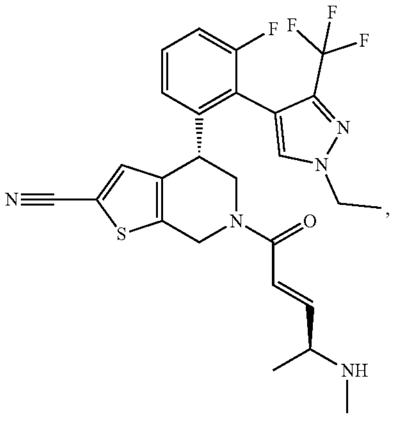

-continued
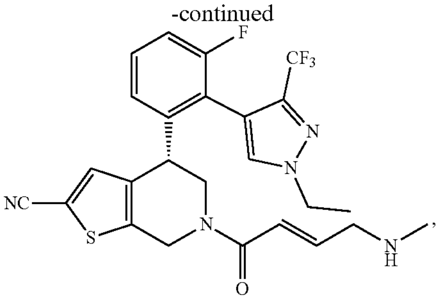
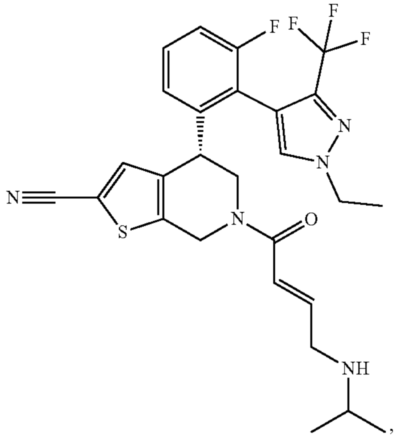
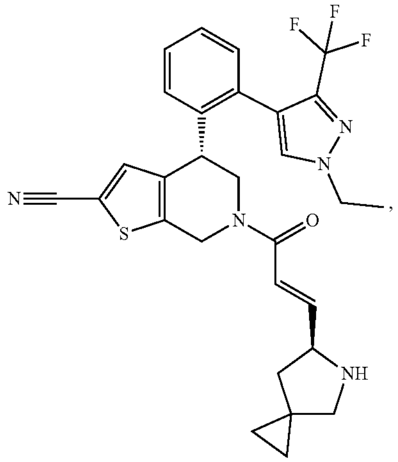
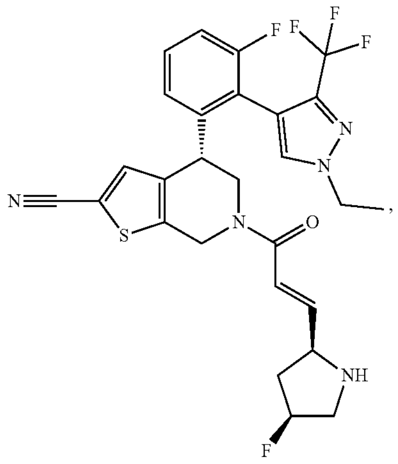
-continued
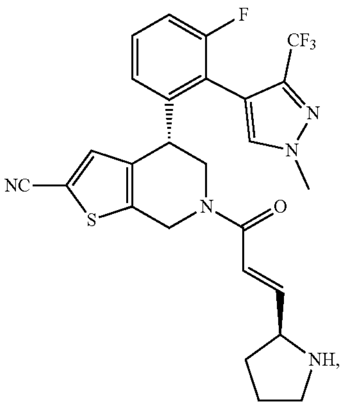
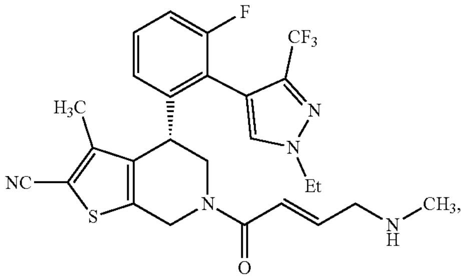
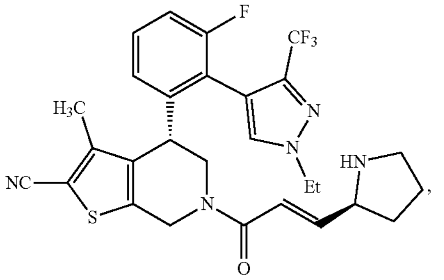
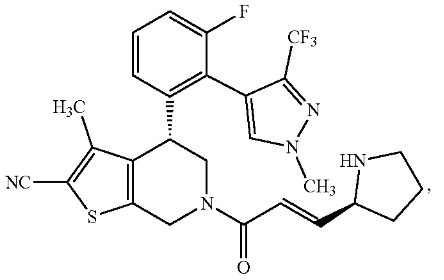
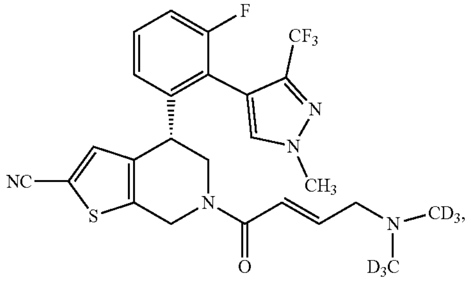

-continued
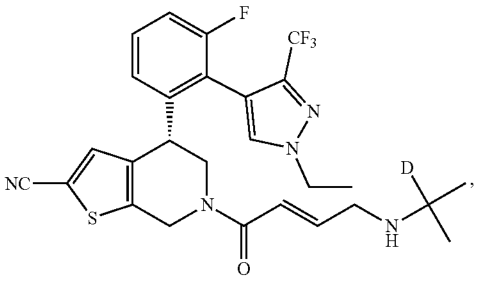
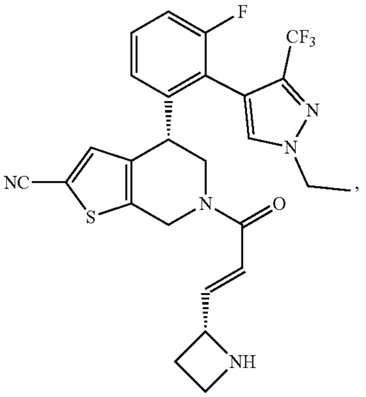
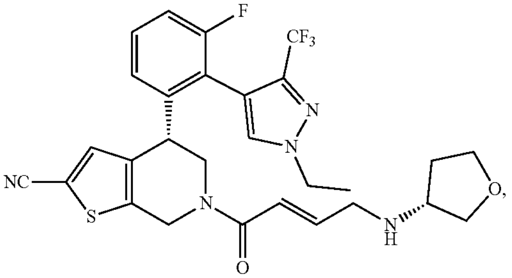
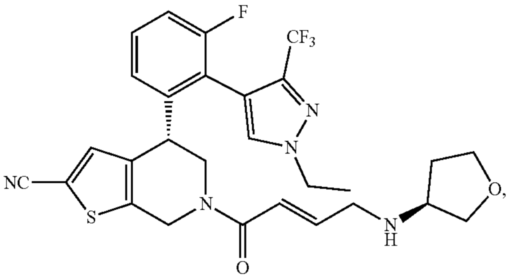
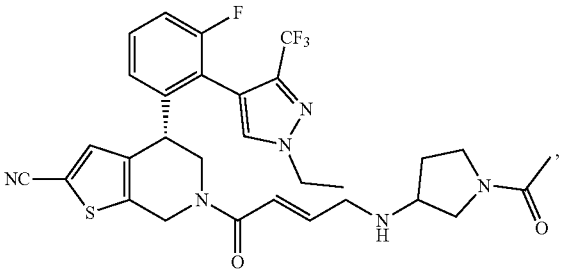
-continued
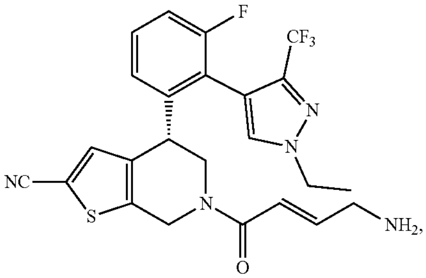
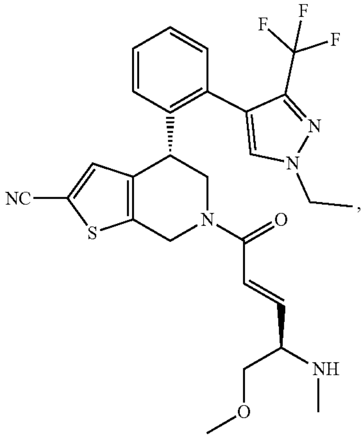
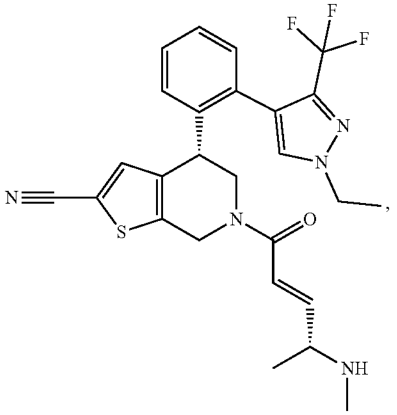
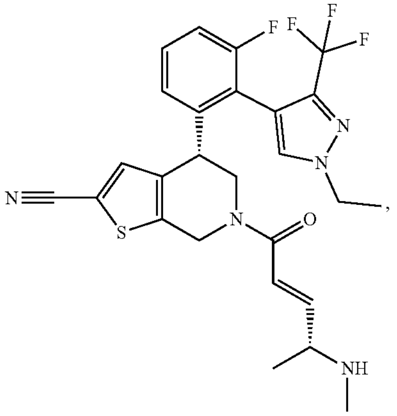

-continued
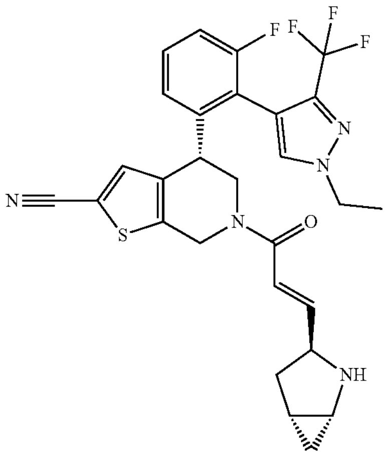
,
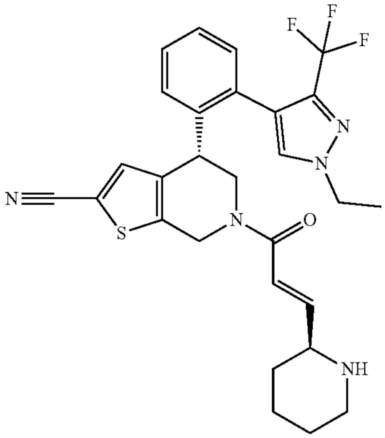
,
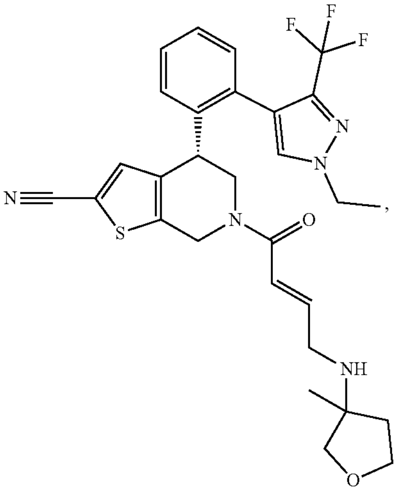
,
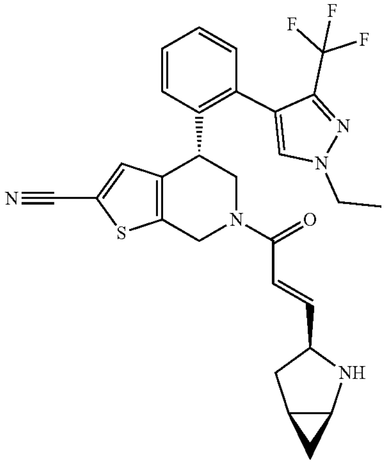
,
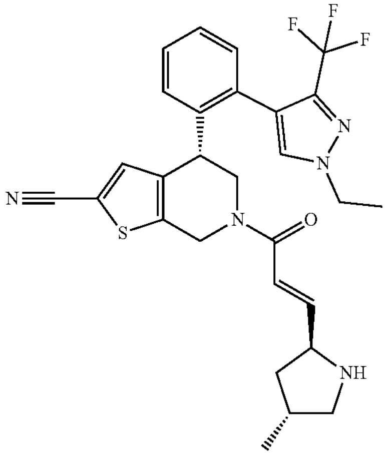
,
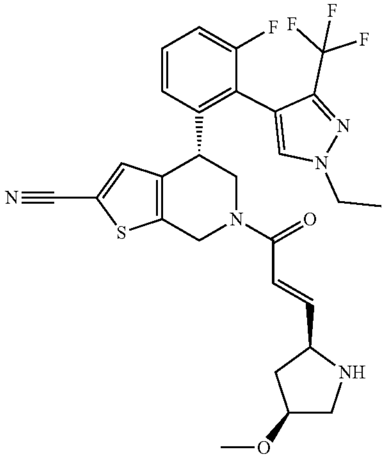
,
-continued -continued
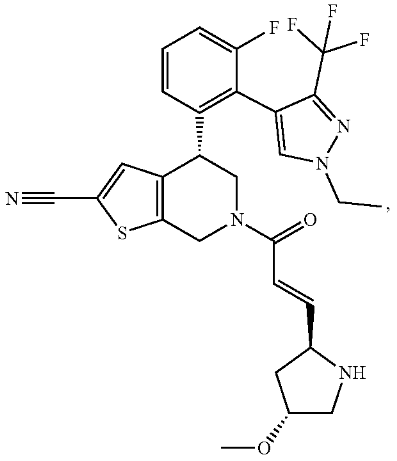
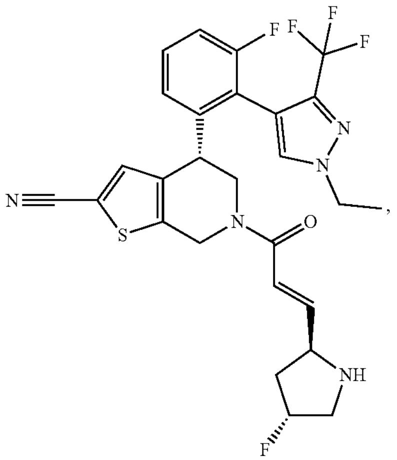
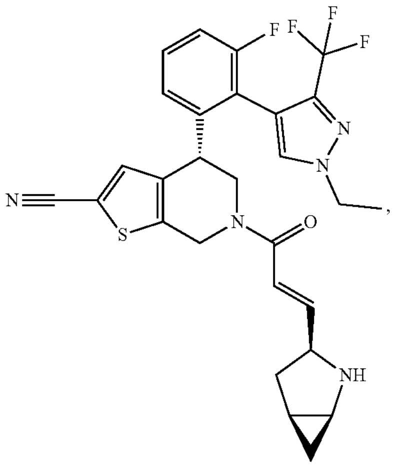
-continued
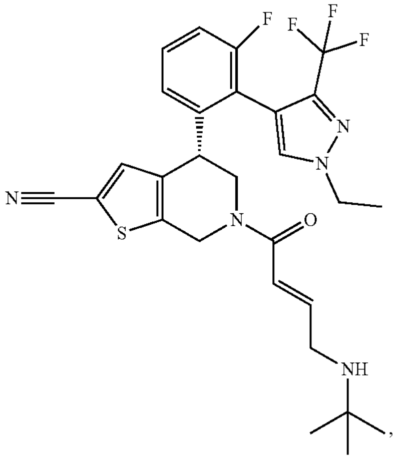
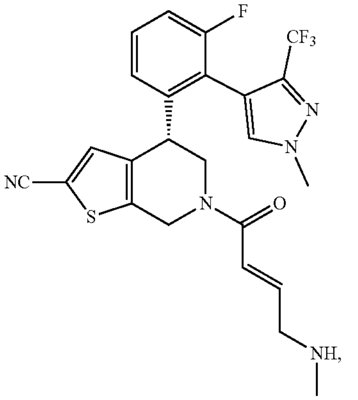
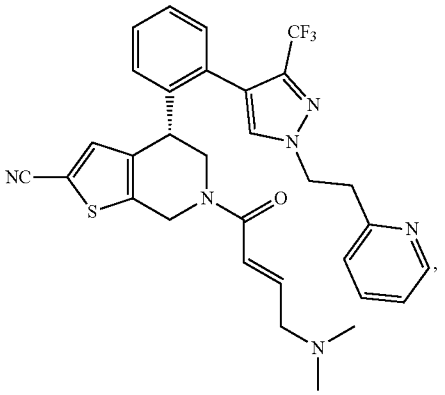
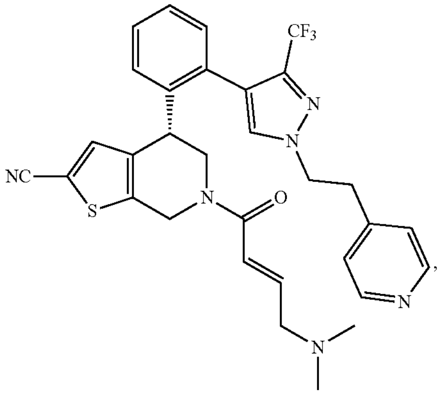

-continued

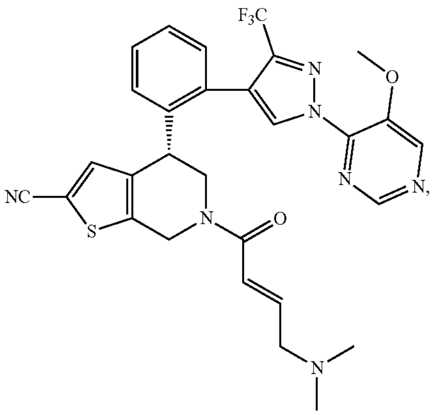

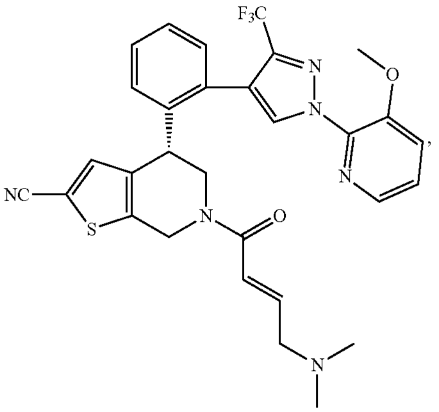

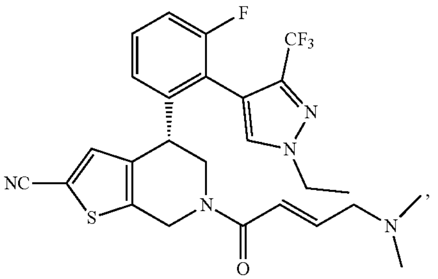

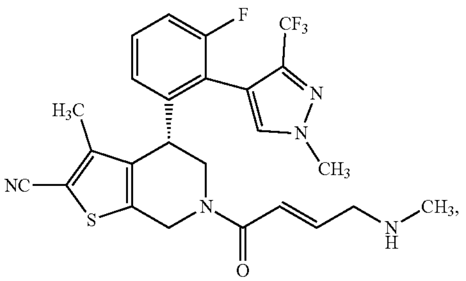

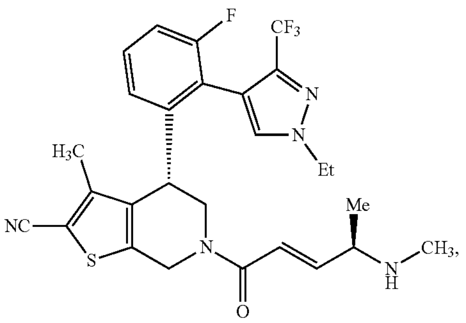

-continued

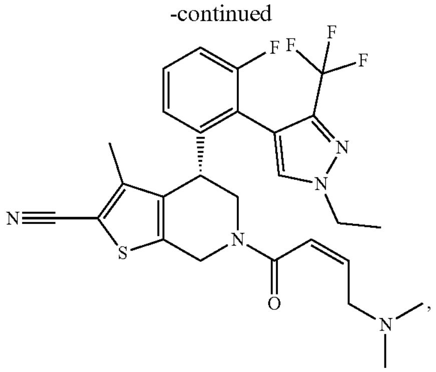

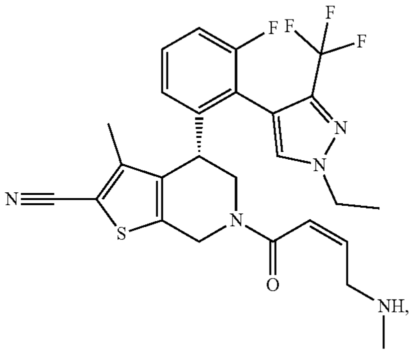

and

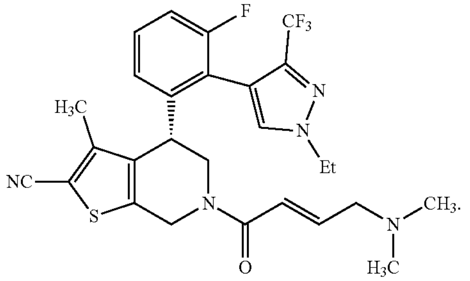

14. A pharmaceutical composition, comprising the compound of claim 1 or a pharmaceutically acceptable salt thereof and at least one carrier, excipient, or diluent.

15. A method of treating cancer in a subject in need thereof, said method comprising administering to said subject a therapeutically effective amount of the compound of claim 1.

16. The compound of claim 13, wherein the compound is the specific isomer

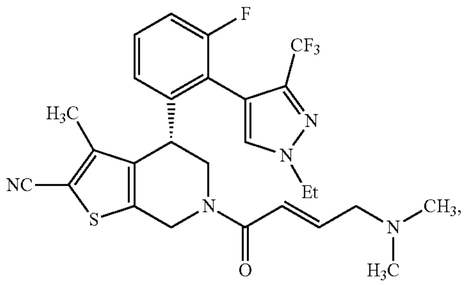 [SMILES: CCn1cc(-c2c(F)cccc2[C@@H]2CN(C(=O)/C=C/CN(C)C)Cc3sc(C#N)c(C)c32)c(C(F)(F)F)n1]

or a pharmaceutically acceptable salt thereof.

17. The compound of claim 13, wherein the compound is the specific isomer

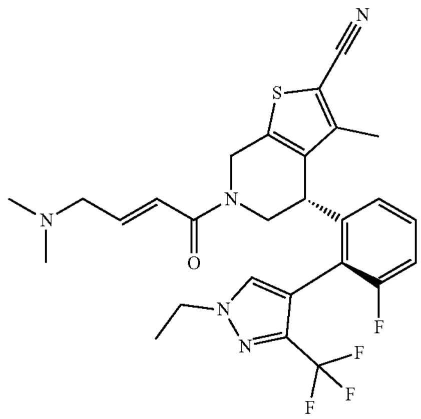
,
or a pharmaceutically acceptable salt thereof.
18. A compound having a structure selected from
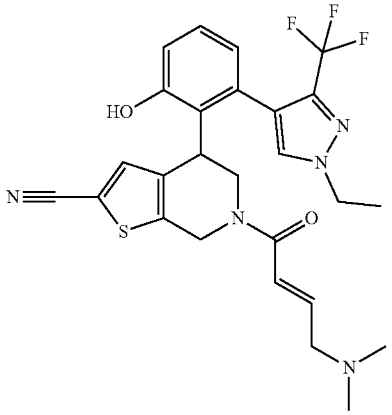
,
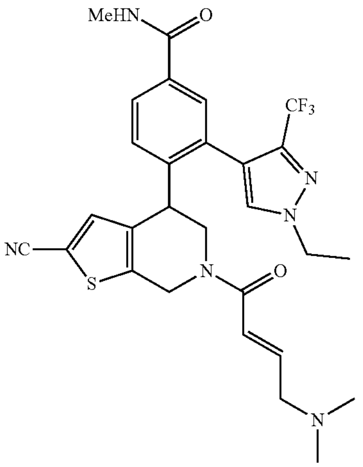
,
-continued
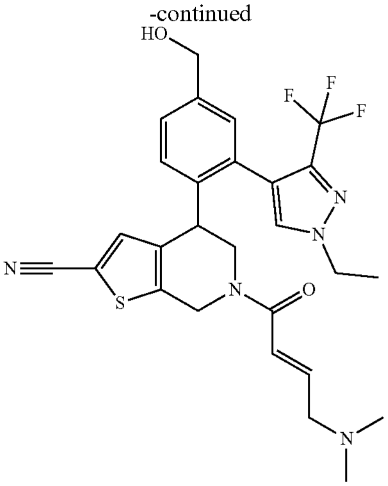
,
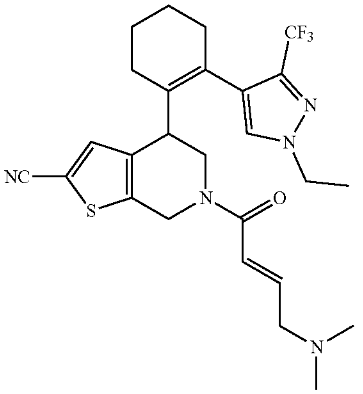
,
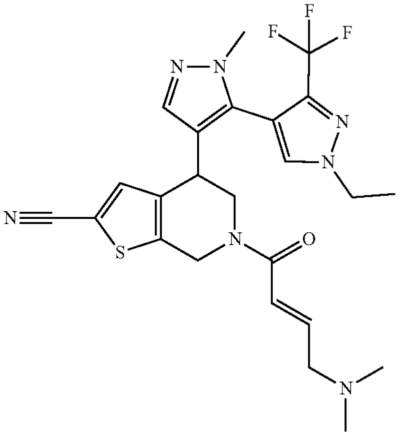
,
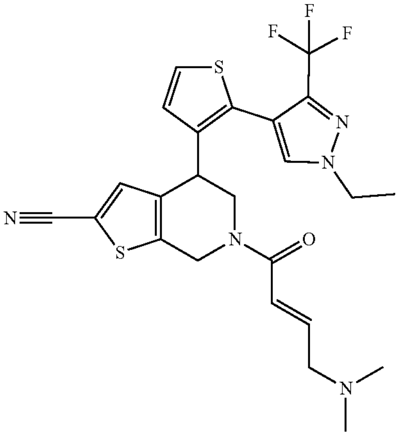
, -continued
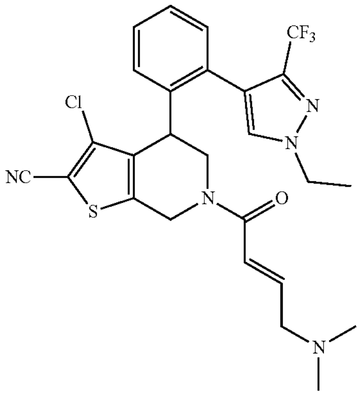
, and
-continued
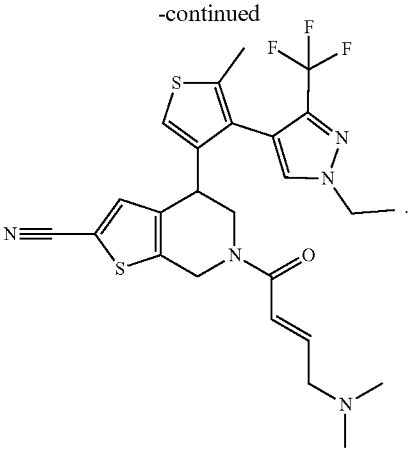
.
* * * * *